(12) United States Patent
Rudolf et al.

(10) Patent No.: US 7,498,325 B2
(45) Date of Patent: Mar. 3, 2009

(54) MODIFIED AMINO ACIDS, PHARMACEUTICALS CONTAINING THESE COMPOUNDS AND METHOD FOR THEIR PRODUCTION

(75) Inventors: Klaus Rudolf, Biberach (DE); Wolfgang Eberlein, Biberach (DE); Wolfhard Engel, Biberach (DE); Helmut Pieper, Biberach (DE); Henri Doods, Warthausen (DE); Gerhard Hallermayer, Maselheim/Sulmingen (DE); Michael Entzeroth, Meudon (FR); Wolfgang Wienen, Biberach (DE)

(73) Assignee: Karl Thomas GmbH, Ingelheim (DE)

( * ) Notice: Subject to any disclaimer, the term of this patent is extended or adjusted under 35 U.S.C. 154(b) by 369 days.

(21) Appl. No.: 10/835,495

(22) Filed: Apr. 29, 2004

(65) Prior Publication Data

US 2004/0214819 A1     Oct. 28, 2004

Related U.S. Application Data

(63) Continuation of application No. 10/119,875, filed on Apr. 10, 2002, now abandoned, which is a continuation of application No. 09/789,391, filed on Feb. 21, 2001, now abandoned, which is a continuation of application No. 09/254,281, filed on Oct. 12, 1999, now Pat. No. 6,344,449.

(30) Foreign Application Priority Data

Sep. 8, 1997  (EP) .................... PCT/EP97/04862

(51) Int. Cl.
  C07D 498/02  (2006.01)
  C07D 285/22  (2006.01)
  A61K 31/50   (2006.01)

(52) U.S. Cl. .............. 514/222.5; 514/260.1; 514/266.3; 544/12; 544/279; 544/285

(58) Field of Classification Search ............... 514/222.5
See application file for complete search history.

(56) References Cited

U.S. PATENT DOCUMENTS 5,798,337 A * 8/1998 Somers et al. ............. 514/19
6,025,372 A * 2/2000 Yang et al. ................ 514/316
6,194,437 B1   2/2001 Horwell et al.

6,300,501 B1  10/2001 Dobrusin et al.

FOREIGN PATENT DOCUMENTS

DE        19636623     *  3/1998
WO     WO 93/25574     * 12/1993
WO     WO 96/15148        5/1996
WO     WO 97/44350       11/1997
WO     WO 98/07718        2/1998

OTHER PUBLICATIONS

Hamilton, et al; A Quantitative Analysis f the Binding f N-Acyl Derivatives f alpha-Amin amides by alpha-Chym trypsin, Pr c. Nat. Acad. Sci. (1996), 55(3), pp. 664-669.
Bachem Bi science, Inc., Datal g US Jun. 1993; E-1160 and E-1170, p. 13.
Fang, et al; Clin. Exp. Allergy 28 (1998) 228-232 (Medline abstract nly).
Edvinss n Funct. Neur I. 15 Suppl. 3 (2000) 50-60 (Medline abstract nly).
Onuoha, et al; Eur. J. Clin. Invest 31 (2001) 253-257 (Medline abstract nly).
Powell, et al; Br. J. Pharmac I. 131 (2000) 875-884 (Medline abstract nly).

* cited by examiner

*Primary Examiner*—James O. Wilson
*Assistant Examiner*—Noble Jarrell
(74) *Attorney, Agent, or Firm*—Michael P. Morris; Mary-Ellen M. Devlin; Alan R. Stempel

(57) ABSTRACT

The present invention relates to modified amino acids of general formula

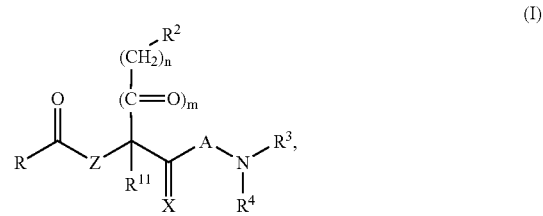

(I)

wherein
A, Z, X, n, m, R, $R^2$, $R^3$, $R^4$ and $R^{11}$ are defined as in claims 1 to 5, their tautomers, their diastereomers, their enantiomers, the mixtures thereof and the salts thereof, particularly the physiologically acceptable salts thereof with inorganic or organic acids or bases, pharmaceutical compositions containing these compounds, the use thereof and processes for preparing them as well as their use for the production and purification of antibodies and as labelled compounds in RIA- and ELISA assays and as diagnostic or analytical aids in neurotransmitter research.

5 Claims, No Drawings

MODIFIED AMINO ACIDS, PHARMACEUTICALS CONTAINING THESE COMPOUNDS AND METHOD FOR THEIR PRODUCTION

This is a continuation of Ser. No. 10/119,875 filed Apr. 10, 2002, which is a continuation of Ser. No. 09/789,391 filed Feb. 21, 2001, now abandoned, which is a continuation of Ser. No. 09/254,281 filed Oct. 12, 1999, now U.S. Pat. No. 6,344,449, which is a 371 of PCT/P97/04862.

The present invention relates to modified amino acids of general formula

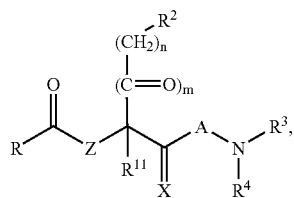

their tautomers, their diastereomers, their enantiomers, their mixtures and salts thereof, particularly physiologically acceptable salts thereof with inorganic or organic acids or bases, pharmaceutical compositions containing these compounds, the use thereof and processes for preparing them.

In the above general formula I

R denotes an unbranched $C_{1-7}$-alkyl group which may be substituted in the ω-position by a $C_{4-10}$-cycloalkyl group, by one or two phenyl groups, by a 1-naphthyl, 2-naphthyl or biphenylyl group, by a 1,3-dihydro-2H-2-oxobenzimidazol-1-yl, 2,4(1H,3H)-di-oxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-2H-2-oxoimidazopyridinyl, 1,3-dihydro-2(2H)-oxoimidazo[4,5-c]quinolin-3-yl, 1,3-dihydro-2H-2-oxoimidazol-1-yl or 3,4-dihydro-2(1H)-oxopyrimidin-3-yl group, wherein the latter two groups may each be mono- or disubstituted in the 4- and/or 5-position or in the 5- and/or 6-position by lower straight chained or branched alkyl groups, by phenyl, biphenylyl, pyridinyl, diazinyl, furyl, thienyl, pyrrolyl, 1,3-oxazolyl, 1,3-thiazolyl, isoxazolyl, pyrazolyl-1-methylpyrazolyl, imidazolyl or 1-methylimidazolyl groups and the substituents may be identical or different, by a 5-membered heteroaromatic ring linked via a carbon atom, which contains a nitrogen, oxygen or sulphur atom or, in addition to a nitrogen atom, contains an oxygen, sulphur or additional nitrogen atom, whilst a nitrogen atom of an imino group may be substituted by an alkyl group, or by a 6-membered heteroaromatic ring linked via a carbon atom, which contains one, two or three nitrogen atoms, whilst a 1,4-butadienylene group may be attached both to the above-mentioned 5-membered heteroaromatic monocyclic rings and to the 6-membered heteroaromatic monocyclic rings, in each case via two adjacent carbon atoms, and the bicyclic heteroaromatic rings thus formed may also be bound via a carbon atom of the 1,4-butadienylene group, an unbranched $C_{1-6}$-alkylamino group optionally substituted at the nitrogen atom by a $C_{1-6}$-alkyl group or by a phenylmethyl group, which may be substituted in the ω-position by a $C_{4-10}$-cycloalkyl group, by one or two phenyl groups, by a 1-naphthyl, 2-naphthyl or biphenylyl group, by a 1H-indol-3-yl, 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-4-(3-thienyl)-2H-2-oxoimidazol-1-yl, 1,3-dihydro-4-phenyl-2H-2-oxoimidazol-1-yl, 1,3-dihydro-5-phenyl-2H-2-oxoimidazol-1-yl, 1,3-dihydro-2(2H)-oxoimidazo[4,5-c]quinolin-3-yl, 3,4-dihydro-5-phenyl-2(1H)-oxopyrimidin-3-yl, 3,4-dihydro-6-phenyl-2(1H)-oxopyrimidin-3-yl- or 1,3-dihydro-2H-2-oxoimidazo-[4,5-b]pyridin-3-yl- group, by a 5-membered heteroaromatic ring linked via a carbon atom, which contains a nitrogen, oxygen or sulphur atom or, in addition to a nitrogen atom, contains an oxygen, sulphur or an additional nitrogen atom, whilst a nitrogen atom of an imino group may be substituted by an alkyl group, or by a 6-membered heteroaromatic ring linked via a carbon atom, containing 1, 2 or 3 nitrogen atoms, whilst a 1,4-butadienylene group may be attached both to the 5-membered and to the 6-membered heteroaromatic monocyclic rings, in each case via two adjacent carbon atoms, and the bicyclic heteroaromatic rings thus formed may also be bound via a carbon atom of the 1,4-butadienylene group, whilst the phenyl, naphthyl and biphenylyl groups mentioned above for the substitution of the alkyl and alkylamino groups in the ω-position and optionally also partially hydrogenated mono- and bicyclic heteroaromatic rings in the carbon skeleton may additionally be mono-, di- or trisubstituted by fluorine, chlorine or bromine atoms or by alkyl groups, $C_{3-8}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl)carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl or trifluoromethylsulphonyl groups, wherein the substituents may be identical or different and the above-mentioned benzoyl, benzoylamino and benzoylmethylamino groups may in turn additionally be substituted in the phenyl moiety by a fluorine, chlorine or bromine atom or by an alkyl, trifluoromethyl, amino or acetylamino group, or the group of formula

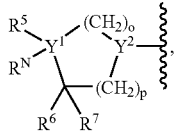

(II)

wherein
p denotes the number 1 or 2,
o denotes the number 2 or 3 or, if $Y^1$ and $Y^2$ are not simultaneously nitrogen atoms, o may also denote 1.
$Y^1$ denotes the nitrogen atom if $R^5$ is a free pair of electrons, or the carbon atom,
$Y^2$ is the nitrogen atom or the group >CH—,
$R^5$ is a free pair of electrons if $Y^1$ denotes the nitrogen atom or, if $Y^1$ denotes the carbon atom, $R^5$ denotes a hydrogen atom, a $C_{1-3}$-alkyl group, a hydroxy, cyano, aminocarbonyl, carboxy, alkoxycarbonyl, aminocarbonylamino, phenylmethyl or phenyl group,
$R^6$ denotes the hydrogen atom or, provided that $Y^1$ is not a nitrogen atom, $R^6$ together with $R^5$ may denote an additional bond,
$R^7$ denotes the hydrogen atom or, provided that $Y^1$ is not a nitrogen atom and $R^5$ and $R^6$ together constitute an additional bond, $R^7$ together with $R^N$ may also denote a 1,4-butadienylene group,
$R^N$ denotes a hydrogen atom or a $C_{1-6}$-alkyl group which may be mono- or disubstituted in the ω-position
by a $C_{5-7}$-cycloalkyl group, by a 1-naphthyl, 2-naphthyl, hydroxy, alkoxy, amino, alkylamino, dialkylamino, piperidinyl, morpholinyl, pyrrolidinyl, hexahydro-1H-1-azepinyl, aminocarbonyl, alkylaminocarbonyl, acetylamino, cyano, aminocarbonylamino or alkylaminocarbonylamino group or by phenyl, pyridinyl or diazinyl groups, whilst these substituents may be identical or different,
a $C_{5-7}$-cycloalkyl group, a phenyl, pyridinyl, cyano, amino, benzoylamino, aminocarbonyl, alkylaminocarbonyl, alkoxycarbonyl, phenylalkoxycarbonyl, aminocarbonylamino, alkylaminocarbonylamino, dialkylaminocarbonylamino, N-(aminocarbonyl)-N-alkylamino, N-(alkylaminocarbonyl)-N-alkylamino, N-(alkylaminocarbonyl)-N-phenylamino, phenylaminocarbonylamino, [phenyl(alkylamino)]carbonylamino, N-(phenylaminocarbonyl)-N-alkylamino, N-(phenylaminocarbonyl)-N-phenylamino, benzoylaminocarbonylamino, phenylalkylaminocarbonylamino, pyridinylaminocarbonylamino, N-(aminocarbonyl)-N-phenylamino, N-(alkylaminocarbonyl)-N-phenylamino, N-(aminocarbonylaminocarbonyl)-N-phenylamino, N-(pyridinyl)-N-(aminocarbonyl)amino, N-(pyridinyl)-N-(alkylaminocarbonyl)amino, phenylamino, pyridinylamino, 4-[3,4-dihydro-2(1H)-oxoquinazolin-3-yl]-1-piperidinyl or diazinylamino group,
a saturated, mono- or diunsaturated 5- to 7-membered aza, diaza, triaza, oxaza, thiaza, thiadiaza- or S,S-dioxidothiadiaza-heterocycle.
wherein the above-mentioned heterocycles may be linked via a carbon or nitrogen atom and
may contain one or two carbonyl groups adjacent to a nitrogen atom,
may be substituted at one of the nitrogen atoms by an alkyl, alkanoyl, aroyl, hydroxycarbonylalkyl, alkoxycarbonylalkyl, phenylalkoxycarbonylalkyl, phenylmethyl or phenyl group,
may be substituted at one or two carbon atoms by a branched or unbranched alkyl group or by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl group, wherein the substituents may be the same or different,
and wherein a $C_{3-6}$-alkylene group may additionally be attached to the above-mentioned heterocycles via two adjacent carbon atoms or an olefinic double bond of one of the above-mentioned unsaturated heterocycles may be fused with a benzene, pyridine, diazine, 1,3-oxazole, thiophene, furan, thiazole, pyrrole, N-methyl-pyrrole, quinoline, imidazole or N-methyl-imidazole ring,
or if $Y^1$ is not a nitrogen atom and $R^5$ and $R^6$ together denote an additional bond, $R^N$ together with $R^7$ may also denote the 1,4-butadienylene group,
or, if $Y^1$ is a carbon atom, $R^N$ together with $R^5$, including $Y^1$, also denotes a carbonyl group or a saturated or mono-unsaturated 5- or 6-membered 1,3-diaza-heterocycle which may optionally contain one or two carbonyl groups in the ring and, if it is unsaturated, may be benzofused at the double bond and may be substituted at one of the nitrogen atoms by a methyl, aminocarbonyl, hydroxycarbonylalkyl, alkoxycarbonylalkyl, phenylalkoxycarbonylalkyl, phenylmethyl or phenyl group,
whilst the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl- or 1-methylimidazolyl groups contained in the residues mentioned under $R^5$, $R^7$ and $R^N$, as well as benzo, thieno, pyrido- and diazino-fused heterocycles in the carbon skeleton may additionally be mono-, di- or trisubstituted by fluorine, chlorine or bromine atoms, by alkyl groups, $C_{3-8}$-cycloalkyl groups, nitro, alkoxy, alkylthio, alkylsulphinyl, alkylsulphonyl, alkylsulphonylamino, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, hydroxyalkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, aminocarbonylaminoalkyl, alkylaminocarbonylamino, alkanoyl, cyano, trifluoromethoxy, trifluormethylthio, trifluoromethylsulphinyl- or trifluoromethylsulphonyl groups, wherein the substituents may be identical or different and the above-mentioned benzoyl, benzoylamino, benzoylaminocarbonylamino and benzoylmethylamino groups may in turn additionally be substituted in the phenyl moiety by a fluorine, chlorine or bromine atom or by an alkyl, trifluoromethyl, amino- or acetylamino group
and unless otherwise specified the alkyl groups contained in the above-mentioned radicals may contain 1 to 5 carbon atoms,
X denotes an oxygen atom or 2 hydrogen atoms,
Z denotes a methylene group or the group —$NR^1$, wherein $R^1$ denotes a hydrogen atom or an alkyl or phenylalkyl group, $R^{11}$ denotes a hydrogen atom, a $C_{1-3}$-alkyl group, an alkoxycarbonyl group having a total of 2 to 4 carbon atoms or a phenylmethyl group, n denotes the number 1 or 2 or, if m is 1, n may also be 0, m denotes the number 0 or 1, $R^2$ denotes a phenyl, 1-naphthyl, 2-naphthyl, 1,2,3,4-tetrahydro-1-naphthyl, 1H-indol-3-yl, 1-methyl-1H-indol-3-yl, 1-formyl-1H-indol-3-yl, 1-(1,1-dimethylethoxycarbonyl)-1H-indol-3-yl, 4-imidazolyl, 1-methyl-4-imidazolyl, 2-thienyl, 3-thienyl, thiazolyl, 1H-indazol-3-yl, 1-methyl-1H-indazol-3-yl, benzo[b]fur-3-yl, benzo[b]thien-3-yl, pyridinyl, quinolinyl or isoquinolinyl group, whilst the above-mentioned aromatic and heteroaromatic groups in the carbon skeleton may additionally be mono-, di- or trisubstituted by fluorine, chlorine or bromine atoms or by branched or unbranched alkyl groups, $C_{3-8}$-cycloalkyl groups, phenylalkyl groups, alkenyl, alkoxy, phenyl, phenylalkoxy, trifluoromethyl, alkoxycarbonylalkyl, carboxyalkyl, alkoxycarbonyl, carboxy, dialkylaminoalkyl, dialkylaminoalkoxy, hydroxy, nitro, amino, acetylamino, propionylamino, benzoyl, benzoylamino, benzoylmethylamino, methylsulphonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulphinyl- or trifluoromethylsulphonyl groups, and the substituents may be identical or different and the above-mentioned benzoyl, benzoylamino- and benzoylmethylamino groups may in turn additionally be substituted in the phenyl moiety by a fluorine, chlorine or bromine atom, or by an alkyl, trifluoromethyl, amino or acetylamino group, A denotes a bond or the divalent group of formula

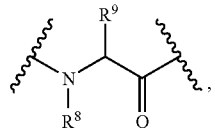

(III)

(which is linked to the $NR^3R^4$ group via the —CX group)

wherein $R^8$ and $R^9$ together denote an n-propylene group or $R^8$ denotes a hydrogen atom or an alkyl- or phenylalkyl group and $R^9$ denotes a hydrogen atom or a branched or unbranched $C_{1-5}$-alkyl group which, if it is unbranched, may be substituted in the ω-position by a hydroxy, mercapto, amino, alkylamino, dialkylamino, 1-azetidinyl, 1-pyrrolidinyl, 1-piperidinyl, hexahydro-1-azepinyl, methylthio, hydroxycarbonyl, aminocarbonyl, aminoiminomethylamino, aminocarbonylamino, phenyl, 1H-indol-3-yl, 1-methyl-1H-indol-3-yl, 1-formyl-1H-indol-3-yl, 4-imidazolyl, 1-methyl-4-imidazolyl, 1-naphthyl, 2-naphthyl- or pyridinyl group, whilst the above-mentioned heterocycles, phenyl and naphthyl groups may in turn be mono-, di- or trisubstituted in the carbon skeleton by fluorine, chlorine or bromine atoms or by methyl, alkoxy, trifluoromethyl, hydroxy, amino, acetylamino, aminocarbonyl, cyano, trifluoromethoxy, methylsulphonyloxy, trifluoromethylthio, trifluoromethylsulphinyl or trifluoromethylsulphonyl groups, wherein the substituents may be identical or different, and wherein the hydroxy, mercapto, amino, guanidino, indolyl and imidazolyl groups contained in the groups mentioned for $R^9$ may be substituted with the protecting groups commonly used in peptide chemistry, preferably with the acetyl, benzyloxycarbonyl or tert.butyloxycarbonyl group, $R^3$ denotes a hydrogen atom, a $C_{1-7}$-alkyl group which may be substituted in the ω-position by a cyclohexyl, phenyl, pyridinyl, diazinyl, hydroxy, amino, alkylamino, dialkylamino, carboxy, aminocarbonyl, aminocarbonylamino, acetylamino, 1-pyrrolidinyl, 1-piperidinyl, 4-(l-piperidinyl)-1-piperidinyl, 4-morpholinyl, hexahydro-1H-1-azepinyl, [bis-(2-hydroxyethyl)]amino, 4-alkyl-1-piperazinyl or 4-(ω-hydroxyalkyl)-1-piperazinyl group, a phenyl or pyridinyl group, wherein the above-mentioned heterocyclic groups and phenyl groups may additionally be mono-, di- or trisubstituted in the carbon skeleton by fluorine, chlorine or bromine atoms or by methyl, alkoxy, trifluoromethyl, hydroxy, amino, acetylamino, aminocarbonyl, cyano, methylsulphonyloxy, trifluoromethoxy, trifluoromethylthio, trifluoromethylsulphinyl or trifluoromethylsulphonyl groups and the substituents may be identical or different, $R^4$ denotes a hydrogen atom or a $C_{1-3}$-alkyl group optionally substituted by a phenyl or pyridinyl group or $R^3$ and $R^4$ together with the enclosed nitrogen atom denote a group of general formula

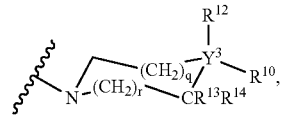

(IV)

wherein $Y^3$ denotes a carbon atom or, if $R^{12}$ denotes a free pair of electrons, $Y^3$ may also be the nitrogen atom, r denotes the number 0, 1 or 2, q denotes the number 0, 1 or 2, $R^{10}$ denotes a hydrogen atom or an amino, alkylamino, dialkylamino, alkyl, cycloalkyl, aminoalkyl, alkylaminoalkyl, dialkylaminoalkyl, aminoiminomethyl, aminocarbonylamino, alkylaminocarbonylamino, cycloalkylaminocarbonylamino, phenylaminocarbonylamino, aminocarbonylalkyl, aminocarbonylaminoalkyl, alkoxycarbonyl, alkoxycarbonylalkyl, carboxyalkyl or carboxy group, a phenyl, pyridinyl, diazinyl, 1-naphthyl, 2-naphthyl, pyridinylcarbonyl- or phenylcarbonyl-group which may be mono-, di- or trisubstituted in the carbon skeleton by fluorine, chlorine or bromine atoms, or by alkyl, alkoxy, methylsulphonyloxy, trifluoromethyl, hydroxy, amino, acetylamino, aminocarbonyl, aminocarbonylamino, aminocarbonylaminomethyl, cyano, carboxy, carbalkoxy, carboxyalkyl, carbalkoxyalkyl, alkanoyl, ω-(dialkylamino)alkanoyl, ω-(dialkylamino)alkyl, ω-(dialkylamino)hydroxyalkyl, ω-(carboxy)alkanoyl, trifluoromethoxy, trifluoromethylthio, trifluoromethylsulphinyl or trifluoromethylsulphonyl groups, whilst the substituents may be identical or different, a 1,3-dihydro-2-oxo-2H-imidazolyl, 2,4(1H,3H)-dioxopyrimidinyl or 3,4-dihydro-2(1H)-oxopyrimidinyl group bound via a nitrogen atom, which may be substituted by a phenyl group or fused at the double bond to a benzene, pyridine or diazine ring, a 1,1-dioxido-3(4H)-oxo-1,2,4-benzothiadiazin-2-yl group, a 4- to 10-membered azacycloalkyl group, a 5- to 10-membered oxaza, thiaza- or diazacycloalkyl group or a 6- to 10-membered azabicycloalkyl group, wherein the above-mentioned mono- and bicyclic heterocycles may be bound via a nitrogen or carbon atom and may be substituted by a $C_{1-7}$-alkyl group, by an alkanoyl, dialkylamino, phenylcarbonyl, pyridinylcarbonyl, carboxyalkanoyl, carboxyalkyl, alkoxycarbonylalkyl, alkoxycarbonyl, aminocarbonyl, alkylaminocarbonyl, alkylsulphonyl, cycloalkyl- or cycloalkylalkyl group, by a cycloalkylcarbonyl, azacycloalkylcarbonyl, diazacycloalkylcarbonyl or oxazacycloalkylcarbonyl group optionally substituted in the ring, whilst the alicyclic parts contained in these substituents may comprise 3 to 10 ring members and the heteroalicyclic parts may comprise 4 to 10 ring members and the above-mentioned phenyl and pyridinyl groups may in turn be mono-, di- or trisubstituted by fluorine, chlorine or bromine atoms, by alkyl, alkoxy, methylsulphonyloxy, trifluoromethyl, hydroxy, amino, acetylamino, aminocarbonyl, aminocarbonylamino, aminocarbonylaminomethyl, cyano, carboxy, carbalkoxy, carboxyalkyl, carbalkoxyalkyl, alkanoyl, ω-(dialkylamino)alkanoyl, ω-(carboxy)alkanoyl, trifluoromethoxy, trifluoromethylthio, trifluoromethylsulphinyl or trifluoromethylsulphonyl groups, whilst the substituents may be identical or different, or $R^{10}$ together with $R^{12}$ and $Y^3$ denotes a 4- to 7-membered cycloaliphatic ring in which a methylene group may be replaced by an —NH— or —N(alkyl)-group, whilst a hydrogen atom bound to a nitrogen atom within the group $R^{10}$ may be replaced by a protecting group, $R^{12}$ denotes a hydrogen atom, a $C_{1-4}$-alkyl group, wherein an unbranched alkyl group may be substituted in the ω-position by a phenyl, pyridinyl, diazinyl, amino, alkylamino, dialkylamino, 1-pyrrolidinyl, 1-piperidinyl, 4-methyl-1-piperazinyl, 4-morpholinyl- or hexahydro-1H-1-azepinyl group, an alkoxycarbonyl, cyano or aminocarbonyl group or a free pair of electrons, if $Y^3$ denotes a nitrogen atom, and $R^{13}$ and $R^{14}$ in each case denote a hydrogen atom or, if $Y^3$ is a carbon atom, $R^{12}$ together with $R^{14}$ also denotes another carbon-carbon bond, wherein $R^{10}$ is as hereinbefore defined and $R^{13}$ denotes a hydrogen atom or if $Y^3$ is a carbon atom, $R^{12}$ together with $R^{14}$ also denotes another carbon-carbon bond and $R^{10}$ together with $R^{13}$ and the enclosed double bond denotes a partially hydrogenated or aromatic 5- to 7-membered mono- or bicyclic carbocycle or heterocycle, whilst all the above-mentioned alkyl and alkoxy groups and the alkyl groups present within the other groups mentioned may contain 1 to 7 carbon atoms, unless otherwise specified, all the above-mentioned cycloalkyl groups and the cycloalkyl groups present within the other groups named may contain 5 to 10 carbon atoms, unless otherwise specified, and the term "aroyl group" used above denotes, for example, the benzoyl or naphthoyl group.

The protecting groups mentioned in the foregoing definitions and hereinafter are the protecting groups which are commonly known from peptide chemistry, particularly a phenylalkoxycarbonyl group having 1 to 3 carbon atoms in the alkoxy moiety, optionally substituted in the phenyl nucleus by a halogen atom, by a nitro or phenyl group or by one or two methoxy groups, for example the benzyloxycarbonyl, 2-nitro-benzyloxycarbonyl, 4-nitro-benzyloxycarbonyl, 4-methoxy-benzyloxycarbonyl, 2-chloro-benzyloxycarbonyl, 3-chloro-benzyloxycarbonyl, 4-chloro-benzyloxycarbonyl, 4-Biphenylyl-α,α-dimethyl-benzyloxycarbonyl or 3,5-dimethoxy-α,α-dimethyl-benzyloxycarbonyl group, an alkoxycarbonyl group having a total of 1 to 5 carbon atoms in the alkyl moiety, for example the methoxycarbonyl, ethoxycarbonyl, n-propoxycarbonyl, isopropoxycarbonyl, n-butoxycarbonyl, 1-methylpropoxycarbonyl, 2-methylpropoxycarbonyl or tert.butyloxycarbonyl group, the allyloxycarbonyl, 2,2,2-trichloro-(1,1-dimethylethoxy)carbonyl or 9-fluorenylmethoxycarbonyl group or the formyl, acetyl or trifluoroacetyl group.

The present invention relates to racemates, where the compounds of general formula I have only one chiral element. However, the application also covers the individual diastereomeric pairs of antipodes or mixtures thereof which occur when there is more than one chiral element in the compounds of general formula (I).

Particularly preferred are compounds of general formula I wherein Z denotes $NR^1$ and m assumes the value 0 and which are in the D- or (R)-configuration with regard to the partial amino acid structure of the formula

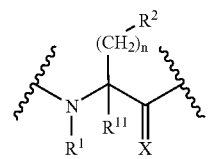

(V)

and which are in the L- or (S)-configuration with regard to the partial amino acid structure of formula

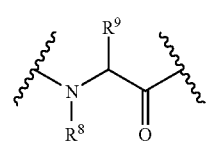

(III)

which may be present in the group A. As for the other compounds covered by general formula I, the preferred isomers are those which are spatially constructed analogously to the (R)-configured partial structure of formula V with regard to the partial structure of formula VI

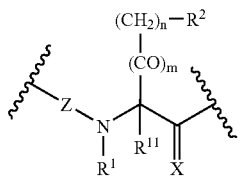
(VI)

The compounds of general formula I have valuable pharmacological properties based on their selective CGRP-antagonistic properties. The invention further relates to medicaments containing these compounds, their use and the preparation thereof.

A subgroup of compounds of general formula I which deserves special mention comprises those wherein A, $R^2$, $R^3$, $R^4$, $R^{11}$, X, Z and m and n are as hereinbefore defined and R denotes an unbranched $C_{1-6}$-alkylamino group optionally substituted at the nitrogen atom by a $C_{1-6}$-alkyl group or by a phenylmethyl group, which may be substituted in the ω-position
  by a $C_{4-10}$-cycloalkyl group,
  by one or two phenyl groups, by a 1-naphthyl, 2-naphthyl or biphenylyl group,
  by a 1H-indol-3-yl, 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-4-(3-thienyl)-2H-2-oxoimidazol-1-yl, 1,3-dihydro-4-phenyl-2H-2-oxoimidazol-1-yl, 1,3-dihydro-5-phenyl-2H-2-oxoimidazol-1-yl, 1,3-dihydro-2(2H)-oxoimidazo[4,5-c]quinolin-3-yl, 3,4-dihydro-5-phenyl-2(1H)-oxopyrimidin-3-yl, 3,4-dihydro-6-phenyl-2(1H)-oxopyrimidin-3-yl- or 1,3-dihydro-2H-2-oxoimidazo[4,5-b]pyridin-3-yl-group,
  by a 5-membered heteroaromatic ring linked via a carbon atom, which contains a nitrogen, oxygen or sulphur atom or, in addition to a nitrogen atom, contains an oxygen, sulphur or an additional nitrogen atom, whilst a nitrogen atom of an imino group may be substituted by an alkyl group, or
  by a 6-membered heteroaromatic ring linked via a carbon atom and containing 1, 2 or 3 nitrogen atoms, whilst a 1,4-butadienylene group may be attached both to the 5-membered and to the 6-membered heteroaromatic monocyclic rings via two adjacent carbon atoms in each case and the bicyclic heteroaromatic rings thus formed may also be bound via a carbon atom of the 1,4-butadienylene group, whilst the phenyl, naphthyl and biphenylyl groups mentioned above for the substitution of the alkylamino groups in the ω-position and optionally partially hydrogenated mono- and bicyclic heteroaromatic rings in the carbon skeleton may additionally be mono-, di- or trisubstituted by fluorine, chlorine or bromine atoms, by alkyl groups, $C_{3-8}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl)carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl- or trifluoromethylsulphonyl groups, whilst the substituents may be identical or different and the above-mentioned benzoyl, benzoylamino- and benzoylmethylamino groups in turn may additionally be substituted in the phenyl moiety by a fluorine, chlorine or bromine atom or by an alkyl, trifluoromethyl, amino or acetylamino group, whilst all the above-mentioned alkyl and alkoxy groups and the alkyl groups present within the other groups mentioned may contain 1 to 4 carbon atoms, unless otherwise stated, their tautomers, their diastereomers, their enantiomers, mixtures thereof and the salts thereof.

Another subgroup of compounds of general formula I deserving special mention comprises those wherein
$R^2$, $R^3$, $R^4$, $R^{11}$, X, Z and m and n are defined as for the first subgroup hereinbefore,
R denotes an unbranched $C_{1-7}$-alkyl group which may be substituted in the ω-position
  by a $C_{4-10}$-cycloalkyl group,
  by one or two phenyl groups, by a 1-naphthyl, 2-naphthyl- or biphenylyl-group,
  by a 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-2H-2-oxoimidazopyridinyl, 1,3-dihydro-2(2H)-oxoimidazo[4,5-c]quinolin-3-yl, 1,3-dihydro-2H-2-oxoimidazol-1-yl- or 3,4-dihydro-2(1H)-oxopyrimidin-3-yl-group, whilst the latter two groups may each be mono- or disubstituted in the 4- and/or 5-position or in the 5- and/or 6-position by lower straight-chained or branched alkyl groups, by phenyl, biphenylyl, pyridinyl, diazinyl, furyl, thienyl, pyrrolyl, 1,3-oxazolyl, 1,3-thiazolyl, isoxazolyl, pyrazolyl-1-methylpyrazolyl, imidazolyl or 1-methylimidazolyl groups, and the substituents may be identical or different,
  by a 5-membered heteroaromatic ring linked via a carbon atom, which contains a nitrogen, oxygen or sulphur atom or in addition to a nitrogen atom contains an oxygen, sulphur or an additional nitrogen atom, whilst a nitrogen atom of an imino group may be substituted by an alkyl group,
  or by a 6-membered heteroaromatic ring linked via a carbon atom, which contains one, two or three nitrogen atoms,
    whilst a 1,4-butadienylene group may be attached both to the above-mentioned 5-membered and to the 6-membered heteroaromatic monocyclic rings, in each case via two adjacent carbon atoms, and the bicyclic heteroaromatic rings thus formed may also be bound via a carbon atom of the 1,4-butadienylene group, whilst the phenyl, naphthyl- and biphenylyl-groups mentioned hereinbefore for the substitution of the alkyl groups in the ω-position and optionally partially hydrogenated mono- and bicyclic heteroaromatic rings in the carbon skeleton may additionally be mono-, di- or trisubstituted by fluorine, chlorine or bromine atoms, by alkyl groups, $C_{3-8}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl)carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl or trifluoromethylsulphonyl groups, whilst the substituents may be identical or different and the above-mentioned benzoyl, benzoylamino and benzoylmethylamino groups may in turn additionally be substituted in the phenyl moiety by a fluorine, chlorine or bromine atom or by an alkyl, trifluoromethyl, amino or acetylamino group, and A denotes a single bond, whilst all the above-mentioned alkyl and alkoxy groups and the alkyl groups present within the other groups mentioned may contain 1 to 4 carbon atoms unless otherwise stated, their tautomers, their diastereomers, their enantiomers and the salts thereof.

Preferred compounds of the above general formula I are those wherein

R denotes an unbranched $C_{1-5}$-alkyl group which may be substituted in the ω-position
   by a $C_{4-7}$-cycloalkyl group,
   by one or two phenyl groups, by a 1-naphthyl, 2-naphthyl or (4-biphenylyl) group,
   by a 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-2H-2-oxoimidazopyridinyl, 1,3-dihydro-2(2H)-oxoimidazo[4,5-c]quinolin-3-yl, 1,3-dihydro-2H-2-oxoimidazol-1-yl or 3,4-dihydro-2(1H)-oxopyrimidin-3-yl group, whilst the latter two groups may each be mono- or disubstituted in the 4- and/or 5-position or in the 5- and/or 6-positions by lower straight-chained or branched alkyl groups, by phenyl, biphenylyl, pyridinyl, diazinyl, furyl, thienyl, pyrrolyl, 1,3-oxazolyl, 1,3-thiazolyl, isoxazolyl, pyrazolyl-1-methylpyrazolyl, imidazolyl or 1-methylimidazolyl groups, and the substituents may be identical or different,
   by a 5-membered heteroaromatic ring linked via a carbon atom and containing a nitrogen, oxygen or sulphur atom or, in addition to a nitrogen atom, an oxygen, sulphur or additional nitrogen atom, whilst a nitrogen atom of an imino group may be substituted by an alkyl group,
   or by a 6-membered heteroaromatic ring linked via a carbon atom and containing one or two nitrogen atoms, whilst a 1,4-butadienylene group may be attached both to the 5-membered and to the 6-membered heteroaromatic monocyclic rings via two adjacent carbon atoms in each case and the bicyclic heteroaromatic rings thus formed may also be bound via a carbon atom of the 1,4-butadienylene group, or an unbranched $C_{1-4}$-alkylamino group optionally substituted at the nitrogen atom by a $C_{1-3}$-alkyl group or by a phenylmethyl group, which may be substituted in the ω-position
   by a $C_{4-7}$-cycloalkyl group,
   by one or two phenyl groups, by a 1-naphthyl, 2-naphthyl or (4-biphenylyl) group,
   by a 1H-indol-3-yl, 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-4-(3-thienyl)-2H-2-oxoimidazol-1-yl, 1,3-dihydro-4-phenyl-2H-2-oxoimidazol-1-yl, 1,3-dihydro-5-phenyl-2H-2-oxoimidazol-1-yl, 1,3-dihydro-2(2H)-oxoimidazo[4,5-c]quinolin-3-yl, 3,4-dihydro-5-phenyl-2(1H)-oxopyrimidin-3-yl, 3,4-dihydro-6-phenyl-2(1H)-oxopyrimidin-3-yl or 1,3-dihydro-2H-2-oxoimidazo[4,5-b]pyridin-3-yl group,
   by a 5-membered heteroaromatic ring linked via a carbon atom and containing a nitrogen, oxygen or sulphur atom or, in addition to a nitrogen atom, an oxygen, sulphur or additional nitrogen atom, whilst a nitrogen atom of an imino group may be substituted by an alkyl group,
   or by a 6-membered heteroaromatic ring linked via a carbon atom and containing 1 or 2 nitrogen atoms, whilst a 1,4-butadienylene group may be attached to both the 5-membered and to the 6-membered heteroaromatic monocyclic rings via two adjacent carbon atoms in each case and the bicyclic heteroaromatic rings thus formed may also be bound via a carbon atom of the 1,4-butadienylene group, whilst the phenyl, naphthyl and biphenylyl groups mentioned above for the substitution of the alkyl and alkylamino groups in the ω-position and optionally also partially hydrogenated mono- and bicyclic heteroaromatic rings in the carbon skeleton may additionally be mono-, di- or trisubstituted by fluorine, chlorine or bromine atoms or by alkyl groups, $C_{5-7}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl)carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl or trifluoromethylsulphonyl groups, wherein the substituents may be identical or different and the above-mentioned benzoyl, benzoylamino and benzoylmethylamino groups may in turn additionally be substituted in the phenyl moiety by a fluorine, chlorine or bromine atom or by an alkyl, trifluoromethyl, amino or acetylamino group, or the group of formula

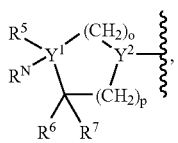
(II)

wherein p denotes the number 1 or 2, o denotes the number 2 or, if $Y^1$ and $Y^2$ are not simultaneously nitrogen atoms, o may also denote 1.

$Y^1$ denotes the nitrogen atom if $R^5$ is a free pair of electrons, or the carbon atom, $Y^2$ is the nitrogen atom or the group >CH—, $R^5$ is a free pair of electrons if $Y^1$ denotes the nitrogen atom or, if $Y^1$ denotes the carbon atom, $R^5$ denotes a hydrogen atom, a $C_{1-3}$-alkyl group, a hydroxy, cyano, aminocarbonyl, carboxy, alkoxycarbonyl, aminocarbonylamino, phenylmethyl or phenyl group, $R^6$ denotes the hydrogen atom or, provided that $Y^1$ is not a nitrogen atom, $R^6$ together with $R^5$ may denote an additional bond, $R^7$ denotes the hydrogen atom or, provided that $Y^1$ is not a nitrogen atom and $R^5$ and $R^6$ together constitute an additional bond, $R^7$ together with $R^N$ may also denote a 1,4-butadienylene group, $R^N$ denotes the hydrogen atom or a $C_{1-3}$-alkyl group, which may be monosubstituted in the ω-position by a $C_{5-7}$-cycloalkyl group or by a 1-naphthyl, 2-naphthyl, hydroxy, alkoxy, amino, alkylamino,.dialkylamino, piperidinyl, morpholinyl, pyrrolidinyl, hexahydro-1H-1-azepinyl, aminocarbonyl, alkylaminocarbonyl, acetylamino, cyano, aminocarbonylamino or alkylaminocarbonylamino group, or may be mono- or disubstituted by phenyl, pyridinyl or diazinyl groups, whilst these substituents may be identical or different, a cyclohexyl, phenyl, pyridinyl, cyano, amino, benzoylamino, aminocarbonyl, alkylaminocarbonyl, alkoxycarbonyl, phenylalkoxycarbonyl, aminocarbonylamino, alkylaminocarbonylamino, dialkylaminocarbonylamino, N-(aminocarbonyl)N-alkylamino, N-(alkylaminocarbonyl)-N-alkylamino, N-(alkylaminocarbonyl)-N-phenylamino, phenylaminocarbonyl-amino, [N-phenyl(alkylamino)]carbonylamino, N-(phenylaminocarbonyl)-N-alkylamino, N-(phenylaminocarbonyl)-N-phenylamino, benzoylaminocarbonylamino, phenylalkylaminocarbonylamino, pyridinylaminocarbonylamino, N-(aminocarbonyl)-N-phenylamino, N-(alkylaminocarbonyl)-N-phenylamino, N-(aminocarbonylaminocarbonyl)-N-phenylamino, N-(pyridinyl)-N-(aminocarbonyl)amino, N-(pyridinyl)-N-(alkylaminocarbonyl)amino, phenylamino, pyridinylamino, diazinylamino or 4-[3,4-dihydro-2(1H)-oxoquinazolin-3-yl]-1-piperidinyl group, a saturated, mono- or diunsaturated 5- to 7-membered aza, diaza, triaza, oxaza, thiaza, thiadiaza- or S,S-dioxidothiadiaza heterocycle, whilst the above-mentioned heterocycles may be linked via a carbon or nitrogen atom and may contain one or two carbonyl groups adjacent to a nitrogen atom, may be substituted at one of the nitrogen atoms by an alkyl, alkanoyl, aroyl, hydroxycarbonylalkyl, alkoxycarbonylalkyl, phenylalkoxycarbonylalkyl, phenylmethyl or phenyl group, may be substituted at one or two carbon atoms by a branched or unbranched alkyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl group, whilst the substituents may be identical or different, and wherein a $C_{3-4}$-alkylene group may additionally be attached to the above-mentioned heterocycles via two adjacent carbon atoms or an olefinic double bond of one of the above-mentioned unsaturated heterocycles may be fused with a benzene, pyridine, diazine, 1,3-oxazole, thiophene, furan, thiazole, pyrrole, N-methyl-pyrrole, quinoline, imidazole or N-methyl-imidazole ring, or, provided that $Y^1$ is not a nitrogen atom and $R^5$ and $R^6$ together denote an additional bond, $R^N$ together with $R^7$ may also denote the 1,4-butadienylene group or, if $Y^1$ denotes a carbon atom, $R^N$ together with $R^5$, with the inclusion of $Y^1$, may also denote a carbonyl group or a saturated or monounsaturated 5- or 6-membered 1,3-diazaheterocycle which may contain one or two carbonyl groups in the ring adjacent to a nitrogen atom and, if it is unsaturated, may also be benzo-fused at the double bond and substituted at one of the nitrogen atoms by a methyl, aminocarbonyl, hydroxycarbonylalkyl, alkoxycarbonylalkyl, phenylalkoxycarbonylalkyl, phenylmethyl or phenyl group, whilst the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups contained in the residues mentioned under $R^5$, $R^7$ and $R^N$, as well as benzo-, thieno-, pyrido- and diazino-fused heterocycles in the carbon skeleton may additionally be mono-, di- or trisubstituted by fluorine, chlorine or bromine atoms, by alkyl groups, $C_{4-7}$-cycloalkyl groups, nitro, alkoxy, alkylthio, alkylsulphinyl, alkylsulphonyl, alkylsulphonylamino, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, hydroxyalkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, aminocarbonylaminoalkyl, alkylaminocarbonylamino, alkanoyl, cyano, trifluoromethoxy, trifluormethylthio, trifluoromethylsulphinyl or trifluoromethylsulphonyl groups, wherein the substituents may be identical or different and the alkyl groups contained in the above-mentioned groups may contain 1 to 3 carbon atoms unless otherwise specified, X denotes the oxygen atom or 2 hydrogen atoms, Z denotes the methylene group or the group —$NR^1$— wherein $R^1$ denotes a hydrogen atom or a $C_{1-3}$-alkyl group, $R^{11}$ denotes a hydrogen atom, a $C_{1-3}$-alkyl group or an alkoxycarbonyl group having 2 to 4 carbon atoms altogether, n denotes the number 1 or 2 or, if m is 1, n may also be 0, m denotes the number 0 or 1, $R^2$ denotes a phenyl, 1-naphthyl, 2-naphthyl, 1,2,3,4-tetrahydro-1-naphthyl, 1H-indol-3-yl, 1-methyl-1H-indol-3-yl, 1-formyl-1H-indol-3-yl, 1-(1,1-dimethylethoxycarbonyl)-1H-indol-3-yl, 1-methyl-4-imidazolyl, 2-thienyl, 3-thienyl, thiazolyl, 1H-indazol-3-yl, 1-methyl-1H-indazol-3-yl, benzo[b]fur-3-yl, benzo[b]thien-3-yl, pyridinyl, quinolinyl or isoquinolinyl group, whilst the above-mentioned aromatic and heteroaromatic groups in the carbon skeleton may additionally be mono-, di- or trisubstituted by fluorine, chlorine or bromine atoms, or by branched or unbranched alkyl groups, $C_{4-7}$-cycloalkyl groups, phenylalkyl groups, alkenyl, alkoxy, phenyl, phenylalkoxy, trifluoromethyl, alkoxycarbonylalkyl, carboxyalkyl, alkoxycarbonyl, carboxy, dialkylaminoalkyl, dialkylaminoalkoxy, hydroxy, nitro, amino, acetylamino, propionylamino, benzoyl, benzoylamino, benzoylmethylamino, methylsulphonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulphinyl or trifluoromethylsulphonyl groups, and the substituents may be identical or different, A denotes a bond or the divalent group of formula

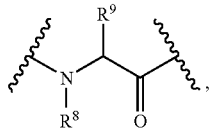

(III)

(linked to the $R^3R^4N$-group of general formula (I) via the carbonyl group)

wherein $R^8$ and $R^9$ together denote an n-propylene group or $R^8$ denotes a hydrogen atom or a $C_{1-3}$-alkyl group and $R^9$ denotes a hydrogen atom or a branched or unbranched $C_{1-4}$-alkyl group which, if it is unbranched, may be substituted in the ω-position by a hydroxy, mercapto, amino, alkylamino, dialkylamino, 1-azetidinyl, 1-pyrrolidinyl, 1-piperidinyl, hexahydro-1-azepinyl, methylthio, hydroxycarbonyl, aminocarbonyl, aminoiminomethylamino, aminocarbonylamino, phenyl, 1H-indol-3-yl, 1-methyl-1H-indol-3-yl, 1-formyl-1H-indol-3-yl, 4-imidazolyl, 1-methyl-4-imidazolyl, 1-naphthyl, 2-naphthyl- or pyridinyl group, whilst the above-mentioned heterocycles and phenyl groups may in turn be mono-, di- or trisubstituted in the carbon skeleton by fluorine, chlorine or bromine atoms, or by methyl, alkoxy, trifluoromethyl, hydroxy, amino, acetylamino, aminocarbonyl, cyano, trifluoromethoxy, methylsulphonyloxy, trifluoromethylthio, trifluoromethylsulphinyl or trifluoromethylsulphonyl groups, whilst the substituents may be identical or different and any hydroxy, mercapto, amino, guanidino, indolyl and imidazolyl groups contained in the groups mentioned for $R^9$ may be substituted by a protecting group, $R^3$ denotes a hydrogen atom, a $C_{1-4}$-alkyl group which may be substituted in the ω-position by a cyclohexyl, phenyl, pyridinyl, diazinyl, hydroxy, amino, alkylamino, dialkylamino, carboxy, aminocarbonyl, aminocarbonylamino, acetylamino, 1-pyrrolidinyl, 1-piperidinyl, 4-(1-piperidinyl)-1-piperidinyl, 4-morpholinyl, hexahydro-1H-azepin-1-yl, [bis-(2-hydroxyethyl)]amino, 4-methyl-1-piperazinyl- or 4-(ω-hydroxyalkyl)-1-piperazinyl group, a phenyl or pyridinyl group, wherein the above-mentioned heterocyclic radicals and phenyl groups may additionally be mono-, di- or trisubstituted in the carbon skeleton by fluorine, chlorine or bromine atoms or by methyl, alkoxy, trifluoromethyl, hydroxy, amino, acetylamino, aminocarbonyl, cyano, methylsulphonyloxy, trifluoromethoxy, trifluoromethylthio, trifluoromethylsulphinyl or trifluoromethylsulphonyl groups and the substituents may be identical or different, $R^4$ denotes a hydrogen atom or a methyl or ethyl group optionally substituted by a phenyl or pyridinyl group or $R^3$ and $R^4$ together with the enclosed nitrogen atom denote a group of general formula

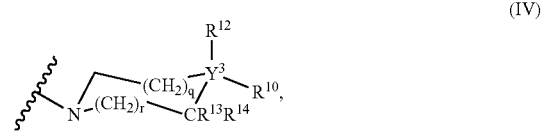

(IV)

wherein $Y^3$ denotes a carbon atom or, if $R^{12}$ denotes a free pair of electrons, $Y^3$ may also be the nitrogen atom, r denotes the number 0, 1 or 2, q denotes the number 0, 1 or 2, $R^{10}$ denotes a hydrogen atom or an amino, alkylamino, dialkylamino, alkyl, cycloalkyl, aminoalkyl, alkylaminoalkyl, dialkylaminoalkyl, aminoiminomethyl, aminocarbonylamino, alkylaminocarbonylamino, cycloalkylaminocarbonylamino, phenylaminocarbonylamino, aminocarbonylalkyl, aminocarbonylaminoalkyl, alkoxycarbonyl, alkoxycarbonylalkyl, carboxyalkyl or carboxy group, a phenyl, pyridinyl, diazinyl, 1-naphthyl, 2-naphthyl, pyridinylcarbonyl or phenylcarbonyl group which may be mono-, di- or trisubstituted in the carbon skeleton by fluorine, chlorine or bromine atoms, or by alkyl, alkoxy, methylsulphonyloxy, trifluoromethyl, hydroxy, amino, acetylamino, aminocarbonyl, aminocarbonylamino, aminocarbonylaminomethyl, cyano, carboxy, carbalkoxy, carboxyalkyl, carbalkoxyalkyl, alkanoyl, ω-(dialkylamino)alkanoyl, ω-(dialkylamino)alkyl, ω-(dialkylamino)hydroxyalkyl, ω-(carboxy)alkanoyl, trifluoromethoxy, trifluoromethylthio, trifluoromethylsulphinyl-oder trifluoromethylsulphonyl groups, whilst the substituents may be identical or different, a 1,3-dihydro-2-oxo-2H-imidazolyl, 2,4(1H,3H)-dioxopyrimidinyl or 3,4-dihydro-2(1H)-oxopyrimidinyl group bound via a nitrogen atom, which may be substituted by a phenyl group or fused at the double bond to a benzene, pyridine or diazine ring, a 1,1-dioxido-3(4H)-oxo-1,2,4-benzothiadiazin-2-yl group, a 4- to 10-membered azacycloalkyl group, a 5- to 10-membered oxaza, thiaza or diazacycloalkyl group or a 6- to 10-membered azabicycloalkyl group, wherein the above-mentioned mono- and bicyclic heterocycles may be bound via a nitrogen or carbon atom and may be substituted by a $C_{1-7}$-alkyl group, by an alkanoyl, dialkylamino, phenylcarbonyl, pyridinylcarbonyl, carboxyalkandyl, carboxyalkyl, alkoxycarbonyl, alkoxycarbonyl, aminocarbonyl, alkylaminocarbonyl, alkylsulphonyl, cycloalkyl or cycloalkylalkyl group, by a cycloalkylcarbonyl, azacycloalkylcarbonyl, diazacycloalkylcarbonyl or oxazacycloalkylcarbonyl group optionally alkyl substituted in the ring, whilst the alicyclic parts contained in these substituents may comprise 3 to 10 ring members and the heteroalicyclic parts may comprise 4 to 10 ring members and the above-mentioned phenyl and pyridinyl groups may in turn be mono-, di- or trisubstituted by fluorine, chlorine or bromine atoms, by alkyl, alkoxy, methylsulphonyloxy, trifluoromethyl, hydroxy, amino, acetylamino, aminocarbonyl, aminocarbonylamino, aminocarbonylaminomethyl, cyano, carboxy, carbalkoxy, carboxyalkyl, carbalkoxyalkyl, alkanoyl, ω-(dialkylamino)alkanoyl, ω(carboxy)alkanoyl, trifluoromethoxy, trifluoromethylthio, trifluoromethylsulphinyl or trifluoromethylsulphonyl groups, whilst the substituents may be identical or different, or $R^{10}$ together with $R^{12}$ and $Y^3$ denotes a 4- to 7-membered cycloaliphatic ring in which a methylene group may be replaced by an —NH— or —N(alkyl)-group, whilst a hydrogen atom bound to a nitrogen atom within the group $R^{10}$ may be replaced by a protecting group, $R^{12}$ denotes a hydrogen atom, a $C_{1-2}$-alkyl group which may be substituted in the ω-position by a phenyl, pyridinyl, diazinyl, amino, alkylamino, dialkylamino, 1-pyrrolidinyl, 1-piperidinyl, 4-methyl-1-piperazinyl, 4-morpholinyl or hexahydro-1H-azepin-1-yl-group, an alkoxycarbonyl, cyano- or aminocarbonyl group or a free pair of electrons, if $Y^3$ denotes a nitrogen atom, and $R^{13}$ and $R^{14}$ in each case denote a hydrogen atom or, if $Y^3$ is a carbon atom, $R^{12}$ together with $R^{14}$ also denotes another carbon-carbon bond, wherein $R^{10}$ is as hereinbefore defined and $R^{13}$ denotes a hydrogen atom or if $Y^3$ is a carbon atom, $R^{12}$ together with $R^{14}$ also denotes another carbon-carbon bond and $R^{10}$ together with $R^{13}$ and the enclosed double bond denotes a partially hydrogenated or aromatic 5- to 7-membered mono- or bicyclic carbocycle or heterocycle, whilst all the above-mentioned alkyl and alkoxy groups and the alkyl groups present within the other groups mentioned may contain 1 to 4 carbon atoms, unless otherwise specified, all the above-mentioned cycloalkyl groups and the cycloalkyl groups present within the other groups named may contain 5 to 7 carbon atoms, unless otherwise specified, and the term "aroyl group" used above denotes, for example, the benzoyl or naphthoyl group;

their tautomers, their diastereomers, their enantiomers and their salts.

One subgroup of preferred compounds of general formula I deserving special mention comprises those wherein A, $R^2$, $R^3$, $R^4$, $R^{11}$, X, Z and m and n are defined as given hereinbefore defined for the preferred compounds of general formula I, R denotes an unbranched $C_{1-4}$-alkylamino group optionally substituted at the nitrogen atom by a $C_{1-3}$-alkyl group or by a phenylmethyl group, which may be substituted in the ω-position by a $C_{4-7}$-cycloalkyl group, by one or two phenyl groups, by a 1-naphthyl, 2-naphthyl or (4-biphenylyl) group, by a 1H-indol-3-yl, 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3 (4H)-oxo-1,2,4-benzothiadiazin-2-yl, 1,3-dihydro-4-(3-thienyl)-2H-2-oxoimidazol-1-yl, 1,3-dihydro-4-phenyl-2H-2-oxoimidazol-1-yl, 1,3-dihydro-5-phenyl-2H-2-oxoimidazol-1-yl, 1,3-dihydro-2(2H)-oxoimidazo[4,5-c]quinolin-3-yl, 3,4-dihydro-5-phenyl-2(1H)-oxopyrimidin-3-yl, 3,4-dihydro-6-phenyl-2 (1H)-oxopyrimidin-3-yl or 1,3-dihydro-2H-2-oxoimidazo[4,5-b]pyridin-3-yl group, by a 5-membered heteroaromatic ring linked via a carbon atom, and containing a nitrogen, oxygen or sulphur atom or, in addition to a nitrogen atom, an oxygen, sulphur or additional nitrogen atom, whilst a nitrogen atom of an imino group may be substituted by an alkyl group, or by a 6-membered heteroaromatic ring linked via a carbon atom and containing 1 or 2 nitrogen atoms, whilst a 1,4-butadienylene group may be attached both to the 5-membered and to the 6-membered heteroaromatic monocyclic rings via two adjacent carbon atoms in each case and the bicyclic heteroaromatic rings thus formed may also be bound via a carbon atom of the 1,4-butadienylene group, whilst the phenyl, naphthyl and biphenylyl groups mentioned above for the substitution of the alkylamino groups in the ω-position and optionally partially hydrogenated mono- and bicyclic heteroaromatic rings in the carbon skeleton may additionally be mono-, di- or trisubstituted by fluorine, chlorine or bromine atoms, by alkyl groups, $C_{5-7}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl)carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl or trifluoromethylsulphonyl groups, whilst the substituents may be identical or different and the above-mentioned benzoyl, benzoylamino- and benzoylmethylamino groups in turn may additionally be substituted in the phenyl moiety by a fluorine, chlorine or bromine atom or by an alkyl, trifluoromethyl, amino or acetylamino group, whilst all the above-mentioned alkyl and alkoxy groups and the alkyl groups present within the other groups mentioned may contain 1 to 4 carbon atoms, unless otherwise stated, their tautomers, their diastereomers, their enantiomers, mixtures thereof and the salts thereof.

Another subgroup of compounds of general formula I deserving special mention comprises those wherein $R^2$, $R^3$, $R^4$, $R^{11}$, X, Z and m and n are defined as for the first preferred subgroup hereinbefore, R denotes an unbranched $C_{1-5}$-alkyl group which may be substituted in the ω-position by a $C_{4-7}$-cycloalkyl group, by one or two phenyl groups, by a 1-naphthyl, 2-naphthyl or (4-biphenylyl) group, by a 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-2H-2-oxoimidazopyridinyl, 1,3-dihydro-2(2H)-oxoimidazo[4,5-c]quinolin-3-yl, 1,3-dihydro-2H-2-oxoimidazol-1-yl or 3,4-dihydro-2(1H)-oxopyrimidin-3-yl group, whilst the latter two groups may each be mono- or disubstituted in the 4- and/or 5-position or in the 5- and/or 6-position by lower straight-chained or branched alkyl groups, by phenyl, biphenylyl, pyridinyl, diazinyl, furyl, thienyl, pyrrolyl, 1,3-oxazolyl, 1,3-thiazolyl, isoxazolyl, pyrazolyl-1-methylpyrazolyl, imidazolyl or 1-methylimidazolyl groups, and the substituents may be identical or different, by a 5-membered heteroaromatic ring linked via a carbon atom, which contains a nitrogen, oxygen or sulphur atom or in addition to a nitrogen atom contains an oxygen, sulphur or an additional nitrogen atom, whilst a nitrogen atom of an imino group may be substituted by an alkyl group, or by a 6-membered heteroaromatic ring linked via a carbon atom, which contains one or two nitrogen atoms, whilst a 1,4-butadienylene group may be attached both to the 5-membered and to the 6-membered heteroaromatic monocyclic rings, in each case via two adjacent carbon atoms, and the bicyclic heteroaromatic rings thus formed may also be bound via a carbon atom of the 1,4-butadienylene group, whilst the phenyl, naphthyl and biphenylyl groups mentioned hereinbefore for the substitution of the alkyl groups in the ω-position and optionally partially hydrogenated mono- and bicyclic heteroaromatic rings in the carbon skeleton may additionally be mono-, di- or trisubstituted by fluorine, chlorine or bromine atoms, by alkyl groups, $C_{5-7}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl)carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl or trifluoromethylsulphonyl groups, whilst the substituents may be identical or different and the above-mentioned benzoyl, benzoylamino and benzoylmethylamino groups may in turn additionally be substituted in the phenyl moiety by a fluorine, chlorine or bromine atom or by an alkyl, trifluoromethyl, amino or acetylamino group, and A denotes a single bond, whilst all the above-mentioned alkyl and alkoxy groups and the alkyl groups present within the other groups mentioned may contain 1 to 4 carbon atoms unless otherwise stated, their tautomers, their diastereomers, their enantiomers, mixtures thereof and the salts thereof.

Preferred compounds of the above general formula I are those wherein

R denotes an unbranched $C_{1-3}$-alkyl group which may be substituted in the ω-position by a $C_{5-7}$-cycloalkyl group, by one or two phenyl groups, by a 1-naphthyl, 2-naphthyl or (4-biphenylyl) group, by a 1,3-dihydro-2H-2-oxobenzimidazol-1-yl, 1,3-dihydro-2H-2-oxoimidazol-1-yl or 3,4-dihydro-2(1H)-oxopyrimidin-3-yl group, whilst the latter two groups may be substituted in the carbon skeleton by a phenyl, pyridinyl or diazinyl group, by a 5-membered heteroaromatic ring linked via a carbon atom and containing a nitrogen, oxygen or sulphur atom or two nitrogen atoms, wherein a nitrogen of an imino group may be substituted by an alkyl group, or may be substituted by a pyridinyl group, whilst a 1,4-butadienylene group may be attached both to the 5-membered heteroaromatic monocyclic rings and to the pyridinyl group, in each case via two adjacent carbon atoms, and the bicyclic heteroaromatic rings thus formed may also be bound via a carbon atom of the 1,4-butadienylene group, or an unbranched $C_{1-4}$-alkylamino group optionally substituted at the nitrogen atom by a methyl or ethyl group, which may be substituted in the ω-position by a $C_{5-7}$-cycloalkyl group, by one or two phenyl groups, by a 1-naphthyl, 2-naphthyl or (4-biphenylyl) group, by a 1H-indol-3-yl, 1,3-dihydro-2H-2-oxobenzimidazol-1-yl, 2(1H)-oxoquinolin-3-yl, 1,3-dihydro-4-phenyl-2H-2-oxoimidazol-1-yl, 1,3-dihydro-5-phenyl-2H-2-oxoimidazol-1-yl, 3,4-dihydro-5-phenyl-2(1H)-oxopyrimidin-3-yl, 3,4-dihydro-6-phenyl-2(1H)-oxopyrimidin-3-yl or 1,3-dihydro-2H-2-oxoimidazo[4,5-b]pyridin-3-yl group, by a 5-membered heteroaromatic ring linked via a carbon atom and containing a nitrogen, oxygen or sulphur atom or two nitrogen atoms, whilst a nitrogen atom of an imino group may be substituted by an alkyl group, or by a pyridinyl group, whilst a 1,4-butadienylene group may be attached both to the 5-membered heteroaromatic monocyclic rings and to the pyridinyl group, in each case via two adjacent carbon atoms, and the bicyclic heteroaromatic rings thus formed may also be bound via a carbon atom of the 1,4-butadienylene group, whilst the phenyl, naphthyl and biphenylyl groups mentioned hereinbefore for the substitution of the alkyl and alkylamino groups in the ω-position as well as optionally partially hydrogenated mono- and bicyclic heteroaromatic rings may additionally be mono- or disubstituted in the carbon skeleton by fluorine, chlorine or bromine atoms or by alkyl, nitro, alkoxy, trifluoromethyl, hydroxy, amino, acetylamino, propionylamino, alkanoyl, cyano or trifluoromethoxy groups, whilst the substituents may be the same or different, or the group of formula

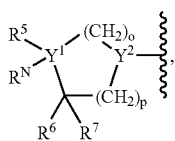

wherein
p denotes the number 1 or 2,
o denotes the number 2 or, if $Y^1$ and $Y^2$ are not simultaneously nitrogen atoms, it may also denote the number 1,
$Y^1$ denotes the nitrogen atom if $R^5$ denotes a free pair of electrons, or the carbon atom,
$Y^2$ denotes the nitrogen atom or the group >CH—,
$R^5$ denotes a free pair of electrons if $Y^1$ denotes the nitrogen atom or, if $Y^1$ denotes the carbon atom, $R^5$ denotes a hydrogen atom, a $C_{1-3}$-alkyl group, a hydroxy, cyano, aminocarbonyl, carboxy, alkoxycarbonyl or aminocarbonylamino group or a phenylmethyl or phenyl group optionally substituted at the aromatic moiety by a fluorine, chlorine or bromine atom or by a methyl, methoxy, ethoxy, trifluoromethyl, hydroxy, amino or acetylamino group,
$R^6$ denotes the hydrogen atom or, if $Y^1$ is not a nitrogen atom, $R^6$ together with $R^5$ may also denote an additional bond,
$R^7$ denotes the hydrogen atom or, provided that $Y^1$ is not a nitrogen atom and $R^5$ and $R^6$ together denote an additional bond, $R^7$ together with $R^N$ may also denote the 1,4-butadienylene group,
$R^N$ denotes the hydrogen atom or a $C_{1-3}$-alkyl group, which may be monosubstituted in the ω-position
by a $C_{5-7}$-cycloalkyl group or by a 1-naphthyl, 2-naphthyl, hydroxy, alkoxy, amino, alkylamino, dialkylamino, piperidinyl, morpholinyl, pyrrolidinyl, hexahydro-1H-1-azepinyl, aminocarbonyl, methylaminocarbonyl, acetylamino, cyano, aminocarbonylamino or alkylaminocarbonylamino group, or may be mono- or disubstituted by phenyl, pyridinyl or diazinyl groups, whilst these substituents may be identical or different,
a cyclohexyl, phenyl, pyridinyl, cyano, amino, benzoylamino, aminocarbonyl, alkylaminocarbonyl, alkoxycarbonyl, phenylalkoxycarbonyl, aminocarbonylamino, alkylaminocarbonylamino, dialkylaminocarbonylamino, N-(aminocarbonyl)-N-alkylamino, N-(alkylaminocarbonyl)-N-alkylamino, N-(alkylaminocarbonyl)-N-phenylamino, phenylaminocarbonylamino, [N-phenyl(alkylamino)]carbonylamino, N-(phenylaminocarbonyl)-N-alkylamino, N-(phenylaminocarbonyl)-N-phenylamino, benzoylaminocarbonylamino, phenylalkylaminocarbonylamino, pyridinylaminocarbonylamino, N-(aminocarbonyl)-N-phenylamino, N-(alkylaminocarbonyl)-N-phenylamino, N-(aminocarbonylaminocarbonyl)-N-phenylamino, N-(pyridinyl)-N-(aminocarbonyl)amino, N-(pyridinyl)-N-(alkylaminocarbonyl)amino, phenylamino, pyridinylamino, diazinylamino or 4-[3,4-dihydro-2(1H)-oxoquinazolin-3-yl]-1-piperidinyl group,
a saturated, mono- or diunsaturated 5- to 7-membered aza, diaza, triaza, oxaza, thiaza, thiadiaza or S,S-dioxidothiadiaza heterocycle,
whilst the above-mentioned heterocycles may be linked via a carbon or nitrogen atom and
may contain one or two carbonyl groups adjacent to a nitrogen atom,
may be substituted at one of the nitrogen atoms by an alkyl, alkanoyl, hydroxycarbonylalkyl, alkoxycarbonylalkyl, phenylalkoxycarbonylalkyl, phenylmethyl or phenyl group,
may be substituted at one or two carbon atoms by a methyl, phenyl, phenylmethyl, naphthyl, biphenylyl, thienyl, pyridinyl or diazinyl group, wherein the substituents may be identical or different,
and wherein a $C_{3-4}$-alkylene group may additionally be attached to the above-mentioned heterocycles via two adjacent carbon atoms or an olefinic double bond of one of the above-mentioned heterocycles may be fused to a thiophene, benzene, pyridine, quinoline or diazine ring,
or, if $Y^1$ is not a nitrogen atom and $R^5$ and $R^6$ together denote an additional bond, $R^N$ together with $R^7$ may also denote a 1,4-butadienylene group or,
if $Y^1$ denotes a carbon atom, $R^N$ together with $R^5$ with the inclusion of $Y^1$ may also denote a carbonyl group or a saturated or monounsaturated 5- or 6-membered 1,3-diazaheterocycle which may contain one or two carbonyl groups in the ring adjacent to a nitrogen atom and, if it is unsaturated, may also be benzo-fused at the double bond and may be substituted at one of the nitrogen atoms by a methyl, aminocarbonyl, hydroxycarbonylalkyl, alkoxycarbonylalkyl, phenylalkoxycarbonylalkyl, phenylmethyl or phenyl group,
whilst the phenyl, pyridinyl or diazinyl groups contained in the groups mentioned under $R^N$ and the thieno-, benzo-, pyrido- or diazino-condensed heterocycles in the carbon skeleton may additionally be mono-, di- or trisubstituted by fluorine, chlorine or bromine atoms, by methyl groups, nitro, methoxy, ethoxy, methylsulphonylamino, trifluoromethyl, alkoxycarbonyl, alkoxycarbonylalkyl, carboxy, carboxyalkyl, hydroxy, amino, acetylamino, propionylamino, aminocarbonyl, methylaminocarbonyl, dimethylaminocarbonyl, hydroxyalkylaminocarbonyl, (4-morpholinyl)-carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, aminocarbonylaminoalkyl, methylaminocarbonylamino, acetyl, cyano or trifluoromethoxy groups, whilst the substituents may be identical or different,
and the alkyl groups contained in the above-mentioned radicals may contain 1 to 3 carbon atoms, unless otherwise specified, X denotes an oxygen atom or 2 hydrogen atoms, Z denotes a methylene group or the group —$NR^1$— wherein $R^1$ is a hydrogen atom or a methyl group, $R^{11}$ denotes the hydrogen atom or a methyl or methoxycarbonyl group, n denotes the number 1 or 2 or, if m is the number 1, n may also denote 0, m denotes the number 0 or 1, $R^2$ denotes a phenyl, 1-naphthyl, 2-naphthyl, 1,2,3,4-tetrahydro-1-naphthyl, 1H-indol-3-yl, 1-methyl-1H-indol-3-yl, 1-formyl-1H-indol-3-yl, 1-(1,1-dimethylethoxycarbonyl)-1H-indol-3-yl, 4-imidazolyl, 1-methyl-4-imidazolyl, 2-thienyl, 3-thienyl, thiazolyl, pyridinyl or quinolinyl group, wherein the above-mentioned aromatic and heteroaromatic groups may additionally be mono-, di- or trisubstituted in the carbon skeleton by fluorine, chlorine or bromine atoms, by branched or unbranched $C_{1-5}$-alkyl groups, allyl, vinyl, methoxy, ethoxy, propoxy, 1-methylethoxy, dimethylaminoethoxy, trifluoromethyl, hydroxy, nitro, amino, acetylamino, propionylamino, aminocarbonyl, methylaminocarbonyl, dimethylaminocarbonyl, acetyl, cyano, methylsulphonyloxy or trifluoromethoxy groups, by tetrazolyl, phenyl pyridinyl, thiazolyl or furyl groups and the substituents may be identical or different, or A denotes a bond or the divalent group of formula

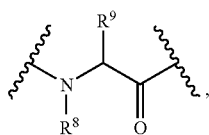

(III)

(linked to the $NR^3R^4$-group of general formula (I) via the carbonyl group)

wherein $R^8$ and $R^9$ together denote an n-propylene group or $R^8$ denotes the hydrogen atom or the methyl group and $R^9$ denotes a hydrogen atom or an unbranched $C_{1-4}$-alkyl group which may be substituted in the ω-position by a hydroxy, amino, methylamino, dimethylamino, hydroxycarbonyl, aminocarbonyl, aminoiminomethylamino, aminocarbonylamino, phenyl or pyridinyl group, wherein the phenyl and pyridinyl group may in turn be substituted in the carbon skeleton by a fluorine, chlorine or bromine atom or by a methyl, methoxy, trifluoromethyl, hydroxy, amino, acetylamino, aminocarbonyl or cyano group and wherein any hydroxy, amino and guanidino groups contained in the groups given for $R^9$ may be substituted by a protecting group, e.g. the phenylmethoxycarbonyl or tert.butyloxycarbonyl group, $R^3$ denotes a hydrogen atom, a $C_{1-4}$-alkyl group optionally substituted in the ω-position by a cyclohexyl, phenyl, pyridinyl, hydroxy, amino, methylamino, dimethylamino, carboxy, aminocarbonyl, aminocarbonylamino, acetylamino, 1-pyrrolidinyl, 1-piperidinyl or 4-(1-piperidinyl)-1-piperidinyl group, a phenyl or pyridinyl group, whilst the above-mentioned phenyl and pyridinyl groups may additionally be substituted in the carbon skeleton by a fluorine, chlorine or bromine atom or by a methyl, methoxy, trifluoromethyl, hydroxy, amino, acetylamino, aminocarbonyl or cyano group, $R^4$ denotes the hydrogen atom or a $C_{1-2}$-alkyl group optionally substituted by a phenyl or pyridinyl group or $R^3$ and $R^4$ together with the enclosed nitrogen atom denote a group of general formula

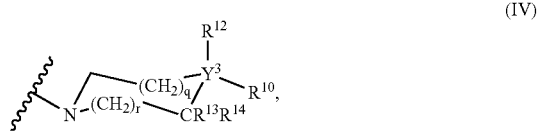

(IV)

wherein $Y^3$ denotes a carbon atom or, if $R^{12}$ denotes a free pair of electrons, $Y^3$ may also be a nitrogen atom, r denotes the number 0, 1 or 2, q denotes the number 0, 1 or 2, with the proviso that the sum of the numbers given for r and q is 0, 1, 2 or 3, $R^{10}$ denotes a hydrogen atom, an alkyl, cycloalkyl, dialkylamino, aminoalkyl, alkylaminoalkyl, dialkylaminoalkyl, phenylaminocarbonylamino, alkoxycarbonyl, alkoxycarbonylmethyl, carboxymethyl or carboxy group, a phenyl, pyridinyl, diazinyl, pyridinylcarbonyl or phenylcarbonyl group which may be mono- or disubstituted in the carbon skeleton by fluorine, chlorine or bromine atoms, or by methyl, ethyl, propyl, methoxy, hydroxy, ω-(dialkylamino)-alkyl, ω-(dialkylamino)hydroxyalkyl or alkanoyl groups, whilst the substituents may be identical or different, a 1,3-dihydro-2-oxo-2H-imidazolyl, 2,4(1H,3H)-dioxopyrimidinyl or 3,4-dihydro-2(1H)-oxopyrimidinyl group bound via a nitrogen atom, which may be substituted by a phenyl group or may be fused at the double bond to a benzene, pyridine or diazine ring, a 5- to 7-membered azacycloalkyl group, a 4- to 7-membered oxaza- or diazacycloalkyl group or a 7- to 9-membered azabicycloalkyl group, wherein the above-mentioned mono- and bicyclic heterocycles are bound via a nitrogen or a carbon atom and may be substituted by a $C_{1-7}$-alkyl group, or by an alkanoyl, dialkylamino, phenylcarbonyl, carboxyalkanoyl, carboxyalkyl, alkoxycarbonylalkyl or alkoxycarbonyl group having 1 to 4 carbon atoms in the alkoxy moiety, alkylsulphonyl, cycloalkyl or cycloalkylalkyl group or by an azacycloalkylcarbonyl or diazacycloalkylcarbonyl group optionally alkyl-substituted in the ring, whilst the alicyclic groups contained in these substituents may comprise 3 to 7 ring members and the heteroalicyclic groups may comprise 4 to 7 ring members and the above-mentioned phenylcarbonyl group may be substituted by a fluorine, chlorine or bromine atom or by a methyl, methoxy, trifluoromethyl, hydroxy, amino or acetylamino group, or $R^{10}$ together with $R^{12}$ and $Y^3$ denotes a 4- to 6-membered cycloaliphatic ring in which a methylene group may be replaced by an —NH— or —N(CH$_3$)-group, whilst a hydrogen atom bound to a nitrogen atom within the group $R^{10}$ may be replaced by a protecting group, e.g. the phenylmethoxycarbonyl or tert.butyloxycarbonyl group, $R^{12}$ denotes a hydrogen atom, a $C_{1-2}$-alkyl group which may be substituted in the ω-position by a phenyl, pyridinyl, amino, alkylamino, dialkylamino, 1-pyrrolidinyl, 1-piperidinyl or 4-methyl-1-piperazinyl group, a methoxycarbonyl or ethoxycarbonyl, cyano or aminocarbonyl group or a free pair of electrons, if $Y^3$ denotes a nitrogen atom, and $R^{13}$ and $R^{14}$ each denote a hydrogen atom or, if $Y^3$ is a carbon atom, $R^{12}$ together with $R^{14}$ also denotes another carbon-carbon bond, wherein $R^{10}$ is as hereinbefore defined and $R^{13}$ denotes a hydrogen atom, or if $Y^3$ is a carbon atom, $R^{12}$ together with $R^{14}$ also denotes another carbon-carbon bond and $R^{10}$ together with $R^{13}$ and the enclosed double bond denotes a partially hydrogenated or aromatic 5- or 6-membered mono- or bicyclic carbocycle or heterocycle, containing one or two nitrogen atoms, whilst all the above-mentioned alkyl and alkoxy groups and the alkyl groups present within the other groups named may contain 1 to 3 carbon atoms, unless otherwise stated, and all the above-mentioned cycloalkyl groups and the cycloalkyl groups present within the other groups named may contain 5 to 7 carbon atoms, unless otherwise specified, their tautomers, their diastereomers, their enantiomers, mixtures thereof and the salts thereof.

One subgroup of particularly preferred compounds of general formula I deserving special mention comprises those wherein A, $R^2$, $R^3$, $R^4$, $R^{11}$, X, Z and m and n are defined as for the particularly preferred compounds of general formula I hereinbefore and R denotes an unbranched $C_{1-4}$-alkylamino group optionally substituted at the nitrogen atom by a methyl or ethyl group, which may be substituted in the ω-position by a $C_{5-7}$-cycloalkyl group, by one or two phenyl groups, by a 1-naphthyl, 2-naphthyl or (4-biphenylyl) group, by a 1H-indol-3-yl, 1,3-dihydro-2H-2-oxobenzimidazol-1-yl, 2(1H)-oxoquinolin-3-yl, 1,3-dihydro-4-phenyl-2H-2-oxoimidazol-1-yl, 1,3-dihydro-5-phenyl-2H-2-oxoimidazol-1-yl, 3,4-dihydro-5-phenyl-2(1H)-oxopyrimidin-3-yl, 3,4-dihydro-6-phenyl-2(1H)-oxopyrimidin-3-yl or 1,3-dihydro-2H-2-oxoimidazo[4,5-b]pyridin-3-yl group, by a 5-membered heteroaromatic ring linked via a carbon atom and containing a nitrogen, oxygen or sulphur atom or two nitrogen atoms, whilst a nitrogen atom of an imino group may be substituted by an alkyl group, or by a pyridinyl group, whilst a 1,4-butadienylene group may be attached both to the 5-membered heteroaromatic monocyclic rings and also to the pyridinyl group, in each case via two adjacent carbon atoms, and the bicyclic heteroaromatic rings thus formed may also be bound via a carbon atom of the 1,4-butadienylene group, whilst the phenyl, naphthyl and biphenylyl groups mentioned hereinbefore for the substitution of the alkylamino groups in the ω-position, as well as optionally any partially hydrogenated mono- and bicyclic heteroaromatic rings, may additionally be mono- or disubstituted in the carbon skeleton by fluorine, chlorine or bromine atoms or by alkyl, nitro, alkoxy, trifluoromethyl, hydroxy, amino, acetylamino, propionylamino, alkanoyl, cyano or trifluoromethoxy groups, whilst the substituents may be identical or different, whilst all the above-mentioned alkyl and alkoxy groups and the alkoxy groups present within the other named radicals may contain 1 to 3 carbon atoms unless otherwise stated, their tautomers, their diastereomers, their enantiomers, mixtures thereof and the salts thereof.

Another subgroup of particularly preferred compounds of general formula I which deserves special mention comprises those compounds wherein $R^2$, $R^3$, $R^4$, $R^{11}$, X, Z and m and n are as hereinbefore defined for the first-mentioned particularly preferred subgroup, R denotes an unbranched $C_{1-3}$-alkyl group which may be substituted in the ω-position by a $C_{5-7}$-cycloalkyl group, by one or two phenyl groups, by a 1-naphthyl, 2-naphthyl or (4-biphenylyl) group, by a 1,3-dihydro-2H-2-oxobenzimidazol-1-yl, 1,3-dihydro-2H-2-oxoimidazol-1-yl or 3,4-dihydro-2(1H)-oxopyrimidin-3-yl group, whilst the latter two groups may be substituted in the carbon skeleton by a phenyl, pyridinyl or diazinyl group, by a 5-membered heteroaromatic ring linked via a carbon atom and containing a nitrogen, oxygen or sulphur atom or two nitrogen atoms, wherein a nitrogen atom of an imino group may be substituted by an alkyl group, or by a pyridinyl group, whilst a 1,4-butadienylene group may be attached both to the 5-membered heteroaromatic monocyclic rings and also to the pyridinyl group via two adjacent carbon atoms in each case and the bicyclic heteroaromatic rings thus formed may also be bound via a carbon atom of the 1,4-butadienylene group, whilst the phenyl, naphthyl and biphenylyl groups mentioned hereinbefore for the substitution of the alkyl groups in the ω-position as well as optionally any partially hydrogenated mono- and bicyclic heteroaromatic rings may additionally be mono- or disubstituted in the carbon skeleton by fluorine, chlorine or bromine atoms or by alkyl, nitro, alkoxy, trifluoromethyl, hydroxy, amino, acetylamino, propionylamino, alkanoyl, cyano or trifluoromethoxy groups wherein the substituents may be identical or different, and A denotes a single bond, whilst all the above-mentioned alkyl and alkoxy groups and the alkyl groups present within the other groups mentioned may contain 1 to 3 carbon atoms unless otherwise specified, their tautomers, their diastereomers, their enantiomers and their salts.

More particularly preferred compounds of the above general formula I are those wherein R denotes an unbranched $C_{1-3}$-alkyl group which may be substituted in the ω-position by a $C_{5-7}$-cycloalkyl group, by one or two phenyl groups, by a 1-naphthyl, 2-naphthyl or (4-biphenylyl) group, whilst the above-mentioned aromatic groups may additionally be substituted by a fluorine, chlorine or bromine atom or by a methyl, methoxy, amino or acetylamino group, by a 2-pyrrolyl, 3-pyrrolyl, pyridinyl, 1H-indol-3-yl, quinolinyl or isoquinolinyl group, or an unbranched $C_{1-4}$-alkylamino group which is optionally additionally substituted at the nitrogen atom by a methyl or ethyl group and which may be substituted in the ω-position by a $C_{5-7}$-cycloalkyl group, by a phenyl group which may be mono- or disubstituted by fluorine, chlorine or bromine atoms, or by methyl, nitro, methoxy, trifluoromethyl, hydroxy, amino or acetylamino groups, whilst the substituents may be identical or different, by a 2-pyrrolyl, 3-pyrrolyl, pyridinyl, 1H-indol-3-yl, quinolinyl or isoquinolinyl group, or the group of formula

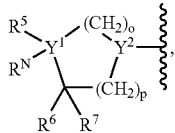

(II)

wherein
p denotes the number 1 or 2,
o denotes the number 2 or, if $Y^1$ and $Y^2$ are not simultaneously nitrogen atoms, it may also denote the number 1,
$Y^1$ denotes the nitrogen atom if $R^5$ denotes a free pair of electrons, or the carbon atom,
$Y^2$ denotes the nitrogen atom or the group >CH—,
$R^5$ denotes a free pair of electrons, if $Y^1$ denotes the nitrogen atom or, if $Y^1$ denotes the carbon atom, $R^5$ may denote the hydrogen atom, a $C_{1-2}$-alkyl group or the cyano or phenyl group,
$R^6$ denotes the hydrogen atom or, provided that $Y^1$ is not a nitrogen atom, $R^6$ together with $R^5$ may also denote an additional bond,
$R^7$ denotes the hydrogen atom or, provided that $Y^1$ is not a nitrogen atom and $R^5$ and $R^6$ together denote an additional bond, $R^7$ together with $R^N$ may also denote the 1,4-butadienylene group,
$R^N$ denotes the hydrogen atom or a $C_{1-3}$-alkyl group, which may be substituted in the ω-position
    by one or two phenyl or pyridinyl groups, wherein the substituents may be identical or different,
    or by a hydroxy or methoxy group,
a phenyl group which may be mono- or disubstituted by fluorine, chlorine or bromine atoms or by methyl groups, nitro, methoxy, ethoxy, trifluoromethyl, hydroxy or cyano groups, whilst the substituents may be identical or different, or a phenyl group substituted by a methylenedioxy group,
a 2-pyridinyl or 4-pyridinyl group,
an amino, benzoylamino, aminocarbonyl, methylaminocarbonyl, methoxycarbonyl, ethoxycarbonyl, aminocarbonylamino, methylaminocarbonylamino, N-(aminocarbonyl)-N-methylamino, N-(methylaminocarbonyl)-N-methylamino, N-(aminocarbonyl)-N-(4-fluorophenyl)amino, N-(methyl-aminocarbonyl)-N-phenylamino, phenylaminocarbonylamino, [N-phenyl(methylamino)]carbonylamino, N-(phenylaminocarbonyl)-N-methylamino, N-(phenylaminocarbonyl)-N-phenylamino, benzoylaminocarbonylamino, N-(aminocarbonyl)-N-phenylamino group or a phenylamino group optionally substituted in the phenyl ring by an aminocarbonylamino or methylsulphonylamino group,
a 1,3-dihydro-4-phenyl-2H-2-oxoimidazol-1-yl, a 1,3-dihydro-4-(3-thienyl)-2H-2-oxoimidazol-1-yl, 1,3-dihydro-5-phenyl-2H-2-oxoimidazol-1-yl, 1,3-dihydro-2(2H)-oxobenzimidazol-1-yl, 1,3,3a,4,5,6,7a-octahydro-2(2H)-oxobenzimidazol-1-yl, 1H-indol-3-yl, 2,4(1H,3H)-dioxoquinazolin-3-yl, 1,3-dihydro-2(2H)-oxoimidazo[4,5-b]pyridin-3-yl, 1,3(2H)-dioxo-1H-isoindol-2-yl, 1H-benzimidazol-1-yl, 3,4-dihydro-2(1H)-oxoquinazolin-3-yl, 3,4-dihydro-2(1H)-oxoquinazolin-1-yl, 2(3H)-oxobenzoxazol-3-yl, 1,3-dihydro-2(2H)-oxoimidazo[4,5-d]pyrimidin-3-yl, 2,3,4,5-tetrahydro-2(1H)-oxo-1,3-benzodiazepin-3-yl, 3,4-dihydro-2(1H)-oxopyrido[2,3-d]pyrimidin-3-yl, 2(1H)-bxoquinolin-3-yl, 3,4-dihydro-2(1H)-oxoquinolin-3-yl, 2(1H)-oxoquinoxalin-3-yl, 3,4,4a,5,6,7,8,8a-octahydro-2(1H)-oxoquinazolin-3-yl, 1,1-dioxido-3(4H)-oxo-1,2,4-benzothiadiazin-2-yl, 2,4(1H,3H)-dioxothieno[3,4-d]-pyrimidin-3-yl, 3,4-dihydro-2(1H)-oxothieno[3,4-d]pyrimidin-3-yl, 3,4-dihydro-2(1H)-oxothieno[3,2-d]pyrimidin-3-yl, 2,4-dihydro-5-phenyl-3(3H)-oxo-1,2,4-triazol-2-yl, 1,3-dihydro-5-methyl-4-phenyl-2(2H)-oxoimidazol-1-yl, 2,5-dioxo-4-phenylimidazolidin-1-yl, 2,5-dioxo-4-(phenylmethyl)-imidazolidin-1-yl, 3,4-dihydro-2,2-dioxido-2,1,3-benzothiadiazin-3-yl, 1,3-dihydro-4-(4-biphenylyl)-2(2H)-oxoimidazol-1-yl, 1,3-dihydro-4-(2-naphthyl)-2(2H)-oxoimidazol-1-yl, 1,3-dihydro-4,5-diphenyl-2(2H)-oxoimidazol-1-yl, 1,3-dihydro-2(2H)-oxoimidazo[4,5-c]quinolin-3-yl, 4-phenyl-2(1H)-oxopyrimidin-1-yl, 4-[3,4-dihydro-2(1H)-oxoquinazolin-3-yl]-1-piperidinyl, 3,4-dihydro-2(1H)-oxopyrido[3,4-d]pyrimidin-3-yl, 3,4-dihydro-2[1H]-oxopyrido[4,3-d]pyrimidin-3-yl or 2,3-dihydro-4(1H)-oxoquinazolin-3-yl group,
    wherein the above-mentioned mono- and bicyclic heterocycles may be substituted at one of the nitrogen atoms by a methoxycarbonylmethyl group and/or
    the above-mentioned mono- and bicyclic heterocycles may be mono-, di- or trisubstituted in the carbon skeleton and/or at the phenyl groups contained in these groups by fluorine, chlorine or bromine atoms, or by methyl, trifluoromethyl, methoxy, hydroxy, amino, nitro, phenyl, phenylmethyl, carboxy, methoxycarbonyl, ethoxycarbonyl, aminocarbonyl, methylaminocarbonyl, hydroxyethylaminocarbonyl, (4-morpholinyl)carbonyl, (1-piperidinyl)carbonyl or (4-methyl-1-piperazinyl)carbonyl groups wherein the substituents may be identical or different and multiple substitution with the last three substituents is ruled out,
or, provided that $Y^1$ is not a nitrogen atom and $R^5$ and $R^6$ together denote an additional bond, $R^N$ together with $R^7$ also denotes the 1,4-butadienylene group,
or, provided that $Y^1$ denotes a carbon atom, $R^N$ together with $R^5$ with the inclusion of $Y^1$ may also denote a carbonyl group or saturated or monounsaturated five- or six-membered 1,3-diaza-heterocycle,
    which may contain a carbonyl group in the ring, adjacent to a nitrogen atom,
    may be substituted by a phenyl group at one of the nitrogen atoms
    and, if it is unsaturated, may also be benzo-condensed at the double bond,
X denotes an oxygen atom or 2 hydrogen atoms,
Z denotes a methylene group or the group —$NR^1$, wherein
    $R^1$ denotes a hydrogen atom or a methyl group,
$R^{11}$ denotes a hydrogen atom, a methoxycarbonyl, ethoxycarbonyl or methyl group,
n denotes the number 1 and m denotes the number 0 or
n denotes the number 0 and m denotes the number 1,
$R^2$ denotes a phenyl, 1-naphthyl, 2-naphthyl, 1,2,3,4-tetrahydro-1-naphthyl, 1H-indol-3-yl, 1-methyl-1H-indol-3-yl, 1-(1,1-dimethylethoxycarbonyl)-1H-indol-3-yl, 2-thienyl, 3-thienyl, thiazolyl or alkylthiazolyl group having 1 to 3 carbon atoms in the alkyl moiety, a pyridinyl or quinolinyl group,
wherein the above-mentioned phenyl and naphthyl groups may be mono-, di- or trisubstituted by fluorine, chlorine or bromine atoms or by branched or unbranched $C_{1-5}$-alkyl groups, by $C_{1-3}$-alkoxy groups, by vinyl, allyl, trifluoromethyl, methylsulphonyloxy, 2-(dimethylamino)ethoxy, hydroxy, cyano, nitro or amino groups, by tetrazolyl, phenyl, pyridinyl, thiazolyl or furyl groups and the substituents may be identical or different, and multiple substitution with the last five substituents is ruled out, A denotes a bond or the divalent group of formula

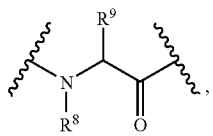

(III)

(linked to the group —$NR^3R^4$ of formula (I) via the carbonyl group)
wherein
$R^8$ and $R^9$ together denote an n-propylene group or
$R^8$ denotes the hydrogen atom or the methyl group and
$R^9$ denotes the hydrogen atom or an unbranched $C_{1-4}$-alkyl group,
which may be substituted in the ω-position by an amino, methylamino, dimethylamino, aminoiminomethylamino or aminocarbonylamino group, whilst in the above-mentioned substituents a hydrogen atom bound to a nitrogen atom may be replaced by a protecting group, e.g. the phenylmethoxycarbonyl or tert.butyloxycarbonyl group,
$R^3$ denotes a hydrogen atom or
a $C_{1-4}$-alkyl group optionally substituted in the (ω-position by an amino, methylamino, dimethylamino- or 4-(1-piperidinyl)-1-piperidinyl group,
$R^4$ denotes a hydrogen atom or a methyl or ethyl group
or $R^3$ and $R^4$ together with the enclosed nitrogen atom denote a group of general formula

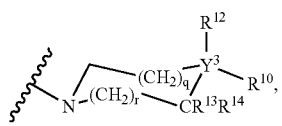

(IV)

wherein
$Y^3$ denotes the carbon atom or, if $R^{12}$ denotes a free pair of electrons, $Y^3$ may also denote a nitrogen atom,
r denotes the number 1,
q denotes the number 1,
$R^{10}$ denotes the hydrogen atom, an alkyl, dialkylamino, aminoalkyl, alkylaminoalkyl, dialkylaminoalkyl, phenylaminocarbonylamino, alkoxycarbonyl, alkoxycarbonylmethyl, carboxymethyl or carboxy group or a cycloalkyl group having 4 to 7 carbon atoms in the ring,
a benzoyl, pyridinylcarbonyl, phenyl, pyridinyl or diazinyl group, each of which may be substituted in the carbon skeleton by a fluorine, chlorine or bromine atom, or by an acetyl, methyl, ethyl or methoxy group, or by a dimethylaminoalkyl group having 1 to 4 carbon atoms in the alkyl moiety optionally hydroxysubstituted in the alkyl moiety,
a 1,3-dihydro-2-oxo-2H-imidazolyl group bound via a nitrogen atom, which may be fused to a benzene or pyridine ring at the double bond,
a 1-pyrrolidinyl, 1-piperidinyl, 4-(dimethylamino)-1-piperidinyl, 4-piperidinyl or 4-morpholinyl group, wherein the nitrogen atom of the 4-piperidinyl group may be substituted by an alkanoyl- or alkyl group each having 1 to 7 carbon atoms or by a benzoyl, methylsulphonyl, 3-carboxy-propionyl, cyclopropylmethyl, alkoxycarbonylmethyl or carboxymethyl group or by a protecting group, e.g. the phenylmethoxycarbonyl or tert.butyloxycarbonyl group, or it may represent a hexahydro-1H-1-azepinyl, 8-methyl-8-azabicyclo[3,2,1]oct-3-yl, 4-alkyl-1-piperazinyl, hexahydro-4-alkyl-1H-1,4-diazepin-1-yl, 1-alkyl-4-piperidinylcarbonyl or 4-alkyl-1-piperazinylcarbonyl group,
or
$R^{10}$ together with $R^{12}$ and $Y^3$ denotes a 5-membered cycloaliphatic ring in which a methylene group may be replaced by an —NH— or —N(CH$_3$)— group,
$R^{12}$ denotes a hydrogen atom, a $C_{1-2}$-alkyl group which may be substituted in the ω-position by a 1-pyrrolidinyl, 1-piperidinyl or 4-methyl-1-piperazinyl group,
a methoxycarbonyl or ethoxycarbonyl or a cyano group,
a free pair of electrons if $Y^3$ denotes a nitrogen atom, and
$R^{13}$ and $R^{14}$ each denote a hydrogen atom or,
provided that $Y^3$ is a carbon atom, $R^{12}$ together with $R^{14}$ may also denote an additional carbon-carbon bond, wherein $R^{10}$ is as hereinbefore defined and $R^{13}$ denotes a hydrogen atom or,
provided that $Y^3$ is a carbon atom, $R^{12}$ together with $R^{14}$ may also denote an additional carbon-carbon bond and $R^{10}$ together with $R^{13}$ and the enclosed double bond denotes an indole group fused on via the 5-membered ring, whilst all the above-mentioned alkyl groups and the alkyl groups present within the other named groups may contain 1 to 3 carbon atoms, unless otherwise specified, their tautomers, their diastereomers, their enantiomers and their salts.

A subgroup of most particularly preferred compounds of general formula I deserving special mention comprises those wherein A, $R^2$, $R^3$, $R^4$, $R^{11}$, X, Z and m and n are as hereinbefore defined for the most particularly preferred compounds of general formula I and R denotes an unbranched $C_{1-4}$-alkylamino group optionally substituted at the nitrogen atom by a methyl or ethyl group, which may be substituted in the ω-position
by a $C_{5-7}$-cycloalkyl group,
by a phenyl group, which may be mono- or disubstituted by fluorine, chlorine or bromine atoms or by methyl, nitro, methoxy, trifluoromethyl, hydroxy, amino or acetylamino groups, wherein the substituents may be identical or different, or
by a 2-pyrrolyl, 3-pyrrolyl, pyridinyl, 1H-indol-3-yl, quinolinyl or isoquinolinyl group, their tautomers, their diastereomers, their enantiomers, mixtures thereof and salts thereof.

Another subgroup of most particularly preferred compounds of general formula I deserving special mention comprises those wherein $R^2, R^3, R^4, R^{11}$, X, Z and m and n are as defined hereinbefore for the first-mentioned particularly preferred subgroup, R denotes an unbranched $C_{1-3}$-alkyl group which may be substituted in the ω-position
  by a $C_{5-7}$-cycloalkyl group,
  by one or two phenyl groups, by a 1-naphthyl, 2-naphthyl or (4-biphenylyl) group, whilst the above-mentioned aromatic groups may be substituted by a fluorine, chlorine or bromine atom or by a methyl, methoxy, amino or acetylamino group,
  or by a 2-pyrrolyl, 3-pyrrolyl, pyridinyl, 1H-indol-3-yl, quinolinyl- or isoquinolinyl group,
and A denotes a single bond, their tautomers, their diastereomers, their enantiomers, mixtures thereof and the salts thereof.

The following are mentioned as examples of most particularly preferred compounds:

(1) 1-[$N^2$—[N-[[[2-(2-Methoxyphenyl)ethyl]amino]carbonyl]-3,5-dibromo-D-tyrosyl]-L-lysyl]-4-(4-pyridinyl)-piperazine
(2) 1-[$N^2$—[N-[[[2-(3-Methoxyphenyl)ethyl]amino]carbonyl]-3,5-dibromo-D-tyrosyl]-L-lysyl]-4-(4-pyridinyl)-piperazine
(3) 1-[$N^2$—[N-[[[2-(2,5-Dimethoxyphenyl)ethyl]amino]carbonyl]-3,5-dibromo-D-tyrosyl]-L-lysyl]-4-(4-pyridinyl)-piperazine
(4) 1-[$N^2$—[N-[[[2-(3-Methoxyphenyl)ethyl]amino]carbonyl]-3,5-dibromo-D-tyrosyl]-L-arginyl]-4-(4-pyridinyl)-piperazine
(5) 1-[$N^2$—[N-[[[2-(2,3-dimethoxyphenyl)ethyl]amino]carbonyl]-3,5-dibromo-D-tyrosyl]-L-lysyl]-4-(4-pyridinyl)-piperazine
(6) 1-[$N^2$—[N-[[[2-(3-Methoxyphenyl)ethyl]amino]carbonyl]-3,5-dibromo-D,L-tyrosyl]-D,L-lysyl]-4-(1-methyl-4-piperidinyl)-piperazine
(7) 1-[$N^2$—[N-[[[2-(3-Methoxyphenyl)ethyl]amino]carbonyl]-3,5-dibromo-D,L-tyrosyl]-D,L-lysyl]-4-(4-piperidinyl)-piperazine
(8) 1-[$N^2$—[N-[[[2-(3,4-dihydroxyphenyl)ethyl]amino]carbonyl]-3,5-dibromo-D,L-tyrosyl]-D,L-lysyl]-4-(4-pyridinyl)-piperazine
(9) 1-[$N^2$—[N-[4-(2-Methoxyphenyl)-1-piperazinyl]carbonyl]-3,5-dibromo-D-tyrosyl]-L-lysyl]-4-(4-pyridinyl)-piperazine
(10) 1-[$N^2$—[N-[4-(3-Methoxyphenyl)-1-piperazinyl]carbonyl]-3,5-dibromo-D-tyrosyl]-L-lysyl]-4-(4-pyridinyl)-piperazine
(11) 1-[$N^2$—[N-[[(2-Phenylethyl)amino]carbonyl]-3,5-dibromo-D-tyrosyl]-L-lysyl]-4-(4-pyridinyl)-piperazine
(12) 1-[$N^2$—[N-[[[2-(4-Methoxyphenyl)ethyl]amino]carbonyl]-3,5-dibromo-D-tyrosyl]-L-lysyl]-4-(4-pyridinyl)-piperazine
(13) 1-[$N^2$—[N-[[[2-(3-Methoxyphenyl)ethyl]amino]carbonyl]-3-(1-naphthyl)-D-alanyl]-L-lysyl]-4-(4-pyridinyl)-piperazine
(14) 1-[$N^2$—[N-[[[2-(3-Hydroxyphenyl)ethyl]amino]carbonyl]-3,5-dibromo-D-tyrosyl]-L-lysyl]-4-(4-pyridinyl)-piperazine
(15) 1-[$N^2$—[N-[3-(3-Methoxyphenyl)-1-oxopropyl]-3,5-dibromo-D-tyrosyl]-L-lysyl]-4-(4-pyridinyl)-piperazine
(16) 1-[$N^2$—[N-[[[2-(3-Methoxyphenyl)ethyl]methylamino]carbonyl]-3,5-dibromo-D-tyrosyl]-L-lysyl]-4-(4-pyridinyl)-piperazine
(17) 1-[$N^2$—[N-(4-Phenyl-1-piperazinyl)carbonyl]-3,5-dibromo-D-tyrosyl]-L-lysyl]-4-(4-pyridinyl)-piperazine
(18) 1-[$N^2$—[N-[4-(2-Methylphenyl)-1-piperazinyl]carbonyl]-3,5-dibromo-D-tyrosyl]-L-lysyl]-4-(4-pyridinyl)-piperazine
(19) 1-[$N^2$—[N-[4-(1,3-Dihydro-2(2H)-oxobenzimidazol-1-yl)-1-piperidinyl]carbonyl]-3,5-dibromo-D-tyrosyl]-L-lysyl]-4-(4-pyridinyl)-piperazine
(20) 1-[$N^2$—[N-[[[2-(3-Methoxyphenyl)ethyl]amino]carbonyl]-3,5-dichloro-D,L-tyrosyl]-D,L-lysyl]-4-(4-pyridinyl)-piperazine
(21) 1-[$N^2$—[N-[4-(2-Methoxyphenyl)-1-piperazinyl]carbonyl]-3,5-dibromo-D-tyrosyl]-L-lysyl]-4-(4-pyridinyl)-piperidin
(22) 1-[$N^2$—[N-(4,4-Diphenyl-1-piperidinyl)carbonyl]-3,5-di-bromo-D-tyrosyl]-L-lysyl]-4-(4-pyridinyl)-piperazine
(23) 1-[$N^2$—[N-(4-Phenyl-1-piperidinyl)carbonyl]-3,5-dibromo-D-tyrosyl]-L-lysyl]-4-(4-pyridinyl)-piperazine
(24) 1-[$N^2$—[N-[4-(4-Fluorophenyl)-1-oxobutyl]-3,5-dibromo-D-tyrosyl]-L-lysyl]-4-(4-pyridinyl)-piperazine
(25) 1-[$N^2$—[N-[4,4-Diphenyl-1-oxobutyl]-3,5-dibromo-D-tyrosyl]-L-lysyl]-4-(4-pyridinyl)-piperazine
(26) 1-[$N^2$—[N-[4-Cyclohexyl-1-oxobutyl]-3,5-dibromo-D-tyrosyl]-L-lysyl]-4-(4-pyridinyl)-piperazine
(27) 1-[$N^2$—[N-[4-(4-Acetylaminophenyl)-1-oxobutyl]-3,5-dibromo-D-tyrosyl]-L-lysyl]-4-(4-pyridinyl)-piperazine
(28) 1-[$N^2$—[N-[4-(2-Methoxyphenyl)-1-piperazinyl]carbonyl]-3,5-dichloro-D,L-tyrosyl]-D,L-lysyl]-4-(4-pyridinyl)-piperazine
(29) 1-[$N^2$—[N-[4-[3-(Trifluoromethyl)phenyl]-1-piperazinyl]-carbonyl]-3,5-dibromo-D,L-tyrosyl]-D,L-lysyl]-4-(4-pyridinyl)-piperazine
(30) 1-[$N^2$—[N-[4-(2-Chlorophenyl)-1-piperazinyl]carbonyl]-3,5-dibromo-D-tyrosyl]-L-lysyl]-4-(4-pyridinyl)-piperazine
(31) 1-[$N^2$—[N-[4-(3,4-Methylenedioxyphenyl)-1-piperazinyl]-carbonyl]-3,5-dibromo-D-tyrosyl]-L-lysyl]-4-(4-pyridinyl)-piperazine
(32) 1-[$N^2$—[N-(4-Methyl-1-piperazinyl)carbonyl]-3,5-dibromo-D-tyrosyl]-L-lysyl]-4-(4-pyridinyl)-piperazine
(33) 1-[$N^2$—[N-[4-(2-Hydroxyethyl)-1-piperazinyl]carbonyl]-3,5-dibromo-D-tyrosyl]-L-lysyl]-4-(4-pyridinyl)-piperazine
(34) 1-[$N^2$—[N-[4-(4-Pyridinyl)-1-piperazinyl]carbonyl]-3,5-dibromo-D-tyrosyl]-L-lysyl]-4-(4-pyridinyl)-piperazine
(35) 1-[$N^2$—[N-[4-(2-Pyridinyl)-1-piperazinyl]carbonyl]-3,5-dibromo-D-tyrosyl]-L-lysyl]-4-(4-pyridinyl)-piperazine
(36) 1-[$N^2$—[N-[4-(Diphenylmethyl)-1-piperazinyl]carbonyl]-3,5-dibromo-D-tyrosyl]-L-lysyl]-4-(4-pyridinyl)-piperazine
(37) 1-[$N^2$—[N-[4-(Phenylmethyl)-1-piperazinyl]carbonyl]-3,5-dibromo-D-tyrosyl]-L-lysyl]-4-(4-pyridinyl)-piperazine
(38) 1-[$N^2$—[N-[4-(4-Nitrophenyl)-1-piperazinyl]carbonyl]-3,5-dibromo-D-tyrosyl]-L-lysyl]-4-(4-pyridinyl)-piperazine
(39) 1-[$N^2$—[N-[4-(Ethoxycarbonyl)-1-piperazinyl]carbonyl]-3,5-dibromo-D-tyrosyl]-L-lysyl]-4-(4-pyridinyl)-piperazine
(40) 1-[$N^2$—[N-[[[3-(2-Methoxyphenyl)propyl]amino]carbonyl]-3,5-dibromo-D-tyrosyl]-L-lysyl]-4-(4-pyridinyl)-piperazine
(41) 1-[$N^2$—[N-[[[2-(3-Bromophenyl)ethyl]amino]carbonyl]-3,5-dibromo-D-tyrosyl]-L-lysyl]-4-(4-pyridinyl)-piperazine

(42) 1-[N²—[N-[[[2-(3-Nitrophenyl)ethyl]amino]carbonyl]-3,5-dibromo-D-tyrosyl]-L-lysyl]-4-(4-pyridinyl)-piperazine
(43) 1-[N²—[N-[[[2-(3-Acetylaminophenyl)ethyl]amino]carbonyl]-3,5-dibromo-D-tyrosyl]-L-lysyl]-4-(4-pyridinyl)-piperazine
(44) 1-[N²—[N-[[[2-(3-Bromophenyl)ethyl]amino]carbonyl]-3,5-dibromo-D-tyrosyl]-N⁶-(1,1-dimethylethoxycarbonyl)-L-lysyl]-4-(4-pyridinyl)-piperazine
(45) 1-[N²—[N-[(1,2,4,5-Tetrahydro-3H-3-benzazepin-3-yl)carbonyl]-3,5-dibromo-D-tyrosyl]-L-lysyl]-4-(4-pyridinyl)-piperazine
(46) 1-[N²—[N-[[[2-[3-(Trifluoromethyl)phenyl]ethyl]amino]-carbonyl]-3,5-dibromo-D-tyrosyl]-L-lysyl]-4-(4-pyridinyl)-piperazine
(47) 1-[N²—[N-[[[2-(3-Fluorophenyl)ethyl]amino]carbonyl]-3,5-dibromo-D-tyrosyl]-L-lysyl]-4-(4-pyridinyl)-piperazine
(48) 1-[N²—[N-[4-(2-Methoxyphenyl)-1-piperazinyl]carbonyl]-3,5-dibromo-D-tyrosyl]-L-lysyl]-4-(4-fluorophenyl)-piperazine
(49) 1-[N²-[4-Amino-3,5-dibromo-N-[[(2-phenylethyl)amino]carbonyl]-D-phenylalanyl]-L-lysyl]-4-(4-pyridinyl)-piperazine
(50) 1-[N²—[N-[4-(2-Methoxyphenyl)-1-piperidinyl]carbonyl]-3,5-dibromo-D-tyrosyl]-L-lysyl]-4-(4-pyridinyl)-piperazine
(51) 1-[N²—[N-[4-(3-Methoxyphenyl)-1,2,5,6-tetrahydro-1-piperidinyl]carbonyl]-3,5-dibromo-D-tyrosyl]-L-lysyl]-4-(4-pyridinyl)-piperazine
(52) 1-[N²—[N-[4-(2-Methoxyphenyl)-1,2,5,6-tetrahydro-1-piperidinyl]carbonyl]-3,5-dibromo-D-tyrosyl]-L-lysyl]-4-(4-pyridinyl)-piperazine
(53) 1-[N²—[N-[(4-Biphenylyl)acetyl]-3,5-dibromo-D-tyrosyl]-L-lysyl]-4-(4-pyridinyl)-piperazine
(54) 1-[N²—[N-[4-(4-Bromophenyl)-1-oxobutyl]-3,5-dibromo-D-tyrosyl]-L-lysyl]-4-(4-pyridinyl)-piperazine
(55) 1-[N²—[N-[4-(1H-Indol-3-yl)-1-oxobutyl]-3,5-dibromo-D-tyrosyl]-L-lysyl]-4-(4-pyridinyl)-piperazine
(56) 1-[N²—[N-(4,4-Diphenyl-1-piperidinyl)carbonyl]-3,5-dibromo-D-tyrosyl]-L-lysyl]-4-(4-pyridinyl)-piperazine
(57) 1-[N²—[N-(4-oxo-1-phenyl-1,3,8-triazaspiro[4,5]dec-8-yl)carbonyl]-3,5-dibromo-D-tyrosyl]-L-lysyl]-4-(4-pyridinyl)-piperazine
(58) 1-[N²—[N-[4-(1,3-Dihydro-2(2H)-oxobenzimidazol-1-yl)-1-piperidinyl]carbonyl]-4-amino-3,5-dibromo-D-phenylalanyl]-L-lysyl]-4-(4-pyridinyl)-piperidine
(59) 1-[N²—[N-[4-(1,3-Dihydro-2(2H)-oxobenzimidazol-1-yl)-1-piperidinyl]carbonyl]-4-amino-3,5-dibromo-D-phenylalanyl]-L-lysyl]-4-(4-pyridinyl)-piperazine
(60) 1-[N²—[N-[4-(2-Chlorophenyl)-1-piperazinyl]carbonyl]-4-amino-3,5-dibromo-D-phenylalanyl]-L-lysyl]-4-(4-pyridinyl)-piperidine
(61) 1-[N²—[N-[4-(2-Chlorophenyl)-1-piperazinyl]carbonyl]-4-amino-3,5-dibromo-D-phenylalanyl]-L-lysyl]-4-(4-pyridinyl)-piperazine
(62) 1-[N²—[N-[4-(1,3-Dihydro-2(2H)-oxobenzimidazol-1-yl)-1-piperidinyl]carbonyl]-3,5-dibromo-D-tyrosyl]-N⁶-(1,1-dimethylethoxycarbonyl)-L-lysyl]-4-(2-pyridinyl)-piperazine
(63) 1-[N²—[N-[[[2-(2-Cyclohexyl)ethyl]amino]carbonyl]-3,5-dibromo-D-tyrosyl]-L-lysyl]-4-(4-pyridinyl)-piperazine
(64) 1-[N²—[N-[4-(2-Chlorophenyl)-1-piperazinyl]carbonyl]-3,5-dibromo-D-tyrosyl]-L-lysyl]-4-(4-pyridinyl)-piperidine
(65) 1-[N²—[N-[4-(1,3-Dihydro-2(2H)-oxobenzimidazol-1-yl)-1-piperidinyl]carbonyl]-3,5-dibromo-D-tyrosyl]-L-lysyl]-4-(4-pyridinyl)-piperidine
(66) 1-[N²—[N-[4-(Aminocarbonyl)-1-piperidinyl]carbonyl]-3,5-dibromo-D-tyrosyl]-L-lysyl]-4-(4-pyridinyl)-piperidine
(67) 1-[N²—[N-[[[2-(1H-Indol-3-yl)ethyl]amino]carbonyl]-3,5-dibromo-D-tyrosyl]-L-lysyl]-4-(4-pyridinyl)-piperazine
(68) 1-[N²—[N-[4-(1,3-Dihydro-2(2H)-oxobenzimidazol-1-yl)-1-piperidinyl]carbonyl]-3,5-dibromo-D-tyrosyl]-L-lysyl]-4-(2-methoxyphenyl)-piperazine
(69) 1-[N²—[N-[4-(1,3-Dihydro-2(2H)-oxobenzimidazol-1-yl)-1-piperidinyl]carbonyl]-3,5-dibromo-D-tyrosyl]-L-lysyl]-4-(2-pyridinyl)-piperazine
(70) 1-[N²—[N-(4-Oxo-1-phenyl-1,3,8-triazaspiro[4,5]dec-8-yl)carbonyl]-3,5-dibromo-D-tyrosyl]-L-lysyl]-4-(2-methoxyphenyl)-piperazine
(71) 1-[N²—[N-(4,4-Diphenyl-1-piperidinyl)carbonyl]-3,5-dibromo-D-tyrosyl]-L-lysyl]-4-(2-pyridinyl)-piperazine
(72) 1-[N²—[N-[4-(1,3-Dihydro-2(2H)-oxobenzimidazol-1-yl)-1-piperidinyl]carbonyl]-3,5-dibromo-D,L-phenylalanyl]-L-lysyl]-4-(4-pyridinyl)-piperazine
(73) 1-[N²—[N-[4-(1,3-Dihydro-2(2H)-oxobenzimidazol-1-yl)-1-piperidinyl]carbonyl]-3,5-dibromo-D,L-phenylalanyl]-N⁶-(1,1-dimethylethoxycarbonyl)-L-lysyl]-4-(4-pyridinyl)-piperazine
(74) 1-[N²—[N-[4-(2,3-Dichlorophenyl)-1-piperazinyl]carbonyl]-3,5-dibromo-D-tyrosyl]-L-lysyl]-4-(4-pyridinyl)-piperazine
(75) 1-[N²—[N-[4-(3,5-Dichlorophenyl)-1-piperazinyl]carbonyl]-3,5-dibromo-D-tyrosyl]-L-lysyl]-4-(4-pyridinyl)-piperazine
(76) 1-[N²—[N-[4-(2-Cyanphenyl)-1-piperazinyl]carbonyl]-3,5-dibromo-D-tyrosyl]-L-lysyl]-4-(4-pyridinyl)-piperazine
(77) 1-[N²—[N-(4-Oxo-1-phenyl-1,3,8-triazaspiro[4,5]dec-8-yl)carbonyl]-3,5-dibromo-D,L-phenylalanyl]-L-lysyl]-4-(4-pyridinyl)-piperazine
(78) 1-[N²—[N-(4-Oxo-1-phenyl-1,3,8-triazaspiro[4,5]dec-8-yl)carbonyl]-3,5-dibromo-D,L-phenylalanyl]-N⁶-(1,1-dimethyl-ethoxycarbonyl)-L-lysyl]-4-(4-pyridinyl)-piperazine
(79) 1-[N²—[N-[4-[4-Chloro-3-(trifluoromethyl)phenyl]-1-piperazinyl]carbonyl]-3,5-dibromo-D-tyrosyl]-L-lysyl]-4-(4-pyridinyl)-piperazine
(80) 1-[N²—[N-[4-(1,3-Dihydro-2(2H)-oxobenzimidazol-1-yl)-1-piperidinyl]carbonyl]-3,5-dibromo-D-tyrosyl]-N⁶-(1,1-dimethylethoxycarbonyl)-L-lysyl]-4-(4-pyridinyl)-piperazine
(81) 1-[4-Amino-3,5-dibromo-N-[[4-(1,3-dihydro-2(2H)-oxobenzimidazol-1-yl)-1-piperidinyl]carbonyl]-D-phenylalanyl]-4-(4-pyridinyl)-piperidine
(82) 1-[4-Amino-3,5-dibromo-N-[[4-(1,3-dihydro-2(2H)-oxobenzimidazol-1-yl)-1-piperidinyl]carbonyl]-D-phenylalanyl]-4-(4-pyridinyl)-piperazine
(83) 1-[3,5-Dibromo-N-[[4-(1,3-dihydro-2(2H)-oxobenzimidazol-1-yl)-1-piperidinyl]carbonyl]-D-tyrosyl]-4-(4-pyridinyl)-piperazine
(84) 1-[N-[[4-[3,4-Dihydro-2(1H)-oxoquinazolin-3-yl]-1-piperidinyl]carbonyl]-3-(trifluoromethyl)-D,L-phenylalanyl]-4-[1-(1-methylethyl)-4-piperidinyl]-piperidine
(85) 1-[4-Amino-3,5-dibromo-N-[[4-(1,3-dihydro-2(2H)-oxo-benzimidazol-1-yl)-1-piperidinyl]carbonyl]-D-phenylalanyl]-4-phenylpiperazine

(86) 1-[4-Amino-3,5-dibromo-N-[[4-(1,3-dihydro-6-methyl-2(2H)-oxobenzimidazol-1-yl)-1-piperidinyl]carbonyl]-D-phenylalanyl]-4-(4-pyridinyl)-piperazine
(87) 1-[4-Amino-3,5-dibromo-N-[[4-(1,3-dihydro-5-methyl-2(2H)-oxobenzimidazol-1-yl)-1-piperidinyl]carbonyl]-D-phenylalanyl]-4-(4-pyridinyl)-piperazine
(88) 1-[4-Amino-3,5-dibromo-N-[[4-(1,3-dihydro-5,6-dichloro-2(2H)-oxobenzimidazol-1-yl)-1-piperidinyl]carbonyl]-D-phenyl-alanyl]-4-(4-pyridinyl)-piperazine
(89) 1-[4-Amino-3,5-dibromo-N-[[4-[1,3-dihydro-3-(methoxy-carbonylmethyl)-2(2H)-oxobenzimidazol-1-yl]-1-piperidinyl]carbonyl]-D-phenylalanyl]-4-(4-pyridinyl)-piperazine
(90) 1-[3,5-Dibromo-N-[[4-(1,3-dihydro-2(2H)-oxobenzimidazol-1-yl)-1-piperidinyl]carbonyl]-D-tyrosyl]-4-(4-piperidinyl)-piperidine
(91) 1-[4-Amino-3,5-dibromo-N-[[4-(1,3,3a,4,5,6,7,7a-octahydro-2(2H)-oxobenzimidazol-1-yl)-1-piperidinyl]carbonyl]-D-phenylalanyl]-4-(4-pyridinyl)-piperazine
(92) 1-[4-Amino-3,5-dibromo-N-[[4-(benzoylamino)-1-piperidinyl]carbonyl]-D-phenylalanyl]-4-(4-pyridinyl)-piperazine
(93) 1-[4-Amino-3,5-dibromo-N-[[4-(aminocarbonyl)-1-piperidinyl]carbonyl]-D-phenylalanyl]-4-(4-pyridinyl)-piperazine
(94) 1-[4-Amino-3,5-dibromo-N-[(4-Oxo-1-phenyl-1,3,8-triazaspiro[4,5]dec-8-yl)carbonyl]-D-phenylalanyl]-4-(4-pyridinyl)-piperazine
(95) 1-[3,5-Dibromo-N-[[4-(benzoylamino)-1-piperidinyl]carbonyl]-D-phenylalanyl]-4-(4-pyridinyl)-piperazine
(96) 1-[3,5-Dibromo-N-[[4-(1,3-dihydro-6-methyl-2(2H)-oxobenzimidazol-1-yl)-1-piperidinyl]carbonyl]-D-tyrosyl]-4-(4-pyridinyl)-piperazine
(97) 1-[3,5-Dibromo-N-[[4-(1,3-dihydro-5-methyl-2(2H)-oxobenzimidazol-1-yl)-1-piperidinyl]carbonyl]-D-tyrosyl]-4-(4-pyridinyl)-piperazine
(98) 3,5-Dibromo-$N^2$-[[4-(1,3-dihydro-2(2H)-oxobenzimidazol-1-yl)-1-piperidinyl]carbonyl]-D-tyrosinamide
(99) 1-[3,5-Dibromo-N-[[4-(1,3-dihydro-2(2H)-oxobenzimidazol-1-yl)-1-piperidinyl]carbonyl]-D-tyrosyl]-4-methylpiperazine
(100) 1-[3,5-Dibromo-N-[[4-(1,3-dihydro-2(2H)-oxobenzimidazol-1-yl)-1-piperidinyl]carbonyl]-D-tyrosyl]-4-(1-methyl-4-piperidinyl)piperazine
(101) 1-[3,5-Dibromo-N-[[4-(1,3-dihydro-2(2H)-oxobenzimidazol-1-yl)-1-piperidinyl]carbonyl]-D-tyrosyl]-4-phenylpiperazine
(102) 3,5-Dibromo-$N^2$-[[4-(1,3-dihydro-2(2H)-oxobenzimidazol-1-yl)-1-piperidinyl]carbonyl]-N,N-diethyl-D-tyrosinamide
(103) 3,5-Dibromo-$N^2$-[[4-(1,3-dihydro-2(2H)-oxobenzimidazol-1-yl)-1-piperidinyl]carbonyl]-N-[(4-(dimethylamino)butyl]-D-tyrosinamide
(104) 1-[3-Bromo-N-[[4-(1,3-dihydro-2(2H)-oxobenzimidazol-1-yl)-1-piperidinyl]carbonyl]-D-tyrosyl]-4-(4-pyridinyl)-piperidine
(105) 1-[3-Bromo-N-[[4-(1,3-dihydro-2(2H)-oxobenzimidazol-1-yl)-1-piperidinyl]carbonyl]-D-tyrosyl]-4-(4-pyridinyl)-piperazine
(106) 1-[3,5-Dibromo-N-[[4-(1,3-dihydro-2(2H)-oxobenzimidazol-1-yl)-1-piperidinyl]carbonyl]-D-tyrosyl]-4-[1-(1,1-di-methylethoxycarbonyl)-4-piperidinyl]piperazine
(107) 1-[4-Amino-3,5-dibromo-N-[(4-cyan-4-phenyl-1-piperidinyl)carbonyl]-D-phenylalanyl]-4-(4-pyridinyl)-piperazine
(108) 1-[3,5-Dibromo-N-[(4-oxo-1-phenyl-1,3,8-triazaspiro-[4,5]dec-8-yl)carbonyl]-D-tyrosyl]-4-(4-pyridinyl)-piperazine
(109) 1-[3,5-Dibromo-N-[(4-cyan-4-phenyl-1-piperidinyl)carbonyl]-D-tyrosyl]-4-(4-pyridinyl)-piperazine
(110) 1-[4-Amino-3,5-dibromo-N-[[4-(1,3-dihydro-2(2H)-oxobenzimidazol-1-yl)-1-piperidinyl]carbonyl]-D-phenylalanyl]-4-(2-pyridinyl)-piperazine
(111) 1-[4-Amino-3,5-dibromo-N-[[4-(1,3-dihydro-2(2H)-oxobenzimidazol-1-yl)-1-piperidinyl]carbonyl]-D-phenylalanyl]-4-(2-pyrimidinyl)-piperazine
(112) 1-[3,5-Dibromo-N-[[4-(1,3-dihydro-2(2H)-oxobenzimidazol-1-yl)-1-piperidinyl]carbonyl]-D-tyrosyl]-4-(2-pyridinyl)-piperazine
(113) 1-[4-Amino-3,5-dibromo-N-[[4-(1,3-dihydro-2(2H)-oxobenzimidazol-1-yl)-1-piperidinyl]carbonyl]-D-phenylalanyl]-4(pyrazinyl)-piperazine
(114) 1-[4-Amino-3,5-dibromo-N-[(4-oxo-1-phenyl-1,3,8-triazaspiro[4,5]dec-8-yl)carbonyl]-D-phenylalanyl]-4-(2-pyridinyl)-piperazine
(115) 1-[3,5-Dibromo-N-[(4-oxo-1-phenyl-1,3,8-triazaspiro-[4,5]dec-8-yl)carbonyl]-D-tyrosyl]-4-(2-pyridinyl)-piperazine
(116) 1-[4-Amino-3,5-dibromo-N-[[4-(2,4(1H,3H)-dioxoquinazolin-3-yl)-1-piperidinyl]carbonyl]-D-phenylalanyl]-4-(4-pyridinyl)-piperazine
(117) 1-[3,5-Dibromo-N-[[4-(2,4(1H,3H)-dioxoquinazolin-3-yl)-1-piperidinyl]carbonyl]-D-tyrosyl]-4-(4-pyridinyl)-piperazine
(118) 1-[3,5-Dibromo-N-[[4-(aminocarbonyl)-1-piperidinyl]carbonyl]-D-tyrosyl]-4-(4-pyridinyl)-piperazine
(119) 1-[4-Amino-3,5-dibromo-N-[(4-oxo-1-phenyl-1,3,8-triazaspiro[4,5]dec-8-yl)carbonyl]-D-phenylalanyl]-4-(pyrazinyl)-piperazine
(120) 1-[3,5-Dibromo-N-[[4-(1,3-dihydro-2(2H)-oxobenzimidazol-1-yl)-1-piperidinyl]carbonyl]-D-tyrosyl]-4-(2-pyrimidinyl)-piperazine
(121) 1-[3,5-Dibromo-N-[[4-(1,3-dihydro-2(2H)-oxo-imidazo-[4,5-b]pyridin-3-yl)-1-piperidinyl]carbonyl]-D-tyrosyl]-4-(4-pyridinyl)-piperazine
(122) 1-[4-Amino-3,5-dibromo-N-[[4-(1,3-dihydro-2(2H)-oxo-imidazo[4,5-b]pyridin-3-yl)-1-piperidinyl]carbonyl]-D-phenyl-alanyl]-4-(4-pyridinyl)-piperazine
(123) cis-1-[3,5-Dibromo-N-[[4-(1,3-dihydro-2(2H)-oxobenzimidazol-1-yl)-1-cyclohexyl]carbonyl]-D-tyrosyl]-4-(4-pyridinyl)-piperazine
(124) trans-1-[3,5-Dibromo-N-[[4-(1,3-dihydro-2(2H)-oxobenzimidazol-1-yl)-1-cyclohexyl]carbonyl]-D-tyrosyl]-4-(4-pyridinyl)-piperazine
(125) 1-[N-[[4-(1,3-Dihydro-2(2H)-oxobenzimidazol-1-yl)-1-piperidinyl]carbonyl]-3,5-dimethyl-D,L-tyrosyl]-4-(4-pyridinyl)-piperazine
(126) 1-[N-[[4-(1,3-Dihydro-2(2H)-oxobenzimidazol-1-yl)-1-piperidinyl]carbonyl]-3,5-dimethyl-D,L-tyrosyl]-4-(4-pyridinyl)-piperidine
(127) 1-[N-[[4-(1,3-Dihydro-2(2H)-oxobenzimidazol-1-yl)-1-piperidinyl]carbonyl]-3,5-dimethyl-D,L-tyrosyl]-4-(1-piperidinyl)-piperidine
(128) 1-[4-Amino-3,5-dibromo-N-[[4-(1,3-dihydro-2(2H)-oxobenzimidazol-1-yl)-1-piperidinyl]carbonyl]-D-phenylalanyl]-4-(4-fluorophenyl)-piperazine
(129) 1-[3,5-Dibromo-N-[[4-(1,3-dihydro-2(2H)-oxobenzimidazol-1-yl)-1-piperidinyl]carbonyl]-D-tyrosyl]-4-(pyrazinyl)-piperazine
(130) 1-[4-Amino-3,5-dibromo-N-[[4-(1,3-dihydro-2(2H)-oxobenzimidazol-1-yl)-1-piperidinyl]carbonyl]-D-phenylalanyl]-4-(2-methoxyphenyl)-piperazine (131) 1-[4-Amino-3,5-dibromo-N-[(4-oxo-1-phenyl-1,3,8-triazaspiro[4,5]dec-8-yl)carbonyl]-D-phenylalanyl]-4-(2-methoxyphenyl)-piperazine
(132) 1-[4-Amino-3,5-dibromo-N-[(4-oxo-1-phenyl-1,3,8-triazaspiro[4,5]dec-8-yl)carbonyl]-D-phenylalanyl]-4-(4-fluorophenyl)-piperazine
(133) 1-[3,5-Dibromo-N-[[4-(1,3-dihydro-2(2H)-oxobenzimidazol-1-yl)-1-piperidinyl]carbonyl]-D-tyrosyl]-4-(2-methoxyphenyl)-piperazine
(134) 1-[4-Amino-3,5-dibromo-N-[[4-(1,3-dihydro-2(2H)-oxobenzimidazol-1-yl)-1-piperidinyl]carbonyl]-D-phenylalanyl]-4-(5-methoxy-4-pyrimidinyl)-piperazine
(135) 1-[3,5-Dibromo-N-[[4-(1,3-dihydro-2(2H)-oxobenzimidazol-1-yl)-1-piperidinyl]carbonyl]-D-tyrosyl]-4-(5-methoxy-4-pyrimidinyl)-piperazine
(136) 1-[N-[[4-(1,3-dihydro-2(2H)-oxobenzimidazol-1-yl)-1-piperidinyl]carbonyl]-D-tyrosyl]-4-(4-pyridinyl)-piperazine
(137) 1-[4-Amino-N-[[4-(1H-benzimidazol-1-yl)-1-piperidinyl]carbonyl]-3,5-dibromo-D-phenylalanyl]-4-(4-pyridinyl)-piperidine
(138) 1-[4-Amino-3,5-dibromo-N-[[4-(1,3(2H)-dioxo-1H-isoindol-2-yl)-1-piperidinyl]carbonyl]-D-phenylalanyl]-4-(1-piperidinyl)-piperidine
(139) 1-[$N^2$-[3,5-Dibromo-N-[[4-(1,3-dihydro-2(2H)-oxoimidazo[4,5-b]pyridin-3-yl)-1-piperidinyl]carbonyl]-D-tyrosyl]-$N^6$-(1,1-dimethylethoxycarbonyl)-L-lysyl]-4-(4-pyridinyl)-piperazine
(140) 1-[$N^2$-[3,5-Dibromo-N-[[4-(2,4(1H,3H)-dioxo-quinazolin-3-yl)-1-piperidinyl]carbonyl]-D-tyrosyl]-$N^6$-(1,1-dimethyl-ethoxycarbonyl)-L-lysyl]-4-(4-pyridinyl)-piperazine
(141) 1-[$N^2$-[3,5-Dibromo-N-[[4-(1,3-dihydro-2(2H)-oxoimidazo[4,5-b]pyridin-3-yl)-1-piperidinyl]carbonyl]-D-tyrosyl]-L-lysyl]-4-(4-pyridinyl)-piperazine
(142) 1-[$N^2$-[3,5-Dibromo-N-[[4-(2,4(1H,3H)-dioxo-quinazolin-3-yl)-1-piperidinyl]carbonyl]-D-tyrosyl]-L-lysyl]-4-(4-pyridinyl)-piperazine
(143) 1-[3,5-Dibromo-N-[[4-(3,4-dihydro-2(1H)-oxo-quinazolin-3-yl)-1-piperidinyl]carbonyl]-D-tyrosyl]-4-(4-pyridinyl)-piperidine
(144) 1-[3,5-Dibromo-N-[(4'(3'H)-oxospiro[piperidine-4,2'(1'H)-quinazolin]-1-yl)carbonyl]-D-tyrosyl]-4-(4-pyridinyl)-piperidine
(145) 1-[3,5-Dibromo-N-[[4-(1,3-dihydro-2(2H)-oxoimidazo-[4,5-b]pyridin-3-yl)-1-piperidinyl]carbonyl]-D-tyrosyl]-4-(4-pyridinyl)-piperidine
(146) 1-[N-[[4-(1,3-Dihydro-2(2H)-oxobenzimidazol-1-yl)-1-piperidinyl]carbonyl]-D,L-3-(4-pyridinyl)alanyl]-4-(4-pyridinyl)-piperazine
(147) 1-[4-Amino-3,5-dibromo-N-[[4-(1,3-dihydro-2(2H)-oxoimidazo[4,5-b]pyridin-3-yl)-1-piperidinyl]carbonyl]-D-phenyl-alanyl]-4-(1-methyl-4-piperidinyl)-piperazine
(148) 1-[3,5-Dibromo-N-[[4-(3,4-dihydro-2(1H)-oxo-quinazolin-3-yl)-1-piperidinyl]carbonyl]-D-tyrosyl]-4-(1-piperidinyl)-piperidine
(149) 1-[3,5-Dibromo-N-[[4-(3,4-dihydro-2(1H)-oxo-quinazolin-1-yl)-1-piperidinyl]carbonyl]-D-tyrosyl]-4-(4-pyridinyl)-piperidine
(150) 1-[3,5-Dibromo-N-[[4-(1,3-dihydro-5-(methoxycarbonyl)-2(2H)-oxobenzimidazol-1-yl)-1-piperidinyl]carbonyl]-D-tyrosyl]-4-(4-pyridinyl)-piperidine
(151) 1-[3,5-Dibromo-N-[[4-(1,3-dihydro-5-(hydroxycarbonyl)-2(2H)-oxobenzimidazol-1-yl)-1-piperidinyl]carbonyl]-D-tyrosyl]-4-(4-pyridinyl)-piperidine
(152) 1-[3,5-Dibromo-N-[[4-(1,3-dihydro-4-phenyl-2(2H)-oxoimidazol-1-yl)-1-piperidinyl]carbonyl]-D-tyrosyl]-4-(4-pyridinyl)-piperidine
(153) 1-[3,5-Dibromo-N-[[4-(1,3-dihydro-5-phenyl-2(2H)-oxoimidazol-1-yl)-1-piperidinyl]carbonyl]-D-tyrosyl]-4-(4-pyridinyl)-piperidine
(154) 1-[$N^2$-[3,5-Dibromo-N-[[4-(3,4-dihydro-2(1H)-oxo-quinazolin-3-yl)-1-piperidinyl]carbonyl]-D-tyrosyl]-L-lysyl]-4-(4-pyridinyl)-piperazine
(155) 1-[3,5-Dibromo-N-[[4-(1,3-dihydro-2(2H)-oxobenzimidazol-1-yl)-1-piperidinyl]carbonyl]-D-tyrosyl]-4-(4-fluorophenyl)-piperazine
(156) 1-[3,5-Dibromo-N-[[4-(1,3-dihydro-2(2H)-oxobenzimidazol-1-yl)-1-piperidinyl]carbonyl]-D-tyrosyl]-4-(2-fluorophenyl)-piperazine
(157) 1-[4-Amino-3,5-dibromo-N-[[4-(1,3-dihydro-2(2H)-oxobenzimidazol-1-yl)-1-piperidinyl]carbonyl]-D-phenylalanyl]-4-(2-fluorophenyl)-piperazine
(158) 1-[4-Amino-3,5-dibromo-N-[[4-(phenylaminocarbonylamino)-1-piperidinyl]carbonyl]-D-phenylalanyl]-4-(4-pyridinyl)-piperazine
(159) 1-[4-Amino-3,5-dibromo-N-[[4-[N-(aminocarbonyl)-N-phenylamino]-1-piperidinyl]carbonyl]-D-phenylalanyl]-4-(1-piperidinyl)-piperidine
(160) 1-[3,5-Dibromo-N-[[4-(aminocarbonylamino)-1-piperidinyl]carbonyl]-D-tyrosyl]-4-(4-pyridinyl)-piperidine
(161) 1-[4-Amino-3,5-dibromo-N-[[4-(1,3-dihydro-2(2H)-oxobenzimidazol-1-yl)-1-piperidinyl]carbonyl]-D-phenylalanyl]-4-(4-pyrimidinyl)-piperazine
(162) 1-[3,5-Dibromo-N-[[4-[2(3H)-oxobenzoxazol-3-yl]-1-piperidinyl]carbonyl]-D-tyrosyl]-4-(4-pyridinyl)-piperidine
(163) 1-[N-[[4-(Aminocarbonylamino)-1-piperidinyl]carbonyl]-3,5-dibromo-D-tyrosyl]-4-(4-pyridinyl)-piperazine
(164) 1-[4-Amino-3,5-dibromo-N-[[4-(phenylaminocarbonylamino)-1-piperidinyl]carbonyl]-D-phenylalanyl]-4-(1-piperidinyl)-piperidine
(165) 1-[3,5-Dibromo-N-[[4-(1,3-dihydro-2(2H)-oxobenzimidazol-1-yl)-1-piperidinyl]carbonyl]-D-tyrosyl]-4-(4-pyrimidinyl)-piperazine
(166) 1-[3,5-Dibromo-N-[[4-(methylaminocarbonylamino)-1-piperidinyl]carbonyl]-D-tyrosyl]-4-(4-pyridinyl)-piperidine
(167) 1-[3,5-Dibromo-N-[[4-[N-(aminocarbonyl)-methylamino]-1-piperidinyl]carbonyl]-D-tyrosyl]-4-(4-pyridinyl)-piperidine
(168) 1-[$N^2$—N-[[4-(Aminocarbonylamino)-1-piperidinyl]carbonyl]-3,5-dibromo-D-tyrosyl]-$N^6$-(1,1-dimethyl-ethoxycarbonyl)-L-lysyl]-4-(4-pyridinyl)-piperidine
(169) 1-[3,5-Dibromo-N-[[4-(1,3-dihydro-2(2H)-oxobenzimidazol-1-yl)-1-piperidinyl]carbonyl]-D-tyrosyl]-4-(3-pyridinyl)-piperazine
(170) 1-[4-Amino-3,5-dibromo-N-[[4-(1,3-dihydro-2(2H)-oxobenzimidazol-1-yl)-1-piperidinyl]carbonyl]-D-phenylalanyl]-4-(3-pyridinyl)-piperazine
(171) 1-[3,5-Dibromo-N-[[4-(phenylaminocarbonylamino)-1-piperidinyl]carbonyl]-D-tyrosyl]-4-(4-pyridinyl)-piperazine
(172) 1-[3,5-Dibromo-N-[[4-(phenylaminocarbonylamino)-1-piperidinyl]carbonyl]-D-tyrosyl]-4-(1-piperidinyl)-piperidine
(173) 1-[2,5-dibromo-N-[[4-(1,3-dihydro-2(2H)-oxobenzimidazol-1-yl)-1-piperidinyl]carbonyl]-D,L-phenylalanyl]-4-(4-pyridinyl)-piperidine
(174) 1-[2,5-dibromo-N-[[4-(1,3-dihydro-2(2H)-oxobenzimidazol-1-yl)-1-piperidinyl]carbonyl]-D,L-phenylalanyl]-4-(4-pyridinyl)-piperazine (175) 1-[3,5-Dibromo-N-[[4-[N-(aminocarbonyl)-N-phenylamino]-1-piperidinyl]carbonyl]-D-tyrosyl]-4-(4-pyridinyl)-piperazine
(176) 1-[N$^2$-[3,5-Dibromo-N-[[4-(methylaminocarbonylamino)-1-piperidinyl]carbonyl]-D-tyrosyl]-N$^6$-(1,1-dimethylethoxycarbonyl)-L-lysyl]-4-(4-pyridinyl)-piperidine
(177) 1-[N$^2$-[3,5-Dibromo-N-[[4-[N-(aminocarbonyl)methylamino]-1-piperidinyl]carbonyl]-D-tyrosyl]-N$^6$-(1,1-dimethylethoxycarbonyl)-L-lysyl]-4-(4-pyridinyl)-piperidine
(178) 1-[3,5-Dibromo-N-[[4-[N-(methylaminocarbonyl)-methyl-amino]-1-piperidinyl]carbonyl]-D-tyrosyl]-4-(4-pyridinyl)-piperidine
(179) 1-[N$^2$—[N-[[4-(Aminocarbonylamino)-1-piperidinyl]carbonyl]-3,5-dibromo-D-tyrosyl]-L-lysyl]-4-(4-pyridinyl)-piperidine
(180) 1-[N$^2$-[3,5-Dibromo-N-[[4-[N-(methylaminocarbonyl)methylamino]-1-piperidinyl]carbonyl]-D-tyrosyl]-N$^6$-(1,1-dimethylethoxycarbonyl)-L-lysyl]-4-(4-pyridinyl)-piperidine
181) 1-[N$^2$-[3,5-Dibromo-N-[[4-[N-(aminocarbonyl)methylamino]-1-piperidinyl]carbonyl]-D-tyrosyl]-L-lysyl]-4-(4-pyridinyl)-piperidine
(182) 1-[N$^2$-[3,5-Dibromo-N-[[4-[N-(methylaminocarbonyl)amino]-1-piperidinyl]carbonyl]-D-tyrosyl]-L-lysyl]-4-(4-pyridinyl)-piperidine
(183) 1-[N$^2$-[3,5-Dibromo-N-[[4-[N-(methylaminocarbonyl)methylamino]-1-piperidinyl]carbonyl]-D-tyrosyl]-L-lysyl]-4-(4-pyridinyl)-piperidine
(184) 1-[N$^2$—[N-[[4-[N-(Aminocarbonyl)phenylamino]-1-piperidinyl]carbonyl]-3,5-dibromo-D-tyrosyl]-L-lysyl]-4-(4-pyridinyl)-piperidine
(185) 1-[N-[[4-[N-(Aminocarbonyl)phenylamino]-1-piperidinyl]carbonyl]-4-amino-3,5-dibromo-D-phenylalanyl]-4-(4-pyridinyl)-piperidine
(186) 1-[N-[[4-[N-(Aminocarbonyl)phenylamino]-1-piperidinyl-carbonyl]-4-amino-3,5-dibromo-D-phenylalanyl]-4-(4-pyridinyl)-piperazine
(187) 1-[N-[[4-[N-(Aminocarbonyl)phenylamino]-1-piperidinyl-carbonyl]-3,5-dibromo-D-tyrosyl]-4-(4-pyridinyl)-piperidine
(188) 1-[N$^2$—[N-[[4-[2(3H)-Oxobenzoxazol-3-yl]-1-piperidinyl]-carbonyl]-3,5-dibromo-D-tyrosyl]-N$^6$-(1,1-dimethylethoxycarbonyl)-L-lysyl]-4-(4-pyridinyl)-piperazine
(189) 1-[4-Amino-3,5-dibromo-N-[[4-(1H-indol-3-yl)-1-piperidinyl]carbonyl]-D-phenylalanyl]-4-(1-piperidinyl)-piperidine
(190) 1-[N$^2$-[3,5-Dibromo-N-[[4-(1,3-dihydro-2(2H)-oxobenzimidazol-1-yl)-1-piperidinyl]carbonyl]-D-tyrosyl]-N$^6$-(1,1-di-methylethoxycarbonyl)-L-lysyl]-4-(5-methoxy-4-pyrimidinyl)-piperazine
(191) 1-[N$^2$-[2,5-Dibromo-N-[[4-(1,3-dihydro-2(2H)-oxobenzimidazol-1-yl)-1-piperidinyl]carbonyl]-D-phenylalanyl]-N$^6$-(1,1-dimethylethoxycarbonyl)-L-lysyl]-4-(4-pyridinyl)-piperazine
(192) 1-[N-[[4-[N-(Aminocarbonyl)phenylamino]-1-piperidinyl-carbonyl]-3,5-dibromo-D-tyrosyl]-4-(4-pyridinyl)-piperazine
(193) 1-[3-Bromo-N-[[4-(1,3-dihydro-2(2H)-oxobenzimidazol-1-yl)-1-piperidinyl]carbonyl]-D-tyrosyl]-4-phenylpiperazine
(194) 1-[3,5-Dibromo-N-[[4-(3,4-dihydro-2(1H)-oxoquinazolin-3-yl)-1-piperidinyl]carbonyl]-D-tyrosyl]-4-(1-cyclohexyl-4-piperidinyl)-piperazine
(195) 1-[N$^2$-[3,5-Dibromo-N-[[4-(1,3-dihydro-2(2H)-oxobenzimidazol-1-yl)-1-piperidinyl]carbonyl]-D-tyrosyl]-N$^6$-(1,1-dimethylethoxycarbonyl)-L-lysyl]-4-(1-piperidinyl)-piperidine
(196) 1-[N$^2$—[N-[[4-(2-Cyanophenyl)-1-piperazinyl]carbonyl]-3,5-dibromo-D-tyrosyl]-N$^6$-(1,1-dimethylethoxycarbonyl)-L-lysyl]-4-(1-piperidinyl)-piperidine
(197) 1-[N$^2$-[3,5-Dibromo-N-[[4-(1,3-dihydro-2(2H)-oxobenzimidazol-1-yl)-1-piperidinyl]carbonyl]-D-tyrosyl]-L-lysyl]-4-(1-piperidinyl)-piperidine
(198) 1-[N$^2$—[N-[[4-(2-Cyanophenyl)-1-piperazinyl]carbonyl]-3,5-dibromo-D-tyrosyl]-L-lysyl]-4-(1-piperidinyl)-piperidine
(199) 1-[3,5-Dichloro-N-[[4-(1,3-dihydro-2(2H)-oxobenzimidazol-1-yl)-1-piperidinyl]carbonyl]-D-tyrosyl]-4-(1-piperidinyl)-piperidine
(200) 1-[3,5-Dichloro-N-[[4-(1,3-dihydro-2(2H)-oxobenzimidazol-1-yl)-1-piperidinyl]carbonyl]-D-tyrosyl]-4-(4-pyridinyl)-piperazine
(201) 1-[4-Amino-3,5-dibromo-N-[[4-(1,3-dihydro-6-hydroxy-2(2H)-oxobenzimidazol-1-yl)-1-piperidinyl]carbonyl]-D-phenyl-alanyl]-4-(1-piperidinyl)-piperidine
(202) 1-[3,5-Dibromo-N-[[4-(1,3-dihydro-2(2H)-oxobenzimidazol-1-yl)-1-piperidinyl]carbonyl]-D-tyrosyl]-4-(4-morpholinyl)-piperidine
(203) 1-[3,5-Dibromo-N-[[4-(1,3-dihydro-2(2H)-oxobenzimidazol-1-yl)-1-piperidinyl]carbonyl]-D-tyrosyl]-4-(ethoxycarbonyl)-piperidine
(204) 1-[3,5-Dibromo-N-[[4-(1,3-dihydro-2(2H)-oxobenzimidazol-1-yl)-1-piperidinyl]carbonyl]-D-tyrosyl]-4-(dimethylamino)-piperidine
(205) 1-[3-Bromo-N-[[4-(1,3-dihydro-2(2H)-oxobenzimidazol-1-yl)-1-piperidinyl]carbonyl]-D-tyrosyl]-4-(1-piperidinyl)-piperidine
(206) 1-[3,5-Dibromo-N-[[4-(1,3-dihydro-2(2H)-oxobenzimidazol-1-yl)-1-piperidinyl]carbonyl]-D-tyrosyl]-4-(1-pyrrolidinyl)-piperidine
(207) 1-[3,5-Dibromo-N-[[4-(1,3-dihydro-2(2H)-oxobenzimidazol-1-yl)-1-piperidinyl]carbonyl]-D-tyrosyl]-4-(methoxycarbonyl)-4-phenylpiperidine
(208) 1-[N$^2$-[3,5-Dibromo-N-[[4-(1,3-dihydro-2(2H)-oxobenzimidazol-1-yl)-1-piperidinyl]carbonyl]-L-tyrosyl]-L-lysyl]-4-(4-pyridinyl)-piperazine
(209) 1-[N$^2$-[3,5-Dibromo-N-[[4-(1,3-dihydro-2(2H)-oxobenzimidazol-1-yl)-1-piperidinyl]carbonyl]-L-tyrosyl]-D-lysyl]-4-(4-pyridinyl)-piperazine
(210) 1-[N$^2$-[3,5-Dibromo-N-[[4-(1,3-dihydro-2(2H)-oxobenzimidazol-1-yl)-1-piperidinyl]carbonyl]-D-tyrosyl]-D-lysyl]-4-(4-pyridinyl)-piperazine
(211) 1-[3,5-Dibromo-N-[[4-(1,3-dihydro-2(2H)-oxobenzimidazol-1-yl)-1-piperidinyl]carbonyl]-D-tyrosyl]-4-(hydroxycarbonyl)-piperidine
(212) 1-[N$^2$-[3,5-Dibromo-N-[[4-(1,3-dihydro-2(2H)-oxobenzimidazol-1-yl)-1-piperidinyl]carbonyl]-D-tyrosyl]-N$^6$,N$^6$-dimethyl-L-lysyl]-4-(4-pyridinyl)-piperazine
(213) 1-[N$^2$-[3-Bromo-N-[[4-(1,3-dihydro-2(2H)-oxobenzimidazol-1-yl)-1-piperidinyl]carbonyl]-D-tyrosyl]-L-lysyl]-4-(1-piperidinyl)-piperidine
(214) 1-[3,5-Dibromo-N-[[4-(1,3-dihydro-2(2H)-oxobenzimidazol-1-yl)-1-piperidinyl]carbonyl]-D-tyrosyl]-4-(4-piperidinyl)-piperazine
(215) 1-[3,5-Dibromo-N-[[4-(1,3-dihydro-2(2H)-oxobenzimidazol-1-yl)-1-piperidinyl]carbonyl]-D-tyrosyl]-4-(1,3-dihydro-2(2H)-oxobenzimidazol-1-yl)-piperidine (216) 1-[3,5-Dibromo-N-[[4-(1,3-dihydro-2(2H)-oxobenzimidazol-1-yl)-1-piperidinyl]carbonyl]-D-tyrosyl]-4-(1,3-dihydro-2(2H)-oxoimidazo[4,5-b]pyridin-3-yl)-piperidine (217) 1-[$N^2$-[3-Bromo-N-[[4-(1,3-dihydro-2(2H)-oxobenzimidazol-1-yl)-1-piperidinyl]carbonyl]-D-tyrosyl]-$N^6$-(1,1-dimethylethoxycarbonyl)-L-lysyl]-4-(4-pyridinyl)-piperazine (218) 1-[$N^2$-[3-Bromo-N-[[4-(1,3-dihydro-2(2H)-oxobenzimidazol-1-yl)-1-piperidinyl]carbonyl]-D-tyrosyl]-L-lysyl]-4-(4-pyridinyl)-piperazine (219) (R)-1-[2-[N-[[4-(1,3-Dihydro-2(2H)-oxobenzimidazol-1-yl)-1-piperidinyl]carbonyl]-N-methylamino]-3-(3,5-dibromo-4-hydroxyphenyl)-propyl]-4-(1-piperidinyl)-piperidine (220) (R)-1-[2-[N-[[4-(1,3-Dihydro-2(2H)-oxobenzimidazol-1-yl)-1-piperidinyl]carbonyl]amino]-3-(3,5-dibromo-4-hydroxyphenyl)-propyl]-4-(1-piperidinyl)-piperidine (221) 1-[$N^2$-[4-Amino-3,5-dibromo-N-[[4-(1,3-dihydro-2(2H)-oxobenzimidazol-1-yl)-1-piperidinyl]carbonyl]-D-phenylalanyl]-$N^6$,$N^6$-dimethyl-L-lysyl]-4-(4-pyridinyl)-piperazine (222) 3,5-Dibromo-$N^2$-[[4-(1,3-dihydro-2(2H)-oxobenzimidazol-1-yl)-1-piperidinyl]carbonyl]-N-[(2-(4-(1-piperidinyl)-1-piperidinyl]ethyl]-D-tyrosinamide (223) 1-[3,5-Dibromo-N-[[4-[5-[(4-morpholinyl)carbonyl]-1,3-dihydro-2(2H)-oxobenzimidazol-1-yl]-1-piperidinyl]carbonyl]-D-tyrosyl]-4-(4-pyridinyl)-piperidine (224) 1-[3,5-Dibromo-N-[[4-[5-[(4-methyl-1-piperazinyl)carbonyl]-1,3-dihydro-2(2H)-oxobenzimidazol-1-yl]-1-piperidinyl]-carbonyl]-D-tyrosyl]-4-(4-pyridinyl)-piperidine (225) 1-[3,5-Dibromo-N-[[4-(3,4-dihydro-2(1H)-oxoquinazolin-3-yl)-1-piperidinyl]carbonyl]-D-tyrosyl]-4-(4-pyridinyl)-piperazine (226) 1-[4-Amino-3,5-dibromo-N-[[4-(3,4-dihydro-2(1H)-oxoquinazolin-3-yl)-1-piperidinyl]carbonyl]-D-phenylalanyl]-4-(1-piperidinyl)-piperidine (227) 1-[4-Amino-3,5-dibromo-N-[[4-(3,4-dihydro-2(1H)-oxoquinazolin-1-yl)-1-piperidinyl]carbonyl]-D-phenylalanyl]-4-(1-piperidinyl)-piperidine (228) 1-[3,5-Dibromo-N-[[4-(3,4-dihydro-2(1H)-oxoquinazolin-1-yl)-1-piperidinyl]carbonyl]-D-tyrosyl]-4-(1-piperidinyl)-piperidine (229) 1-[3,5-Dibromo-N-[[4-(1,3-dihydro-2(2H)-oxoimidazo-[4,5-d]pyrimidin-3-yl)-1-piperidinyl]carbonyl]-D-tyrosyl]-4-(4-pyridinyl)-piperazine (230) 1-[4-Amino-3,5-dibromo-N-[[4-(3,4-dihydro-2(1H)-oxoquinazolin-3-yl)-1-piperidinyl]carbonyl]-D-phenylalanyl]-4-(1-methyl-4-piperidinyl)-piperidine (231) 1-[4-Amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine (232) 1-[$N^2$-[4-Amino-3,5-dibromo-N-[[4-(3,4-dihydro-2(1H)-oxoquinazolin-3-yl)-1-piperidinyl]carbonyl]-D-phenylalanyl]-L-lysyl]-4-(1-piperidinyl)-piperidine (233) 1-[$N^2$-[4-Amino-3,5-dibromo-N-[[4-(3,4-dihydro-2(1H)-oxoquinazolin-3-yl)-1-piperidinyl]carbonyl]-D-phenylalanyl]-L-lysyl]-4-(4-pyridinyl)-piperazine (234) 1-[$N^2$-[4-Amino-3,5-dibromo-N-[[4-(3,4-dihydro-2(1H)-oxoquinazolin-3-yl)-1-piperidinyl]carbonyl]-D-phenylalanyl]-L-lysyl]-4-(4-pyridinyl)-piperazine (235) 1-[$N^2$-[3,5-Dibromo-N-[[4-(3,4-dihydro-2(1H)-oxoquinazolin-3-yl)-1-piperidinyl]carbonyl]-D-tyrosyl]-L-lysyl]-4-(1-piperidinyl)-piperidine (236) 1-[$N^2$-[3,5-Dibromo-N-[[4-(1,3-dihydro-4-phenyl-2(2H)-oxoimidazol-1-yl)-1-piperidinyl]carbonyl]-D-tyrosyl]-L-lysyl]-4-(4-pyridinyl)-piperazine (237) 1-[$N^2$-[4-Amino-3,5-dibromo-N-[[4-(1,3-dihydro-4-phenyl-2(2H)-oxoimidazol-1-yl)-1-piperidinyl]carbonyl]-D-phenylalanyl]-L-lysyl]-4-(1-piperidinyl)-piperidine (238) 1-[$N^2$-[4-Amino-3,5-dibromo-N-[[4-(1,3-dihydro-4-phenyl-2(2H)-oxoimidazol-1-yl)-1-piperidinyl]carbonyl]-D-phenylalanyl]-L-lysyl]-4-(4-pyridinyl)-piperazine (239) 1-[3,5-Dibromo-N-[[4-(1,3-dihydro-4-phenyl-2(2H)-oxoimidazol-1-yl)-1-piperidinyl]carbonyl]-D-tyrosyl]-4-(1-piperidinyl)-piperidine (240) 1-[4-Amino-3,5-dibromo-N-[[4-(1,3-dihydro-4-phenyl-2(2H)-oxoimidazol-1-yl)-1-piperidinyl]carbonyl]-D-phenylalanyl]-4-(1-methyl-4-piperidinyl)-piperazine (241) 1-[4-Amino-3,5-dibromo-N-[[4-(1,3-dihydro-4-phenyl-2(2H)-oxoimidazol-1-yl)-1-piperidinyl]carbonyl]-D-phenyl-alanyl]-4-(1-piperidinyl)-piperidine (242) 1-[4-Amino-3,5-dibromo-N-[[4-(1,3-dihydro-4-phenyl-2(2H)-oxoimidazol-1-yl)-1-piperidinyl]carbonyl]-D-phenylalanyl]-4-(4-pyridinyl)-piperazine (243) 1-[4-Amino-3,5-dibromo-N-[[4-(1,3-dihydro-4-phenyl-2(2H)-oxoimidazol-1-yl)-1-piperidinyl]carbonyl]-D-phenylalanyl]-4-(1-methyl-4-piperidinyl)-piperidine (244) 1-[3,5-Dibromo-N-[[4-(1,3-dihydro-4-phenyl-2(2H)-oxoimidazol-1-yl)-1-piperidinyl]carbonyl]-D-tyrosyl]-4-(1-methyl-4-piperidinyl)-piperazine (245) (R)-1-[2-[N-[[4-(3,4-dihydro-2(1H)-oxopyrido[2,3-d]pyrimidin-3-yl)-1-piperidinyl]carbonyl]amino]-3-(4-amino-3,5-dibromophenyl)-propyl]-4-(1-piperidinyl)-piperidine (246) (R,S)-1-[2-[(3,5-Dibromo-4-hydroxyphenyl)methyl]-4-[4-(1,3-dihydro-2(2H)oxobenzimidazol-1-yl)-1-piperidinyl]-1,4-dioxobutyl]-4-(1-piperidinyl)-piperidine (247) 1-[$N^2$-[2,5-Dibromo-N-[[4-(1,3-dihydro-2(2H)oxobenzimidazol-1-yl)-1-piperidinyl]carbonyl]-D-phenylalanyl]-$N^6$-(1,1-di-methylethoxycarbonyl)-L-lysyl]-4-(4-pyridinyl)-piperidine (248) 1-[$N^2$-[3,5-Dibromo-N-[[4-[2(3H)-oxobenzoxazol-3-yl]-1-piperidinyl]carbonyl]-D-tyrosyl]-L-lysyl]-4-(4-pyridinyl)-piperazine (249) 1-[N-[[4-[N-(Aminocarbonyl)phenylamino]-1-piperidinyl]-carbonyl]-4-amino-3,5-dibromo-D-phenylalanyl]-4-[(1-piperidinyl)methyl]-piperidine (250) 1-[$N^2$-[3,5-Dibromo-N-[[4-(1,3-dihydro-2(2H)-oxobenzimidazol-1-yl)-1-piperidinyl]carbonyl]-D-tyrosyl]-L-lysyl]-4-(5-methoxy-4-pyrimidinyl)-piperazine (251) 1-[$N^2$-[2,5-Dibromo-N-[[4-(1,3-dihydro-2(2H)-oxobenzimidazol-1-yl)-1-piperidinyl]carbonyl]-D-phenylalanyl]-L-lysyl]-4-(4-pyridinyl)-piperidine (252) 1-[$N^2$-[2,5-Dibromo-N-[[4-(1,3-dihydro-2(2H)-oxobenzimidazol-1-yl)-1-piperidinyl]carbonyl]-L-phenylalanyl]-L-lysyl]-4-(4-pyridinyl)-piperidine (253) 1-[$N^2$-[2,5-Dibromo-N-[[4-(1,3-dihydro-2(2H)-oxobenzimidazol-1-yl)-1-piperidinyl]carbonyl]-D-phenylalanyl]-L-lysyl]-4-(4-pyridinyl)-piperazine (254) 1-[$N^2$-[3,5-Dibromo-N-[[4-[N-(Aminocarbonyl)phenylamino]-1-piperidinyl]carbonyl]-D-tyrosyl]-$N^6$-(1,1-dimethylethoxycarbonyl)-L-lysyl]-4-(4-pyridinyl)-piperazine (255) 1-[$N^2$-[3,5-Dibromo-N-[[4-[N-(Aminocarbonyl)phenylamino]-1-piperidinyl]carbonyl]-D-tyrosyl]-L-lysyl]-4-(4-pyridinyl)-piperazine (256) 1-[N²-[4-Amino-3,5-dibromo-N-[[4-(1,3-dihydro-2 (2H)-oxobenzimidazol-1-yl)-1-piperidinyl]carbonyl]-D-phenylalanyl]-L-lysyl]-4-(5-methoxy-4-pyrimidinyl)-piperazine
(257) 1-[N-[4-Amino-3,5-dibromo-N-[[4-(1,3-dihydro-2 (2H)-oxobenzimidazol-1-yl)-1-piperidinyl]carbonyl]-D-phenylalanyl]-glycyl]-4-(4-pyridinyl)-piperazine
(258) 1-[4-Amino-3,5-dibromo-N-[[4-(benzoylaminocarbonylamino)-1-piperidinyl]carbonyl]-D-phenylalanyl]-4-(4-pyridinyl)-piperazine
(259) 1-[4-Amino-3,5-dibromo-N-[[4-(benzoylaminocarbonylamino)-1-piperidinyl]carbonyl]-D-phenylalanyl]-4-(1-piperidinyl)-piperidine
(260) 1-[N-[4-Amino-3,5-dibromo-N-[[4-(1,3-dihydro-2 (2H)-oxobenzimidazol-1-yl)-1-piperidinyl]carbonyl]-D-phenylalanyl]-β-alanyl]-4-(4-pyridinyl)-piperazine
(261) 1-[N-[4-Amino-3,5-dibromo-N-[[4-(1,3-dihydro-2 (2H)-oxobenzimidazol-1-yl)-1-piperidinyl]carbonyl]-D-phenylalanyl]-N-methylglycyl]-4-(4-pyridinyl)-piperazine
(262) 1-[4-Amino-3,5-dibromo-N-[[4-[N-(phenylaminocarbonyl)-phenylamino)-1-piperidinyl]carbonyl]-D-phenylalanyl]-4-(4-pyridinyl)-piperazine
(263) 1-(N-[[4-(1,3-Dihydro-2(2H)-oxobenzimidazol-1-yl)-1-piperidinyl]carbonyl]-[3-(2-thienyl)-D-alanyl]-4-(1-piperidinyl)-piperidine
(264) 4-Amino-3,5-dibromo-N²-[[4-(1,3-dihydro-2(2H)-oxobenzimidazol-1-yl)-1-piperidinyl]carbonyl]-N-methyl-N-[3-(4-methyl-1-piperazinyl)propyl]-D-phenylalaninamide
(265) 1-[N-[4-Amino-3,5-dibromo-N-[[4-(1,3-dihydro-2 (2H)-oxobenzimidazol-1-yl)-1-piperidinyl]carbonyl]-D-phenylalanyl]-glycyl]-4-(1-piperidinyl)-piperidine
(266) 1-[N-[4-Amino-3,5-dibromo-N-[[4-(1,3-dihydro-2 (2H)-oxobenzimidazol-1-yl)-1-piperidinyl]carbonyl]-D-phenylalanyl]-L-alanyl]-4-(4-pyridinyl)-piperazine
(267) 1-[N²-[4-Amino-3,5-dibromo-N-((4-[N-(methylaminocarbonyl)phenylamino]-1-piperidinyl]carbonyl]-D-phenylalanyl]-N⁶-(1,1-dimethylethoxycarbonyl)-L-lysyl]-4-(1-piperidinyl)-piperidine
(268) 1-[N-[4-Amino-3,5-dibromo-N-[[4-(1,3-dihydro-2 (2H)-oxobenzimidazol-1-yl)-1-piperidinyl]carbonyl]-D-phenylalanyl]-L-alanyl]-4-(1-piperidinyl)-piperidine
(269) 1-[4-Amino-3,5-dibromo-N-[[4-[2(1H)-oxoquinolin-3-yl]-1-piperazinyl]carbonyl]-D-phenylalanyl]-4-(1-piperidinyl)-piperidine
(270) 1-[4-Amino-3,5-dibromo-N-[[4-[2(1H)-oxoquinolin-3-yl]-1-piperazinyl]carbonyl]-D-phenylalanyl]-4-(4-pyridinyl)-piperazine
(271) 1-[N²-[4-Amino-3,5-dibromo-N-[[4-[N-(methylaminocarbonyl)phenylamino]-1-piperidinyl]carbonyl]-D-phenylalanyl]-L-lysyl]-4-(1-piperidinyl)-piperidine
(272) 1-[N²-[[4-(1,3-Dihydro-2(2H)oxobenzimidazol-1-yl)-1-piperidinyl]carbonyl]-1-(1,1-dimethylethoxycarbonyl)-D-tryptyl]-4-(1-piperidinyl)-piperidine
(273) 1-[N-[4-Amino-3,5-dibromo-N-[[4-(1,3-dihydro-2 (2H)-oxobenzimidazol-1-yl)-1-piperidinyl]carbonyl]-D-phenylalanyl]-N-methylglycyl]-4-(1-piperidinyl)-piperidine
(274) 1-[4-Amino-3,5-dibromo-N-[[4-[2(1H)-oxoquinoxalin-3-yl]-1-piperazinyl]carbonyl]-D-phenylalanyl]-4-(4-pyridinyl)-piperazine
(275) 1-[4-Amino-3,5-dibromo-N-[[4-[2(1H)-oxoquinoxalin-3-yl]-1-piperazinyl]carbonyl]-D-phenylalanyl]-4-(1-piperidinyl)-piperidine (276) 1-[4-Amino-3,5-dibromo-N-[[4-[N-(aminocarbonyl)-N-(4-fluorophenyl)amino]-1-piperidinyl]carbonyl]-D-phenylalanyl]-4-(4-pyridinyl)-piperazine
(277) 1-[4-Amino-3,5-dibromo-N-[[4-(1,3-dihydro-2(2H)-oxobenzimidazol-1-yl)-4-methyl-1-piperidinyl]carbonyl]-D-phenylalanyl]-4-(1-piperidinyl)-piperidine
(278) 1-[N²-[4-Amino-3,5-dibromo-N-[[4-(1,3-dihydro-2 (2H)-oxobenzimidazol-1-yl)-4-methyl-1-piperidinyl]carbonyl]-D-phenylalanyl]-N⁶-(1,1-dimethylethoxycarbonyl)-L-lysyl]-4-(4-pyridinyl)-piperidine
(279) 1-[4-Amino-3,5-dibromo-N-[[4-(1,3-dihydro-2(2H)-oxobenzimidazol-1-yl)-1-piperidinyl]carbonyl]-D-phenylalanyl]-4-[3-dimethylamino)propyl]-piperidine
(280) 1-[N²-[4-Amino-3,5-dibromo-N-[[4-(1,3-dihydro-2 (2H)-oxobenzimidazol-1-yl)-4-methyl-1-piperidinyl]carbonyl]-D-phenylalanyl]-L-lysyl]-4-(4-pyridinyl)-piperidine
(281) 1-[N-[[4-(1,3-Dihydro-2(2H)-oxobenzimidazol-1-yl)-1-piperidinyl]carbonyl]-D-tryptyl]-4-(1-piperidinyl)-piperidine
(282) 1-[4-Amino-3,5-dibromo-N-[[4-(3,4-dihydro-2(1H)-oxoquinazolin-3-yl)-1-piperidinyl]carbonyl]-D-phenylalanyl]-4-(5-methoxy-4-pyrimidinyl)-piperazine
(283) 1-[N²-[4-Amino-3,5-dibromo-N-[[4-[2(1H)-oxoquinolin-3-yl]-1-piperazinyl]carbonyl]-D-phenylalanyl]-L-lysyl]-4-(4-pyridinyl)-piperidine
(284) 1-[3,5-Dibromo-N-[[4-(3,4-dihydro-2(1H)-oxoquinazolin-3-yl)-1-piperidinyl]carbonyl]-D-tyrosyl]-4-(5-methoxy-4-pyrimidinyl)-piperazine
(285) (R,S)-1-[2-[(3,5-Dibromo-4-hydroxyphenyl)methyl]-4-[4-(1,3-dihydro-2(2H)-oxobenzimidazol-1-yl)-1-piperidinyl]-1,4-dioxobutyl]-4-(4-pyridinyl)-piperidine
(286) 3,5-Dibromo-N²-[[4-(1,3-dihydro-2(2H)-oxobenzimidazol-1-yl)-1-piperidinyl]carbonyl]-N-[2-(4-methyl-1-piperazinyl)ethyl]-D-tyrosinamide
(287) 1-[N²-[3,5-Dibromo-N-[[4-(1,3-dihydro-2(2H)-oxobenzimidazol-1-yl)-1-piperidinyl]carbonyl]-D-tyrosyl]-L-lysyl]-4-(4-pyridinyl)-piperazine
(288) 1-[3,5-Dibromo-N-[[4-(7,9-dihydro-6,8-dioxo-1H-purin-9-yl)-1-piperidinyl]carbonyl]-D-tyrosyl]-4-(1-piperidinyl)-piperidine
(289) (R,S)-1-[2-[(3,5-Dibromo-4-hydroxyphenyl)methyl]-4-[4-(3,4-dihydro-2(1H)-oxoquinazolin-3-yl)-1-piperidinyl]-1,4-dioxobutyl]-4-(1-piperidinyl)-piperidine
(290) (R,S)-1-[2-[(3,5-Dibromo-4-hydroxyphenyl)methyl]-4-[4-(3,4-dihydro-2(1H)-oxoquinazolin-3-yl)-1-piperidinyl]-1,4-dioxobutyl]-4-(4-pyridinyl)-piperidine
(291) (R,S)-1-[2-(4-Amino-3,5-dibromobenzoyl)-4-[4-(3,4-dihydro-2(1H)-oxoquinazolin-3-yl)-1-piperidinyl]-4-oxobutyl]-4-(4-pyridinyl)-piperidine
(292) (R)-1-[3-(3,5-Dibromo-4-hydroxyphenyl)-2-[N-[[4-(3,4-dihydro-2(1H)-oxoquinazolin-3-yl)-1-piperidinyl]carbonyl]amino]propyl]-4-(1-piperidinyl)-piperidine
(293) 1-[N⁶-Acetyl-N²-[3,5-dibromo-N-[[4-(3,4-dihydro-2 (1H)-oxoquinazolin-3-yl)-1-piperidinyl]carbonyl]-D-tyrosyl]-L-lysyl]-4-(4-pyridinyl)-piperazine
(294) 1-[N²-[4-Amino-3,5-dibromo-N-[[4-(3,4-dihydro-2 (1H)-oxoquinazolin-3-yl)-1-piperidinyl]carbonyl]-D-phenylalanyl]-N⁶,N⁶-dimethyl-L-lysyl]-4-(4-pyridinyl)-piperazine
(295) 1-[N²-[3,5-Dibromo-N-[[4-(3,4-dihydro-2(1H)-oxoquinazolin-3-yl)-1-piperidinyl]carbonyl]-D-tyrosyl]-N⁶,N⁶-dimethyl-L-lysyl]-4-(4-pyridinyl)-piperazine
(296) (R,S)-1-[2-(4-Amino-3,5-dibromobenzoyl)-4-[4-(3,4-dihydro-2(1H)-oxoquinazolin-3-yl)-1-piperidinyl]-4-oxobutyl]-4-(1-piperidinyl)-piperidine (297) (R)-1-[3-(4-Amino-3,5-dibromophenyl)-2-[N-[[4-(1,3-dihydro-4-phenyl-2(2H)-oxoimidazol-1-yl)-1-piperidinyl]carbonyl]amino]propyl]-4-(1-piperidinyl)-piperidine (298) (R)-1-[3-(4-Amino-3-bromophenyl)-2-[N-[[4-(1,3-dihydro-4-phenyl-2(2H)-oxoimidazol-1-yl)-1-piperidinyl]carbonyl]amino]propyl]-4-(1-piperidinyl)-piperidine (299) (R)-1-[3-(4-Amino-3,5-dibromophenyl)-2-[N-[[4-(3,4-dihydro-2(1H)-oxoquinazolin-3-yl)-1-piperidinyl]carbonyl]amino]propyl]-4-(1-piperidinyl)-piperidine (300) (R)-1-[3-(4-Amino-3-bromophenyl)-2-[N-[[4-(3,4-dihydro-2(1H)-oxoquinazolin-3-yl)-1-piperidinyl]carbonyl]amino]propyl]-4-(1-piperidinyl)-piperidine (301) (R)-1-[3-(3,5-Dibromo-4-hydroxyphenyl)-2-[N-[[4-(1,3-dihydro-4-phenyl-2(2H)-oxoimidazol-1-yl)-1-piperidinyl]carbonyl]amino]propyl]-4-(1-piperidinyl)-piperidine (302) (R,S)-1-[2-(4-Amino-3,5-dibromobenzoyl)-4-[4-(1,3-dihydro-4-phenyl-2(2H)-oxoimidazol-1-yl)-1-piperidinyl]-4-oxobutyl]-4-(1-piperidinyl)-piperidine (303) 1-[4-Amino-N-[[4-[2-(aminocarbonylamino)phenylamino]-1-piperidinyl]carbonyl]-3,5-dibromo-D-phenylalanyl]-4-(1-piperidinyl)-piperidine (304) 1-[4-Amino-3,5-dibromo-N-[[4-[3,4-dihydro-7-(methoxycarbonyl)-2(1H)-oxoquinazolin-3-yl]-1-piperidinyl]carbonyl]-D-phenylalanyl]-4-(1-piperidinyl)-piperidine (305) 1-(4-Amino-N-[[4-[2-(methylsulphonylamino)phenylamino]-1-piperidinyl]carbonyl]-3,5-dibromo-D-phenylalanyl]-4-(1-piperidinyl)-piperidine (306) 1-[4-Amino-3,5-dibromo-N-[[4-[3,4-dihydro-7-(hydroxycarbonyl)-2(1H)-oxoquinazolin-3-yl]-1-piperidinyl]carbonyl]-D-phenylalanyl]-4-(1-piperidinyl)-piperidine (307) 1-[4-Amino-3,5-dibromo-N-[[4-[3,4-dihydro-7-(methoxy-carbonyl)-2(1H)-oxoquinazolin-3-yl]-1-piperidinyl]carbonyl]-D-phenylalanyl]-4-(4-pyridinyl)-piperidine (308) 1-[4-Amino-3,5-dibromo-N-[[4-[3,4,4a,5,6,7,8,8a-octahydro-2(1H)-oxoquinazolin-3-yl]-1-piperidinyl]carbonyl]-D-phenylalanyl]-4-(1-piperidinyl)-piperidine (309) 1-[4-Amino-3,5-dibromo-N-[[4-[3,4-dihydro-7-(hydroxycarbonyl)-2(1H)-oxoquinazolin-3-yl]-1-piperidinyl]carbonyl]-D-phenylalanyl]-4-(4-pyridinyl)-piperidine (310) 1-[4-Amino-N-[[4-[7-(aminocarbonyl)-3,4-dihydro-2(1H)-oxoquinazolin-3-yl]-1-piperidinylicarbonyl]-3,5-dibromo-D-phenylalanyl]-4-(1-piperidinyl)-piperidine (311) 1-[4-Amino-3,5-dibromo-N-[[4-[7-(2-hydroxyethylaminocarbonyl)-3,4-dihydro-2(1H)-oxoquinazolin-3-yl]-1-piperidinyl]-carbonyl]-D-phenylalanyl]-4-(1-piperidinyl)-piperidine (312) 1-[4-Amino-N-[[4-[7-(aminocarbonyl)-3,4-dihydro-2(1H)-oxoquinazolin-3-yl]-1-piperidinyl]carbonyl]-3,5-dibromo-D-phenylalanyl]-4-(4-pyridinyl)-piperidine (313) 1-[4-Amino-3,5-dibromo-N-[[4-[7-(2-hydroxyethylaminocarbonyl)-3,4-dihydro-2(1H)-oxoquinazolin-3-yl]-1-piperidinyl]carbonyl]-D-phenylalanyl]-4-(4-pyridinyl)-piperidine (314) 1-[4-Amino-3,5-dibromo-N-[[4-(1,1-dioxido-3(4H)-oxo-1,2,4-benzothiadiazin-2-yl)-1-piperidinyl]carbonyl]-D-phenylalanyl]-4-(1-piperidinyl)-piperidine (315) 1-[4-Amino-3,5-dibromo-N-[[4-(1,1-dioxido-3(4H)-oxo-1,2,4-benzothiadiazin-2-yl)-1-piperidinyl]carbonyl]-D-phenylalanyl]-4-(4-pyridinyl)-piperazine (316) 1-[3,5-Dibromo-N-[[4-(1,3-dihydro-4-phenyl-2(2H)-oxoimidazol-1-yl)-1-piperidinyl]carbonyl]-D-tyrosyl]-4-(5-methoxy-4-pyrimidinyl)-piperazine (317) 1-[4-Amino-3,5-dibromo-N-[[4-(3,4-dihydro-2(1H)-oxoquinazolin-3-yl)-1-piperidinyl]carbonyl]-D-phenylalanyl]-4-(4-fluorophenyl)-piperazine (318) 1-[3,5-Dibromo-N-[[4-(3,4-dihydro-2(1H)-oxoquinazolin-3-yl)-1-piperidinyl]carbonyl]-D-tyrosyl]-4-(4-fluorophenyl)-piperazine (319) 1-[4-Amino-3,5-dibromo-N-[[4-(3,4-dihydro-2(1H)-oxo-quinazolin-3-yl)-1-piperidinyl]carbonyl]-D-phenylalanyl]-4-(2-fluorophenyl)-piperazine (320) 1-[4-Amino-3,5-dibromo-N-[[4-(1,3-dihydro-4-phenyl-2(2H)-oxoimidazol-1-yl)-1-piperidinyl]carbonyl]-D-phenyl-alanyl]-4-(2-fluorophenyl)-piperazine (321) 1-[3,5-Dibromo-N-[[4-(1,1-dioxido-3(4H)-oxo-1,2,4-benzothiadiazin-2-yl)-1-piperidinyl]carbonyl]-D-tyrosyl]-4-(4-pyridinyl)-piperidine (322) trans-1-[3,5-Dibromo-N-[[4-(1,3-dihydro-2(2H)-oxobenzimidazol-1-yl)-1-cyclohexyl]carbonyl]-D-tyrosyl]-4-(1-piperidinyl)-piperidine (323) 1-[3,5-Dibromo-N-[[4-(3,4-dihydro-6,7-dimethoxy-2(1H)-oxoquinazolin-3-yl)-1-piperidinyl]carbonyl]-D-tyrosyl]-4-(4-pyridinyl)-piperidine (324) 1-[N-[[4-(5-Chloro-3,4-dihydro-2(1H)-oxoquinazolin-3-yl)-1-piperidinyl]carbonyl]-3,5-dibromo-D-tyrosyl]-4-(4-pyridinyl)-piperidine (325) 1-[3,5-Dibromo-N-[[3-(3,4-dihydro-2(1H)-oxoquinazolin-3-yl)-1-pyrrolidinyl]carbonyl]-D-tyrosyl]-4-(4-pyridinyl)-piperidine (326) 1-[3,5-Dibromo-N-[[4-(1,3-dihydro-4-phenyl-2(2H)-oxoimidazol-1-yl)-1-piperidinyl]carbonyl]-D-tyrosyl]-4-(4-pyridinyl)-piperazine (327) 1-[4-Amino-3,5-dibromo-N-[[4-(1,3-dihydro-4-phenyl-2(2H)-oxoimidazol-1-yl)-1-piperidinyl]carbonyl]-D-phenylalanyl]-4-(4-pyridinyl)-piperidine (328) 1-[3,5-Dibromo-N-[[4-(3,4-dihydro-8-methoxy-2(1H)-oxoquinazolin-3-yl)-1-piperidinyl]carbonyl]-D-tyrosyl]-4-(4-pyridinyl)-piperidine (329) 1-[3,5-Dibromo-N-[[4-(1,3-dihydro-4-(4-methoxyphenyl)-2(2H)-oxoimidazol-1-yl)-1-piperidinyl]carbonyl]-D-tyrosyl]-4-(4-pyridinyl)-piperidine (330) 1-[4-Amino-3,5-dibromo-N-[[4-(1,3-dihydro-4-(4-methoxy-phenyl)-2(2H)-oxoimidazol-1-yl)-1-piperidinyl]carbonyl]-D-phenylalanyl]-4-(4-pyridinyl)-piperazine (331) 1-[4-Amino-3,5-dibromo-N-[[4-(1,3-dihydro-4-(4-methoxy-phenyl)-2(2H)-oxoimidazol-1-yl)-1-piperidinyl]carbonyl]-D-phenylalanyl]-4-(1-methyl-4-piperidinyl)-piperidine (332) 1-[3,5-Dibromo-N-[[4-(3,4-dihydro-2(1H)-oxothieno[3,4-d]pyrimidin-3-yl)-1-piperidinyl]carbonyl]-D-tyrosyl]-4-(4-pyridinyl)-piperidine (333) 1-[3,5-Dibromo-N-[[4-(3,4-dihydro-2(1H)-oxothieno[3,2-d]pyrimidin-3-yl)-1-piperidinyl]carbonyl]-D-tyrosyl]-4-(4-pyridinyl)-piperidine (334) 1-[N-[[4-(1,3-dihydro-4-[3-(trifluoromethyl)-phenyl]-2(2H)-oxoimidazol-1-yl)-1-piperidinyl]carbonyl]-3-(4-pyridinyl)-D,L-alanyl]-4-(4-pyridinyl)-piperazine (335) 1-[4-Amino-3,5-dibromo-N-[[4-(3,4-dihydro-2(1H)-oxothieno[3,4-d]pyrimidin-3-yl)-1-piperidinyl]carbonyl]-D-phenylalanyl]-4-(4-pyridinyl)-piperidine (336) 1-[3,5-Dibromo-N-[[4-(3,4-dihydro-2(1H)-oxothieno[3,2-d]pyrimidin-3-yl)-1-piperidinyl]carbonyl]-D-tyrosyl]-4-(1-piperidinyl)-piperidine (337) 1-[3,5-Dibromo-N-[[4-(3,4-dihydro-2(1H)-oxothieno[3,4-d]pyrimidin-3-yl)-1-piperidinyl]carbonyl]-D-tyrosyl]-4-(1-piperidinyl)-piperidine (338) (R)-1-[3-(4-Amino-3,5-dibromophenyl)-2-[N-[[4-(3,4-dihydro-2(1H)-oxothieno[3,4-d]pyrimidin-3-yl)-1-piperidinyl]carbonyl]amino]propyl]-4-(1-piperidinyl)-piperidine (339) (R)-1-[3-(4-Amino-3,5-dibromophenyl)-2-[N-[[4-(3,4-dihydro-2(1H)-oxothieno[3,2-d]pyrimidin-3-yl)-1-piperidinyl]carbonyl]amino]propyl]-4-(1-piperidinyl)-piperidine (340) 1-[3,5-Dibromo-N-[[4-(3,4-dihydro-2(1H)-oxoquinazolin-3-yl)-1-piperidinyl]carbonyl]-D-tyrosyl]-4-(1-methyl-4-piperidinyl)-piperidine (341) 1-[3,5-Dibromo-N-[[4-(1,3-dihydro-4-phenyl-2(2H)-oxoimidazol-1-yl)-1-piperidinyl]carbonyl]-D-tyrosyl]-4-(1-methyl-4-piperidinyl)-piperidine (342) 1-[4-Amino-3,5-dibromo-N-[[4-(1,3-dihydro-4-(3-thienyl)-2(2H)-oxoimidazol-1-yl)-1-piperidinyl]carbonyl]-D-phenylalanyl]-4-(1-methyl-4-piperidinyl)-piperidine (343) 1-[3,5-Dibromo-N-[[4-(1,3-dihydro-4-(3-thienyl)-2(2H)-oxoimidazol-1-yl)-1-piperidinyl]carbonyl]-D-tyrosyl]-4-(1-methyl-4-piperidinyl)-piperidine (344) 1-[3,5-Dibromo-N-[[4-(1,3-dihydro-4-phenyl-2(2H)-oxoimidazol-1-yl)-1-piperidinyl]carbonyl]-D-tyrosyl]-4-(hexahydro-1H-1-azepinyl)-piperidine (345) 1-[3,5-Dibromo-N-[[4-(3,4-dihydro-2(1H)-oxoquinazolin-3-yl)-1-piperidinyl]carbonyl]-D-tyrosyl]-4-(hexahydro-1H-1-azepinyl)-piperidine (346) 1-[4-Amino-3,5-dibromo-N-[[4-(1,3-dihydro-4-phenyl-2(2H)-oxoimidazol-1-yl)-1-piperidinyl]carbonyl]-D-phenylalanyl]-4-(hexahydro-1H-1-azepinyl)-piperidine (347) 1-[4-Amino-3,5-Dibromo-N-[[4-(3,4-dihydro-2(1H)-oxoquinazolin-3-yl)-1-piperidinyl]carbonyl]-D-phenylalanyl]-4-(hexahydro-1H-1-azepinyl)-piperidine (348) 1-[4-Amino-3,5-dibromo-N-[[4-(2,4-dihydro-5-phenyl-3(3H)-oxo-1,2,4-triazol-2-yl)-1-piperidinyl]carbonyl]-D-phenylalanyl]-4-(1-methyl-4-piperidinyl)-piperidine (349) 1-[4-Amino-3,5-dibromo-N-[[4-(2,4-dihydro-5-phenyl-3(3H)-oxo-1,2,4-triazol-2-yl)-1-piperidinyl]carbonyl]-D-phenylalanyl]-4-(1-piperidinyl)-piperidine (350) 1-[4-Amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-methyl-4-piperidinyl)-piperidine (351) 1-[4-Amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-piperidinyl)-piperidine (352) 1-[3,5-Dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(1-piperidinyl)-piperidine (353) 1-[3,5-Dibromo-N-[[4-(1,3-dihydro-4-(3-thienyl)-2(2H)-oxoimidazol-1-yl)-1-piperidinyl]carbonyl]-D-tyrosyl]-4-(1-piperidinyl)-piperidine (354) 1-[3,5-Dibromo-N-[[4-(1,3-dihydro-2(2H)-oxobenzimidazol-1-yl)-1-piperidinyl]carbonyl]-D,L-tyrosyl]-4-(4-pyridinyl)-piperidine (355) 1-[4-Amino-3,5-dibromo-N-[[4-(2,4-dihydro-5-phenyl-3(3H)-oxo-1,2,4-triazol-2-yl)-1-piperidinyl]carbonyl]-D-phenylalanyl]-4-(1-methyl-4-piperidinyl)-piperazine (356) 1-[4-Amino-3,5-dibromo-N-[[4-(3,4-dihydro-2(1H)-oxoquinazolin-3-yl)-1-piperidinyl]carbonyl]-D-phenylalanyl]-4-(exo-8-methyl-8-azabicyclo[3,2,1]oct-3-yl)-piperazine (357) 1-[4-Amino-3,5-dibromo-N-[[4-(1,3-dihydro-4-(3-thienyl)-2(2H)-oxoimidazol-1-yl)-1-piperidinyl]carbonyl]-D-phenylalanyl]-4-(1-methyl-4-piperidinyl)-piperazine (358) 1-[3,5-Dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(1-methyl-4-piperidinyl)-piperazine (359) 1-[4-Amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-methyl-4-piperidinyl)-piperazine (360) 1-[4-Amino-3,5-dibromo-N-[[4-(3,4-dihydro-2(1H)-oxothieno[3,4-d]pyrimidin-3-yl)-1-piperidinyl]carbonyl]-D-phenyl-alanyl]-4-(1-piperidinyl)-piperidine (361) 1-[4-Amino-3,5-dibromo-N-[[4-(3,4-dihydro-2(1H)-oxothieno[3,2-d]pyrimidin-3-yl)-1-piperidinyl]carbonyl]-D-phenylalanyl]-4-(1-methyl-4-piperidinyl)-piperazine (362) 1-[4-Amino-3,5-dibromo-N-[[4-(3,4-dihydro-2(1H)-oxothieno[3,2-d]pyrimidin-3-yl)-1-piperidinyl]carbonyl]-D-phenylalanyl]-4-(1-piperidinyl)-piperidine (363) 1-[4-Amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(hexahydro-1H-1-azepinyl)-piperidine (364) 1-[3,5-Dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(hexahydro-1H-1-azepinyl)-piperidine (365) 1-[N2-[3,5-Dibromo-N-[[4-[1,3-dihydro-4-[3-(trifluoromethyl)phenyl]-2(2H)-oxoimidazol-1-yl]-1-piperidinyl]carbonyl]-D-tyrosyl]-L-lysyl]-4-(4-pyridinyl)-piperazine (366) 1-[4-Amino-3,5-Dibromo-N-[[4-(3,4-dihydro-2(1H)-oxoquinazolin-3-yl)-1-piperidinyl]carbonyl]-D-phenylalanyl]-4-(1-ethyl-4-piperidinyl)-piperidine (367) 1-[4-Amino-3,5-dibromo-N-[[4-(1,3-dihydro-4-phenyl-2(2H)-oxoimidazol-1-yl)-1-piperidinyl]carbonyl]-D-phenylalanyl]-4-(1-ethyl-4-piperidinyl)-piperidine (368) 1-[4-Amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-ethyl-4-piperidinyl)-piperidine (369) 1-[4-Amino-3,5-dibromo-N-[[4-[1,3-dihydro-4-[4-(trifluoromethyl)phenyl]-2(2H)-oxoimidazol-1-yl]-1-piperidinyl]carbonyl]-D-phenylalanyl]-4-(1-piperidinyl)-piperazine (370) 1-[4-Amino-3,5-Dibromo-N-[[4-(3,4-dihydro-2(1H)-oxoquinazolin-3-yl)-1-piperidinyl]carbonyl]-D-phenylalanyl]-4-(1-ethyl-4-piperidinyl)-piperazine (371) 1-[4-Amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-ethyl-4-piperidinyl)-piperazine (372) 4-(1-Acetyl-4-piperidinyl)-1-[4-amino-3,5-dibromo-N-[[4-(3,4-dihydro-2(1H)-oxoquinazolin-3-yl)-1-piperidinyl]carbonyl]-D-phenylalanyl]-piperidine (373) 1-[4-Amino-N-[[4-(6-bromo-3,4-dihydro-2(1H)-oxoquinazolin-3-yl)-1-piperidinyl]carbonyl]-3,5-dibromo-D-phenylalanyl]-4-(1-piperidinyl)-piperidine (374) 1-[4-Amino-3,5-dibromo-N-[[4-(1,3-dihydro-5-methyl-4-phenyl-2(2H)-oxoimidazol-1-yl)-1-piperidinyl]carbonyl]-D-phenylalanyl]-4-(1-methyl-4-piperidinyl)-piperidine (375) 1-[4-Amino-3,5-dibromo-N-[[4-[1,3-dihydro-4-(3-nitrophenyl)-2(2H)-oxoimidazol-1-yl]-1-piperidinyl]carbonyl]-D-phenylalanyl]-4-(1-methyl-4-piperidinyl)-piperidine
(376) 1-[4-Amino-3,5-dibromo-N-[[4-[1,3-dihydro-4-(3-methoxyphenyl)-2(2H)-oxoimidazol-1-yl]-1-piperidinyl]carbonyl]-D-phenylalanyl]-4-(1-methyl-4-piperidinyl)-piperidine
(377) 1-[47Amino-N-[[4-[4-(3-bromophenyl)-1,3-dihydro-2(2H)-oxoimidazol-1-yl]-1-piperidinyl]carbonyl]-3,5-dibromo-D-phenylalanyl]-4-(1-methyl-4-piperidinyl)-piperidine
(378) 1-[$N^2$-[3,5-Dibromo-N-[[4-(1,3-dihydro-2(2H)-oxobenzimidazol-1-yl)-1-piperidinyl]carbonyl]-D-tyrosyl]-$N^6$-(1,1-dimethylethoxycarbonyl)-L-lysyl]-4-(4-pyridinyl)-piperazine
(379) 1-[3,5-Dibromo-N-[[4-[1,3-dihydro-4-phenyl-2(2H)-oxoimidazol-1-yl]-1-piperidinyl]carbonyl]-D-tyrosyl]-4-(4-fluorophenyl)-piperazine
(380) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-(4-fluorophenyl)-piperazine
(381) 1-[3,5-Dibromo-N-[[4-[1,3-dihydro-4-phenyl-2(2H)-oxoimidazol-1-yl]-1-piperidinyl]carbonyl]-D-tyrosyl]-4-(3-pyridinyl)-piperazine
(382) 1-[3,5-Dibromo-N-[[4-(3,4-dihydro-2(1H)-oxoquinazolin-3-yl)-1-piperidinyl]carbonyl]-D-tyrosyl]-4-(3-pyridinyl)-piperazine
(383) 1-[4-Amino-3,5-dibromo-N-[[4-(3,4-dihydro-2(1H)-oxoquinazolin-3-yl)-1-piperidinyl]carbonyl]-D-phenylalanyl]-4-(3-pyridinyl)-piperazine
(384) 1-[3,5-Dibromo-N-[[4-[1,1-dioxido-3(4H)-oxo-1,2,4-benzothiadiazin-2-yl]-1-piperidinyl]carbonyl]-D-tyrosyl]-4-(4-pyridinyl)-piperazine
(385) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-(3-pyridinyl)-piperazine
(386) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-(5-methoxy-4-pyrimidinyl)-piperazine
(387) 1-[4-Amino-3,5-dibromo-N-[[4-(3,4-dihydro-2(1H)-oxoquinazolin-3-yl)-1-piperidinyl]carbonyl]-D-phenylalanyl]-4-(2-pyridinyl)-piperazine
(388) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-(2-pyridinyl)-piperazine
(389) 1-[4-Amino-3,5-dibromo-N-[[4-(3,4-dihydro-2(1H)-oxoquinazolin-3-yl)-1-piperidinyl]carbonyl]-D-phenylalanyl]-4-(phenylaminocarbonylamino)-piperidine
(390) 1-[4-Amino-3,5-dibromo-N-[[4-[4-[3,4-dihydro-2(1H)-oxoquinazolin-3-yl]-1-piperidinyl]-1-piperidinyl]carbonyl]-D-phenylalanyl]-4-(5-methoxy-4-pyrimidinyl)-piperazine
(391) 1-[3,5-Dibromo-N-[[4-[4-[3,4-dihydro-2(1H)-oxoquinazolin-3-yl]-1-piperidinyl]-1-piperidinyl]carbonyl]-D-tyrosyl]-4-(5-methoxy-4-pyrimidinyl)-piperazine
(392) 1-[3,5-Dibromo-N-[[4-[4-phenyl-2(1H)-oxopyrimidin-1-yl]-1-piperidinyl]carbonyl]-D-tyrosyl]-4-(4-pyridinyl)-piperidine
(393) 4-Cyano-1-[3,5-dibromo-N-[[4-(3,4-dihydro-2(1H)-oxoquinazolin-3-yl)-1-piperidinyl]carbonyl]-D-tyrosyl]-4-phenylpiperidine
(394) 1-[4-Amino-3,5-dibromo-N-[[4-(3,4-dihydro-2(1H)-oxoquinazolin-3-yl)-1-piperidinyl]carbonyl]-D-phenylalanyl]-4-(4-pyrimidinyl)-piperazine
(395) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-(4-pyrimidinyl)-piperazine
(396) 1-[3,5-Dibromo-N-[[4-[1,3-dihydro-4-phenyl-2(2H)-oxoimidazol-1-yl]-1-piperidinyl]carbonyl]-D-tyrosyl]-4-(4-pyrimidinyl)-piperazine
(397) 1-[3,5-Dibromo-N-[[4-(3,4-dihydro-2(1H)-oxoquinazolin-3-yl)-1-piperidinyl]carbonyl]-D-tyrosyl]-4-(4-pyrimidinyl)-piperazine
(398) 1-[4-Amino-3,5-dibromo-N-[[4-[3,4-dihydro-2(1H)-oxoquinolin-3-yl]-1-piperidinyl]carbonyl]-D-phenylalanyl]-4-(1-piperidinyl)-piperidine
(399) 1-[4-Amino-3,5-dibromo-N-[[4-[1,3-dihydro-4-(4-fluorophenyl)-2(2H)-oxoimidazol-1-yl]-1-piperidinyl]carbonyl]-D-phenylalanyl]-4-(5-methoxy-4-pyrimidinyl)-piperazine
(400) 1-[4-Amino-3,5-dibromo-N-[[4-[2(1H)-oxoquinolin-3-yl]-1-piperidinyl]carbonyl]-D-phenylalanyl]-4-(1-piperidinyl)-piperidine
(401) 2-[3,5-Dibromo-N-[[4-(3,4-dihydro-2(1H)-oxoquinazolin-3-yl)-1-piperidinyl]carbonyl]-D-tyrosyl]-1,2,3,4-tetrahydro-5H-pyrido[4,3-b]indole
(402) 1-[4-Amino-3,5-dibromo-N-[[4-[2(1H)-oxoquinolin-3-yl]-1-piperidinyl]carbonyl]-D-phenylalanyl]-4-(4-pyridinyl)-piperazine
(403) 1-[4-Amino-3,5-dibromo-N-[[4-[3,4-dihydro-2(1H)-oxoquinolin-3-yl]-1-piperidinyl]carbonyl]-D-phenylalanyl]-4-(4-pyridinyl)-piperazine
(404) 1-[4-Amino-3,5-dibromo-N-[[4-(3,4-dihydro-2(1H)-oxoquinazolin-3-yl)-1-piperidinyl]carbonyl]-D-phenylalanyl]-4-(4-ethylphenyl)-piperazine
(405) 1-[3,5-Dibromo-N-[[4-(3,4-dihydro-2(1H)-oxoquinazolin-3-yl)-1-piperidinyl]carbonyl]-D-tyrosyl]-4-(4-fluorophenyl)-1,2,5,6-tetrahydropyridine
(406) 1-[3,5-Dibromo-N-[[4-[2(1H)-oxoquinolin-3-yl]-1-piperidinyl]carbonyl]-D-tyrosyl]-4-(4-pyridinyl)-piperazine
(407) 1-[3,5-Dibromo-N-[[4-[3,4-dihydro-2(1H)-oxoquinolin-3-yl]-1-piperidinyl]carbonyl]-D-tyrosyl]-4-(4-pyridinyl)-piperazine
(408) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-[4-(1-oxoethyl)phenyl]-piperazine
(409) 1-[4-Amino-3,5-dibromo-N-[[4-[3,4-dihydro-2(1H)-oxoquinazolin-3-yl]-1-piperidinyl]carbonyl]-D-phenylalanyl]-4-[4-(1-oxoethyl)phenyl]-piperazine
(410) 1-[3,5-Dibromo-N-[[4-(3,4-dihydro-2(1H)-oxoquinazolin-3-yl)-1-piperidinyl]carbonyl]-D-tyrosyl]-4-(4-fluorobenzoyl)-piperidine
(411) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-cyano-4-phenylpiperidine
(412) 1-[3,5-Dibromo-N-[[4-(3,4-dihydro-2(1H)-oxoquinazolin-3-yl)-1-piperidinyl]carbonyl]-D-tyrosyl]-4-(4-fluorophenyl)-piperidine
(413) 1-[3,5-Dibromo-N-[[4-(3,4-dihydro-2(1H)-oxoquinazolin-3-yl)-1-piperidinyl]carbonyl]-D-tyrosyl]-4-[(hexahydro-1-methyl-4-pyridinyl)carbonyl]-piperazine
(414) 1-[4-Amino-3,5-dibromo-N-[[4-[3,4-dihydro-2(1H)-oxoquinazolin-3-yl]-1-piperidinyl]carbonyl]-D-phenylalanyl]-4-[3-(dimethylamino)propyl]-piperazine
(415) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-[3-(dimethylamino)propyl]-piperazine
(416) 1-[4-Amino-3,5-dibromo-N-[[4-[3,4-dihydro-2(1H)-oxoquinazolin-3-yl]-1-piperidinyl]carbonyl]-D-phenylalanyl]-4-(4-methyl-1-piperazinyl)-piperidine (417) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-(4-methyl-1-piperazinyl)-piperidine
(418) 1-[4-Amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(exo-8-methyl-8-azabicyclo[3,2,l]oct-3-yl)-piperazine
(419) 1-[N-[4-[[1,3-Dihydro-2(2H)-oxoimidazol-1-yl]-1-piperidinyl]carbonyl]-3-(trifluoromethyl)-D,L-phenylalanyl]-4-(exo-8-methyl-8-azabicyclo[3,2,1]oct-3-yl)-piperazine
(420) 1-[3,5-Dibromo-N-[[4-[7-(methoxycarbonyl)-3,4-dihydro-2(1H)-oxoquinazolin-3-yl]-1-piperidinyl]carbonyl]-D-tyrosyl]-4-(4-pyridinyl)-piperidine
(421) 1-[3,5-Dibromo-N-[[4-[7-(hydroxycarbonyl)-3,4-dihydro-2(1H)-oxoquinazolin-3-yl]-1-piperidinyl]carbonyl]-D-tyrosyl]-4-(4-pyridinyl)-piperidine
(422) 1-[3,5-Dibromo-N-[[4-[7-(methoxycarbonyl)-3,4-dihydro-2(1H)-oxoquinazolin-3-yl]-1-piperidinyl]carbonyl]-D-tyrosyl]-4-(1-piperidinyl)-piperidine
(423) 1-[3,5-Dibromo-N-[[4-[7-(hydroxycarbonyl)-3,4-dihydro-2(1H)-oxoquinazolin-3-yl]-1-piperidinyl]carbonyl]-D-tyrosyl]-4-(1-piperidinyl)-piperidine
(424) 1-[4-Amino-3,5-dibromo-N-[[4-[7-(methylaminocarbonyl)-3,4-dihydro-2(1H)-oxoquinazolin-3-yl]-1-piperidinyl]carbonyl]-D-phenylalanyl]-4-(4-pyridinyl)-piperidine
(425) 1-[3,5-Dibromo-N-[[4-[3,4-dihydro-2(1H)-oxoquinazolin-3-yl]-1-piperidinyl]carbonyl]-D-tyrosyl]-4-(4-morpholinyl)-piperidine
(426) 1-[4-Amino-3,5-dibromo-N-[[4-[3,4-dihydro-2(1H)-oxo-quinazolin-3-yl]-1-piperidinyl]carbonyl]-D-phenylalanyl]-4-(dimethylamino)-piperidine
(427) 1-[3,5-Dibromo-N-[[4-[3,4-dihydro-2(1H)-oxoquinazolin-3-yl]-1-piperidinyl]carbonyl]-D-tyrosyl]-4-(1-pyrrolidinyl)-piperidine
(428) 1-[4-Amino-3,5-dibromo-N-[[4-[3,4-dihydro-2(1H)-oxoquinazolin-3-yl]-1-piperidinyl]carbonyl]-D-phenylalanyl]-4-(4-morpholinyl)-piperidine
(429) 1-[3,5-Dibromo-N-[[4-[3,4-dihydro-2(1H)-oxoquinazolin-3-yl]-1-piperidinyl]carbonyl]-D-tyrosyl]-4-(dimethylamino)-piperidine
(430) 1-[4-Amino-3,5-dibromo-N-[[4-[7-[(4-methyl-1-piperazinyl)carbonyl]-3,4-dihydro-2(1H)-oxoquinazolin-3-yl]-1-piperidinyl]carbonyl]-D-phenylalanyl]-4-(4-pyridinyl)-piperidine
(431) 1-[4-Amino-3,5-dibromo-N-[[4-(2,5-dioxo-4-phenylimidazolidin-1-yl)-1-piperidinyl]carbonyl]-D-phenylalanyl]-4-(1-piperidinyl)-piperidine
(432) 1-[3,5-Dibromo-N-[[4-(2,5-dioxo-4-phenylimidazolidin-1-yl)-1-piperidinyl]carbonyl]-D-tyrosyl]-4-(4-pyridinyl)-piperidine
(433) 1-[4-Amino-3,5-dibromo-N-[[4-[2,5-dioxo-4-(phenyl-methyl)-imidazolidin-1-yl)-1-piperidinyl]carbonyl]-D-phenylalanyl]-4-(4-pyridinyl)-piperidine
(434) 1-[3,5-Dibromo-N-[[4-[2,5-dioxo-4-(phenylmethyl)imidazolidin-1-yl)-1-piperidinyl]carbonyl]-D-tyrosyl]-4-(1-piperidinyl)-piperidine
(435) 1-[4-Amino-3,5-dibromo-N-[[4-[3,4-dihydro-2(1H)-oxoquinazolin-3-yl]-1-piperidinyl]carbonyl]-D-phenylalanyl]-4-(1-pyrrolidinyl)-piperidine
(436) 1-[3,5-Dibromo-N-[[4-[3,4-dihydro-2(1H)-oxoquinazolin-3-yl]-1-piperidinyl]carbonyl]-D-tyrosyl]-4-(1-methyl-4-piperidinyl)-piperazine
(437) 1-[4-Amino-3,5-dibromo-N-[[4-[3,4-dihydro-2(1H)-oxoquinazolin-3-yl]-1-piperidinyl]carbonyl]-D-phenylalanyl]-4-(1-methyl-4-piperidinyl)-piperazine
(438) 1-[4-Amino-3,5-dibromo-N-[[4-[3,4-dihydro-2(1H)-oxoquinazolin-3-yl]-1-piperidinyl]carbonyl]-D-phenylalanyl]-4-cyclohexylpiperazine
(439) 1-[3,5-Dibromo-N-[[4-[3,4-dihydro-2(1H)-oxoquinazolin-3-yl]-1-piperidinyl]carbonyl]-D-tyrosyl]-4-cyclohexylpiperazine
(440) 1-[4-Amino-3,5-dibromo-N-[[4-(3,4-dihydro-2,2-dioxido-2,1,3-benzothiadiazin-3-yl)-1-piperidinyl]carbonyl]-D-phenyl-alanyl]-4-(1-piperidinyl)-piperidine
(441) 1-[4-Amino-3,5-dibromo-N-[[4-(3,4-dihydro-2,2-dioxido-2,1,3-benzothiadiazin-3-yl)-1-piperidinyl]carbonyl]-D-phenyl-alanyl]-4-(1-methyl-4-piperidinyl)-piperidine
(442) 1-[4-Amino-3,5-dibromo-N-[[4-(3,4-dihydro-2,2-dioxido-2,1,3-benzothiadiazin-3-yl)-1-piperidinyl]carbonyl]-D-phenyl-alanyl]-4-(4-pyridinyl)-piperidine
(443) 1-[3,5-Dibromo-N-[[4-[1,3-dihydro-4-(4-fluorophenyl)-2(2H)-oxoimidazol-1-yl]-1-piperidinyl]carbonyl]-D-tyrosyl]-4-(1-methyl-4-piperidinyl)-piperazine
(444) 1-[3,5-Dibromo-N-[[4-[1,3-dihydro-4-(4-fluorophenyl)-2(2H)-oxoimidazol-1-yl]-1-piperidinyl]carbonyl]-D-tyrosyl]-4-(1-piperidinyl)-piperidine
(445) 1-[3,5-Dibromo-N-[[4-[1,3-dihydro-4-(4-fluorophenyl)-2(2H)-oxoimidazol-1-yl]-1-piperidinyl]carbonyl]-D-tyrosyl]-4-(4-pyridinyl)-piperazine
(446) 1-[3,5-Dibromo-N-[[4-[1,3-dihydro-4-(4-fluorophenyl)-2(2H)-oxoimidazol-1-yl]-1-piperidinyl]carbonyl]-D-tyrosyl]-4-(1-methyl-4-piperidinyl)-piperidine
(447) 1-[4-Amino-3,5-dibromo-N-[[4-[1,3-dihydro-4-(4-fluorophenyl)-2(2H)-oxoimidazol-1-yl]-1-piperidinyl]carbonyl]-D-phenylalanyl]-4-(4-pyridinyl)-piperazine
(448) 1-[4-Amino-3,5-dibromo-N-[[4-[1,3-dihydro-4-(4-fluorophenyl)-2(2H)-oxoimidazol-1-yl]-1-piperidinyl]carbonyl]-D-phenylalanyl]-4-(1-methyl-4-piperidinyl)-piperidine
(449) 1-[4-Amino-3,5-dibromo-N-[[4-[1,3-dihydro-4-(4-fluorophenyl)-2(2H)-oxoimidazol-1-yl]-1-piperidinyl]carbonyl]-D-phenylalanyl]-4-(1-piperidinyl)-piperidine
(450) 1-[3,5-Dibromo-N-[[4-[3,4-dihydro-2(1H)-oxoquinazolin-3-yl]-1-piperidinyl]carbonyl]-N-methyl-D-tyrosyl]-4-(4-pyridinyl)-piperidine
(451) (R,S)-1-[2-[(3,5-Dibromo-4-hydroxyphenyl)methyl]-4-[4-[3,4-dihydro-2(1H)-oxoquinazolin-3-yl]-1-piperidinyl]-1,4-dioxobutyl]-4-(4-pyridinyl)-piperazine
(452) (R,S)-1-[2-[(3,5-Dibromo-4-hydroxyphenyl)methyl]-4-[4-[1,3-dihydro-4-phenyl-2(2H)-oxoimidazol-1-yl]-1-piperidinyl]-1,4-dioxobutyl]-4-(4-pyridinyl)-piperazine
(453) (R,S)-1-[2-[(3,5-Dibromo-4-hydroxyphenyl)methyl]-4-[4-[3,4-dihydro-2(1H)-oxoquinazolin-3-yl]-1-piperidinyl]-1,4-dioxobutyl]-4-(1-methyl-4-piperidinyl)-piperazine
(454) (R,S)-1-[2-[(3,5-Dibromo-4-hydroxyphenyl)methyl]-4-[4-[3,4-dihydro-2(1H)-oxoquinazolin-3-yl]-1-piperidinyl]-1,4-dioxobutyl]-4-(1-methyl-4-piperidinyl)-piperidine
(455) (R,S)-1-[2-[(3,5-Dibromo-4-hydroxyphenyl)methyl]-4-[4-[1,3-dihydro-4-phenyl-2(2H)-oxoimidazol-1-yl]-1-piperidinyl]-1,4-dioxobutyl]-4-(1-piperidinyl)-piperidine
(456) 1-[3,4-Dichloro-N-[[4-[3,4-dihydro-2(1H)-oxoquinazolin-3-yl]-1-piperidinyl]carbonyl]-D,L-phenylalanyl]-4-(1-piperidinyl)-piperidine
(457) (R,S)-1-[2-[(3,5-Dibromo-4-hydroxyphenyl)methyl]-4-[4-[1,3-dihydro-4-phenyl-2(2H)-oxoimidazol-1-yl]-1-piperidinyl]-1,4-dioxobutyl]-4-(4-pyridinyl)-piperidine (458) (R,S)-1-[2-[(3,5-Dibromo-4-hydroxyphenyl)methyl]-4-[4-[1,3-dihydro-4-phenyl-2(2H)-oxoimidazol-1-yl]-1-piperidinyl]-1,4-dioxobutyl]-4-(hexahydro-1H-1-azepinyl)-piperidine (459) (R,S)-1-[2-[(3,5-Dibromo-4-hydroxyphenyl)methyl]-4-[4-[3,4-dihydro-2(1H)-oxoquinazolin-3-yl]-1-piperidinyl]-1,4-dioxobutyl]-4-(hexahydro-1H-1-azepinyl)-piperidine (460) 1-[3,5-Dibromo-N-[[4-[3,4-dihydro-2(1H)-oxoquinazolin-3-yl]-1-piperidinyl]carbonyl]-D-tyrosyl]-4-cycloheptylpiperazine (461) 1-[3,5-Dibromo-N-[[4-[3,4-dihydro-2(1H)-oxoquinazolin-3-yl]-1-piperidinyl]carbonyl]-D-tyrosyl]-4-cyclopentylpiperazine (462) 1-[3,5-Dibromo-N-[[4-[3,4-dihydro-2(1H)-oxoquinazolin-3-yl]-1-piperidinyl]carbonyl]-4-methoxy-D-phenylalanyl]-4-(1-piperidinyl)-piperidine (463) 1-[3,5-Bis-(trifluoromethyl)-N-[[4-[3,4-dihydro-2(1H)-oxoquinazolin-3-yl]-1-piperidinyl]carbonyl]-D,L-phenylalanyl]-4-(4-pyridinyl)-piperazine (464) 1-[3,5-Bis-(trifluoromethyl)-N-[[4-[3,4-dihydro-2(1H)-oxoquinazolin-3-yl]-1-piperidinyl]carbonyl]-D,L-phenylalanyl]-4-(1-piperidinyl)-piperidine (465) 1-[3,5-Bis-(trifluoromethyl)-N-[[4-[3,4-dihydro-2(1H)-oxoquinazolin-3-yl]-1-piperidinyl]carbonyl]-D,L-phenylalanyl]-4-(hexahydro-1H-1-azepinyl)-piperidine (466) 1-[4-Amino-3,5-dibromo-N-[[4-[1,3-dihydro-4-(biphenylyl)-2(2H)-oxoimidazol-1-yl]-1-piperidinyl]carbonyl]-D-phenylalanyl]-4-(1-piperidinyl)-piperidine (467) 1-[4-Amino-3,5-dibromo-N-[[4-[1,3-dihydro-4-(2-naphthyl)-2(2H)-oxoimidazol-1-yl]-1-piperidinyl]carbonyl]-D-phenylalanyl]-4-(1-piperidinyl)-piperidine (468) 1-[3,5-Dibromo-N-[[4-[1,3-dihydro-4-(2-naphthyl)-2(2H)-oxoimidazol-1-yl]-1-piperidinyl]carbonyl]-D-tyrosyl]-4-(1-piperidinyl)-piperidine (469) 1-[3-Bromo-N-[[4-[3,4-dihydro-2(1H)-oxoquinazolin-3-yl]-1-piperidinyl]carbonyl]-D,L-phenylalanyl]-4-(1-piperidinyl)-piperidine (470) 1-[3,5-Dibromo-N-[[4-[1,3-dihydro-4-(4-biphenylyl)-2(2H)-oxoimidazol-1-yl]-1-piperidinyl]carbonyl]-D-tyrosyl]-4-(1-piperidinyl)-piperidine (471) 1-[N-[[4-[3,4-dihydro-2(1H)-oxoquinazolin-3-yl]-1-piperidinyl]carbonyl]-3-(4-biphenylyl)-D,L-alanyl]-4-(1-piperidinyl)-piperidine (472) 1-[3,5-Dibromo-N-[[4-[1,3-dihydro-4-biphenylyl-2(2H)-oxoimidazol-1-yl]-1-piperidinyl]carbonyl]-D,L-phenylalanyl]-4-(1-piperidinyl)-piperidine (473) 1-[3,5-Dibromo-N-[[4-[1,3-dihydro-4-(2-methoxyphenyl)-2(2H)-oxoimidazol-1-yl]-1-piperidinyl]carbonyl]-D-tyrosyl]-4-(1-piperidinyl)-piperidine (474) 1-[4-Amino-3,5-dibromo-N-[[4-[1,3-dihydro-4-(2-methoxyphenyl)-2(2H)-oxoimidazol-1-yl]-1-piperidinyl]carbonyl]-D-phenylalanyl]-4-(1-piperidinyl)-piperidine (475) 1-[3,5-Bis-(trifluoromethyl)-N-[[4-[3,4-dihydro-2(1H)-oxoquinazolin-3-yl]-1-piperidinyl]carbonyl]-D,L-phenylalanyl]-4-(1-methyl-4-piperidinyl)-piperidine (476) 1-[3,5-Bis-(trifluoromethyl)-N-[[4-[3,4-dihydro-2(1H)-oxoquinazolin-3-yl]-1-piperidinyl]carbonyl]-D,L-phenylalanyl]-4-(1-methyl-4-piperidinyl)-piperazine (477) 1-[3,4-Dichloro-N-[[4-[3,4-dihydro-2(1H)-oxoquinazolin-3-yl]-1-piperidinyl]carbonyl]-D,L-phenylalanyl]-4-(4-pyridinyl)-piperazine (478) 1-[3-Bromo-N-[[4-[3,4-dihydro-2(1H)-oxoquinazolin-3-yl]-1-piperidinyl]carbonyl]-D,L-phenylalanyl]-4-(hexahydro-1H-1-azepinyl)-piperidine (479) 1-[3-Bromo-N-[[4-[3,4-dihydro-2(1H)-oxoquinazolin-3-yl]-1-piperidinyl]carbonyl]-D,L-phenylalanyl]-4-(1-methyl-4-piperidinyl)-piperidine (480) 1-[3-Bromo-N-[[4-[3,4-dihydro-2(1H)-oxoquinazolin-3-yl]-1-piperidinyl]carbonyl]-D,L-phenylalanyl]-4-(4-pyridinyl)-piperidine (481) 1-[4-Amino-3,5-dibromo-N-[[4-[4-(3,4-dichlorophenyl)-1,3-dihydro-2(2H)-oxoimidazol-1-yl]-1-piperidinyl]carbonyl]-D-phenylalanyl]-4-(hexahydro-1H-1-azepinyl)-piperidine (482) 1-[4-Amino-3,5-dibromo-N-[[4-[4-(3,4-dichlorophenyl)-1,3-dihydro-2(2H)-oxoimidazol-1-yl]-1-piperidinyl]carbonyl]-D-phenylalanyl]-4-(1-methyl-4-piperidinyl)-piperidine (483) 1-[4-Amino-N-[[4-[4-(3-chlorophenyl)-1,3-dihydro-2(2H)-oxoimidazol-1-yl]-1-piperidinyl]carbonyl]-3,5-dibromo-D-phenylalanyl]-4-(1-methyl-4-piperidinyl)-piperidine (484) 1-[4-Amino-N-[[4-[4-(3-chlorophenyl)-1,3-dihydro-2(2H)-oxoimidazol-1-yl]-1-piperidinyl]carbonyl]-3,5-dibromo-D-phenylalanyl]-4-(hexahydro-1H-1-azepinyl)-piperidine (485) 1-[4-Amino-3,5-dibromo-N-[[4-[3,4-dihydro-2(1H)-oxoquinazolin-3-yl]-1-piperidinyl]carbonyl]-D-phenylalanyl]-4-(1-benzoyl-4-piperidinyl)-piperidine (486) 1-[4-Amino-3,5-dibromo-N-[[4-[3,4-dihydro-2(1H)-oxoquinazolin-3-yl]-1-piperidinyl]carbonyl]-D-phenylalanyl]-4-(1-methylsulphonyl-4-piperidinyl)-piperidine (487) 1-[4-Amino-3,5-dibromo-N-[[4-[3,4-dihydro-2(1H)-oxoquinazolin-3-yl]-1-piperidinyl]carbonyl]-D-phenylalanyl]-4-[1-(3-carboxy-1-oxopropyl)-4-piperidinyl]-piperidine (488) 1-[4-Amino-3,5-dibromo-N-[[4-[3,4-dihydro-2(1H)-oxoquinazolin-3-yl]-1-piperidinyl]carbonyl]-D-phenylalanyl]-4-(1-hexyl-4-piperidinyl)-piperidine (489) 1-[4-Amino-3,5-dibromo-N-[[4-[3,4-dihydro-2(1H)-oxoquinazolin-3-yl]-1-piperidinyl]carbonyl]-D-phenylalanyl]-4-(1-cyclopropylmethyl-4-piperidinyl)-piperidine (490) 1-[3,5-Dibromo-N-[[4-(2,4-dihydro-5-phenyl-3(3H)-oxo-1,2,4-triazol-2-yl)-1-piperidinyl]carbonyl]-D-tyrosyl]-4-(1-methyl-4-piperidinyl)-piperidine (491) 1-[3,5-Dibromo-N-[[4-(2,4-dihydro-5-phenyl-3(3H)-oxo-1,2,4-triazol-2-yl)-1-piperidinyl]carbonyl]-D-tyrosyl]-4-(1-piperidinyl)-piperidine (492) 1-[3,5-Dibromo-N-[[4-(2,4-dihydro-5-phenyl-3(3H)-oxo-1,2,4-triazol-2-yl)-1-piperidinyl]carbonyl]-D-tyrosyl]-4-(1-methyl-4-piperidinyl)-piperazine (493) 1-[4-Amino-3,5-dibromo-N-[[4-[3,4-dihydro-2(1H)-oxoquinazolin-3-yl]-1-piperidinyl]carbonyl]-D-phenylalanyl]-4-[1-(ethoxycarbonylmethyl)-4-piperidinyl]-piperidine (494) 1-[4-Amino-3,5-dibromo-N-[[4-[3,4-dihydro-2(1H)-oxoquinazolin-3-yl]-1-piperidinyl]carbonyl]-D-phenylalanyl]-4-[1-(carboxymethyl)-4-piperidinyl]-piperidine (495) 1-[4-Amino-3,5-dibromo-N-[[4-[1,3-dihydro-4,5-diphenyl-2(2H)-oxoimidazol-1-yl]-1-piperidinyl]carbonyl]-D-phenylalanyl]-4-(1-methyl-4-piperidinyl)-piperidine (496) 1-[4-Amino-3,5-dibromo-N-[[4-[3,4-dihydro-2(1H)-oxoquinazolin-3-yl]-1-piperidinyl]carbonyl]-D-phenylalanyl]-4-[(4-pyridinyl)carbonyl]-piperazine (497) 1-[3,5-Dibromo-N-[[4-[3,4-dihydro-2(1H)-oxoquinazolin-3-yl]-1-piperidinyl]carbonyl]-D-tyrosyl]-4-(4-methyl-1-piperazinyl)piperidine (498) 1-[4-Amino-3,5-dibromo-N-[[4-[3,4-dihydro-2(1H)-oxoquinazolin-3-yl]-1-piperidinyl]carbonyl]-D-phenylalanyl]-4-(hexahydro-4-methyl-1H-1,4-diazepin-1-yl)piperidine (499) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-(hexahydro-4-methyl-1H-1,4-diazepin-1-yl)piperidine (500) 1-[4-Amino-3,5-dibromo-N-[[4-[3,4-dihydro-2(1H)-oxoquinazolin-3-yl]-1-piperidinyl]carbonyl]-D-phenylalanyl]-4-[(1-methyl-4-piperidinyl)carbonyl]-piperazine (501) 1-[3,5-Dibromo-N-[[4-[1,3-dihydro-4-phenyl-2(2H)-oxoimidazol-1-yl]-1-piperidinyl]carbonyl]-D-tyrosyl]-4-(4-methyl-1-piperazinyl)piperidine (502) 1-[3,5-Dibromo-N-[[4-[3,4-dihydro-2(1H)-oxoquinazolin-3-yl]-1-piperidinyl]carbonyl]-D-tyrosyl]-4-(hexahydro-4-methyl-1H-1,4-diazepin-1-yl)piperidine (503) 1-[3,5-Dibromo-N-[[4-[1,3-dihydro-4-phenyl-2(2H)-oxoimidazol-1-yl]-1-piperidinyl]carbonyl]-D-tyrosyl]-4-(hexahydro-4-methyl-1H-1,4-diazepin-1-yl)piperidine (504) 1-[4-Amino-3,5-dibromo-N-[[4-[3,4-dihydro-2(1H)-oxoquinazolin-3-yl]-1-piperidinyl]carbonyl]-D-phenylalanyl]-4-[(4-methyl-1-piperazinyl)carbonyl]-piperidine (505) 1-[4-Amino-3,5-dibromo-N-[[4-[1,3-dihydro-2(2H)-oxoimidazo[4,5-c]quinolin-3-yl]-1-piperidinyl]carbonyl]-D-phenylalanyl]-4-(1-piperidinyl)carbonyl]-piperidine (506) 1-[N-[[4-[3,4-Dihydro-2(1H)-oxoquinazolin-3-yl]-1-piperidinyl]carbonyl]-3-(trifluoromethyl)-D,L-phenylalanyl]-4-(1-methyl-4-piperidinyl)-piperidine (507) 1-[3-Chloro-N-[[4-[3,4-dihydro-2(1H)-oxoquinazolin-3-yl]-1-piperidinyl]carbonyl]-D,L-phenylalanyl]-4-(1-piperidinyl)-piperidine (508) (R,S)-1-[[4-[3,4-Dihydro-2(1H)-oxoquinazolin-3-yl]-1-piperidinyl]-2-[[3-(trifluoromethyl)phenyl]methyl]-1,4-dioxobutyl]-4-(1-methyl-4-piperidinyl)-piperidine (509) 1-[4-Amino-3,5-dibromo-N-[[4-[4-(3-bromophenyl)-1,3-dihydro-2(2H)-oxoimidazol-1-yl]-1-piperidinyl]carbonyl]-D-phenylalanyl]-4-(exo-8-methyl-8-azabicyclo[3,2,1]oct-3-yl)-piperazine (510) 1-[4-Amino-3,5-dibromo-N-[[4-[1,3-dihydro-4-(3-methoxyphenyl)-2(2H)-oxoimidazol-1-yl]-1-piperidinyl]carbonyl]-D-phenylalanyl]-4-(exo-8-methyl-8-azabicyclo[3,2,1]oct-3-yl)-piperazine (511) 1-[N-[[4-(3,4-Dihydro-2(1H)-oxoquinazolin-3-yl]-1-piperidinyl]carbonyl]-3-methoxy-D,L-phenylalanyl]-4-(1-piperidinyl)-piperidine (512) 1-[N-[[4-(3,4-Dihydro-2(1H)-oxoquinazolin-3-yl)-1-piperidinyl]carbonyl]-3-methoxy-D,L-phenylalanyl]-4-(1-methyl-4-piperidinyl)-piperazine (513) 1-[N-[[4-(3,4-Dihydro-2(1H)-oxoquinazolin-3-yl)-1-piperidinyl]carbonyl]-3-methoxy-D,L-phenylalanyl]-4-(4-pyridinyl)-piperazine (514) 1-[N-[[4-(3,4-Dihydro-2(1H)-oxoquinazolin-3-yl)-1-piperidinyl]carbonyl]-3-methoxy-D,L-phenylalanyl]-4-(exo-8-methyl-8-azabicyclo[3,2,1]oct-3-yl)-piperazine (515) 1-[N-[[4-(3,4-Dihydro-2(1H)-oxoquinazolin-3-yl)-1-piperidinyl]carbonyl]-3-methoxy-D,L-phenylalanyl]-4-(1-ethyl-4-piperidinyl)-piperazine (516) 1-[$N^2$-[3,5-Dibromo-N-[[4-(3,4-dihydro-2(1H)-oxoquinazolin-3-yl)-1-piperidinyl]carbonyl]-L-tyrosyl]-D-lysyl]-4-(4-pyridinyl)-piperazine (517) 1-[$N^2$-[3,5-Dibromo-N-[[4-(3,4-dihydro-2(1H)-oxoquinazolin-3-yl)-1-piperidinyl]carbonyl]-D-tyrosyl]-D-lysyl]-4-(4-pyridinyl)-piperazine (518) 1-[$N^2$-[3,5-Dibromo-N-[[4-(3,4-dihydro-2(1H)-oxoquinazolin-3-yl)-1-piperidinyl]carbonyl]-L-tyrosyl]-L-lysyl]-4-(4-pyridinyl)-piperazine (519) 1-[4-Amino-3,5-dibromo-N-[[4-(1,3-dihydro-4-(3-hydroxyphenyl)-2(2H)-oxoimidazol-1-yl)-1-piperidinyl]carbonyl]-D-phenylalanyl]-4-(1-methyl-4-piperidinyl)-piperidine (520) 1-[4-Amino-N-[[4-[4-[3,5-bis-(trifluoromethyl)phenyl]-1,3-dihydro-2(2H)-oxoimidazol-1-yl]-1-piperidinyl]carbonyl]-3,5-dibromo-D-phenylalanyl]-4-(1-methyl-4-piperidinyl)-piperidine (521) 1-[4-Amino-3,5-dibromo-N-[[4-(3,4-dihydro-2(1H)-oxoquinazolin-3-yl)-1-piperidinyl]carbonyl]-D-phenylalanyl]-4-(4-piperidinyl)-piperidine (522) 1-[3,5-Dibromo-N-[[4-(3,4-dihydro-2(1H)-oxoquinazolin-3-yl)-1-piperidinyl]carbonyl]-D-tyrosyl]-4-(4-piperidinyl)-piperidine (523) 1-[3,5-Dibromo-N-[[4-(3,4-dihydro-2(1H)-oxoquinazolin-3-yl)-1-piperidinyl]carbonyl]-4-(methylsulphonyloxy)-D-phenylalanyl]-4-[1-(methylsulphonyl)-4-piperidinyl]-piperidine (524) 1-[3,5-Dibromo-N-[[4-(3,4-dihydro-2 (1H) -oxoquinazolin-3-yl)-1-piperidinyl]carbonyl]-D-tyrosyl]-4-[1-(methylsulphonyl)-4-piperidinyl]-piperidine (525) 1-[3,5-Dibromo-N-[[4-(3,4-dihydro-2(1H)-oxoquinazolin-3-yl)-1-piperidinyl]carbonyl]-D-tyrosyl]-4-[1-(cyclopropylmethyl)-4-piperidinyl]-piperidine (526) 1-[3,5-Dibromo-N-[[4-(3,4-dihydro-2(1H)-oxoquinazolin-3-yl)-1-piperidinyl]carbonyl]-D-tyrosyl]-4-[1-(hydroxycarbonylmethyl)-4-piperidinyl]-piperidine (527) 1-[N-[[4-(3,4-Dihydro-2(1H)-oxoquinazolin-3-yl)-1-piperidinyl]carbonyl]-3-(2-methyl-4-thiazolyl)-D,L-alanyl]-4-(1-piperidinyl)-piperidine (528) 1-[N-[[4-(3,4-Dihydro-2(1H)-oxoquinazolin-3-yl)-1-piperidinyl]carbonyl]-3-(2-methyl-4-thiazolyl)-D,L-alanyl]-4-(4-pyridinyl)-piperazine (529) (R,S)-1-[2-[(1-Naphthyl)methyl]-4-[4-(3,4-dihydro-2(1H)-oxoquinazolin-3-yl)-1-piperidinyl]-1,4-dioxobutyl]-4-(1-piperi-dinyl)-piperidine (530) (R,S)-1-[2-[(1-Naphthyl)methyl]-4-[4-(3,4-dihydro-2(1H)-oxoquinazolin-3-yl)-1-piperidinyl]-1,4-dioxobutyl]-4-(1-methyl-4-piperidinyl)-piperidine (531) (R,S)-1-[2-[(3-Methoxyphenyl)methyl]-4-[4-(3,4-dihydro-2(1H)-oxoquinazolin-3-yl)-1-piperidinyl]-1,4-dioxobutyl]-4-(1-piperidinyl)-piperidine (532) 1-[N-[[4-[3,4-Dihydro-2(1H)-oxoquinazolin-3-yl]-1-piperidinyl]carbonyl]-3-ethenyl-D,L-phenylalanyl]-4-(hexahydro-1H-1-azepinyl)-piperidine (533) 1-[3,5-Dibromo-N-[[4-(3,4-dihydro-2(1H)-oxopyrido-[3,4-d]pyrimidin-3-yl)-1-piperidinyl]carbonyl]-D-tyrosyl]-4-(1-piperidinyl)-piperidine (534) 1-[4-Amino-3,5-dibromo-N-[[4-(3,4-dihydro-2(1H)-oxopyrido[3,4-d]pyrimidin-3-yl)-1-piperidinyl]carbonyl]-D-phenylalanyl]-4-(1-methyl-4-piperidinyl)-piperidine (535) 1-[3,5-Dibromo-N-[[4-(3,4-dihydro-2(1H)-oxopyrido[3,4-d]pyrimidin-3-yl)-1-piperidinyl]carbonyl]-D-tyrosyl]-4-(1-methyl-4-piperazinyl)-piperidine (536) 1-[4-Amino-3,5-dibromo-N-[[4-(3,4-dihydro-2(1H)-oxopyrido[4,3-d]pyrimidin-3-yl)-1-piperidinyl]carbonyl]-D-phenylalanyl]-4-(1-piperidinyl)-piperidine (537) 1-[3,5-Dibromo-N-[[4-(3,4-dihydro-2(1H)-oxopyrido[4,3-d]pyrimidin-3-yl)-1-piperidinyl]carbonyl]-D-tyrosyl]-4-(1-piperidinyl)-piperidine (538) (R,S)-1-[2-[(1-Naphthyl)methyl]-4-[4-(3,4-dihydro-2(1H)-oxopyrido[3,4-d]pyrimidin-3-yl)-1-piperidinyl]-1,4-dioxobutyl]-4-(1-methyl-4-piperidinyl)-piperidine (539) (R,S)-1-[2-[(1-Naphthyl)methyl]-4-[4-(3,4-dihydro-2 (1H)-oxopyrido[3,4-d]pyrimidin-3-yl)-1-piperidinyl]-1, 4-dioxobutyl]-4-(1-methyl-4-piperazinyl)-piperidine
(540) (R,S)-1-[2-[(1-Naphthyl)methyl]-4-[4-(3,4-dihydro-2 (1H)-oxopyrido[3,4-d]pyrimidin-3-yl)-1-piperidinyl]-1, 4-dioxobutyl]-4-(1-piperidinyl)-piperidine
(541) (R,S)-1-[2-[(3-Ethoxyphenyl)methyl]-4-[4-(3,4-dihydro-2(1H)-oxoquinazolin-3-yl)-1-piperidinyl]-1,4-dioxobutyl]-4-(1-methyl-4-piperazinyl)-piperidine
(542) (R,S)-1-[2-[(3-Ethoxyphenyl)methyl]-4-[4-(3,4-dihydro-2(1H) -oxoquinazolin-3-yl)-1-piperidinyl]-1,4-dioxobutyl]-4-(1-piperidinyl)-piperidine
(543) (R,S)-1-[2-[(3-Ethoxyphenyl)methyl]-4-[4-(3,4-dihydro-2(1H)-oxoquinazolin-3-yl)-1-piperidinyl]-1,4-dioxobutyl]-4-(1-methyl-4-piperidinyl)-piperidine
(544) (R,S)-1-[4-[4-(3,4-Dihydro-2(1H)-oxoquinazolin-3-yl)-1-piperidinyl]-2-[[3-(1-methylethoxy)phenyl]methyl]-1,4-dioxobutyl]-4-(1-methyl-4-piperidinyl)-piperidine
(545) (R,S)-1-[4-[4-(3,4-Dihydro-2(1H)-oxoquinazolin-3-yl)-1-piperidinyl]-2-[[3-(1-methylethoxy)phenyl]methyl]-1,4-dioxobutyl]-4-(1-methyl-4-piperazinyl)-piperidine
(546) (R,S)-1-[4-[4-(3,4-Dihydro-2(1H)-oxoquinazolin-3-yl)-1-piperidinyl]-2-[[3-(1-methylethoxy)phenyl]methyl]-1,4-dioxobutyl]-4-(1-piperidinyl)-piperidine
(547) (R,S)-1-[4-[4-(3,4-Dihydro-2(1H)-oxoquinazolin-3-yl)-1-piperidinyl]-2-[(3,5-dimethylphenyl)methyl]-1,4-dioxobutyl]-4-(1-piperidinyl)-piperidine
(548) (R,S)-1-[4-[4-(3,4-Dihydro-2(1H)-oxoquinazolin-3-yl)-1-piperidinyl]-2-[(3,5-dimethylphenyl)methyl]-1,4-dioxobutyl]-4-(1-methyl-4-piperazinyl)-piperidine
(549) (R,S)-1-[4-[4-(3,4-Dihydro-2(1H)-oxoquinazolin-3-yl)-1-piperidinyl]-2-[(3,5-dimethylphenyl)methyl]-1,4-dioxobutyl]-4-(1-methyl-4-piperidinyl)-piperidine
(550) (R,S)-1-[4-[4-(3,4-Dihydro-2(1H)-oxoquinazolin-3-yl)-1-piperidinyl]-2-[[3-[2-(dimethylamino)ethoxy]phenyl]methyl]-1,4-dioxobutyl]-4-(1-methyl-4-piperazinyl)-piperidine
(551) 1-[3,5-Dibromo-N-[[4-(3,4-dihydro-2(1H)-oxoquinazolin-3-yl)-1-piperidinyl]carbonyl]-D-tyrosyl]-4-[(1-methyl-4-piperazinyl)carbonyl]-piperidine
(552) 1-[4-Amino-3,5-dibromo-N-[[4-[3,4-dihydro-2(1H)-oxoquinazolin-3-yl]-1-piperidinyl]carbonyl]-D-phenylalanyl]-4-[4-(1-oxoethyl)-1-piperazinyl]-piperidine
(553) 1-[3,5-Dibromo-N-[[4-(3,4-dihydro-2(1H)-oxoquinazolin-3-yl)-1-piperidinyl]carbonyl]-D-tyrosyl]-4-[4-(1-oxoethyl)-1-piperazinyl]-piperidine
(554) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-[4-(1-oxoethyl)-1-piperazinyl]-piperidine
(555) 1-[3,5-Dibromo-N-[[4-[1,3-dihydro-4-phenyl-2(2H)-oxoimidazol-1-yl]-1-piperidinyl]carbonyl]-D-tyrosyl]-4-[4-(1-oxoethyl)-1-piperazinyl]-piperidine
(556) 1-[4-Amino-3,5-dibromo-N-[[4-[3,4-dihydro-2(1H)-oxoquinazolin-3-yl]-1-piperidinyl]carbonyl]-D-phenylalanyl]-4-[(1-methyl-4-piperazinyl)carbonyl]-piperazine
(557) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-[(1-methyl-4-piperazinyl)carbonyl]-piperazine
(558) 1-[3,5-Dibromo-N-[[4-(3,4-dihydro-2(1H)-oxoquinazolin-3-yl)-1-piperidinyl]carbonyl]-D-tyrosyl]-4-[(4-pyridinyl)carbonyl]-piperazine
(559) 1-[4-Amino-3,5-dibromo-N-[(4-oxo-1-piperidinyl)carbonyl]-D-phenylalanyl]-4-(1-methyl-4-piperidinyl)-piperidine
(560) 1-[4-Amino-3,5-dibromo-N-[[4-(3,4-dihydro-2(1H)-oxoquinazolin-3-yl)-1-piperidinyl]carbonyl]-D-phenylalanyl]-4-[4-[4-(dimethylamino)butyl]phenyl]-piperazine
(561) 1-[4-Amino-3,5-dibromo-N-[[4-[1,3-dihydro-4-phenyl-2(2H)-oxoimidazol-1-yl]-1-piperidinyl]carbonyl]-D-phenylalanyl]-4-[4-[4-(dimethylamino)butyl]phenyl]-piperazine
(562) 1-[3,5-Dibromo-N-[[4-(3,4-dihydro-2(1H)-oxoquinazolin-3-yl)-1-piperidinyl]carbonyl]-D-tyrosyl]-4-[(1-methyl-4-piperazinyl)carbonyl]-piperazine
(563) 1-[3,5-Dibromo-N-[[4-(1,3-dihydro-4-phenyl-2(2H)-oxoimidazol-1-yl)-1-piperidinyl]carbonyl]-D-tyrosyl]-4-[(1-methyl-4-piperazinyl)carbonyl]-piperazine
(564) 1-[4-Amino-N-[(4-amino-1-piperidinyl)carbonyl]-3, 5-dibromo-D-phenylalanyl]-4-(1-methyl-4-piperidinyl)-piperidine
(565) 1-[4-Amino-3,5-dibromo-N-[[4-(3,4-dihydro-2(1H)-oxoquinazolin-3-yl)-1-piperidinyl]carbonyl]-D-phenylalanyl]-4-[4-(dimethylamino)-1-piperidinyl]-piperidine
(566) 1-[4-Amino-3,5-dibromo-N-[[4-(1,3-dihydro-4-phenyl-2(2H)-oxoimidazol-1-yl)-1-piperidinyl]carbonyl]-D-phenylalanyl]-4-[4-(dimethylamino)-1-piperidinyl]-piperidine
(567) 1-[4-Amino-3,5-dibromo-N-[[4-[2(1H)-oxoquinolin-3-yl]-1-piperidinyl]carbonyl]-D-phenylalanyl]-4-(4-methyl-1-piperazinyl)-piperidine
(568) 1-[4-Amino-3,5-dibromo-N-[[4-[2(1H)-oxoquinolin-3-yl]-1-piperidinyl]carbonyl]-D-phenylalanyl]-4-[4-(dimethylamino)-1-piperidinyl]-piperidine
(569) 1-[3,5-Dibromo-N-[[4-[2(1H)-oxoquinolin-3-yl]-1-piperidinyl]carbonyl]-D-tyrosyl]-4-(4-methyl-1-piperazinyl)-piperidine
(570) 1-[$N^2$-[[4-(3,4-Dihydro-2(1H)-oxoquinazolin-3-yl)-1-piperidinyl]carbonyl]-N'-methyl-D-tryptyl]-4-(1-methyl-4-piperidinyl)-piperidine
(571) 1-[$N^2$-[[4-(3,4-Dihydro-2(1H)-oxoquinazolin-3-yl)-1-piperidinyl]carbonyl]-N'-methyl-D-tryptyl]-4-(4-methyl-1-piperazinyl)-piperidine
(572) 1-[$N^2$-[[4-(1,3-dihydro-4-phenyl-2(2H)-oxoimidazol-1-yl)-1-piperidinyl]carbonyl]-N'-methyl-D-tryptyl]-4-(1-methyl-4-piperidinyl)-piperidine
(573) 1-[$N^2$-[[4-(1,3-dihydro-4-phenyl-2(2H)-oxoimidazol-1-yl)-1-piperidinyl]carbonyl]-N'-methyl-D-tryptyl]-4-(4-methyl-1-piperazinyl)-piperidine
(574) (R,S)-1-[4-[4-(3,4-Dihydro-2(1H)-oxoquinazolin-3-yl)-1-piperidinyl]-2-[(3,4-dichlorophenyl)methyl]-1,4-dioxobutyl]-4-(1-methyl-4-piperidinyl)-piperidine
(575) (R,S)-1-[4-[4-(3,4-Dihydro-2(1H)-oxoquinazolin-3-yl)-1-piperidinyl]-2-[(3,4-dichlorophenyl)methyl]-1,4-dioxobutyl]-4-(4-methyl-1-piperazinyl)-piperidine
(576) 1-[$N^2$-[[4-(3,4-Dihydro-2(1H)-oxoquinazolin-3-yl)-1-piperidinyl]carbonyl]-N'-(1,1-dimethylethoxycarbonyl)-D-tryptyl]-4-(4-methyl-1-piperazinyl)-piperidine
(577) 1-[$N^2$-[[4-(1,3-dihydro-4-phenyl-2(2H)-oxoimidazol-1-yl)-1-piperidinyl]carbonyl]-N'-(1,1-dimethylethoxycarbonyl)-D-tryptyl]-4-(4-methyl-1-piperazinyl)-piperidine
(578) (R,S)-1-[4-[4-(3,4-Dihydro-2(1H)-oxoquinazolin-3-yl)-1-piperidinyl]-2-[(3,5-dibromophenyl)methyl]-1,4-dioxobutyl]-4-(4-methyl-1-piperazinyl)-piperidine
(579) (R,S)-1-[4-[4-(3,4-Dihydro-2(1H)-oxoquinazolin-3-yl)-1-piperidinyl]-2-[(3,5-dibromophenyl)methyl]-1,4-dioxobutyl]-4-(1-methyl-4-piperidinyl)-piperidine (580) 1-[N²-[[4-(1,3-dihydro-4-phenyl-2(2H)-oxoimidazol-1-yl)-1-piperidinyl]carbonyl]-N'-(1,1-dimethylethoxycarbonyl)-D-tryptyl]-4-(1-methyl-4-piperidinyl)-piperidine (581) 1-[N²-[[4-(1,3-dihydro-4-phenyl-2(2H)-oxoimidazol-1-yl)-1-piperidinyl]carbonyl]-N'-(1,1-dimethylethoxycarbonyl)-D-tryptyl]-4-(1-methyl-4-piperidinyl)-piperidine (582) 1-[4-Amino-3,5-dibromo-N-[[4-(2,3-dihydro-4(1H)-oxoquinazolin-3-yl)-1-piperidinyl]carbonyl]-D-phenylalanyl]-4-(1-methyl-4-piperidinyl)-piperidine (583) 1-[N²-[[4-(3,4-Dihydro-2(1H)-oxoquinazolin-3-yl)-1-piperidinyl]carbonyl]-N'-methyl-D-tryptyl]-4-[4-(dimethylamino)-1-piperidinyl]-piperidine (584) 1-[N²-[[4-(1,3-dihydro-4-phenyl-2(2H)-oxoimidazol-1-yl)-1-piperidinyl]carbonyl]-N'-methyl-D-tryptyl]-4-[4-(dimethylamino)-1-piperidinyl]-piperidine (585) 1-[4-Amino-N-[[4-[4-(4-amino-3,5-dibromophenyl)-1,3-dihydro-2(2H)-oxoimidazol-1-yl]-1-piperidinyl]carbonyl]-3,5-dibromo-D-phenylalanyl]-4-(1-piperidinyl)-piperidine (586) 1-[4-Amino-N-[[4-[4-(4-amino-3,5-dibromophenyl)-1,3-dihydro-2(2H)-oxoimidazol-1-yl]-1-piperidinyl]carbonyl]-3,5-dibromo-D-phenylalanyl]-4-(4-methyl-1-piperazinyl)-piperidine (587) 1-[N²-[[4-(3,4-Dihydro-2(1H)-oxoquinazolin-3-yl)-1-piperidinyl]carbonyl]-N'-(1,1-dimethylethoxycarbonyl)-D-tryptyl]-4-[4-(dimethylamino)-1-piperidinyl]-piperidine (588) 1-[N²-[[4-(1,3-dihydro-4-phenyl-2(2H)-oxoimidazol-1-yl)-1-piperidinyl]carbonyl]-N'-(1,1-dimethylethoxycarbonyl)-D-tryptyl]-4-[(dimethylamino)-1-piperidinyl]-piperidine (589) (R,S)-1-[4-[4-(3,4-Dihydro-2(1H)-oxoquinazolin-3-yl)-1-piperidinyl]-2-[(3,5-dibromo-4-methylphenyl)methyl]-1,4-dioxobutyl]-4-(4-methyl-1-piperazinyl)-piperidine (590) (R,S)-1-[4-[4-(3,4-Dihydro-2(1H)-oxoquinazolin-3-yl)-1-piperidinyl]-2-[(3,5-dibromo-4-methylphenyl)methyl]-1,4-dioxobutyl]-4-(1-methyl-4-piperidinyl)-piperidine (591) (R,S)-1-[4-[4-(3,4-Dihydro-2(1H)-oxoquinazolin-3-yl)-1-piperidinyl]-2-[[3,4-difluoro-5-(trifluoromethyl)-phenyl]methyl]-1,4-dioxobutyl]-4-(1-methyl-4-piperidinyl)-piperidine (592) (R,S)-1-[4-[4-(3,4-Dihydro-2(1H)-oxoquinazolin-3-yl)-1-piperidinyl]-2-[[3,4-difluoro-5-(trifluoromethyl)-phenyl]methyl]-1,4-dioxobutyl]-4-(4-methyl-1-piperazinyl)-piperidine (593) (R,S)-1-[4-[4-(3,4-Dihydro-2(1H)-oxoquinazolin-3-yl)-1-piperidinyl]-2-[(3,4-dichlorophenyl)methyl]-1,4-dioxobutyl]-4-(ethoxycarbonyl)-piperidine (594) (R,S)-1-[4-[4-(3,4-Dihydro-2(1H)-oxoquinazolin-3-yl)-1-piperidinyl]-2-[(3,4-dichlorophenyl)methyl]-1,4-dioxobutyl]-4-(ethoxycarbonylmethyl)-piperidine (595) (R,S)-2-[4-[4-(3,4-Dihydro-2(1H)-oxoquinazolin-3-yl)-1-piperidinyl]-2-[(3,4-dichlorophenyl)methyl]-1,4-dioxobutyl]-6-methyl-2,6-diazaspiro[3,4]octane (596) (R,S)-1-[4-[4-(3,4-Dihydro-2(1H)-oxoquinazolin-3-yl)-1-piperidinyl]-2-[(3,4-dichlorophenyl)methyl]-1,4-dioxobutyl]-4-(hydroxycarbonylmethyl)-piperidine (597) (R,S)-1-[4-[4-(3,4-Dihydro-2(1H)-oxoquinazolin-3-yl)-1-piperidinyl]-2-[[1-methyl-1H-indol-3-yl]methyl]-1,4-dioxobutyl]-4-(4-methyl-1-piperazinyl)-piperidine (598) (R,S)-1-[4-[4-(3,4-Dihydro-2(1H)-oxoquinazolin-3-yl)-1-piperidinyl]-2-[[1-methyl-1H-indol-3-yl]methyl]-1,4-dioxobutyl]-4-(1-methyl-4-piperidinyl)-piperidine (599) (R,S)-1-[4-[4-(3,4-Dihydro-2(1H)-oxoquinazolin-3-yl)-1-piperidinyl]-2-(ethoxycarbonyl)-2-[[1-methyl-1H-indol-3-yl]methyl]-1,4-dioxobutyl]-4-(4-methyl-1-piperazinyl)-piperidine (600) (R,S)-1-[4-[4-(Aminocarbonylamino)-1-piperidinyl]-2-[[1-methyl-1H-indol-3-yl]methyl]-1,4-dioxobutyl]-4-(1-methyl-4-piperidinyl)-piperidine (601) (R,S)-1-[4-[4-(Aminocarbonylamino)-1-piperidinyl]-2-(ethoxycarbonyl)-2-[[1-methyl-1H-indol-3-yl]methyl]-1,4-dioxobutyl]-4-(4-methyl-1-piperazinyl)-piperidine (602) (R,S)-1-[4-[4-(3,4-Dihydro-2(1H)-oxoquinazolin-3-yl)-1-piperidinyl]-2-[(3,5-dibromo-4-methoxyphenyl)methyl]-1,4-dioxobutyl]-4-(4-methyl-1-piperazinyl)-piperidine (603) (R,S)-1-[4-[4-(3,4-Dihydro-2(1H)-oxoquinazolin-3-yl)-1-piperidinyl]-2-[(3,4-dichlorophenyl)methyl]-1,4-dioxobutyl]-4-carboxypiperidine (604) (R,S)-1-[4-[4-(3,4-Dihydro-2(1H)-oxoquinazolin-3-yl)-1-piperidinyl]-2-[(3,5-dibromo-4-methoxyphenyl)methyl]-1,4-dioxobutyl]-4-(1-methyl-4-piperidinyl)-piperidine (605) (R,S)-1-[4-[4-(3,4-Dihydro-2(1H)-oxoquinazolin-3-yl)-1-piperidinyl]-2-[[4-fluor-3-(trifluoromethyl)-phenyl]methyl]-1,4-dioxobutyl]-4-(4-methyl-1-piperazinyl)-piperidine (607) (R,S)-1-[4-[4-(3,4-Dihydro-2(1H)-oxoquinazolin-3-yl)-1-piperidinyl]-2-[[4-fluor-3-(trifluoromethyl)-phenyl]methyl]-1,4-dioxobutyl]-4-(1-methyl-4-piperidinyl)-piperidine (607) 1-[N-[[4-[3,4-Dihydro-2(1H)-oxoquinazolin-3-yl]-1-piperidinyl]carbonyl]-3-(trifluoromethyl)-D,L-phenylalanyl]-4-(1-ethyl-4-piperidinyl)-piperazine (608) 1-[N-[[4-[3,4-Dihydro-2(1H)-oxoquinazolin-3-yl]-1-piperidinyl]carbonyl]-3-(trifluoromethyl)-D,L-phenylalanyl]-4-(1-methyl-4-piperidinyl)-piperazine (609) 1-[N-[[4-[3,4-Dihydro-2(1H)-oxoquinazolin-3-yl]-1-piperidinyl]carbonyl]-3-(trifluoromethyl)-D,L-phenylalanyl]-4-(1-piperidinyl)-piperidine (610) 1-[N-[[4-[3,4-Dihydro-2(1H)-oxoquinazolin-3-yl]-1-piperidinyl]carbonyl]-3-(trifluoromethyl)-D,L-phenylalanyl]-4-(4-pyridinyl)-piperazine (611) 1-[N-[[4-[3,4-Dihydro-2(1H)-oxoquinazolin-3-yl]-1-piperidinyl]carbonyl]-3-(trifluoromethyl)-D,L-phenylalanyl]-4-(4-pyridinyl)-piperidine (612) (R,S)-1-[2-[(4-Amino-3,5-dibromophenyl)methyl]-4-[4-(3,4-dihydro-2(1H)-oxoquinazolin-3-yl)-1-piperidinyl]-1,4-dioxobutyl]-4-(1-piperidinyl)-piperidine (613) 1-[3-Chloro-N-[[4-[3,4-dihydro-2(1H)-oxoquinazolin-3-yl]-1-piperidinyl]carbonyl]-D,L-phenylalanyl]-4-(1-methyl-4-piperidinyl)-piperidine (614) 1-[3-Chloro-N-[[4-[3,4-dihydro-2(1H)-oxoquinazolin-3-yl]-1-piperidinyl]carbonyl]-D,L-phenylalanyl]-4-(hexahydro-1H-1-azepinyl)-piperidine (615) 1-[3-Chloro-N-[[4-[3,4-dihydro-2(1H)-oxoquinazolin-3-yl]-1-piperidinyl]carbonyl]-D,L-phenylalanyl]-4-(cyclopentyl)-piperazine (616) (R,S)-1-[4-[4-(3,4-Dihydro-2(1H)-oxoquinazolin-3-yl)-1-piperidinyl]-2-[(3-methylphenyl)methyl]-1,4-dioxobutyl]-4-(1-piperidinyl)-piperidine (617) (R,S)-1-[4-[4-(3,4-Dihydro-2(1H)-oxoquinazolin-3-yl)-1-piperidinyl]-2-[[3-(trifluoromethyl)-phenyl]methyl]-1,4-dioxobutyl]-4-(hexahydro-1H-1-azepinyl)-piperidine (618) (R,S)-1-[4-[4-(3,4-Dihydro-2(1H)-oxoquinazolin-3-yl)-1-piperidinyl]-2-[[3-(trifluoromethyl)-phenyl]methyl]-1,4-dioxobutyl]-4-(exo-8-methyl-8-azabicyclo[3,2,1]oct-3-yl)-piperazine (619) 1-[3-Bromo-N-[[4-(1,3-dihydro-4-phenyl-2(2H)-oxoimidazol-1-yl)-1-piperidinyl]carbonyl]-D,L-phenylalanyl]-4-(1-piperidinyl)-piperidine
(620) 1-[3-cyano-N-[[4-[3,4-dihydro-2(1H)-oxoquinazolin-3-yl]-1-piperidinyl]carbonyl]-D,L-phenylalanyl]-4-(1-piperidinyl)-piperidine
(621) 1-[N-[[4-[3,4-Dihydro-2(1H)-oxoquinazolin-3-yl]-1-piperidinyl]carbonyl]-3-methyl-D,L-phenylalanyl]-4-(1-piperidinyl)-piperidine
(622) 1-[N-[[4-(1,3-Dihydro-4-phenyl-2(2H)-oxoimidazol-1-yl)-1-piperidinyl]carbonyl]-3-methyl-D,L-phenylalanyl]-4-(1-piperidinyl)-piperidine
(623) 1-[3-Methyl-N-[[4-[3,4-dihydro-2(1H)-oxothieno[3,4-d]-pyrimidin-3-yl]-1-piperidinyl]carbonyl]-D,L-phenylalanyl]-4-(1-piperidinyl)-piperidine
(624) 1-[N-[[4-[1,3-Dihydro-4-(3-methoxyphenyl)-2(2H)-oxoimidazol-1-yl]-1-piperidinyl]carbonyl]-3-methyl-D,L-phenylalanyl]-4-(1-piperidinyl)-piperidine
(625) 1-[N-[[4-[1,3-Dihydro-4-[(3-(trifluoromethyl)-phenyl]-2(2H)-oxoimidazol-1-yl]-1-piperidinyl]carbonyl]-3-methyl-D,L-phenylalanyl]-4-(1-piperidinyl)-piperidine
(626) 1-[3-Bromo-N-[[4-[1,3-dihydro-4-[(3-(trifluoromethyl)-phenyl]-2(2H)-oxoimidazol-1-yl]-1-piperidinyl]carbonyl]-D,L-phenylalanyl]-4-(1-piperidinyl)-piperidine
(627) 1-[3-Bromo-N-[[4-[3,4-dihydro-2(1H)-oxothieno[3,4-d]-pyrimidin-3-yl]-1-piperidinyl]carbonyl]-D,L-phenylalanyl]-4-(1-piperidinyl)-piperidine
(628) (R,S)-1-[4-[4-(3,4-Dihydro-2(1H)-oxoquinazolin-3-yl)-1-piperidinyl]-2-[[3-(trifluoromethyl)-phenyl]methyl]-1,4-dioxobutyl]-4-(1-piperidinyl)-piperidine
(629) (R,S)-1-[4-[4-(3,4-Dihydro-2(1H)-oxoquinazolin-3-yl)-1-piperidinyl]-2-[[3-(trifluoromethyl)-phenyl]methyl]-1,4-dioxobutyl]-4-(1-methyl-4-piperidinyl)-piperazine
(630) (R,S)-1-[4-[4-(3,4-Dihydro-2(1H)-oxoquinazolin-3-yl)-1-piperidinyl]-2-[[3-(trifluoromethyl)-phenyl]methyl]-1,4-dioxobutyl]-4-(4-pyridinyl)-piperazine
(631) (R,S)-4-[4-(3,4-Dihydro-2(1H)-oxoquinazolin-3-yl)-1-piperidinyl]-4-oxo-2-[[3-(trifluoromethyl)-phenyl]methyl]-N-[2-(4-methyl-1-piperazinyl)ethyl]-butanamide
(632) 1-[N-[[4-[3,4-Dihydro-2(1H)-oxoquinazolin-3-yl]-1-piperidinyl]carbonyl]-3-(1H-tetrazol-5-yl)-D,L-phenylalanyl]-4-(1-piperidinyl)-piperidine
(633) 1-[3-Bromo-N-[[4-[1,3-dihydro-4-(3-methoxyphenyl)-2(2H)-oxoimidazol-1-yl]-1-piperidinyl]carbonyl]-D,L-phenylalanyl]-4-(1-piperidinyl)-piperidine
(634) (R,S)-1-[4-[4-(3,4-Dihydro-2(1H)-oxoquinazolin-3-yl)-1-piperidinyl]-2-[(2-naphthyl)methyl]-1,4-dioxobutyl]-4-(1-piperidinyl)-piperidine
(635) (R,S)-1-[4-[4-(3,4-Dihydro-2(1H)-oxoquinazolin-3-yl)-1-piperidinyl]-2-[[2-(trifluoromethyl)phenyl]methyl]-1,4-dioxobutyl]-4-(1-piperidinyl)-piperidine
(636) 1-[N-[[4-[3,4-Dihydro-2(1H)-oxoquinazolin-3-yl]-1-piperidinyl]carbonyl]-3-nitro-D,L-phenylalanyl]-4-(1-methyl-4-piperidinyl)-piperidine
(637) (R,S)-1-[2-[(4-Amino-3,5-dibromophenyl)methyl]-4-[4-(3,4-dihydro-2(1H)-oxoquinazolin-3-yl)-1-piperidinyl]-1,4-dioxobutyl]-4-(1-methyl-4-piperidinyl)-piperidine
(638) (R,S)-1-[4-[4-(3,4-Dihydro-2(1H)-oxoquinazolin-3-yl)-1-piperidinyl]-2-[[2-(trifluoromethyl)phenyl]methyl]-1,4-dioxobutyl]-4-(1-methyl-4-piperidinyl)-piperidine
(639) (R,S)-1-[2-[[3,5-Bis-(trifluoromethyl)phenyl]methyl]-4-[4-(3,4-dihydro-2(1H)-oxoquinazolin-3-yl)-1-piperidinyl]-1,4-dioxobutyl]-4-(1-methyl-4-piperidinyl)-piperidine
(640) (R,S)-1-[4-[4-(3,4-Dihydro-2(1H)-oxoquinazolin-3-yl)-1-piperidinyl]-2-[(3,4-dimethoxyphenyl)methyl]-1,4-dioxobutyl]-4-(1-methyl-4-piperidinyl)-piperidine
(641) (R,S)-1-[4-[4-(3,4-Dihydro-2(1H)-oxoquinazolin-3-yl)-1-piperidinyl]-2-[(2-naphthyl)methyl]-1,4-dioxobutyl]-4-(1-methyl-4-piperidinyl)-piperidine
(642) (R,S)-1-[4-[4-(3,4-Dihydro-2(1H)-oxoquinazolin-3-yl)-1-piperidinyl]-2-[(3,4-dimethoxyphenyl)methyl]-1,4-dioxobutyl]-4-(1-piperidinyl)-piperidine
(643) (R,S)-1-[4-[4-(3,4-Dihydro-2(1H)-oxoquinazolin-3-yl)-1-piperidinyl]-2-[[3-(trifluoromethyl)phenyl]methyl]-1,4-dioxobutyl]-4-(4-piperidinyl)-piperidine
(644) (R,S)-1-[4-[4-(3,4-Dihydro-2(1H)-oxothieno[3,4-d]pyrimidin-3-yl)-1-piperidinyl]-2-[[3-(trifluoromethyl)phenyl]methyl]-1,4-dioxobutyl]-4-(1-methyl-4-piperidinyl)-piperidine
(645) (R,S)-1-[2-[(3-Bromophenyl)methyl]-4-[4-(3,4-dihydro-2(1H)-oxoquinazolin-3-yl)-1-piperidinyl]-1,4-dioxobutyl]-4-(1-methyl-4-piperidinyl)-piperidine
(646) (R,S)-1-[2-[(3-Bromophenyl)methyl]-4-[4-(3,4-dihydro-2(1H)-oxoquinazolin-3-yl)-1-piperidinyl]-1,4-dioxobutyl]-4-(1-piperidinyl)-piperidine
(647) (R,S)-1-[4-[4-(3,4-Dihydro-2(1H)-oxoquinazolin-3-yl)-1-piperidinyl]-2-[[3-(1-propen-3-yl)phenyl]methyl]-1,4-dioxobutyl]-4-(1-piperidinyl)-piperidine
(648) (R,S)-1-[2-[3-(Biphenylyl)methyl]-4-[4-(3,4-dihydro-2(1H)-oxoquinazolin-3-yl)-1-piperidinyl]-1,4-dioxobutyl]-4-(1-piperidinyl)-piperidine
(649) (R,S)-1-[4-[4-(3,4-Dihydro-2(1H)-oxoquinazolin-3-yl)-1-piperidinyl]-2-[[3-(pyridinyl)phenyl]methyl]-1,4-dioxobutyl]-4-(1-piperidinyl)-piperidine
(650) (R,S)-1-[4-[4-(3,4-Dihydro-2(1H)-oxoquinazolin-3-yl)-1-piperidinyl]-2-[[3-(2-thiazolyl)phenyl]methyl]-1,4-dioxobutyl]-4-(1-piperidinyl)-piperidine
(651) (R,S)-1-[4-[4-(3,4-Dihydro-2(1H)-oxoquinazolin-3-yl)-1-piperidinyl]-2-[[3-(2-furyl)phenyl]methyl]-1,4-dioxobutyl]-4-(1-piperidinyl)-piperidine
(652) (R,S)-1-[4-[4-(3,4-Dihydro-2(1H)-oxoquinazolin-3-yl)-1-piperidinyl]-2-[(3-propylphenyl)methyl]-1,4-dioxobutyl]-4-(1-piperidinyl)-piperidine
(653) (R,S)-1-[4-(2,4-Dihydro-5-phenyl-3(3H)-oxotriazol-2-yl)-1-piperidinyl]-2-[[3-(trifluoromethyl)phenyl]methyl]-1,4-dioxobutyl]-4-(1-methyl-4-piperidinyl)-piperidine
(654) (R,S)-1-[4-[1,3-Dihydro-2(2H)-oxoimidazo[4,5-c]quinolin-3-yl]-1-piperidinyl]-2-[[3-(trifluoromethyl)phenyl]methyl]-1,4-dioxobutyl]-4-(1-methyl-4-piperidinyl)-piperidine
(655) (R,S)-1-[2-[(4-Quinolinyl)methyl]-4-[4-(3,4-dihydro-2(1H)-oxoquinazolin-3-yl)-1-piperidinyl]-1,4-dioxobutyl]-4-(1-methyl-4-piperidinyl)-piperidine
(656) (R,S)-1-[2-[(4-Quinolinyl)methyl]-4-[4-(3,4-dihydro-2(1H)-oxoquinazolin-3-yl)-1-piperidinyl]-1,4-dioxobutyl]-4-(1-piperidinyl)-piperidine
(657) 1-[2-[((1,2,3,4-Tetrahydro-1-naphthyl)methyl]-4-[4-(3,4-dihydro-2(1H)-oxoquinazolin-3-yl)-1-piperidinyl]-1,4-dioxobutyl]-4-(1-methyl-4-piperidinyl)-piperidine (mixture of diastereomers)
(658) (R,S)-1-[4-[4-(3,4-Dihydro-2(1H)-oxoquinazolin-3-yl)-1-piperidinyl]-2-[(3,4-dibromophenyl)methyl]-1,4-dioxobutyl]-4-(1-methyl-4-piperidinyl)-piperidine
(659) (R,S)-1-[4-[4-(3,4-Dihydro-2(1H)-oxoquinazolin-3-yl)-1-piperidinyl]-2-[(3,4-dibromophenyl)methyl]-1,4-dioxobutyl]-4-(4-methyl-1-piperazinyl)-piperidine
(660) (R,S)-1-[2-[(4-Quinolinyl)methyl]-4-[4-(3,4-dihydro-2(1H)-oxoquinazolin-3-yl)-1-piperidinyl]-1,4-dioxobutyl]-4-(4-methyl-1-piperazinyl)-piperidine (661) (R,S)-1-[4-[4-(3,4-Dihydro-2(1H)-oxoquinazolin-3-yl)-1-piperidinyl]-2-[(4-hydroxy-3,5-dimethylphenyl)methyl]-1,4-dioxobutyl]-4-(1-piperidinyl)-piperidine (662) (R,S)-1-[4-[4-(3,4-Dihydro-2(1H)-oxoquinazolin-3-yl)-1-piperidinyl]-2-[(4-hydroxy-3,5-dimethylphenyl)methyl]-1,4-dioxobutyl]-4-(4-methyl-1-piperazinyl)-piperidine (663) (R,S)-1-[4-[4-(3,4-Dihydro-2(1H)-oxoquinazolin-3-yl)-1-piperidinyl]-2-[(4-hydroxy-3,5-dimethylphenyl)methyl]-1,4-dioxobutyl]-4-(1-methyl-4-piperidinyl)-piperidine (664) (R,S)-1-[4-[4-(3,4-Dihydro-2(1H)-oxoquinazolin-3-yl)-1-piperidinyl]-2-[(4-methoxy-3,5-dimethylphenyl)methyl]-1,4-dioxobutyl]-4-(1-piperidinyl)-piperidine (665) (R,S)-1-[4-[4-(3,4-Dihydro-2(1H)-oxoquinazolin-3-yl)-1-piperidinyl]-2-[(4-methoxy-3,5-dimethylphenyl)methyl]-1,4-dioxobutyl]-4-(4-methyl-1-piperazinyl)-piperidine (666) (R,S)-1-[4-[4-(3,4-Dihydro-2(1H)-oxoquinazolin-3-yl)-1-piperidinyl]-2-[(4-methoxy-3,5-dimethylphenyl)methyl]-1,4-dioxobutyl]-4-(1-methyl-4-piperidinyl)-piperidine (667) (R,S)-1-[4-[4-(3,4-Dihydro-2(1H)-oxoquinazolin-3-yl)-1-piperidinyl]-2-[(1-naphthyl)methyl]-1,4-dioxobutyl]-4-(4-methyl-1-piperazinyl)-piperidine (668) (R,S)-1-[4-[4-(3,4-Dihydro-2(1H)-oxoquinazolin-3-yl)-1-piperidinyl]-2-[(1-naphthyl)methyl]-1,4-dioxobutyl]-4-(1-methylsulphonyl-4-piperidinyl)-piperidine (669) (R,S)-1-[2-[3,5-Dibromo-4-methylphenyl)methyl]-4-[4-(3,4-dihydro-2(1H)-oxoquinazolin-3-yl)-1-piperidinyl]-1,4-dioxobutyl]-4-[4-[4-(dimethylamino)butyl]phenyl]-piperazine (670) (R,S)-1-[4-[4-(3,4-Dihydro-2(1H)-oxoquinazolin-3-yl)-1-piperidinyl]-2-[[4-(1,1-dimethylethyl)phenyl]methyl]-1,4-dioxobutyl]-4-(1-methyl-4-piperidinyl)-piperidine (671) (R,S)-1-[4-[4-(3,4-Dihydro-2(1H)-oxoquinazolin-3-yl)-1-piperidinyl]-2-[[4-(1,1-dimethylethyl)phenyl]methyl]-1,4-dioxobutyl]-4-(1-methyl-4-piperidinyl)-piperidine (672) (R,S)-1-[2-[(3,4-Dichlorophenyl)methyl]-4-[4-(3,4-dihydro-2(1H)-oxoquinazolin-3-yl)-1-piperidinyl]-1,4-dioxobutyl]-4-[4-(dimethylaminomethyl)phenyl]-piperidine and the salts thereof.

The compounds of general formula I are prepared by methods which are known in principle, particularly using processes derived from peptide chemistry (cf. for example Houben-Weyl, Methoden der Organischen Chemie, Vol. 15/2). The amino protecting groups used may be those described in Houben-Weyl, Methoden der Organischen Chemie, Vol. 15/1, of which urethane protecting groups such as the fluorenylmethoxycarbonyl, phenylmethoxycarbonyl or tert.-butyloxycarbonyl group are preferred. Any functional groups present in the groups $R^2$ and/or A of the compounds of general formula I or in the precursors thereof are additionally protected by suitable protecting groups in order to prevent side reactions (cf. for example: G. B. Fields et al., Int. J. Peptide Protein Res. 35, 161 (1990); T. W. Greene, Protective Groups in Organic Synthesis). Examples of side-chain-protected amino acids of this kind include, in particular, Arg (NO₂), Arg(Mtr), Arg(di-Z), Arg(Pmc), Lys(Boc), Lys(Z), Orn(Boc), Orn(Z), Lys(Cl-Z) which are commercially obtainable, possibly in the form of derivatives. Particular care should be taken to ensure that so-called orthogonal combinations of protecting groups are used to protect the α-amino and the side chain amino group, e.g.:

| Protection of the N (side chain) | N$^\alpha$-protection |
|---|---|
| p-Toluenesulphonyl | Phenylmethoxycarbonyl |
|  | tert.Butyloxycarbonyl |
| Phenylmethoxycarbonyl | (4-Methoxyphenyl)methoxycarbonyl |
|  | tert.Butoxycarbonyl |
|  | Adamantyloxycarbonyl |
|  | Biphenylylisopropyloxycarbonyl |
|  | Isonicotinoyloxycarbonyl |
|  | o-Nitrophenylsulphenyl |
|  | Formyl |
| tert.Butoxycarbonyl | Phenylmethoxycarbonyl |
|  | p-Toluenesulphonyl |
|  | o-Nitrophenylsulphenyl |
|  | Biphenylylisopropyloxycarbonyl |
|  | 9-Fluorenylmethoxycarbonyl |
| Acetyl, Trifluoroacetyl, Formyl, (2-Chlorophenyl)-methoxycarbonyl, (4-Chlorophenyl)methoxycarbonyl, 4-(Nitrophenyl)methoxycarbonyl, Phthaloyl | tert.Butyloxycarbonyl |

Instead of protecting amino groups in the side chain, amino acids or derivatives thereof which carry precursor functions and in particular are substituted by nitro or cyano in the side chain, such as 5-o-cyanonorvalin may also be used.

The basic functions in the side chains of α-amino acids which are not commercially obtainable and which are characterised, for example, by (aminoiminomethyl) groups, may be protected in the same way as is used for protecting the side chains of arginine and its derivatives (cf. also M. Bodanszky, "Peptide Chemistry", Springer-Verlag, 1988, p. 94-97); protecting groups which are particularly suitable for the (aminoiminomethyl)- group are the p-toluenesulphonyl, mesitylene sulphonyl- (Mts), methoxytrimethylphenylsulphonyl- (Mtr), 2,2,5,7,8-pentamethyl-chroman-6-sulphonyl- (Pmc), pentachlorophenoxycarbonyl- and nitro-protecting groups.

For the actual coupling, the methods known from peptide chemistry are used (see Houben-Weyl, for example, Methoden der Organischen Chemie, Vol. 15/2). It is preferable to use carbodiimides such as dicyclohexylcarbodiimide (DCC), diisopropylcarbodiimide (DIC) or ethyl-(3-dimethylaminopropyl)-carbodiimide, O-(1H-benzotriazol-1-yl)N,N-N',N'-tetramethyluronium-hexafluorophosphate (HBTU) or tetrafluoroborate (TBTU) or 1H-benzotriazol-1-yloxy-tris-(dimethylamino)-phosphonium hexafluorophosphate (BOP). By the addition of 1-hydroxybenzotriazole (HOBt) or 3-hydroxy-4-oxo-3,4-dihydro-1,2,3-benzotriazine (HOObt) racemisation may additionally be suppressed, if desired, or the reaction rate may be increased. The couplings are normally carried out with equimolar amounts of the coupling components and the coupling reagent in solvents such as dichloromethane, tetrahydrofuran, acetonitrile, dimethylformamide (DMF), dimethylacetamide (DMA), N-methylpyrrolidone (NMP) or mixtures thereof and at temperatures between −30 and +30° C., preferably between −20 and +20° C. If necessary, N-ethyl-diisopropylamine (DIEA) is preferred as an additional auxiliary base (Hünig base).

The so-called "anhydride method" (cf. also M. Bodanszky, "Peptide Chemistry", Springer-Verlag 1988, p. 58-59; M. Bodanszky, "Principles of Peptide Synthesis", Springer-Verlag 1984, p. 21-27) was used as another coupling method for the synthesis of compounds of general formula I. The "mixed anhydride method" is preferred, in the variant according to Vaughan (J. R. Vaughan Jr., J. Amer. Chem. Soc. 73, 3547 (1951)), in which the mixed anhydride is obtained from the optionally $N^2$-protected α-amino acid which is to be coupled, and the mono-isobutylcarbonate, using isobutylchlorocarbonate in the presence of base such as 4-methylmorpholine or 4-ethylmorpholine. The preparation of this mixed anhydride and the coupling with amines are carried out in a one-pot process using the above-mentioned solvents at temperatures between −20 and +20° C., preferably between 0 and +20° C.

Any protecting groups present in the side chains of α-amino acid partial structures are finally cleaved, after the formation of the N— and C-terminally substituted amino acid derivative, with suitable reagents which are also known from the literature in principle, specifically arylsulphonyl and hetarylsulphonyl protecting groups, preferably by acidolysis, i.e. by the action of strong acids, preferably trifluoroacetic acid, nitro- and arylmethoxycarbonyl protecting groups are preferably cleaved by hydrogenolysis, e.g. using hydrogen in the presence of palladium black and with glacial acetic acid as solvent. If the substrate contains functions which are sensitive to hydrogenolysis, e.g. halogen atoms such as chlorine, bromine or iodine, a phenylmethanol or hetarylmethanol function or some other benzyl heteroatom bond, particularly a benzyl-oxygen bond, the nitro group may also be cleaved non-hydrogenolytically, e.g. with zinc/2N trifluoroacetic acid (cf. also A. Turan, A. Patthy and S. Bajusz, Acta Chim. Acad. Sci. Hung, Tom. 85 (3), 327-332 [1975]; C.A. 83, 206526y [1975]), with tin(II)-chloride in 60% aqueous formic acid (see also: SUNSTAR KK, JA-A-3271-299), with zinc in the presence of acetic acid (cf. also: A. Malabarba, P. Ferrari, G. Cietto, R. Pallanza and M. Berti, J. Antibiot. 42 (12), 1800-1816 (1989)) or excess aqueous 20% titanium(III)-chloride in aqueous methanol and in the presence of aqueous ammonium acetate buffer at 24° C. (see also: R. M. Freidinger, R. Hirschmann and D. F. Veber, J. Org. Chem. 43 (25), 4800-4803 [1978]).

Any precursor functions which may be present in the side chain of the α-amino acid may also subsequently be converted by hydrogenolysis into the desired amino functions; nitroalkyl groups yield aminoalkyl groups under conditions which will be familiar to the chemist, whilst the cyano group is converted into the aminomethyl group.

Alternatively, nitrile functions may also be reduced with complex hydrides which are selective in relation to other critical functions contained in the molecule, particularly amide groups (cf. also: J. Seyden-Penne, "Reductions by the Alumino- and Borohydrides in Organic Synthesis", VCH Publishers Inc., 1991, p. 132ff.), e.g. with sodium borohydride in methanol and in the presence of cobalt(II)-chloride, with sodium borohydride in tetrahydrofuran in the presence of trifluoroacetic acid or with tetrakis-(n-butyl)-ammonium borohydride in dichloromethane; the reduction of aliphatic nitro function to the primary amino-function is also possible with sodium borohydride in the presence of tin(II)-chloride or copper(II)-acetylacetonate, without affecting the carboxamide groups present in type I compounds (see also: J. Seyden-Penne, ibid. p. 137ff.).

The following methods are particularly suitable for preparing the compounds of general Formula I according to the invention:

a) In order to prepare compounds of general formula I, wherein
R denotes an unbranched $C_{1-7}$-alkyl group which may be substituted in the ω-position
by a $C_{4-10}$-cycloalkyl group,
by one or two phenyl groups, by a 1-naphthyl, 2-naphthyl or biphenylyl group, by a 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-2H-2-oxoimidazopyridinyl, 1,3-dihydro-2(2H)-oxoimidazo[4,5-c]quinolin-3-yl, 1,3-dihydro-2H-2-oxoimidazol-1-yl or 3,4-dihydro-2(1H)-oxopyrimidin-3-yl group, wherein the latter two groups may each be mono- or disubstituted in the 4- and/or 5-position or in the 5- and/or 6-position by lower straight chained or branched alkyl groups, by phenyl, biphenylyl, pyridinyl, diazinyl, furyl, thienyl, pyrrolyl, 1,3-oxazolyl, 1,3-thiazolyl, isoxazolyl, pyrazolyl-1-methylpyrazolyl, imidazolyl- or 1-methylimidazolyl-groups and the substituents may be identical or different, by a 5-membered heteroaromatic ring linked via a carbon atom, which contains a nitrogen, oxygen or sulphur atom or, in addition to a nitrogen atom, contains an oxygen, sulphur or additional nitrogen atom, whilst a nitrogen atom of an imino group may be substituted by an alkyl group, or by a 6-membered heteroaromatic ring linked via a carbon atom, which contains one, two or three nitrogen atoms, whilst a 1,4-butadienylene group may be attached both to the above-mentioned 5-membered heteroaromatic monocyclic rings and to the 6-membered heteroaromatic monocyclic rings, in each case via two adjacent carbon atoms, and the bicyclic heteroaromatic rings thus formed may also be bound via a carbon atom of the 1,4-butadienylene group, and whilst the phenyl, naphthyl and biphenylyl groups mentioned above for the substitution of the alkyl groups in the (ω-position and optionally also partially hydrogenated mono- and bicyclic heteroaromatic rings in the carbon skeleton may additionally be mono-, di- or trisubstituted by fluorine, chlorine or bromine atoms or by alkyl groups, $C_{3-8}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl)carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl- or trifluoromethylsulphonyl groups, wherein the substituents may be identical or different and the above-mentioned benzoyl, benzoylamino and benzoylmethylamino groups may in turn additionally be substituted in the phenyl moiety by a fluorine, chlorine or bromine atom or by an alkyl, trifluoromethyl, amino or acetylamino group, or the group of formula

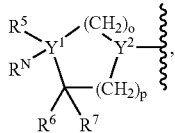

(II)

wherein
$R^5, R^6, R^7, R^N, Y^1$, o and p are as hereinbefore defined,
$Y^2$ denotes a CH— group and
Z denotes an $NR^1$— group, wherein $R^1$ is as hereinbefore defined:
coupling carboxylic acids of general formula VII, $$RCO_2H \qquad (VII)$$

wherein
R is as hereinbefore defined,
with compounds of general formula VIII,

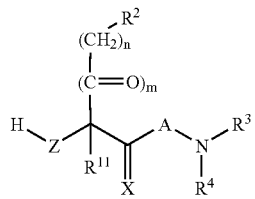

(VIII)

wherein
$R^2, R^3, R^4, R^{11}, A, X, m$ and n are as hereinbefore defined, and
Z denotes an $NR^1$— group, wherein $R^1$ is as hereinbefore defined, and, if necessary, subsequently cleaving any protecting groups or modifying precursor functions in accordance with the methods described hereinbefore.

The coupling is carried out using the methods known from peptide chemistry described above, particularly using DCC, DIC, HBTU, TBTU or BOP as reagents or using the mixed anhydride method.

b) In order to prepare compounds of general formula I wherein R is defined as in a), Z denotes the $NR^1$— group and $R^1, R^2, R^3, R^4, R^{11}, A, X, m$ and n are as hereinbefore defined:
coupling compounds of general formula IX, $$R-CO-Nu \qquad (IX)$$

wherein
R is defined as in a) and
Nu denotes a leaving group, for example a halogen atom such as the chlorine, bromine- or iodine atom, an alkylsulphonyloxy group having 1 to 10 carbon atoms in the alkyl moiety, a phenylsulphonyloxy or naphthylsulphonyloxy group optionally mono-, di- or trisubstituted by chlorine or bromine atoms or by methyl- or nitro groups, wherein the substituents may be identical or different, a 1H-imidazol-1-yl, a 1H-pyrazol-1-yl-optionally substituted by 1 or 2 methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yloxy, 2,5-dioxopyrrolidin-1-yloxy, phthalimidyloxy, 1H-benzotriazol-1-yloxy or azide group, with compounds of general formula VIII,

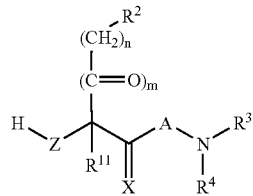

(VIII)

wherein
$R^2, R^3, R^4, R^{11}, A, X, m$ and n are as hereinbefore defined and
Z denotes an $NR^1$— group, whilst $R^1$ is as hereinbefore defined,
and, if necessary, subsequently cleaving protecting groups or modifying precursor functions using the methods described above.

The reaction is carried out under Schotten-Baumann- or Einhorn-conditions, i.e. the components are reacted in the presence of at least one equivalent of an auxiliary base at temperatures between −50° C. and +120° C., preferably between −10° C. and +30° C., optionally in the presence of solvents. Auxiliary bases which may be used are preferably alkali-metal and alkaline earth metal hydroxides, e.g. sodium hydroxide, potassium hydroxide or barium hydroxide, alkali metal carbonates, e.g. sodium carbonate, potassium carbonate or cesium carbonate, alkali metal acetate, e.g. sodium- or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-Diazabicyclo[2,2,2]octane or 1,8-diazabicyclo-[5,4,0]undec-7-ene, whilst the solvents which may be used include, for example, dichloromethane, tetrahydrofuran, 1,4-dioxane, acetonitrile, dimethylformamide, dimethylacetamide, N-methyl-pyrrolidone or mixtures thereof; if alkali metal or alkaline earth metal hydroxides, alkali metal carbonates or -acetates are used as auxiliary bases, water may also be added to the reaction mixture as a cosolvent.

c) In order to prepare compounds of general formula I wherein
R denotes an unbranched $C_{1-6}$-alkylamino group optionally substituted at the nitrogen atom by a $C_{1-6}$-alkyl group or by a phenylmethyl group, which may be substituted in the ω-position
by a $C_{4-10}$-cycloalkyl group,
by one or two phenyl groups, by a 1-naphthyl, 2-naphthyl- or biphenylyl group,
by a 1H-indol-3-yl, 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-4-

(3-thienyl)-2H-2-oxoimidazol-1-yl, 1,3-dihydro-4-phenyl-2H-2-oxoimidazol-1-yl, 1,3-dihydro-5-phenyl-2H-2-oxoimidazol-1-yl, 1,3-dihydro-2(2H)-oxoimidazo[4,5-c]quinolin-3-yl, 3,4-dihydro-5-phenyl-2(1H)-oxopyrimidin-3-yl, 3,4-dihydro-6-phenyl-2(1H)-oxopyrimidin-3-yl- or 1,3-dihydro-2H-2-oxoimidazo[4,5-b]pyridin-3-yl-group, by a 5-membered heteroaromatic ring linked via a carbon atom, which contains a nitrogen, oxygen or sulphur atom or, in addition to a nitrogen atom, contains an oxygen, sulphur or an additional nitrogen atom, whilst a nitrogen atom of an imino group may be substituted by an alkyl group, or by a 6-membered heteroaromatic ring linked via a carbon atom and containing 1, 2 or 3 nitrogen atoms, whilst a 1,4-butadienylene group may be attached both to the 5-membered and to the 6-membered heteroaromatic monocyclic rings via two adjacent carbon atoms in each case and the bicyclic heteroaromatic rings thus formed may also be bound via a carbon atom of the 1,4-butadienylene group, whilst the phenyl, naphthyl and biphenylyl groups mentioned above for the substitution of the alkyl moiety of the alkylamino groups in the ω-position and optionally partially hydrogenated mono- and bicyclic heteroaromatic rings in the carbon skeleton may additionally be mono-, di- or trisubstituted by fluorine, chlorine or bromine atoms, by alkyl groups, $C_{3-8}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl)carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl- or trifluoromethylsulphonyl groups, whilst the substituents may be identical or different and the above-mentioned benzoyl, benzoylamino- and benzoylmethylamino groups in turn may additionally be substituted in the phenyl moiety by a fluorine, chlorine or bromine atom or by an alkyl, trifluoromethyl, amino- or acetylamino group, or the group of formula

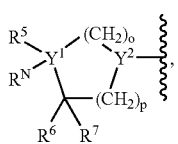

(II)

wherein $R^5$, $R^6$, $R^7$, $R^N$, $Y^1$, o and p are as hereinbefore defined, $Y^2$ denotes the N-atom and Z denotes the $NR^1$— group, wherein $R^1$ is as hereinbefore defined:

reacting amines of general formula X

R—H         (X)

wherein

R is as hereinbefore defined, with carbonic acid derivatives of general XI

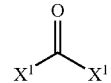

(XI)

wherein $X^1$ is a nucleofugic group, preferably the 1H-imidazol-1-yl, 1H-1,2,4-triazol-1-yl, trichloromethoxy- or 2,5-dioxopyrrolidin-1-yloxy group, and with compounds of general formula VIII,

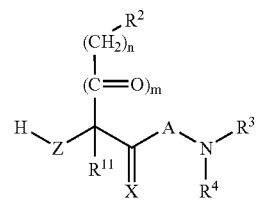

(VIII)

wherein $R^2$, $R^3$, $R^4$, $R^{11}$, A, X, m and n are as hereinbefore defined and Z denotes an $NR^1$— group, wherein $R^1$ is as hereinbefore defined, and, if necessary, subsequently cleaving any protecting groups or modifying any precursor functions using the method described hereinbefore.

The theoretically two-step reactions are generally carried out as one-pot processes, preferably by reacting one of the two components X or VIII with equimolar amounts of the carbonic acid derivative of general formula XI in a suitable solvent at fairly low temperature, in the first step, and then adding at least equimolar amounts of the other component VIII or X and finishing the reaction at elevated temperature. The reactions with bis-(trichloromethyl)-carbonate are preferably carried out in the presence of at least 2 equivalents (based on bis-(trichloromethyl)-carbonat) of a tertiary base, e.g. triethylamine, N-ethyl-diisopropylamine, pyridine, 1,5-diazabicyclo[4,3,0]non-5-ene, 1,4-diazabicyclo[2,2,2]octane or 1,8-diazabicyclo-[5,4,0]undec-7-ene. Examples of solvent, which should be anhydrous, include tetrahydrofuran, dioxane, dimethylformamide, dimethylacetamide, N-methyl-2-pyrrolidone, 1,3-dimethyl-2-imidazolidinone or acetonitrile, if bis-(trichloromethyl)-carbonate is used as the carbonyl component, anhydrous chlorohydrocarbons such as dichloromethane, 1,2-dichloroethane or trichloroethylene are preferred. The reaction temperatures are between −30 and +25° C. for the first step of the reaction, preferably between −5 and +10° C., and between +15° C. and the boiling temperature of the solvent used, preferably between +20° C. and +70° C. for the second step of the reaction (cf. also: H. A. Staab and W. Rohr, "Synthesen mit heterocyclischen Amiden (Azoliden)", Neuere Methoden der Praparativen Organischen Chemie, Band V, p. 53-93, Verlag Chemie, Weinheim/Bergstr., 1967; P. Majer and R. S. Randad, J. Org. Chem. 59, 1937-1938 (1994); K. Takeda, Y. Akagi, A. Saiki, T. Sukahara und H. Ogura, Tetrahedron Letters 24 (42), 4569 -4572 (1983)).

d) In order to prepare compounds of general formula I wherein the carbonyl group linked to the groups R and Z denotes a urea carbonyl group, in which the urea carbonyl is flanked by at least one NH— group, and wherein R denotes an unbranched $C_{1-6}$-alkylamino group optionally additionally substituted at the nitrogen atom by a $C_{1-6}$-alkyl group or by a phenylmethyl group, which may be substituted in the ω-position by a $C_{4-10}$-cycloalkyl group, by one or two phenyl groups, by a 1-naphthyl, 2-naphthyl- or biphenylyl group, by a 1H-indol-3-yl, 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-1-yl, 3,4-dihydro-2(1H)-oxothieno[3,2-d]pyrimidin-3-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-4-(3-thienyl)-2H-2-oxoimidazol-1-yl, 1,3-dihydro-4-phenyl-2H-2-oxoimidazol-1-yl, 1,3-dihydro-5-phenyl-2H-2-oxoimidazol-1-yl, 1,3-dihydro-2(2H)-oxoimidazo[4,5-c]quinolin-3-yl, 3,4-dihydro-5-phenyl-2(1H)-oxopyrimidin-3-yl, 3,4-dihydro-6-phenyl-2(1H)-oxopyrimidin-3-yl- or 1,3-dihydro-2H-2-oxoimidazo[4,5-b]pyridin-3-yl-group, by a 5-membered heteroaromatic ring linked via a carbon atom, which contains a nitrogen, oxygen or sulphur atom or, in addition to a nitrogen atom, contains an oxygen, sulphur or an additional nitrogen atom, whilst a nitrogen atom of an imino group may be substituted by an alkyl group, or by a 6-membered heteroaromatic ring linked via a carbon atom and containing 1, 2 or 3 nitrogen atoms, whilst a 1,4-butadienylene group may be attached both to the 5-membered and to the 6-membered heteroaromatic monocyclic rings via two adjacent carbon atoms in each case and the bicyclic heteroaromatic rings thus formed may also be bound via a carbon atom of the 1,4-butadienylene group, whilst the phenyl, naphthyl and biphenylyl groups mentioned above for the substitution of the alkyl moiety of the alkylamino groups in the ω-position and optionally partially hydrogenated mono- and bicyclic heteroaromatic rings in the carbon skeleton may additionally be mono-, di- or trisubstituted by fluorine, chlorine or bromine atoms, by alkyl groups, $C_{3-8}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl)carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl- or trifluoromethylsulphonyl groups, whilst the substituents may be identical or different and the above-mentioned benzoyl, benzoylamino- and benzoylmethylamino groups in turn may additionally be substituted in the phenyl moiety by a fluorine, chlorine or bromine atom or by an alkyl, trifluoromethyl, amino or acetylamino group, or the group of formula

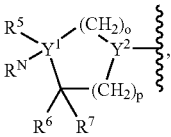

wherein
$R^5, R^6, R^7, R^N, Y^1$, o and p are as hereinbefore defined and $Y^2$ denotes the N-atom, Z denotes the group $NR^1$ and $R^1$ denotes a hydrogen atom or, provided that, R denotes an unbranched alkylamino group unsubstituted at the nitrogen atom and optionally substituted in the ω-position, $R^1$ may also denote an alkyl or phenylalkyl group:

Reacting amines of general formula X',

R—H  (X')

wherein R is as hereinbefore defined, with carbonic acid derivatives of general formula XI',

wherein $X^2$ denotes a phenoxy group, if $X^3$ is the (1H)-1,2,3,4-tetrazol-1-yl group, the 4-nitrophenoxy group, if $X^3$ is the 4-nitropheoxy group, and the chlorine atom if $X^3$ is the 2,4,5-trichlorophenoxy group, and with compounds of general formula VIII',

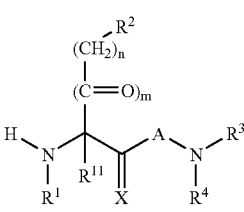

wherein $R^2, R^3, R^4, R^{11}, X, A$, m and n are as hereinbefore defined and $R^1$ denotes a hydrogen atom or, provided that R is an unbranched alkylamino group unsubstituted at the nitrogen and optionally substituted in the ω-position, $R^1$ may also denote an alkyl or phenylalkyl group, and if necessary, subsequently cleaving protecting groups or modifying precursor functions using the methods described hereinbefore.

The reactions are in two steps, in principle, with intermediate formation of urethanes, which can be isolated. However, the reactions may also be carried out as one-pot reactions. Preferably, in the first step, one of the two components X' or VIII' is reacted with equimolar amounts of the carbonic acid derivative of general formula XI'in a suitable solvent at low temperature, then at least equimolar amounts of the other component VIII' or X' are added and the reaction is completed at elevated temperature. The reactions are preferably carried out in anhydrous solvents, e.g. in tetrahydrofuran, dioxane, dimethylformamide, dimethylacetamide, N-methyl-2-pyrrolidone, 1,3-dimethyl-2-imidazolidinone, acetonitrile or anhydrous chlorohydrocarbons e.g. dichloromethane, 1,2-dichloroethane or trichloroethylene. The reaction temperatures are between −15 and +40° C., preferably between −10 and +25° C. for the first step, between +20° C. and the boiling temperature of the solvent used, preferably between +20° C. and 100° C. for the second reaction step (cf. also: R. W. Adamiak and J. Stawinski, Tetrahedron Letters 1977, 22, 1935 -1936; A. W. Lipkowski, S. W. Tam and P. S. Portoghese, J. Med. Chem. 29, 1222 -1225 (1986); J. Izdebski and D. Pawlak, Synthesis 1989, 423 -425).

e) In order to prepare compounds of general formula I wherein Z denotes the group NH and R denotes an unbranched $C_{1-6}$-alkylamino group optionally substituted at the nitrogen atom by a $Cl_{1-6}$-alkyl group or by a phenylmethyl group, which may be substituted in the ω-position by a $C_{4-10}$-cycloalkyl group, by one or two phenyl groups, by a 1-naphthyl, 2-naphthyl or biphenylyl group, by a 1H-indol-3-yl, 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d] pyrimidin-3-yl, 3,4-dihydro-2(1H)-oxothieno[3,4-d] pyrimidin-1-yl, 3,4-dihydro-2(1H)-oxothieno[3,2-d] pyrimidin-3-yl, 3,4-dihydro-2(1H)-oxothieno[3,2-d] pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3 (4H)-oxo-1,2,4-benzothiadiazin-2-yl, 1,3-dihydro-4-(3-thienyl)-2H-2-oxoimidazol-1-yl, 1,3-dihydro-4-phenyl-2H-2-oxoimidazol-1-yl, 1,3-dihydro-5-phenyl-2H-2-oxoimidazol-1-yl, 1,3-dihydro-2(2H)-oxoimidazo[4,5-c]quinolin-3-yl, 3,4-dihydro-5-phenyl-2(1H)-oxopyrimidin-3-yl, 3,4-dihydro-6-phenyl-2 (1H)-oxopyrimidin-3-yl or 1,3-dihydro-2H-2-oxoimidazo[4,5-b]pyridin-3-yl group, by a 5-membered heteroaromatic ring linked via a carbon atom, which contains a nitrogen, oxygen or sulphur atom or, in addition to a nitrogen atom, contains an oxygen, sulphur or an additional nitrogen atom, whilst a nitrogen atom of an imino group may be substituted by an alkyl group, or by a 6-membered heteroaromatic ring linked via a carbon atom and containing 1, 2 or 3 nitrogen atoms, whilst a 1,4-butadienylene group may be attached both to the 5-membered and to the 6-membered heteroaromatic monocyclic rings via two adjacent carbon atoms in each case and the bicyclic heteroaromatic rings thus formed may also be bound via a carbon atom of the 1,4-butadienylene group, whilst the phenyl, naphthyl and biphenylyl groups mentioned above for the substitution of the alkyl groups in the ω-position and optionally partially hydrogenated mono- and bicyclic heteroaromatic rings in the carbon skeleton may additionally be mono-, di- or trisubstituted by fluorine, chlorine or bromine atoms, by alkyl groups, $C_{3-8}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl) carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl or trifluoromethylsulphonyl groups, whilst the substituents may be identical or different and the above-mentioned benzoyl, benzoylamino- and benzoylmethylamino groups in turn may additionally be substituted in the phenyl moiety by a fluorine, chlorine or bromine atom or by an alkyl, trifluoromethyl, amino or acetylamino group, or the group of formula

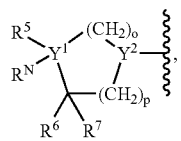

(II)

wherein $R^5, R^6, R^7, R^N, Y^1$, o and p are as hereinbefore defined and $Y^2$ denotes an N-atom:

Reacting isocyanates of general formula XII,

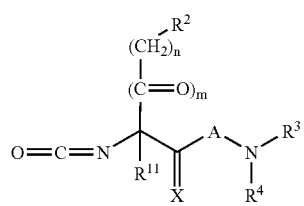

(XII)

wherein $R^2, R^3, R^4, R^{11}$, A, X, m and n are as hereinbefore defined, with amines of general formula X,

R—H  (X)

wherein

R is as hereinbefore defined and, if necessary, subsequently cleaving protecting groups or modifying precursor functions using the processes described above.

The reaction is carried out at temperatures between 0° C. and 150° C., preferably between 20° C. and 100° C., optionally in the presence of anhydrous solvents, e.g. tetrahydrofuran, 1,4-dioxane, dimethylformamide, dimethylacetamide, N-methyl-2-pyrrolidone or 1,3-dimethyl-2-imidazolidinone or mixtures thereof.

f) In order to prepare compounds of general formula I wherein R denotes an unbranched $C_{1-6}$-alkylamino group unsubstituted at the nitrogen atom, which may be substituted in the ω-position by a $C_{4-10}$-cycloalkyl group, by one or two phenyl groups, by a 1-naphthyl, 2-naphthyl- or biphenylyl group, by a 1H-indol-3-yl, 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-4-(3-thienyl)-2H-2-oxoimidazol-1-yl, 1,3-dihydro-4-phenyl-2H-2-oxoimidazol-1-yl, 1,3-dihydro-5-phenyl-2H-2-oxoimidazol-1-yl, 1,3-dihydro-2(2H)-oxoimidazo[4,5-c]quinolin-3-yl, 3,4-dihydro-5-phenyl-2(1H)-oxopyrimidin-3-yl, 3,4-dihydro-6-phenyl-2(1H)-oxopyrimidin-3-yl- or 1,3-dihydro-2H-2-oxoimidazo[4,5-b]pyridin-3-yl-group, by a 5-membered heteroaromatic ring linked via a carbon atom, which contains a nitrogen, oxygen or sulphur atom or, in addition to a nitrogen atom, contains an oxygen, sulphur or an additional nitrogen atom, whilst a nitrogen atom of an imino group may be substituted by an alkyl group, or by a 6-membered heteroaromatic ring linked via a carbon atom and containing 1, 2 or 3 nitrogen atoms, whilst a 1,4-butadienylene group may be attached both to the 5-membered and to the 6-membered heteroaromatic monocyclic rings via two adjacent carbon atoms in each case and the bicyclic heteroaromatic rings thus formed may also be bound via a carbon atom of the 1,4-butadienylene group, whilst the phenyl, naphthyl and biphenylyl groups mentioned above for the substitution of the alkylamino groups in the ω-position and optionally partially hydrogenated mono- and bicyclic heteroaromatic rings in the carbon skeleton may additionally be mono-, di- or trisubstituted by fluorine, chlorine or bromine atoms, by alkyl groups, $C_{3-8}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl)carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl- or trifluoromethylsulphonyl groups, whilst the substituents may be identical or different and the above-mentioned benzoyl, benzoylamino- and benzoylmethylamino groups in turn may additionally be substituted in the phenyl moiety by a fluorine, chlorine or bromine atom or by an alkyl, trifluoromethyl, amino- or acetylamino group, and Z denotes the $NR^1$— group wherein $R^1$ is as hereinbefore defined:

Reacting isocyanates of general formula XIII, $$R\!=\!C\!=\!O \qquad \qquad (XIII)$$

wherein R is as hereinbefore defined, with compounds of general formula VIII,

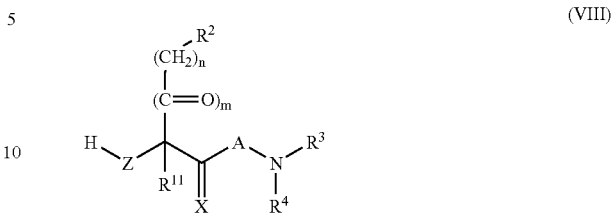

(VIII)

wherein $R^2$, $R^3$, $R^4$, $R^{11}$, A, X, m and n are as hereinbefore defined and Z denotes an $NR^1$— group, wherein $R^1$ is as hereinbefore defined, and, if necessary, subsequently cleaving any protecting groups or modifying the precursor functions using the methods described hereinbefore.

The reaction is carried out at temperatures between 0 and 150° C., preferably at temperatures between 20 and 100° C., and optionally in the presence of anhydrous solvents, e.g. tetrahydrofuran, 1,4-dioxane, dimethylformamide, dimethylacetamide, N-methyl-2-pyrrolidone or 1,3-dimethyl-2-imidazolidinone.

g) In order to prepare compounds of general formula I wherein R, Z, $R^2$, $R^3$, $R^4$, $R^{11}$, A, m and n have the meanings given hereinbefore and X is as hereinbefore defined, provided that A does not denote a bond or X denotes an oxygen atom, if A denotes a single bond:

Coupling carboxylic acids of general formula XIV,

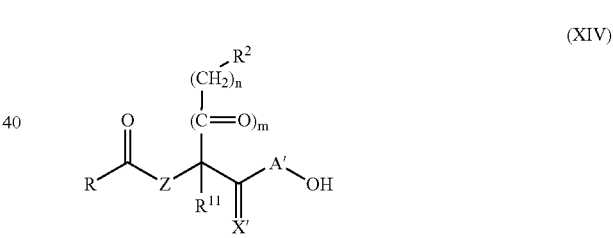

(XIV)

wherein

R, Z, $R^{11}$, m and n are as hereinbefore defined, $R^{2\prime}$ has the meanings given for $R^2$ hereinbefore or denotes a group $R^2$ substituted by the above-mentioned protecting groups, A' has the meanings given for A hereinbefore or, if A denotes the divalent group of an amino acid, it optionally bears in the side chain a precursor group for the group $R^9$, e.g. a cyanopropyl group, to compounds of general formula XV,

$$H\!-\!NR^3R^4 \qquad \qquad (XV)$$

wherein $R^3$ and $R^4$ are as hereinbefore defined, and if necessary subsequent cleaving of protective groups or modification of precursor functions using the methods described above.

The coupling is carried out using the methods known from peptide chemistry and described hereinbefore, particularly using DCC, DIC, HBTU, TBTU or BOP as reagents or using the mixed anhydride method.

If the starting compound XIV used is enantiomerically pure, partial racemisation of the C-terminal amino acid must be expected during the coupling step and possibly quantitative racemisation must be expected if triethylamine is used as the auxiliary base and dimethylformamide, dimethylacetamide or N-methyl-pyrrolidone is used as solvent.

h) In order to prepare compounds of general formula I wherein X denotes the oxygen atom:

Coupling carboxylic acids of general formula XVI,

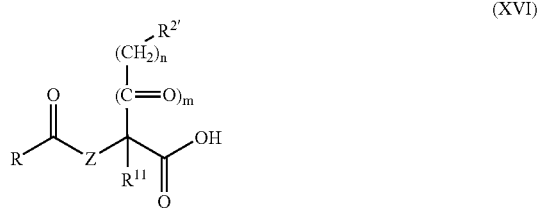

wherein
R, Z, $R^{11}$, m and n are as hereinbefore defined and
$R^{2'}$ has the meanings given for $R^2$ hereinbefore or denotes a group $R^2$ substituted by the above-mentioned protecting groups, to compounds of general formula XVII,

wherein
A' has the meanings given for A hereinbefore or, if A denotes the divalent group of an amino acid, A' optionally bears in the side chain a precursor group for the group $R^9$, e.g. a cyanopropyl group, and
$R^3$ and $R^4$ are as hereinbefore defined, and if necessary subsequently cleaving protecting groups or modifying precursor functions using the methods described above.

The coupling is carried out using the methods known from peptide chemistry and described above, particularly using DCC, DIC, HBTU, TBTU or BOP as reagents or using the mixed anhydride method.

If the starting compound XVI used is enantiomerically pure, during the coupling step partial racemisation must be expected or, if triethylamine is used as the auxiliary base and dimethylformamide, dimethylacetamide or N-methyl-pyrrolidone is used as solvent, quantitative racemisation must be expected based on the chiral centre of XVI.

i) In order to prepare compounds of general formula I wherein R denotes an unbranched $C_{1-6}$-alkylamino group optionally substituted at the nitrogen atom by a $C_{1-6}$-alkyl group or by a phenylmethyl group, which may be substituted in the ω-position
by a $C_{4-10}$-cycloalkyl group,
by one or two phenyl groups, by a 1-naphthyl, 2-naphthyl or biphenylyl group,
by a 1H-indol-3-yl, 1,3-dihydro-2H-2-oxobenzimidazol-1-yl, 2,4(1H,3H)-dioxoquinazolin-1-yl, 2,4(1H,3H)-dioxoquinazolin-3-yl, 2,4(1H,3H)-dioxothieno[3,4-d]pyrimidin-3-yl, 3,4-dihydro-2(1H)-oxothieno[3,4-d]pyrimidin-3-yl, 3,4-dihydro-2(1H)-oxothieno[3,4-d]pyrimidin-1-yl, 3,4-dihydro-2(1H)-oxothieno[3,2-d]pyrimidin-3-yl, 3,4-dihydro-2(1H)-oxothieno[3,2-d]pyrimidin-1-yl, 3,4-dihydro-2(1H)-oxoquinazolin-1-yl, 3,4-dihydro-2(1H)-oxoquinazolin-3-yl, 2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-4-(3-thienyl)-2H-2-oxoimidazol-1-yl, 1,3-dihydro-4-phenyl-2H-2-oxoimidazol-1-yl, 1,3-dihydro-5-phenyl-2H-2-oxoimidazol-1-yl, 1,3-dihydro-2(2H)-oxoimidazo[4,5-c]quinolin-3-yl, 3,4-dihydro-5-phenyl-2(1H)-oxopyrimidin-3-yl, 3,4-dihydro-6-phenyl-2(1H)-oxopyrimidin-3-yl- or 1,3-dihydro-2H-2-oxoimidazo[4,5-b]pyridin-3-yl-group, by a 5-membered heteroaromatic ring linked via a carbon atom, which contains a nitrogen, oxygen or sulphur atom or, in addition to a nitrogen atom, contains an oxygen, sulphur or an additional nitrogen atom, whilst a nitrogen atom of an imino group may be substituted by an alkyl group, or by a 6-membered heteroaromatic ring linked via a carbon atom and containing 1, 2 or 3 nitrogen atoms, whilst a 1,4-butadienylene group may be attached both to the 5-membered and to the 6-membered heteroaromatic monocyclic rings via two adjacent carbon atoms in each case and the bicyclic heteroaromatic rings thus formed may also be bound via a carbon atom of the 1,4-butadienylene group, whilst the phenyl, naphthyl and biphenylyl groups mentioned above for the substitution of the alkyl moiety of the alkylamino groups in the ω-position and optionally partially hydrogenated mono- and bicyclic heteroaromatic rings in the carbon skeleton may additionally be mono-, di- or trisubstituted by fluorine, chlorine or bromine atoms, by alkyl groups, $C_{3-8}$-cycloalkyl groups, nitro, alkoxy, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, (1-pyrrolidinyl)carbonyl, (1-piperidinyl)carbonyl, (hexahydro-1H-azepin-1-yl)carbonyl, (4-methyl-1-piperazinyl)carbonyl, (4-morpholinyl)carbonyl, alkanoyl, cyano, trifluoromethoxy, trifluoromethylthio, trifluoromethylsulphinyl or trifluoromethylsulphonyl groups, whilst the substituents may be identical or different and the above-mentioned benzoyl, benzoylamino and benzoylmethylamino groups in turn may additionally be substituted in the phenyl moiety by a fluorine, chlorine or bromine atom or by an alkyl, trifluoromethyl, amino or acetylamino group, or the group of formula

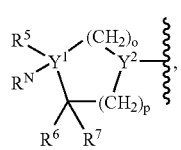

wherein
$R^5$, $R^6$, $R^7$, $R^N$, $Y^1$, o and p are as hereinbefore defined and $Y^2$ denotes an N-atom,
Z represents the methylene group,
X denotes two hydrogen atoms,
A denotes a single bond, m denotes the value 1 and
n denotes the value 0:

Coupling carboxylic acids of general formula XVIII,

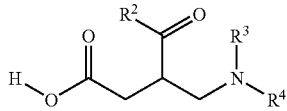

(XVIII)

wherein
R², R³ and R⁴ are as hereinbefore defined,
with amines of general formula X,

R—H (X)

wherein R is as hereinbefore defined.

The coupling is carried out using the methods known from peptide chemistry and described above, particularly using DCC, DIC, HBTU, TBTU or BOP as reagents or using the mixed anhydride method.

j) In order to prepare compounds of general formula I wherein R³ and R⁴ have the meanings given hereinbefore with the exception of the hydrogen atoms, Z denotes a methylene group, X denotes two hydrogen atoms, A denotes a single bond, m is the number 1 and n is the number 0:

Reacting secondary amines of general formula XVa,

H—NR³'R⁴' (XVa)

wherein
R³' and R⁴' have the meanings given for R³ and R⁴ hereinbefore with the exception of hydrogen atoms, with formaldehyde and CH-acid compounds of general formula XIX,

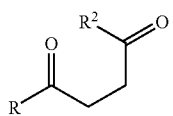

(XIX)

wherein
R is as hereinbefore defined and
R² is as hereinbefore defined, but with the proviso that any acid functions present such as hydroxy groups are appropriately protected by suitable protecting groups.

The reaction is preferably carried out in a slightly acidic medium, using alcohols, e.g. methanol or ethanol, or lower aliphatic carboxylic acids, such as glacial acetic acid, as solvents and at temperatures between room temperature and the boiling point of the solvent in question. In a preferred variant, an inorganic acid salt such as the hydrochloride of a secondary amine of general formula XVa is heated with paraformaldehyde and a ketone of general formula XIX in glacial acetic acid to temperatures between 50° C. and 80° C.

k) In order to prepare compounds of general formula I wherein
R, R², R³, R⁴, R¹¹, X, Z, m and n are as hereinbefore defined
and A denotes the divalent group of formula III

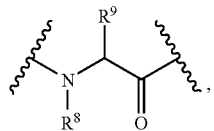

(III)

(linked to the NR³R⁴-group via the —CX— group)

wherein
R⁸ denotes the hydrogen atom or an alkyl or phenylalkyl group and
R⁹ denotes an unbranched $C_{1-5}$-alkyl group substituted in the ω-position by an aminoiminomethylamino group:

Reacting compounds of general formula XX,

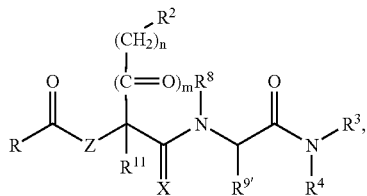

(XX)

wherein
R, R², R³, R⁴, R¹¹, X, Z, m and n are as hereinbefore defined,
R⁸ denotes a hydrogen atom or an alkyl or phenylalkyl group and
R⁹ denotes an unbranched $C_{1-5}$-alkyl group substituted in the ω-position by a primary amino group, with carbonic acid derivatives of general formula XXI,

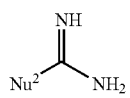

(XXI)

wherein
Nu² is a leaving group, e.g. an alkoxy, alkylthio, alkylsulphinyl or alkylsulphonyl group each having 1 to 10 carbon atoms in alkyl moiety, e.g. a methoxy, ethoxy, methylthio, ethylthio, methylsulphinyl, ethylsulphinyl, propylsulphinyl, isopropylsulphinyl, methylsulphonyl or ethylsulphonyl group, the chlorine atom, the SO₂H, SO₃H— or OPOCl₂— group, or the group of general formula XXII,

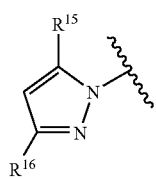

(XXII)

wherein

R$^{15}$ and R$^{16}$, which may be identical or different, denote hydrogen atoms or C$_{1-3}$-alkyl groups.

Occasionally, for example when Nu$^2$ is an alkoxy group, instead of using the compounds of general formula XXI it is advantageous to use the inorganic acid salts thereof, e.g. the neutral sulphates or hydrochlorides thereof.

The reactions are carried out analogously to methods known from the literature (see G. B. L. Smith, J. Amer. Chem. Soc. 51, 476 [1929]; B. Rathke, Chem. Ber. 17, 297 [1884]; R. Phillips and H. T. Clarke, J. Amer. Chem. Soc. 45, 1755 [1923]; S. J. Angyal and W. K. Warburton, J. Amer. Chem. Soc. 73, 2492 [1951]; H. Lecher and F. Graf, Chem. Ber. 56, 1326 [1923]; J. Wityak, S. J. Gould, S. J. Hein and D. A. Keszler, J. Org. Chem. 52, 2179 [1987]; T. Teraji, Y. Nakai, G. J. Durant, WO-A-81/00109, Chem. Abstr. 94, 192336z [1981]; C. A. Maryanoff, R. C. Stanzione, J. N. Plampin and J. E. Mills, J. Org. Chem. 51, 1882-1884 [1986]; A.E. Miller and J.J. Bischoff, Synthesis 1986, 777; R. A. B. Bannard, A. A. Casselman, W. F. Cockburn and G. M. Brown, Can. J. Chem. 36, 1541 [1958]; Aktieselskabet Grea, Kopenhagen, DE 28 26 452-C2; K. Kim. Y-T. Lin and H. S. Mosher, Tetrah. Letters, 29, 3183-3186 [1988]; H. B. Arzeno et al., Synth. Commun. 20, 3433-3437 [1990]; H. Bredereck and K. Bredereck, Chem. Ber. 94, 2278 [1961]; H. Eilingsfeld, G. Neubauer, M. Seefelder and H. Weidinger, Chem. Ber. 97, 1232 [1964]; P. Pruszynski, Can. J. Chem. 65, 626 [1987]; D. F. Gavin, W. J. Schnabel, E. Kober and M. A. Robinson, J. Org. Chem. 32, 2511 [1967]; N. K. Hart, S. R. Johns, J. A. Lamberton and R. I. Willing, Aust. J. Chem. 23, 1679 [1970]; CIBA Ltd., Belgisches Patent 655 403; Chem. Abstr. 64, 17481 [1966]; R. A. B. Bannard, A. A. Casselman, W. F. Cockburn and G. M. Brown, Can. J. Chem. 36, 1541 [1958]; J. P. Greenstein, J. Org. Chem. 2, 480 [1937]; F. L. Scott and J. Reilly, J. Amer. Chem. Soc. 74, 4562 [1952]; W. R. Roush and A. E. Walts, J. Amer. Chem. Soc. 106, 721 [1984], M. S. Bernatowicz, Y. Wu and G. R. Matsueda, J. Org. Chem. 57, 2497-2502 [1992]; H. Tsunematsu, T. Imamura and S. Makisumi, J. Biochem. 94, 123-128 [1983]) at temperatures between 0° C. and +100° C., preferably between +40° C. and +80° C., using inert solvents, e.g. dichloromethane, tetrahydrofuran, 1,4-dioxane, acetonitrile, dimethylformamide, dimethylacetamide, N-methyl-pyrrolidone or mixtures thereof and, depending on the nature of the Nu$^2$-group, frequently in the presence of auxiliary bases, especially alkali metal carbonates such as sodium- or potassium carbonate, or tertiary amines, preferably N-ethyl-diisopropylamine or triethylamine.

The amino acids of general formula I modified according to the invention contain at least one chiral centre. If the group A is also chiral, the compounds may occur in the form of two diastereomeric pairs of antipodes. The invention includes the individual isomers as well as the mixtures thereof.

The diastereomers are separated on the basis of their different physicochemical properties, e.g. by fractional crystallisation from suitable solvents, by high pressure liquid or column chromatography using chiral or preferably achiral stationary phases.

Racemates covered by general formula I may be separated, for example, by HPLC on suitable chiral stationary phases (e.g. Chiral AGP, Chiralpak AD). Racemates which contain a basic or acidic function can also be separated by means of the diastereomeric optically active salts which are formed on reacting with an optically active acid, e.g. (+)- or (−)-tartaric acid, (+)- or (−)-diacetyl tartaric acid, (+)- or (−)-monomethyltartrate or (+)-camphor sulphonic acid or an optically active base such as (R)-(+)-1-phenylethylamine, (S)-(−)-1-phenylethylamine or (S)-brucine.

According to a conventional process for separating isomers, the racemate of a compound of general formula I is reacted with one of the above-mentioned optically active acids or bases in equimolar amounts in a solvent and the crystalline, diastereomeric, optically active salts obtained are separated on the basis of their different solubilities. This reaction may be carried out in solvents of any kind provided that they are sufficiently different in terms of the solubility of the salts. Preferably, methanol, ethanol or mixtures thereof are used, e.g. in a ratio by volume of 50:50. Then each of the optically active salts is dissolved in water, neutralised with a base such as sodium carbonate or potassium carbonate, sodium hydroxide solution or potassium hydroxide solution, and in this way the corresponding free compound is obtained in the (+)- or (−)-form.

The (R)-enantiomer alone or a mixture of two optically active diastereomeric compounds coming within the scope of general formula I may also be obtained by carrying out the syntheses described above with a suitable reaction component in the (R)-configuration.

The starting materials of general formulae VII, IX, X, X', XI, XI', XIII, XV, XVa, XVII, XXI, XXII required to synthesis the compounds of general formula I as well as the amino acids used are commercially available or may be prepared by methods known from the literature.

Compounds of general formula VIII wherein Z denotes the group NR$^1$ and those of general formula VIII' wherein X denotes the oxygen atom may be obtained from commonly available starting materials using methods familiar to peptide chemists.

Isocyanates of general formula XII can easily be obtained from α-amino acid derivatives of general formula VIII' wherein R$^1$ denotes a hydrogen atom and the other groups are as hereinbefore defined, or from the hydrochlorides thereof by reacting with phosgene, diphosgene or triphosgene in the presence of pyridine (see also: J. S. Nowick, N. A. Powell, T. M. Nguyen and G. Noronha, J. Org. Chem. 57, 7364-7366 [1992]).

Carboxylic acids of general formulae XIV and XVI may be obtained from the corresponding carboxylic acid esters by saponification, preferably in the presence of lithium hydroxide.

The carboxylic acids of general formula XVIII are obtained by saponifying corresponding carboxylic acid esters which are in turn prepared from suitable secondary amines, 4-aryl-4-oxobutanoic acid esters and formaldehyde by Mannich reaction.

Compounds of general formula XIX may be obtained from suitable 4-oxobutanoic acids and amines of general formula X using conventional methods.

The intermediate compounds of general formula XX come under general formula I and are thus within the scope of the present application. These compounds may be obtained, for example, using processes a) to h) described herein.

The compounds of general formula I may be converted into their physiologically acceptable salts with inorganic or organic acids, particularly for pharmaceutical applications. Examples of suitable acids for this purpose include hydrochloric acid, hydrobromic acid, phosphoric acid, nitric acid, sulphuric acid, methanesulphonic acid, p-toluenesulphonic acid, acetic acid, fumaric acid, succinic acid, lactic acid, mandelic acid, malic acid, citric acid, tartaric acid or maleic acid.

Moreover, if the new compounds of formula I thus obtained contain an acid function, for example a carboxy group, they may if desired be converted into the addition salts thereof with inorganic or organic bases, more particularly for pharmaceutical use, into the physiologically acceptable addition salts thereof. Bases which may be considered include, for example, sodium hydroxide, potassium hydroxide, ammonia, cyclohexylamine, dicyclohexylamine, ethanolamine, diethanolamine and triethanolamine.

The new compounds of general formula I and the physiologically acceptable salts thereof have CGRP-antagonistic properties and exhibit good affinities in CGRP-receptor binding studies. The compounds exhibit CGRP-antagonistic properties in the pharmacological test systems described hereinafter.

The following experiments were carried out to demonstrate the affinity of compounds of general formula I for human CGRP-receptors and their antagonistic properties:

A. Binding Studies with SK-N-MC-Cells Expressing Human CGRP-Receptor

SK-N-MC-cells are cultivated in Dulbecco's modified Eagle Medium. The medium of confluent cultures is removed. The cells are washed twice with PBS-buffer (Gibco 041-04190 M), detached by the addition of PBS-buffer mixed with 0.02% EDTA and isolated by centrifuging. After resuspension in 20 ml of Balanced Salts Solution [BSS (in mM): NaCl 120, KCl 5.4, NaHCO$_3$ 16.2, MgSO$_4$ 0.8, NaHPO$_4$ 1.0, CaCl$_2$ 1.8, D-Glucose 5.5, HEPES 30, pH7.40] the cells are centrifuged twice at 100×g and resuspended in BSS. After the cell number has been determined the cells are homogenised using an Ultra-Turrax and centrifuged for 10 minutes at 3000×g. The supernatent is discarded and the pellet is recentrifuged and resuspended (1 ml/1000000 cells) in Tris-buffer (10 mM Tris, 50 mM NaCl, 5 mM MgCl$_2$, 1 mM EDTA, pH 7.40), enriched with 1% bovine serum albumin and 0.1% bacitracin. The homogenate is frozen at −80° C. The membrane preparations are stable for more than 6 weeks under these conditions.

After thawing, the homogenate is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 µl of the homogenate are incubated at ambient temperature for 180 minutes with 50 pM of $^{125}$I-Iodotyrosyl-Calcitonin-Gene-Related Peptide (Amersham) and increasing concentrations of the test substances in a total volume of 250 µl. Incubation is ended by rapid filtration using GF/B-glass fibre filters treated with polyethyleneimine (0.1%) by means of a cell harvester. The protein-bound radioactivity is measured using a gammacounter. The non-specific binding is defined as the radioactivity bound after the presence of 1 µM of human CGRP-alpha during incubation.

The concentration binding curves are analysed using a computer-aided non-linear curve adaptation.

The compounds of general formula I show IC$_{50}$ values ≦10000 nM in the test described.

B. CGRP-Antagonism in SK-N-MC-cells

SK-N-MC-cells (1 million cells) are washed twice with 250 µl of incubation buffer (Hanks' HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations ($10^{-11}$ to $10^{-6}$ M) or additionally of substance in 3 to 4 different concentrations, incubation is continued for a further 15 minutes.

Intracellular cAMP is then extracted by the addition of 20 µl of 1M HCl and centrifugation (2000×g, 4° C. for 15 minutes). The supernatants are frozen in liquid nitrogen and stored at −20° C.

The cAMP contents of the samples are determined by radioimmunoassay (Amersham) and the pA$_2$-values of antagonistically acting substances are determined graphically.

The compounds of general formula I display CGRP-antagonistic properties in a dosage range between $10^{-11}$ and $10^{-5}$ M in the in vitro test model described.

In view of their pharmacological properties the compounds of general formula I and the salts thereof with physiologically acceptable acids or bases are thus suitable for acute and prophylactic treatment of headache, particularly migraine and cluster headaches. Moreover, the compounds of general formula I also have a beneficial effect on the following diseases: non-insulin-dependent diabetes mellitis (NIDDM), cardiovascular diseases, skin diseases, particularly thermal and radiation-induced skin damage including sunburn, inflammatory diseases, e.g. inflammatory joint diseases (arthritis), inflammatory lung diseases, allergic rhinitis, asthma, diseases which involve excessive vasodilation and resultant reductions in circulation, e.g. shock and sepsis, as well as morphine tolerance. In addition, the compounds of general formula I have the effect of alleviating pain in general.

The dosage needed to achieve such effects is appropriately 0.0001 to 3 mg/kg of body weight, preferably 0.01 to 1 mg/kg of body weight, by intravenous or subcutaneous route, and 0.01 to 10 mg/kg of body weight, preferably 0.1 to 10 mg/kg of body weight, when administered orally, nasally or by inhalation, in each case 1 to 3 times a day.

For this purpose, the compounds of general formula I prepared according to the invention may be formulated, optionally in combination with other active substances, such as antiemetics, prokinetics, neuroleptics, antidepressants, neurokinin-antagonists, anti-convulsants, histamine-H1-receptor antagonists, antimuscarinics, β-blockers, α-agonists and α-antagonists, ergot alkaloids, mild analgesics, non-steroidal antiphlogistics, corticosteroids, calcium-antagonists, 5-HT$_{1D}$-agonists or other antimigraine agents, together with one or more inert conventional carriers and/or diluents, e.g. corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearylalcohol, carboxymethyl-cellulose or fatty substances such as hard fat or suitable mixtures thereof, to produce conventional galenic preparations such as plain or coated tablets, capsules, powders, suspensions, solutions, metering aerosol or suppositories.

Thus, additional active substances which may be considered for the above-mentioned combinations include, for example, meloxicam, ergotamine, dihydroergotamine, metoclopramide, domperidon, diphenhydramine, cyclizine, promethazine, chlorpromazine, dexamethasone, flunarizine, dextropropoxyphene, meperidine, propranolol, nadolol, atenolol, clonidine, indoramine, carbamazepine, phenytoin, valproate, amitryptilin, lidocaine, diltiazem or sumatriptan and other 5-HT$_{1D}$-agonists such as naratriptan, zolmitriptan, avitriptan, rizatriptan and eletriptan. The dosage for these active substances is appropriately 1/5 of the lowest dose normally recommended up to 1/1 of the normally recommended dosage, i.e. 20 to 100 mg of sumatriptan, for example.

The invention further relates to the use of the compounds of general formula I as valuable auxiliary agents for the production and purification (by affinity chromatography) of antibodies and, after suitable radiolabelling, e.g. by direct labelling with $^{125}$I or $^{131}$I or by tritiation of suitable precursors for example by replacing halogen atoms with tritium, in RIA- and ELISA assays and as diagnostic or analytical aids in neurotransmitter research.

The Examples which follow are intended to illustrate the invention:

Preliminary Remarks:

There are satisfactory elementary analyses, IR, UV, $^1$H-NMR and generally mass spectra as well, for all the compounds. Unless otherwise specified, $R_f$ values were determined using TLC ready-made plates of silica gel 60 $F_{254}$ (E. Merck, Darmstadt, Product No. 5729) without chamber saturation. If there are no details of configuration, it is undecided whether this is the pure enantiomer or whether partial or total racemisation has occurred. The following eluants or eluant mixtures were used for chromatography:

FM1=dichloromethane/cyclohexane/methanol/ammonia 7/1.5/1.5/0.2 (v/v/v/v)
FM2=dichloromethane/methanol/ammonia 7.5/2.5/0.5 (v/v/v)
FM3=dichloromethane/methanol 8/2 (v/v)
FM4=dichloromethane/ethyl acetate/methanol/cyclohexane/conc. aqueous ammonia=59/25/7,5/7,5/1 (v/v/v/v/v)
FM5=ethyl acetate/dichloromethane=7/3 (v/v)
FM6=ethyl acetate/petroleum ether=1/1 (v/v)
FM7=dichloromethane/methanol/conc. aqueous ammonia=80/20/1 (v/v/v)

The following abbreviations were used in the descriptions of the experiments:
Mp.: melting point
(D): (decomposition)
DIEA: N,N-diisopropyl-ethylamine
Boc: (1,1-dimethylethoxy)carbonyl
TBTU: 2-(1H-benzotriazol-1-yl)-1,1,3,3-tetramethyluronium-tetrafluoroborate
HOBt: 1-hydroxybenzotriazole-hydrate
CDT: 1,1'-carbonyldi(1,2,4-triazole)
THF: tetrahydrofuran
DMF: dimethylformamide
Fmoc: (9-fluorenylmethoxy)carbonyl
EE: ethyl acetate
PE: petroleum ether
LM: solvent
Lfd. No.: item number The meanings of the symbols made up of letters and numbers used in the Examples are given in the following summary:

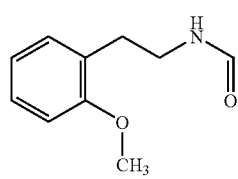

N1

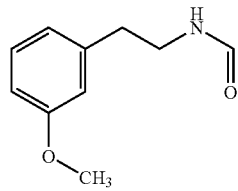

N2

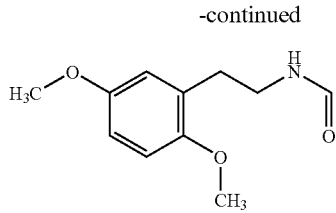

N3

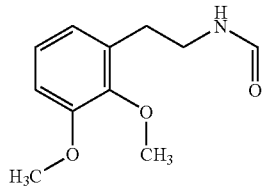

N4

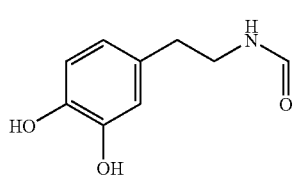

N5

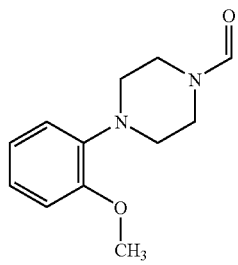

N6

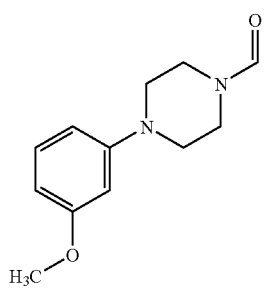

N7

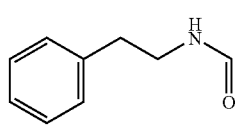

N8

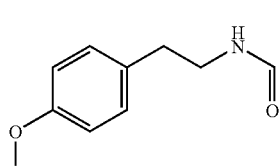

N9

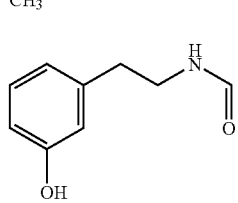

N10

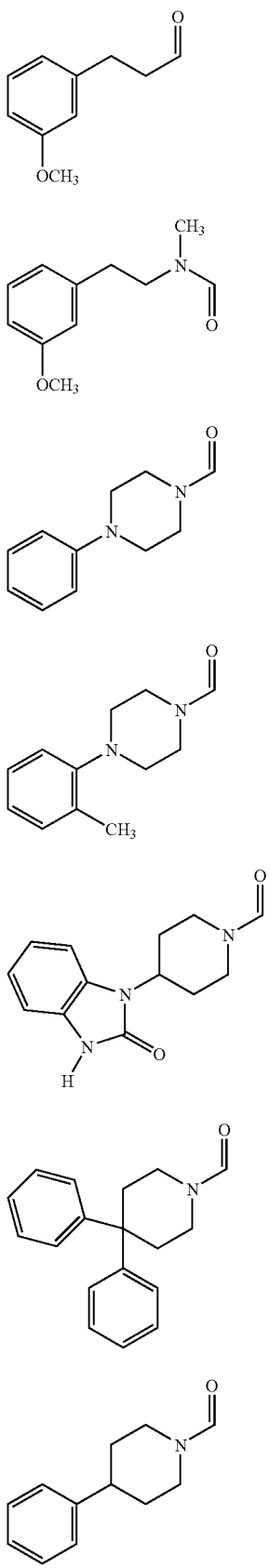
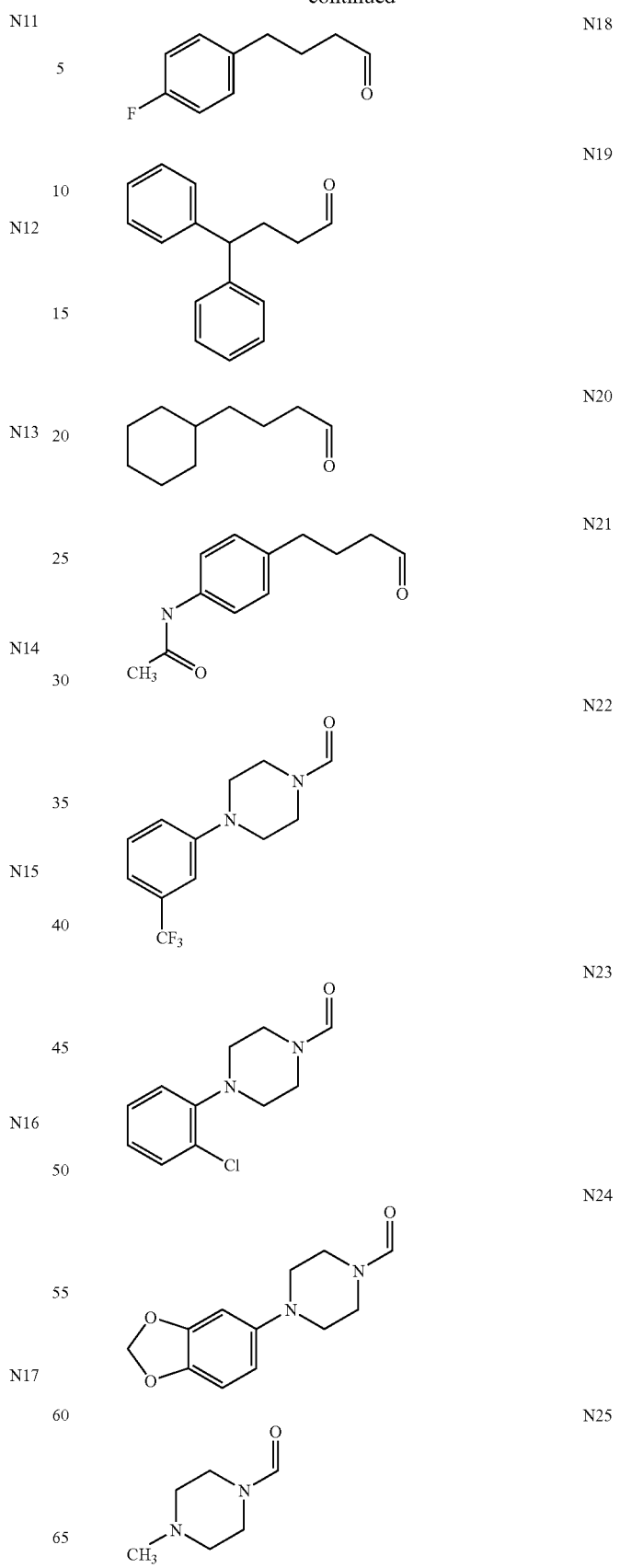

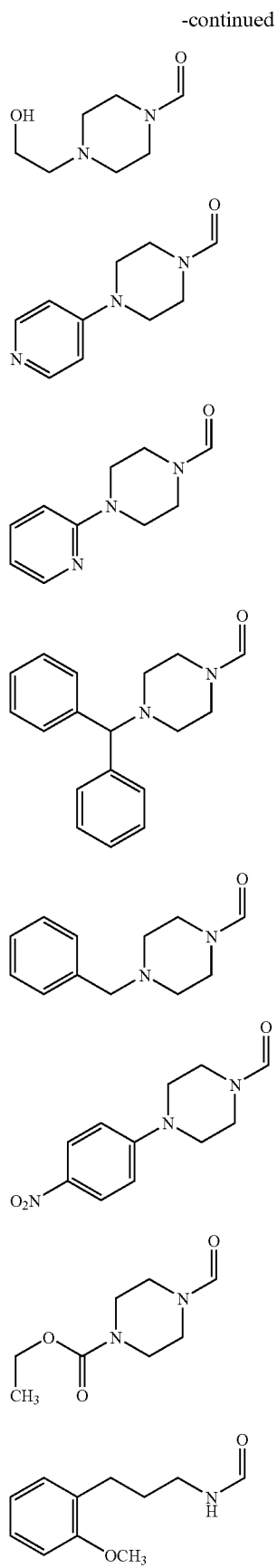
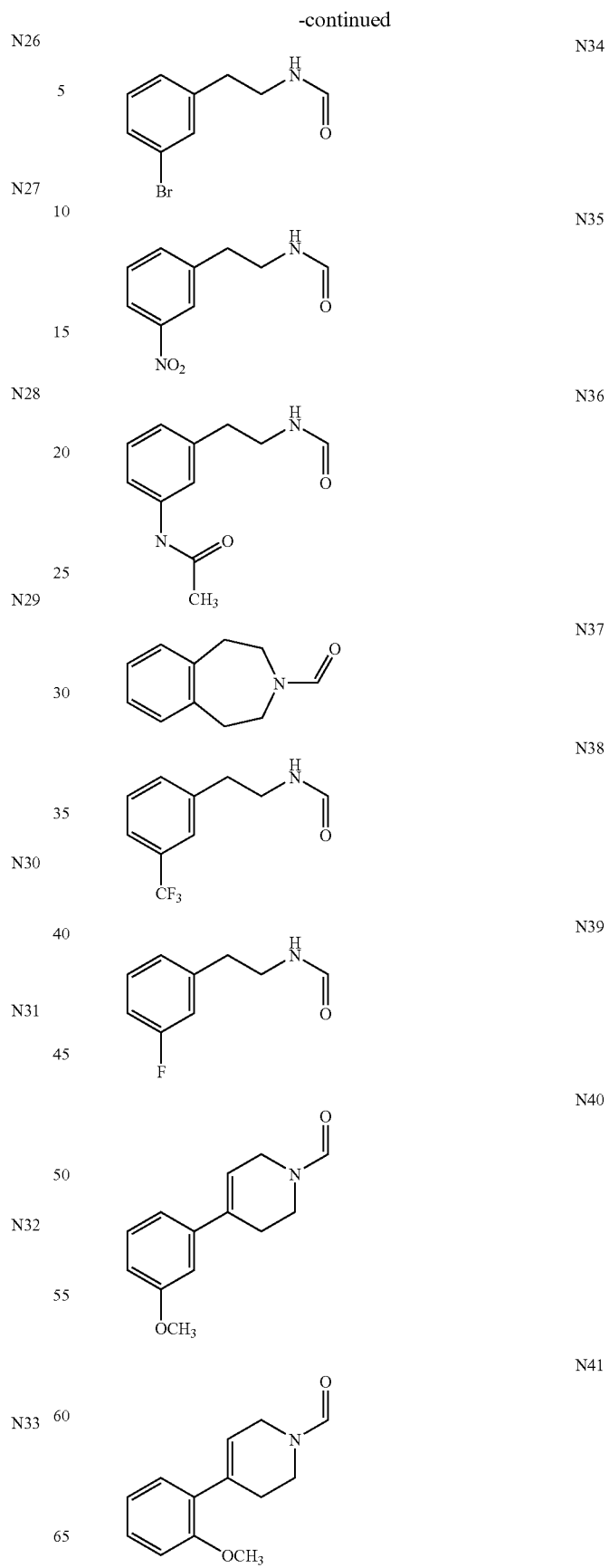

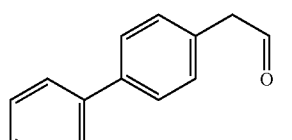
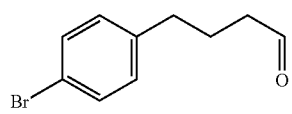
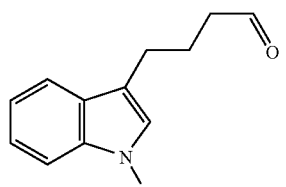
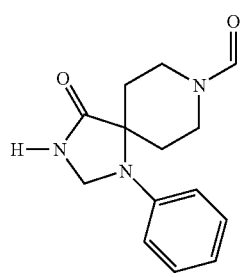
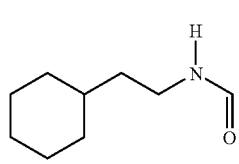
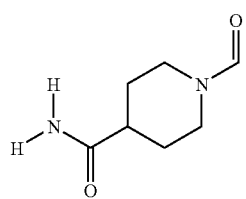
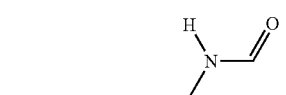
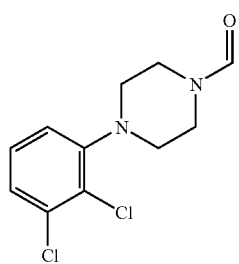
N42
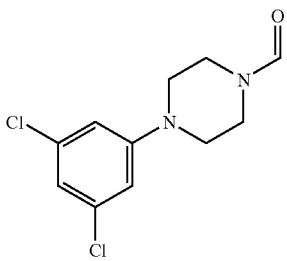
N43
N44
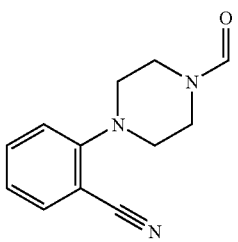
N45
N46
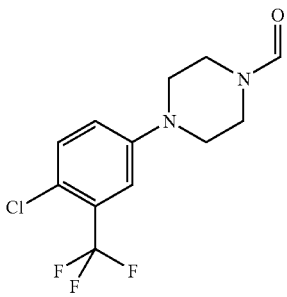
N47
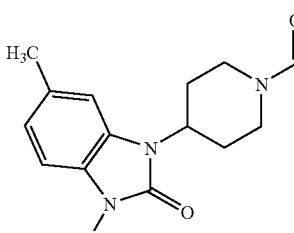
N48
N49
N50
N51
N52
N53
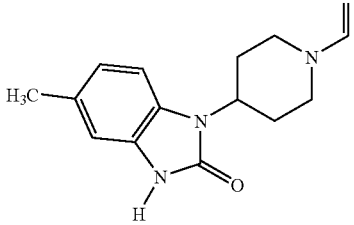
N54
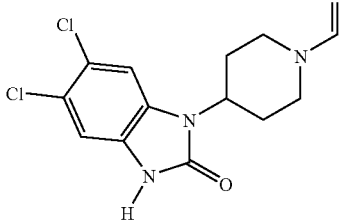
N55

-continued
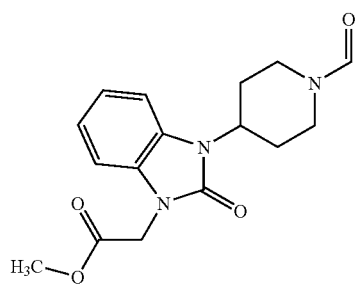
N56
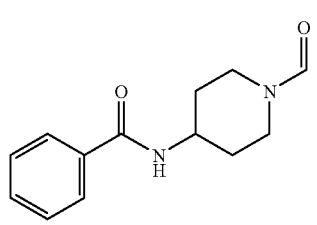
N57
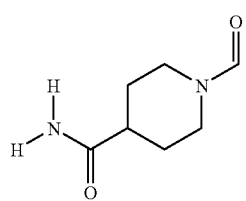
N58
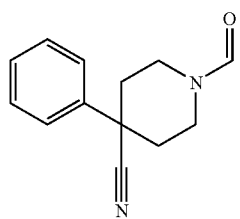
N59
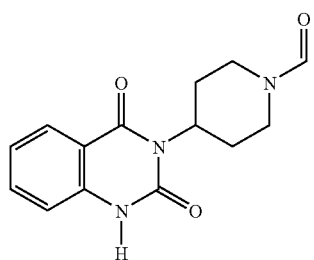
N60
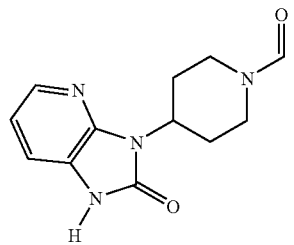
N61
-continued
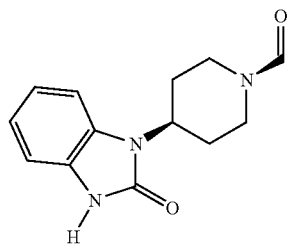
N62
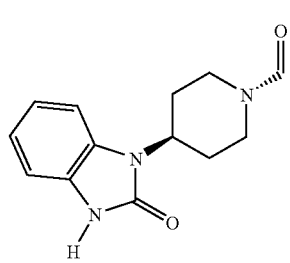
N63
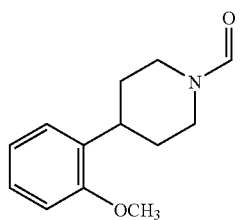
N64
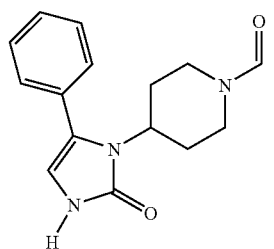
N65
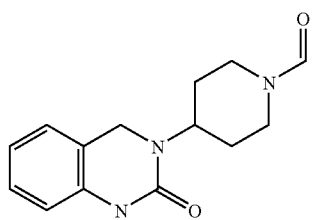
N66
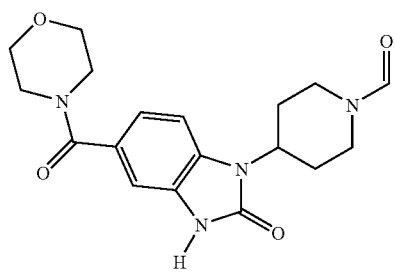
N67

-continued
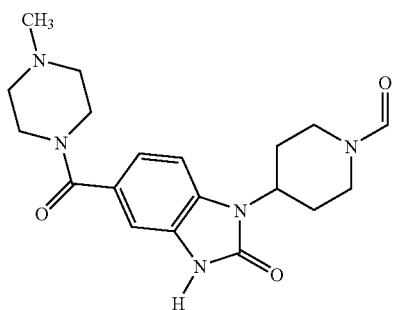
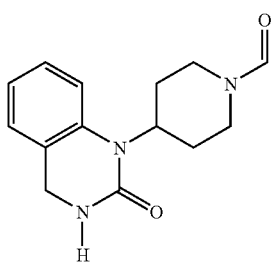
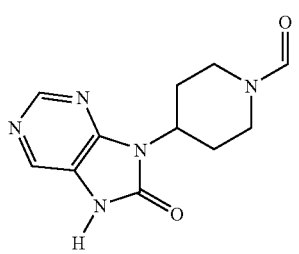
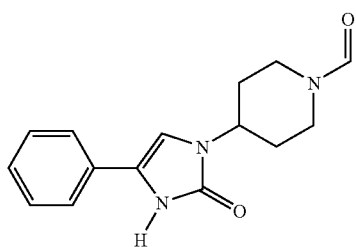
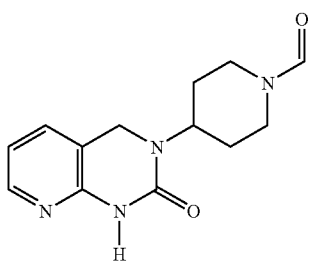
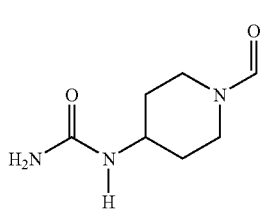
-continued
N68
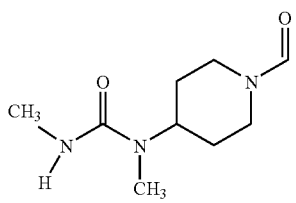
N69
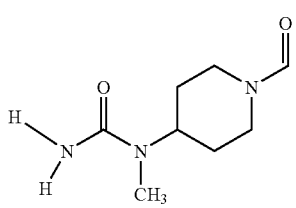
N70
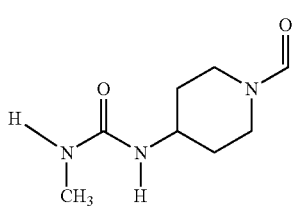
N71
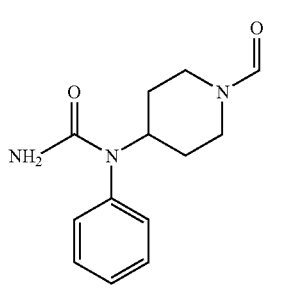
N72
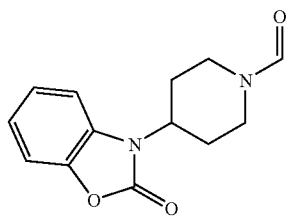
N73
N74
N75
N76
N77
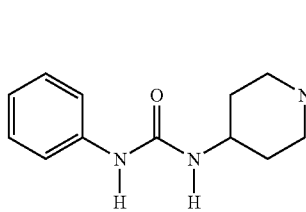
N78
N79
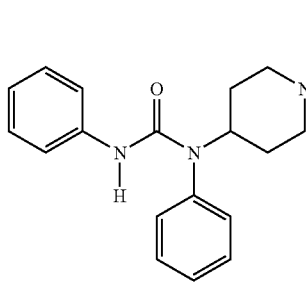
N80

-continued
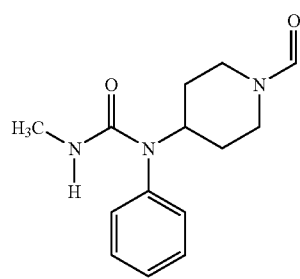
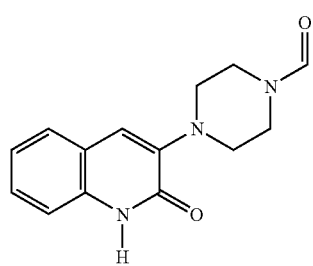
N82
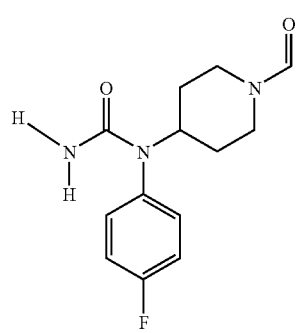
N83
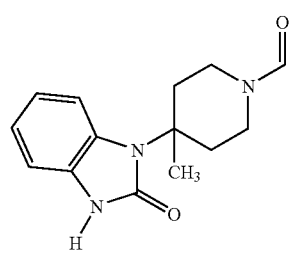
N84
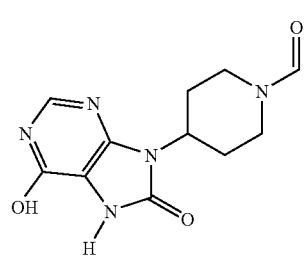
N85
N81
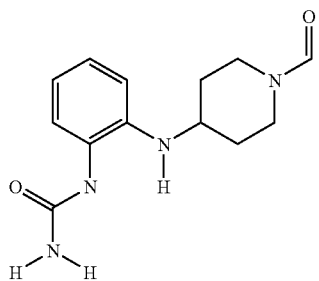
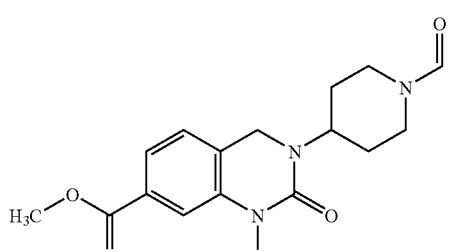
N86
N87
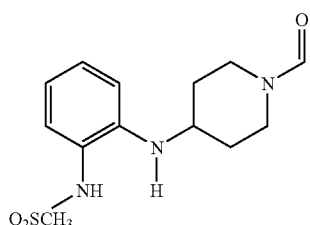
N88
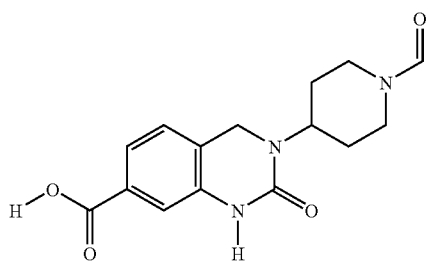
N89
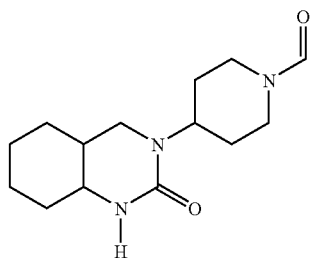
N90
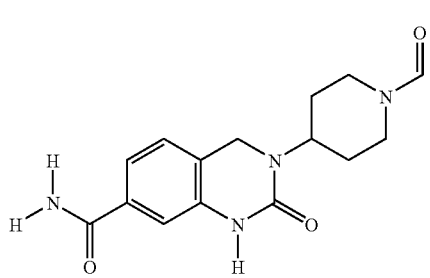
N91

-continued
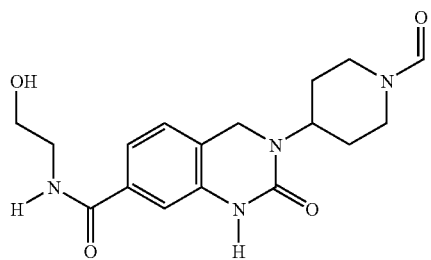
N92
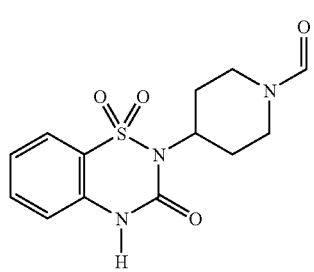
N93
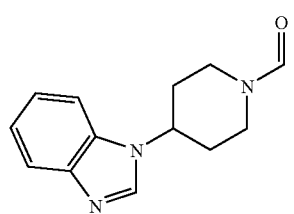
N94
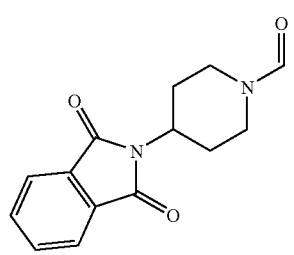
N95
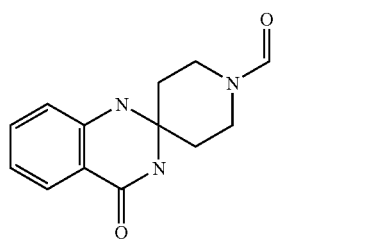
N96
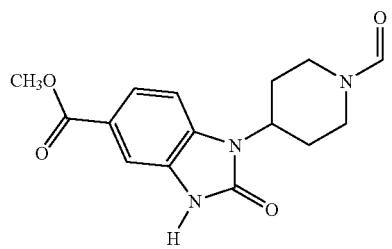
N97
-continued
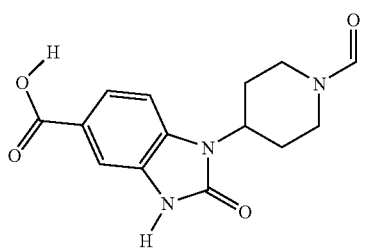
N98
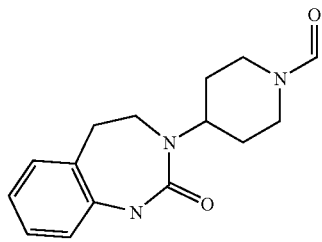
N99
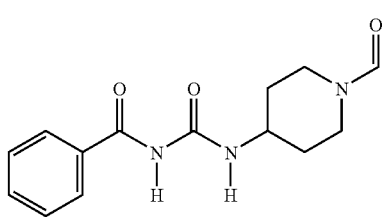
N100
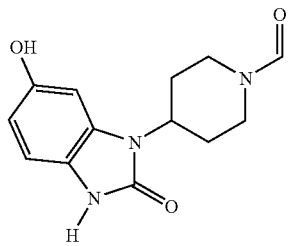
N101
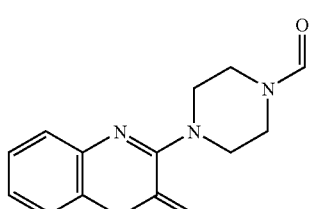
N102
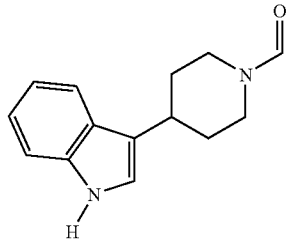
N103

-continued

-continued
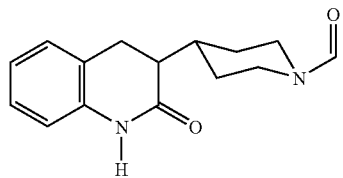
N121
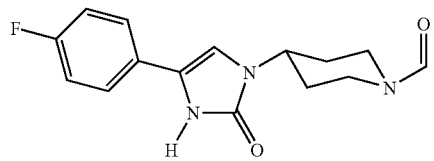
N122
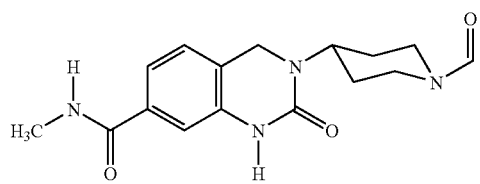
N123
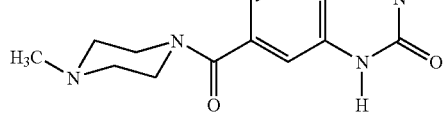
N24
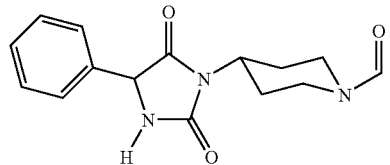
N125
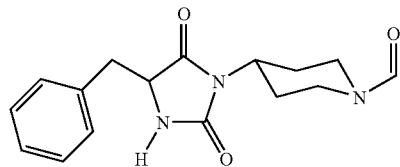
N126
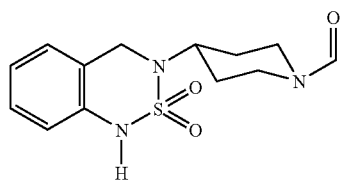
N127
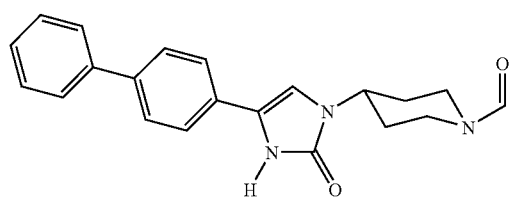
N128
-continued
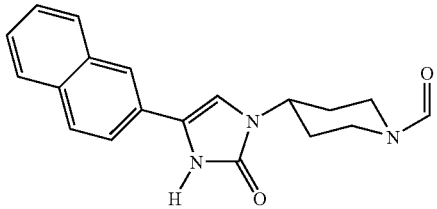
N129
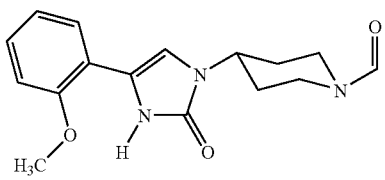
N130
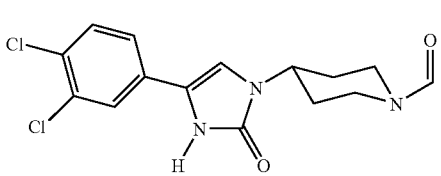
N131
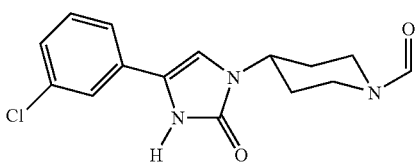
N132
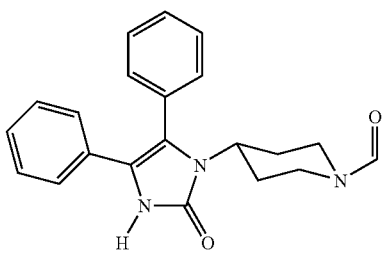
N133
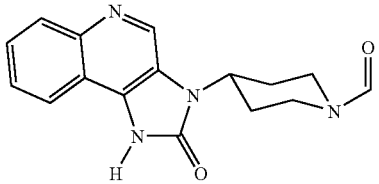
N134
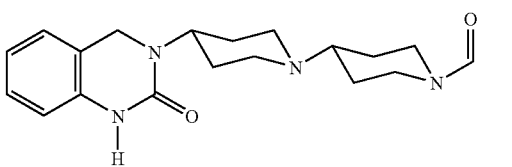
N135
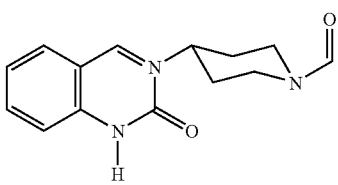
N136

-continued
| | | |
|---|---|---|
| 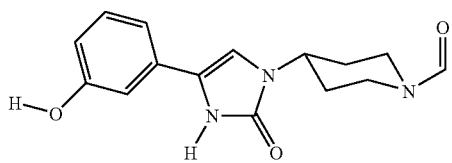 | N137 | |
| 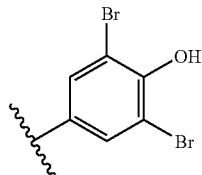 | | AS1 |
| | N138 | |
| | | AS2 |
| 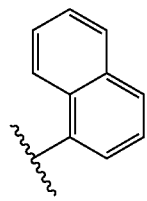 | N139 | |
| | | AS3 |
| | N140 | |
| 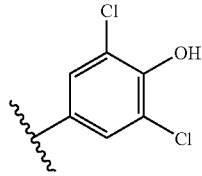 | | AS4 |
| | N141 | |
| 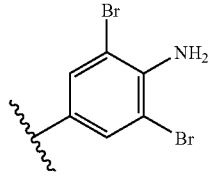 | | AS5 |
| | N142 | |
| 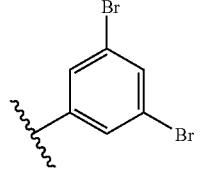 | N143 | AS6 |
| | N144 | |
| 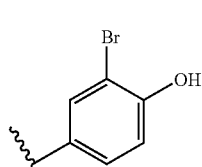 | | AS7 |
| 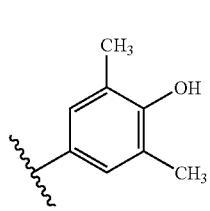 | | |

-continued
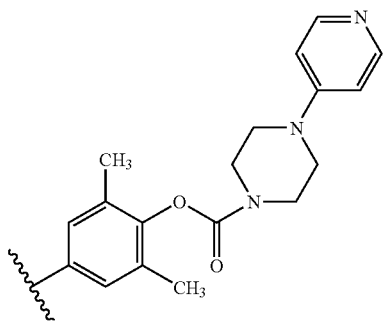
AS8
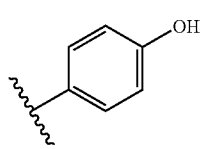
AS9
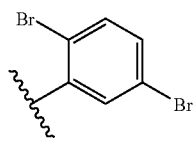
AS10
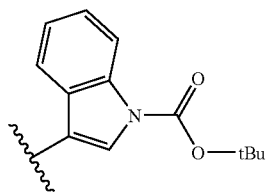
AS11
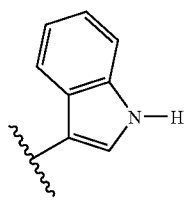
AS12
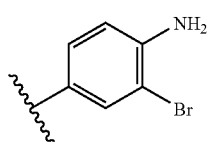
AS13
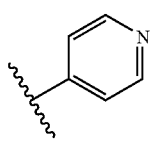
AS14
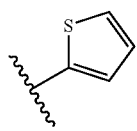
AS15
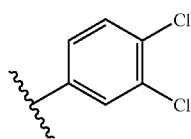
AS16
-continued
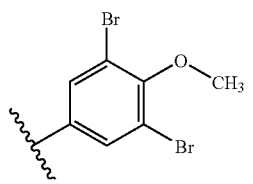
AS17
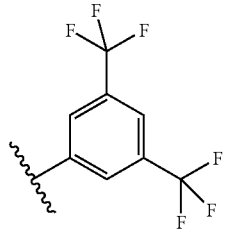
AS18
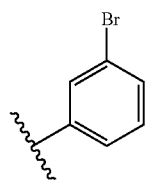
AS19
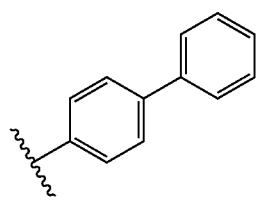
AS20
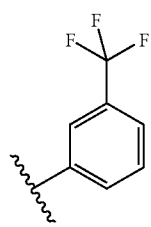
AS21
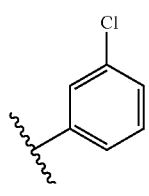
AS22
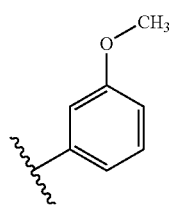
AS23

-continued
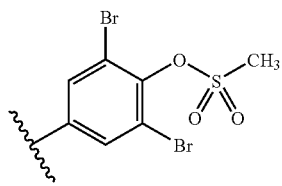 AS24
 AS25
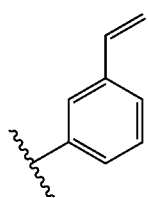 AS26
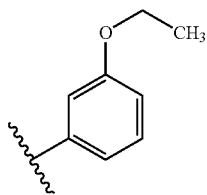 AS27
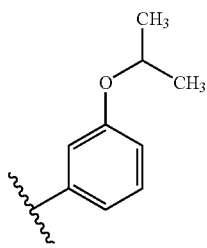 AS28
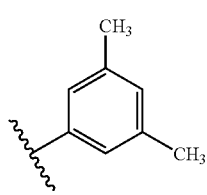 AS29
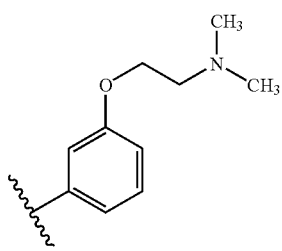 AS30
-continued
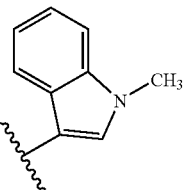 AS31
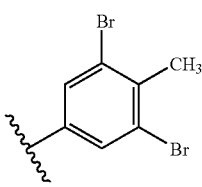 AS32
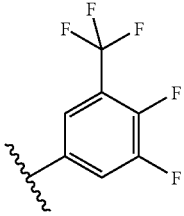 AS33
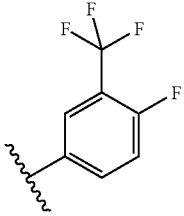 AS34
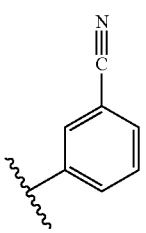 AS35
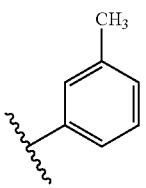 AS36
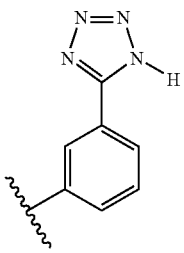 AS37

-continued
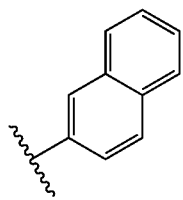 AS38
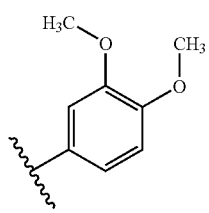 AS39
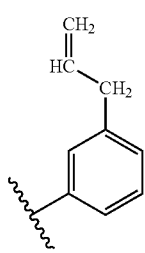 AS40
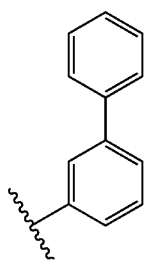 AS41
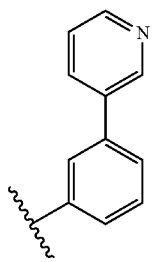 AS42
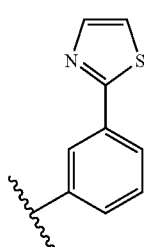 AS43
-continued
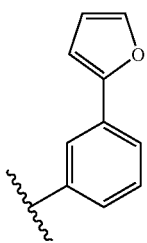 AS44
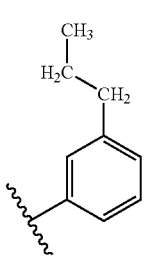 AS45
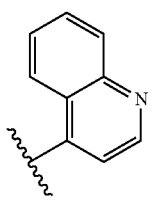 AS46
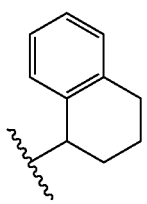 AS47
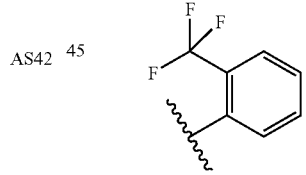 AS48
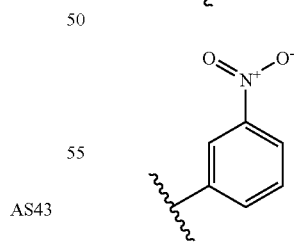 AS49
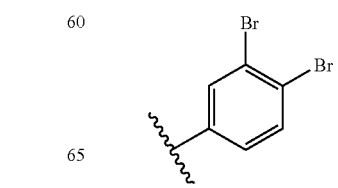 AS50

-continued
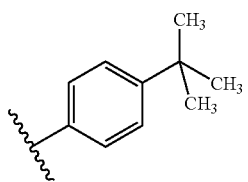
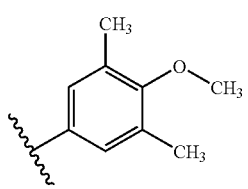
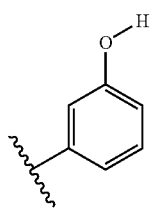
— bond
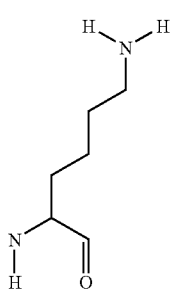
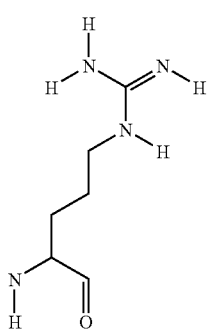
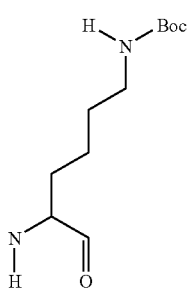
-continued
AS51
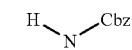
AS52
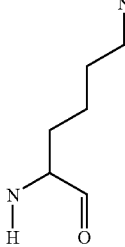
AS53
A0
A1
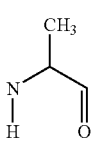
A2
A3
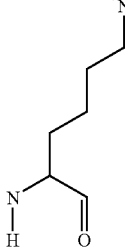
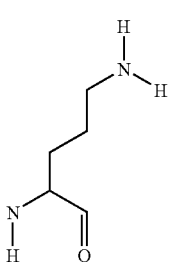
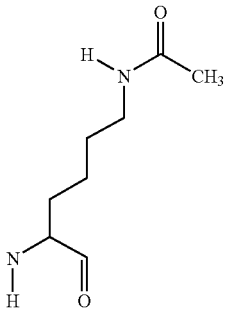
A4
A5
A6
A7
A8
A9
A10

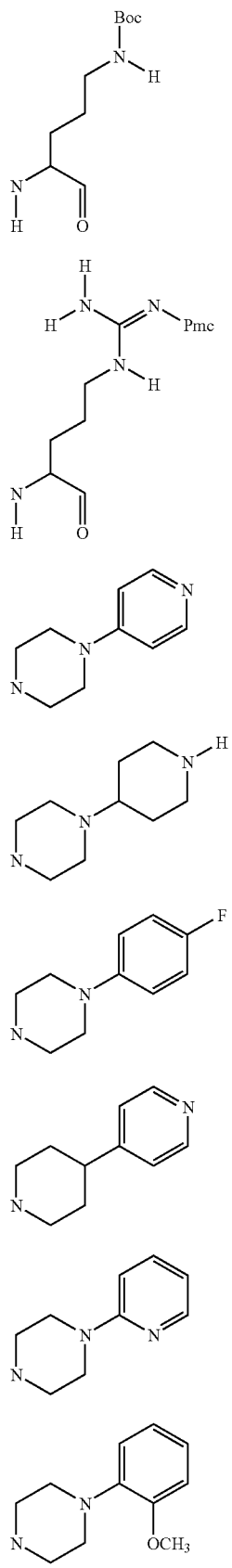
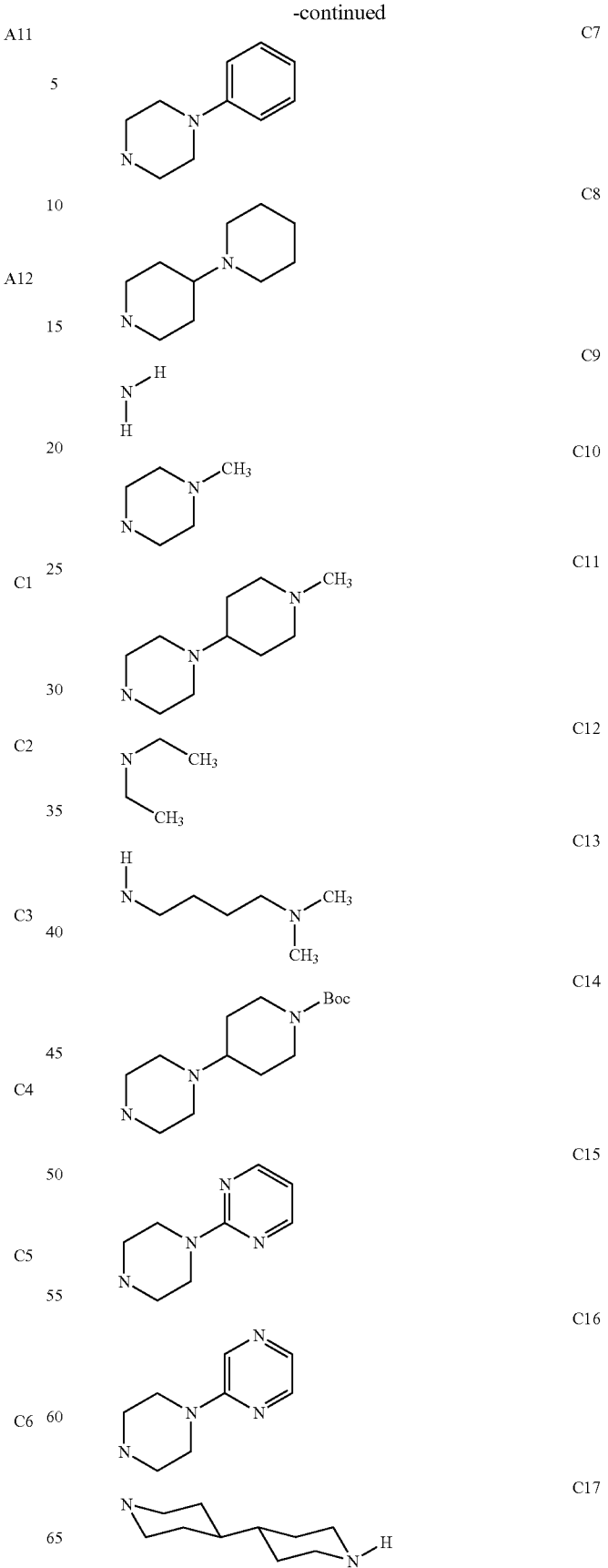

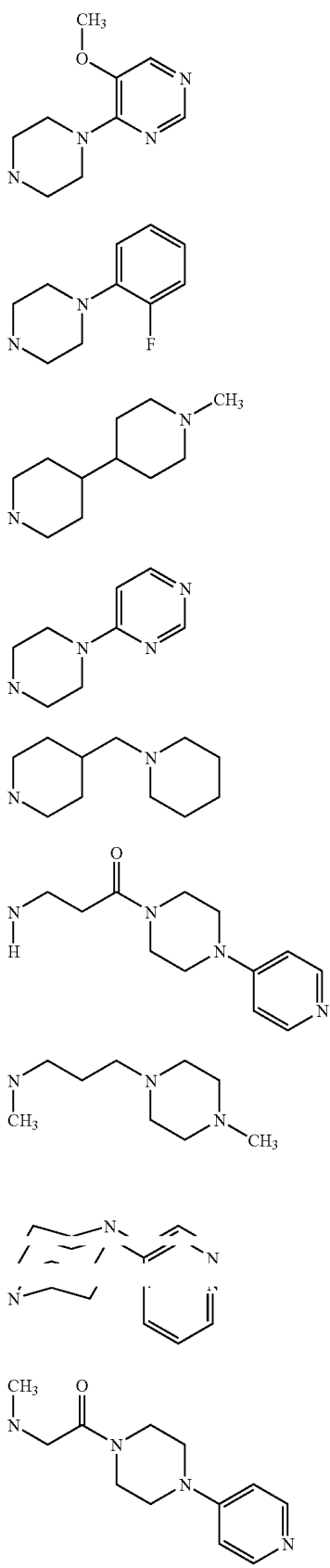
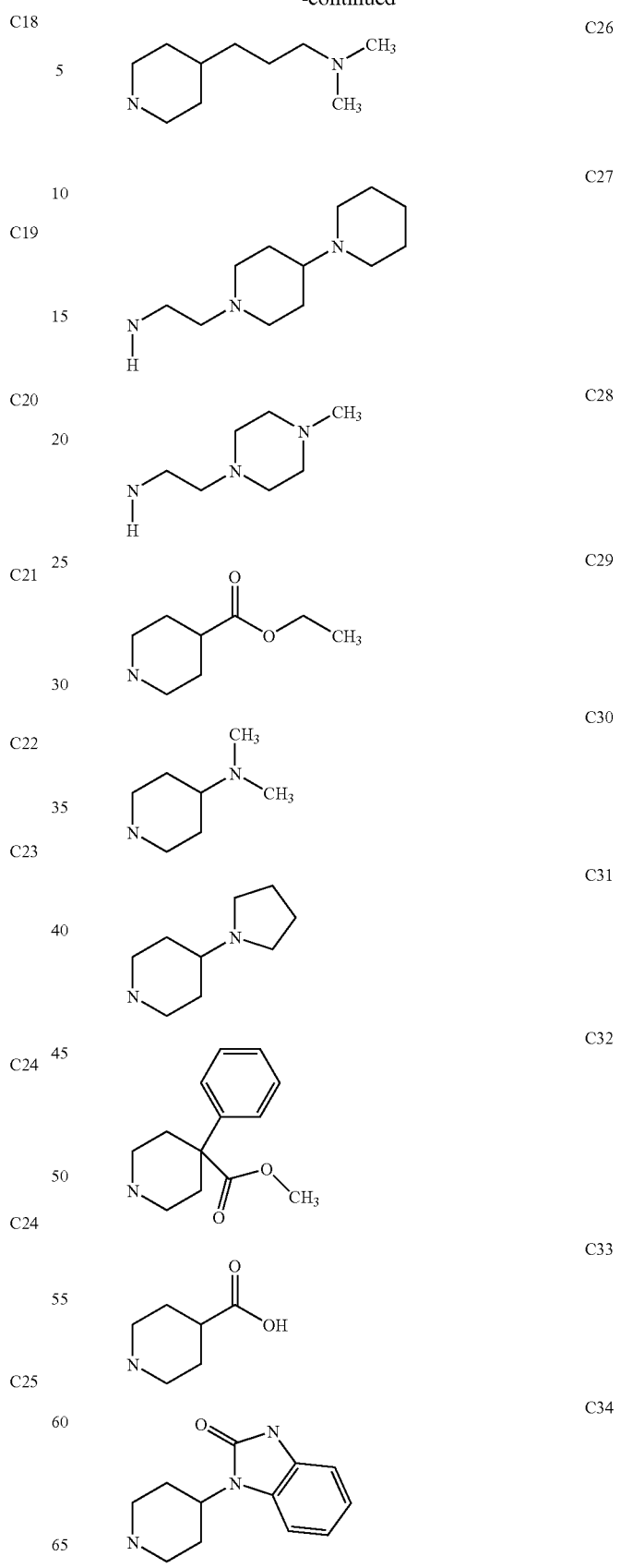

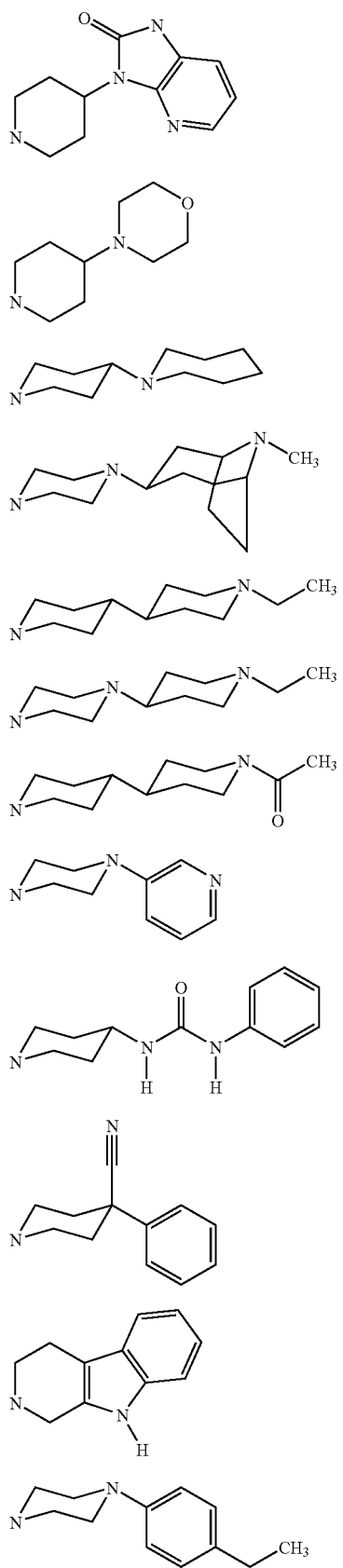
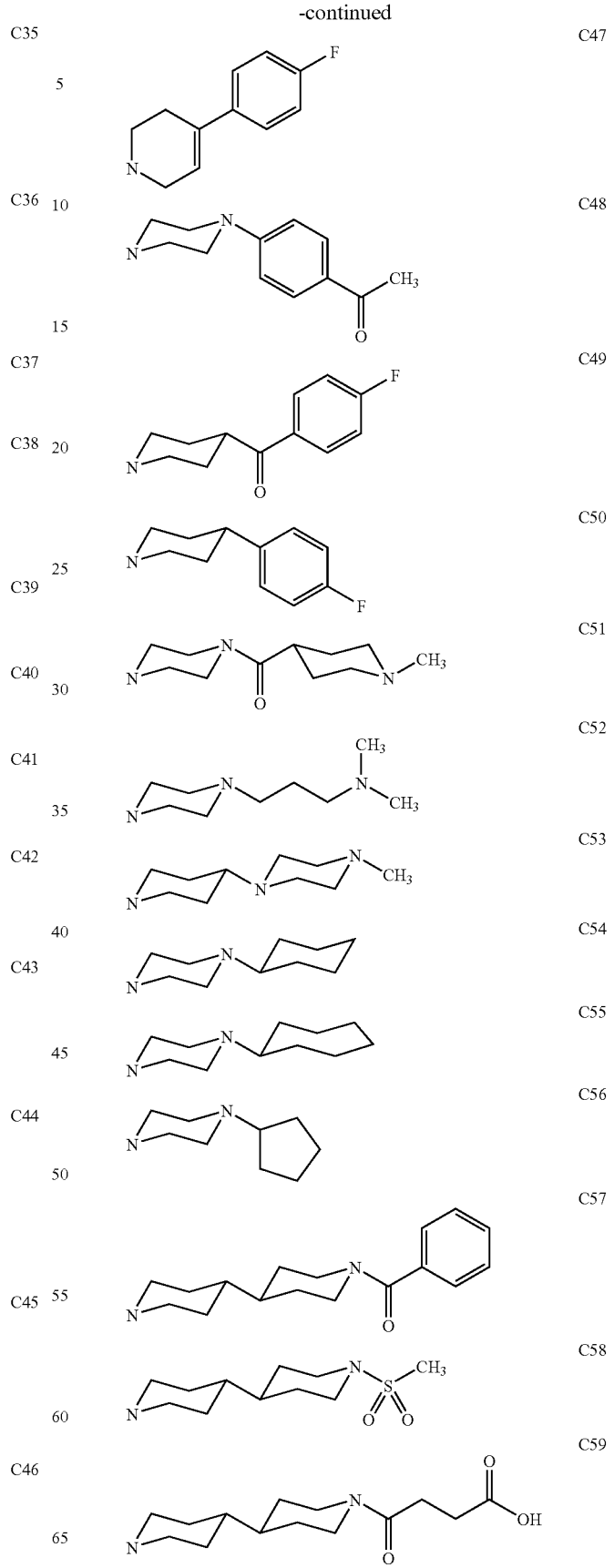

-continued

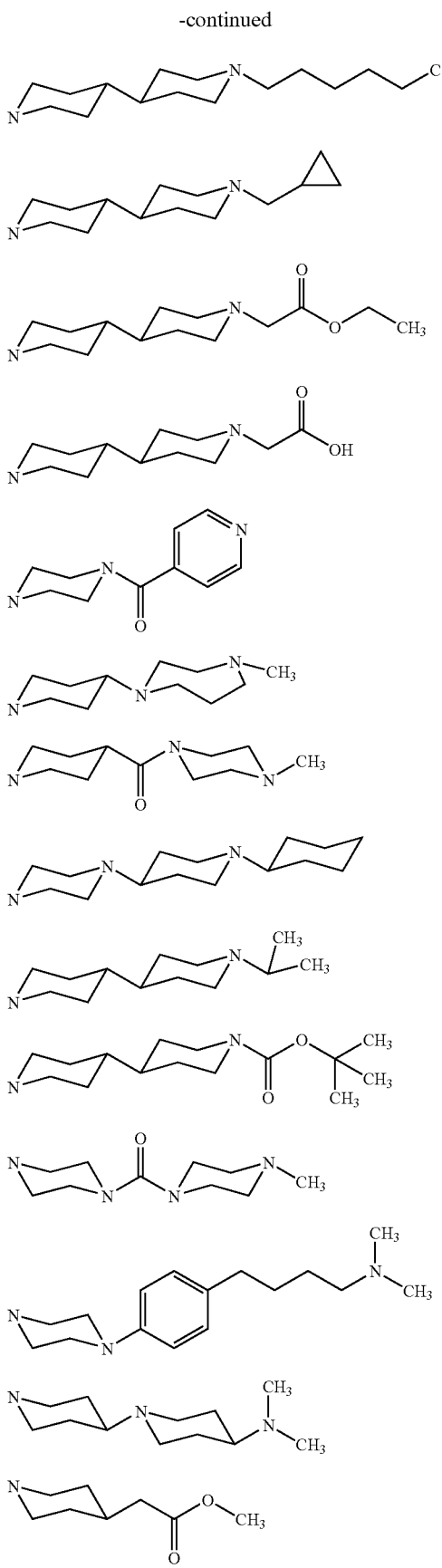

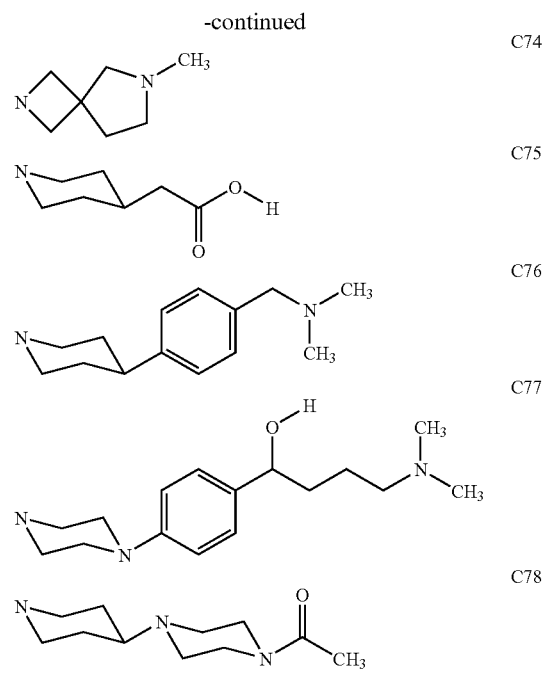

A. Preparation of Intermediate Compounds

EXAMPLE A1

Preparation of compounds of the general structure:

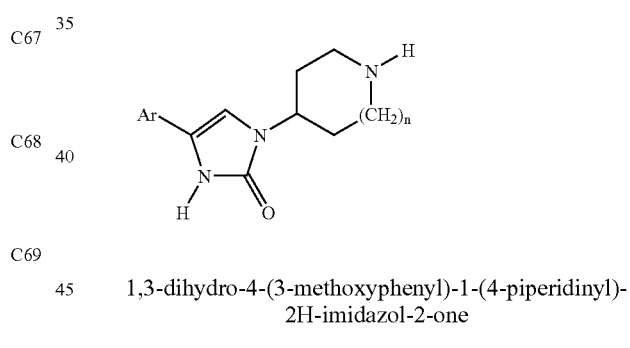

1,3-dihydro-4-(3-methoxyphenyl)-1-(4-piperidinyl)-2H-imidazol-2-one a) 4-[1,3-dihydro-4-(3-methoxyphenyl)-2(2H)-oxoimidazol-1-yl]-1-(1,1-dimethylethoxycarbonyl)-piperidine To a mixture of 20.0 g (0.10 mol) of 4-amino-1-(1,1-dimethylethoxycarbonyl)piperidine, 8.2 g (0.1 mol) of anhydrous sodium acetate and 150 ml of dichloromethane was added dropwise, with stirring and whilst maintaining a reaction temperature of from 0° C. to +10° C., a solution of 25.0 g (0.109 mol) of 3-methoxyphenacylbromide in 50 ml of dichloromethane was added dropwise. The mixture was stirred for 5 hours at room temperature, then 19.5 g (0.296 mol) of sodium cyanate, 18 ml of glacial acetic acid and 10 ml of water were added and stirring was continued for 12 hours at room temperature. The mixture was stirred into 1 l of ice water, the dichloromethane phase was separated off, washed twice with 200 ml of water, 5% aqueous sodium hydrogen carbonate solution, 20% aqueous citric acid solution and once more with water, dried over magnesium sulphate and evaporated down in vacuo. The residue was taken up in methanol.

It was left to stand overnight, the precipitate which crystallised out was suction filtered, washed thoroughly with tert. butyl-methylether and after drying in vacuo 11.5 g (30.8% of theory) of colourless crystals were obtained.

MS: M$^+$=373

The following were obtained accordingly:

(1) 4-[1,3-dihydro-4-phenyl-2(2H)-oxoimidazol-1-yl]-1-(1,1-dimethylethoxycarbonyl)-piperidine
R$_f$: 0.51 (FM4)

(2) 4-[1,3-dihydro-4-(4-methoxyphenyl)-2(2H)-oxoimidazol-1-yl]-1-(1,1-dimethylethoxycarbonyl)-piperidine
yield: 23.8% of theory (3) 4-[1,3-dihydro-4-[3-(trifluoromethyl)phenyl]-2(2H)-oxoimidazol-1-yl]-1-(1,1-dimethylethoxycarbonyl)-piperidine
IR(KBr): 1685.7 cm$^{-1}$ (C=O)

(4) 4-[1,3-dihydro-5-methyl-4-phenyl-2(2H)-oxoimidazol-1-yl]-1-(1,1-dimethylethoxycarbonyl)-piperidine
R$_f$: 0.23 (dichloromethane/methanol 9/1 v/v)
IR(KBr): 1687.6 cm$^{-1}$ (C=O)
MS: M$^+$=357

(5) 4-[1,3-dihydro-4-(3-nitrophenyl)-2(2H)-oxoimidazol-1-yl]-1-(1,1-dimethylethoxycarbonyl)-piperidine
yield: 29.1% of theory
MS: M$^+$=388

(6) 4-[4-(3-bromophenyl)-1,3-dihydro-2(2H)-oxoimidazol-1-yl]-1-(1,1-dimethylethoxycarbonyl)-piperidine
yield: 13.1% of theory
IR(KBr): 1685 cm$^{-1}$ (C=O)
MS: M$^+$=421/423 (Br)

(7) 4-[1,3-dihydro-4,5-diphenyl-2(2H)-oxoimidazol-1-yl]-1-(1,1-dimethylethoxycarbonyl)-piperidine
IR(KBr): 1680, 1699 cm$^{-1}$ (C=O)
MS: M$^+$=419

(8) 4-[1,3-dihydro-4-(4-fluorophenyl)-2(2H)-oxoimidazol-1-yl]-1-(1,1-dimethylethoxycarbonyl)-piperidine
IR(KBr): 1682 cm$^{-1}$ (C=O)
MS: M$^+$=388

(9) 4-[4-(4-biphenylyl)-1,3-dihydro-2(2H)-oxoimidazol-1-yl]-1-(1,1-dimethylethoxycarbonyl)-piperidine
yield: 21.6% of theory, colourless crystals
R$_f$: 0.6 (ethyl acetate)
IR(KBr): 1681.8 cm$^{-1}$ (C=O)

(10) 4-[1,3-dihydro-4-(2-naphthyl)-2(2H)-oxoimidazol-1-yl]-1-(1,1-dimethylethoxycarbonyl)-piperidine
yield: 30% of theory, crystals
IR(KBr): 1679.9 cm$^{-1}$ (C=O)

(11) 4-[1,3-dihydro-4-(2-methoxyphenyl)-2(2H)-oxoimidazol-1-yl]-1-(1,1-dimethylethoxycarbonyl)-piperidine
R$_f$: 0.86 (FM1)

(12) 4-[4-(3,4-dichlorophenyl)-1,3-dihydro-2(2H)-oxoimidazol-1-yl]-1-(1,1-dimethylethoxycarbonyl)-piperidine
yield: 62% of theory, colourless crystals
R$_f$: 0.34 (ethyl acetate)
IR(KBr): 1687 cm$^{-1}$ (C=O)

(13) 4-[4-(3-chlorophenyl)-1,3-dihydro-2(2H)-oxoimidazol-1-yl]-1-(1,1-dimethylethoxycarbonyl)-piperidine
yield: 21% of theory
R$_f$: 0.6 (ethyl acetate/methanol 9/1 v/v)

(14) 4-[1,3-dihydro-4-(3-hydroxyphenyl)-2(2H)-oxoimidazol-1-yl]-1-(1,1-dimethylethoxycarbonyl)-piperidine
Yield: 60% of theory
IR(KBr): 1682 cm$^{-1}$ (C=O)
MS: M$^+$=359

(15) 4-[4-[3,5-bis-(trifluoromethyl)phenyl]-1,3-dihydro-2(2H)-oxoimidazol-1-yl]-1-(1,1-dimethylethoxycarbonyl)-piperidine
Yield: 3.2% of theory
IR(KBr): 1687.6 cm$^{-1}$ (C=O)
R$_f$: 0.95 (dichloromethane/methanol 9/1 v/v)

(16) 4-[4-(4-amino-3,5-dibromophenyl)-1,3-dihydro-2(2H)-oxoimidazol-1-yl]-1-(1,1-dimethylethoxycarbonyl)-piperidine
Yield: 4.6% of theory
IR(KBr): 1684 cm$^{-1}$ (C=O)
R$_f$: 0.48 (FM4; Macherey-Nagel POLYGRAM® SIL G/TV$_{254}$ ready-made films for TLC)

b) 1,3-dihydro-4-(3-methoxyphenyl)-1-(4-piperidinyl)-2H-imidazol-2-one

The solution of 11.5 g (0.0308 mol) of 4-[1,3-dihydro-4-(3-methoxyphenyl)-2(2H)-oxoimidazol-1-yl]-1-(1,1-dimethylethoxy-carbonyl)-piperidine in 150 ml of dichloromethane was mixed with 15 ml of trifluoroacetic acid and then stirred overnight at room temperature. The reaction mixture was evaporated down in vacuo, the residue was taken up in 10 ml of water and made distinctly ammoniacal. The resulting precipitate was suction filtered, washed thoroughly with water and dried overnight at 50° C. in vacuo. 7.0 g (83.1% of theory) of colourless crystals were obtained, R$_f$ value 0.2 (dichloromethane/methanol 9/1 v/v).

The following were obtained accordingly:

(1) 1,3-dihydro-4-phenyl-1-(4-piperidinyl)-2H-imidazol-2-one,
R$_f$: 0.22 (FM1; Macherey-Nagel POLYGRAM® SIL G/UV$_{254}$ ready-made films for TLC)
IR(KBr): 1672 cm$^{-1}$ (C=O)

(2) 1,3-dihydro-4-(4-methoxyphenyl)-1-(4-piperidinyl)-2H-imidazol-2-one
IR(KBr): 1670 cm$^{-1}$ (C=O)
MS: M$^+$=273

(3) 1,3-dihydro-4-[3-(trifluoromethyl)phenyl]-1-(4-piperidinyl)-2H-imidazol-2-one
IR(KBr): 1687.6 cm$^{-1}$ (C=O)

(4) 1,3-dihydro-5-methyl-4-phenyl-1-(4-piperidinyl)-2H-imidazol-2-one
yield: 76.2% of theory
IR (KBr): 1679.9 cm$^{-1}$ (C=O)
MS: M$^+$=257

(5) 1,3-dihydro-4-(3-nitrophenyl)-1-(4-piperidinyl)-2H-imidazol-2-one
yield: 94% of theory
IR(KBr): 1677.8 (C=O); 1137.8, 1197.6, 1349.9 (NO$_2$) cm$^{-1}$ (6) 4-(3-bromophenyl)-1,3-dihydro-1-(4-piperidinyl)-2H-imidazol-2-one
yield: quantitative
IR(KBr): 1676 cm$^{-1}$ (C=O)

(7) 1,3-dihydro-4,5-diphenyl-1-(4-piperidinyl)-2H-imidazol-2-one
IR(KBr): 1670 cm$^{-1}$ (C=O)
MS: M$^+$=319

(8) 1,3-dihydro-4-(4-fluorophenyl)-1-(4-piperidinyl)-2H-imidazol-2-one
yield: 30% of theory
R$_f$: 0.2 (eluant: ethyl acetate/methanol/conc. ammonia 9/1/0.3 v/v/v)
IR(KBr): 1682 cm$^{-1}$ (C=O)

(9) 4-(4-biphenylyl)-1,3-dihydro-1-(4-piperidinyl)-2H-imidazol-2-one
yield: quantitative
IR(KBr) of the trifluoroacetate: 1679.9 cm$^{-1}$ (C=O)

(10) 1,3-dihydro-4-(2-naphthyl)-1-(4-piperidinyl)-2H-imidazol-2-one
yield: 28.2% of theory
$R_f$: 0.03 (FM1)
IR(KBr) of the trifluoroacetate: 1678 cm$^{-1}$ (C=O)
(11) 7-(2-methoxyphenyl)-1-(4-piperidinyl)-2H-imidazol-2-one
yield: 18.8% of theory
$R_f$: 0.22 (FM1)
IR(KBr) of the trifluoroacetate: 1681.6 cm$^{-1}$ (C=O)
(12) 4-(3,4-dichlorophenyl)-1,3-dihydro-1-(4-piperidinyl)-2H-imidazol-2-one
yield: quantitative
IR(KBr) of the trifluoroacetate: 3197 (N—H); 1685 (C=O)cm$^{-1}$
(13) 4-(3-chlorophenyl)-1,3-dihydro-1-(4-piperidinyl)-2H-imidazol-2-one
Yield: 98% of theory
$R_f$: 0.25 (eluant: ethyl ethanoate/methanol/conc. ammonia 9/1/0.3 v/v/v)
(14) 1,3-dihydro-4-(3-hydroxyphenyl)-1-(4-piperidinyl)-2H-imidazol-2-one
Yield: 90% of theory
$R_f$: 0.075 (FM1)
IR(KBr): 1670 (C=O) cm$^{-1}$
MS: M$^+$=259
(15) 4-[3,5-bis-(trifluoromethyl)phenyl]-1,3-dihydro-1-(4-piperidinyl)-2H-imidazol-2-one
Yield: 71% of theory
$R_f$: 0.15 (FM1)
IR(KBr): 1701 (C=O) cm$^{-1}$
MS: M$^+$=379
(16) 4-(4-amino-3,5-dibromophenyl)-1,3-dihydro-1-(4-piperidinyl)-2H-imidazol-2-one
Yield: 44% of theory
$R_f$: 0.71 (FM1; Macherey-Nagel POLYGRAM® SIL G/UV$_{254}$ ready-made films for TLC)
IR(KBr): 1676 (C=O) cm$^{-1}$

EXAMPLE A2

2,4-dihydro-5-phenyl-2-(4-piperidinyl)-3H-1,2,4-triazol-3-one a) 1-(9H-fluoren-9-ylmethoxycarbonyl)-4-piperidinone-(1,1-dimethylethoxycarbonyl)hydrazone A mixture of 16.0 g (0.05 mol) of 1-(9H-fluoren-9-ylmethoxycarbonyl)-4-piperidinone, 7.25 g (0.055 mol) of tert. butyl hydrazinoformate and 250 ml of ethanol was refluxed for 1 hour. The solvent was distilled off in vacuo, the oily residue remaining was triturated with diethylether. The crystalline precipitate thus formed was suction filtered and washed with a little diethylether. After the product had been dried in vacuo 21.7 g (99.7% of theory) of colourless crystals were obtained, m.p. 156-158° C. (decomposition).

b) N-(1,1-dimethylethoxycarbonyl)-N'-[1-(9H-fluoren-9-yl-methoxycarbonyl)-4-piperidinyl]-hydrazine A solution of 21.7 g (0.05 mol) of 1-(9H-fluoren-9-ylmethoxycarbonyl)-4-piperidinone-(1,1-dimethylethoxycarbonyl)-hydrazone in 200 ml of glacial acetic acid was hydrogenated in the presence 2.0 g platinum (IV) oxide at room temperature and 3 bar of hydrogen pressure until the calculated volume of hydrogen had been taken up. The catalyst was filtered off, the filtrate was evaporated down in vacuo and the residue was dissolved in a little diethylether. The crystals precipitated after standing for 3 hours at room temperature were suction filtered, washed with a little diethylether and dried in vacuo at room temperature. 21.8 g (99.6% of theory) of colourless crystals of m.p. 135-137° C. and $R_f$=0.235 (eluant 3) were obtained.
ESI-MS: (M+H)$^+$=438 c) [1-(9H-fluoren-9-ylmethoxycarbonyl)-4-piperidinyl]-hydrazine-hydrochloride 21.8 g (0.0498 mol) of N-(1,1-dimethylethoxycarbonyl)-N'-[1-(9H-fluoren-9-ylmethoxycarbonyl)-4-piperidinyl]-hydrazine were dissolved in 100 ml of trifluoroacetic acid and stirred for 1 hour at room temperature. The excess trifluoroacetic acid was removed in vacuo, the residue was dissolved in 50 ml of water and made alkaline with 10% aqueous sodium carbonate solution. The solution was extracted thoroughly with dichloromethane, the combined extracts were dried over magnesium sulphate and evaporated down in vacuo. The residue thus obtained was taken up in ethyl acetate and converted into the hydrochloride by the addition of ethereal hydrogen chloride solution. After recrystallisation from anhydrous ethanol 6.2 g (33.3% of theory) of colourless crystals of melting point 160-162° C. were obtained.

$C_{20}H_{23}N_3O_2$+HCl (373.88)

| | | | | |
|---|---|---|---|---|
| Calculated: | C 64.25 | H 6.47 | N 11.24 | Cl 9.48 |
| Found: | 64.14 | 6.46 | 10.99 | 9.46 | d) 2,4-dihydro-5-phenyl-2-[1-(9H-fluoren-9-ylmethoxycarbonyl)-4-piperidinyl]-3H-1,2,4-triazol-3-one The solutions of 5.56 g (0.0165 mol) of [1-(9H-fluoren-9-ylmethoxycarbonyl)-4-piperidinyl]-hydrazine in 60 ml of tetrahydrofuran and 3.7 g (0.0177 mol) of N-(ethoxycarbonyl)-benzothionamide in 30 ml of tetrahydrofuran were combined and refluxed for 1 hour, whereupon hydrogen sulphide was released. The solvent was distilled off in vacuo, the oily residue remaining was boiled with a little acetonitrile. The mixture was allowed to cool, then additionally cooled from outside with ice water and the resulting precipitate was suction filtered. 4.0 g (52% of theory) of colourless crystals were obtained, melting point 142° C. and $R_f$=0.38 (eluant 4).
IR (KBr): 1685.7 cm$^{-1}$ (C=O)

e) 2,4-dihydro-5-phenyl-2-(4-piperidinyl)-3H-1,2,4-triazol-3-one

A mixture of 9.0 g (0.0193 mol) of 2,4-dihydro-5-phenyl-2-[1-(9H-fluoren-9-ylmethoxycarbonyl)-4-piperidinyl]-3H-1,2,4-triazol-3-one, 50 ml of tetrahydrofuran and 70 ml of diethylamine was stirred at room temperature until the end of the reaction monitored by thin layer chromatography. The solvent was removed in vacuo, the residue remaining was mixed with 300 ml of water and subjected to ultrasound treatment for 30 minutes. The insoluble matter was separated off by suction filtering and the aqueous filtrate was evaporated down in vacuo. The residue thus obtained was boiled with a little methanol and after cooling it was suction filtered. After drying 0.58 g (12.3% of theory) of colourless crystals of melting point 294° C. (D) and $R_f$=0.1 (eluant 1) were obtained.

IR (KBr): 1681.8 cm$^{-1}$ (C=O)

EXAMPLE A3

Preparation of Compounds of General Structure:

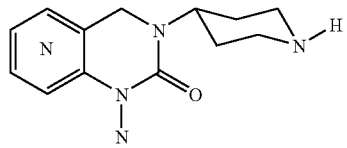

3,4-dihydro-3-(4-piperidinyl)-2 (1H-pyrido[2,3-d]-pyrimidinone a) N-(2-Pyridinyl)-2,2-dimethylpropanamide

To a solution of 94.1 g (1.0 mol) of 2-aminopyridine and 173 ml (1.25 mol) of triethylamine in 400 ml of dichloromethane were added dropwise, whilst cooling with ice water, 132.5 g (1.099 mol) of pivaloyl chloride in 150 ml of dichloromethane. The. mixture was stirred for 2 hours at room temperature and filtered to remove the triethylamine hydrochloride formed. The filtrate was washed with water and twice with 5% aqueous sodium hydrogen carbonate solution, then dried over sodium sulphate. After working up in the usual way 157.5 g (88.4% of theory) of colourless crystals of melting point 74-76° C. were obtained.

The following was obtained in the same way:
N-(4-Pyridinyl)-2,2-dimethylpropanamide
Yield: 74% of theory
Mp. 137-140° C. (diisopropylether)
IR (KBr): 1687 cm$^{-1}$ (C=O)

b) N-(3-formyl-2-pyridinyl)-2,2-dimethylpropanamide whilst maintaining a reaction temperature of −78° C., 781 ml (1.25 mol) of a 1.6-molar solution of n-butyllithium in n-hexane were added dropwise to a solution of 89.1 g (0.5 mol) of N-(2-pyridinyl)-2,2-dimethylpropanamide in 300 ml of anhydrous tetrahydrofuran. The mixture was allowed to heat slowly up to 0° C. and stirred for 3 hours at this temperature. Then the mixture was again cooled to −78° C. and whilst maintaining this temperature the solution of 109.6 g (1.5 mol) of dimethyformamide in 150 ml of anhydrous tetrahydrofuran was added dropwise thereto. The mixture was allowed to come up to 0° C. and then stirred into 1 l of ice water. It was initially acidified with 12% aqueous hydrochloric acid, then made alkaline by the addition of solid potassium carbonate and extracted thoroughly with diethylether. The combined ether extracts were dried over sodium sulphate and evaporated down. The crystalline residue, after recrystallisation from diisopropylether, had an m.p. of 83° C. Yield: 94.0 g (91.2% of theory).

The following were obtained in the same way:
(1) N-(4-formyl-3-pyridinyl)-2,2-dimethylpropanamide
Yield: 52% of theory
$R_f$: 0.5 (dichloromethane/methanol/conc. ammonia 90/10/0.1 v/v/v)
IR (KBr) of the hydrochloride: 1695 cm$^{-1}$ (C=O)
MS: M$^+$=206
(2) N-(3-formyl-4-pyridinyl)-2,2-dimethylpropanamide
The reddish oil obtained in a quantitative yield was further processed without more purification c) N-[3-[[[1-(phenylmethyl)-4-piperidinyl]amino]methyl]-2-pyridinyl]-2,2-dimethylpropanamide A solution of 8.2 g (0.0398 mol) of N-(3-formyl-2-pyridinyl)-2,2-dimethylpropanamide and 7.6 g (0.04 mol) of 4-amino-1-(phenylmethyl)piperidine in 80 ml of methanol was combined in batches with a total of 1.7 g (0.045 mol) of sodium borohydride and refluxed for a total of 24 hours. The solvent was removed in vacuo, the residue was distributed between water and ethyl acetate. The organic phase was dried over sodium sulphate and freed from solvent. The residue was triturated with diisopropylether and suction filtered. 6.0 g (39.6% of theory) of colourless crystals of melting point 138° C. were obtained.

The following were obtained in the same way:
(1) N-[4-[[[1-(phenylmethyl)-4-piperidinyl]amino]methyl]-3-pyridinyl]-2,2-dimethylpropanamide
Yield: 94% of theory
$R_f$: 0.4 (dichloromethane/methanol/conc. ammonia 90/10/0.1 v/v/v)
The yellowish oil was used in the following stage without further purification
(2) N-[3-[[[1-(phenylmethyl)-4-piperidinyl]amino]methyl]-4-pyridinyl]-2,2-dimethylpropanamide
Yield: 11.6% of theory
IR(KBr): 1689 (C=O) cm$^{-1}$ d) 2-amino-3-[[[1-(phenylmethyl)-4-piperidinyl]-amino]methyl]-pyridine

A mixture of 6.0 g (0.0158 mol) of N-[3-[[[1-(phenylmethyl)-4-piperidinyl]amino]methyl]-2-pyridinyl]-2,2-dimethylpropanamide and 100 ml of conc. hydrochloric acid was refluxed for 3 hours. The mixture was evaporated down in vacuo, the residue remaining was dissolved in a little water and made alkaline by the addition of solid potassium carbonate. It was extracted thoroughly with ethyl acetate, the combined extracts were dried over sodium sulphate and evaporated down in vacuo. The residue was thoroughly triturated with diisopropylether and yielded 4.2 g (89.7% of theory) of colourless crystals of melting point 114° C.

The following were obtained in the same way:
(1) 3-amino-4-[[[1-(phenylmethyl)-4-piperidinyl]amino] methyl]-pyridine
Yield: 96% of theory
$R_f$: 0.42 (dichloromethane/methanol/conc. ammonia 90/10/0.1 v/v/v)
The yellowish oil was used in the following stage without further purification
(2) 4-amino-3-[[[1-(phenylmethyl)-4-piperidinyl]amino] methyl]-pyridine
Yield: quantitative
The yellowish oil was used in the following stage without further purification e) 3,4-dihydro-3-[1-(phenylmethyl)-4-piperidinyl]-2 (1H)-pyrido[2,3-d]-pyrimidinone A mixture of 4.2 g (0.0142 mol) of 2-amino-3-[[[1-(phenylmethyl)-4-piperidinyl]amino]methyl]-pyridine, 2.4 g (0.0148 mol) of N,N'-carbonyldiimidazole and 50 ml of dimethylformamide was heated to 100° C. for 30 minutes. The still warm mixture was stirred into 300 ml of ice water, the precipitate formed was suction filtered and recrystallised from acetonitrile. After drying in vacuo 4.5 g (98.3% of theory) of colourless crystals of melting point 187° C. were obtained.

The following were obtained in the same way:
(1) 3,4-dihydro-3-[1-(phenylmethyl)-4-piperidinyl]-2(1H)-pyrido[3,4-d]-pyrimidinone Colourless crystals
    Yield: 33% of theory
    IR (KBr): 1676 cm$^{-1}$ (C=O)
    MS: M$^+$=322
(2) 3,4-dihydro-3-[1-(phenylmethyl)-4-piperidinyl]-2(1H)-pydrio[4,3-d]-pyrimidinone
    Mp. 155° C. (D)
    Yield: 99% of theory
    IR (KBr): 1680 cm$^{-1}$ (C=O)

f) 3,4-dihydro-3-(4-piperidinyl]-2(1H)-pyrido[2,3-d]-pyrimidinone

A solution of 4.7 g (0.0146 mol) of 3,4-dihydro-3-[1-(phenylmethyl)-4-piperidinyl]-2(1H)-pyrido[2,3-d]-pyrimidinone in 50 ml of methanol was hydrogenated at a temperature of 50° C. and in the presence of 2.0 g of 20% palladium/charcoal until the uptake of hydrogen ceased. After removal of the catalyst and solvent 3.3 g (97.3% of theory) of a colourless oil of $R_f$=0.35 (FM1) were obtained.
    IR (KBr): 1660.6 cm$^{-1}$ (C=O)

The following were obtained in the same way:
(1) 3,4-dihydro-3-(4-piperidinyl]-2(1H)-pyrido[3,4-d]-pyrimidinone
    Colourless crystals
    Yield: 95% of theory
    IR (KBr): 1662 cm$^{-1}$ (C=O)
    MS: M$^+$=232
(2) 3,4-dihydro-3-(4-piperidinyl]-2(1H)-pyrido[4,3-d]-pyrimidinone
    Yellowish resin
    Yield: 97% of theory
    IR (KBr): 1672 cm$^{-1}$ (C=O)
    $R_f$: 0.12 (FM1)

EXAMPLE A4

Methyl 3,4-dihydro-3-(4-piperidinyl)-2(1H)-oxoquinazoline-7-carboxylate a) (E)-1-(dimethylamino)-2-[4-(methoxycarbonyl)-2-nitrophenyl]-ethene

A mixture of 98.3 g (0.504 mol) of methyl 4-methyl-3-nitrobenzoate, 78.0 g (0.655 mol) of N,N-dimethylformamide dimethylacetal and 1 l of dimethylformamide was heated to 140° C. for 3 hours. The solvent was distilled off in vacuo, the residue was triturated thoroughly with 1 l methanol. After drying in vacuo 119.5 g (94.7% of theory) of a red amorphous substance was obtained, which was further processed without any more purification.

b) 4-(Methoxycarbonyl)-2-nitrobenzaldehyde

To a mixture of 119.5 g (0.478 mol) of (E)-1-(dimethylamino)-2-[4-(methoxycarbonyl)-2-nitrophenyl]-ethene and 1.3 l of water/tetrahydrofuran mixture (1/1 v/v) were added, in batches, 308.0 g (1.44 mol) of sodium metaperiodate, whilst the reaction temperature was regulated at under +30° C. by external cooling with ice water. The mixture was stirred for a further 2.5 hours at room temperature and then filtered. The precipitate was thoroughly washed with ethyl acetate. The organic phase was separated off, the aqueous phase was thoroughly extracted with ethyl acetate. The combined ethyl acetate phases were dried over sodium sulphate and evaporated down in vacuo. The oil which crystallised after one day was further processed without any more purification. Yield: 87 g (87% of theory).

c) Methyl 4-[[[1-(phenylmethyl)-4-piperidinyl]amino]methyl]-3-nitrobenzoate To a solution of 41.0 g (0.215 mol) of 4-amino-1-(phenylmethyl)-piperidine and 45.0 g (0.215 mol) of 4-(methoxycarbonyl)-2-nitrobenzaldehyde in 1 l methanol were added in batches, at room temperature, 8.3 g (0.22 mol) of sodium borohydride and the mixture was then stirred for 30 minutes at the same temperature. The mixture was stirred into 1 l of ice water and thoroughly extracted with tert. butyl-methylether. The combined extracts were dried over sodium sulphate and evaporated down in vacuo, the residue was dissolved in as little methanol as possible and converted into the hydrochloride by treatment with methanolic hydrogen chloride solution. The crystalline salt was suction filtered, washed with methanol and diethylether, then taken up in water and made alkaline with saturated aqueous potassium carbonate solution. The mixture obtained was extracted thoroughly with ethyl acetate, the combined ethyl acetate extracts were dried over sodium sulphate and evaporated down. 58.2 g (70.6% of theory) of a brownish-yellow oil were obtained, which was further processed without any more purification.

d) Methyl 3-amino-4-[[[1-(phenylmethyl)-4-piperidinyl]amino]methyl]-benzoate A solution of 58.0 g (0.151 mol) of methyl 4-[[[1-(phenylmethyl)-4-piperidinyl]amino]methyl]-3-nitrobenzoate in 800 ml of methanol was hydrogenated in the presence of 10 g of 5% rhodium/charcoal for 7 hours at room temperature. The catalyst was filtered off, the filtrate was evaporated down in vacuo. 50.0 g (93.7% of theory) of colourless crystals were obtained, which were further processed without any more purification.

e) Methyl 3,4-dihydro-3-[1-(phenylmethyl)-4-piperidinyl]-2(1H)-oxoquinazolin-7-carboxylate Prepared analogously to Example A3e) from methyl 3-amino-4-[[[1-(phenylmethyl)-4-piperidinyl]amino]methyl]-benzoate and N,N'-carbonyl-diimidazole in a yield of 66.3% of theory.
    Slightly yellowish crystals.
    IR (KBr): 1714.6; 1664.5 cm$^{-1}$ (C=O)

f) Methyl 3,4-dihydro-3-(4-piperidinyl)-2(1H)-oxoquinazolin-7-carboxylate

A solution of 35.5 g (0.0936 mol) of methyl 3,4-dihydro-3-[1-(phenylmethyl)-4-piperidinyl]-2(1H)-oxoquinazolin-7-carboxylate in 400 ml of methanol was hydrogenated in the presence of 5 g of 10% palladium/charcoal for 5 hours at 50° C. The catalyst was filtered off, the filtrate was evaporated down in vacuo. The residue was triturated with 150 ml of ethyl acetate and then suction filtered. After drying in vacuo 20.4 g (75.3w of theory) of colourless crystals were obtained, which were further processed without any more purification.

IR (KBr): 1718.5; 1672.2 cm$^{-1}$ (C=O)

The following were prepared analogously:
(1) 3,4-dihydro-3-(4-piperidinyl)-2(1H)-quinazolinone
R$_f$: 0.3 (FM1)
IR (KBr): 1662.5 cm$^{-1}$ (C=O)
(2) 3,4-dihydro-8-methoxy-3-(4-piperidinyl)-2(1H)-quinazolinone
R$_f$: 0.35 (FM1)
(3) 3,4-dihydro-6,7-dimethoxy-3-(4-piperidinyl)-2(1H)-quinazolinone
R$_f$: 0.40 (FM1)

EXAMPLE A5

3,4-dihydro-3-(4-piperidinyl)-1H-thieno[3,4-d]pyrimidin-2-one-trifluoroacetate a) Methyl 4-(ethoxycarbonylamino)-thiophene-3-carboxylate

A mixture of 50.0 g (0.258 mol) of methyl 4-aminothiophen-3-carboxylate-hydrochloride, 700 ml of toluene, 26 g (0.257 mol) of triethylamine and 27 ml (0.283 mol) of ethyl chlorocarbonate was refluxed for 5 hours. The insoluble matter was filtered off, the filtrate was evaporated down in vacuo and the residue was crystallised from petroleum ether. 59.0 g (99.8% of theory) of colourless crystals of melting point 52° C. were obtained.

In the same way, crystalline methyl 3-(ethoxycarbonylamino)-thiophen-2-carboxylate was obtained from methyl 3-aminothiophene-2-carboxylate and ethyl chlorocarbonate in a yield of 98.7% of theory.

IR (KBr): 1739.7; 1622 cm$^{-1}$ (C=O, C=C)

b) 4-(ethoxycarbonylamino)-thiophene-3-carboxaldehyde

Into an ice-cold suspension of 12.9 g (0.34 mol) of lithium aluminium hydride in 800 ml of tert. butyl-methylether was added dropwise, at a reaction temperature of about 0° C., a solution of 59.1 g (0.258 mol) of methyl 4-(ethoxycarbonylamino)-thiophene-3-carboxylate in 200 ml of tert. butyl-methylether, and the mixture was then stirred for a further 2 hours at 10° C. Then 13 ml of water, 13 ml of 2N aqueous sodium hydroxide solution and 39 ml of water were added dropwise one after another and the mixture was stirred for 1 hour at room temperature. It was filtered, and 500 g of activated manganese (IV) oxide were added in batches to the filtrate with stirring. After the completion of the reaction, which could be monitored by thin layer chromatography, the mixture was filtered again and the filtrate was then evaporated down in vacuo. The crystalline residue which solidified was further processed without any more purification. yield: 28.2 g (54.9% of theory).

In the same way 3-(ethoxycarbonylamino)-thiophene-2-carboxaldehyde was obtained from methyl 3-(ethoxycarbonylamino)-thiophene-2-carboxylate in a yield of 71.9% of theory.

c) 4-[[[1-(1,1-dimethylethoxycarbonyl)-4-piperidinyl]amino]methyl]-3-(ethoxycarbonylamino)-thiophene A mixture of 28.2 g (0.142 mol) of 4-(ethoxycarbonylamino)-thiophene-3-carboxaldehyde, 28.2 g (0.141 mol) of 4-amino-1-(1,1-dimethyl-ethoxycarbonyl)piperidine and 300 ml of toluene was refluxed using a water separator until water formation had ceased. The solvent was removed in vacuo, the residue was dissolved in 300 ml of methanol and at room temperature combined batchwise with 5.5 g (0.145 mol) of sodium borohydride. The mixture was stirred for a further hour at room temperature, then evaporated down in vacuo and the residue was distributed between water and tert. butyl-methylether. The organic phase was dried over sodium sulphate and freed from solvent in vacuo. The oily residue was further processed without purification.

Yield: 54.0 g (99.9% of theory).

In the same way 2-[[[1-(1,1-dimpethylethoxycarbonyl)-4-piperidinyl]amino]methyl]-3-(ethoxycarbonylamino)-thiophene was obtained from 3-(ethoxycarbonylamino)-thiophene-2-carboxaldehyde, 4-amino-1-(1,1-dimethylethoxycarbonyl)piperidine and sodium borohydride in a yield of 100% of theory.

IR (KBr): 1728.1; 1693.4 cm$^{-1}$ (C=O)

d) 3,4-dihydro-3-[1-(1,1-dimethylethoxycarbonyl)-4-piperidinyl]-1H-thieno[3,4-d]pyrimidin-2-one A solution of 54.0 g (0.141 mol) of 4-[[[1-(1,1-dimethylethoxycarbonyl)-4-piperidinyl]amino]methyl]-3-(ethoxycarbonylamino)-thiophene in 300 ml of dimethylformamide was refluxed for 4 hours. After the end of the reaction, which could be monitored by thin layer chromatography, the still warm mixture was stirred into 1 l of ice water. The crystalline precipitate was suction filtered and dried at 30° C. in a circulating air drier.

Yield: 47.5 g (99.8% of theory).

In the same way 3,4-dihydro-3-[1-(1,1-dimthylethoxycarbonyl)-4-piperidinyl]-1H-thieno[3,2-d]pyrimidin-2-one was obtained from 2-[[[1-(1,1-dimethylethoxycarbonyl)-4-piperidinyl]amino]methyl]-3-(ethoxycarbonyl-amino)-thiophene in a yield of 71% of theory. Colourless crystals of melting point 200° C. (acetonitrile).

IR (KBr): 1683.8; 1654.8 cm$^{-1}$ (C=O)

e) 3,4-dihydro-3-(4-piperidinyl)-1H-thieno[3,4-d]pyrimidin-2-one-trifluoroacetate A mixture of 10.0 g (0.0296 mol) of 3,4-dihydro-3-[1-(1,1-dimethylethoxycarbonyl)-4-piperidinyl]-1H-thieno[3,4-d]pyrimidin-2-one and 50 ml of trifluoroacetic acid was stirred at room temperature for 30 minutes. The residue remaining after removal of the excess trifluoroacetic acid was triturated with diethylether and suction filtered. 5.8 g (55.8% of theory) of colourless crystals were obtained, which were used without further purification.

IR (KBr): 1664.5 cm$^{-1}$ (C=O)

In the same way, crystalline 3,4-dihydro-3-(4-piperidinyl)-1H-thieno[3,2-d]pyrimidin-2-one-trifluoracetate was obtained from 3,4-dihydro-3-[1-(1,1-dimethylethoxycarbonyl)-4-piperidinyl]-1H-thieno-[3,2-d]pyrimidin-2-one and trifluoroacetic acid in a yield of 100% of theory.

IR (KBr): 1685.7; 1656.8 cm$^{-1}$ (C=O)

EXAMPLE A6

3,4-dihydro-3-(4-piperidinyl)-2(1H)quinolone-hydrochloride

A mixture of 1.1 g (4.949 mmol) of 3-(4-pyridinyl)-2(1H)-quinolone (D. R. Bragg and D. G. Wibberley, J. Chem. Soc. 1961, 5074-5077), 100 ml of ethanol, 5 ml (5 mmol) of 1N hydrochloric acid and 0.2 g platinum (IV) oxide was hydrogenated for 4 hours at room temperature. The catalyst was filtered off, the filtrate evaporated down in vacuo and the residue was triturated with isopropanol. The precipitated crystals were suction filtered, washed with isopropanol and diethylether and dried in vacuo. Yield: 0.64 g (56.2% of theory).

IR (KBr): 1666.4 cm$^{-1}$ (C=O)
MS: M$^+$=230 m/e=146, 84

EXAMPLE A7

3-(4-Piperidinyl-2(1H)-quinolone

A mixture of 8.6 g (0.0387 mol) of 3-(4-pyridinyl)-2(1H)-quinolone, 1.2 l of ethanol, 39 ml (0.039 mol) of 1N hydrochloric acid and 8.0 g of 10% palladium/charcoal was hydrogenated at a temperature of 40° C. until about 0.08 mol of hydrogen had been taken up. The mixture was freed from catalyst, the filtrate was evaporated down in vacuo, the residue was taken up in 200 ml of water and made ammoniacal. Common salt was added up to saturation point and the mixture was continuously extracted with dichloromethane using a perforator. The dichloromethane phase was evaporated down, the residue remaining was separated from byproducts by chromatography over silica gel using FM1 as eluant. The appropriate fractions were combined, freed from solvent, dissolved in a little isopropanol and converted with ethanolic hydrogen chloride solution into the hydrochloride. Colourless crystals. Yield: 2.68 g (26.2% of theory).

MS: M$^+$=228
IR (KBr): 1651 cm$^{-1}$ (C=O)

EXAMPLE A8

5-chloro-3,4-dihydro-3-(4-piperidinyl)-2(1H)-quinazolinone

An ice-cold solution of 6.3 g (0.0177 mol) of 5-chloro-3,4-dihydro-3-[1-(phenylmethyl)-4-piperidinyl]-2(1H)-quinazolinone (prepared analogously to Example A4e)) in 50 ml of dichloromethane was mixed dropwise with 3.34 g (0.0234 mol) of (α-chloroethyl chlorocarbonate whilst maintaining a reaction temperature of 0° C., after which the mixture was allowed to come back slowly to room temperature. The reaction mixture was evaporated down in vacuo, the residue was taken up in 50 ml of methanol and refluxed for 4 hours. After cooling, the colourless precipitate formed was suction filtered. Yield: 2.0 g (42.5% of theory).

IR (KBr): 1666.4 cm$^{-1}$ (C=O)

6-bromo-3,4-dihydro-3-(4-piperidinyl)-2(1H)-quinazolinone-hydrobromide

To a solution of 6.16 g (0.075 mol) of sodium acetate and 11.565 g (0.05 mol) of 3,4-dihydro-3-(4-piperidinyl)-2(1H)-quinazolinone in a mixture of 150 ml of glacial acetic acid and 35 ml of water a solution of 8.8 g (0.055 mol) of anhydrous bromine in 20 ml of glacial acetic acid was added dropwise, with stirring and whilst maintaining a reaction temperature of 13 to 15° C. The mixture was filtered and the filtrate was evaporated down in vacuo. To remove any inorganic components the residue was taken up five times in 50 ml of dichloromethane, filtered and evaporated down, then triturated with a little acetonitrile, whereupon crystallisation occurred. The crystals were suction filtered, washed with acetonitrile/diethylether (1/1 v/v) and after drying in vacuo 5.5 g of colourless crystals of melting point 288° C. (decomposition) were obtained. By working up the mother liquors a further 4.5 g of material of the same quality was obtained. Total yield: 10.0 g (51% of theory).

$C_{13}H_{17}Br_2N_3O$ (391.10)

| Calculated: | C 39.92 | H 4.38 | Br 40.86 | N 10.74 |
|---|---|---|---|---|
| Found: | 39.72 | 4.36 | 41.56 | 10.24 |
| IR (KBr): | 1670.3 cm−1 (C=O) | | | |

EXAMPLE A10

3-(4-piperidinyl)-2,4 (1H,3H)-quinazolindione a) 2-amino-N-[1-(phenylmethyl)-4-piperidinyl]-benzamide To an ice-cold solution of 28 ml (134 mmol) of 4-amino-1-(phenylmethyl)piperidine in 200 ml of tetrahydrofuran were added, batchwise, 21.9 g (134 mmol) of isatoic acid anhydride. The resulting suspension was stirred for 2½ hours at room temperature and 2½ hours at reflux temperature, then freed from solvent. The residue was dissolved in 100 ml of hot ethanol, the resulting solution was filtered whilst hot after the addition of 5 g of activated charcoal. The crystal mass precipitated after cooling was suction filtered, washed with diisopropylether and dried in vacuo at 50° C. 28.3 g of colourless crystals were obtained. A further 5.1 g of a product of the same quality were isolated from the combined mother liquors. Total yield: 33.4 g (80.6% of theory).

IR (KBr): 1620 cm$^{-1}$ (C=O)
MS: M$^+$=309 b) 3-[1-(phenylmethyl)-4-piperidinyl]-2,4(1H,3H)-quinazolindione

Prepared analogously to Example A3e) from 2-amino-N-[1-(phenylmethyl)-4-piperidinyl]-benzamide and N,N'-carbonyldiimidazole in a yield of 97.8% of theory. Colourless crystals of melting point 223° C.

IR (KBr): 1720; 1647 cm$^{-1}$ (C=O)
MS: M$^+$=335 c) 3-(4-piperidinyl)-2,4(1H,3H)-qinazolindione

Prepared analogously to Example A3f) from 3-[1-(phenylmethyl)-4-piperidinyl]-2,4(1H,3H)-quinazolindione by hydrogenolysis in the presence of palladium/charcoal in a yield of 70% of theory.

R$_f$: 0.075 (FM1)
IR (KBr): 1703; 1657 cm$^{-1}$ (C=O)

EXAMPLE A11

3,4-dihydro-3-[1-(4-piperidinyl)-4-piperidinyl]-2 (1H)-quinazolinone a) 3,4-dihydro-3-[1-[1-(phenylmethyl)-4-piperidinyl]-4-piperidinyl]-2(1H)-quinazolinone A mixture of 5.75 g (0.0249 mol) of 3,4-dihydro-3-(4-piperidinyl-2(1H)-quinazolinone, 4.75 g (0.0251 mol) of 1-(phenylmethyl)-4-piperidinone and 100 ml of ethanol was treated for 30 minutes in an ultrasound bath, then mixed with 9.5 ml (0.031 mol) of titanium (IV) isopropoxide, whereby after 10 minutes a crystal mass was formed. Then heating was continued using the ultrasound bath for a further 2½ hours to a maximum of 35° C., the mixture was allowed to cool to room temperature and 1.05 g (0.0167 mol) of sodium cyanoborohydride were then added in batches, whilst maintaining the pH at 5-6 using dilute methanolic hydrogen chloride solution, and it was then kept for 24 hours at room temperature. After this time another 1.05 g (0.0167 mol) of sodium cyanoborohydride were added and the same procedure was used as above. After a total of 48 hours reaction time the mixture was decomposed by the addition of water and worked up in the usual way. The crude product obtained was purified by column chromatography over silica gel using FM4 as eluant. 7.05 g (70% of theory)of a colourless crystalline substance were obtained.

In the same way exo-4-(8-methyl-8-azabicyclo[3,2,1]oct-3-yl)-1-(phenylmethyl)piperazine was obtained from tropinone and 1-(phenylmethyl)piperazine in a yield of 48.9% of theory.

Colourless, amorphous substance, $R_f$=0.36 (FM1).

b) 3,4-dihydro-3-[1-(4-piperidinyl)-4-piperidinyl]-2(1H)-quinazolinone

Prepared analogously to Example A3f) from 3,4-dihydro-3-[1-[1-(phenylmethyl)-4-piperidinyl]-4-piperidinyl]-2(1H)-quinazolinone by hydrogenolysis, but using Pearlman's catalyst, in a yield of 92% of theory. Colourless crystals, $R_f$=0.48 (Macherey-Nagel, POLYGRAM® SIL G/UV$_{254}$ready-made films for TLC; eluant: dichloromethane/methanol/cyclohexane/conc. ammonia 68/20/10/5 v/v/v/v).

IR (KBr): 1660.6 cm$^{-1}$ (C=O)
MS: M$^+$=314

EXAMPLE A12

3-(4-piperidinyl)-3,4,4a,5,6,7,8,8a-octahydro-2(1H)-quinazolinone-acetate

A solution of 5.0 g (17.17 mmol) of 3,4-dihydro-3-(4-piperidinyl)-2(1H)-quinazolinone-acetate in 70 ml of methanol was hydrogenated at room temperature and in the presence of 1.0 g rhodium (III) oxide-platinum (IV) oxide hydrate catalyst (46.45% rhodium, 20.15% platinum) until the hydrogen uptake had ceased. The catalyst and solvent were removed, the residue was triturated with 10 ml of diisopropylether and a few drops of isopropanol and the resulting crystals were suction filtered. After drying in vacuo 4.4 g (86.2% of theory) of colourless crystals were obtained, $R_f$=0.3 (eluant: dichloromethane/methanol/conc. ammonia 7.5/2.5/0.5 v/v/v).

IR (KBr): 1641 cm$^{-1}$ (C=O)
MS: M$^+$=237

EXAMPLE A13

1,1-dioxido-2-(4-piperidinyl)-3(4H-1,2,4-benzothiadiazinone a) 2-nitro-N-[1-(phenylmethyl)-4-piperidinyl]-benzenesulphonic acid amide Whilst carrying out external cooling with ice water a solution of 44.3 g (0.2 mol) of 2-nitrobenzenesulphonyl chloride in 250 ml of chloroform was added dropwise to a solution of 38.0 g (0.2 mol) of 4-amino-1-(phenylmethyl)piperidine and 22.0 g (0.22 mol) of triethylamine in 250 ml of chloroform. After the cooling was stopped the mixture was stirred for a further 30 minutes at room temperature, the reaction mixture was then extracted twice with 1 l water. The aqueous extracts were extracted once more with 100 ml of dichloromethane, the combined organic phases were then dried over sodium sulphate and evaporated down in vacuo. The highly viscous light-brown substance obtained in a yield of 75.0 g (99.9% of theory) was further processed without any more purification.

IR (KBr): 3363.7 (NH); 1541.0 (NO$_2$); 1365.5 (NO$_2$ or SO$_2$); 1346.2 (NO$_2$ or SO$_2$); 1168.8 (SO$_2$) cm$^{-1}$ b) 2-amino-N-[1-(phenylmethyl)-4-piperidinyl]-benzenesulphonic acid amide To a solution of 75.0 g (0.2 mol) of 2-nitro-N-[1-(phenylmethyl)-4-piperidinyl]-benzenesulphonic acid amide in 2.0 l ethanol was added dropwise, at room temperature, a solution of 174.0 g ( 0.828 mol) of sodium dithionite-dihydrate in 700 ml of water. After the heat of the exothermic reaction had died away the mixture was refluxed for 4.5 hours, then the ethanol was distilled off and the aqueous phase remaining was extracted thoroughly with dichloromethane.

The combined dichloromethane extracts were dried over sodium sulphate and evaporated down, the residue remaining was purified by column chromatography over silica gel using dichloromethane/methanol/conc. ammonia 80/20/0.25 (v/v/v) as eluant. 6.5 g (8.6% of theory) of a highly viscous oil were obtained.

IR(KBr): 1319.2, 1153.4 cm$^{-1}$ (SO$_2$)

c) 1,1-dioxido-2-[1-(phenylmethyl)-4-piperidinyl]-3(4H)-1,2,4-benzothiadiazinone Prepared analogously to Example A3e) from 2-amino-N-[1-(phenylmethyl)-4-piperidinyl]-benzenesulphonic acid amide and N, N'-carbonyldiimidazole in a yield of 78% of theory. Colourless crystals of melting point 169-171° C.

IR(KBr): 1693.4 (C=O); 1359.7, 1340.4, 1188.1 (SO$_2$) cm$^{-1}$ d) 1,1-dioxido-2-(4-piperidinyl)-3(4H)-1,2,4-benzothiadiazinone Prepared analogously to Example A3f), but using Pearlman's catalyst instead of palladium/charcoal, in a yield of 90% of theory. Colourless, amorphous substance.

IR(KBr): 1705.0 (C=O) cm$^{-1}$

EXAMPLE A14

3,4-dihydro-2,2-dioxido-3-(4-piperidinyl)-2,1,3-benzothiadiazine a) 3,4-dihydro-2,2-dioxido-3-[1-(phenylmethyl)-4-piperidinyl]-2,1,3-benzothiadiazine A solution of 11.0 g (0.0372 mol) of 2-amino-N-[1-(phenylmethyl)-4-piperidinyl]-benzenemethanamine in 200 ml of pyridine was added dropwise within 1.5 hours and at reflux temperature to a solution of 3.4 g (0.0354 mol) of sulphamide in 200 ml of pyridine and the mixture was then refluxed for 6 hours. The mixture was freed from solvent, the residue was purified by column chromatography using ethyl acetate/methanol 9/1 (v/v) as eluant. 5.5 g (43.5% of theory) of a colourless amorphous substance were obtained.

IR(KBr): 1344.3, 1166.9 cm$^{-1}$ (SO$_2$)

b) 3,4-dihydro-2,2-dioxido-3-(4-piperidinyl)-2,1,3-benzothiadiazine

Prepared analogously to Example A3f) from 3,4-dihydro-2,2-dioxide-3-[1-(phenylmethyl)-4-piperidinyl]-2,1,3-benzothiadiazine by catalytic hydrogenation in the presence of palladium/charcoal in a quantitative yield. Colourless, amorphous substance.

IR(KBr): 1263.3, 1105.1 cm$^{-1}$ (SO$_2$)

EXAMPLE A15

D,L-4-phenyl-1-(4-piperidinyl)-imidazolidine-2,5-dione a) N$^2$-(1,1-dimethylethoxycarbonyl)-N-[1-(phenylmethyl)-4-piperidinyl]-D,L-phenylglycinamide A mixture of 10.0 g (0.0398 mol) of N$^2$-(1,1-dimethylethoxycarbonyl)-D,L-phenylglycine, 7.57 g (0.0398 mol) of 4-amino-1-(phenylmethyl)piperidine, 10 ml of triethylamine, 12.8 g (0.0399 mol) of TBTU and 5.4 g (0.0353 mol) of N-hydroxy-benzotriazole-hydrate in 200 ml of THF-DMF mixture (1/1 v/v) was stirred overnight at room temperature. The residue remaining after removal of the solvent was taken up in ethyl acetate, washed with saturated sodium hydrogen carbonate solution, dried over sodium sulphate and evaporated down in vacuo. 14.8 g (87.8% of theory) of a colourless, amorphous substance were obtained.

IR(KBr): 1701.1, 1676.0, 1652.9 cm$^{-1}$ (C=O)

Analogously N$^2$-(1,1-dimethylethoxycarbonyl)-N-[1-(phenylmethyl)-4-piperidinyl]-D,L-phenylalaninamide was obtained from N$^2$-(1,1-dimethylethoxycarbonyl)-D,L-phenylalanine and 4-amino-1-(phenylmethyl)piperidine in a yield of 85% of theory. Colourless, amorphous substance, R$_f$=0.83 (eluant: dichloromethane/cyclohexane/metha-nol/conc. ammonia=70/15/15/2 v/v/v/v).

IR(KBr): 1683.8, 1651.0 cm$^{-1}$ (C=O)

b) N-[1-(phenylmethyl)-4-piperidinyl]-D,L-phenylglycinamide-bis-trifluoroacetate Prepared analogously to Example A5e) from N$^2$-(1,1-dimethylethoxycarbonyl)-N-[1-(phenylmethyl)-4-piperidinyl]-D,L-phenylglycinamide and trifluoroacetic acid in a quantitative yield. Colourless, amorphous substance, R$_f$=0.56 (FM1)

Analogously N-[1-(phenylmethyl)-4-piperidinyl]-D,L-phenylalaninamide-bis-trifluoracetate was obtained from N$^2$-(1,1-dimethylethoxycarbonyl)-N-[1-(phenylmethyl)-4-piperidinyl]-D,L-phenylalaninamide in a yield of 92% of theory.

IR(KBr): 1670.3 cm$^{-1}$ (C=O)

c) D,L-4-phenyl-1-[1-(phenylmethyl)-4-piperidinyl]-imidazolidine-2,5-dione

Prepared analogously to Example A3e) from N-[1-(phenylmethyl)-4-piperidinyl]-D,L-phenylglycinamide and N, N'-carbonyldiimidazole in a yield of 57.3% of theory. Colourless crystals, R$_f$=0.68. IR(KBr): 1774.4, 1712.7 cm$^{-1}$ (C=O)

Analogously D,L-4-(phenylmethyl)-1-[1-(phenylmethyl)-4-piperidinyl]-imidazolidine-2,5-dione was obtained from N-[1-(phenylmethyl)-4-piperidinyl]-D,L-phenylalaninamide in a yield of 93% of theory. Colourless, fine crystals, R$_f$=0.6 (eluant: dichloromethane/methanol/cyclohexane/conc. ammonia=7/1.5/1.5/0.2 v/v/v/v).

IR(KBr): 1764.8, 1708.8 cm$^{-1}$ (C=O)
MS: M$^+$=363 d) D,L-4-phenyl-1-(4-piperidinyl)-imidazolidine-2,5-dione

Prepared analogously to Example A3f) from D,L-4-phenyl-1-[1-(phenylmethyl)-4-piperidinyl]-imidazolidine-2,5-dione by hydrogenolysis in the presence of palladium/charcoal in a yield of 84.3% of theory. Colourless, amorphous substance, R$_f$=0.5.

IR(KBr): 1766.7, 1706.9 cm$^{-1}$ (C=O)

Analogously D,L-4-(phenylmethyl)-1-(4-piperidinyl)-imidazolidine-2,5-dione was obtained from D,L-4-(phenylmethyl)-1-[1-(phenylmethyl)-4-piperidinyl]-imidazolidine-2,5-dione. Colourless crystals, R$_f$=0.24 (eluant: dichloromethane/methanol/cyclohexane/conc. ammonia=7/1.5/1.5/0.2 v/v/v/v).

IR(KBr): 1766.7, 1705.0 cm$^{-1}$ (C=O)

EXAMPLE A16

1,3-dihydro-3-(4-piperidinyl)-2(2H)-imidazo[4,5-c]quinolone a) 1-[2-(acetylamino)phenyl]-2-bromoethanone 45.0 g (0.282 mol) of dry bromine were added dropwise to a boiling solution of 50.0 g (0.282 mol) of 1-[2-(acetylamino)phenyl]ethanone in 400 ml of chloroform at room temperature. The solvent was distilled off, the residue was distributed between dichloromethane and saturated ice-cold sodium hydrogen carbonate solution. The organic phase was dried over sodium sulphate, evaporated down in vacuo, the residue was triturated with diethylether and suction filtered. After drying in vacuo 35.4 g (49% of theory) of colourless crystals were obtained, R$_f$=0.48 (eluant: petroleum ether/ethyl acetate 2/1 v/v).

IR(KBr): 1685.69, 1664.47 cm$^{-1}$ (C=O)
MS: M$^+$=255/257 (Br)

b) 4-[2-(acetylamino)phenyl]-1,3-dihydro-1-[1-(phenylmethyl)-4-piperidinyl]-2H-benzimidazol-2-one To a solution of 26.3 g (0.138 mol) of 4-amino-1-(phenylmethyl)piperidine and 17.8 g (0.138 mol) of DIEA in 300 ml of dichloromethane was added dropwise a solution of 35.4 g (0.138 mol) of 1-[2-(acetylamino)phenyl]-2-bromoethanone in 150 ml of dichloromethane and the mixture was kept for a further 2 hours at room temperature. With external cooling with ice 13.5 g (0.20 mol) of sodium cyanate and 12 ml of glacial acetic acid were then added and the mixture was stirred overnight in a thawing ice bath. It was washed with water and saturated sodium hydrogen carbonate solution, dried over sodium sulphate and freed from solvent. The residue was triturated with 50 ml of ethyl acetate-methanol mixture (9/1 v/v), the resulting crystals were suction filtered, washed with ethyl acetate and dried in vacuo. 37.0 g (68.7% of theory) of colourless crystals were obtained, R$_f$=0.41 (eluant: dichloromethane/methanol 9/1 v/v).

IR(KBr): 1678 cm$^{-1}$ (C=O)
MS: M$^+$=390 (Br)

c) 4-(2-aminophenyl)-1,3-dihydro-1-[1-(phenylmethyl)-4-piperidinyl]-2H-imidazol-2-one A mixture of 3.0 g (7.68 mmol) of 4-[2-(acetylamino)phenyl]-1,3-dihydro-1-[1-(phenylmethyl)-4-piperidinyl]-2H-imidazol-2-one, 50 ml of 5 N sodium hydroxide solution and 25 ml of ethanol was refluxed for 3 hours. After cooling the organic phase was separated off, dried over sodium sulphate and evaporated down in vacuo. A colourless amorphous substance was obtained in a quantitative yield, $R_f$=0.53 (eluant: dichloromethane/methanol 9/1 v/v).

d) 1,3-dihydro-3-[1-(phenylmethyl)-4-piperidinyl]-2(2H)-imidazo[4,5-c]quinolone A solution of 2.67 g (7.66 mmol) of 4-(2-aminophenyl)-1,3-dihydro-1-[1-(phenylmethyl)-4-piperidinyl]-2H-imidazol-2-one in 50 ml of chloroform was mixed with 3.0 g of paraformaldehyde and refluxed for 3.5 hours. The residue remaining after evaporation of the solvent was taken up in 100 ml of methanol and acidified with methanolic hydrogen chloride solution. After stirring for one hour at room temperature the mixture was poured into 300 ml of saturated sodium hydrogen carbonate solution. The resulting mixture was extracted thoroughly with ethyl acetate, the combined extracts were dried over sodium sulphate and evaporated down in vacuo. The residue was purified by column chromatography over silica gel using FM4 as eluant. From the appropriate fractions 0.5 g (18.2% of theory) of a colourless, amorphous substance were isolated, $R_f$=0.24 (FM4).

IR(KBr): 1689 cm$^{-1}$ (C=O)
MS: M$^+$=358 (Br)

e) 1,3-dihydro-3-(4-piperidinyl)-2(2H)-imidazo[4,5-c]quinolone

Prepared analogously to Example A3f) from 1,3-dihydro-3-[1-(phenylmethyl)-4-piperidinyl]-2(2H)-imidazo[4,5-c]quinolone by hydrogenolysis in the presence of palladium/charcoal in a yield of 98.5% of theory. Colourless crystals, $R_f$=0.63 (FM1).

EXAMPLE A17

Preparation of β-(methoxycarbonyl)-arenebutanoic acids 3,5-dibromo-4-hydroxy-β-(methoxycarhonyl)-benzenebutanoic acid a) 4-(phenylmethoxy)-benzaldehyde

To a solution of 36.6 g (0.3 mol) of 4-hydroxybenzaldehyde in 100 ml of ethanol were added dropwise, one after another, a solution of 12.0 g (0.3 mol) of sodium hydroxide in 100 ml of water and a solution of 36.5 ml of (0.307 mol) of benzylbromide in 100 ml of ethanol and the mixture was then kept for 1 hour at 50° C. The ethanol was extensively distilled off, finally in vacuo, the remaining aqueous emulsion was divided between water and ethyl acetate. The ethyl acetate phase was dried over sodium sulphate and evaporated down in vacuo. The residue remaining crystallised on trituration with petroleum ether and was recrystallised from diisopropyl ether. 48.0 g (75.4% of theory) of colourless crystals of melting point 118-122° C. were obtained.

b) 3-(methoxycarbonyl)-4-[(4-phenylmethoxy)phenyl]-3-butenoic acid

To a freshly prepared solution of 2.3 g (0.1 mol) of sodium in 300 ml of anhydrous methanol were added 14.6 g (0.1 mol) of dimethyl succinate and after half an hour's stirring a solution of 21.2 g (0.1 mol) of 4-(phenylmethoxy)-benzaldehyde in 100 ml of anhydrous methanol were added dropwise. Then the mixture was refluxed for 6 hours, the methanol was distilled off under normal pressure and the remaining residue was kept for 30 minutes at a reaction temperature of 80° C. The viscous slurry obtained was stirred into 1 l of a glacial acetic acid-water mixture (1/1 v/v), the resulting mixture was extracted thoroughly with ethyl acetate. The combined ethyl acetate extracts were in turn extracted with saturated potassium carbonate solution. The potassium carbonate extracts were carefully acidified with acetic acid and then extracted thoroughly with ethyl acetate. These extracts were washed with water, dried over sodium sulphate and freed from solvent in vacuo. The residue was purified by column chromatography over silica gel using dichloromethane/petroleum ether/glacial acetic acid 25/74/1 (v/v/v). The colourless, partly crystallised mixture of diastereomers was obtained in a yield of 16.0 g (49% of theory). $R_f$=0.68 (eluant: ethyl acetate/petroleum ether 1:2 v/v).

IR(KBr): 1699.2 cm$^{-1}$ (C=O)

The following were obtained analogously:

(1) 3-(methoxycarbanyl)-4-[3-(trifluoromethyl)phenyl]-3-butenoic acid was obtained from 3-(trifluoromethyl)benzaldehyde and dimethyl succinate in a yield of 21% of theory.

| IR (KBr): | 1738, 1726 cm$^{-1}$ (C=O) | |
|---|---|---|
| ESI-MS: | (M − H)$^-$ = | 287 |
| | (M + H)$^+$ = | 289 |
| | (M + Na)$^+$ = | 311 |

(2) 3-(methoxycarbonyl)-4-(1-naphthyl)-3-butenoic acid was obtained from 1-naphthaldehyde and dimethyl succinate in a yield of 60% of theory.
Colourless oil
IR(KBr): 1712 cm$^{-1}$ (C=O)
MS: M$^+$=270

(3) 3-(methoxycarbonyl)-4-[3,5-dimethyl-4-phenylmethoxyphenyl]-3-butenoic acid was obtained from 3,5-dimethyl-4-phenyl-methoxybenzaldehyde and dimethyl succinate in a yield of 66% of theory.
Colourless oil which could be further processed without purification.

(4) 4-(4-amino-3,5-dibromophenyl)-3-(methoxycarbonyl)-3-butenoic acid was obtained from 4-amino-3,5-dibromobenzaldehyde and dimethyl succinate in a yield of 21% of theory.

(5) 3-(Methoxycarbonyl)-4-(3-phenylmethoxyphenyl)-3-butenoic acid was obtained from 3-phenylmethoxybenzaldehyde and dimethyl succinate in a yield of 37% of theory.

c) 4-hydroxy-β-(methoxycarbonyl)-benzenebutanoic acid

Prepared analogously to Example A3f) from 3-(methoxycarbonyl)-4-[(4-phenylmethoxy)phenyl]-3-butenoic acid by hydrogenolysis in the presence of palladium/charcoal in a yield of 96% of theory. Colourless oil, $R_f$=0.5 (eluant: ethyl acetate/petroleum ether/glacial acetic acid 66.3/33.3/0.4 v/v/v).

The following were obtained analogously:

(1) β-(methoxycarbonyl)-3-(trifluoromethyl)-benzenebutanoic acid was obtained from 3-(methoxycarbonyl)-4-[3-(trifluoromethyl)phenyl]-3-butenoic acid in a yield of 80% of theory. $R_f$=0.59 (eluant: ethyl acetate/petroleum ether 1/1/ v/v).

ESI-MS: (M–H)⁻=289

(2) β-(methoxycarbonyl)-1-naphthalinebutanoic acid was obtained from 3-(methoxycarbonyl)-4-(1-naphthyl)-3-butenoic acid, however using platinum(IV)-oxide as a catalyst, in a yield of 31% of theory.

IR (KBr): 1734, 1711 (C=O) cm⁻¹
MS: M⁺=272

β-(methoxycarbonyl)-1,2,3,4-tetrahydro-1-naphthalinebutanoic acid was isolated as a by-product in a yield of 8.4% of theory IR (KBr): 1736, 1712 (C=O) cm⁻¹
MS: M⁺=276

(3) 3,5-dimethyl-4-hydroxy-β-(methoxycarbonyl)-benzene butanoic acid was obtained from 3-(methoxycarbonyl)-4-[3,5-dimethyl-4-phenylmethoxyphenyl]-3-butenoic acid in a yield of 48% of theory.

$R_f$=0.11 (FM1)
IR (KBr): 1716 (C=O) cm⁻¹
MS: M⁺=266

(4) 3-Hydroxy-β-(methoxycarbonyl)-benzene butanoic acid was obtained from 3-(Methoxycarbonyl)-4-(3-phenylmethoxyphenyl)-3-butenoic acid in a yield of 59% of theory.

$R_f$=0.24 (petroleum ether/ethyl acetate/glacial acetic acid 6/4/0.2 v/v/v)
IR (KBr): 1714 (C=O) cm⁻¹
MS: M⁺=238

(5) 4-Amino-β-(methoxycarbonyl)-benzene butanoic acid was obtained from 3-(methoxycarbonyl)-4-(4-amino-3,5-dibromophenyl)-3-butenoic acid and in the presence of triethylamine in a quantitative yield.

$R_f$=0.53 (eluant: dichloromethane/methanol/glacial acetic acid 90/10/1.5 v/v/v))
IR (KBr): 1728 (C=O) cm⁻¹
MS: M⁺=237 d) 3,5-dibromo-4-hydroxy-β-(methoxycarbonyl)-benzenebutanoic acid

To a solution of 12.0 g (0.05 mol) of 4-hydroxy-β-(methoxycarbonyl)-benzenebutanoic acid in 200 ml of glacial acetic acid were added 150 ml of water and 8.0 g sodium acetate and then a solution of 15.58 g (0.0975 mol) of bromine in 60 ml of glacial acetic acid was added dropwise. The mixture was stirred for a further hour at room temperature, then evaporated down to two thirds in vacuo and the residue was divided between water and ethyl acetate. The ethyl acetate extracts were washed with water, dried over sodium sulphate and evaporated down in vacuo. After stirring with diisopropylether a colourless crystal was obtained. Yield: 12.0 g (62.2% of theory). $R_f$=0.4 (eluant: ethyl acetate/petroleum ether/glacial acetic acid 49.8/49.8/0.4 v/v/v).

IR(KBr): 1724 cm⁻¹ (C=O)
MS: M⁺=394/396/398 (Br₂)

EXAMPLE A18

1-(3-pyridinyl)piperazine a) 1-(phenylmethyl)-3-(3-pyridinyl)piperazine

To a solution of 5.0 g (0.0515 mol) of 3-fluoropyridine and 43.5 ml of 1-(phenylmethyl)piperazine in 300 ml of anhydrous diethylether was added dropwise, at boiling temperature, within 2.5 hours, 56 ml (0.112 mol) of a 2 molar solution of phenyl-lithium in a cyclohexane-diethylether mixture (7/3 v/v) and the resulting mixture was then kept at reflux temperature for a further 4 hours. The crude reaction product obtained as an oil after working up in the usual way was purified by column chromatography over silica gel (30-60 μm) using FM1/cyclohexane (7/3 v/v) as eluant. 12.0 g (92% of theory) of a colourless oil were obtained, $R_f$ 0.52 (FM4; Macherey-Nagel, POLYGRAM® SIL G/UV$_{254}$ Pre-coated plastic sheets for TLC).

MS: M⁺=253 b) 1-(3-Pyridinyl)piperazine

Prepared analogously to Example A3f) from 1-(phenylmethyl)-3-(3-pyridinyl)piperazine by hydrogenolysis in the presence of palladium/charcoal in a yield of 55% of theory. Colourless oil, $R_f$ 0.35 (FM1).
IR(KBr): 1652.9 cm¹ (C=N)

EXAMPLE A19

1-(1-cyclohexyl-4-piperidinyl)piperazine-tris-trifuoroacetate a) 1-(1,1-dimethylethoxycarbonyl)-4-[1-(phenylmethyl)-4-piperidinyl]piperazine A solution of 15.0 g ( 0.8054 mol) of 1-(1,1-dimethylethoxycarbonyl)piperazine and 14.26 ml (0.08053 mol) of 1-(phenylmethyl)-4-piperidinone in 250 ml of methanol was adjusted to a pH of between 5 and 6 by dropwise addition of acetic acid and mixed in batches with a total of 4.13 g (0.0624 mol) of 95% sodium cyanoborohydride, whilst taking care to maintain a pH of 5 to 6 by further dropwise addition of acetic acid. After stirring for 18 hours at room temperature the mixture was evaporated down in vacuo, the residue was made alkaline with soda and divided between water and ethyl acetate. After working up the ethyl acetate phase in the usual way 21.76 g (75.2% of theory) of a highly viscous colourless oil were obtained, $R_f$ 0.66 (FM1).

b) 1-(1,1-dimethylethoxycarbonyl)-4-(4-piperidinyl)piperazine

Prepared analogously to Example A3f) from 1-(1,1-dimethyl-ethoxycarbonyl)-4-[1-(phenylmethyl)-4-piperidinyl]piperazine by hydrogenolysis, but using Pearlman's catalyst instead of palladium/charcoal, in a yield of 79.7% of theory.

Colourless crystals, $R_f$=0.3 (FM1).

c) 1-(1,1-dimethylethoxycarbonyl)-4-(1-cyclohexyl-4-piperidinyl)piperazine

Prepared analogously to Example A19a) from 1-(1,1-dimethyl-ethoxycarbonyl)-4-(4-piperidinyl)piperazine and cyclohexanone in a yield of 99% of theory. Colourless, highly viscous oil.
MS: $M^+=251$ d) 1-(1-cyclohexyl-4-piperidinyl)piperazine-tris-trifluoroacetate Prepared analogously to Example A5e) from 1-(1,1-dimethylethoxycarbonyl)-4-(1-cyclohexyl-4-piperidinyl)piperazine and trifluoroacetic acid in a quantitative yield. Colourless crystals, $R_f$=0.2 (FM1).

EXAMPLE A20

1-(1-ethyl-4-piperidinyl)piperazine-trihydrochloride a) 1-(1-ethyl-4-piperidinyl)-4-(phenylmethyl)piperazine Prepared analogously to Example A19a) from 1-ethyl-4-piperidinone and 1-(phenylmethyl)piperazine in a yield of 71% of theory. Colourless, amorphous substance, $R_f$=0.46 (FM4).

b) 1-(1-ethyl-4-piperidinyl)piperazine-trihydrochloride

A mixture of 36.3 g (0.126 mol) of 1-(1-ethyl-4-piperidinyl)-4-(phenylmethyl)piperazine, 300 ml of 1N hydrochloric acid and 200 ml of methanol was hydrogenated at room temperature and in the presence of 4.0 g of 10% palladium/charcoal until the up-take of hydrogen had ceased. After working up in the usual way 22.9 g (59.3% of theory) of a colourless, crystalline substance was obtained.
MS: $M^+=197$
In the same way exo-1-(8-methyl-8-azabicyclo[3,2,1]oct-3-yl)piperazine-trihydrochloride was obtained from exo-4-(8-methyl-8-azabicyclo[3,2,1]oct-3-yl)-1-(phenylmethyl)piperazine (see Example A11a)) by hydrogenolysis in the presence of palladium/charcoal in a yield of 91% of theory.
MS: $M^+=209$

EXAMPLE A21

1-ethyl-4-(4-piperidinyl)piperidine a) 1-(phenylmethoxycarbonyl)-4-(4-piperidinyl)piperidine To a mixture of 72.375 g (0.3 mol) of bipiperidine-dihydrochloride, 1500 ml of methanol, 75 ml of water and 100 mg of bromophenol blue were added dropwise, simultaneously, with stirring and at room temperature, a solution of 51.18 g (0.3 mol) of benzyl chlorocarbonate in 75 ml of toluene and 6 N sodium hydroxide solution (about 80 ml) were added, so that the indicator colour changed continuously. After all had been added, which took about 4 hours, the mixture was diluted with 300 ml of water and the organic solvent was distilled off in vacuo. The aqueous phase remaining was acidified with hydrochloric acid, whilst being externally cooled, extracted thoroughly with diethylether and then made alkaline with 50% potassium hydroxide solution. The mixture was extracted thoroughly with dichloromethane, the combined dichloromethane extracts were dried over magnesium sulphate and evaporated down in vacuo. The colourless, highly viscous, slowly crystallising oil remaining was further processed without any more purification.
Yield: 87.3 g (96.2% of theory).
IR(KBr): 1701.1 cm$^{-1}$ (C=O)

b) 1-ethyl-4-[1-(phenylmethoxycarbonyl)-4-piperidinyl]piperidine

To a solution of 18.14 g (0.061 mol) of 1-(phenylmethoxycarbonyl)-4-(4-piperidinyl)piperidine in 450 ml of a methanol/water mixture (1/1 v/v) were added, with stirring, whilst maintaining a temperature of 15 to 20° C., 10.05 g (0.152 mol) of 95% sodium cyanoborohydride and 50 mg of bromocresol purple. Then a solution of 10.57 g (0.24 mol) of acetaldehyde in 50 ml of methanol and 1N hydrochloric acid were alternately added dropwise so that the colour of the mixture changed continuously from blue to yellow. After all had been added and the reaction had finished the mixture was adjusted to pH 2 with hydrochloric acid and extracted twice with 200 ml of diethylether. The aqueous phase was then made alkaline and extracted thoroughly with dichloromethane. The combined dichloromethane extracts were dried over magnesium sulphate and evaporated down in vacuo. The colourless crystallising residue remaining was purified by column chromatography over silica gel (30-60 µm) using FM1 as eluant. Yield of colourless crystals of melting point 93-96° C.: 7.9 g (39.2% of theory).
IR(KBr): 1699.2 cm$^{-1}$ (C=O)

c) 1-ethyl-4-(4-piperidinyl)piperidine

A solution of 7.6 g (0.023 mol) of 1-ethyl-4-[1-(phenylmethoxy-carbonyl)-4-piperidinyl]piperidine in a mixture of 70 ml of methanol, 30 ml of water and 10 ml of glacial acetic acid was hydrogenated in the presence of 10% palladium/charcoal at room temperature and 3 bar of hydrogen pressure until the uptake of hydrogen had ceased. After working up in the usual way the desired compound was obtained as a colourless oil in a quantitative yield.

EXAMPLE A22

Hexahydro-1-methyl-4-(4-piperidinyl)-1H-1,4-diazepine a) Hexahydro-1-methyl-4-[1-(phenylmethyl)-4-piperidinyl]-1H-1,4-diazepine Prepared analogously to Example A11a) from hexahydro-1-methyl-1H-1,4-diazepine and 1-(phenylmethyl)-4-piperidinone in a yield of 35% of theory. Colourless viscous oil.
MS: $M^+=287$
The following were prepared in the same way:
(1) 1-methyl-4-[1-(phenylmethyl)-4-piperidinyl]-piperazine from 1-methylpiperazine and 1-(phenylmethyl)-4-piperidinone
Yield: 39.9% of theory, colourless viscous oil
(2)  1-acetyl-4-[1-(phenylmethyl)-4-peridinyl]piperazine from 1-acetylpiperazine and 1-(phenylmethyl)-4-piperidinone
Yield: 24.2% of theory, colourless viscous oil
$R_f$: 0.46 (eluant: ethyl acetate/methanol/conc. ammonia 50/50/2 v/v/v)

IR(KBr): 1647 cm$^{-1}$ (C=O)

MS: M$^+$=301

(3) 4-(dimethylamino)-1-[1-(phenylmethyl)-4-piperidinyl]-piperidine from 4-(dimethylamino)piperidine and 1-(phenylmethyl)-4-piperidinone Yield: 28.9% of theory; colourless viscous oil $R_f$: 0.58 (eluant: ethyl acetate/methanol/conc. ammonia 50/50/2 v/v/v)

MS: M$^+$=301

(4) 1-(1,1-dimethylethoxycarbonyl)-4-[4-(phenylmethyl)-1-piperazinyl]piperidine from 1-(1,1-dimethylethoxycarbonyl)-4-piperidinone and 1-(phenylmethyl)piperazine Yield: 86.6% of theory. Colourless, amorphous substance $R_f$: 0.58 (eluant: dichloromethane/methanol 9/1 v/v)

b) Hexahydro-1-methyl-4-(4-piperidinyl)-1H-1,4-diazepine

Prepared analogously to Example A3f) from hexahydro-1-methyl-4-[1-(phenylmethyl)-4-piperidinyl]-1H-1,4-diazepine by hydrogenolysis, but using Pearlman's catalyst instead of palladium/charcoal, in a quantitative yield. Colourless viscous oil.

MS: M$^+$=197

The following were obtained in the same way:

(1) 1-methyl-4-(4-piperidinyl)piperazine from 1-methyl-4-[1-(phenylmethyl)-4-piperidinyl]piperazine in a quantitative yield. Colourless viscous oil.

MS: M$^+$=183

(2) 1-acetyl-4-(4-piperidinyl)piperazine from 1-acetyl-4-[1-(phenylmethyl)-4-piperidinyl]piperazine in a yield of 81.9% of theory. Colourless crystals.

IR(KBr): 1631 cm$^{-1}$ (C=O)

(3) 4-(dimethylamino)-1-(4-piperidinyl)piperidine from 4-(dimethylamino)-1-[1-(phenylmethyl)-4-piperidinyl]-piperidine in a yield of 76.8% of theory. Colourless, amorphous substance.

(4) 1-(1,1-dimethylethoxycarbonyl)-4-(1-piperazinyl)piperidine-hydrochloride from 1-(1,1-dimethylethoxycarbonyl)-4-[4-(phenylmethyl)-1-piperazinyl]piperidine-hydrochloride.

Yield: 96% of theory. Colourless crystals $R_f$: 0.23 (eluant: dichloromethane/methanol 9/1 v/v)

EXAMPLE A23

4-[(4-methyl-1-piperazinyl)carbonyl]-piperidine-bis-trifluoroacetate a) 1-(1,1-dimethylethoxycarbonyl)-4-piperidinecarboxylic acid

To a mixture of 25.9 g (0.2 mol) of piperidine-4-carboxylic acid, 200 ml (0.2 mol) of 1N sodium hydroxide solution and 200 ml of tetrahydrofuran were added 48.0 g (0.22 mol) of di-tert.-butyl pyrocarbonate and the mixture was stirred overnight at room temperature. The tetrahydrofuran was distilled off, finally in vacuo, and the remaining aqueous solution was acidified with citric acid. The colourless crystals precipitated were suction filtered and dried at 40° C. in a circulating air drier. Yield: 45.5 g (99.2% of theory).

IR(KBr): 1733.9, 1662.5 cm$^{-1}$ (C=O)

b) 1-(1,1-dimethylethoxycarbonyl)-4-[(4-methyl-1-piperazinyl)-carbonyl]-piperidine Prepared analogously to Example A15a) from 1-(1,1-dimethylethoxycarbonyl)-4-piperidinecarboxylic acid and 1-methylpiperazine in the presence of TBTU in a yield of 76% of theory. Colourless, amorphous substance, $R_f$=0.64 (eluant: dichloromethane/methanol/conc. ammonia 50/50/1 v/v/v).

IR(KBr): 1693, 1678 cm$^{-1}$ (C=O)

The following were prepared in the same way:

(1) 1-methyl-4-[[4-(1,1-dimethylethoxycarbonyl)-1-piperazinyl]carbonyl]-piperidine from 1-methyl-4-piperidinecarboxylic acid and 1-(1,1-dimethyl-ethoxycarbonyl)piperazine in a yield of 97% of theory.

Colourless crystals.

IR(KBr): 1683.8, 1629.8 cm$^{-1}$ (C=O)

(2) 1-(1,1-methylethoxycarbonyl)-4-(isonicotinoyl)piperazine from 1-(1,1-dimethylethoxycarbonyl)-piperazine and 4-pyridine-carboxylic acid in a yield of 76.8% of theory. Colourless crystals of melting point 139.2-140.2° C. and $R_f$=0.84 (eluant: dichloromethane/methanol/conc. ammonia 90/10/1 v/v/v).

IR(KBr): 1689.5, 1625.9 cm$^{-1}$ (C=O)

c) 4-[(4-methyl-1-piperazinyl)carbonyl]-piperidine-bis-trifluoroacetate prepared analogously to Example A5e) from 1-(1,1-dimethyl-ethoxycarbonyl)-4-[(4-methyl-1-piperazinyl)carbonyl]-piperidine and trifluoroacetic acid in a yield of 89% of theory.

Colourless, amorphous substance.

The following were prepared in the same way:

(1) 1-methyl-4-[(1-piperazinyl)carbonyl]-piperidine from 1-methyl-4-[[4-(1,1-dimethylethoxycarbonyl)-1-piperazinyl]carbonyl]-piperidine and trifluoroacetic acid in a yield of 57% of theory. Colourless, amorphous substance.

IR(KBr): 1679.9, 1645.2 cm$^{-1}$ (C=O)

MS: M$^+$=211

(2) 4-(isonicotinoyl)piperazine-trifluoroacetate from 1-(1,1-dimethylethoxycarbonyl)-4-(isonicotinoyl)piperazine and trifluoroacetic acid in a yield of 98.3% of theory.

Colourless, amorphous substance.

IR(KBr): 1676.0 cm$^{-1}$ (C=O)

EXAMPLE A24

Preparation of Compounds of the General Structure:

Boc-A-NR$^3$R$^4$

1-[N$^2$-(1,1-dimethylethoxycarbonyl)-N$^6$-(phenylmethoxycarbonyl)-L-lysyl]-4-(4-pyridinyl)piperazine To a mixture of 18.8 g (0.0494 mol) of Boc-Lys(Z)-OH, 6.5 g (0.05 mol) of DIEA, 16 g (0.05 mol) of TBTU, 6.6 g (0.049 mol) of HOBt and 100 ml of dimethylformamide were added dropwise, with stirring, 8.1 g (0.0494 mol) of 1-(4-pyridinyl)piperazine, dissolved in 40 ml of DMF, and the mixture was stirred over-night at room temperature. The solvent was removed in vacuo and the residue was taken up in ethyl acetate. The ethyl acetate phase was then washed three times successively with 70 ml of saturated aqueous sodium hydrogen carbonate solution and once with 70 ml of saturated aqueous saline solution, dried over sodium sulphate and evaporated down in vacuo. 24.2 g (93.2% of theory) of a yellowish oil were obtained, which was used for the following reactions without further purification.

IR (KBr): 1650, 1713 cm$^{-1}$ (C=O)

$R_f$(FM1): 0.59

The following were prepared analogously:

| A | NR$^3$R$^4$ | Remarks | % Yield | $R_f$ | Eluant | IR [cm$^{-1}$] |
|---|---|---|---|---|---|---|
| A9 | C1 | THF as LM KHSO$_4$/NaCl soln | 63.2 | 0.4 | FM1 | (KBr): C=O 1705.0; 1649 |
| A4 | C1 | | 93.2 | 0.59 | FM1 | (KBr): C=O 1647.7; 1712.7 |
| A5 | C1 | | 66 | 0.55 | FM1 | (KBr): C=O 1655; 1709 |

-continued

| A | NR$^3$R$^4$ | Remarks | % Yield | $R_f$ | Eluant | IR [cm$^{-1}$] |
|---|---|---|---|---|---|---|
| A5 | C8 | | 54 | 0.8 | FM1 | (KBr): C=O 1653; 1713 |
| A6 | C8 | | 91 | 0.8 | FM1 | (KBr): C=O 1645; 1710.8 |
| A10 | C1 | | 63 | 0.5 | FM1 | (KBr): C=O 1665; 1695 |
| A10 | C8 | | 30 | 0.41 | FM4 | (KBr): C=O 1662; 1699 |

EXAMPLE A25

Preparation of Compounds of General Formula:

Cbz-A-NR$^3$R$^4$

1-[N$^2$-(phenylmethoxycarbonyl)-N$^6$-(1,1-dimethyl-ethoxycarbonyl)-L-lysyl]-4-(4-pyridinyl)piperazine To a mixture of 100 g (0.263 mol) of Z-Lys(Boc)-OH, 86.1 g (0.268 mol) of TBTU and 36.3 g (0.263 mol) of HOBt in 600 ml of dimethylformamide were added 43.0 g (0.263 mol) of 1-(4-pyridinyl)-piperazine and 47.2 ml (0.268 mol) of DIEA with stirring and the mixture was stirred overnight at room temperature. The reaction mixture was evaporated down in vacuo and the residue divided between ethyl acetate and aqueous saturated sodium hydrogen carbonate solution. The aqueous phase was extracted twice more with a mixture of ethyl acetate/methanol (10/1, v/v) and the combined organic phases were washed once with saturated sodium hydrogen carbonate solution. The organic phase was, after drying over sodium sulphate, evaporated down in vacuo and the residue was taken up in 750 ml of ethyl acetate and washed four times with 100 ml of water, six times with 100 ml of 1% potassium hydrogen sulphate solution, once with 100 ml of water, twice with 100 ml of 3% aqueous ammonia solution and twice with 100 ml of water. The organic phase was evaporated down after drying over sodium sulphate. 120 g (87% of theory) of the desired product were obtained as an oil, which was used without further purification for the subsequent reactions.

IR (KBr): 1709 cm$^{-1}$ (C=O)

$R_f$(FM1): 0.59

EI-MS: M$^+$=525

The following were prepared analogously:

| A | NR$^3$R$^4$ | Remarks | % Yield | MS | $R_f$ | Eluant | IR [cm$^{-1}$] |
|---|---|---|---|---|---|---|---|
| A3 | C4 | | 100 | | | | |
| A3 | C3 | Triethylamine as base | 100 | | 0.8 | FM1 | (KBr): C=O 1643.3; 1710.8 |
| A11 | C1 | | 98.8 | | 0.5 | FM1 | (KBr): C=O 1705.0; 1643.3 |
| A3 | C1 | | 81 | EI: M + = 525 | 0.59 | FM1 | (KBr): C=O 1708.8; |
| A3 | C5 | LC/SiO$_2$/FM4 | 95 | YED: M = 525 | 0.67 | FM4 | |
| A3 | C6 | THF, LC/SiO$_2$/FM4 | 92 | | 0.82 | FM4 | (KBr): C=O 1710.8; 1641.3 |
| A3 | C8 | Further reacted as crude product | 100 | | | | |

EXAMPLE 26

Preparation of Compounds of General Formula:

H-A-NR$^3$R$^4$

1-[N$^6$-(phenylmethoxycarbonyl)-L-lysyl]-4-(4-pyridinyl)piperazine

To a mixture of 24.2 g (46 mmol) of 1-[N$^2$-(1,1-dimethyl-ethoxycarbonyl)-N$^6$-(phenylmethoxycarbonyl)-L-lysyl]-4-(4-pyridinyl)piperazine and 150 ml of methylene chloride were added 50 ml of trifluoroacetic acid and the reaction mixture was stirred overnight at room temperature. The reaction mixture was neutralised by the addition of saturated aqueous sodium hydrogen carbonate solution, the organic phase was dried and evaporated down in vacuo. 12 g (62% of theory) of the desired compound were obtained as a colourless oil.

IR (KBr): 1648 cm$^{-1}$ (C=O)

$R_f$(FMl) 0.5

The following were prepared analogously:

| A | NR$^3$R$^4$ | Remarks | % Yield | $R_f$ | Eluant | IR [cm$^{-1}$] |
|---|---|---|---|---|---|---|
| A9 | C1 | | 100 | 0.4 | FM2 | (KBr): C=O 1676.0; 1645.2 |
| A4 | C1 | | 61.5 | 0.48 | FM1 | (KBr): C=O 1647.7; 1712.7 |

-continued

| A | NR³R⁴ | Remarks | % Yield | R_f | Eluant | IR [cm⁻¹] |
|---|---|---|---|---|---|---|
| A5 | C1 | | 55 | 0.42 | FM1 | (KBr): C=O 1651 |
| A5 | C8 | further reacted as crude product | 100 | 0.19 | FM1 | |
| A6 | C1 | | 82 | 0.3 | FM1 | (KBr): C=O 1647; 1676 |
| A6 | C8 | further reacted as crude product | 100 | 0.23 | FM1 | (KBr): C=O 1674 |
| A10 | C1 | | 38 | 0.55 | FM1 | (KBr): C=O 1643 |
| A10 | C8 | further reacted as crude product | 100 | 0.15 | FM1 | |

EXAMPLE A27

Preparation of Compounds of General Formula:

H-A-NR³R⁴

1-[N⁶-(1,1-dimethylethoxycarbonyl)-L-lysyl]-4-(4-pyridinyl)-piperazine

A solution of 120 g (0.228 mol) of 1-[N²-(phenylmethoxycarbonyl)-N⁶-(1,1-dimethylethoxycarbonyl)-L-lysyl]-4-(4-pyridinyl)piperazine in 1000 ml of methanol and 240 ml of 1M aqueous potassium hydrogen sulphate solution was hydrogenated in the presence of 30 g palladium on charcoal (10%) at 20° C. and 3 bar of hydrogen pressure until the uptake of hydrogen had ceased. The catalyst was filtered off, the filtrate evaporated down in vacuo, the residue was taken up in isopropanol/methanol and adjusted to pH 7-8 by the addition of a concentrated aqueous ammonia solution. The solution was filtered and evaporated to dryness. 87 g (97w of theory) of an oil were obtained.

IR (KBr): 1634, 1701 cm⁻¹ (C=O) R_f: 0.79 (ethyl acetate/methanol/conc. aqueous ammonia=6/4/1 (v/v/v)

The following were prepared analogously:

EXAMPLE A28

Preparation of Compounds of General Formula:

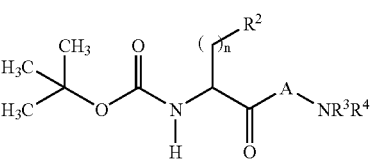

1-[N²—[N-(1,1-dimethylethoxycarbonyl)-3,5-dibromo-D-tyrosyl]-N⁶-(phenylmethoxycarbonyl)-L-lysyl]-4-(4-pyridinyl)-piperazine To a mixture of 2.58 g (5.88 mmol) of N-[(1,1-dimethylethoxy)-carbonyl]-3,5-dibromo-D-tyrosine, 1.03 g (8 mmol) of DIEA, 1.93 g (6 mmol) of TBTU, 0.79 g (5.8 mmol) of HOBt and 100 ml of dimethylformamide were added dropwise, 2.5 g (5.88 mmol) of 1-[N⁶-[(phenylmethoxy)-carbonyl]-L-lysyl]-4-(4-pyridinyl)piperazine, dissolved in 50 ml of dimethylformamide, with stirring. The reaction mixture was stirred overnight at room temperature, then evaporated down in vacuo and the residue was taken up in ethyl acetate. The organic phase was washed twice with aqueous saturated sodium hydrogen carbonate solution and once with aqueous saturated saline solution, dried and evaporated down in vacuo. The purification was carried out by column chromatography (aluminium oxide, activity stage III (6% water content) (ICN Biomedical), eluant: ethyl acetate/methanol/ammonia=8/2/0.5 (v/v/v), followed by methanol/ammonia=7/3 (v/v)). 4.0 g (80% of theory) of an amorphous substance were obtained.

IR (KBr): 1643, 1709 cm⁻¹ (C=O)

R_f: 0.52(FM1)

ESI-MS: (M+H)⁺=845/847/849 (Br₂)

| A | NR³R⁴ | Remarks | % Yield | MS | R_f | Eluant | IR [cm⁻¹] |
|---|---|---|---|---|---|---|---|
| A3 | C4 | | 93 | ESI: M + H = 391 (M + Na = 413) | 0.6 | FM1 | (KBr): C=O 1637.5; 1706.9 |
| A3 | C3 | | 100 | | 0.3 | FM1 | (KBr): C=O 1641.3; 1705 |
| A11 | C1 | | 78.5 | | 0.2 | FM1 | (KBr): C=O 1701.1; 1641.3 |
| A7 | C1 | without KHSO₄ | 80.2 | | 0.2 | FM7 | |
| A3 | C1 | | 97 | | 0.79 | ethyl acetate/methanol/ conc. aqueous ammonia 6/4/1 (v/v/v) | (KBr): C=O 1633.6; 1701.1 |
| A3 | C5 | without KHSO₄ | 53 | | 0.39 | FM4 | (KBr): C=O 1733.9; 1624.0 |
| A3 | C6 | without KHSO₄ | 89 | | 0.38 | FM4 | (KBr): C=O 1706.9; 1645.2 |
| A3 | C8 | further reacted as crude product | 100 | | 0.3 | FM1 | |

The following were prepared analogously (in each case n=1):

| R² | A | NR³R⁴ | Remarks | % Yield | MS | $R_f$ | Eluant | IR [cm⁻¹] |
|---|---|---|---|---|---|---|---|---|
| AS7 | A0 | C4 | LM: THF; reacted as crude product | 100 | | | | |
| AS1 | A0 | C11 | reacted as crude product | 69 | | | | |
| AS4 | A0 | C20 | | 59 | ESI: (M + H)⁺ = 600/2/4 (Br₂) | | | (KBr): C=O 1639; 1707 |
| AS1 | A0 | C4 | | 71 | | | | |
| AS4 | A0 | C11 | | 53 | | 0.5 | FM1 | |
| AS7 | A0 | C1 | reacted as crude product | 100 | | | | (KBr): C=O 1644 |
| AS4 | A7 | C1 | NEt₃ as base; reacted as crude product | 100 | | 0.4 | FM8 | |
| AS1 | A4 | C1 | | 80 | ESI: (M + H)⁺ = 845/7/9 (Br₂) | 0.52 | FM1 | (KBr): C=O 1643.3; 1708.8 |
| AS4 | A0 | C5 | Boc-AS4 LC/SiO₂/FM5 | 83 | EI: M⁺ = 581/3/5(Br₂) | 0.69 | FM5 | (KBr): C=O 1706.9; 1641.3 |
| AS4 | A0 | C15 | LC/SiO₂/FM4 | 86 | EI: M⁺ = 382/4/6(Br₂) | 0.83 | FM4 | (KBr): C=O 1706.9; 1641.3 |
| AS1 | A0 | C5 | LC/SiO₂/FM5 | 81 | | 0.5 | FM5 | (KBr): C=O 1705.0; 1637.5 |
| AS4 | A0 | C16 | LC/SiO₂/FM4 THF | 85 | EI: (M + H)⁺ = 582/4/6(Br₂) | 0.42 | FM4 | (KBr): C=O 1706.9; 1643.3 |
| AS1 | A0 | C15 | THF LC/SiO₂/FM4 | 76 | | 0.53 | FM4 | (KBr): C=O 1701.1; 1637.5 |
| AS4 | A0 | C3 | LC/SiO₂/FM6 | 83 | ESI: (M + H)⁺ = 598/600/2(Br₂) | 0.71 | FM6 | (KBr): C=O 1706.9; 1641.3 |
| AS1 | A0 | C16 | LC/SiO₂/FM4 | 85 | | 0.35 | FM1 | (KBr): C=O 1705; 1641.3 |
| AS1 | A0 | C6 | LC/SiO₂/FM6 | 84 | | 0.54 | FM6 | (KBr): C=O 1701.1; 1635.5 |
| AS4 | A0 | C18 | LC/SiO₂/FM4 | 95 | | 0.66 | FM4 | (KBr): C=O 1705; 1641.3 |
| AS1 | A0 | C37 | | 90 | | 0.43 | FM1 | (KBr): C=O 1645; 1714.5 |
| AS4 | A0 | C37 | | 95 | | 0.51 | FM4 | (KBr): C=O 1643.3; 1705 |
| AS4 | A0 | C22 | | 75 | | | | (KBr): C=O 1635.5; 1708.8 |
| AS4 | A0 | C21 | | 92 | M⁺ = 582/4/6(Br₂) | 0.42 | FM4 | (KBr): C=O 1643; 1705 |
| AS4 | A5 | C1 | | 69 | ESI: (M + H)⁺ = 939/41/43(Br₂) | | | (KBr): C=O 1653; 1709 |
| AS4 | A0 | C23 | | 85 | | | | (KBr): C=O 1645; 1709 |
| AS4 | A10 | C1 | | 65 | M⁺: 652/4/6 | | | (KBr): C=O 1649; 1707 |
| AS4 | A0 | C24 | | 79 | M⁺: 589/91/93 | | | (KBr): C=O 1643; 1707 |
| AS4 | A5 | C8 | | 76 | | | | (KBr): C=O 1643; 1713 |
| AS4 | A6 | C1 | | 95 | | | | (KBr): C=O 1645; 1710.8 |
| AS4 | A6 | C8 | | 88 | M⁺: 657/9/61 | | | (KBr): C=O 1628; 1713 |
| AS4 | A10 | C8 | | 46 | ESI: (M + H)⁺ = 858/60/62(Br₂) | | | (KBr): C=O 1647; 1707 |
| AS4 | A0 | C26 | | 46 | | | | (KBr): C=O 1637.5; 1707 |
| AS1 | A0 | C1 | further reacted as crude product | 100 | | | | |

-continued

| R² | A | NR³R⁴ | Remarks | % Yield | MS | R_f | Eluant | IR [cm⁻¹] |
|---|---|---|---|---|---|---|---|---|
| AS1 | A0 | C8 | | 55 | | 0.3 | dichloro-methane/ methanol 9/1 | (KBr): C=O 1632 |
| AS1 | A0 | C18 | | 84 | ESI: (M + H)⁺ = 613/5/7(Br₂) | 0.4 | FM4 | (KBr): C=O 1641; 1707 |
| AS1 | A0 | C3 | | 81 | | | | (KBr): C=O 1638; 1701 |
| AS1 | A0 | C21 | | 70 | | 0.28 | FM4 | (KBr): C=O 1643; 1707 |
| AS4 | A0 | C6 | | 47 | | | | (KBr): C=O 1639; 1707 |
| AS4 | A0 | C19 | | 90 | | | | (KBr): C=O 1639; 1707 |
| AS9 | A0 | C1 | further reacted as crude product | 47 | | | | |
| AS1 | A7 | C1 | NEt₃ as base; further reacted as crude product | 83 | | 0.28 | FM1 | |
| AS4 | A0 | C38 | | 67 | | 0.5 | FM1 | |
| AS4 | A0 | C37 | | 84 | | | | |
| AS4 | A0 | C39 | | 100 (raw) | | 0.68 | FM1 | |
| AS4 | A0 | C40 | | 36 | | | | |
| AS1 | A0 | C42 | | 90 | | 0.43 | FM1 | (KBr): C=O 1645/1715 |
| AS4 | A0 | C42 | | 100 | | 0.51 | FM4 | (KBr): C=O 1643/1705 |
| AS1 | A0 | C43 | | 78 | | 0.9 | EE/MeOH 95/5 | (KBr): C=O 1636/1676/ 1659 |
| AS1 | A0 | C44 | | 47 | | 0.9 | EE/MeOH 95/5 | (KBr): C=O 1638/1701 |
| AS1 | A0 | C45 | | 72 | EI: M⁺ = 591/3/5 (Br₂) | 0.9 | EE/MeOH 9/1 | (KBr): C=O 1638/1695 |
| AS1 | A0 | C47 | | 80 | EI: M⁺ = 596/98/600 (Br₂) | 0.95 | EE/MeOH 9/1 | (KBr): C=O 1636/1705 |
| AS1 | A0 | C49 | | 89 | | 0.9 | EE/MeOH 9/1 | (KBr): C=O 1636/1684 |
| AS4 | A0 | C44 | | 69 | | 0.9 | EE/MeOH 9/1 | (KBr): C=O 1643/1707; CN 2235 |
| AS1 | A0 | C50 | | 93 | EI: M⁺ = 598/600/602 (Br₂) | 0.9 | EE/MeOH 9/1 | (KBr): C=O 1636/1705 |
| AS1 | A0 | C51 | | 100 | | 0.1 | EE/MeOH/ NH₄OH 5/5/0.1 | (KBr): C=O 1638/1707 |
| AS4 | A0 | C52 | | 63 | | 0.56 | FM1 | (KBr): C=O 1641/1705 |
| AS4 | A0 | C53 | | 83 | EI: M⁺ = 601/3/5 (Br₂) | | | (KBr): C=O 1638/1705 |
| AS4 | A0 | C64 | | 41 | ESI: (M + H)⁺ = 610/12/14 (Br₂) | | | (KBr): C=O 1639/1701 |
| AS1 | A0 | C53 | | 66 | | 0.45 | CH₂Cl₂/ MeOH/ NH₄OH 70/30/1 | (KBr): C=O 1639/1709 |
| AS4 | A0 | C51 | | 88 | | 0.35 | CH₂Cl₂/ MeOH/ NH₄OH 50/50/0.5 | (KBr): C=O 1641/1691 |
| AS4 | A0 | C66 | | 77 | EI: M⁺ = 629/31/33 (Br₂) | 0.75 | CH₂Cl₂/ MeOH/ NH₄OH 9/1/0.1 | (KBr): C=O 1641/1707 |
| AS16 | A0 | C8 | | 100 | | 0.8 | FM1 | |
| AS16 | A0 | C1 | | 56 | | 0.5 | EE/MeOH NH₄OH 9/1/1 | (KBr): C=O 1695 |
| AS4 | A0 | C8 | | 100 | | | | |
| AS1 | A0 | C53 | | 70.0 | EI: M⁺ = 502/4/6 (Br₂) | 0.10 | CH₂Cl₂/MeOH/ NH4OH 70/30/1 | (KBr): C=O 1676 |

-continued

| R² | A | NR³R⁴ | Remarks | % Yield | MS | $R_f$ | Eluant | IR [cm⁻¹] |
|---|---|---|---|---|---|---|---|---|
| AS4 | A0 | C70 | | 47.0 | | | | (KBr): C=O 1645/1707 |
| AS1 | A0 | C64 | | 31.0 | | 0.50 | CH₂Cl₂/MeOH/ NH4OH 90/10/1 | (KBr): C=O 1639/1707 |
| AS1 | A0 | C70 | | 20.0 | | | | |
| AS4 | A0 | C72 | | 50.0 | | 0.50 | CH₂Cl₂/MeOH/ NH4OH 90/10/1 | |
| AS19 | A0 | C8 | | 98.0 | | | | |
| AS35 | A0 | C8 | | 92.0 | | 0.70 | FM1 | |
| AS36 | A0 | C8 | | 65.0 | | | | |

EXAMPLE A29

Preparation of Compounds of General Formula:

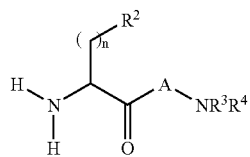

1-(4-amino-3,5-dibromo-D-phenylalanyl)-4-(4-pyridinyl)-piperazine

A mixture of 39 g (0.089 mol) of 4-amino-3,5-dibromo-N-[(1,1-dimethylethoxy)carbonyl]-D-phenylalanine, 35.7 g (0.111 mol) of TBTU, 12.3 g (0.089 mol) of HOBt, 14.5 g.(0.089 mol) of 1-(4-pyridinyl)-piperazine and 19.6 ml of (0.111 mol) of DIEA in 1000 ml of tetrahydrofuran was stirred overnight at room temperature. The reaction mixture was extracted once with saturated aqueous saline solution and twice with saturated aqueous sodium hydrogen carbonate solution. The combined aqueous phases were extracted once with tetrahydrofuran and the combined tetrahydrofuran phases were washed once with saturated aqueous saline solution. After drying the organic phase with sodium sulphate it was evaporated down in vacuo and the residue was taken up in ethyl acetate. The ethyl acetate phase was filtered after drying again and evaporated down in vacuo. 52.5 g of the intermediate compound were obtained as a viscous oil, which was then mixed with 300 ml of methylene chloride and 8.0 ml of trifluoroacetic acid and stirred overnight at room temperature. The reaction mixture was evaporated down in vacuo, the residue formed was triturated with ether. 45.8 g (72% of theory) of the desired product were obtained as a white amorphous solid.

IR (KBr): 1643, 1674 cm⁻¹ (C=O)

$R_f$: 0.36 (ethyl acetate/methanol=6/4 (v/v))

The following were prepared analogously (in each case n=1):

| R² | A | NR³R⁴ | Remarks | % Yield | MS | $R_f$ | Eluant | IR [cm⁻¹] |
|---|---|---|---|---|---|---|---|---|
| AS7 | A0 | C8 | Crude product; Boc-cleaving with pure TFA | 84 | | | | |
| AS4 | A0 | C8 | | 63 | ESI: (M + H)⁺ = 486/88/90(Br₂) | | | (KBr): C=O 1632 |
| AS4 | A0 | C4 | | 63 | ESI: (M + H)⁺ = 481/3/5(Br₂) | | | (KBr): C=O 1620 |
| AS1 | A9 | C1 | | 55 | | 0.25 | FM2 | (KBr): C=O 1674.1; 1643.3 |
| AS4 | A0 | C8 | | 81 | ESI: (M + H)⁺ = 486/8/90(Br₂) | 0.6 | FM2 | (KBr): C=O 1629.8 |
| AS4 | A0 | C1 | | 72 | | 0.38 | ethyl acetate/ methanol = 6/4 (v/v) | (KBr): C=O 1643.3; 1674.1 |
| AS1 | A0 | C20 | | 30 | | | | |
| AS4 | A0 | C65 | | 41 | EI: M⁺ = 515/17/19(Br₂) | | | (KBr): C=O 1618 |
| AS1 | A0 | C65 | | 15 | ESI: (M + H)⁺ = 517/19/21(Br₂) | 0.08 | FM1 | (KBr): C=O 1635 |
| AS4 | A0 | C78 | | 77.0 | ESI: (M + H)⁺ = 529/31/33(Br₂) | 0.30 | CH₂Cl₂/MeOH/ NH4OH = 90/10/1 | (KBr): C=O 1674 |
| AS1 | A0 | C78 | | 60.0 | ESI: (M + H)⁺ = 531/33/35(Br₂) | 0.10 | CH₂Cl₂/MeOH/ NH₄OH = 80/20/1 | (KBr): C=O 1670 |
| AS4 | A0 | C71 | | 43.0 | | 0.20 | CH₂Cl₂/MeOH/ NH₄OH = 90/10/1 | (KBr): C=O 1678 |
| AS31 | A0 | C20 | | 39.0 | EI: M⁺ = 382 | 0.30 | CH₂Cl₂/MeOH/ NH₄OH = 80/20/1 | (KBr): C=O 1678 |
| AS31 | A0 | C53 | | 83.0 | EI: M⁺ = 383 | | | (KBr): C=O 1678 |

EXAMPLE A30

Preparation of Compounds of General Formula:

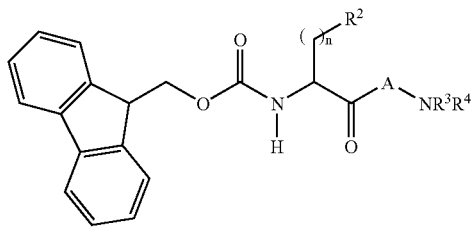

1-[$N^2$—[N-(9-fluorenylmethoxycarbonyl)-3,5-dibromo-D-tyrosyl]-$N^6$-(1,1-dimethylethoxycarbonyl)-L-lysyl]-4-(4-pyridinyl)-piperazine A mixture of 63 g (0.1123 mol) of N-[(9-fluorenylmethoxy)-carbonyl]-3,5-dibromo-D-tyrosine, 44 g (0.1123 mol) of 1-[$N^6$-(1,1-dimethylethoxycarbonyl)-L-lysyl]-4-(4-pyridinyl)-piperazine, 39.7 g (0.1235 mol) of TBTU, 15.5 g (0.1123 mol) of HOBt, 21.7 ml (0.1235 mol) of DIEA and 600 ml of dimethylformamide was stirred for 20 hours at room temperature. The reaction mixture was evaporated down in vacuo and the residue divided between ethyl acetate/methanol (10/1 v/v) and saturated aqueous sodium hydrogen carbonate solution. The organic phase was washed once with saturated aqueous sodium hydrogen carbonate solution and after drying evaporated down in vacuo. The residue was recrystallised twice from isopropanol (22.6 g; 22% of theory), the mother liquors were combined, evaporated down and purified by column chromatography (MN-silica gel 60, Macherey-Nagel, 70-230 mesh ASTM; eluant: ethyl acetate/methanol=8/2 (v/v)). A further 28.0 g (26.7% of theory) of the desired end product were obtained. Total yield: 49% of theory.

IR (KBr): 1641, 1705 cm$^{-1}$ (C=O)
$R_f$: 0.46 (ethyl acetate/methanol=6/4 (v/v))
ESI-MS: (M+H)$^+$=933/935/937 (Br$_2$)

The following were prepared analogously:

| $R^2$ | A | $NR^3R^4$ | Remarks | % Yield | MS | $R_f$ | Eluant | IR [cm$^{-1}$] |
|---|---|---|---|---|---|---|---|---|
| AS1 | A3 | C1 | | 48 | ESI: (M + H)$^+$ = 933/5/7(Br$_2$) | 0.46 | Ethyl acetate/methanol = 6/4 (v/v) | (KBr): C=O 1641.3; 1705.5 |
| AS1 | A3 | C5 | THF/SiO$_2$/FM4 | 80 | ESI: (M + H)$^+$ = 933/5/7(Br$_2$) | 0.72 | FM1 | (KBr): C=O 1701.1; 1635.5 |
| AS1 | A3 | C6 | THF | 60 | ESI: M$^-$ = 960/2/4(Br$_2$) | 0.47 | FM4 | (KBr): C=O 1712.7; 1631.7 |
| AS5 | A3 | C1 | THF LC/SiO$_2$/FM4 Diastereomers | 61 | ESI: (M + H)$^+$ = 917/19/21(Br$_2$) | 0.36 | FM4 | (KBr): C=O 1708.8; 1645.2 |
| AS10 | A0 | C1 | THF | 90 | | 0.52 | FM4 | |
| AS1 | A3 | C18 | | 73 | | 0.46 | FM1 | (KBr): C=O 1635.5; 1712.7 |
| AS10 | A3 | C1 | THF | 85 | | | | (KBr): C=O 1643.3; 1708.8 |
| AS10 | A3 | C4 | THF | 82 | | | | (KBr): C=O 1639.4; 1710.8 |
| AS10 | A3 | C1 | THF | 85 | | | | (KBr): C=O 1643; 1709 |
| AS4 | A3 | C18 | | 94 | ESI: (M + H)$^+$ = 963/5/7(Br$_2$) | | | (KBr): C=O 1633.6; 1711 |
| AS15 | A0 | C8 | | 90 | | | | (KBr): C=O 1635.5; 1617.5 |
| AS12 | A0 | C8 | | 44 | ESI: (M + H)$^+$ = 577 | | | (KBr): C=O 1630; 1714.6 |
| AS10 | A0 | C4 | | 88 | | 0.49 | FM4 | (KBr): C=O 1635.5; 1716.5 |
| AS1 | A3 | C1 | | 70 | | 0.7 | FM7 | |

EXAMPLE A31

Preparation of Compounds of GeneralFormula:

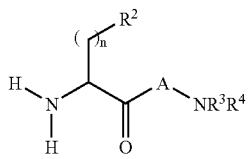

1-[N²-(3,5-dibromo-D-tyrosyl)-N⁶-(1,1-dimethyl-ethoxycarbonyl)-L-lysyl]-4-(4-pyridinyl)-piperazine To a mixture of 63 g (0.1123 mol) of N-[(9-fluorenyl-methoxy)-carbonyl]-3,5-dibromo-D-tyrosine, 44 g (0.1123 mol) of 1-[N⁶-(1,1-dimethylethoxycarbonyl)-L-lysyl]-4-(4-pyridinyl)piperazine, 39.7 g (0.1235 mol) of TBTU, 15.5 g (0.1123 mol) of HOBt and 1500 ml of tetrahydrofuran were slowly added dropwise 21.7 ml (0.1235 mol) of DIEA and the reaction mixture was then stirred for 2 hours at room temperature. After the addition of 200 ml of diethylamine the mixture was again stirred overnight at room temperature. The reaction mixture was mixed with 1000 ml of saturated saline solution, stirred thoroughly and the aqueous phase was separated off. After extracting the aqueous phase three times with 500 ml of tetrahydrofuran and combining the organic phases the mixture was washed three times with 500 ml of saturated aqueous saline solution, three times with 200 ml of saturated aqueous sodium hydrogen carbonate solution and once with 500 ml of saturated aqueous saline solution. The organic phase was dried and then evaporated down in vacuo. The residue was purified by column chromatography (MN-silica gel 60, Macherey-Nagel, 70-230 mesh ASTM, eluant: ethyl acetate/methanol/conc. aqueous ammonia=8/1/0.25 (v/v/v)). 40.0 g (50w of theory)of the desired end product were obtained.

IR (KBr): 1641, 1699 cm$^{-1}$ (C=O)

$R_f$: 0.2 (ethyl acetate/methanol/conc. aqueous ammonia=6/4/1 (v/v/v))

ESI-MS: $(M+H)^+$=711/713/715 $(Br_2)$

The following were prepared analogously (in each case n=1):

| R² | A | NR³R⁴ | Remarks | % Yield | MS | $R_f$ | Eluant | IR [cm$^{-1}$] |
|---|---|---|---|---|---|---|---|---|
| AS4 | A3 | C8 | crude | 43 | | | | |
| AS4 | A3 | C1 | crude | 100 | | 0.4 | FM1 | |
| AS4 | A3 | C4 | | 79 | ESI: $(M + H)^+$ = 709/11/13 $(Br_2)$ | 0.7 | FM7 | (KBr): C=O 1637.5; 1705 |
| AS4 | A0 | C69 | | 82 | ESI: $(M + H)^+$ = 587/9/81 $(Br_2)$ | | | (KBr): C=O 1618/1645/ 1690 |
| AS4 | A0 | C46 | | 38 | | 0.55 | CH$_2$Cl$_2$/ MeOH/ NH$_4$OH 90/10/1 | (KBr): C=O 1614/1639 |
| AS4 | A0 | C48 | | 54 | EI: M$^+$ = 522/4/6(Br$_2$) | 0.52 | CH$_2$Cl$_2$/ MeOH/ NH$_4$OH 90/10/2 | (KBr): C=O 1638 |
| AS11 | A0 | C53 | | 71.0 | EI: M$^+$ = 469 | 0.20 | CH$_2$Cl$_2$/ MeOH/ NH4OH 90/10/1 | (KBr): C=O 1637/1732 |
| AS11 | A0 | C20 | | 45.0 | EI: M$^+$ = 468 | 0.40 | CH$_2$Cl$_2$/ MeOH/ NH$_4$OH 90/10/1 | (KBr): C=O 1635/1732 |
| AS31 | A0 | C72 | | 100.0 | EI: M$^+$ = 411 | 0.45 | FM1 | (KBr): C=O 1664 |
| AS11 | A0 | C72 | | 33.0 | EI: M$^+$ = 497 | 0.30 | FM1 | (KBr): C=O 1630/1641 |

EXAMPLE A32

Preparation of Compounds of GeneralFormula:

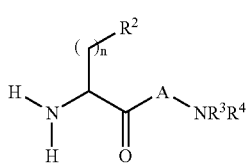

1-[N²-(3,5-dibromo-D-tyrosyl)-N⁶-(phenylmethoxycarbonyl)-L-lysyl]-4-(4-pyridinyl)-piperazine To a mixture of 4 g (4.7 mmol) of 1-[N²—[N-(1,1-dimethylethoxycarbonyl)-3,5-dibromo-D-tyrosyl]-N⁶-(phenylmethoxycarbonyl)-L-lysyl]-4-(4-pyridinyl)-piperazine and 80 ml of methylene chloride were added 20 ml of trifluoroacetic acid and the reaction mixture was stirred overnight at room temperature. The reaction mixture was neutralised by the addition of saturated aqueous sodium hydrogen carbonate solution, the organic phase was dried over sodium sulphate and evaporated down in vacuo. 2.2 g (64% of theory) of an amorphous solid were obtained.

IR (KBr): 1643, 1680 cm⁻¹ (C=O)
$R_f$: 0.5 (FM1)
ESI-MS: (M+H)⁺=745/747/749 (Br₂)

The following were prepared analogously (in each case n=1):

| $R^2$ | A | $NR^3R^4$ | Remarks | % Yield | MS | $R_f$ | Eluant | IR [cm⁻¹] | Mp. (°C.) |
|---|---|---|---|---|---|---|---|---|---|
| AS7 | A0 | C4 | crude product; pure TFA | 51 | | 0.30 | FM1 | | |
| AS1 | A0 | C11 | | 95 | ESI: (M + H)⁺ = 503/5/7 (Br₂) | | | (KBr): C=O 1676 | |
| AS4 | A0 | C20 | | 100 | ESI: (M + H)⁺ = 500/2/4 (Br₂) | | | | |
| AS1 | A0 | C4 | | 100 | ESI: (M + H)⁺ = 481/3/5 (Br₂) | | | (KBr): C=O 1678 | |
| AS4 | A0 | C11 | | 74 | | | | | |
| AS7 | A0 | C1 | reacted as crude product | 100 | | | | | |
| AS4 | A7 | C1 | reacted as crude product | 100 | | 0.40 | EE/MeOH 7/3 v/v | | |
| AS1 | A4 | C1 | | 64 | ESI: (M + H)⁺ = 745/7/9 (Br₂) | 0.50 | FM1 | (KBr): C=O 1643.3; 1679.9 | |
| AS4 | A0 | C5 | | 89 | | 0.32 | FM4 | (KBr): C=O 1637.5 | |
| AS4 | A0 | C15 | | 93 | | 0.33 | FM4 | (KBr): C=O 1618.2 | |
| AS1 | A0 | C5 | | 89 | | 0.25 | FM4 | (KBr): C=O 1639.4 | 154-157 |
| AS4 | A0 | C16 | LC/SiO₂/ FM4 | 90 | | 0.30 | FM4 | (KBr): C=O 1635.5 | |
| AS1 | A0 | C15 | | 89 | | 0.20 | FM4 | (KBr): C=O 1639.4 | 160-164 |
| AS4 | A0 | C3 | LC/SiO₂/ FM4 | 98 | | 0.37 | FM4 | (KBr): C=O 1683.8; | |
| AS4 | A0 | C6 | | 89 | | 0.28 | FM4 | (KBr): C=O 1637.5 | |
| AS1 | A0 | C16 | | 95 | | 0.57 | FM1 | (KBr): C=O 1683.8 | |
| AS1 | A0 | C6 | LC/SiO₂/ FM4 | 56 | EI: M⁺ = 511/3/5 (Br₂) | 0.24 | FM4 | (KBr): C=O 1637.5 | |
| AS4 | A0 | C18 | | 90 | EI: M⁺ = 512/4/6 (Br₂) | 0.50 | FM1 | (KBr): C=O 1624.0 | |
| AS4 | A0 | C37 | | 93 | | 0.24 | FM4 | (KBr): C=O 1635.5; 1684 | |
| AS4 | A0 | C22 | | 88 | M⁺ = 502/4/6 (Br₂) | | | (KBr): C=O 1618.2 | |
| AS4 | A0 | C21 | | 52 | M⁺ = 482/4/6 (Br₂) | 0.55 | FM1 | (KBr): C=O 1681.8 | |
| AS1 | A0 | C37 | | 89 | | 0.32 | FM1 | (KBr): C=O 1681.8 | |
| AS4 | A5 | C1 | | crude | | | | (KBr): C=O 1645; 1676 | |
| AS4 | A0 | C23 | | 88 | | | | (KBr): C=O 1643 | |
| AS4 | A10 | C1 | | 47 | ESI: (M + H)⁺ = 553/5/7 (Br₂) | | | (KBr): C=O 1653 | |
| AS4 | A5 | C8 | | 67 | M⁺ = 543/5/7 | | | (KBr): C=O 1645 | |
| AS4 | A6 | C1 | | 59 | | | | (KBr): C=O 1643 | |
| AS4 | A0 | C24 | | 94 | M⁺ = 489/91/93 | | | (KBr): C=O 1618; 1637.5 | |
| AS4 | A6 | C8 | | 70 | | | | (KBr): C=O 1639.4 | |
| AS4 | A10 | C8 | | 82 | M⁺ = 557/9/61 | | | (KBr): C=O 1651 | |
| AS4 | A0 | C26 | | 88 | | | | (KBr): C=O 1626 | |

-continued

| R² | A | NR³R⁴ | Remarks | % Yield | MS | R_f | Eluant | IR [cm⁻¹] | Mp. (°C.) |
|---|---|---|---|---|---|---|---|---|---|
| AS1 | A0 | C1 | | 96 | ESI: (M + H)⁺ = 483/5/7 (Br₂) | 0.18 | FM1 | (KBr): C=O 1680 | |
| AS1 | A0 | C8 | crude | 69 | | | | | |
| AS1 | A0 | C18 | | 82 | | 0.27 | FM1 | (KBr): C=O 1684 | |
| AS1 | A0 | C3 | | 100 | | 0.38 | FM1 | (KBr): C=O 1682 | |
| AS1 | A0 | C21 | | 89 | | 0.26 | FM1 | (KBr): C=O 1595; 1615 | |
| AS4 | A0 | C3 | | 99 | | 0.37 | FM4 | (KBr): C=O 1618; 1636; 1683 | |
| AS4 | A0 | C19 | | 98 | ESI: (M + H)⁺ = 498/500/502 (Br₂) | 0.47 | FM4 | (KBr): C=O 1638; 1682 | |
| AS9 | A0 | C1 | Crude product | 96 | | | | | |
| AS1 | A7 | C1 | | 37 | | 0.42 | FM7 | | |
| AS4 | A0 | C38 | | 80 | | 0.25 | FM1 | | |
| AS4 | A0 | C37 | | 86 | | | | | |
| AS4 | A0 | C39 | | 73 | | | | | |
| AS4 | A0 | C40 | | 92 | EI: M⁺ = 515/7/9 | | | (KBr): C=O 1674 | |
| AS1 | A0 | C42 | | 100 crude | | 0.32 | FM1 | (KBr): C=O 1682 | |
| AS4 | A0 | C42 | | 95 | | 0.24 | FM4 | (KBr): C=O 1636/1684 | |
| AS1 | A0 | C43 | | 66 | | 0.1 | FM7 | (KBr): C=O 1659 | |
| AS1 | A0 | C44 | | 59 | | 0.15 | CH₂Cl₂/MeOH/NH₄OH 90/10/1 | (KBr): C=O 1676 | |
| AS1 | A0 | C45 | | 82 | ESI: (M + H)⁺ = 492/4/6 (Br₂) | 0.10 | EE/MeOH 9/1 | (KBr): C=O 1678 | |
| AS1 | A0 | C47 | | 89 | | 0.52 | FM7 | (KBr): C=O 1634/1666 | |
| AS1 | A0 | C49 | | 84 | | 0.15 | CH₂Cl₂/MeOH/NH₄OH | (KBr): C=O 1678 | |
| AS4 | A0 | C44 | | 93 | EI: M⁺ = 504/6/8 (Br₂) | 0.45 | EE/MeOH 9/1 | (KBr): C=O 1653; CN 2239 | |
| AS1 | A0 | C50 | | 100 | EI: M⁺ = 498/500/502 (Br₂) | 0.10 | EE/MeOH 9/1 | (KBr): C=O 1636 | |
| AS1 | A0 | C51 | | 100 | EI: M⁺ = 530/2/4 (Br₂) | 0.05 | EE/MeOH/NH4OH 5/5/0.1 | (KBr): C=O 1678 | |
| AS4 | A0 | C52 | | 97 | | 0.15 | FM1 | (KBr): C=O 1620/1688 | |
| AS4 | A0 | C53 | | 58 | ESI: (M + H)M⁺ = 502/4/6 (Br₂) | 0.05 | EE/MeOH/NH₄OH 5/5/0.1 | (KBr): C=O 1678 | |
| AS4 | A0 | C64 | | 100 | | | | (KBr): C=O 1647/1678 | |
| AS1 | A0 | C53 | | 70 | EI: M⁺ = 502/4/6 (Br₂) | 0.15 | CH₂Cl₂/MeOH/NH₄OH 70/30/1 | (KBr): C=O 1676 | |
| AS4 | A0 | C51 | | 100 | | 0.05 | CH₂Cl₂/MeOH/NH₄OH | (KBr): C=O 1680 | |
| AS4 | A0 | C66 | | 100 | | 0.27 | CH₂Cl₂/MeOH/NH₄ | | |
| AS16 | A0 | C8 | | 76 | | 0.40 | FM1 | | |
| AS16 | A0 | C1 | | 28 | | 0.20 | EE/MeOH/NH₄OH 9/1/1 | | |
| AS4 | A0 | C70 | | 96 | | 0.20 | EE/MeOH/NH₄OH 80/20/0.5 | (KBr): C=O 1676 | |
| AS1 | A0 | C64 | | 100 | EI: M⁺ = 510/1214 | | | (KBr): C=O 1674 | |
| AS1 | A0 | C70 | | 100 | | | | (KBr): C=O 1674 | |
| AS4 | A0 | C72 | | 100 | ESI: (M + H)M⁺ = 530/2/4 (Br₂) | 0.10 | CH₂Cl₂/MeOH/NH₄OH 80/20/1 | (KBr): C=O 1678 | |

-continued

| $R^2$ | A | $NR^3R^4$ | Remarks | % Yield | MS | $R_f$ | Eluant | IR [cm$^{-1}$] | Mp. (°C.) |
|---|---|---|---|---|---|---|---|---|---|
| AS19 | A0 | C8 | | 100 | | | | | |
| AS35 | A0 | C8 | | 72 | | 0.60 | FM1 | | |
| AS36 | A0 | C8 | | 80 | | 0.52 | FM1 | (KBr): C=O 1674 | |

EXAMPLE A33

4-(4-pyridinyl)-1-[3-(4-pyridinyl)-D,L-alanyl]-piperazine-hydrochloride 16.4 g (0.04 mol) of 1-[N-[(1,1-dimethylethoxy)carbonyl]-3-(4-pyridinyl)-D,L-alanyl]-4-(4-pyridinyl)-piperazine, dissolved in 100 ml of methanol, were mixed with 20 ml of ethereal hydrochloric acid and the reaction mixture was heated to 40° C. The desired compound crystallised out of the reaction mixture.

yield: 9.2 g (60% of theory)
$R_f$: 0.1 (FM1)
Mp.: 198-200° C.

EXAMPLE A34

Preparation of Compounds of GeneralFormula:

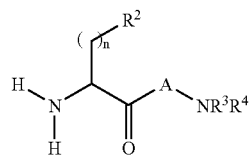

1-[$N^2$-(3,5-dibromo-D-tyrosyl)-$N^6$-(1,1-dimethylethoxycarbonyl)-L-lysyl]-4-(4-pyridinyl)-piperazine A mixture of 50 g (53.5 mmol) of 1-[$N^2$—[N-(9-fluorenylmethoxycarbonyl)-3,5-dibromo-D-tyrosyl]-$N^6$-(1,1-dimethylethoxycarbonyl)-L-lysyl]-4-(4-pyridinyl)-piperazine and 300 ml of diethylamine was heated to 60° C. with stirring. 100 ml of methanol were added and stirring was continued for a further 5 hours at 60° C. The reaction mixture was evaporated down in vacuo and the residue was purified by column chromatography (MN-silica gel 60, Macherey-Nagel, 70-230 mesh ASTM, eluant: ethyl acetate/methanol=6/4 (v/v)). 26 g (68% of theory) of a white foam were obtained.

IR (KBr): 1641, 1691 cm$^{-1}$ (C=O)
$R_f$: 0.2 (ethyl acetate/methanol/conc. aqueous ammonia=6/4/1 (v/v/v)) Ele;2q
SI-MS: (M+H)$^+$=710/712/714 (Br$_2$)

The following were prepared analogously:

| $R^2$ | A | $NR^3R^4$ | n | Remarks | % Yield | MS | $R_f$ | Eluant | IR [cm$^{-1}$] |
|---|---|---|---|---|---|---|---|---|---|
| AS1 | A3 | C4 | 1 | | 85 | ESI: M + H = 710/2/4(Br$_2$) | 0.2 | FM1 | (KBr): C=O 1635.5; 1695.3 |
| AS1 | A3 | C8 | 1 | | 98 | | | | (KBr): C=O 1635; 1705 |
| AS1 | A3 | C1 | 1 | | 68 | EI: M$^+$ = 71 0/2/4 (Br$_2$) | 0.2 | ethyl acetate/ methanol/ NH$_4$OH = 6/4/1 (v/v/v) | (KBr): C=O 1641.3; 1691.5 |
| AS1 | A3 | C5 | 1 | THF as solvent; purified by column chromatography: silica gel/FM1 | 56 | ESI: M + H = 711/3/5(Br$_2$) | 0.3 | FM1 | (KBR):C=O 1695.3; 1635.5 |
| AS1 | A3 | C6 | 1 | THF as solvent; purified by column chromatography: silica gel/FM1 | 90 | EI: M$^+$ = 739/41/43 (Br$_2$) | 0.49 | FM1 | (KBr): C=O 1695.3; 1629.8 |
| AS5 | A3 | C1 | 1 | THF as solvent; purified by column chromatography: silica gel/FM4; diastereomers | 93 | | 0.25/ 0.37 | FM4 | (KBr): C=O 1705.0; 1643.3 |
| AS10 | A0 | C1 | 1 | | 71 | | 0.5 | FM1 | (KBr): C=O 1641.3 |
| AS1 | A3 | C18 | 1 | | 94 | | | | (KBr): C=O 1647; 1722.5 |
| AS10 | A3 | C1 | 1 | | 49 | M$^+$ = 694/6/8 (Br$_2$) | | | (KBr): C=O 1643; 1703 |
| AS10 | A3 | C4 | 1 | | 46 | ESI: M + H = 694/6/8 (Br$_2$) | | | (KBr): C=O 1639.4; 1705 |

-continued

| R² | A | NR³R⁴ | n | Remarks | % Yield | MS | $R_f$ | Eluant | IR [cm⁻¹] |
|---|---|---|---|---|---|---|---|---|---|
| AS10 | A3 | C4 | 1 | | 46 | ESI: M + H = 694/6/8(Br₂) | | | (KBr): C=O 1639.4; 1705 |
| AS10 | A3 | C1 | 1 | | 49 | M⁺ = 694/68/70 (Br₂) | | | (KBr): C=O 1643; 1703 |
| AS4 | A3 | C18 | 1 | | 46 | ESI: M + H = 741/3/5 (Br₂) | | | (KBr): C=O 1641.3; 1705 |
| AS15 | A0 | C8 | 1 | | 100 | M⁺: 321 | | | (KBr): C=O 1637.5 |
| AS12 | A0 | C8 | 1 | | 81 | | | | (KBr): C=O 1630 |
| AS10 | A0 | C4 | 1 | THF as solvent | 68 | | 0.38 | FM4 | (KBr): C=O 1635.5 |
| AS1 | A3 | C1 | 0 | crude product | 100 | | 0.3 | FM7 | |

EXAMPLE A35

1-[N²—[N-[[[2-(2-methoxyphenyl)ethyl]amino]carbonyl]-3,5-dibromo-D-tyrosyl]-N⁶-(phenylmethoxycarbonyl)-L-lysyl]-4-(4-pyridinyl)-piperazine To a solution of 1.0 g (1.34 mmol) of 1-[N²-(-3,5-dibromo-D-tyrosyl)-N⁶-(phenylmethoxycarbonyl)-L-lysyl]-4-(4-pyridinyl)-piperazine in 80 ml of tetrahydrofuran were added 0.28 g (1.6 mmol) of 2-methoxyphenethyl isocyanate and the mixture was stirred for 3 days at room temperature. The reaction mixture was evaporated down in vacuo and the residue was purified by column chromatography (MN-silica gel 60, Macherey-Nagel, 70-230 mesh ASTM, eluant: methylene chloride/methanol/cyclohexane/ammonia=350/75/75/10 (v/v/v/v)). 0.5 g (40% of theory) of a colourless amorphous solid was obtained.

IR (KBr): 1639 cm¹ (C=O)
$R_f$: 0.49 (FM1)
ESI-MS: (M+H)⁺=922/924/926 (Br₂)

EXAMPLE A36

Preparation of Compounds of General Formula:

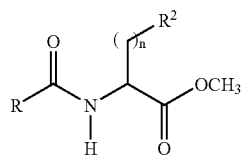

methyl 4-amino-3,5-dibromo-N²-[[(2-phenylethyl)amino]-carbonyl]-D-phenylalanine

A mixture of 1.27 g (7.73 mmol) of CDT in 150 ml of tetrahydrofuran was mixed, whilst cooling with ice, with 0.72 ml (5.15 mmol) of triethylamine and 2.0 g (5.15 mmol) of methyl-4-amino-3,5-dibromo-D-phenylalanine-hydrochloride, stirred for a further 30 minutes whilst cooling with ice and stirred for 1 hour at room temperature. Then 0.82 ml (6.44 mmol) of benzene ethanamine were added and the mixture was refluxed for 5 hours. The reaction mixture was evaporated down in vacuo, the residue was taken up in ethyl acetate and washed with saturated aqueous sodium hydrogen carbonate solution. After drying the organic phase the solvent was removed in vacuo, the residue was stirred with ether and the precipitate was filtered off. 1.69 g (66% of theory) of an amorphous solid were obtained.

IR (KBr): 1632, 1732 cm⁻¹ (C=O)

$R^f$: 0.63 (ethyl acetate)

ESI-MS: (M+H)⁺=498/500/502 (Br₂)

The following were prepared in the same way (in each case n=1):

| RCO | R² | Remarks | % Yield | MS | $R_f$ | Eluant | IR [cm⁻¹] |
|---|---|---|---|---|---|---|---|
| N6 | AS1 | further reacted as crude product | 100 | | 0.60 | FM1 | |
| N15 | AS6 | DMF/THF = 1/1 (v/v) as solvent | 100 | ESI: (M + H)⁺ = 517/9 (Br) | 0.65 | FM1 | (KBr): C=O 1745.5; 1676.0 |
| N2 | AS1 | | 99 | | 0.53 | FM1 | (KBr): C=O 1716.5 |

-continued

| RCO | R² | Remarks | % Yield | MS | R_f | Eluant | IR [cm⁻¹] |
|---|---|---|---|---|---|---|---|
| N8 | AS4 | | 66 | ESI: (M + H)⁺ = 498/500/502 (Br₂) | 0.63 | ethyl acetate | (KBr): C=O 1631.7; 1732.0 |
| N15 | AS4 | | 92 | | 0.85 | ethyl acetate/ methanol = 8/2 (v/v) | (KBr): C=O 1620.1; 1737.8 |
| N23 | AS4 | | 95 | EI: M⁺ = 572/4/6/8 (Br₂Cl) | 0.86 | ethyl acetate/ methanol = 8/2 (v/v) | (KBr): C=O 1732.0; 1641.3 |
| N2 | AS2 | | 100 | EI: M⁺ = 406 | 0.86 | FM1 | (KBr): C=O 1629.8; 1722.3; 1741.6 |
| N15 | AS1 | DIEA | 47 | | 0.75 | FM1 | |
| N15 | AS3 | | 38 | | 0.60 | t-butyl-methylether/ petroleum ether = 9/1 (v/v) | (KBr): C=O 1695.5 |
| N66 | AS21 | | 76 | | 0.60 | EE | (KBr): C=O 1662/1734 |
| N66 | AS1 | | 100 | | | | |
| N66 | AS4 | | 63 | | 0.56 | FM1 | |
| N122 | AS1 | | 95 | | | | |
| N122 | AS4 | | 88 | | | | |
| N66 | AS17 | | 22 | ESI: (M + H)⁺ = 623/5/7 (Br₂) | 0.25 | FM1 | (KBr): C=O 1663/1740 |
| N66 | AS18 | | 65 | | 0.53 | EE | |
| N66 | AS19 | | 79 | | 0.50 | FM1 | (KBr): C=O 1663/1734 |
| N66 | AS5 | | 90 | ESI: (M + H)⁺ = 607/09/11 (Br₂) | 0.78 | FM1 | (KBr): C=O 1637/1663/ 1740 |
| N66 | AS22 | | 68 | | 0.74 | FM1 | |
| N66 | AS23 | | 100 | | | | (KBr): C=O 1738/1662 |
| N66 | AS25 | | 100 | ESI: (M + H)⁺ = 472 | 0.52 | FM1 | |
| N66 | AS49 | | 100 | | 0.80 | FM1 | |

EXAMPLE A37

Preparation of Compounds of General Formula:

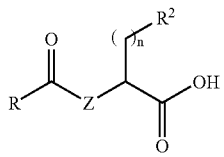

4-amino-3,5-dibromo-N²-[4-(2-chlorophenyl)-1-piperazinyl]carbonyl]-D-phenylalanine To a solution of 2.8 g (4.9 mmol) of methyl 4-amino-3,5-dibromo-N²-[4-(2-chlorophenyl)-1-piperazinyl]carbonyl]-D-phenyl-alanine in a mixture of 30 ml of methanol and 20 ml of water were added 0.25 g (10.0 mmol) of lithium hydroxide and the mixture was then stirred for 3 hours at room temperature. After the addition of 2.0 g (50 mmol) of sodium hydroxide the mixture was diluted with 50 ml of water. The reaction mixture was stirred for 15 minutes in an ultrasound bath, then stirred over-night at room temperature and evaporated down in vacuo. The residue was mixed with 100 ml of water and the aqueous phase was extracted twice with 50 ml of ether. By the addition of 2 M aqueous hydrochloric acid the aqueous phase was adjusted to a pH of 3-4 and extracted three times with ethyl acetate. The combined ethyl acetate phases were washed once with water, then dried and evaporated down in vacuo. 1.6 g (58% of theory) of a yellowish-brown oil were obtained.

IR (KBr): 1616, 1724 cm⁻¹ (C=O)
R_f: 0.33 (ethyl acetate/methanol=8/2 (v/v))
ESI-MS: (M+H)⁺=557/559/561/563 (Br₂, Cl)

The following were prepared in the same way (in each case n=1):

| RCO | Z | R² | Remarks | % Yield | MS | R_f | Eluant | IR [cm⁻¹] |
|---|---|---|---|---|---|---|---|---|
| N8 | N—H | AS4 | | 62 | ESI: (M − H)⁻ = 482/4/6 (Br₂) | 0.61 | Ethyl acetate/ methanol = 6/4 (v/v) | (KBr): C=O 1612.4; 1724.3; —OH, —NH— 3386.8; 3483.2 |

-continued

| RCO | Z | R² | Remarks | % Yield | MS | R_f | Eluant | IR [cm⁻¹] |
|---|---|---|---|---|---|---|---|---|
| N15 | N—H | AS4 | | 64 | ESI: (M − H)⁻ = 578/80/82 (Br₂); (M + H)⁺ = 580/2/4 (Br₂); (M + Na)⁺ = 602/4/6 (Br₂) | 0.10 | Ethyl acetate/ methanol = 8/2 (v/v) | (KBr): C=O 1703.0 |
| N23 | N—H | AS4 | | 58 | ESI: (M − H)⁻ = 557/59/61/63 (Br₂, Cl) | 0.33 | Ethyl acetate/ methanol = 8/2 (v/v) | (KBr): C=O 1616.3; 1724.3 |
| N15 | N—H | AS1 | No addition of sodium hydroxide | 59 | ESI: (M − H)⁻ = 579/81/83 (Br₂) | 0.72 | EE/MeOH/ NH₄OH = 6/4/1 (v/v/v) | (KBr): C=O 1695.3 |
| N66 | N—H | AS21 | | 95 | | 0.48 | EE/AcOH 10/0.02 (v/v) | (KBr): C=O 1639 |
| N66 | CH₂ | AS1 | | 85 | | 0.38 | CH₂Cl₂/MeOH/ AcOH 9/1/0.15 (v/v/v) | |
| N71 | CH₂ | AS1 | | 66.6 | ESI: (M + H)⁺ = 606/08/10 (Br₂) | 0.38 | CH₂Cl₂/MeOH/ AcOH 9/1/0.15 (v/v/v) | (KBr): C=O 1622/1680 |
| N66 | N—H | AS18 | | 100 | ESI: (M − H)⁻ = 557 | 0.26 | EE/AcOH 9/0.01 (v/v) | |
| N66 | N—H | AS19 | | 98 | | 0.22 | CH₂Cl₂/MeOH/ AcOH 9/1/0.15 (v/v/v) | (KBr): C=O 1665/1740 |
| N66 | N—H | AS5 | | 73 | ESI: (M − H)⁻ = 577/79/81 (Br₂) | 0.23 | FM1 | (KBr): C=O 1632/1705 |
| N66 | N—H | AS22 | | 78 | | 0.30 | FM1 | (KBr): C=O 1668/1739 |
| N66 | CH₂ | AS21 | | 79 | | 0.34 | EE/AcOH 9/0.01 (v/v) | (KBr): C=O 1643/1703 |
| N66 | CH₂ | AS1 | | 90 | | 0.30 | EE/MeOH 9/1 (v/v) | |
| N15 | CH₂ | AS1 | | 78 | ESI: (M − H)⁻ = 578/80/82 (Br₂) | 0.30 | EE/AcOH 9/0.01 (v/v) | (KBr): C=O 1728/1672 |
| N66 | N—H | AS25 | | 99 | | | | |
| N66 | CH₂ | AS2 | | 100 | | | | (KBr): C=O 1645/1712 |
| N66 | CH₂ | AS23 | | 70 | | | | |
| N139 | CH₂ | AS2 | | 50 | | | | (KBr): C=O 1630/1662/ 1707 |
| N66 | CH₂ | AS27 | | 93 | | 0.20 | FM1 | |
| N66 | CH₂ | AS28 | LiOH | 100 | | 0.30 | FM1 | |
| N66 | CH₂ | AS4 | | 72 | | 0.53 | FM1 | (KBr): C=O 1639/1701 |
| N66 | CH₂ | AS36 | | 74 | ESI: (M − H)⁻ = 434 | 0.36 | FM1 | (KBr): C=O 1645/1701 |
| N66 | CH₂ | AS38 | | 69 | | | | |
| N66 | CH₂ | AS48 | | 47 | EI: M⁺ = 489 | 0.30 | FM1 | (KBr): C=O 1645 |
| N66 | N—H | AS49 | | 47 | | 0.10 | FM1 | |
| N66 | CH₂ | AS18 | | 60 | | 0.15 | EE | |
| N66 | CH₂ | AS39 | | 96 | | | | |
| N109 | CH₂ | AS21 | | 81 | | | | |
| N113 | CH₂ | AS21 | | 76 | | 0.20 | EE/AcOH 99/1 | |
| N134 | CH₂ | AS21 | | 89 | | 0.15 | EE/AcOH 99/1 | |
| N66 | CH₂ | AS47 | | 100 | ESI: (M + H)⁺ = 476 | | | (KBr): C=O 1645/1716 |
| N66 | CH₂ | AS7 | | 60 | | 0.20 | FM1 | (KBr): C=O 1649/1722 |
| N66 | CH₂ | AS52 | | 95 | ESI: (M + H)⁺ = 480 | 0.15 | FM1 | (KBr): C=O 1643/1722 |

EXAMPLE A38

Preparation of Compounds of General Formula:

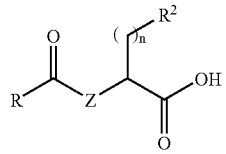

3,5-dibromo-N-[[[2-(3-methoxyphenyl)ethyl]amino]carbonyl]-D-tyrosine

A mixture of 24 g (46.3 mmol) of methyl 3,5-dibromo-N-[[[2-(3-methoxyphenyl)ethyl]amino]carbonyl]-D-tyrosine and 5.0 g (50 mmol) of lithium hydroxide in 200 ml of water was stirred for 1 hour at 60 C. The solid product was suction filtered and the filtrate was washed with 200 ml of ethyl acetate. By the addition of 1 M aqueous hydrochloric acid the aqueous phase was adjusted to a pH of 3-4 and extracted 3 times with 150 ml of ethyl acetate. The combined ethyl acetate phases were washed once with water, dried over sodium sulphate and evaporated down in vacuo. The residue was triturated with ether. 9.1 g (38% of theory) of a colourless solid were obtained.

IR (KBr): 1719 cm$^{-1}$ (C=O)
$R_f$: 0.57 (ethyl acetate/methanol/glacial acetic acid=9.5/0.5/0.2 (v/v/v))

The following were prepared in the same way (in each case n=1):

EXAMPLE A39 methyl $N^6$-[(1,1-dimethylethoxy)carbonyl]-$N^2$—[N-[[[2-(3-methoxyphenyl)ethyl]amino]carbonyl]-3,5-dibromo-D-tyrosyl]-L-lysine To a mixture of 10 g (19.4 mmol) of 3,5-dibromo-N-[[[2-(3-methoxyphenyl)ethyl]amino]carbonyl]-D-tyrosine, 2.6 g (20 mmol) of DIEA, 6.4 g (20 mmol) of TBTU, 2.64 g (19.5 mmol) of HOBt and 200 ml of dimethylformamide was added dropwise, with stirring, a solution of 5.04 g (19.4 mmol) of H-Lys(Boc)-OMe in 50 ml of dimethylformamide and the mixture was stirred over-night at room temperature. The reaction mixture was evaporated down in vacuo and the residue was taken up in 250 ml of ethyl acetate. The ethyl acetate phase was then washed twice with 100 ml of saturated aqueous sodium hydrogen carbonate solution, once with 100 ml of 20% aqueous citric acid solution and finally once with 100 ml of saturated aqueous saline solution. The organic phase was dried with sodium sulphate, evaporated down in vacuo and the residue was purified by column chromatography (MN-silica gel 60, Macherey-Nagel, 70-230 mesh ASTM, eluant: ethyl acetate/petroleum ether=2/1 (v/v)). After removal of the solvent in vacuo the residue was triturated with ether, the amorphous solid obtained (9.5 g; 660 of theory) was suction filtered and dried.

| IR (KBr): | 1632, 1657, 1682, 1734 cm$^{-1}$ (C=0) | |
|---|---|---|
| $R_f$: | 0.64 (ethyl acetate) | |
| ESI-MS: | (M + H)$^+$ = | 757/759/761 (Br$_2$) |
| | (M + Na)$^+$ = | 779/781/783 (Br$_2$) |

| RCO | Z | R$^2$ | Remarks | % Yield | MS | R$_1$ | Eluant | IR [cm$^{-1}$] |
|---|---|---|---|---|---|---|---|---|
| N6 | N—H | AS1 | | 100 | | 0.20 | FM1 | (KBr): C=O 1625.9; 1730 |
| N15 | N—H | AS6 | H$_2$O/MeOH = 1/1 (v/v) as solvent | 85 | ESI: (M − H)$^-$ = 501/3 (Br) | 0.53 | EE/MeOH/AcOH = 9/1/0.1 (v/v/v) | (KBr): C=O 1695.3 |
| N2 | N—H | AS1 | | 75 | | 0.57 | EE/methanol/glacial acetic acid = 9.5/0.5/0.2 (v/v/v) | (KBr): C=O 1718.5 |
| N2 | N—H | AS2 | | 71 | | 0.20 | FM1 | (KBr): C=O 1625.9; 1693.4; 1718.5; —NH— 3357.9 |
| N15 | N—H | AS3 | H$_2$O/MeOH = 1/1 (v/v) as solvent | 57 | | 0.30 | EE/MeOH = 1/1 (v/v) | (KBr): C=O 1693.4 |
| N66 | | AS1 | | 75 | | 0.05 | EE/MeOH 8/2 | |
| N66 | | AS4 | | 85 | | | | |
| N122 | | AS1 | | 44 | | | | |
| N122 | | AS4 | | 85 | | | | |
| N66 | N—CH$_3$ | AS1 | | 58 | ESI: (M − H)$^-$ = 607/09/11 (Br$_2$) | 0.20 | EE | (KBr): C=O 1607/1655/1711 |
| N66 | N—H | AS17 | | 55 | | 0.03 | FM1 | |
| N15 | CH$_2$ | AS1 | | 78 | ESI: (M − H)$^-$ = 578/80/82 (Br$_2$) | 0.30 | EE/MeOH 9/1 (v/v) | (KBr): C=O 1672/1728 |
| N66 | N—H | AS23 | | 79.0 | | 0.22 | FM1 | (KBr): C=O 1738/1664 |

EXAMPLE A40

N⁶-[(1,1-dimethylethoxy)carbonyl]-N²—[N-[[(2-(3-methoxyphenyl)ethyl]amino]carbonyl]-3,5-dibromo-n-tyrosyl]-L-lysine A mixture of 7.75 g (10.4 mmol) of methyl N⁶-[(1,1-dimethyl-ethoxy)carbonyl]-N²-[N-[[[2-(3-methoxyphenyl)ethyl]amino]carbonyl]-3,5-dibromo-D-tyrosyl]-L-lysine, 3.5 g (140 mmol) of lithium hydroxide and 150 ml of water was stirred overnight at room temperature. The aqueous phase was washed once with ethyl acetate, acidified by the addition of 1 M aqueous potassium hydrogen sulphate solution and then extracted with ethyl acetate. The organic phase was dried over sodium sulphate and evaporated down in vacuo. 6.9 g (910 of theory) of a yellowish oil were obtained.

IR (KBr): 1653 cm⁻¹ (C=O)

$R_f$: 0.7 (ethyl acetate/methanol/glacial acetic acid=9/0.5/0.5 (v/v/v))

ESI-MS (M-H)⁻=741/743/745 (Br₂)

EXAMPLE A41

1-[N²—[N-(phenylmethoxycarbonyl)-3,5-dichloro-D-tyrosyl]-N⁶-(1,1-dimethylethoxycarbonyl)-L-lysyl]-4-(4-pyridinyl)-piperazine A mixture of 5 g (13.0 mmol) of 3,5-dichloro-N-[(phenylmethoxy)carbonyl]-D-tyrosine, 5.1 g (13.0 mmol) of 1-[N⁶-[(1,1-dimethylethoxy)carbonyl]-L-lysyl]-4-(4-pyridinyl)-piperazine, 1.81 g (14 mmol) of DIEA, 4.17 g (13 mmol) of TBTU, 1.75 g (13.0 mmol) of HOBt and 200 ml of tetrahydrofuran was stirred at room temperature overnight. The reaction mixture was evaporated down in vacuo, the residue was taken up in ethyl acetate/methanol (95/5) and washed twice with saturated aqueous sodium hydrogen carbonate solution. The organic phase was dried, evaporated down in vacuo and the residue was purified by column chromatography (MN-silica gel 60, Macherey-Nagel, 70-230 mesh ASTM, eluant: ethyl acetate/methanol=6/4 (v/v)). 6.0 g (61% of theory) of a yellowish oil were obtained.

$R_f$: 0.47 (FM1)

ESI-MS (M+H)⁺=757/759/761 (Cl₂)

EXAMPLE A42

Preparation of Compounds of General Formula:

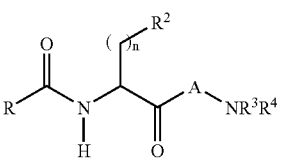

1-[N²—[N-[[[2-(3-methoxyphenyl)ethyl]amino]carbonyl]-3,5-dibromo-D-tyrosyl]-N6-[(1,1-dimethylethoxy)-carbonyl]-L-lysyl]-4-(1-methyl-4 -]piperidinyl)-piperazine To a mixture of 1.1 g (1.5 mmol) of N⁶-[(dimethylethoxy)-carbonyl]-N²-[N-[[[2-(3-methoxyphenyl)ethyl]amino]carbonyl]-3,5-dibromo-D-tyrosyl]-L-lysine, 0.79 g (6.1 mmol) of DIEA, 0.52 g (1.6 mmol) of TBTU, 0.2 g (1.5 mmol) of HOBt and 100 ml of dimethylformamide was added dropwise a solution of 0.44 g (1.5 mmol) of 1-(1-methyl-4-piperidinyl)-piperazine in 30 ml of dimethylformamide at room temperature, the mixture was then stirred overnight and evaporated down in vacuo. The residue was taken up in ethyl acetate/methanol (95/5), washed twice with 70 ml of aqueous saturated sodium hydrogen carbonate solution, dried over sodium sulphate and evaporated down in vacuo. 1.1 g (81% of theory) of a colourless foam were obtained.

$R_f$: 0.34 (ethyl acetate/methanol/conc. aqueous ammonia 7/2/1 (v/v/v))

The following was prepared analogously (n=1)

| RCO | R² | A | NR³R⁴ | Remarks | % Yield | $R_f$ | Eluant | IR [cm⁻¹] |
|---|---|---|---|---|---|---|---|---|
| N15 | AS1 | A11 | C1 | KHSO₄ solution | 70 | 0.40 | FM3 | (KBr): C=O 1697.3; 1641.3 |

EXAMPLE A43

1-[N²-(3,5-dichloro-D-tyrosyl)-N⁶-[(1,1-dimethylethoxy)carbonyl]-L-lysyl]-4-(4-pyridinyl)-piperazine A solution of 6 g (7.9 mmol) of 1-[N²—[N-[(phenylmethoxy)carbonyl-3,5-dichloro-D-tyrosyl]-N⁶-[(1,1-dimethylethoxy)carbonyl]-L-lysyl]-4-(4-pyridinyl)-piperazine in a mixture of 200 ml of methanol and 20 ml of aqueous 1 M potassium hydrogen sulphate solution was hydrogenated in the presence of 0.5 g palladium black as catalyst at room temperature under 3 bar of hydrogen pressure for 40 minutes. The catalyst was filtered off, the reaction mixture was evaporated to dryness in vacuo and the residue adjusted to a pH of about 10 by the addition of 2 ml of concentrated aqueous ammonia solution. The product was extracted several times with isopropanol, the combined isopropanol extracts were evaporated down in vacuo and the residue was purified by column chromatography (LiChroprep, Si60 particle size: 20-40 µm, Messrs. Merck (Darmstadt); eluant: methylene chloride/methanol/ammonia=350/75/75/10 (v/v/v/v)). 2.5 g (51% of theory) of a colourless amorphous solid substance were obtained.

IR (KBr): 1641, 1705 cm$^{-1}$ (C=O)

$R_f$: 0.27 (FM1)

EXAMPLE A44

Preparation of Compounds of General Formula:

Fmoc-A-NR$^3$R$^4$

1-[N$^2$-[(9-fluorenylmethoxy)carbonyl]-N$^G$-(2,2,5,7,8-pentamethylchroman-6-sulphonyl)-L-arginyl]-4-(4-pyridinyl)-piperazine To a mixture of 7.0 g (10.6 mmol) of Fmoc-Arg(Pmc)-OH, 1.42 g (11.0 mmol) of DIEA, 3.53 g (11.0 mmol) of TBTU, 1.35 g (11.0 mmol) of HOBt and 50 ml of DMF was added dropwise with stirring a solution of 1.74 g (10.6 mmol) of 1-(4-pyridinyl)-piperazine in 20 ml of DMF. The reaction mixture was stirred for a further 3.5 hours at room temperature and then evaporated down at 40° C. in a high vacuum. The residue was dissolved in ethyl acetate, the organic phase was washed twice with saturated aqueous sodium hydrogen carbonate solution, dried over sodium sulphate and evaporated down in vacuo. The residue was triturated with diethylether, suction filtered and dried. 7.85 g (96% of theory) of the desired end product were obtained, which was reacted without further purification.

$R_f$: 0.5 (FM1)

The following was prepared analogously:

| A | NR$^3$R$^4$ | % Yield | $R_f$ | Eluant | IR [cm$^{-1}$] |
|---|---|---|---|---|---|
| A3 | C18 | 60 | 0.55 | FM4 | (KBr): C=O 1643; 1711 |

EXAMPLE A45

Preparation of compounds of general formula:

H-A-NR$^3$R$^4$

1-[N$^G$-(2,2,5,7,8-pentamethylchroman-6-sulphonyl)-L-arginyl]-4-(4-pyridinyl)-piperazine A solution of 8.5 g (11.1 mmol) of 1-[N$^2$-[(9-fluorenylmethoxy)carbonyl]-N$^G$-(2,2,5,7,8-pentamethylchroman-6-sulphonyl)-L-arginyl]-4-(4-pyridinyl)-piperazine in 100 ml of THF was mixed with 16 ml of diethylamine and then stirred for 2.5 hours at room temperature. The reaction mixture was evaporated down in vacuo and the residue was purified by column chromatography (MN-silica gel 60, Macherey-Nagel, 70-230 mesh ASTM, eluant: FM1). 3.3 g (54% of theory) of an amorphous solid were obtained.

$R_f$=0.19(FM1)

IR(KBr): 1637 cm$^{-1}$ (C=O)

The following was prepared analogously:

| A | NR$^3$R$^4$ | % Yield | $R_f$ | Eluant | IR [cm$^{-1}$] |
|---|---|---|---|---|---|
| A3 | C18 | 80 | | | (KBr): C=O 1637.5; 1705 |

EXAMPLE A46

1-[N$^6$,N$^6$-dimethyl-N$^2$-[(phenylmethoxy)carbonyl]-L-lysyl]-4-(4-pyridinyl)-piperazine 9.6 g (18.3 mmol) of 1-[N$^6$-[(1,1-dimethylethoxy)carbonyl]-N$^2$-[(phenylmethoxy)carbonyl]-L-lysyl]-4-(4-pyridinyl)-piperazine were stirred overnight in 200 ml of a 5% solution of trifluoroacetic acid in dichloromethane. The reaction mixture was then evaporated down in vacuo. 13.47 g (97% of theory) of the desired 1-[N$^2$-[(phenylmethoxy)carbonyl]-L-lysyl]-4-(4-pyridinyl)-piperazine were obtained as the trifluoroacetate salt. Then 7.0 g (9.1 mmol) of the crude product were dissolved in 200 ml of water and 4.1 ml of a 40% formaldehyde solution (45.6 mmol) were added whilst cooling with an ice bath. The reaction mixture was stirred for 10 minutes at room temperature, carefully mixed with 1.5 g (40 mmol) of sodium borohydride whilst cooling with an ice bath, then mixed with 4.1 ml of a 40% formaldehyde solution (45.6 mmol) whilst cooling externally with ice, after which the reaction mixture was stirred for a further 10 minutes at room temperature and again mixed with 1.5 g (40 mmol) of sodium borohydride whilst cooling with an ice bath. The pH of the reaction mixture was monitored continuously during the reaction and kept between pH 3 and pH 6 by dropwise addition of trifluoroacetic acid. The mixture was then stirred for 30 minutes at 5° C., adjusted to pH 10 by the addition of potassium carbonate and extracted four times with 50 ml of ethyl acetate. The combined organic phases were dried, evaporated down in vacuo and the residue was purified by column chromatography (MN-silica gel 60, Macherey-Nagel, 70-230 mesh ASTM, eluant: ethyl acetate/methanol/conc. aqueous ammonia=6.5/3/0.3 (v/v/v)). 2.3 g (56% of theory) of a colourless oil were obtained.

IR (KBr): 1711, 1649 cm$^{-1}$ (C=O)

$R_f$: 0.2 (FM7)

ESI-MS: (M+H)$^+$=454.

EXAMPLE A47

Preparation of compounds of general formula:

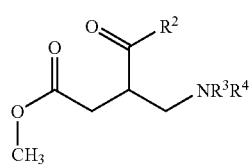

methyl (R,S)-4-amino-3,5-dibromo-γ-oxo-β-[[4-(4-pyridinyl)-1-piperidinyl]methyl]-benzenebutanoate A mixture of 10 g (27 mmol) of methyl 4-amino-3,5-dibromo-γ-oxo-benzenebutanoate, 5.4 g (27 mmol) of 4-(4-pyridinyl)-piperidine and 1.5 g (45 mmol) of paraformaldehyde was suspended in 20 ml of glacial acetic acid and heated with stirring in an oil bath (bath temperature: 100° C.). After 3 hours a further 1.5 g (45 mmol) of paraformaldehyde were added and the mixture was stirred for a further 3 hours at 100° C. and then for 1 hour at 125° C. The solvent was removed in vacuo and the residue was taken up in 800 ml of water. The aqueous phase was made alkaline by the addition of sodium carbonate and extracted twice with 500 ml of ethyl acetate. The combined ethyl acetate extracts were dried, evaporated down in vacuo and the residue was purified by column chromatography (MN-silica gel 60, Macherey Nagel, 70-230 mesh ASTM, eluant: ethyl acetate/methanol=9:1)). 1.0 g (6.8% of theory) of the desired end product were obtained as an oil.

IR(KBr): 1716.5 cm$^{-1}$
$R_f$: 0.7 (FM1)

The following was prepared analogously:

| A | NR$^3$R$^4$ | % Yield | $R_f$ | Eluant | IR [cm$^{-1}$] |
|---|---|---|---|---|---|
| AS4 | C8 | 35 | 0.68 | FM1 | KBr: C=O 1672.2; 1733.9 |

EXAMPLE A48

Preparation of compounds of general formula:

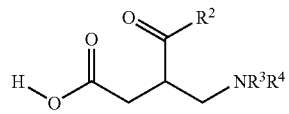

(R,S)-4-amino-3,5-dibromo-γ-oxo-β-[[4-(4-pyridinyl)-1-piperidinyl]methyl]-benzenebutanoic acid A mixture of 1.0 g (1.9 mmol) of methyl (R,S)-4-amino-3,5-dibromo-γ-oxo-β-[[4-(4-pyridinyl)-1-piperidinyl]methyl]-phenyl-butanoate, 5 ml of 1 N sodium hydroxide solution and 50 ml of dioxane was stirred overnight at room temperature and for 1 hour at 60° C. The reaction mixture was then neutralised by the addition of 5 ml of 1N hydrochloric acid, evaporated down in vacuo and the residue was dried in a vacuum drying chamber. 0.97 g (100% of theory) of the desired product was obtained, which was further reacted without any purification.

$R_f$: 0.15 (FM1)

The following was prepared analogously:

| A | NR$^3$R$^4$ | % Yield | $R_f$ | Eluant | IR [cm$^{-1}$] |
|---|---|---|---|---|---|
| AS4 | C8 | 96 | 0.2 | FM1 | KBr: C=O 1660 |

EXAMPLE A49

3,5-dibromo-4-hydroxy-β-(methoxycarbonyl)-benzenitannic acid

To a solution of 12 g (0.043 mol) of 4-hydroxy-β-(methoxycarbonyl)-benzenebutanoic acid in 200 ml of acetic acid were added 150 ml of water and 8 g of sodium acetate, a solution of 5 ml of bromine in 60 ml of acetic acid was added dropwise with stirring, then the reaction mixture was extensively evaporated down in vacuo and the residue was stirred into water. The aqueous phase was repeatedly extracted with ethyl acetate, and the combined organic phases were washed with water. The organic extracts were dried, evaporated down in vacuo and the solid residue was recrystallised from diisopropylether. 12 g (70% of theory) of the desired end product were obtained.

$R_f$: 0.4 (ethyl acetate/petroleum ether/glacial acetic acid=5/5/0.4 (v/v/v)
ESI-MS: (M+H)$^+$=394/6/8 (Br$_2$)

EXAMPLE A50

Preparation of compounds of general formula:

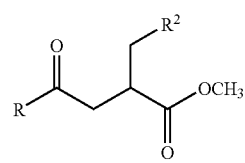

methyl (R,S)-2-[(3,5-dibromo-4-hydroxyphenyl)methyl]-4-[4-(1,3-dihydro-2(2H)-oxobenzimidazol-1-yl)-1-piperidinyl]-4-oxo-butanoate A solution of 2.0 g (5 mmol) of 3,5-dibromo-4-hydroxy-β-(methoxycarbonyl)-benzenebutanoic acid in 80 ml of THF was mixed with 1.6 g (5 mmol) of TBTU, 0.76 g (5 mmol) of HOBt, 1.25 g (5 mmol) of 4-(1,3-dihydro-2(2H)-oxobenzimidazol-1-yl)piperidine and 1.03 g (8 mmol) of DIEA with stirring. The reaction mixture was stirred for 6 hours at room temperature and then evaporated down in vacuo. The residue was mixed with saturated aqueous sodium hydrogen carbonate solution and extracted several times with ethyl acetate. The combined organic extracts were washed successively with saturated aqueous sodium hydrogen carbonate solution and water, dried over sodium sulphate and evaporated down in vacuo. 3.0 g (50% of theory) of the desired product was obtained, which was further reacted without purification.

IR (KBr): 1714.8 cm$^{-1}$ (C=O)
$R_f$: 0.7 (ethyl acetate/petroleum ether=7/3 (v/v))

The following were prepared analogously:

| RCO | R² | % Yield | MS | R_f | Eluant | IR [cm⁻¹] |
|---|---|---|---|---|---|---|
| N66 | AS1 | 98 | | 0.66 | FM1 | |
| N66 | AS2 | 100 | | 0.77 | FM1 | (KBr): C=O 1664/1734 |
| N139 | AS2 | 100 | EI: M⁺ = 486 | 0.30 | FM1 | (KBr): C=O 1643/1672/1732 |
| N66 | AS4 | 28 | EI: M⁺ = 606/08/10 (Br₂) | 0.33 | FM4 | (KBr): C=O 1666/1734 |
| N66 | AS36 | 63 | | 0.56 | FM4 | |
| N66 | AS38 | 92 | | | | |
| N66 | AS48 | 100 | | 0.68 | FM1 | |
| N66 | AS18 | 22 | | | | |
| N66 | AS39 | 100 | | | | |
| N109 | AS21 | 39 | | 0.35 | EE | (KBr): C=O 1639/1734 |
| N113 | AS21 | 57 | | 0.15 | EE/PE 95/5 | |
| N134 | AS21 | 80 | | 0.15 | EE | |
| N66 | AS7 | 100 | | 0.75 | FM1 | |
| N66 | AS53 | 40 | | | | |

EXAMPLE A51

(R)-1-[2-amino-3-(3,5-dibromo-4-hydroxyphenyl) propyl]-4-(1-piperidinyl)-piperidine To a suspension of 3.8 g (100 mmol) of lithium aluminium hydride in 400 ml of THF were added in batches, with stirring and at room temperature, 14.4 g (20 mmol) of 1-(3,5-dibromo-D-tyrosyl)-4-(1-piperidinyl)-piperidine within 30 minutes. The reaction mixture was kept for 30 minutes at room temperature and refluxed for 2 hours and then neutralised by the careful addition of 1 ml of water and 5.1 ml of concentrated aqueous hydrochloric acid. After the addition of 100 ml of methanol the solid precipitate was suction filtered and the filtrate was evaporated down in vacuo. The residue was purified by column chromatography (MN-silica gel 60, Macherey-Nagel, 70-230 mesh ASTM, eluant: methylene chloride/methanol/conc. aqueous ammonia=8/2/0.2 (v/v/v)). 5.4 g (57% of theory) of the desired product was obtained as an amorphous solid.

IR (KBr): 3420 cm⁻¹ (NH₂)
R_f: 0.4 (FM2)
ESI-MS: M⁺=473/475/477 (Br₂)

The following was prepared analogously:
(R)-1-[2-amino-3-(4-amino-3,5-dibromophenyl)propyl]-4-(1-piperidinyl)-piperidine from 1-(4-amino-3,5-dibromo-D-phenylalanyl)-4-(1-piperidinyl)-piperidine in a yield of 56.5% of theory, R_f 0.12 (eluant: dichloromethane/methanol/cyclohexane/conc. ammonia 7/1.5/1.5/0.2 (v/v/v/v)).

EXAMPLE A52

(R)-1-[3-(4-amino-3,5-dibromophenyl)-2-[N-[(1,1-dimethylethoxy)carbonyl]amino]propyl]-4-(1-piperidinyl)-piperidine To a solution of 10 g (0.017 mol) of 1-[4-amino-3,5-dibromo-N-[(1,1-dimethylethoxy)carbonyl]-D-phenylalanyl]-4-(1-piperidinyl)-piperidine in 350 ml of dioxane were added 3.1 g (0.082 mol) of sodium borohydride and the reaction mixture was cooled to 5° C. Then a solution of 4.92 g (0.082 mol) of acetic acid in 100 ml of dioxane was added dropwise with stirring. The reaction mixture was stirred for a further hour at room temperature and for 3 hours at 85° C. Then ice water was added, the organic solvent was removed in vacuo and the aqueous residue was repeatedly extracted with methylene chloride. The combined organic phases were dried, evaporated down in vacuo and the residue was purified by column chromatography (MN-silica gel 60, Macherey-Nagel, 70-230 mesh ASTM, eluant: methylene chloride/methanol/cyclohexane/conc. aqueous ammonia=3600/150/150/20 (v/v/v/v). 4.1 g (42% of theory) of a colourless foam were obtained.

IR (KBr): 1705 cm⁻¹ (C=O)

EXAMPLE A53

(R)-1-[2-amino-3-(4-amino-3,5-dibromophenyl) propyl]-4-(1-piperidinyl)-piperidine To a mixture of 4 g (7 mmol) of (R)-1-[3-(4-amino-3,5-dibromophenyl)-2-[N-[(1,1-dimethylethoxy)carbonyl]-amino]propyl]-4-(1-piperidinyl)-piperidine and 100 ml of methylene chloride, 40 ml of trifluoroacetic acid were slowly added dropwise, with stirring, at 10° C. The reaction mixture was stirred for 2 hours at room temperature and then evaporated down in vacuo. The residue was mixed with ice water, made basic by the addition of concentrated aqueous ammonia solution and extracted three times with 200 ml of diethylether. The combined ether extracts were dried and evaporated down in vacuo. 3.4 g (100% of theory) of an amorphous solid were obtained.

IR (KBr): 1683.8, 1616.3 (C=O)
R_f: 0.02(FM 4)

EXAMPLE A54 methyl (R,S)-4-[4-[3,4-dihydro-2(1H)-oxoquinazolin-3-yl]-1-piperidinyl]-4-oxo-2-[[3-(trifluoromethyl) phenyl]-methyl]-butannate Prepared analogously to Example A15a) from methyl (R,S)-3-carboxy-2-[[3-(trifluoromethyl)phenyl]methyl]-propanoate and 3,4-dihydro-3-(4-piperidinyl)-2(1H)-quinazolinone in a yield of 27.3% of theory. Colourless, amorphous substance, R_f=0.25 (eluant: ethyl acetate).
MS: M⁺=503

The following was obtained in the same way:
methyl (R,S)-4-[4-[3,4-dihydro-2(1H)-oxoquinazolin-3-yl]-1-piperidinyl]-4-oxo-2-[(3,5-dibromo-4-hydroxyphenyl)methyl]-butanoate from methyl (R,S)-3-carboxy-2-[(3,5-dibromo-4-hydroxyphenyl)methyl]-propanoate and 3,4-dihydro-3-(4-piperidinyl)-2(1H)-quinazolinone in a yield of 98% of theory, R_f=0.66 (eluant: dichloromethane/cyclohexane/methanol/conc. ammonia 7/1.5/1.5/0.2 (v/v/v/v)).

EXAMPLE A55

(R,S)-4-[4-[3,4-dihydro-2(1H)-oxoquinazolin-3-yl]-1-piperidinyl]-4-oxo-2-[(3,5-dibromo-4-hydroxyphenyl)methyl]-butanoic acid A mixture of 3.0 g (4.92 mmol) of methyl (R,S)-4-[4-[3,4-dihydro-2(1H)-oxoquinazolin-3-yl]-1-piperidinyl]-4-oxo-2-[(3,5-dibromo-4-hydroxyphenyl)methyl]-butanoate, 30 ml (30 mmol) of 1N sodium hydroxide solution and 20 ml of methanol was stirred for 3 hours at room temperature, then diluted with 100 ml of water and 30 ml of 1N hydrochloric acid were added dropwise. The precipitate was suction filtered and dried at 50° C. in a circulating air drier. Colourless, amorphous substance, $R_f$=0.38 (eluant: dichloromethane/methanol/glacial acetic acid 9/1/0.15 (v/v/v)). Yield: 2.5 g (85.4% of theory).

The following was obtained in the same way:

(R,S)-4-[4-[3,4-dihydro-2(1H)-oxoquinazolin-3-yl]-1-piperidinyl]-4-oxo-2-[[3-(trifluoromethyl)phenyl]methyl]-butanoic acid from methyl(R,S)-4-[4-[3,4-dihydro-2(1H)-oxoquinazolin-3-yl]-1-piperidinyl]-4-oxo-2-[[3-(trifluoromethyl)-phenyl]methyl]-butanoate in a yield of 79% of theory, $R_f$=0.34 (eluant: ethyl acetate/glacial acetic acid 99.8/0.2 (v/v)).

IR(KBr): 1703, 1643 cm$^{-1}$ (C=O)

EXAMPLE A56

Methyl 3,5-dibromo-N-[[4-[3,4-dihydro-2(1H)-oxoquinazolin-3-yl]-1-piperidinyl]carbonyl]-N-methyl-D-tyrosine a) 1-(chlorocarbonyl)-4-[3,4-dihydro-2(1H)-oxoquinazolin-yl]piperidine To a mixture of 7.0 ml (about 14 mmol) of a 20% solution of phosgene in toluene and 2.02 g (20 mmol) of triethylamine in 300 ml of tetrahydrofuran was added in batches, while maintaining a reaction temperature of about 0° C., a suspension of 1.5 g (5.60 mmol) of 4-[3,4-dihydro-2(1H)-oxoquinazolin-3-yl]piperidine-hydrochloride in 100 ml of tetrahydrofuran. The mixture was stirred for another hour at a temperature between 0° C. and +5° C., filtered to remove the resulting triethylamine-hydrochloride and the filtrate was freed from solvent. The residue was triturated with diisopropyl ether and suction filtered. After drying in vacuo 0.7 g (42.6% of theory) of colourless crystals were obtained, $R_f$=0.17 (eluant: dichloromethane/acetone 9.5/0.5 (v/v)), which was further processed without any further purification.

b) Methyl 3,5-dibromo-N-[[4-[3,4-dihydro-2(1H)-oxoquinazolin-3-yl]-1-piperidinyl]carbonyl]-N-methyl-D-tyrosine To a solution of 4.9 g (13.3 mmol) of methyl 3,5-dibromo-N-methyl-D-tyrosine and 4.04 g (40 mmol) of triethylamine in 500 ml of tetrahydrofuran was added dropwise, at room temperature, within 3 hours, a solution of 3.92 g (13.34 mmol) of 1-(chlorocarbonyl)-4-[3,4-dihydro-2(1H)-oxoquinazolin-3-yl]piperidine in 1 l tetrahydrofuran. The mixture was then heated for 12 hours to reflux temperature, left to cool and filtered to remove the precipitated triethylamine. The filtrate was evaporated down, the residue was divided between ethyl acetate and 20% aqueous citric acid. The organic phase was dried over sodium sulphate, again evaporated down in vacuo, the residue was purified by column chromatography over silica gel using ethyl acetate/petroleum ether 9/1 (v/v) as eluant. Working up the appropriate fractions yielded 3.2 g (38.5% of theory) of a colourless, amorphous substance, $R_f$=0.45 (eluant: ethyl acetate)

| IR (KBr): | 1739.7, 1660.6 cm$^{-1}$ (C=O) |
|---|---|
| ESI-MS: | (M + H)$^+$ = 623/625/627 (Br$_2$) |
| | (M + Na)$^+$ = 0 645/647/649 (Br$_2$) |
| | (M + K)$^+$ = 661/663/665 (Br$_2$) |

EXAMPLE A57

Methyl 3,5-dibromo-4-methoxy-D-phenylalanine

To a mixture of 5.5 g (14.12 mmol) of 3,5-dibromo-4-methoxy-D-phenylalanine-hydrochloride and 55 ml of methanol were added 150 ml of a saturated methanolic hydrogen chloride solution and the mixture was stirred for 20 hours at room temperature. The residue remaining after evaporation of the solvent was stirred with 50 ml of water and adjusted to pH 8 with saturated sodium hydrogen carbonate solution. The precipitate was suction filtered, stirred with 10 ml of isopropanol and left to stand overnight. The insoluble matter was filtered off and the filtrate was evaporated down in vacuo. The residue was further reacted as a crude product. Yield: 1.0 g (28.7% of theory) of a colourless oil, $R_f$=0.55 (eluant:dichloromethane/ethyl acetate/cyclohexane/methanol/conc. ammonia=300/80/25/25/3 (v/v/v/v/v)).

EXAMPLE A58

1-(4-amino-3,5-dibromo-D-phenylalanyl)-4-(4-pyrimidinyl)-piperazine a) 1-(2-chloro-4-pyrimidinyl)-4-(phenylmethyl)piperazine A mixture of 9.9 g (0.0664 mol) of 2,4-dichloropyrimidine, 200 ml of water and 11.7 ml (0.0673 mol) of 1-(phenylmethyl)piperazine was heated to 40° C. for 2 hours in an ultrasound bath. After cooling the mixture was made alkaline with potassium carbonate and extracted thoroughly with ethyl acetate. The crude product obtained after working up in the usual way was purified by column chromatography over silica gel (30-60 µm) using FM2 and FM4 (2/1 v/v) as eluant. Working up the appropriate fractions yielded 7.4 g (38.6% of theory) of a colourless oil, $R_f$=0.51 (FM4; Macherey-Nagel POLYGRAM® SIL G/UV$_{254}$, ready-made films for TLC).

MS: M$^+$=288/290 (Cl)

b) 1-(4-pyrimidinyl)piperazine

A solution of 7.4 g (0.0256 mol) of 1-(2-chloro-4-pyrimidinyl)-4-(phenylmethyl)piperazine in 100 ml of ethanol was hydrogenated in the presence of 2 g of 10% palladium/charcoal for 4 hours at 40° C. under 5 bar of hydrogen pressure. The crude product obtained after conventional working up was purified by column chromatography over silica gel (30-60 µm) using FM1/cyclohexane 9/1 (v/v) as eluant. Colourless crystals, $R_f$=0.3 (FM1/cyclohexane 9/1 (v/v)); Macherey-Nagel POLYGRAM® SIL G/UV$_{254}$, ready-made films for TLC). Yield: 1.7 g (40.7% of theory).

c) 1-[4-amino-3,5-dibromo-N-(1,1-dimethylethoxycarbonyl)-D-phenylalanyl]-4-(4-pyrimidinyl)piperazine Prepared analogously to Example A15a) from 4-amino-3,5-dibromo-N-(1,1-dimethylethoxycarbonyl)-D-phenylalanine and 1-(4-pyrimidinyl)piperazine in the presence of TBTU in a yield of 92% of theory. Colourless, amorphous substance, $R_f$=0.42 (FM4; Macherey-Nagel POLYGRAM® SIL G/UV$_{254}$, ready-made films for TLC).

IR(KBr): 1705.0, 1643.3 cm$^{-1}$ (C=O)

MS: M$^+$=582/584/586 (Br$_2$)

d) 1-(4-amino-3,5-dibromo-D-phenylalanyl)-4-(4-pyrimidinyl)piperazine

Prepared analogously to Example A1b) from 1-[4-amino-3,5-dibromo-N-(1,1-dimethylethoxycarbonyl)-D-phenylalanyl]-4-(4-pyrimidinyl)piperazine in a yield of 52% of theory. Colourless, amorphous substance, $R_f$=0.55 (FM1; Macherey-Nagel POLYGRAM® SIL G/UV$_{254}$, ready-made films for TLC).

The ethanol was removed in vacuo, then the residue was diluted with 50 ml of water and adjusted to pH 3 with 1N aqueous hydrochloric acid. The precipitated substance was suction filtered, thoroughly washed with water and then dried in vacuo. 3.8 g (96w of theory) of colourless crystals of Mp. 139▓141° C. were obtained, $R_f$=0.65 (eluant:EE/MeOH/glacial acetic acid 90/10/1 v/v/v).

IR(KBr): 1724, 1647 cm$^{-1}$ (C═O)
MS: no M$^+$, m/e=246, 231, 147
The following were prepared analogously:

| $R^2$ | Remarks | % Yield | MS | $R_f$ | Eluant | IR [cm$^{-1}$] |
|---|---|---|---|---|---|---|
| AS29 | | 100 | | | | |
| AS16 | | 17 | ESI: (M + H)$^+$ = 488/90/92 (Cl$_2$) | 0.30 | EE/MeOH/ AcOH 80/10/1 | |
| AS5 | | 62 | | 0.60 | CH$_2$Cl$_2$/MeOH/ NH$_4$OH 90/10/1 | |
| AS32 | | 100 | ESI: (M + Na)$^+$ = 614/6/8 (Br$_2$) | 0.67 | EE/MeOH/ AcOH 90/10/1 | (KBr): C═O 1645/1728 |
| AS33 | | 90 | EI: M$^+$ = 525 | 0.20 | EE/MeOH/ AcOH 90/10/1 | (KBr): C═O 1643/1701 |
| AS31 | | 100 | | 0.20 | CH$_2$Cl$_2$/MeOH/ NH$_4$OH 80/20/1 | |
| AS17 | | 100 | ESI: (M + H)$^+$ = 608/10/12 (Br$_2$) | 0.50 | EE/MeOH/ AcOH 90/10/1 | (KBr): C═O 1643 |
| AS34 | | 76 | ESI: (M − H)$^-$ = 506 | 0.65 | EE/MeOH/ AcOH 90/10/1 | |
| AS19 | | 70 | | 0.46 | EE/MeOH/ AcOH 9/1/0.5 | (KBr): C═O 1643/1701 |
| AS46 | | 78 | ESI: (M − H)$^-$ = 471 | 0.20 | FM1 | (KBr): C═O 1647 |
| AS50 | | 97 | | 0.05 | EE | |
| AS2 | LiOH instead of NaOH | 86 | ESI: (M + H)$^+$ = 472 | | | (KBr): C═O 1643/1705 |
| AS29 | | 100 | ESI: (M − H)$^-$ = 448 | | | (KBr): C═O 1645/1705 |
| AS31 | | 87 | | | | |

IR(KBr): 1681.8 cm$^{-1}$ (C═O)
MS: M$^+$=482/484/486 (Br$_2$)

EXAMPLE A59

Preparation of Compounds of General Formula:

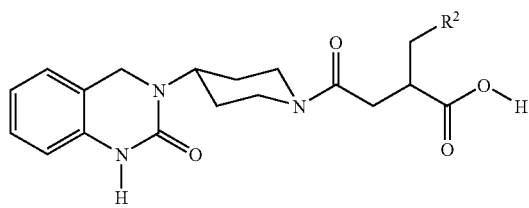

(R,S)-4-[4-(3,4-dihydro-2(1H)-oxoquinazolin-3-yl)-1-piperidinyl]-2-[[4-(1,1-dimpthylathyl)phenyl]methyl]-4-oxobutanoic acid A mixture of 4.8 g (8.3 mMol) of ethyl 4-[4-(3,4-dihydro-2(1H)-oxoquinazolin-3-yl)-1-piperidinyl]-2-[[4-(1,1-dimethylethyl)-phenyl]methyl]-2-(ethoxycarbonyl)-4-oxobutanoate, 200 ml of ethanol and 41.5 ml of 1N sodium hydroxide solution was refluxed for 3 hours.

EXAMPLE A60

Preparation of Compounds of General Formula:

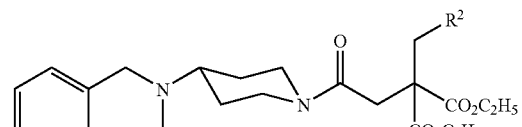

Ethyl 4-[4-(3,4-dihydro-2(1H)-oxoquinazolin-3-yl)-1-piperidinyl]-2-[[4-(1,1-dimethylethyl)phenyl]methyl]-2-(ethoxy-carbonyl)-4-oxobutanoate A mixture of 2.31 g (10 mMol) of 4-(3,4-dihydro-2(1H)-oxo-quinazolin-3-yl)-piperidine, 3.64 g (10 mMol) of β,β-bis-(ethoxycarbonyl)-4-(1,1-dimethylethyl)-benzenebutanoic acid, 5 ml of triethylamine, 3.5 g (11 mMol) of TBTU, 200 ml of tetrahydrofuran and 20 ml dimethylformamide was stirred for 5 hours at room temperature. The solvent was removed in vacuo and the residue taken up in dichloromethane, the resulting solution was dried over sodium sulphate and freed from the solvent. After purification by column chromatography on 400 g of silica gel (Amicon, 35-70 μm, ethyl acetate as eluant), 4.8 g (83% of theory) of a colourless, amorphous substance were obtained, $R_f$=0.63 (eluant:EE).

IR(KBr): 1734, 1668, 1653 cm$^{-1}$ (C=O)

MS: M$^+$=577 (Br$_2$)

The following were prepared analogously:

| R$^2$ | % Yield | MS | $R_f$ | Eluant | IR [cm$^{-1}$] |
|---|---|---|---|---|---|
| AS29 | 75 | | 0.8 | FM1 | |
| AS16 | 59 | | 0.5 | EE | |
| AS5 | 65 | EI: M$^+$ = 677/79/81 (Br$_2$) | 0.7 | FM4 | (KBr): C=O 1649/1668/1734 |
| AS32 | 74 | | 0.5 | FM4 | (KBr): C=O 1647/1668/1734 |
| AS33 | 85 | | 0.5 | EE | (KBr): C=O 1649/1734 |
| AS31 | 82 | EI: M$^+$ = 574 | 0.5 | CH$_2$Cl$_2$/MeOH/ NH$_4$OH 90/10/1 | (KBr): C=O 1658/1741 |
| AS17 | 93 | EI: M$^+$ = 707/09/11 (Br$_2$) | 0.5 | EE | (KBr): C=O 1645/1666/ 1736/1759 |
| AS34 | 75 | EI: M$^+$ = 607 | 0.8 | EE | (KBr): C=O 1649/1668/1736 |
| AS19 | 67 | | 0.8 | FM1 | (KBr): C=O 1647/1668/1734 |
| AS46 | 80 | EI: M$^+$ = 572 | 0.8 | FM1 | (KBr): C=O 1737 |
| AS50 | 78 | EI: M$^+$ = 677/9/81 (Br$_2$) | 0.6 | EE | (KBr): C=O 1645/1666/1730 |
| AS2 | 51 | | | | |

-continued

| R$^2$ | % Yield | MS | $R_f$ | Eluant | IR [cm$^{-1}$] |
|---|---|---|---|---|---|
| AS32 | 100 | | 0.58 | PE/EE 2/1 | (KBr): C=O 1759/1711 |
| AS33 | 100 | | | | (KBr): C=O 1736 |
| AS17 | 52 | | | | (KBr): C=O 1707/1726/ 1755 |
| AS34 | 90 | | 0.8 | EE/MeOH/ AcOH 97.5/2.5/0.25 | (KBr): C=O 1705/1743 |
| AS19 | 100 | | 0.76 | PE/EE/ AcOH 6/3/1 | (KBr): C=O 1738 |
| AS46 | 92 | | 0.35 | FM1 | (KBr): C=O 1732 |
| AS50 | 71 | | | | (KBr): C=O 1712/1734/ 1759 |
| AS2 | 31 | EI: M$^+$ = 272 | 0.42 | PE/EE/ AcOH 6/4/0.2 | (KBr): C=O 1711/1734 |

EXAMPLE A61

Preparation of Compounds of General Formula:

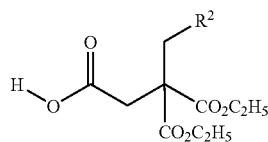

β,β-bis-(ethoxycarbonyl)-1-methyl-1H-indol-3-butanoic acid

Produced analogously to Example A1b) from tert.-butyl β,β-bis-(ethoxycarbonyl)-1-methyl-1H-indol-3-butanoate through the action of trifluoroacetic acid in dichloromethane in a yield of 63.5% of theory. Colourless crystals of Mp. 127-130° C. (diisopropylether).

IR(KBr): 1738, 1712 cm$^-$(C=O)

The following were prepared analogously:

| R$^2$ | % Yield | MS | $R_f$ | Eluant | IR [cm$^{-1}$] |
|---|---|---|---|---|---|
| AS29 | 100 | | | | |
| AS16 | 100 | | 0.7 | EE/MeOH/ AcOH 97.5/2.2/0.25 | |
| AS5 | 100 | | 0.5 | PE/EE 2/1 | |

EXAMPLE A62

Preparation of Compounds of General Formula:

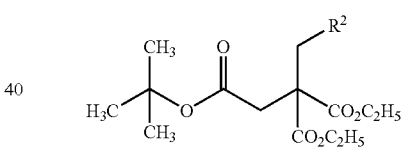

Tert.-butyl β,β-bis-(ethoxycarbonyl)-3,5-dimethyl-benzene-butanoate

To a solution of 13.8 g (50.2 mMol) of diethyl [(1,1-dimethyl-ethoxycarbonyl)methyl]-malonoate in 400 ml of anhydrous tetrahydrofuran, 2.3 g (52.7 mMol) of sodium hydride was added whilst being externally cooled with iced water. After stirring for 30 minutes, and maintaining a reaction temperature of 0 to +5° C., the solution of 10.0 g (50.2 mMol) of 3,5-dimethylbenzylbromide in 80 ml tetrahydrofuran was added dropwise and the mixture allowed to warm to room temperature within 14 hours. The reaction mixture was freed from the solvent in vacuo, 200 ml of 10% citric acid was added to the residue and the resulting mixture was thoroughly extracted with ethyl acetate. After the usual working up, the combined extracts yielded 19.7 g (100% of theory) of a colourless oil of $R_f$=0.67 (eluant:dichloromethane), which was used in the following steps without further purification.

The following were prepared analogously:

| R² | Remarks | % Yield | MS | R_f | Eluant | IR [cm⁻¹] |
|---|---|---|---|---|---|---|
| AS29 | | 100 | | | | |
| AS16 | | 62 | | 0.6 | $CH_2Cl_2$ | |
| AS5 | | 91 | ESI: $(M + H)^+$ = 521/3/5 ($Br_2$) | 0.8 | PE/EE 2/1 | (KBr): C=O 1734 |
| AS32 | | 96 | | 0.76 | PE/EE 2/1 | (KBr): C=O 1734 |
| AS33 | | 78 | | 0.55 | $CH_2Cl_2$ | (KBr): C=O 1736 |
| AS31 | with use of 3-(dimethylaminomethyl)-1-methyl-1H-indol-methoiodide | 74 | EI: $M^+$ = 417 | 0.7 | toluene/ t-BME 4/1 | (KBr): C=O 1734 |
| AS17 | | 70 | EI: $M^+$ = 550/52/54 ($Br_2$) | 0.5 | $CH_2Cl_2$ | (KBr): C=O 1734 |
| AS34 | | 93 | EI: $M^+$ = 450 | 0.5 | $CH_2Cl_2$/ PE 1/1 | (KBr): C=O 1736 |
| AS19 | | 87 | | 0.89 | $CH_2Cl_2$ | (KBr): C=O 1736 |
| AS46 | | 54 | EI: $M^+$ = 415 | 0.7 | FM4 | |
| AS50 | | 60 | EI: $M^+$ = 520/22/24 ($Br_2$) | 0.7 | $CH_2Cl_2$ | (KBr): C=O 1734 |

EXAMPLE A63

(phenylmethyl)-β,β-bis-(ethoxycarbonyl)-4-(1,1-dimethylethyl)-benzenebutanoate

Prepared analogously to Example A62 from diethyl[(phenylmethoxycarbonyl)methyl]-malonoate and 4-(1,1-dimethylethyl)-benzylbromide in the presence of sodium hydride in a yield of 53% of theory.

Colourless oil of $R_f$=0.21 (eluant:dichloromethane/petroleum ether 2/1 v/v).

IR(KBr): 1738 cm⁻¹ (C=O)

EXAMPLE A64

Methyl 4-[4-(3,4-dihydro-2(1H)-oxoquinazolin-3-yl)-1-piperidinyl]-2-[[3-(1-methylethoxy)phenyl]methyl]-4-oxobutanoate To a solution of 2.0 g (4.43 mMol) of methyl 4-[4-(3,4-dihydro-2(1H)-oxoquinazolin-3-yl)-1-piperidinyl]-2-[(3-hydroxyphenyl)-methyl]-4-oxobutanoate in 30 ml of anhydrous dimethylformamide, 0.2 g (4.4 mMol) of a 55% suspension of sodium hydride in paraffin oil was added. After stirring for 30 minutes at room temperature, 0.5 ml (4.8 mMol) of isopropyliodide was added dropwise, and kept for two hours each at room temperature and at 70° C. The residue remaining after removal of the volatile constituents was divided between water and ethyl acetate. The organic phase was washed with saturated sodium chloride solution, dried over magnesium sulphate and was again evaporated down. The raw product was purified by column chromatography on silica gel (60 μm), first using dichloromethane, later methanol/conc. ammonia (9/1 v/v) as eluants. Yield was 0.9 g (42% of theory) of a colourless, amorphous substance of $R_f$=0.32 (FM4).

IR(KBr): 1734, 1668 cm⁻¹ (C=O)
MS: $M^+$=493

In the same way, methyl 4-[4-(3,4-dihydro-2(1H)-oxoquinazolin-3-yl)-1-piperidinyl]-2-[(3-ethoxyphenyl)methyl]-4-oxobutanoate was obtained from methyl 4-[4-(3,4-dihydro-2(1H)-oxoquinazolin-3-yl)-1-piperidinyl]-2-[(3-hydroxyphenyl)methyl]-4-oxobutanoate and ethyliodide in a yield of 67% of theory. Colourless, amorphous substance of $R_f$=0.29 (FM4).

IR(KBr): 1734, 1666 cm⁻¹ (C=O)
MS: $M^+$=479

EXAMPLE A65

β,β-bis-(ethoxycarbonyl)-4-(1,1-dimethylethyl)-benzenebutanoic acid

Prepared analogously to example A58b) from phenyl methyl β,β-bis-(ethoxycarbonyl)-4-(1,1-dimethylethyl)-benzenebutanoate by catalytic hydrogenation in the presence of palladium/charcoal in a yield of 95% of theory. Colourless, highly-viscous oil of $R_f$=0.16 (eluant:dichloromethane).

IR(KBr): 1739 cm⁻¹ (C=O)

EXAMPLE A66

1-methyl-4-[(1-piperazinyl)carbonyl]-piperazine-bis-(trifluoro-acetate)

a) 4-[[4-(1,1-dimethylethoxycarbonyl)-1-piperazinyl]carbonyl]-1-methylpiperazine To a solution of 1.1 g of triphosgene (3.7 mMol) in 20 ml of dichloromethane, a mixture of 1.2 g (10 mMol) of 1-methylpiperazine, 0.38 ml (22 mMol) of DIEA and 35 ml of dichloromethane was added dropwise at room temperature within 30 minutes, and then the solution of 1.9 g (10 mMol) of 1-(1,1-dimethyl-ethoxycarbonyl)piperazine and 0.38 ml of DIEA in 20 ml dichloromethane were added. After stirring for an hour at room temperature, insoluble matter was filtered off and the filtrate evaporated down in vacuo. After purification of the raw product on silica gel (Amicon, 35-70 μm), using dichloromethane/methanol/conc. ammonia(80/20/1 v/v/v) for elution, 700 mg (22% of theory) of colourless crystals were obtained of Mp. 130° C.

IR(KBr): 1691, 1641 cm⁻¹ (C=O)

b) 1-methyl-4-[(1-piperazinyl)carbonyl]-piperazine-bis-(trifluoroacetate)

Prepared analogously to Example A1b), but omitting the treatment with aqueous ammonia, from 4-[[4-(1,1-dimethylethoxycarbonyl)-1-piperazinyl]carbonyl]-1-methylpiperazine and trifluoroacetic acid in a yield of 99.6% of theory. Colourless, amorphous substance of $R_f$=0.17 (eluant:dichloromethane/methanol/conc. ammonia 50/50/0.5).

IR(KBr): 1678 cm$^{-1}$ (C=O)
MS: M$^+$=212

EXAMPLE A67

1-[4-[4-(dimethylamino)butyl]phenyl]-piperazine-dihydrochloride a) N,N-dimethyl-4-fluoro-γ-oxobenzenebutanoic acid amide

To a solution of 30.5 g (0.155 Mol) of 4-fluoro-γ-oxobenzenebutanoic acid in 470 ml tetrahydrofuran, 35.0 g (0.216 Mol) of N,N'-carbonyldiimidazole was added with stirring and at room temperature and held at room temperature for a further 2.5 hours. Then, 13.7 g (0.304 Mol) of dimethylamine was added under strong external cooling by means of an ice-ethanol mixture. After the mixture had stood at room temperature for 12 hours, the solvent was removed in vacuo, the residue was divided between dichloromethane and 10% aqueous citric acid solution, the organic phase was dried over sodium sulphate and once again evaporated down in vacuo. After purification by column chromatography (eluant:ethyl acetate) on silica gel the crude product yielded 30.22 g (87% of theory) of colourless crystals of $R_f$=0.31 (eluant:ethyl acetate/glacial acetic acid 99.99/0.01).

IR(KBr): 1680, 1647 cm$^{-1}$ (C=O)

b) N,N-dimethyl-γ-oxo-4-[4-(phenylmethyl)-1-piperazinyl]-benzenebutanoic acid amide The mixture of 33.48 g (0.15 Mol) of N,N-dimethyl-4-fluoro-γ-oxobenzenebutanoic acid amide, 29.6 g (0.168 Mol) of 1-(phenyl-methyl)piperazine and 6 ml of DIEA was refluxed for 6 hours. Another 30 g (0.17 Mol) of (phenylmethyl)piperazine was added, and the mixture was refluxed for a further 7 hours. The mixture was taken up in a little dichloromethane, and purified by column chromatography on silica gel, using dichloromethane/methanol/conc. ammonia 99/1/0.5 for elution. The residue obtained from the appropriate fractions was stirred with diisopropylether, the formed crystals were then recrystallised from ethanol. 42.22 g (74% of theory) of colourless crystals were obtained, $R_f$=0.69 (eluant: dichloromethane/methanol/conc. ammonia 95/5/0.5 v/v/v).

IR(KBr): 1662, 1643 cm$^{-1}$ (C=O)

c) 4-[4-[4-(dimethylamino)-1-hydroxybutyl]phenyl]-1-(phenyl-methyl)piperazine Prepared analogously to example A51 from N,N-dimethyl-γ-oxo-4-[4-(phenylmethyl)-1-piperazinyl]-benzenebutanoic acid amide by reduction with lithium aluminium hydride in a yield of 61% of theory. Colourless, amorphous substance of $R_f$=0.62 (eluant:ethyl acetate/methanol 1/1 v/v).

MS: Me$^+$=367 d) 1-[4-[4-(dimethylamino)butyl]phenyl]-piperazine-dihydrochloride

Prepared analogously to example A20b) from 4-[4-[4-(dimethylamino)-1-hydroxybutyl]phenyl]-1-(phenylmethyl)piperazine by catalytic hydrogenation in the presence of palladium/charcoal and hydrochloric acid in a quantitative yield. Colourless, amorphous substance of $R_f$=0.37 (eluant:ethyl acetate/methanol 50/50/0.5 v/v/v).

B. Preparation of the Final Compounds

EXAMPLE 1

Preparation of Compounds of General Formula:

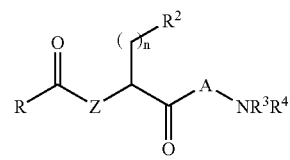

1-[N-[4-(1,3-dihydro-2(2H)-oxobenzimidazol-1-yl)-1-piperidinyl]carbonyl]-3,5-dibromo-D-tyrosyl]-4-(4-pyridinyl)-piperazine (No. 83)

A mixture of 2 g (3.44 mmol) of 3,5-dibromo-N$^2$-[4-(1,3-dihydro-2(2H)-oxobenzimidazol-1-yl)-1-piperidinyl)-carbonyl]-D-tyrosine, 0.59 g (3.6 mmol) of 1-(4-pyridinyl)-piperazine, 1.27 g (3.96 mmol) of TBTU, 0.47 g (3.44 mmol) of HOBt, 0.7 ml (3.96 mmol) of DIEA and 100 ml tetrahydrofuran was stirred overnight at ambient temperature. The reaction mixture was extracted once with saturated aqueous saline solution, twice with saturated aqueous sodium hydrogen carbonate solution and again with saturated aqueous saline solution. The organic phase was dried, evaporated down in vacuo and the crude product was then purified by column chromatography (MN-silica gel 60, Macherey-Nagel, 70-230 mesh ASTM, eluant:ethyl acetate/methanol=9/1/(v/v/)). 550 mg (22% of theory) of an amorphous solid were obtained.

IR (KBr): 1601, 1636, 1696 cm$^{-1}$ (C=O)
$R_f$: 0.67 (FM2)
ESI-MS: (M+H)$^+$=726/728/730 (Br$_2$)

The following were prepared analogously (in each case n=1):

| No. | RCO | Z | R² | A | NR³R⁴ | Remarks | % Yield | MS | $R_f$ | Eluant | IR [cm⁻¹] |
|---|---|---|---|---|---|---|---|---|---|---|---|
|  | N6 | N—H | AS1 | A3 | C4 |  | 88 | ESI: (M + H)⁺ = 928/30/32 (Br₂) | 0.8 | FM1 | (KBr): C=O 1629.8; 1708.8 |
| 193 | N15 | N—H | AS6 | A0 | C7 | DMF as solvent | 26 | ESI: (M + H)⁺ = 647/9 (Br) | 0.9 | EE/MeOH/ AcOH 75/23/2 v/v/v | (KBr): C=O 1693.4; 1622.0 |
| 194 | N66 | N—H | AS1 | A0 | C67 |  | 49 | ESI: (M + H)⁺ = 828/30/32 (Br₂) | 0.33 | FM1 | (KBr): C=O 1622/1664 |
| 202 | N15 | N—H | AS1 | A0 | C36 | DMF as solvent; DIEA | 9 | ESI: (M + H)⁺ = 733/5/7 (Br₂) | 0.49 | FM1 | (KBr): C=O 1695.3; 1622.0 NH 3417.7 |
| 203 | N15 | N—H | AS1 | A0 | C29 | DMF as solvent; DIEA | 41 | ESI: (M − H)⁻ = 718/20/22 (Br₂) | 0.58 | EE/MeOH 9/1 v/v | (KBr): C=O 1695.3 |
| 204 | N15 | N—H | AS1 | A0 | C30 | DMF as solvent; DIEA | 27 | ESI: (M + H)⁺ = 691/3/5 (Br₂) | 0.1 | FM1 | (KBr): C=O 1695.3; 1624.0 |
| 205 | N15 | N—H | AS6 | A0 | C8 | DMF as solvent; DIEA | 23 | ESI: (M + H)⁺ = 653/5 (Br) | 0.46 | FM1 | (KBr): C=O 1695.3; 1622.0 |
| 206 | N15 | N—H | AS1 | A0 | C31 | DMF as solvent; DIEA | 33 | ESI: (M + H)⁺ = 717/19/21 (Br₂) | 0.25 | FM1 | (KBr): C=O 1695.3; 1624.0 |
| 207 | N15 | N—H | AS1 | A0 | C32 | DMF as solvent; DIEA | 55 | ESI: (M − H)⁻ = 780/2/4 (Br₂) | 0.46 | FM1 | (KBr): C=O 1690; 1650 |
| 212 | N15 | N—H | AS1 | A7 | C1 | DMF as solvent; DIEA | 37 | ESI: (M + H)⁺ = 882/4/6 (Br₂) | 0.27 | FM1 | (KBr): C=O 1697.3; 1639.4 NH 3423.4 |
| 217 | N15 | N—H | AS6 | A3 | C1 |  | 51 |  | 0.9 | FM1 | (KBr): C=O 1693.4; 1641.3 |
| 222 | N15 | N—H | AS1 | A0 | C27 | THF/DMF 1/1 as solvent; NEt₃ as base | 10 | ESI: (M + H)⁺ = 774/6/8 (Br₂) | 0.35 | FM1 | (KBr): C=O 1695.3 |
| 286 | N15 | N—H | AS1 | A0 | C28 | THF/DMF 1/1 as solvent; NEt₃ as base | 9 | ESI: (M + H)⁺ = 706/8/10 (Br₂) | 0.4 | FM1 | (KBr): C=O 1699.2 |
| 81 | N15 | N—H | AS4 | A0 | C4 |  | 64 | ESI: (M + H)⁺ = 724/6/8 (Br₂); (M + Na)⁺ = 746/48/50 (Br₂) | 0.75 | FM1 | (KBr): C=O 1618.2; 1703.0 |
| 82 | N15 | N—H | AS4 | A0 | C1 |  | 53 | ESI: (M + H)⁺ = 725/7/9 (Br₂) | 0.55 | FM3 | (KBr): C=O 1620.1; 1703.0 |
| 84 | N66 | N—H | AS21 | A0 | C68 |  | 31 | ESI: (M + H)⁺ = 683 | 0.52 | FM1 | (KBr): C=O 1608/1628/ 1666 |
| 85 | N15 | N—H | AS4 | A0 | C7 |  | 42 | ESI: (M + H)⁺ = 724/6/8 (Br₂); (M + Na)⁺ = 746/48/50 (Br₂) | 0.8 | FM1 | (KBr): C=O 1618.2; 1697.3; —NH—, —NH₂ 3379.1 |
| 90 | N15 | N—H | AS1 | A0 | C8 |  | 40 | ESI: (M + H)⁺ = 731/3/5 (Br₂) | 0.78 | FM2 | (KBr): C=O 1624.0; 1697.3 |
|  | N2 | N—H | AS2 | A3 | C1 | DMF as solvent; DIEA | 73 | ESI: (M + H)⁺ = 766 | 0.42 | FM1 | (KBr): C=O 1654.2; 1708.8 |

-continued

| No. | RCO | Z | R² | A | NR³R⁴ | Remarks | % Yield | MS | R_f | Eluant | IR [cm⁻¹] |
|---|---|---|---|---|---|---|---|---|---|---|---|
| 354 | N15 | N—H | AS1 | A0 | C4 | | 21 | ESI: (M + H)⁺ = 725/7/9 (Br₂); (M + Na)⁺ = 747/49/51 (Br₂) | 0.76 | FM2 | (KBr): C=O 1622.0; 1695.3; —OH, —NH— 3417.7 |
| 98 | N15 | N—H | AS1 | A0 | C9 | | 60 | ESI: (M + H)⁺ = 580/2/4 (Br₂); (M − H)⁻ = 578/80/82 (Br₂); (M + Na)⁺ = 602/4/6 (Br₂) | 0.41 | FM2 | (KBr): C=O 1624.0; 1685.7; —OH, —NH— 3421.5 |
| 102 | N15 | N—H | AS1 | A0 | C12 | | 43 | ESI: (M + H)⁺ = 636/38/40 (Br₂); (M + Na)⁺ = 658/60/62 (Br₂) | 0.76 | FM2 | (KBr): C=O 1622.0; 1695.3; |
| 99 | N15 | N—H | AS1 | A0 | C10 | | 54 | ESI: (M + H)⁺ = 663/5/7 (Br₂) | 0.61 | FM2 | (KBr): C=O 1622.9; 1700.9; —OH, —NH— 3421.5 |
| 100 | N15 | N—H | AS1 | A0 | C11 | | 54 | ESI: (M + H)⁺ = 746/48/50 (Br₂) | 0.5 | FM2 | (KBr): C=O 1624.0; 1695.3; —NH—, —OH 3423.4; |
| 101 | N15 | N—H | AS1 | A0 | C7 | | 62 | ESI: (M + H)⁺ = 725/7/9 (Br₂); (M + Na)⁺ = 747/49/51 (Br₂) | 0.82 | FM2 | (KBr): C=O 1622.0; 1695.3; —OH, —NH— 3253.7 |
| 103 | N15 | N—H | AS1 | A0 | C13 | | 37 | ESI: (M + H)⁺ = 679/81/83 (Br₂) | 0.72 | FM2 | (KBr): C=O 1625.9; 1693.4; 1666.4; —OH, —NH— 3409.9 |
| 106 | N15 | N—H | AS1 | A0 | C14 | | 72 | ESI: (M + H)⁺ = 832/4/6 (Br₂); (M + Na)⁺ = 854/6/8 (Br₂) | 0.66 | FM1 | (KBr): C=O 1674.1; 1689.5 |
| 104 | N15 | N—H | AS6 | A0 | C4 | | 36 | ESI: (M + H)⁺ = 647/9 (Br); (M + Na)⁺ = 669/71 (Br); (M − H)⁻ 645/7 (Br) | 0.71 | FM1 | (KBr): C=O 1695.3 |
| 105 | N15 | N—H | AS6 | A0 | C1 | | 25 | ESI: (M + H)⁺ = 648/50 (Br) | 0.25 | FM3 | (KBr): C=O 1695.3 |
| | N2 | N—H | AS1 | A12 | C1 | DMF as solvent; DIEA | 72 | ESI: (M + H)⁺ = 1082/4/6 (Br₂) | 0.4 | FM1 | KBr: C=O 1641 |
| 199 | N15 | N—H | AS3 | A0 | C8 | THF/DMF = 9/1 (v/v) as solvent | 86 | ESI: (M + H)⁺ = 643/5/7 (Br₂) | 0.37 | ethyl acetate/ methanol/ petroleum ether = 1/2/1 (v/v/v) | KBr: C=O 1697; 1624 |
| 200 | N15 | N—H | AS3 | A0 | C1 | | 40 | ESI: (M + H)⁺ = 638/40/42 (Br₂) | 0.45 | ethyl acetate/ methanol/ petroleum ether = 1/2/1 (v/v/v) | KBr: C=O 1695; 1636 |
| 419 | N66 | N—H | AS21 | A0 | C38 | | 28 | ESI: (M + H)⁺ = 682 | 0.1 | FM1 | (KBr): C=O 1628/1662 |
| 425 | N66 | N—H | AS1 | A0 | C36 | | 42 | ESI: (M + H)⁺ = 747/49/51 (Br₂) | 0.4 | FM1 | (KBr): C=O 1624/1657 |
| 426 | N66 | N—H | AS4 | A0 | C30 | | 66 | ESI: (M + H)⁺ = 704/6/8 (Br₂) | 0.45 | FM1 | (KBr): C=O 1618/1663 |

-continued

| No. | RCO | Z | R² | A | NR³R⁴ | Remarks | % Yield | MS | R_f | Eluant | IR [cm⁻¹] |
|---|---|---|---|---|---|---|---|---|---|---|---|
| 427 | N66 | N—H | AS1 | A0 | C31 | | 38 | ESI: (M + H)⁺ = 731/3/5 (Br₂) | 0.2 | FM1 | (KBr): C=O 1630/1653 |
| 428 | N66 | N—H | AS4 | A0 | C36 | | 40 | ESI: (M + H)⁺ = 746/48/50 (Br₂) | 0.6 | FM1 | (KBr): C=O 1618/1662 |
| 429 | N66 | N—H | AS1 | A0 | C30 | | 47 | ESI: (M + H)⁺ = 705/7/9 (Br₂) | 0.15 | FM1 | (KBr): C=O 1635/1653 |
| 435 | N66 | N—H | AS4 | A0 | C31 | | 20 | ESI: (M + H)⁺ = 730/2/4 (Br₂) | 0.55 | FM1 | (KBr): C=O 1608/1631 |
| 436 | N66 | N—H | AS1 | A0 | C11 | | 15 | ESI: (M + H)⁺ = 760/2/4 (Br₂) | 0.1 | FM1 | (KBr): C=O 1624/1653 |
| 437 | N66 | N—H | AS4 | A0 | C11 | | 25 | ESI: (M + H)⁺ = 759/61/63 (Br₂) | 0.5 | FM1 | (KBr): C=O 1622/1661 |
| 438 | N66 | N—H | AS4 | A0 | C54 | | 13 | ESI: (M + H)⁺ = 744/6/8 (Br₂) | 0.7 | FM1 | (KBr): C=O 1620/1660 |
| 439 | N66 | N—H | AS1 | A0 | C54 | | 31 | ESI: (M + H)⁺ = 745/7/9 (Br₂) | 0.5 | FM1 | (KBr): C=O 1626/1661 |
| 443 | N122 | N—H | AS1 | A0 | C11 | | 44 | ESI: (M + H)⁺ = 790/2/4 (Br₂) | 0.1 | FM1 | (KBr): C=O 1624/1680 |
| 444 | N122 | N—H | AS1 | A0 | C8 | | 62 | ESI: (M + H)⁺ = 775/7/9 (Br₂) | 0.18 | FM1 | (KBr): C=O 1624/1678 |
| 445 | N122 | N—H | AS1 | A0 | C1 | | 60 | ESI: (M + H)⁺ = 770/2/4 (Br₂) | 0.2 | FM1 | (KBr): C=O 1630/1680 |
| 446 | N122 | N—H | AS1 | A0 | C20 | | 59 | ESI: (M + H)⁺ = 789/91/93 (Br₂) | 0.15 | FM1 | (KBr): C=O 1622/1680 |
| 447 | N122 | N—H | AS4 | A0 | C1 | | 54 | ESI: (M + H)⁺ = 769/71/73 (Br₂) | 0.6 | FM1 | (KBr): C=O 1622/1682 |
| 448 | N122 | N—H | AS4 | A0 | C20 | | 68 | ESI: (M + H)⁺ = 788/90/92 (Br₂) | 0.5 | FM1 | (KBr): C=O 1620/1682 |
| 449 | N122 | N—H | AS4 | A0 | C8 | | 59 | ESI: (M + H)⁺ = 774/6/8 (Br₂) | 0.58 | FM1 | (KBr): C=O 1620/1682 |
| 450 | N66 | N—CH₃ | AS1 | A0 | C4 | | 36 | ESI: (M + H)⁺ = 753/5/7 (Br₂) | 0.39 | FM1 | (KBr): C=O 1653 |
| 451 | N66 | CH₂ | AS1 | A0 | C1 | | 20 | ESI: (M + H)⁺ = 739/41/43 (Br₂) | 0.3 | FM1 | (KBr): C=O 1638 |
| 452 | N71 | CH₂ | AS1 | A0 | C1 | | 16 | ESI: (M + H)⁺ = 751/53/55 (Br₂) | 0.4 | FM1 | (KBr): C=O 1638/1680 |
| 453 | N66 | CH₂ | AS1 | A0 | C11 | | 17 | ESI: (M + H)⁺ = 758/60/62 (Br₂) | 0.13 | FM1 | (KBr): C=O 1636 |
| 454 | N66 | CH₂ | AS1 | A0 | C20 | | 33 | ESI: (M + H)⁺ = 757/59/61 (Br₂) | 0.23 | FM1 | (KBr): C=O 1632 |
| 455 | N71 | CH₂ | AS1 | A0 | C8 | | 35 | EI: M⁺ = 755/7/9 (Br₂) | 0.42 | FM1 | (KBr): C=O 1624/1684 |
| 457 | N71 | CH₂ | AS1 | A0 | C4 | | 49 | ESI: (M + H)⁺ = 750/2/4 (Br₂) | 0.77 | FM1 | (KBr): C=O 1626/1682 |
| 458 | N71 | CH₂ | AS1 | A0 | C37 | | 25 | ESI: (M + H)⁺ = 769/71/73 (Br₂) | 0.2 | FM1 | (KBr): C=O 1638/1682 |
| 459 | N66 | CH₂ | AS1 | A0 | C37 | | 50 | EI: M⁺ = 757/59/61 (Br₂) | 0.2 | FM1 | (KBr): C=O 1636 |
| 460 | N66 | N—H | AS1 | A0 | C55 | | 72 | ESI: (M + H)⁺ = 759/61/63 (Br₂) | 0.27 | EE/MeOH/NH₄OH = 8/1.5/0.1 v/v/v | (KBr): C=O 1626/1661 |
| 461 | N66 | N—H | AS1 | A0 | C56 | | 77 | ESI: (M + H)⁺ = 731/3/5 (Br₂) | 0.77 | FM1 | (KBr): C=O 1626/1661 |

-continued

| No. | RCO | Z | R² | A | NR³R⁴ | Remarks | % Yield | MS | R_f | Eluant | IR [cm⁻¹] |
|---|---|---|---|---|---|---|---|---|---|---|---|
| 462 | N66 | N—H | AS17 | A0 | C8 | | 51 | ESI: (M + H)⁺ = 759/61/63 (Br₂) | 0.44 | FM1 | (KBr): C=O 1628/1663 |
| 463 | N66 | N—H | AS18 | A0 | C1 | | 59 | ESI: (M + H)⁺ = 704 | 0.7 | FM1 | (KBr): C=O 1661 |
| 464 | N66 | N—H | AS18 | A0 | C8 | | 51 | ESI: (M + H)⁺ = 709 | 0.76 | FM1 | (KBr): C=O 1628/1663 |
| 465 | N66 | N—H | AS18 | A0 | C37 | | 73 | ESI: (M + H)⁺ = 723 | 0.7 | FM1 | (KBr): C=O 1628/1663 |
| 469 | N66 | N—H | AS19 | A0 | C8 | | 34 | ESI: (M + H)⁺ = 651/53 (Br) | 0.34 | FM1 | (KBr): C=O 1626/1664 |
| 471 | N66 | N—H | AS20 | A0 | C8 | | 41 | ESI: (M + H)⁺ = 649 | 0.68 | FM1 | (KBr): C=O 1624/1684 |
| 472 | N66 | N—H | AS5 | A0 | C8 | | 26 | ESI: (M + H)⁺ = 729/31/33 (Br₂) | 0.73 | FM1 | (KBr): C=O 1626/1664 |
| 475 | N66 | N—H | AS18 | A0 | C20 | | 58 | ESI: (M + H)⁺ = 723 | 0.22 | FM1 | (KBr): C=O 1628/1664 |
| 476 | N66 | N—H | AS18 | A0 | C11 | | 44 | ESI: (M + H)⁺ = 724 | 0.27 | MeOH | (KBr): C=O 1630/1662 |
| 478 | N66 | N—H | AS19 | A0 | C37 | | 62 | ESI: (M + H)⁺ = 665/7 (Br) | 0.8 | FM1 | (KBr): C=O 1626/1662 |
| 479 | N66 | N—H | AS19 | A0 | C20 | | 55 | ESI: (M + H)⁺ = 665/7 (Br) | 0.64 | FM1 | (KBr): C=O 1664 |
| 480 | N66 | N—H | AS19 | A0 | C4 | | 55 | ESI: (M + H)⁺ = 645/7 (Br) | 0.77 | FM1 | (KBr): C=O 1628/1662 |
| 506 | N66 | N—H | AS21 | A0 | C20 | | 46 | ESI: (M + H)⁺ = 655 | 0.75 | FM1 | (KBr): C=O 1626/1664 |
| 507 | N66 | N—H | AS22 | A0 | C8 | | 65 | ESI: (M + H)⁺ = 607/9 (Cl) | 0.78 | FM1 | (KBr): C=O 1624/1664 |
| 508 | N66 | CH₂ | AS21 | A0 | C20 | | 15 | ESI: (M + H)⁺ = 654 | 0.15 | MeOH | (KBr): C=O 1639/1670 |
| 246 | N15 | CH₂ | AS1 | A0 | C8 | | 19 | ESI: (M + H)⁺ = 730/2/4 (Br₂) | 0.35 | EE/MeOH/ NH₄OH 9/1/0.5 v/v/v | (KBr): C=O 1635/1707 |
| 285 | N15 | CH₂ | AS1 | A0 | C4 | | 42 | ESI: (M + H)⁺ = 724/6/8 (Br₂) | 0.45 | EE/MeOH/ NH₄OH 9/1/0.5 v/v/v | (KBr): C=O 1684/1711 |
| 289 | N66 | CH₂ | AS1 | A0 | C8 | | 40 | ESI: (M + H)⁺ = 744/6/8 (Br₂) | 0.38 | EE/MeOH/ NH₄OH 9/1/0.5 v/v/v | (KBr): C=O 1635/1668 |
| 290 | N66 | CH₂ | AS1 | A0 | C4 | | 30 | ESI: (M + H)⁺ = 738/40/42 (Br₂) | 0.45 | EE/MeOH/ NH₄OH 9/1/0.5 v/v/v | (KBr): C=O 1634/1664 |
| 511 | N66 | N—H | AS23 | A0 | C8 | DMF | 80 | ESI: (M + H)⁺ = 603 | 0.57 | FM1 | (KBr): C=O 1664/1626 |
| 512 | N66 | N—H | AS23 | A0 | C11 | DMF | 60 | ESI: (M + H)⁺ = 618 | 0.30 | FM1 | (KBr): C=O 1645 |
| 513 | N66 | N—H | AS23 | A0 | C1 | DMF | 54 | ESI: (M + H)⁺ = 598 | 0.50 | FM1 | (KBr): C=O 1662/1712 |
| 514 | N66 | N—H | AS23 | A0 | C38 | DMF | 65 | ESI: (M + H)⁺ = 644 | 0.20 | FM1 | (KBr): C=O 1664/1626/ 1712 |
| 515 | N66 | N—H | AS23 | A0 | C40 | DMF | 7 | ESI: (M + H)⁺ = 632 | 0.40 | FM1 | (KBr): C=O 1630/1662 |
| 527 | N66 | N—H | AS25 | A0 | C8 | | 49 | ESI: (M + H)⁺ = 594 | 0.48 | FM1 | (KBr): C=O 1647 |
| 528 | N66 | N—H | AS25 | A0 | C1 | | 29 | ESI: (M + H)⁺ = 589 | 0.48 | FM1 | (KBr): C=O 1646 |
| 529 | N66 | CH₂ | AS2 | A0 | C8 | | 27 | ESI: (M + H)⁺ = 622 | 0.50 | FM1 | (KBr): C=O 1635/1668/ 1716 |
| 530 | N66 | CH₂ | AS2 | A0 | C20 | | 5 | EI: M⁺ = 635 | 0.49 | FM1 | (KBr): C=O 1637/1668/ 1714 |
| 531 | N66 | CH₂ | AS23 | A0 | C8 | | 30 | EI: M⁺ = 601 | 0.50 | FM1 | |
| | N66 | CH₂ | AS23 | | | | 95 | | | | |
| 538 | N139 | CH₂ | AS2 | A0 | C20 | | 49 | EI: M⁺ = 636 | 0.30 | FM1 | (KBr): C=O 1635/1674 |
| 539 | N139 | CH₂ | AS2 | A0 | C53 | | 52 | EI: M⁺ = 637 | 0.30 | FM1 | (KBr): C=O 1637/1674 |
| 540 | N139 | CH₂ | AS2 | A0 | C8 | | 60 | | 0.37 | FM1 | (KBr): C=O 1635/1674 |
| 541 | N66 | CH₂ | AS27 | A0 | C53 | | 32 | EI: M⁺ = 630 | 0.65 | FM1 | (KBr): C=O 1639/1670 |
| 542 | N66 | CH₂ | AS27 | A0 | C8 | | 32 | EI: M⁺ = 615 | 0.80 | FM1 | (KBr): C=O 1639/1670 |

-continued

| No. | RCO | Z | R² | A | NR³R⁴ | Remarks | % Yield | MS | R_f | Eluant | IR [cm⁻¹] |
|---|---|---|---|---|---|---|---|---|---|---|---|
| 543 | N66 | CH₂ | AS27 | A0 | C20 | | 21 | EI: M⁺ = 629 | 0.59 | FM1 | (KBr): C=O 1639/1672 |
| 544 | N66 | CH₂ | AS28 | A0 | C20 | | 35 | EI: M⁺ = 643 | 0.50 | FM1 | (KBr): C=O 1641/1670 |
| 545 | N66 | CH₂ | AS28 | A0 | C53 | | 54 | EI: M⁺ = 644 | 0.50 | FM1 | (KBr): C=O 1639/1670 |
| 546 | N66 | CH₂ | AS28 | A0 | C8 | | 53 | EI: M⁺ = 629 | 0.60 | FM1 | (KBr): C=O 1639/1672 |
| 547 | N66 | CH₂ | AS29 | A0 | C8 | | 14 | EI: M⁺ = 599 | 0.53 | FM1 | (KBr): C=O 1630 |
| 548 | N66 | CH₂ | AS29 | A0 | C53 | | 12 | EI: M⁺ = 614 | 0.48 | FM1 | |
| 549 | N66 | CH₂ | AS29 | A0 | C20 | | 15 | EI: M⁺ = 613 | 0.48 | FM1 | (KBr): C=O 1637/1668 |
| 550 | N66 | CH₂ | AS30 | A0 | C53 | | 4 | | 0.48 | FM1 | |
| 574 | N66 | CH₂ | AS16 | A0 | C20 | | 55 | EI: M⁺ = 653/5/7 (Cl₂) | 0.80 | CH₂Cl₂/MeOH/NH₄OH 80/20/1 | (KBr): C=O 1635/1670 |
| 575 | N66 | CH₂ | AS16 | A0 | C53 | | 54 | EI: M⁺ = 654/6/8 (Cl₂) | 0.20 | EE/MeOH/NH₄OH 70/30/3 | (KBr): C=O 1635/1668 |
| 578 | N66 | CH₂ | AS5 | A0 | C53 | | 32 | EI: M⁺ = 742/4/6 (Br₂) | 0.30 | FM5 | (KBr): C=O 1637/1670 |
| 579 | N66 | CH₂ | AS5 | A0 | C20 | | 37 | EI: M⁺ = 741/3/5 (Br₂) | 0.50 | FM5 | (KBr): C=O 1635/1670 |
| 589 | N66 | CH₂ | AS32 | A0 | C53 | | 49 | EI: M⁺ = 756/58/60 (Br₂) | 0.33 | FM5 | (KBr): C=O 1639/1670 |
| 590 | N66 | CH₂ | AS32 | A0 | C20 | | 36 | EI: M⁺ = 755/7/9 (Br₂) | 0.47 | FM5 | (KBr): C=O 1658/1672 |
| 591 | N66 | CH₂ | AS33 | A0 | C20 | | 43 | EI: M⁺ = 689 | 0.40 | EE/MeOH/NH₄OH 50/50/0.5 | (KBr): C=O 1637/1670 |
| 592 | N66 | CH₂ | AS33 | A0 | C53 | | 52 | EI: M⁺ = 690 | 0.20 | EE/MeOH/NH₄OH 70/30/5 | (KBr): C=O 1633/1668 |
| 593 | N66 | CH₂ | AS16 | A0 | C29 | | 11 | EI: M⁺ = 628/30/32 (Cl₂) | 0.65 | EE/MeOH 9/1 | (KBr): C=O 1606/1637/1668/1728 |
| 594 | N66 | CH₂ | AS16 | A0 | C73 | | 48 | EI: M⁺ = 628/30/32 (Cl₂) | 0.50 | EE/MeOH 9/1 | (KBr): C=O 1637/1668/1736 |
| 595 | N66 | CH₂ | AS16 | A0 | C74 | | 10 | EI: M⁺ = 597/99/601 (Cl₂) | 0.30 | EE/MeOH/NH₄OH 50/50/0.5 | |
| 597 | N66 | CH₂ | AS31 | A0 | C53 | | 25 | EI: M⁺ = 639 | 0.30 | CH₂Cl₂/MeOH/NH₄OH 90/10/1 | (KBr): C=O 1635/1668 |
| 598 | N66 | CH₂ | AS31 | A0 | C20 | | 31 | EI: M⁺ = 638 | 0.10 | CH₂Cl₂/MeOH/NH₄OH 90/10/0.3 | (KBr): C=O 1635/1668 |
| 600 | N73 | CH₂ | AS31 | A0 | C20 | | 10 | ESI: (M + H)⁺ = 551 | 0.15 | CH₂Cl₂/MeOH/NH₄OH 90/10/1 | (KBr): C=O 1628 |
| 602 | N66 | CH₂ | AS17 | A0 | C53 | | 56 | EI: M⁺ = 772/4/6 (Br₂) | 0.25 | EE/MeOH/NH₄OH 50/50/0.5 | (KBr): C=O 1637/1668 |
| 603 | N66 | CH₂ | AS16 | A0 | C33 | | 93 | EI: M⁺ = 600/02/04 (Br₂) | 0.75 | EE/MeOH/AcOH 70/30/1 | (KBr): C=O 1635/1716 |
| 604 | N66 | CH₂ | AS17 | A0 | C20 | | 47 | EI: M⁺ = 771/3/5 (Br₂) | 0.20 | EE/MeOH/NH₄OH 50/50/0.5 | (KBr): C=O 1635/1668 |
| 605 | N66 | CH₂ | AS34 | A0 | C53 | | 70 | EI: M⁺ = 672 | 0.25 | EE/MeOH/NH₄OH 60/40/0.5 | (KBr): C=O 1633/1666 |
| 606 | N66 | CH₂ | AS34 | A0 | C20 | | 45 | EI: M⁺ = 671 | 0.15 | EE/MeOH/NH₄OH 50/50/0.5 | (KBr): C=O 1635/1668 |
| 607 | N66 | N—H | AS21 | A0 | C40 | | 27 | ESI: (M + H)⁺ = 670 | 0.65 | FM1 | (KBr): C=O 1608/1628/1664 |

-continued

| No. | RCO | Z | R² | A | NR³R⁴ | Remarks | % Yield | MS | R_f | Eluant | IR [cm⁻¹] |
|---|---|---|---|---|---|---|---|---|---|---|---|
| 608 | N66 | N—H | AS21 | A0 | C11 | | 34 | ESI: (M + H)⁺ = 656 | 0.50 | FM1 | (KBr): C═O 1606/1628/1664 |
| 609 | N66 | N—H | AS21 | A0 | C8 | | 30 | ESI: (M + H)⁺ = 641 | 0.80 | FM1 | (KBr): C═O 1626/1664 |
| 610 | N66 | N—H | AS21 | A0 | C1 | | 55 | ESI: (M + H)⁺ = 636 | 0.80 | FM1 | (KBr): C═O 1635/1662 |
| 611 | N66 | N—H | AS21 | A0 | C4 | | 80 | ESI: (M + H)⁺ = 635 | 0.70 | FM1 | (KBr): C═O 1606/1628/1664 |
| 612 | N66 | CH₂ | AS4 | A0 | C8 | | 43 | EI: M⁺ = 742/4/6 (Br₂) | 0.85 | FM1 | (KBr): C═O 1668/1631/1606 |
| 613 | N66 | N—H | AS22 | A0 | C20 | | 62 | ESI: (M + H)⁺ = 621/23 (Cl) | 0.73 | FM1 | (KBr): C═O 1626/1664 |
| 614 | N66 | N—H | AS22 | A0 | C37 | | 55 | ESI: (M + H)⁺ = 621/23 (Cl) | 0.68 | FM1 | (KBr): C═O 1626/1664 |
| 615 | N66 | N—H | AS22 | A0 | C56 | | 77 | ESI: (M + H)⁺ = 593 | 0.76 | FM1 | (KBr): C═O 1628/1664 |
| 616 | N66 | CH₂ | AS36 | A0 | C8 | | 32 | ESI: (M + H)⁺ = 585 | 0.76 | FM1 | (KBr): C═O 1637/1668 |
| 617 | N66 | CH₂ | AS21 | A0 | C37 | | 15 | EI: M⁺ = 653 | 0.15 | MeOH | (KBr): C═O 1639/1670 |
| 618 | N66 | CH₂ | AS21 | A0 | C38 | | 24 | EI: M⁺ = 680 | 0.10 | MeOH | (KBr): C═O 1639/1670 |
| 628 | N66 | CH₂ | AS21 | A0 | C8 | | 31 | EI: M⁺ = 639 | 0.25 | MeOH | (KBr): C═O 1639/1670 |
| 629 | N66 | CH₂ | AS21 | A0 | C11 | | 43 | EI: M⁺ = 654 | 0.10 | MeOH | (KBr): C═O 1641/1668 |
| 630 | N66 | CH₂ | AS21 | A0 | C1 | | 74 | EI: M⁺ = 634 | 0.10 | MeOH | (KBr): C═O 1641/1668 |
| 631 | N66 | CH₂ | AS21 | A0 | C28 | | 63 | EI: M⁺ = 614 | 0.30 | MeOH | (KBr): C═O 1666 |
| 634 | N66 | CH₂ | AS38 | A0 | C8 | | 35 | ESI: (M + H)⁺ = 622 | 0.25 | MeOH | (KBr): C═O 1635/1668 |
| 635 | N66 | CH₂ | AS48 | A0 | C8 | | 40 | EI: M⁺ = 639 | 0.68 | FM1 | (KBr): C═O 1643/1670 |
| 636 | N66 | N—H | AS49 | A0 | C20 | | 25 | ESI: (M + H)⁺ = 632 | 0.40 | EE/MeOH/NH₄OH 9/1/0.5 | (KBr): C═O 1664 |
| 637 | N66 | CH₂ | AS4 | A0 | C20 | | 11 | ESI: (M + H)⁺ = 757/59/61 (Br₂) | 0.60 | FM1 | (KBr): C═O 1635/1668 |
| 638 | N66 | CH₂ | AS48 | A0 | C20 | | 11 | ESI: (M + H)⁺ = 654 | 0.66 | FM1 | (KBr): C═O 1641/1668 |
| 639 | N66 | CH₂ | AS18 | A0 | C20 | | 4 | EI: M⁺ = 721 | 0.10 | MeOH | (KBr): C═O 1637/1670 |
| 640 | N66 | CH₂ | AS39 | A0 | C20 | | 38 | EI: M⁺ = 645 | 0.80 | CH₂Cl₂/MeOH/NH₄OH 8/2/0.3 | (KBr): C═O 1635/1670 |
| 641 | N66 | CH₂ | AS38 | A0 | C20 | | 49 | EI: M⁺ = 635 | 0.80 | CH₂Cl₂/MeOH/NH₄OH 8/2/0.3 | (KBr): C═O 1635/1668 |
| 642 | N66 | CH₂ | AS39 | A0 | C8 | | 45 | EI: M⁺ = 631 | 0.10 | EE/MeOH/NH₄OH 9/1/0.3 | (KBr): C═O 1635/1670 |
| | N66 | CH₂ | AS21 | A0 | C69 | | 70 | EI: M⁺ = 739 | | | (KBr): C═O 1684 |
| 644 | N109 | CH₂ | AS21 | A0 | C20 | | 46 | ESI: (M + H)⁺ = 659 | 0.10 | MeOH | (KBr): C═O 1643 |
| 645 | N66 | CH₂ | AS19 | A0 | C20 | | 21 | EI: M⁺ = 763/5 (Br) | 0.53 | FM1 | (KBr): C═O 1669/1634 |
| 646 | N66 | CH₂ | AS19 | A0 | C8 | | 45 | EI: M⁺ = 649/651 (Br) | 0.60 | FM1 | (KBr): C═O 1637/1668 |
| 653 | N113 | CH₂ | AS21 | A0 | C20 | | 55 | EI: M⁺ = 666 | 0.60 | FM1 | (KBr): C═O 1630/1701 |
| 654 | N134 | CH₂ | AS21 | A0 | C20 | | 22 | EI: M⁺ = 690 | 0.60 | FM1 | (KBr): C═O 1714 |
| 655 | N66 | CH₂ | AS46 | A0 | C20 | | 43 | EI: M⁺ = 636 | 0.50 | FM1 | (KBr): C═O 1630/1664 |
| 656 | N66 | CH₂ | AS46 | A0 | C8 | | 71 | EI: M⁺ = 622 | 0.60 | FM1 | (KBr): C═O 1635 |

-continued

| No. | RCO | Z | R² | A | NR³R⁴ | Remarks | % Yield | MS | $R_f$ | Eluant | IR [cm⁻¹] |
|---|---|---|---|---|---|---|---|---|---|---|---|
| 657 | N66 | CH₂ | AS47 | A0 | C20 | | 63 | EI: M⁺ = 639 | 0.50 | FM1 | (KBr): C=O 1635/1668/1716 |
| 658 | N66 | CH₂ | AS50 | A0 | C20 | | 70 | ESI: (M + H)⁺ = 741/3/5 (Br₂) | 0.20 | EE/MeOH/ NH₄OH 50/50/0.5 | (KBr): C=O 1635/1668 |
| 659 | N66 | CH₂ | AS50 | A0 | C53 | | 60 | ESI: (M + H)⁺ = 743/5/7 (Br₂) | 0.20 | EE/MeOH/ NH₄OH 50/50/0.5 | (KBr): C=O 1635/1668 |
| 660 | N66 | CH₂ | AS46 | A0 | C53 | | 41 | EI: M⁺ = 637 | 0.65 | FM1 | (KBr): C=O 1630 |
| 661 | N66 | CH₂ | AS7 | A0 | C8 | | 75 | EI: M⁺ = 615 | 0.70 | FM1 | (KBr): C=O 1626/1660 |
| 662 | N66 | CH₂ | AS7 | A0 | C53 | | 41 | EI: M⁺ = 630 | 0.55 | FM1 | (KBr): C=O 1628/1662 |
| 663 | N66 | CH₂ | AS7 | A0 | C20 | | 78 | EI: M⁺ = 629 | 0.60 | FM1 | (KBr): C=O 1628/1662 |
| 664 | N66 | CH₂ | AS52 | A0 | C8 | | 66 | EI: M⁺ = 629 | 0.75 | FM1 | (KBr): C=O 1635 |
| 665 | N66 | CH₂ | AS52 | A0 | C53 | | 37 | EI: M⁺ = 644 | 0.70 | FM1 | (KBr): C=O 1633/1664 |
| 666 | N66 | CH₂ | AS52 | A0 | C20 | | 61 | EI: M⁺ = 643 | 0.80 | FM1 | (KBr): C=O 1635/1664 |
| 667 | N66 | CH₂ | AS2 | A0 | C53 | | 47 | EI: M⁺ = 636 | 0.60 | FM1 | (KBr): C=O 1630/1664 |
| | N66 | CH₂ | AS2 | A0 | C69 | | 78 | | 0.75 | FM1 | |
| 669 | N66 | CH₂ | AS32 | A0 | C71 | | 44 | EI: M⁺ = 834/6/8 (Br₂) | 0.20 | EE/MeOH/ NH₄OH 50/50/0.5 | (KBr): C=O 1641/1670 |
| 670 | N66 | CH₂ | AS51 | A0 | C20 | Preliminary stage special cases | 47 | EI: M⁺ = 641 | 0.15 | EE/MeOH/ NH₄OH 50/50/0.5 | (KBr): C=O 1635/1664 |
| 671 | N66 | CH₂ | AS51 | A0 | C53 | | 45 | EI: M⁺ = 642 | 0.15 | EE/MeOH/ NH₄OH 50/50/0.5 | (KBr): C=O 1637/1670 |
| 672 | N66 | CH₂ | AS16 | A0 | C76 | | 55 | EI: M⁺ = 689/91/93 (Cl₂) | 0.66 | FM1 | (KBr): C=O 1635 |

EXAMPLE 2

Preparation of Compounds of GeneralFormula:

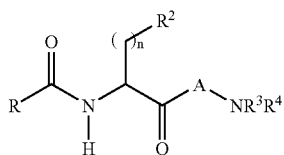

1-[N²-[4-amino-N-[[4-(2-chlorophenyl)-1-piperazinyl]-carbonyl]-3,5-dibromo-D-phenylalanyl]-L-lysyl]-4-(4-pyridinyl)piperazine-bis-(trifluoroacetate) (No. 61)

A mixture of 0.56 g (1.0 mmol) of 4-amino-N²-[[4-(2-chlorophenyl)-nyl]-1-piperazinyl]carbonyl]-3.5-dibromo-D-phenylalanine, 0.41 g (1.05 mmol) of 1-[N⁶-(1.1-dimethylethoxycarbonyl)-L-lysyl]-4-(4-pyridinyl)piperazine, 0.35 g (1.10 mmol) of TBTU, 0.14 g (1.0 mmol) of HOBt, 0.2 ml (1.10 mmol) of DIEA and 100 ml of dimethylformamide was stirred overnight at ambient temperature. The reaction mixture was evaporated down in vacuo and divided between methylene chloride and saturated aqueous sodium hydrogen carbonate solution. The organic phase was then extracted once with saturated aqueous sodium hydrogen carbonate solution and with water, dried and evaporated down in vacuo. The crude product was purified by column chromatography (MN-silica gel 60, Macherey-Nagel, 70-230 mesh ASTM, eluant:ethyl acetate/methanol=8/2 (v/v/)), taken up in 30 ml of methylene chloride and stirred with 3 ml of trifluoroacetic acid for 3 hours at ambient temperature. The reaction mixture was evaporated down in vacuo, the residue was triturated with ether and the obtained amorphous solid (0.43 g, 37% of theory) was suction filtered.

IR (KBr): 1643, 1678 cm⁻¹ (C=O)

$R_f$: 0.6 (FM1)

ESI-MS: (M+H)⁺=832/834/836/838 (Br₂, Cl)

The following were prepared analogously (in each case n=1):

| No. | RCO | R² | A | NR³R⁴ | % Yield | MS | $R_f$ | Eluant | IR [cm⁻¹] |
|---|---|---|---|---|---|---|---|---|---|
| 48 | N6 | AS1 | A1 | C3 | 79 | ESI: M + H = 946/48/50 (Br₂) | 0.3 | FM1 | (KBr): C=O 1652.9; 1674.1 |
| 213 | N15 | AS6 | A1 | C8 | 14.7 | ESI: M + H = 781/3 (Br) | 0.45 | FM2 | (KBr): C=O 1691.5; 1629.8 |
| 49 | N8 | AS4 | A1 | C1 | 57.14 | ESI: M + H = 757/59/61 (Br₂) | 0.5 | FM1 | (KBr): C=O 1643.3; 1676.0 |
| 58 | N15 | AS4 | A1 | C4 | 21 | ESI: M + H = 852/4/6 (Br₂) | 0.57 | FM1 | (KBr): C=O 1635.5; 1695.3 |
| 59 | N15 | AS4 | A1 | C1 | 45.6 | ESI: M + H = 853/5/7 (Br₂) | 0.44 | FM1 | (KBr): C=O 1635.5; 1695.3 |
| 60 | N23 | AS4 | A1 | C4 | 19.2 | ESI: M + H = 831/3/5/7 (Br₂, Cl) | 0.65 | FM1 | (KBr): C=O 1633.6 |
| 61 | N23 | AS4 | A1 | C1 | 36.6 | ESI: M + H = 832/4/6/8 (Br₂, Cl) | 0.6 | FM1 | (KBr): C=O 1643.3; 1678.0 |

EXAMPLE 3

Preparation of Compounds of General Formula:

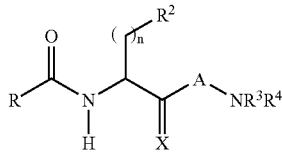

1-[$N^2$-[3,5-dibromo-N-[[[(2-methoxyphenyl)methyl]amino]-carbonyl]-D,L-tyrosyl]-$N^6$-(phenylmethoxycarbonyl)-L-lysyl]-4-(4-pyridinyl)-piperazine A tetrahydrofuran solution (50 ml) of 1.0 g (1.34 mmol) of 1-[$N^2$-(3,5-dibromo-D-tyrosyl)-$N^6$-(phenylmethoxycarbonyl)-L-lysyl]-4-(4-pyridinyl)-piperazine was added dropwise over a period of 40 minutes to a suspension of 0.33 g (2.01 mmol) of CDT in 50 ml of tetrahydrofuran cooled to $-10\,°$C. and stirred. The reaction mixture was then stirred for 2 hours at ambient temperature and mixed with 0.22 ml (1.675 mmol) of 2-methoxy-benzenemethanamine. Then the mixture was refluxed for 2 hours and stirred overnight at ambient temperature. The reaction mixture was evaporated down in vacuo, the residue was triturated with ether and the solid obtained (1.1 g; 90% of theory) was suction filtered and dried.

| IR (KBr): | 1641, 1717 cm⁻¹ (C=O) |
|---|---|
| ESI-MS: | (M + H)⁺ = 908/910/912 (Br₂) |
| | (M + H + Na)⁺⁺ = 466.7 (Br₂) |

The following were prepared analogously:

| No. | RCO | R² | n | X | A | NR³R⁴ | Remarks | % Yield | MS | $R_f$ | Eluant | IR [cm⁻¹] | Mp. (° C.) |
|---|---|---|---|---|---|---|---|---|---|---|---|---|---|
| 195 | N15 | AS1 | 1 | O | A2 | C8 | | 21 | ESI: (M + H)⁺ = 959/61/63 (Br₂) | 0.8 | FM7 | (KBr): C=O 1699.2; 1635.5 | |
| 196 | N51 | AS1 | 1 | O | A2 | C8 | | 26; 1 | ESI: (M + H)⁺ = 929/31/33 (Br₂) | 0.85 | FM7 | (KBr): C=O 1710; CN 2219.8 | |
| 201 | N101 | AS4 | 1 | O | A0 | C8 | DIEA | 34 | ESI: (M + H)⁺ = 746/8/50 (Br₂) | 0.58 | FM1 | (KBr): C=O 1693.4; 1618.2 | |
| 215 | N15 | AS1 | 1 | O | A0 | C34 | NEt₃ as base | 92 | ESI: (M − H)⁻ = 778/80/82 (Br₂) | 0.36 | FM1 | (KBr): C=O 1695.3 | |
| 216 | N15 | AS1 | 1 | O | A0 | C35 | NEt₃ as base | 69 | ESI: (M − H)⁻ = 779/81/82 (Br₂) | 0.3 | FM1 | (KBr): C=O 1701.1 | |
| 221 | N15 | AS4 | 1 | O | A2 | C1 | NEt₃ as base | 39 | ESI: (M + H)⁺ = 881/3/5 (Br₂) | 0.38 | FM1 | (KBr): C=O 1697.3; 1637.5 | |
| 288 | N85 | AS1 | 1 | O | A0 | C8 | THF/DMF as solvent; NEt₃ as base | 30 | ESI: (M + H)⁺ = 749/51/53 (Br₂) | 0.3 | MeOH | (KBr): C=O 1683.8; 1624.0; OH 3429.2 | |

-continued

| No. | RCO | R² | n | X | A NR³R⁴ | Remarks | % Yield | MS | R_f | Eluant | IR [cm⁻¹] | Mp. (° C.) |
|---|---|---|---|---|---|---|---|---|---|---|---|---|
| 293 | N66 | AS1 | 1 | O | A9C1 | DIEA | 11 | ESI: (M + H)⁺ = 910/2/4 (Br₂) | 0.4 | FM1 | (KBr): C=O 1645.2 | |
| 295 | N66 | AS1 | 1 | O | A7C1 | NEt₃ as base | 70 | ESI: (M + H)⁺ = 896/8/900 (Br₂) | 0.45 | FM1 | (KBr): C=O 1716.5; 1647.1 | |
| 303 | N86 | AS4 | 1 | O | A0C8 | DIEA | 20 | ESI: (M + H)⁺ = 747/9/51 (Br₂) | 0.7 | FM 2 | (KBr): C=O 1618.2 | |
| 304 | N87 | AS4 | 1 | O | A0C8 | THFas solvent; NEt₃ as base | 30 | ESI: (M + H)⁺ = 802/4/6 (Br₂) | 0.75 | FM1 | (KBr): C=O 1720.4; 1668.3; 1620.1; NH, NH2 3431.2; 3379.1 | |
| 305 | N88 | AS4 | 1 | O | A0C8 | DIEA | 45 | ESI: (M + H)⁺ = 782/4/6 (Br₂) | 0.6 | FM1 | (KBr): C=O 1616; SO2 1323.1; 1151.4 | |
| 308 | N90 | AS4 | 1 | O | A0C8 | DIEA | 27 | ESI: (M + H)⁺ = 750/2/4 (Br₂) | 0.5 | FM1 | (KBr): C=O 1637.5 | |
| 80 | N15 | AS1 | 1 | O | A3C1 | | 62 | ESI: (M + H)⁺ = 954/6/8 (Br₂) | 0.8 | FM2 | (KBr): C=O 1697.3; 1639.4 | |
| | N8 | AS1 | 1 | O | A3C1 | | 66 | ESI: (M + H)⁺ = 858/60/62 (Br₂) | 0.22 | EtOAc/ methanol = 6/4 (v/v) | (KBr): C=O 1641.3 | |
| | N9 | AS1 | 1 | O | A3C1 | | 59 | ESI: (M + H)⁺ = 888/90/92 (Br₂) | 0.22 | EtOAc/ methanol = 6/4 (v/v) | (KBr): C=O 1652.9 | |
| | N2 | AS1 | 1 | O | A4C1 | | 40 | ESI: (M + H)⁺ = 922/4/6 (Br₂); (M + Na)⁺= 944/6/8 (Br₂) | 0.45 | FM1 | (KBr): C=O 1641.3; 1710.8; OH, NH 3396.4 | |
| | N4 | AS1 | 1 | O | A4C1 | | 73 | ESI: (M + H)⁺ = 952/4/6 (Br₂) | 0.13 | FM1 | (KBr): C=O 1641.3; 1714.6 | |
| 62 | N15 | AS1 | 1 | O | A3C5 | purified by column chromatography: silica gel/FM4 | 65 | ESI: (M + H)⁺ = 1003/5/7 (Br₂); (M + Na)⁺= 1025/7/9 (Br₂) | 0.27 | FM1 | (KBR): C=O 1685.7; 1635.5; OH, NH: 3419.6 | |
| | N15 | AS1 | 1 | O | A3C6 | purified by column chromatography: silica gel/FM4 | 86 | ESI: (M + H)⁺ = 983/5/7 (Br₂) | 0.45 | FM1 | (KBr): C=O 1695.3; 1633.6 | |
| 73 | N15 | AS5 | 1 | O | A3C1 | purified by column chromatography: silica gel/FM4; diastereomers | 64 | ESI: (M + H)⁺ = 938/40/42 (Br₂) | 0.75 | FM1 | (KBr): C=O 1699.2; 1641.3 | |
| 78 | N45 | AS5 | 1 | O | A3C1 | purified by column chromatography: silica gel/FM4; diastereomers | 44 | ESI: (M + H)⁺ = 952/4/6 (Br₂) | 0.73 | FM1 | (KBr): C=O 1712.7, 1637.5; —NH— 3300.0 | |
| 110 | N15 | AS4 | 1 | O | A0C5 | purified by column chromatography: silica gel/FM4 | 82 | ESI: (M + H)⁺ = 725/7/9 (Br₂) | 0.79 | FM1 | (KBr): C=O 1620.1; 1514.0 | |
| 111 | N15 | AS4 | 1 | O | A0C15 | purified by column chromatography: silica gel/FM4 | 58 | ESI: M⁺ = 726/28/30 (Br₂) | 0.77 | FM1 | (KBr): C=O 1697.3; 1620.1 | |
| 114 | N45 | AS4 | 1 | O | A0C5 | purified by column | 75 | ESI: (M + H)⁺ = 739/41/43 (Br₂) | 0.78 | FM1 | (KBr): C=O 1710.8; | |

-continued

| No. | RCO | R² | n | X | A NR³R⁴ | Remarks | % Yield | MS | R_f | Eluant | IR [cm⁻¹] | Mp. (° C.) |
|---|---|---|---|---|---|---|---|---|---|---|---|---|
| 112 | N15 | AS1 | 1 | O | A(C5 | purified by column chromatography: silica gel/FM4 | 45 | ESI: (M + H)⁺ = 726/28/30 (Br₂) | 0.33 | FM1 | (KBr): C=O 1620.1 1695.3; 1624.0 | |
| 115 | N45 | AS1 | 1 | O | A(C5 | purified by column chromatography: silica gel/FM4 | 28 | ESI: (M + H)⁺ = 740/2/4 (Br₂) | 0.35 | FM1 | (KBr): C=O 1710.8; 1622 | |
| 113 | N15 | AS4 | 1 | O | A(C16 | purified by column chromatography: silica gel/FM4 | 56 | ESI: (M + H)⁺ = 726/8/30 (Br₂) | 0.68 | FM1 | (KBr): C=O 1699.2; 1618.2 | 173-176 |
| 119 | N45 | AS4 | 1 | O | A(C16 | purified by column chromatography: silica gel/FM4 | 81 | ESI: (M + H)⁺ = 762/4/6 (Br₂) | 0.69 | FM1 | (KBr): C=O 1710.8; 1618.2 | 148-152 |
| 120 | N15 | AS1 | 1 | O | A(C15 | purified by column chromatography: silica gel/FM4 | 27 | ESI: (M + H)⁺ = 749/51/53 (Br₂) | 0.31 | FM1 | (KBr): C=O 1695.3 | 173-175 |
| 128 | N15 | AS4 | 1 | O | A(C3 | purified by column chromatography: silica gel/FM4 | 61 | ESI: (M + Na)⁺ = 764/6/8 (Br₂) | 0.72 | FM1 | (KBr): C=O 1699.2; 1618.2 | 174-177 |
| 130 | N15 | AS4 | 1 | O | A(C6 | purified by column chromatography: silica gel/FM4 | 60 | ESI: (M + H)⁺ = 754/6/8 (Br₂) | 0.7 | FM1 | (KBr): C=O 1703; 1620.1 | 150-154 |
| 129 | N15 | AS1 | 1 | O | A(C16 | purified by column chromatography: silica gel/FM4 | 18 | ESI: (M − H)⁻ = 725/7/9 (Br₂) | 0.27 | FM1 | (KBr): C=O 1693.4; 1627.8 | 173-176 |
| 131 | N45 | AS4 | 1 | O | A(C6 | purified by column chromatography: silica gel/FM4 | 69 | ESI: (M + H)⁺ = 768/70/72 (Br₂) | 0.73 | FM1 | (KBr): C=O 1712.7; 1620.1 | 159-162 |
| 132 | N45 | AS4 | 1 | O | A(C3 | purified by column chromatography: silica gel/FM4 | 27 | ESI: (M + Na)⁺ = 778/80/2 (Br₂) | 0.72 | FM1 | (KBr): C=O 1712.7; 1618.2 | 142-146 |
| 133 | N15 | AS1 | 1 | O | A(C6 | purified by column chromatography: silica gel/FM4 | 24 | ESI: (M + H)⁺ = 755/7/9 (Br₂) | 0.33 | FM1 | (KBr): C=O 1697.3; 1624.0 | 161-164 |
| 134 | N15 | AS4 | 1 | O | A(C18 | purified by column chromatography: silica gel/FM4 | 69 | ESI: (M + H)⁺ = 756/8/60 (Br₂) | 0.59 | FM1 | (KBr): C=O 1699.2; 1618.2 | 171-174 |
| 135 | N15 | AS1 | 1 | O | A(C18 | Purified by column chromatography: silica gel/FM4 | 17 | ESI: (M + H)⁺ = 757/9/61 (Br₂) | 0.25 | FM1 | (KBr): C=O 1691.5; 1625.9 | 74-77 |
| | N29 | AS1 | 1 | O | A)C1 | | 61 | ESI: (M + H)⁺ = 903/5/7 (Br₂) | 0.62 | FM7 | (KBr): C=O 1641.3 | |
| | N36 | AS1 | 1 | O | A)C1 | | 33 | ESI: (M + H)⁺ = 915/7/9 (Br₂) | 0.49 | FM7 | (KBr): C=O 1641.3 | |
| 44 | N34 | AS1 | 1 | O | A)C1 | | 35 | ESI: (M + H)⁺ = 936/38/40/42 (Br₃) | 0.3 | FM1 | (KBr): C=O 1641.3 | |

-continued

| No. | RCO | R² | n | X | A NR³R⁴ | Remarks | % Yield | MS | R_f | Eluant | IR [cm⁻¹] | Mp. (° C.) |
|---|---|---|---|---|---|---|---|---|---|---|---|---|
| 378 | N15 | AS1 | 0 | O | A3C1 | | 30 | ESI: (M + H)⁺ = 940/2/4 (Br₂) | 0.13 | FM1 | (KBr): C=O 1701.1; 1641.3 | |
| | N48 | AS1 | 1 | O | A3C1 | | 52 | | 0.58 | FM7 | (KBr): C=O 1641.3 | |
| | N77 | AS1 | 1 | O | A3C4 | | 32 | ESI: (M + H)⁺ = 955/7/9 (Br₂) | | | (KBr): C=O 1645; 1713 | |
| 294 | N66 | AS4 | 1 | O | A7C1 | NEt₃ as base | 31 | ESI: (M + H)⁺ = 895/7/9 (Br₂) | 0.3 | FM1 | (KBr): C=O 1653; 1772.5; 1716.5 | |
| 323 | N104 | AS1 | 1 | O | A0C4 | DIEA | 18 | ESI: (M + H)⁺ = 799/801/803 (Br₂) | 0.4 | FM1 | (KBr): C=O 1624 | |
| 324 | N105 | AS1 | 1 | O | A0C4 | DIEA | 24 | ESI: (M + H)⁺ = 773/5/7/9 (Br₂/Cl) | 0.38 | FM1 | (KBr): C=O 1624/1667 | |
| 325 | N106 | AS1 | 1 | O | A0C4 | DIEA | 22 | ESI: (M + H)⁺ = 725/7/9 (Br₂) | 0.35 | FM1 | (KBr): C=O 1626/1662.5 | |
| 326 | N71 | AS1 | 1 | O | A0C1 | DIEA | 20 | ESI: (M + H)⁺ = 752/4/6 (Br₂) | 0.16 | FM1 | (KBr): C=O 1624/1680 | |
| 327 | N71 | AS4 | 1 | O | A0C4 | DIEA | 24 | ESI: (M + H)⁺ = 750/2/4 (Br₂) | 0.48 | FM1 | (KBr): C=O 1618/1682 | |
| 328 | N107 | AS1 | 1 | O | A0C4 | DIEA | 17 | ESI: (M + H)⁺ = 769/71/73 (Br₂) | 0.38 | FM1 | (KBr): C=O 1651 | |
| 329 | N108 | AS4 | 1 | O | A0C4 | DIEA | 16 | ESI: (M + H)⁺ = 781/83/85 (Br₂) | 0.31 | FM1 | (KBr): C=O 1620/1674 | |
| 330 | N108 | AS4 | 1 | O | A0C1 | DIEA/DMF | 15 | ESI: (M + H)⁺ = 781/83/85 (Br₂) | 0.45 | FM1 | (KBr): C=O 1620/1678 | |
| 331 | N108 | AS4 | 1 | O | A0C20 | DIEA/DMF | 15 | ESI: (M + H)⁺ = 800/802/804 (Br₂) | 0.4 | FM1 | (KBr): C=O 1616/1680 | |
| 332 | N109 | AS1 | 1 | O | A0C4 | DIEA/DMF | 39 | ESI: (M + H)⁺ = 745/7/9 (Br₂) | 0.32 | FM1 | (KBr): C=O 1665 | |
| 333 | N110 | AS1 | 1 | O | A0C4 | DIEA/DMF | 52 | ESI: (M + H)⁺ = 745/7/9 (Br₂) | 0.34 | FM1 | (KBr): C=O 1636 | |
| 334 | N111 | AS14 | 1 | O | A0C1 | DIEA/DMF | 18 | ESI: (M + H)⁺ = 649 | 0.5 | FM1 | (KBr): C=O 1626/1688 | |
| 335 | N109 | AS4 | 1 | O | A0C4 | DIEA/DMF | 46 | ESI: (M + H)⁺ = 744/6/8 (Br₂) | 0.47 | FM1 | (KBr): C=O 1618 | |
| 336 | N110 | AS1 | 1 | O | A0C8 | DIEA/DMF | 25 | ESI: (M + H)⁺ = 751/3/5 (Br₂) | 0.22 | FM1 | (KBr): C=O 1645 | |
| 337 | N109 | AS1 | 1 | O | A0C8 | DIEA/DMF | 32 | ESI: (M + H)⁺ = 751/3/5 (Br₂) | 0.21 | FM1 | (KBr): C=O 1645 | |
| 338 | N109 | AS4 | 1 | H2 | A0C8 | DIEA/DMF | 38 | ESI: (M + H)⁺ = 736/8/40 (Br₂) | 0.44 | FM1 | (KBr): C=O 1653 | |
| 339 | N110 | AS4 | 1 | H2 | A0C8 | DIEA/DMF | 39 | ESI: (M + H)⁺ = 736/8/40 (Br₂) | 0.44 | FM1 | (KBr): C=O 1653 | |
| 340 | N66 | AS1 | 1 | O | A0C20 | DIEA/DMF | 33 | ESI: (M + H)⁺ = 759/61/63 (Br₂) | 0.12 | FM1 | (KBr): C=O 1618/1657 | |
| 341 | N71 | AS1 | 1 | O | A0C20 | DIEA/DMF | 31 | ESI: (M + H)⁺ = 771/3/5 (Br₂) | 0.1 | FM1 | (KBr): C=O 1620/1680 | |
| 342 | N112 | AS4 | 1 | O | A0C20 | DIEA/DMF | 27 | ESI: (M + H)⁺ = 776/8/80 (Br₂) | 0.47 | FM1 | (KBr): C=O 1618/1682 | |
| 343 | N112 | AS1 | 1 | O | A0C20 | DIEA/DMF | 26 | ESI: (M + H)⁺ = 777/9/81 (Br₂) | 0.11 | FM1 | (KBr): C=O 1624/1678 | |
| 344 | N71 | AS1 | 1 | O | A0C37 | DIEA/DMF | 52 | ESI: (M + H)⁺ = 771/3/5 (Br₂) | 0.65 | FM1 | (KBr): C=O 1622/1680 | |
| 345 | N66 | AS1 | 1 | O | A0C37 | DIEA/DMF | 50 | ESI: (M + H)⁺ = 759/61/63 (Br₂) | 0.7 | FM1 | (KBr): C=O 1626/1659 | |
| 346 | N71 | AS4 | 1 | O | A0C37 | DIEA/DMF | 37 | ESI: (M + H)⁺ = 770/72/74 (Br₂) | 0.75 | FM1 | (KBr): C=O 1620/1682 | |
| 347 | N6 | AS4 | 1 | O | A0C37 | DIEA/DMF | 45 | ESI: (M + H)⁺ = 758/60/62 (Br₂) | 0.8 | FM1 | (KBr): C=O 1620/1663 | |
| 348 | N113 | AS4 | 1 | O | A0C20 | DIEA/DMF | 24 | ESI: (M + H)⁺ = 771/3/5 (BR₂) | 0.8 | FM1 | (KBr): C=O 1616/1701 | |
| 349 | N113 | AS4 | 1 | O | A0C8 | DIEA/DMF | 40 | ESI: (M + H)⁺ = 757/59/61 (Br₂) | 0.8 | FM1 | (KBr): C=O 1616/1699 | |
| 350 | N111 | AS4 | 1 | O | A0C20 | | 33 | ESI: (M + H)⁺ = 838/40/42 (Br₂) | 0.63 | FM1 | (KBr): C=O 1620/1688 | |
| 351 | N111 | AS4 | 1 | O | A0C8 | | 39 | ESI: (M + H)⁺ = 824/6/8 (Br₂) | 0.64 | FM1 | (KBr): C=O 1620/1688 | |
| 352 | N111 | AS1 | 1 | O | A0C8 | | 36 | ESI: (M + H)⁺ = 825/7/9 (Br₂) | 0.37 | FM1 | (KBr): C=O 1644/1688 | |
| 353 | N112 | AS1 | 1 | O | A0C8 | | 24 | ESI: (M + H)⁺ = 763/5/7 (Br₂) | 0.28 | FM1 | (KBr): C=O 1624/1684 | |
| 355 | N113 | AS4 | 1 | O | A0C11 | DIEA/DMF | 6 | ESI: (M + H)⁺ = 772/4/6 (Br₂) | 0.5 | FM1 | (KBr): C=O 1620/1697 | |

-continued

| No. | RCO | R² | n | X | A NR³R⁴ | Remarks | % Yield | MS | R_f | Eluant | IR [cm⁻¹] | Mp. (° C.) |
|---|---|---|---|---|---|---|---|---|---|---|---|---|
| 356 | N66 | AS4 | 1 | O | A(C38 | DIEA/DMF | 31 | ESI: (M + H)⁺ = 785/7/9 (Br₂) | 0.23 | FM1 | (KBr): C=O 1624/1664 | |
| 357 | N112 | AS4 | 1 | O | A(C11 | DIEA/DMF | 5 | ESI: (M + H)⁺ = 777/79/81 (Br₂) | 0.37 | FM1 | | |
| 358 | N111 | AS1 | 1 | O | A(C11 | DIEA/DMF | 13 | ESI: (M + H)⁺ = 840/42/44 (Br₂) | 0.09 | FM1 | (KBr): C=O 1624/1686 | |
| 359 | N111 | AS4 | 1 | O | A(C11 | DIEA/DMF | 24 | | 0.39 | FM1 | (KBr): C=O 1622/1686 | |
| 360 | N109 | AS4 | 1 | O | A(C8 | DIEA/DMF | 25 | ESI: (M + H)⁺ = 750/52/54 (Br₂) | 0.7 | FM1 | (KBr): C=O 1618/1657 | |
| 361 | N110 | AS4 | 1 | O | A(C11 | DIEA/DMF | 35 | ESI: (M + H)⁺ = 750/52/54 (Br₂) | 0.5 | FM1 | (KBr): C=O 1622/1649 | |
| 362 | N110 | AS4 | 1 | O | A(C8 | DIEA/DMF | 24 | ESI: (M + H)⁺ = 750/52/54 (Br₂) | 0.5 | FM1 | (KBr): C=O 1649 | |
| 363 | N111 | AS4 | 1 | O | A(C37 | DIEA/DMF | 25 | | 0.53 | FM1 | (KBr): C=O 1622/1688 | |
| 364 | N111 | AS1 | 1 | O | A(C37 | DIEA/DMF | 24 | ESI: (M + H)⁺ = 839/41/43 (Br₂) | 0.3 | FM1 | (KBr): C=O 1624/1686 | |
| 366 | N66 | AS4 | 1 | O | A(C39 | | 67 | ESI: (M + H)⁺ = 772/4/6 (Br₂) | 0.53 | FM1 | (KBr): C=O 1618/1665 | |
| 367 | N71 | AS4 | 1 | O | A(C39 | DIEA/DMF | 12 | ESI: (M + H)⁺ = 784/6/8 (Br₂) | 0.52 | FM1 | (KBr): C=O 1618/1684 | |
| 368 | N111 | AS4 | 1 | O | A(C39 | DIEA/DMF | 37 | ESI: (M + H)⁺ = 852/4/6 (Br₂) | 0.8 | FM1 | (KBr): C=O 1618/1686 | |
| 369 | N114 | AS4 | 1 | O | A(C8 | | 15 | ESI: (M + H)⁺ = 824/6/8 (Br₂) | 0.58 | FM1 | (KBr): C=O 1618/1686 | |
| 370 | N66 | AS4 | 1 | O | A(C40 | DIEA/DMF | 35 | ESI: (M + H)⁺ = 773/5/7 (Br₂) | 0.44 | FM1 | (KBr): C=O 1622/1660 | |
| 371 | N111 | AS4 | 1 | O | A(C40 | DIEA/DMF | 58 | ESI: (M + H)⁺ = 853/5/7 (Br₂) | 0.44 | FM1 | (KBr): C=O 1622/1687 | |
| 373 | N115 | AS4 | 1 | O | A(C8 | DIEA/DMF | 43 | ESI: (M + H)⁺ = 822/4/6/8 (Br₃) | 0.7 | FM1 | (KBr): C=O 1620/1670 | |
| 374 | N116 | AS4 | 1 | O | A(C20 | | 27 | ESI: (M + H)⁺ = 784/6/8 (Br) | 0.53 | FM1 | (KBr): C=O 1618/1680 | |
| 375 | N117 | AS4 | 1 | O | A(C20 | | 23 | ESI: (M + H)⁺ = 815/7/9 (Br) | 0.52 | FM1 | (KBr): C=O 1620/1687 | |
| 376 | N118 | AS4 | 1 | O | A(C20 | | 30 | | 0.56 | FM1 | (KBr): C=O 1620/1684 | |
| 377 | N119 | AS4 | 1 | O | A(C20 | | 74 | ESI: (M + H)⁺ = 848/50/52/54 (Br₃) | 0.61 | FM1 | (KBr): C=O 1616/1685 | |
| 418 | N111 | AS4 | 1 | O | A(C38 | DIEA/DMF | 23 | ESI: (M + H)⁺ = 865/7/9 (Br) | 0.27 | FM1 | (KBr): C=O 1622/1687 | |
| 490 | N113 | AS1 | 1 | O | A(C20 | DIEA/DMF | 37 | ESI: (M + H)⁺ = 772/4/6 (Br₂) | 0.1 | FM1 | (KBr): C=O 1622/1699 | |
| 491 | N113 | AS1 | 1 | O | A(C8 | DIEA/DMF | 94 | ESI: (M + H)⁺ = 758/60/62 (Br₂) | 0.37 | FM1 | (KBr): C=O 1624/1691 | |
| 492 | N113 | AS1 | 1 | O | A(C11 | DIEA/DMF | 42 | ESI: (M + H)⁺ = 773/5/7 (Br₂) | 0.1 | FM1 | (KBr): C=O 1678 | |
| 495 | N133 | AS4 | 1 | O | A(C20 | | 45 | ESI: (M + H)⁺ = 846/48/50 (Br₂) | 0.5 | FM1 | (KBr): C=O 1620/1682 | |
| 379 | N71 | AS1 | 1 | O | A(C3 | | 39 | ESI: (M + H)⁺ = 769/71/73 (Br₂) | 0.41 | FM4 | (KBr): C=O 1680 | |
| 380 | N71 | AS4 | 1 | O | A(C3 | | 40 | ESI: (M + H)⁺ = 768/70/72 (Br₂) | 0.47 | FM4 | (KBr): C=O 1618/1682 | |
| 381 | N71 | AS1 | 1 | O | A(C42 | | 11 | ESI: (M + H)⁺ = 752/54/56 (Br₂) | 0.53 | FM1 | (KBr): C=O 1624/1682 | |
| 382 | N66 | AS1 | 1 | O | A(C42 | | 18 | ESI: (M + H)⁺ = 740/42/44 (Br₂) | 0.16 | FM4 | (KBr): C=O 1630/1653 | |
| 383 | N66 | AS4 | 1 | O | A(C42 | | 47 | ESI: (M + H)⁺ = 739/41/43 (Br₂) | 0.25 | FM4 | (KBr): C=O 1626/1659 | |
| 384 | N93 | AS1 | 1 | O | A(C1 | | 11 | ESI: (M + H)⁺ = 790/92/94 (Br₂) | 0.20 | FM7 | (KBr): C=O 1636/1705 | |
| 385 | N71 | AS4 | 1 | O | A(C42 | | 37 | ESI: (M + H)⁺ = 751/53/55 (Br₂) | 0.30 | FM4 | (KBr): C=O 1620/1680 | |
| 386 | N71 | AS4 | 1 | O | A(C18 | | 26 | ESI: (M + H)⁺ = 782/4/6 (Br₂) | 0.27 | FM4 | (KBr): C=O 1620/1682 | |
| 387 | N66 | AS4 | 1 | O | A(C5 | | 62 | ESI: (M + H)⁺ = 739/41/43 (Br₂) | 0.38 | FM4 | (KBr): C=O 1626/1663 | |
| 388 | N71 | AS4 | 1 | O | A(C5 | | 55 | ESI: (M + H)⁺ = 751/3/5 (Br₂) | 0.39 | FM4 | (KBr): C=O 1618/1684 | |
| 389 | N66 | AS1 | 1 | O | A(C43 | | 59 | ESI: (M + H)⁺ = 796/98/800 (Br₂) | 0.32 | CH₂Cl₂/MeOH/ NH₄OH 9/1/0.1 | (KBr): C=O 1653 | |
| 390 | N135 | AS4 | 1 | O | A(C18 | | 5 | ESI: (M + H)⁺ = 853/5/7 (Br₂) | 0.71 | FM1 | (KBr): C=O 1622/1653 | |

-continued

| No. | RCO | R² | n | X | A NR³R⁴ | Remarks | % Yield | MS | $R_f$ | Eluant | IR [cm⁻¹] | Mp. (° C.) |
|---|---|---|---|---|---|---|---|---|---|---|---|---|
| 391 | N135 | AS1 | 1 | O | A(C18 | | 6 | ESI: (M + H)⁺ = 854/6/8 (Br₂) | 0.54 | FM1 | (KBr): C=O 1659 | |
| 392 | N120 | AS1 | 1 | O | A(C4 | | 12 | ESI: (M + H)⁺ = 763/5/7 (Br₂) | 0.41 | CH₂Cl₂/MeOH/ NH₄OH 9/1/0.1 | (KBr): C=O 1618/1639 | |
| 393 | N66 | AS1 | 1 | O | A(C44 | | 28 | ESI: (M + H)⁺ = 763/5/7 (Br₂) | 0.50 | CH₂Cl₂/MeOH/ NH₄OH 9/1/0.1 | (KBr): C=O 1659 | |
| 394 | N66 | AS4 | 1 | O | A(C21 | | 37 | ESI: (M + H)⁺ = 740/42/44 (Br₂) | 0.35 | EE/MeOH/ AcOH 75/25/0.5 | (KBr): C=O 1659 | |
| 396 | N71 | AS1 | 1 | O | A(C21 | | 49 | ESI: (M + H)+ = 753/5/7 (Br₂) | 0.30 | EE/MeOH/ AcOH 75/25/0.5 | (KBr): C=O 1622/1678 | |
| 397 | N66 | AS1 | 1 | O | A(C21 | | 62 | ESI: (M + H)⁺ = 741/3/5 (Br₂) | 0.35 | EE/MeOH/ AcOH 75/25/0.5 | (KBr): C=O 1649 | |
| 398 | N121 | AS4 | 1 | O | A(C8 | | 80 | ESI: (M + H)⁺ = 743/5/7 (Br₂) | 0.55 | CH₂Cl₂/MeOH/ NH₄OH 9/1/0.1 | (KBr): C=O 1618/1668 | |
| 399 | N122 | AS4 | 1 | O | A(C18 | | 40 | ESI: (M + H)+ = 800/2/4 (Br₂) | 0.62 | FM1 | (KBr): C=O 1622/1682 | |
| 400 | N136 | AS4 | 1 | O | A(C8 | | 11 | ESI: (M + H)⁺ = 741/3/5 (Br₂) | 0.65 | FM1 | (KBr): C=O 1622/1653 | |
| 401 | N66 | AS1 | 1 | O | A(C45 | | 19 | ESI: (M + H)⁺ = 749/51/53 (Br₂) | 0.65 | CH₂Cl₂/MeOH/ NH₄OH 9/1/0.1 | (KBr): C=O 1659 | |
| 402 | N136 | AS4 | 1 | O | A(C1 | | 10 | ESI: (M + H)⁺ = 736/8/40 (Br₂) | 0.42 | CH₂Cl₂/MeOH/ NH₄OH 9/1/0.1 | (KBr): C=O 1649 | |
| 403 | N121 | AS4 | 1 | O | A(C1 | | 25 | ESI: (M + H)⁺ = 738/40/42 (Br₂) | 0.43 | CH₂Cl₂/MeOH/ NH₄OH 9/1/0.1 | (KBr): C=O 1626/1676 | |
| 404 | N66 | AS4 | 1 | O | A(C46 | | 58 | ESI: (M + H)⁺ = 766/8/70 (Br₂) | 0.29 | CH₂Cy MeOH/ NH₄OH 9/1/0.1 | (KBr): C=O 1624/1663 | |
| 405 | N66 | AS1 | 1 | O | A(C47 | | 40 | ESI: (M − H)⁻ = 752/4/6 (Br₂) | 0.3 | EE/MeOH 9/1 | (KBr): C=O 1659 | |
| 406 | N136 | AS1 | 1 | O | A(C1 | | 16 | ESI: (M + H)⁺ = 737/39/41 (Br₂) | 0.34 | FM7 | (KBr): C=O 1645 | |
| 407 | N121 | AS1 | 1 | O | A(C1 | | 15 | ESI: (M + H)⁺ = 739/41/43 (Br₂) | 0.36 | FM7 | (KBr): C=O 1638 | |
| 408 | N71 | AS4 | 1 | O | A(C48 | | 47 | ESI: (M + Hr = 792/4/6 (Br₂) | 0.17 | CH₂Cl₂/MeOH/ NH₄OH 9/1/0.1 | (KBr): C=O 1620/1680 | |
| 409 | N66 | AS4 | 1 | O | A(C48 | | 31 | ESI: (M + H)⁺ = 780/2/4 (Br₂) | 0.43 | CH₂Cl₂/MeOH/ NH₄OH 9/1/0.1 | (KBr): C=O 1665/1736 | |
| 410 | N66 | AS1 | 1 | O | A(C49 | | 51 | | 0.24 | EE/MeOH 9/1 | (KBr): C=O 1661 | |
| 411 | N71 | AS4 | 1 | O | A(C44 | | 45 | ESI: (M + Na)⁺ = 796/98/800 (Br₂) | 0.35 | EE/MeOH 9/1 | (KBr): C=O 1728 | |
| 412 | N66 | AS1 | 1 | O | A(C50 | | 58 | ESI: (M + H)⁺ = 756/58/60 (Br₂) | 0.47 | EE/MeOH 9/1 | (KBr): C=O 1642/1661 | |
| 413 | N66 | AS1 | 1 | O | A(C51 | | 16 | ESI: (M + H)⁺ = 788/90/92 (Br₂) | 0.47 | EE/MeOH/ NH₄OH 5/5/0.1 | (KBr): C=O 1631 | |
| 414 | N66 | AS4 | 1 | O | A(C52 | | 34 | ESI: (M + H)⁺ = 747/49/51 (Br₂) | 0.54 | FM1 | (KBr): C=O 1622/1662 | |
| 415 | N71 | AS4 | 1 | O | A(C52 | | 35 | ESI: (M + H)⁺ = 759/61/63 (Br₂) | 0.52 | FM1 | (KBr): C=O 1620/1682 | |
| 416 | N66 | AS4 | 1 | O | A(C53 | | 53 | ESI: (M + H)⁺ = 759/61/63 (Br₂) | 0.45 | CH₂Cl₂/MeOH/ NH₄OH 9/1/0.1 | (KBr): C=O 1620/1664 | |
| 417 | N71 | AS4 | 1 | O | A(C53 | | 39 | ESI: (M + H)⁺ = 771/3/5 (Br₂) | 0.43 | | (KBr): C=O 1620/1684 | |
| 496 | N66 | AS4 | 1 | O | A(C64 | | 57 | | 0.5 | CH₂Cl₂/MeOH/ NH₄OH 9/1/0.1 | (KBr): C=O 1635 | |
| 497 | N66 | AS1 | 1 | O | A(C53 | | 60 | ESI: (M + H)⁺ = 760/2/4 (Br₂) | 0.31 | CH₂Cl₂/MeOH/ NH₄OH 50/50/0.5 | (KBr): C=O 1676 | |
| 498 | N66 | AS4 | 1 | O | A(C65 | | 60 | ESI: (M + H)⁺ = 760/2/4 (Br₂) | 0.39 | FM1 | (KBr): C=O 1676 | |
| 499 | N71 | AS4 | 1 | O | A(C65 | | 53 | ESI: (M + H)⁺ = 785/7/9 (Br₂) | 0.39 | FM1 | (KBr): C=O 1618/1684 | |
| 500 | N66 | AS4 | 1 | O | A(C51 | | 71 | ESI: (M + H)⁺ = 787/89/91 (Br₂) | 0.15 | CH₂Cl₂/MeOH/ NH₄OH 9/1/0.1 | (KBr): C=O 1628 | |
| 501 | N71 | AS1 | 1 | O | A(C53 | | 71 | ESI: (M + H)⁺ = 772/4/6 (Br₂) | 0.25 | CH₂Cl₂/MeOH/ NH₄OH 50/50/0.5 | (KBr): C=O 1676 | |
| 502 | N66 | AS1 | 1 | O | A(C65 | | 42 | ESI: (M + H)⁺ = 774/6/8 (Br₂) | 0.15 | FM1 | (KBr): C=O 1626/1657 | |
| 503 | N71 | AS1 | 1 | O | A(C65 | | 48 | ESI: M + H)⁺ = 786/88/90 (Br₂) | 0.12 | FM1 | (KBr): C=O 1620/1682 | |
| 504 | N66 | AS4 | 1 | O | A(C66 | | 67 | ESI: (M + H)⁺ = 787/89/91 (Br₂) | 0.65 | CH₂Cl₂MeOH/ NH₄OH 50/50/0.5 | (KBr): C=O 1624 | |
| 297 | N71 | AS4 | 1 | H2 | A(C8 | | 9 | ESI: (M + H)⁺ = 742/4/6 (Br₂) | 0.2 | FM1 | (KBr): C=O 1684 | |

-continued

| No. | RCO | R² | n | X | A NR³R⁴ | Remarks | % Yield | MS | $R_f$ | Eluant | IR [cm⁻¹] | Mp. (° C.) |
|---|---|---|---|---|---|---|---|---|---|---|---|---|
| 298 | N71 | AS13 | 1 | H2 | A(C8 | | 6 | ESI: (M + H)⁺ = 664/6 (Br) | 0.16 | FM1 | (KBr): C=O 1622/1682 | |
| 299 | N66 | AS4 | 1 | H2 | A(C8 | | 21 | ESI: (M + H)⁺ = 730/2/4 (Br₂) | 0.25 | FM1 | (KBr): C=O 1666 | |
| 300 | N66 | AS13 | 1 | H2 | A(C8 | | 14 | ESI: (M + H)⁺ = 652/4 (Br) | 0.19 | FM1 | (KBr): C=O 1666 | |
| 301 | N71 | AS1 | 1 | H2 | A(C8 | | 26 | ESI: (M + H)⁺ = 743/5/7 (Br₂) | 0.2 | FM1 | (KBr): C=O 1682 | |
| 420 | N87 | AS1 | 1 | O | A(C4 | | 45 | ESI: (M + H)⁺ = 797/99/801 (Br₂) | 0.5 | FM1 | (KBr): C=O 1624/1665/ 1719 | |
| 422 | N87 | AS1 | 1 | O | A(C8 | | 35 | ESI: (M + H)⁺ = 805/7/9 (Br₂) | 0.54 | FM1 | (KBr): C=O 1628/1668/ 1720 | |
| 431 | N125 | AS4 | 1 | O | A(C8 | | 89 | ESI: (M + H)⁺ = 772/4/6 (Br₂) | 0.75 | FM1 | (KBr): C=O 1713/1773 | |
| 432 | N125 | AS1 | 1 | O | A(C4 | | 59 | ESI: (M + H)⁺ = 767/69/71 (Br₂) | 0.65 | FM1 | (KBr): C=O 1622/1711/ 1773 | |
| 433 | N126 | AS4 | 1 | O | A(C4 | | 33 | ESI: (M + H)⁺ = 780/2/4 (Br₂) | 0.65 | FM1 | (KBr): C=O 1709/1769 | |
| 434 | N126 | AS1 | 1 | O | A(C8 | | 53 | ESI: (M + H)⁺ = 787/89/91 (Br₂) | 0.53 | FM1 | (KBr): C=O 1626/1707 | |
| 440 | N127 | AS4 | 1 | O | A(C8 | | 67 | ESI: (M + H)⁺ = 780/2/4 (Br₂) | 0.67 | FM1 | (KBr): C=O 1618 | |
| 441 | N127 | AS4 | 1 | O | A(C20 | | 89 | ESI: (M + H)⁺ = 794/6/8 (Br₂) | 0.24 | EE/MeOH/ NH₄OH 8/1.5/0.3 | (KBr): C=O 1618 | |
| 442 | N127 | AS4 | 1 | O | A(C4 | | 83 | ESI: (M + H)⁺ = 774/6/8 (Br₂) | 0.37 | EE/MeOH/ NH₄OH 8/1.5/0.3 | (KBr): C=O 1616/1732 | |
| 456 | N66 | AS16 | 1 | O | A(C8 | | 83 | ESI: (M + H)⁺ = 641/3/5 (Cl₂) | 0.32 | EE/MeOH/ NH₄OH 8/1.5/0.1 | (KBr): C=O 1624/1665 | |
| 466 | N128 | AS4 | 1 | O | A(C8 | | 13 | ESI: (M + H)⁺ = 832/4/6 (Br₂) | 0.63 | FM1 | (KBr): C=O 1684 | |
| 467 | N129 | AS4 | 1 | O | A(C8 | | 16 | ESI: (M + H)⁺ = 806/08/10 (Br₂) | 0.63 | FM1 | (KBr): C=O 1618/1682 | |
| 468 | N129 | AS1 | 1 | O | A(C8 | | 28 | ESI: (M + H)⁺ = 807/09/11 (Br₂) | 0.29 | FM1 | (KBr): C=O 1630/1680 | |
| 470 | N128 | AS1 | 1 | O | A(C8 | | 81 | ESI: (M + H)⁺ = 835/7/9 (Br₂) | 0.63 | FM1 | (KBr): C=O 1684 | |
| 473 | N130 | AS1 | 1 | O | A(C8 | | 40 | ESI: (M + H)⁺ = 787/89/91 (Br₂) | 0.51 | FM1 | (KBr): C=O 1624/1678 | |
| 474 | N130 | AS4 | 1 | O | A(C8 | | 17 | ESI: (M + Hr = 786/88/90 (Br₂) | 0.71 | FM1 | (KBr): C=O 1618/1684 | |
| 477 | N66 | AS16 | 1 | O | A(C1 | | 33 | ESI: (M + H)+ = 636/38/40 (Cl₂) | 0.53 | EE/MeOH/ NH₄OH 9/1/1 (v/v/v) | (KBr): C=O 1661 | |
| 481 | N131 | AS4 | 1 | O | A(C37 | | 30 | ESI: (M + H)⁺ = 838/40/42/44 (Br₂; Cl₂) | 0.15 | CH₂Cl₂/ MeOH 7/3 (v/v) | (KBr): C=O 1618/1685 | |
| 482 | N131 | AS4 | 1 | O | A(C20 | | 24 | ESI: (M + H)⁺ = 838/40/42/44 (Br₂; Cl₂) | 0.15 | CH₂Cl₂/ MeOH 7/3 (v/v) | (KBr): C=O 1618/1685 | |
| 483 | N132 | AS4 | 1 | O | A(C20 | | 62 | ESI: (M + H)⁺ = 804/6/8/10 (Br₂; Cl) | 0.55 | FM1 | (KBr): C=O 1684 | |
| 484 | N132 | AS4 | 1 | O | A(C37 | | 85 | ESI: (M + H)⁺ = 804/6/8/10 (Br₂; Cl) | 0.60 | FM1 | (KBr): C=O 1616/1686 | |
| 505 | N134 | AS4 | 1 | O | A(C8 | | 81 | ESI: (M + H)⁺ = 781/3/5 (Br₂) | 0.74 | FM1 | (KBr): C=O 1616/1714 | |
| 292 | N66 | AS1 | 1 | H2 | A(C8 | | 6 | ESI: (M + H)⁺ = 731/3/5 (Br₂) | 0.25 | FM1 | (KBr): C=O 1607/1664 | |
| 245 | N72 | AS4 | 1 | H2 | A(C8 | | 19 | ESI: (M + H)⁺ = 731/3/5 (Br₂) | 0.30 | FM1 | (KBr): C=O 1668 | |
| 220 | N15 | AS1 | 1 | H2 | A(C8 | | 6 | ESI: (M + H)⁺ = 717/19/21 (Br₂) | 0.30 | FM1 | (KBr): C=O 1697.3 | |
| 307 | N87 | AS4 | 1 | O | A(C4 | | 27 | ESI: (M + H)⁺ = 796/98/800 (Br₂) | 0.50 | FM1 | (KBr): C=O 1618/1670/ 1718 | |
| 178 | N74 | AS1 | 1 | O | A(C4 | | 33 | ESI: (M + H)⁺ = 679/81/83 (Br₂) | 0.60 | EE/MeOH/ AcOH 50/50/1 (v/v/v) | (KBr): C=O 1624 | |

-continued

| No. | RCO | R² | n | X | A NR³R⁴ | Remarks | % Yield | MS | R_f | Eluant | IR [cm⁻¹] | Mp. (° C.) |
|---|---|---|---|---|---|---|---|---|---|---|---|---|
| 395 | N71 | AS4 | 1 | O | A(C21 | | 22 | ESI: (M + H)⁺ = 752/4/6 (Br₂) | 0.25 | EE/MeOH/ AcOH 50/25/0.5 (v/v/v) | | |
| 509 | N119 | AS4 | 1 | O | A(C38 | DMF | 45 | ESI: (M + H)⁺ = 875/7/9/81 (Br₃) | 0.2 | FM1 | (KBr): C═O 1687/1618 | |
| 510 | N118 | AS4 | 1 | O | A(C38 | DMF | 34 | ESI: (M + H)⁺ = 827/29/31 (Br₂) | 0.4 | FM1 | (KBr): C═O 1682/1620 | |
| 519 | N137 | AS4 | 1 | O | A(C20 | THF/ DMF | 62 | ESI: (M + H)⁺ = 786/88/90 (Br₂) | 0.1 | FM1 | (KBr): C═O 1618/1678 | |
| 520 | N138 | AS4 | 1 | O | A(C20 | THF/DMF | 31 | ESI: (M + H)⁺ = 906/08/10 (Br₄) | 0.45 | FM1 | (KBr): C═O 1693 | |
| | N66 | AS4 | 1 | O | A(C69 | DMF | 100 | | | | | |
| 533 | N139 | AS1 | 1 | O | A(C8 | | 44 | ESI: (M + H)⁺ = 746/48/50 (Br₂) | 0.1 | FM5 | (KBr): C═O 1628 | |
| 534 | N139 | AS4 | 1 | O | A(C20 | | 60 | ESI: (M + H)⁺ = 759/61/63 (Br₂) | 0.2 | FM5 | (KBr): C═O 1618/1672 | |
| 535 | N139 | AS1 | 1 | O | A(C53 | | 34 | ESI: (M + H)⁺ = 761/63/65 (Br₂) | 0.1 | FM5 | (KBr): C═O 1624/1670 | |
| 536 | N140 | AS4 | 1 | O | A(C8 | | 40 | ESI: (M + H)⁺ = 745/7/9 (Br₂) | 0.37 | FM1 | (KBr): C═O 1616/1676 | |
| 537 | N140 | AS1 | 1 | O | A(C8 | | 33.4 | ESI: (M + H)⁺ = 746/48/50 (Br₂) | 0.3 | FM1 | (KBr): C═O 1614/1672 | |
| 551 | N66 | AS1 | 1 | O | A(C66 | | 41 | ESI: (M + H)⁺ = 788/90/92 (Br₂) | 0.3 | EE/MeOH/ NH₄OH 50/50/0.5 | (KBr): C═O 1628 | |
| 552 | N66 | AS4 | 1 | O | A(C78 | | 83 | ESI: (M + H)⁺ = 787/89/91 (Br₂) | 0.6 | CH₂Cl₂/MeOH/ NH₄OH 80/20/1 | (KBr): C═O 1620 | |
| 553 | N66 | AS1 | 1 | O | A(C78 | | 30 | ESI: (M + H)⁺ = 788/90/92 (Br₂) | 0.5 | CH₂Cl₂/MeOH/ NH₄OH 80/20/1 | (KBr): C═O 1626 | |
| 554 | N71 | AS4 | 1 | O | A(C78 | | 67 | ESI: (M + H)⁺ = 799/801/803 (Br₂) | 0.5 | CH₂Cl₂/MeOH/ NH₄OH 80/20/1 | (KBr): C═O 1622/1684 | |
| 555 | N71 | AS1 | 1 | O | A(C78 | | 26 | ESI: (M + H)⁺ = 800/02/04 (Br₂) | 0.5 | CH₂Cl₂/MeOH/ NH₄OH 80/20/1 | (KBr): C═O 1624/1684 | |
| 556 | N66 | AS4 | 1 | O | A(C70 | | 71 | ESI: (M + H)⁺ = 788/90/92 (Br₂) | 0.6 | CH₂Cl₂/MeOH/ NH₄OH 50/50/0.5 | (KBr): C═O 1653 | |
| 557 | N71 | AS4 | 1 | O | A(C70 | | 27 | ESI: (M + H)⁺ = 800/02/04 (Br₂) | 0.8 | CH₂Cl₂/MeOH/ NH₄OH 50/50/0.5 | | |
| 558 | N66 | AS1 | 1 | O | A(C64 | | 61 | ESI: (M + H)⁺ = 790/92/94 (Br₂) | 0.3 | CH₂Cl₂/MeOH/ NH₄OH 90/10/1 | (KBr): C═O 1635 | |
| 559 | N141 | AS4 | 1 | O | A(C20 | | 80 | ESI: (M + H)⁺ = 626/28/30 (Br₂) | 0.3 | CH₂Cl₂/MeOH/ NH₄OH 90/10/1 | (KBr): C═O 1618/1714 | |
| 560 | N66 | AS4 | 1 | O | A(C71 | | 59 | ESI: (M + H)⁺ = 837/39/41 (Br₂) | 0.3 | CH₂Cl₂/MeOH/ NH₄OH 90/10/1 | (KBr): C═O 1628/62 | |
| 561 | N71 | AS4 | 1 | O | A(C71 | | 56 | ESI: (M + H)⁺ = 849/51/53 (Br₂) | 0.2 | CH₂Cl₂/ MeOH/ NH₄OH 90/10/1 | (KBr): C═O 1618/1684 | |
| 562 | N66 | AS1 | 1 | O | A(C70 | | 15 | ESI: (M + H)⁺ = 789/91/93 (Br₂) | 0.6 | CH₂Cl₂/ MeOH/ NH₄OH 50/50/0.5 | (KBr): C═O 1676 | |
| 563 | N71 | AS1 | 1 | O | A(C70 | | 27 | ESI: (M + H)⁺ = 801/3/5 (Br₂) | 0.6 | CH₂Cl₂/ MeOH/ NH₄OH 70/30/1 | (KBr): C═O 1678 | |
| 565 | N66 | AS4 | 1 | O | A(C72 | | 51 | ESI: (M + H)⁺ = 787/89/91 (Br₂) | 0.2 | CH₂Cl₂/ MeOH/ NH₄OH 80/20/1 | (KBr): C═O 1622/1658 | |

-continued

| No. | RCO | R² | n | X | A NR³R⁴ | Remarks | % Yield | MS | $R_f$ | Eluant | IR [cm⁻¹] | Mp. (° C.) |
|---|---|---|---|---|---|---|---|---|---|---|---|---|
| 566 | N71 | AS4 | 1 | O | A(C72 | | 65 | ESI: (M + H)⁺ = 799/801/803 (Br₂) | 0.2 | CH₂Cl₂/ MeOH/ NH₄OH 80/20/1 | (KBr): C═O 1620/1682 | |
| 567 | N136 | AS4 | 1 | O | A(C53 | | 65 | ESI: (M + H)⁺ = 756/58/60 (Br₂) | 0.5 | CH₂Cl₂/ MeOH/ NH₄OH 80/20/1 | (KBr): C═O 1641 | |
| 568 | N136 | AS4 | 1 | O | A(C72 | | 76 | ESI: (M + H)⁺ = 784/6/8 (Br₂) | 0.2 | CH₂Cl₂/ MeOH/ NH₄OH 80/20/1 | (KBr): C═O 1637 | |
| 569 | N136 | AS1 | 1 | O | A(C53 | | 63 | ESI: (M + H)⁺ = 757/59/61 (Br₂) | 0.4 | CH₂Cl₂/ MeOH/ NH₄OH 80/20/1 | (KBr): C═O 1643 | |
| 570 | N66 | AS31 | 1 | O | A(C20 | | 88 | ESI: (M + H)⁺ = 640 | 0.6 | CH₂Cl₂/ MeOH/ NH₄OH 80/20/1 | (KBr): C═O 1622/1664 | |
| 571 | N66 | AS31 | 1 | O | A(C53 | | 82 | ESI: (M + H)⁺ = 641 | 0.8 | CH₂Cl₂/ MeOH/ NH₄OH 80/20/1 | (KBr): C═O 1664 | |
| 572 | N71 | AS31 | 1 | O | A(C20 | | 100 | ESI: (M + H)⁺ = 652 | 0.4 | CH₂Cl₂/ MeOH/ NH₄OH 80/20/1 | (KBr): C═O 1620/1684 | |
| 573 | N71 | AS31 | 1 | O | A(C53 | | 48 | ESI: (M + H)⁺ = 653 | 0.4 | CH₂Cl₂/ MeOH/ NH₄OH 80/20/1 | (KBr): C═O 1622/1684 | |
| 576 | N66 | AS11 | 1 | O | A(C53 | | 35 | ESI: (M + H)⁺ = 727 | 0.65 | CH₂Cl₂/ MeOH/ NH₄OH 80/20/1 | (KBr): C═O 1664/1732 | |
| 577 | N71 | AS11 | 1 | O | A(C53 | | 73 | ESI: (M + H)⁺ = 739 | 0.18 | EE/ MeOH/ NH₄OH 50/50/0.5 | (KBr): C═O 1684/1734 | |
| 580 | N66 | AS11 | 1 | O | A(C20 | | 65 | ESI: (M + H)⁺ = 706 | 0.5 | CH₂Cl₂/ MeOH/ NH₄OH 80/20/1 | (KBr): C═O 1664/1732 | |
| 581 | N71 | AS11 | 1 | O | A(C20 | | 38 | ESI: (M + H)⁺ = 738 | 0.2 | CH₂Cl₂/ MeOH/ NH₄OH 90/10/1 | (KBr): C═O 1684/1734 | |
| 582 | N143 | AS4 | 1 | O | A(C20 | | 61 | ESI: (M + H)⁺ = 758/60/62 | 0.5 | CH₂Cl₂/ MeOH/ NH₄OH 90/10/1 | (KBr): C═O 1615 | |
| 583 | N66 | AS31 | 1 | O | A(C72 | | 50 | ESI: (M + H)⁺ = 669 | 0.35 | FM1 | (KBr): C═O 1664 | |
| 584 | N71 | AS31 | 1 | O | A(C72 | | 68 | ESI: (M + H)⁺ = 681 | 0.35 | FM1 | (KBr): C═O 1622/1684 | |
| 585 | N144 | AS4 | 1 | O | A(C8 | | 50 | ESI: (M + H)⁺ = 927/29/31/33 (Br₄) | 0.43 | FM5 | (KBr): C═O 1616/1684 | |
| 586 | N144 | AS4 | 1 | O | A(C53 | | 85 | ESI: (M + H)⁺ = 942/4/6/8 (Br₄) | 0.67 | FM1 | (KBr): C═O 1680 | |
| 587 | N66 | AS11 | 1 | O | A(C72 | | 37 | ESI: (M + H)⁺ = 755 | 0.35 | FM1 | (KBr): C═O 1622/1658/ 1732 | |
| 588 | N71 | AS11 | 1 | O | A(C72 | | 81 | ESI: (M + H)⁺ = 767 | 0.5 | FM1 | (KBr): C═O 1684/1732 | |
| 619 | N71 | AS19 | 1 | O | A(C8 | | 27.9 | | 0.3 | EE/MeOH/ NH₄OH 9/1/0.3 | (KBr): C═O 1622/1684 | |
| 620 | N66 | AS35 | 1 | O | A(C8 | | 36 | ESI: (M − H)⁻ = 598 | 0.25 | MeOH | (KBr): C═O 1628/1664 | |
| 621 | N66 | AS36 | 1 | O | A(C8 | | 32 | ESI: (M − H)⁻ = 587 | 0.56 | FM1 | (KBr): C═O 1626/1666 | |
| 622 | N71 | AS36 | 1 | O | A(C8 | | 32 | ESI: (M − H)⁻ = 599 | 0.44 | FM1 | (KBr): C═O 1622/1684 | |

| No. | RCO | R² | n | X | A | NR³R⁴ | Remarks | % Yield | MS | Rf | Eluant | IR [cm⁻¹] | Mp. (° C.) |
|---|---|---|---|---|---|---|---|---|---|---|---|---|---|
| 623 | N109 | AS36 | 1 | O | A | C8 | | 37 | ESI: (M − H)⁻ = 593 | 0.6 | FM1 | (KBr): C=O 1626/1649 | |
| 624 | N118 | AS36 | 1 | O | A | C8 | | 55 | ESI: (M − H)⁻ = 629 | 0.6 | FM1 | (KBr): C=O 1622/1684 | |
| 625 | N111 | AS36 | 1 | O | A | C8 | | 47 | ESI: (M − H)⁻ = 667 | 0.61 | FM1 | (KBr): C=O 1624/1687 | |
| 626 | N111 | AS19 | 1 | O | A | C8 | | 20 | ESI: (M − H)⁻ = 731/3 (Br) | 0.28 | EE/MeOH/ NH₄OH 9/1/0.3 | (KBr): C=O 1624/1687 | |
| 627 | N109 | AS19 | 1 | O | A | C8 | | 16 | ESI: (M − H)⁻ = 657/9 (Br) | 0.28 | EE/MeOH/ NH₄OH 9/1/0.3 | (KBr): C=O 1653 | |
| 633 | N118 | AS19 | 1 | O | A | C8 | | 20 | ESI: (M + H)⁺ = 693/5 (Br) | 0.18 | EE/MeOH/ NH₄OH 9/1/0.3 | (KBr): C=O 1622/1684 | |
| | N66 | AS1 | 1 | O | A | C69 | | 100 | | 0.3 | FM4 | (KBr): C=O 1668 | |

EXAMPLE 4

Preparation of Compounds of General Formula:

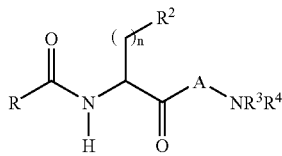

1-[4-amino-3,5-dibromo-N-[4-(1,3,3a,4,5,6,7,7a-octahydro-2(2H)-oxobenzimidazol-1-yl)-1-piperidinyl]carbonyl]-D-phenylalanyl]-4-(4-pyridinyl)-piperazine (No. 91)

A mixture of 0.35 g (2.1 mmol) of CDT, 1.0 g (1.4 mmol) of 4-(1,3,3a,4,5,6,7,7a-octahydro-2(2H)-oxobenzimidazol-1-yl)-piperidine, 0.5 ml of (2.8 mmol) of DIEA and 100 ml of tetrahydrofuran was stirred for 1 hour whilst cooling with ice and then for 30 minutes at ambient temperature. With stirring 0.46 g (1.75 mmol) of 1-(4-amino-3,5-dibromo-D-phenylalanyl)-4-(4-pyridinyl)piperazine and 0.32 ml of (1.8 mmol) of DIEA were added and refluxed for 3 hours. The reaction mixture was diluted with 100 ml of ethyl acetate and the organic phase was washed twice with aqueous saturated sodium hydrogen carbonate solution. The combined aqueous phases were then extracted once with ethyl acetate/tetrahydrofuran=1/1 (v/v) and the combined organic phases were washed once with saturated aqueous saline solution. After drying the organic phase and eliminating the solvent in vacuo the residue was purified by column chromatography (MN-silica gel 60, Macherey-Nagel, 70-230 mesh ASTM, eluant: ethyl acetate/methanol=9/1 (v/v)). 120 mg (12% of theory) of a colourless foam were obtained.

IR (KBr): 1626. 1686 cm⁻¹ (C=O)

| | |
|---|---|
| IR (KBr): | 1626. 1686 cm⁻¹ (C=O) |
| Rf: | 0.62 (FM3) |
| ESI-MS: | (M + H)⁺ = 731/733/735 (Br₂) |
| | (M + H + Na)⁺⁺ = 377/378/379 (Br₂) |

The following were prepared analogously (in each case n=1):

| No. | RCO | R² | A | NR³R⁴ | n | Remarks | % Yield | MS | Rf | Eluant | IR [cm⁻¹] | M.p. (° C.) |
|---|---|---|---|---|---|---|---|---|---|---|---|---|
| | N16 | AS1 | A3 | C1 | 1 | NEt₃ as base | 31 | ESI: (M + H)⁺ = 974/6/8 (Br₂) | 0.2 | FM1 | (KBr): C=O 1641.3; 1695.3 | |
| 86 | N53 | AS4 | A0 | C1 | 1 | DMF as solvent | 23 | ESI: (M + H)⁺ = 739/41/43 (Br₂) | 0.5 | FM1 | (KBr): C=O 1641.3; 1697.3 | |
| 87 | N54 | AS4 | A0 | C1 | 1 | DMF als Lösemittel | 81 | ESI: (M + H)⁺ = 739/41/43 (Br₂) | 0.5 | FM1 | (KBr): C=O 1620.1; 1697.3 | |
| 92 | N57 | AS4 | A0 | C1 | 1 | DMF as solvent | 60 | ESI: (M + H)⁺ = 712/4/6 (Br₂) | 0.6 | FM1 | (KBr): C=O 1597; 1635.5 | |
| 93 | N47 | AS4 | A0 | C1 | 1 | | 23 | ESI: (M + H)⁺ = 636/8/40 (Br₂) | 0.4 | FM1 | (KBr): C=O 1622; 1675 | |
| 94 | N45 | AS4 | A0 | C1 | 1 | | 45 | ESI: (M + H)⁺ = 739/41/43 (Br₂) | 0.6 | FM1 | (KBr): C=O 1598.9; 1620.1 | |
| 95 | N57 | AS1 | A0 | C1 | 1 | DMF as solvent | 13 | ESI: (M + H)⁺ = 713/5/7 (Br₂) | 0.2 | FM1 | (KBr): C=O 1637.5 | |
| 96 | N53 | AS1 | A0 | C1 | 1 | DMF as solvent | 15 | ESI: (M + H)⁺ = 740/2/4 (Br₂) | 0.2 | FM1 | (KBr): C=O 1633.6; 1687.6 | |

-continued

| No. | RCO | R² | A | NR³R⁴ | n | Remarks | % Yield | MS | $R_f$ | Eluant | IR [cm⁻¹] | M.p. (° C.) |
|---|---|---|---|---|---|---|---|---|---|---|---|---|
| 97 | N54 | AS1 | A0 | C1 | 1 | DMF as solvent | 31 | ESI: (M + H)⁺ = 740/2/4 (Br₂) | 0.2 | FM1 | (KBr): C=O 1635.5; 1695.3 | |
| 107 | N59 | AS4 | A0 | C1 | 1 | | 76 | ESI: (M + H)⁺ = 694/6/8 (Br₂) | 0.7 | FM1 | (KBr): C=O 1597; 1635.5 | |
| 108 | N45 | AS1 | A0 | C1 | 1 | | 37 | ESI: (M + H)⁺ = 740/2/4 (Br₂) | 0.3 | FM1 | (KBr): C=O 1633.6; 1708.8 | |
| 109 | N59 | AS1 | A0 | C1 | 1 | | 30 | ESI: (M + H)⁺ = 695/7/9 (Br₂) | 0.3 | FM1 | (KBr): C=O 1647.4 | |
| 116 | N60 | AS4 | A0 | C1 | 1 | DMF as solvent | 80 | ESI: (M + H)⁺ = 753/5/7 (Br₂) | 0.6 | FM1 | (KBr): C=O 1623.7; 1676.1; 1712.7 | |
| 117 | N60 | AS1 | A0 | C1 | 1 | DMF as solvent | 50 | ESI: (M + H)⁺ = 754/6/8 (Br₂) | 0.4 | FM1 | (KBr): C=O 1617; 1650; 1670; 1712.7 | |
| 118 | N47 | AS1 | A0 | C1 | 1 | | 29 | ESI: (M + H)⁺ = 637/9/41 (Br₂) | 0.1 | FM1 | (KBr): C=O 1639.4 | |
| 121 | N61 | AS1 | A0 | C1 | 1 | | 12.4 | ESI: (M + H)⁺ = 727/9/31 (Br₂) | 0.2 | FM1 | (KBr): C=O 1635.5; 1705 | |
| 122 | N61 | AS4 | A0 | C1 | 1 | | 42 | ESI: (M + H)⁺ = 726/8/30 (Br₂) | 0.6 | FM1 | (KBr): C=O 1620.1; 1706.9 | |
| 125 | N15 | AS7 | A0 | C1 | 1 | NEt₃ as base | 4.4 | ESI: (M + H)⁺ = 598 | 0.6 | FM1 | (KBr): C=O 1708.8 | |
| 126 | N15 | AS7 | A0 | C4 | 1 | NEt₃ as base | 57 | ESI: (M + H)⁺ = 597 | 0.6 | FM1 | (KBr): C=O 1622; 1708.8 | 188.0 |
| 127 | N15 | AS7 | A0 | C8 | 1 | NEt₃ as base | 16 | ESI: (M + H)⁺ = 603 | 0.6 | FM1 | (KBr): C=O 1622; 1697.3 | 168-170 |
| 137 | N94 | AS4 | A0 | C4 | 1 | | 42 | ESI: (M + H)⁺ = 708/10/12 (Br₂) | 0.8 | FM1 | (KBr): C=O 1618 | |
| 138 | N95 | AS4 | A0 | C8 | 1 | NEt₃ as base | 29 | ESI: (M + H)⁺ = 743/5/7 (Br₂) | 0.8 | FM1 | (KBr): C=O 1713 | |
| 139 | N61 | AS1 | A3 | C1 | 1 | | 41 | ESI: (M + H)⁺ = 955/7/9 (Br₂) | 0.4 | FM1 | (KBr): C=O 1640; 1709 | |
| 140 | N60 | AS1 | A3 | C1 | 1 | | 66 | ESI: (M + H)⁺ = 982/4/6 (Br₂) | 0.5 | FM1 | (KBr): C=O 1645; 1712 | |
| 143 | N66 | AS1 | A0 | C4 | 1 | DMF as solvent | 69 | ESI: (M + H)⁺ = 739/41/43 (Br₂) | 0.4 | FM1 | (KBr): C=O 1624; 1659 | |
| 144 | N96 | AS1 | A0 | C4 | 1 | | 54 | ESI: (M + H)⁺ = 725/7/9 (Br₂) | 0.54 | FM1 | (KBr): C=O 1616 | |
| 145 | N61 | AS1 | A0 | C4 | 1 | | 48 | ESI: (M + H)⁺ = 724/6/8 (Br₂) | 0.6 | FM1 | (KBr): C=O 1624; 1709 | |
| 146 | N15 | AS14 | A0 | C1 | 1 | DMF as solvent | 53 | ESI: (M + H)⁺ = 555 | 0.15 | FM1 | (KBr): C=O 1636; 1701 | |
| 147 | N61 | AS4 | A0 | C11 | 1 | | 30 | ESI: (M + H)⁺ = 746/48/50 (Br₂) | 0.7 | FM1 | (KBr): C=O 1620; 1713 | |
| 148 | N66 | AS1 | A0 | C8 | 1 | THF/DMF as solvent | 58 | ESI: (M + H)⁺ = 745/7/9 (Br₂) | 0.68 | FM1 | (KBr): C=O 1628; 1663 | |
| 149 | N69 | AS1 | A0 | C4 | 1 | THF/DMF as solvent | 61 | ESI: (M + H)⁺ = 739/41/43 (Br₂) | 0.68 | FM1 | (KBr): C=O 1624; 1675 | |
| 150 | N97 | AS1 | A0 | C4 | 1 | THF/DMSO as solvent | 32 | ESI: (M + H)⁺ = 783/85/87 (Br₂) | 0.4 | FM1 | (KBr): C=O 1709 | |
| 152 | N71 | AS1 | A0 | C4 | 1 | | 40 | ESI: (M + H)⁺ = 751/53/55 (Br₂) | 0.68 | FM1 | (KBr): C=O 1622; 1684 | |
| 153 | N65 | AS1 | A0 | C4 | 1 | | 51 | ESI: (M + H)⁺ = 751/53/55 (Br₂) | 0.68 | FM1 | (KBr): C=O 1626; 1678 | |
| | N66 | AS1 | A3 | C1 | 1 | | 37 | | | | | |
| 225 | N66 | AS1 | A0 | C1 | 1 | THF/DMF as solvent | 48 | ESI: (M + H)⁺ = 740/42/44 (Br₂) | 0.35 | FM1 | (KBr): C=O 1650; 1670 | |
| 226 | N66 | AS4 | A0 | C8 | 1 | THF/DMF as solvent | 88 | ESI: (M + H)⁺ = 744/6/8 (Br₂) | 0.6 | FM1 | (KBr): C=O 1618; 1661 | |
| 227 | N69 | AS4 | A0 | C8 | 1 | THF/DMF as solvent | 72 | ESI: (M + H)⁺ = 744/6/8 (Br₂) | 0.6 | FM1 | (KBr): C=O 1618; 1680 | |
| 228 | N69 | AS1 | A0 | C8 | 1 | THF/DMF as solvent | 69 | ESI: (M + H)⁺ = 745/7/9 (Br₂) | 0.45 | FM1 | (KBr): C=O 1628 | |
| 229 | N70 | AS1 | A0 | C4 | 1 | THF/DMF as solvent | 39 | ESI: (M + H)⁺ = 727/29/31 (Br₂) | 0.3 | FM1 | (KBr): C=O 1730 | |
| 230 | N66 | AS4 | A0 | C20 | 1 | | 49 | ESI: (M + H)⁺ = 758/60/62 (Br₂) | 0.55 | FM1 | (KBr): C=O 1614 | |
| 231 | N99 | AS4 | A0 | C8 | 1 | THF/DMF as solvent | 68 | ESI: (M + H)⁺ = 758/60/62 (Br₂) | 0.6 | FM1 | (KBr): C=O 1624 | |
| 239 | N71 | AS1 | A0 | C8 | 1 | THF/DMF as solvent | 59 | ESI: (M + H)⁺ = 757/59/61 (Br₂) | 0.45 | FM1 | (KBr): C=O 1626; 1680 | |
| 240 | N71 | AS4 | A0 | C11 | 1 | | 35 | ESI: (M + H)⁺ = 771/3/5 (Br₂) | 0.68 | FM1 | (KBr): C=O 1615; 1684 | |
| 241 | N71 | AS4 | A0 | C8 | 1 | | 88 | ESI: (M + H)⁺ = 756/58/60 (Br₂) | 0.68 | FM1 | (KBr): C=O 1620; 1682 | |

-continued

| No. | RCO | R² | A | NR³R⁴ | n | Remarks | % Yield | MS | R_f | Eluant | IR [cm⁻¹] | M.p. (° C.) |
|---|---|---|---|---|---|---|---|---|---|---|---|---|
| 242 | N71 | AS4 | A0 | C1 | 1 | | 40 | ESI: (M + H)⁺ = 751/3/5 (Br₂) | 0.64 | FM1 | (KBr): C═O 1615; 1684 | |
| 243 | N71 | AS4 | A0 | C20 | 1 | | 38 | ESI: (M + H)⁺ = 770/2/4 (Br₂) | 0.65 | FM1 | (KBr): C═O 1618; 1684 | |
| 244 | N71 | AS1 | A0 | C11 | 1 | | 36 | ESI: (M + H)⁺ = 772/4/6 (Br₂) | 0.35 | FM1 | (KBr): C═O 1622; 1684 | |
| | N5 | AS1 | A3 | C1 | 1 | NEt₃ as base | 24 | ESI: (M + H)⁺ = 890/2/4 (Br₂) | 0.06 | FM1 | (KBr): C═O 1641.3 | |
| | N10 | AS1 | A3 | C1 | 1 | NEt₃ as base | 55 | ESI: (M + H)⁺ = 874/6/8 (Br₂) | 0.38 | FM1 | (KBr): C═O 1641.3 | |
| | N12 | AS1 | A3 | C1 | 1 | NEt₃ as base | 35480 | ESI: (M + H)⁺ = 902/4/6 (Br₂) | 0.43 | FM1 | (KBr): C═O 1639.4 | |
| | N22 | AS1 | A3 | C1 | 1 | NEt₃ as base | 35.5 | | 0.5 | FM1 | | |
| | N23 | AS1 | A3 | C1 | 1 | NEt₃ as base | 31 | | 0.5 | FM1 | | |
| | N24 | AS1 | A3 | C1 | 1 | NEt₃ as base | 35607 | | 0.5 | FM1 | | |
| | N46 | AS1 | A3 | C1 | 1 | NEt₃ as base | 36.2 | | 0.5 | FM1 | (KBr): C═O 1641.3 | |
| 83 | N15 | AS1 | A0 | C1 | 1 | | 36.7 | ESI: (M + H)⁺ = 726/28/30 (Br₂) | 0.62 | FM2 | (KBr): C═O 1641.3; 1695.3 | |
| 84 | N15 | AS1 | A0 | C4 | 1 | | 36.3 | ESI: (M + H)⁺ = 725/7/9 (Br₂); (M + Na)⁺= 747/49/51 (Br₂) | 0.69 | FM2 | (KBr): C═O 1624.0; 1699.2 | |
| 88 | N55 | AS4 | A0 | C1 | 1 | | 93.6 | ESI: (M + H)⁺ = 793/5/7/9 (Br₂; Cl₂) | 0.75 | FM3 | (KBr): C═O 1641.3; 1708.8 | |
| 89 | N56 | AS4 | A0 | C1 | 1 | | 30 | ESI: (M + H)⁺ = 797/799/801 (Br₂) | 0.81 | FM1 | (KBr): C═O 1641.3; 1697.3; 1749.3 | |
| 136 | N15 | AS9 | A0 | C1 | 1 | | 14.6 | ESI: (M + H)⁺ = 570 | 0.55 | FM3 | (KBr): C═O 1635.5; 1701.1 | |
| 91 | N64 | AS4 | A0 | C1 | 1 | | 11.7 | ESI: (M + H)⁺ = 731/733/735 | 0.62 | FM3 | (KBr): C═O 1625.9; 1685.7 | |
| | N16 | AS1 | A3 | C5 | 1 | Purification by column chromatography: silica gel/FM4 | 74 | ESI: (M + H)⁺ = 974/976/978 (Br₂) | 0.48 | FM4 | (KBr): C═O 1685.7; 1635.5 | |
| 155 | N15 | AS1 | A0 | C3 | 1 | | 34 | ESI: (M + H)⁺ = 743/5/7 (Br₂) | 0.45 | FM1 | (KBr): C═O 1626; 1695 | 165-9 |
| 156 | N15 | AS1 | A0 | C19 | 1 | | 40 | ESI: (M + H)⁺ = 743/5/7 (Br₂) | 0.47 | FM1 | (KBr): C═O 1624; 1695 | 155-9 |
| 157 | N15 | AS4 | A0 | C19 | 1 | | 54 | ESI: (M + H)⁺ = 742/4/6 (Br₂) | 0.79 | FM1 | (KBr): C═O 1616; 1697 | 151-4 |
| 158 | N79 | AS4 | A0 | C1 | 1 | | 15 | ESI: (M + H)⁺ = 727/29/31 (Br₂) | 0.63 | FM1 | (KBr): C═O 1616; 1695; 1732 | 132-5 |
| 159 | N77 | AS4 | A0 | C8 | 1 | | 34 | ESI: (M + H)⁺ = 732/4/6 (Br₂) | 0.63 | FM1 | (KBr): C═O 1632 | |
| 160 | N73 | AS1 | A0 | C4 | 1 | | 12 | ESI: (M − H)⁻ = 649/651/653 (Br₂) | 0.14 | FM1 | (KBr): C═O 1626 | |
| 170 | N15 | AS4 | A0 | C37 | 1 | | 62 | ESI: (M − H)⁻ = 725/7/9 (Br₂) | 0.45 | FM1 | (KBr): C═O 1620; 1701 | 165-70 |
| 171 | N79 | AS1 | A0 | C1 | 1 | | 60 | ESI: (M + H)⁺ = 728/30/32 (Br₂) | 0.21 | FM1 | (KBr): C═O 1637.5 | 193-7 |
| 172 | N79 | AS1 | A0 | C8 | 1 | | 27 | ESI: (M + H)⁺ = 733/5/7 (Br₂) | 0.32 | FM1 | (KBr): C═O 1622 | 163-9 |
| 185 | N77 | AS4 | A0 | C4 | 1 | | 66 | ESI: (M + H)⁺ = 726/28/30 (Br₂) | 0.49 | FM1 | (KBr): C═O 1624 | |
| 186 | N77 | AS4 | A0 | C1 | 1 | | 76 | ESI: (M + H)⁺ = 727/29/31 (Br₂) | 0.63 | FM1 | (KBr): C═O 1635.5 | |
| 187 | N77 | AS1 | A0 | C4 | 1 | | 67 | ESI: (M + H)⁺ = 727/29/31 (Br₂) | 0.33 | FM1 | (KBr): C═O 1627.8 | |
| 188 | N78 | AS1 | A3 | C1 | 1 | | 63 | ESI: (M + H)⁺ = 955/7/9 (Br₂) | 0.45 | FM1 | (KBr): C═O 1637.5; 1774.4; 1701 | |
| 189 | N103 | AS4 | A0 | C8 | 1 | | 50 | ESI: (M + H)⁺ = 713/5/7 (Br₂) | 0.71 | FM1 | (KBr): C═O 1616.3 | |
| 192 | N77 | AS1 | A0 | C1 | 1 | | 47 | ESI: (M + H)⁺ = 728/30/32 (Br₂) | 0.2 | FM1 | (KBr): C═O 1643.3 | |
| 247 | N15 | AS10 | A3 | C4 | 1 | | 60 | ESI: (M + H)⁺ = 937/39/41 (Br₂) | 0.6 | FM1 | (KBr): C═O 1639.4; 1701 | |
| 249 | N15 | AS4 | A0 | C22 | 1 | | 52 | ESI: (M + H)⁺ = 744/6/8 (Br₂) | 0.59 | FM1 | (KBr): C═O 1695.3 | |
| 161 | N15 | AS4 | A0 | C21 | 1 | | 32 | ESI: (M + H)⁺ = 726/28/30 (Br₂) | 0.61 | FM1 | (KBr): C═O 1622; 1701 | 163-7 |

| No. | RCO | R² | A | NR³R⁴ | n | Remarks | % Yield | MS | R_f | Eluant | IR [cm⁻¹] | M.p. (° C.) |
|---|---|---|---|---|---|---|---|---|---|---|---|---|
| 162 | N78 | AS1 | A0 | C4 | 1 | | 15 | ESI: (M + H)⁺ = 726/28/30 (Br₂) | 0.48 | FM1 | (KBr): C=O 1624; 1772.5 | |
| 163 | N73 | AS1 | A0 | C1 | 1 | | 43 | ESI: (M + H)⁺ = 752/4/6 (Br₂) | 0.07 | FM1 | (KBr): C=O 1637.5 | |
| 164 | N79 | AS4 | A0 | C8 | 1 | | 48 | ESI: (M + H)⁺ = 732/4/6 (Br₂) | 0.6 | FM1 | (KBr): C=O 1616.3 | 127-32 |
| 165 | N15 | AS1 | A0 | C21 | 1 | | 27 | ESI: (M + H)⁺ = 727/29/31 (Br₂) | 0.26 | FM1 | (KBr): C=O 1697.3 | 184-9 |
| 166 | N76 | AS1 | A0 | C4 | 1 | | 17 | ESI: (M + H)⁺ = 665/7/9 (Br₂) | 0.23 | FM1 | (KBr): C=O 1616; 1734 | |
| 167 | N75 | AS1 | A0 | C4 | 1 | | 20 | ESI: (M + H)⁺ = 665/7/9 (Br₂) | 0.18 | FM1 | (KBr): C=O 1624 | |
| 168 | N73 | AS1 | A3 | C4 | 1 | | 39 | ESI: (M + H)⁺ = 879/81/83 (Br₂) | 0.15 | FM1 | (KBr): C=O 1631.7 | |
| 169 | N15 | AS1 | A0 | C37 | 1 | | 17 | ESI: (M + H)⁺ = 726/28/30 (Br₂) | 0.31 | FM1 | (KBr): C=O 1627.8; 1697.3 | 156-61 |
| 173 | N15 | AS10 | A0 | C4 | 1 | | 66 | ESI: (M + H)⁺ = 709/11/13 (Br₂) | 0.68 | FM1 | (KBr): C=O 1627.8; 1656.8; 1695.3 | 283-4 |
| 174 | N15 | AS10 | A0 | C1 | 1 | | 42 | ESI: (M + H)⁺ = 710/2/4 (Br₂) | 0.61 | FM1 | (KBr): C=O 1706.9 | 266-9 |
| 175 | N77 | AS1 | A0 | C8 | 1 | | 36 | ESI: (M + H)⁺ = 733/5/7 (Br₂) | 0.24 | FM1 | (KBr): C=O 1641.3 | |
| 176 | N76 | AS1 | A3 | C4 | 1 | | 47 | ESI: (M + H)⁺ = 893/5/7 (Br₂) | 0.21 | FM1 | (KBr): C=O 1635.5 | |
| 177 | N75 | AS1 | A3 | C4 | 1 | | 53 | ESI: (M + H)⁺ = 893/5/7 (Br₂) | 0.14 | FM1 | (KBr): C=O 1637.5 | |
| 180 | N74 | AS1 | A3 | C4 | 1 | | 44 | ESI: (M + H)⁺ = 907/9/11 (Br₂) | 0.26 | FM1 | (KBr): C=O 1631.7; 1689.5 | |
| 190 | N15 | AS1 | A3 | C18 | 1 | | 44 | ESI: (M + H)⁺ = 985/7/9 (Br₂) | 0.38 | FM1 | (KBr): C=O 1635.5; 1695.3 | |
| 191 | N15 | AS10 | A3 | C1 | 1 | | 64 | ESI: (M + H)⁺ = 938/40/42 (Br₂) | 0.56 | FM1 | (KBr): C=O 1645.2; 1701 | |
| | N15 | AS10 | A3 | C4 | 1 | | 91 | ESI: (M + H)⁺ = 937/39/41 (Br₂) | | | (KBr): C=O 1643.3; 1701 | |
| | N15 | AS10 | A3 | C1 | 1 | | 64 | ESI: (M + H)⁺ = 938/40/42 (Br₂) | | | (KBr): C=O 1645; 1701 | |
| 254 | N77 | AS1 | A3 | C1 | 1 | | 37 | ESI: (M + H)⁺ = 956/8/60 (Br₂) | 0.3 | FM1 | (KBr): C=O 1641 | |
| | N15 | AS4 | A3 | C18 | 1 | | 90 | ESI: (M + H)⁺ = 984/6/8 (Br₂) | | | (KBr): C=O 1641.3; 1699 | |
| 257 | N15 | AS4 | A5 | C1 | 1 | | 17 | ESI: (M + H)⁺ = 782/4/6 (Br₂) | 0.53 | FM1 | (KBr): C=O 1643; 1697 | |
| 258 | N100 | AS4 | A0 | C1 | 1 | | 69 | ESI: (M + H)⁺ = 755/7/9 (Br₂) | 0.54 | FM1 | (KBr): C=O 1627.8; 1705 | |
| 259 | N100 | AS4 | A0 | C8 | 1 | | 70 | ESI: (M + H)⁺ = 760/2/4 (Br₂) | 0.54 | FM1 | (KBr): C=O 1695 | |
| 260 | N15 | AS4 | A0 | C23 | 1 | | 39 | ESI: (M + H)⁺ = 796/798/800 (Br₂) | 0.36 | FM1 | (KBr): C=O 1635.5; 1699 | |
| 261 | N15 | AS4 | A10 | C1 | 1 | | 26 | ESI: (M + H)⁺ = 796/798/800 (Br₂) | 0.38 | FM1 | (KBr): C=O 1631.4; 1701 | |
| 265 | N15 | AS4 | A5 | C8 | 1 | | 20 | ESI: (M + H)⁺ = 787/9/91 (Br₂) | 0.41 | FM1 | (KBr): C=O 1635.5; 1697 | |
| 266 | N15 | AS4 | A6 | C1 | 1 | | 24 | ESI: (M + H)⁺ = 796/798/800 (Br₂) | 0.43 | FM1 | (KBr): C=O 1647; 1689.5 | |
| 262 | N80 | AS4 | A0 | C1 | 1 | | 25 | ESI: (M + H)⁺ = 803/5/7 (Br₂) | 0.54 | FM1 | (KBr): C=O 1637.5 | |
| 263 | N15 | AS15 | A0 | C8 | 1 | | 64 | ESI: (M + H)⁺ = 565 | 0.43 | FM1 | (KBr): C=O 1627.8; 1707 | |
| 264 | N15 | AS4 | A0 | C24 | 1 | | 62 | ESI: (M + H)⁺ = 733/5/7 (Br₂) | 0.4 | FM1 | (KBr): C=O 1622; 1701 | |
| 267 | N81 | AS4 | A3 | C8 | 1 | | 46 | ESI: (M + H)⁺ = 974/6/8 (Br₂) | 0.55 | FM1 | (KBr): C=O 1641; 1707 | |
| 268 | N15 | AS4 | A6 | C8 | 1 | | 27 | ESI: (M + H)⁺ = 801/3/5 (Br₂) | 0.5 | FM1 | (KBr): C=O 1633.6; 1697 | |
| 269 | N82 | AS4 | A0 | C8 | 1 | | 86 | ESI: (M + H)⁺ = 742/4/6 (Br₂) | 0.66 | FM1 | (KBr): C=O 1620; 1649 | |
| 270 | N82 | AS4 | A0 | C1 | 1 | | 56 | ESI: (M + H)⁺ = 737/39/41 (Br₂) | 0.59 | FM1 | (KBr): C=O 1641 | |
| 272 | N15 | AS11 | A0 | C8 | 1 | | 76 | ESI: (M + H)⁺ = 698 | 0.6 | FM1 | (KBr): C=O 1627.8; 1714.6 | |
| 273 | N15 | AS4 | A10 | C8 | 1 | | 68 | ESI: (M + H)⁺ = 801/3/5 (Br₂) | 0.52 | FM1 | (KBr): C=O 1637.5; 1701 | |
| 274 | N102 | AS4 | A0 | C1 | 1 | | 76 | ESI: (M + H)⁺ = 738/40/42 (Br₂) | 0.56 | FM1 | (KBr): C=O 1664.5 | |

-continued

| No. | RCO | R² | A | NR³R⁴ | n | Remarks | % Yield | MS | $R_f$ | Eluant | IR [cm⁻¹] | M.p. (° C.) |
|---|---|---|---|---|---|---|---|---|---|---|---|---|
| 275 | N102 | AS4 | A0 | C8 | 1 | | 55 | ESI: (M + H)⁺ = 743/5/7 (Br₂) | 0.59 | FM1 | (KBr): C═O 1618; 1664.5 | |
| 276 | N83 | AS4 | A0 | C1 | 1 | | 30 | ESI: (M + H)⁺ = 745/7/9 (Br₂) | 0.48 | FM1 | (KBr): C═O 1633.6 | |
| 277 | N84 | AS4 | A0 | C8 | 1 | | 63 | ESI: (M + H)⁺ = 744/6/8 (Br₂) | 0.54 | FM1 | (KBr): C═O 1616; 1691.5 | |
| 278 | N84 | AS4 | A3 | C4 | 1 | | 88 | ESI: (M + H)⁺ = 966/8/70(Br₂) | 0.53 | FM1 | (KBr): C═O 1633.6; 1691.5 | |
| 279 | N15 | AS4 | A0 | C26 | 1 | | 75 | ESI: (M + H)⁺ = 732/4/6 (Br₂) | 0.44 | FM1 | (KBr): C═O 1618; 1709 | |
| 281 | N15 | AS12 | A0 | C8 | 1 | | 21 | ESI: (M + H)⁺ = 598 | 0.42 | FM1 | (KBr): C═O 1697 | |
| 282 | N66 | AS1 | A0 | C18 | 1 | | 19 | ESI: (M + H)⁺ = 770/2/4 (Br₂) | 0.51 | FM1 | (KBr): C═O 1624; 1660.6; 1734 | |
| 284 | N66 | AS1 | A0 | C18 | 1 | | 29 | ESI: (M + H)⁺ = 771/3/5 (Br₂) | 0.3 | FM1 | (KBr): C═O 1630; 1655 | |
| 314 | N93 | AS4 | A0 | C8 | 1 | | 81 | ESI: (M + H)⁺ = 794/6/8 (Br₂) | 0.5 | FM1 | (KBr): C═O 1618; 1701 | |
| 315 | N93 | AS4 | A0 | C1 | 1 | | 77 | ESI: (M + H)⁺ = 789/91/93 (Br₂) | 0.49 | FM1 | (KBr): C═O 1627.6; 1705 | |
| 316 | N65 | AS1 | A0 | C18 | 1 | | 15 | ESI: (M + H)⁺ = 783/5/7 (Br₂) | 0.3 | FM1 | (KBr): C═O 1624; 1681.8 | |
| 317 | N66 | AS4 | A0 | C3 | 1 | | 51 | ESI: (M + H)⁺ = 778/80/82 (Br₂) | 0.62 | FM1 | (KBr): C═O 1627.6; 1662.5 | |
| 318 | N66 | AS1 | A0 | C3 | 1 | | 40 | ESI: (M + H)⁺ = 557/559/561 (Br₂) | 0.41 | FM1 | (KBr): C═O 1659 | |
| 319 | N66 | AS4 | A0 | C19 | 1 | | 55 | ESI: (M + H)⁺ = 778/780/782 (Br₂) | 0.68 | FM1 | (KBr): C═O 1664.5 | |
| 320 | N65 | AS4 | A0 | C19 | 1 | | 61 | ESI: (M + H)⁺ = 768/70/72 (Br₂) | 0.62 | FM1 | (KBr): C═O 1618; 1682 | |
| 321 | N93 | AS1 | A0 | C4 | 1 | | 29 | ESI: (M + H)⁺ = 789/91/93 (Br₂) | 0.35 | FM1 | (KBr): C═O 1622; 1705 | |
| | N15 | AS1 | A3 | C5 | 1 | | 47 | | 0.32 | FM1 | | |
| | N19 | AS1 | A3 | C1 | 1 | | 80 | ESI: (M + H)⁺ = 933/5/7 (Br₂) | | | (KBr): C═O 1641.3 | |

EXAMPLE 5

Preparation of Compounds of General Formula:

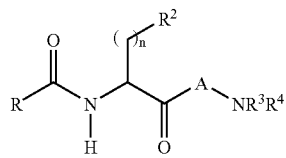

1-[N²—[N-(4-phenyl-1-piperazinyl)carbonyl]-3,5-dibromo-D-tyrosyl]-L-lysyl]-4-(4-pyridinyl)-piperazine (No. 17)

To a solution of 800 mg (0.86 mmol) of 1-[N²—[N-(4-phenyl-1-piperazinyl)carbonyl]-3,5-dibromo-D-tyrosyl]-N⁶-[(1,1-dimethyl-ethoxy)carbonyl]-L-lysyl]-4-(4-pyridinyl)-piperazine in methanol were added 2 ml of methanol saturated with hydrogen chloride and the mixture was stirred overnight at ambient temperature. The reaction mixture was mixed with ethyl acetate until the hydrochloride was totally precipitated and the precipitate formed was filtered off. After washing the precipitate with water it was purified by column chromatography (MN-silica gel 60, Macherey-Nagel, 70-230 mesh ASTM, eluant:ethyl acetate/methanol/conc. aqueous ammonia=5/5/0.5 (v/v/v)). 0.38 g (55% of theory) of an amorphous solid were obtained.

| | |
|---|---|
| IR (KBr): | 1639 cm⁻¹ (C═O) |
| Rf: | 0.55 (FM2) |
| ESI-MS: | (M + H)⁺ = 799/801/803 (Br₂) |
| | (M + 2H)⁺⁺ = 400/401/402 (Br₂) |

The following were prepared analogously (in each case n=1):

| No. | RCO | R² | A | n | NR³R⁴ | % Yield | MS | $R_f$ | Eluant | IR [cm⁻¹] |
|---|---|---|---|---|---|---|---|---|---|---|
| 11 | N8 | AS1 | A1 | 1 | C1 | 70 | ESI: (M + H)⁺ = 758/60/62 (Br₂) | 0.43 | FM2 | (KBr): C═O 1656.8 |
| 12 | N9 | AS1 | A1 | 1 | C1 | 60 | ESI: (M + H)⁺ = 788/90/92 (Br₂) | 0.46 | FM2 | (KBr): C═O 1643.3 |

-continued

| No. | RCO | R² | A | n | NR³R⁴ | % Yield | MS | $R_f$ | Eluant | IR [cm⁻¹] |
|---|---|---|---|---|---|---|---|---|---|---|
| 8 | N5 | AS1 | A1 | 1 | C1 | 53.7 | ESI: (M + H)⁺ = 790/2/4 (Br₂) | 0.2 | methanol/ glacial acetic acid/water = 9/1/1 (v/v/v) | (KBr): C=O 1641.3 |
| 15 | N11 | AS1 | A1 | 1 | C1 | 56 | ESI: (M + H)⁺ = 773/5/7 (Br₂) | 0.4 | FM2 | |
| 6 | N2 | AS1 | A1 | 1 | C11 | 66.4 | ESI: (M + H)⁺ = 808/10/12 (Br₂) | 0.39 | FM2 | (KBr): C=O 1656.8 |
| 7 | N2 | AS1 | A1 | 1 | C2 | 46.2 | ESI: (M + H)⁺ = 794/6/8 (Br₂) | 0.13 | FM2 | (KBr): C=O 1637.5 |
| 13 | N2 | AS2 | A1 | 1 | C1 | 84.7 | ESI: (M + H)⁺ = 666 | 0.46 | FM2 | (KBr): C=O 1641.3 |

EXAMPLE 6

Preparation of Compounds of General Formula:

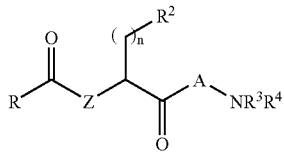

1-[4-amino-3,5-dibromo-N²—[N-[4-(2-chlorophenyl)-1-piperazinyl]carbonyl]-D-phenylalanyl]-L-lysyl]-4-(4-pyridinyl)-piperazine-bis-(trifluoroacetate) (No. 61)

To a mixture of 0.42 g (0.45 mmol) of 1-[4-amino-3,5-dibromo-N²-[4-(2-chlorophenyl)-1-piperazinyl]carbonyl]-D-phenylalanyl]-N6-[(1.1-dimethylethoxy)carbonyl]-L-lysyl]-4-(4-pyridinyl)-piperazine in 30 ml of methylene chloride were added 3 ml of trifluoroacetic acid. The reaction mixture was stirred for 3 hours at ambient temperature and then evaporated down in vacuo. The remaining residue was triturated with ether and the resulting beige amorphous solid (0.43 g; 37% of theory) was suction filtered.

IR (KBr): 1643, 1678 cm⁻¹ (C=O)
$R_f$: 0.6 (FM1)
ESI-MS: (M+H)⁺=832/834/836/838 (Br₂, Cl)
The following were prepared analogously:

| No. | RCO | Z | R² | A | NR³R⁴ | n | Remarks | % Yield | MS | $R_f$ | Eluant | IR [cm⁻¹] |
|---|---|---|---|---|---|---|---|---|---|---|---|---|
| 21 | N6 | N—H | AS1 | A1 | C4 | 1 | | 65 | ESI: (M + H)⁺ = 828/30/32 (Br₂) | 0.3 | FM1 | (KBr): C=O 1635.5 |
| 22 | N16 | N—H | AS1 | A1 | C1 | 1 | | 98 | ESI: (M + H)⁺ = 874/6/8 (Br₂) | 0.2 | FM1 | (KBr): C=O 1643.3; 1676 |
| 141 | N61 | N—H | AS1 | A1 | C1 | 1 | | 46 | ESI: (M + H)⁺ = 855/7/9 (Br₂) | 0.1 | FM1 | (KBr): C=O 1634; 1705 |
| 142 | N60 | N—H | AS1 | A1 | C1 | 1 | | 50 | ESI: (M + H)⁺ = 882/4/6 (Br₂) | 0.1 | FM1 | (KBr): C=O 1643; 1711 |
| 154 | N66 | N—H | AS1 | A1 | C1 | 1 | | 60 | ESI: (M + H)⁺ = 868/70/72 (Br₂) | 0.1 | FM1 | (KBr): C=O 1645; 1653 |
| 197 | N15 | N—H | AS1 | A1 | C8 | 1 | | 21 | ESI: (M + H)⁺ = 859/61/63 (Br₂) | 0.18 | FM7 | (KBr): C=O 1678; 1201.6; CF3 1180.4; 1134.1 |
| 198 | N51 | N—H | AS1 | A1 | C8 | 1 | | 27 | ESI: (M + H)⁺ = 829/31/33 (Br₂) | 0.22 | FM7 | (KBr): C=O 1676; CN 2221.9; CF3 1203.5; 1180.4; 1132 |
| 218 | N15 | N—H | AS6 | A1 | C1 | 1 | | 25.7 | ESI: (M + H)⁺ = 776/8 (Br) | 0.45 | FM1 | (KBr): C=O 1695.3; 1635.5 |
| 287 | N15 | N—H | AS1 | A8 | C1 | 1 | | 36.5 | ESI: (M + H)⁺ = 840/2/4 (Br₂) | 0.5 | FM2 | (KBr): C=O 1695.3; 1637.5 |
| 19 | N15 | N—H | AS1 | A1 | C1 | 1 | | 44 | ESI: (M + H)⁺ = 854/6/8 (Br₂) | 0.43 | FM2 | (KBr): C=O 1695.3; 1637.5 |
| 14 | N10 | N—H | AS1 | A1 | C1 | 1 | | 25.5 | ESI: (M + H)⁺ = 774/6/8 (Br₂) | 0.33 | FM2 | (KBr): C=O 1683.8 |
| 16 | N12 | N—H | AS1 | A1 | C1 | 1 | | 64.4 | ESI: (M + H)⁺ = 802/4/6 (Br₂) | 0.55 | FM2 | (KBr): C=O 1639.4 |
| 29 | N22 | N—H | AS1 | A1 | C1 | 1 | | 91.2 | ESI: (M + H)⁺ = 867/69/71 (Br₂) | 0.5 | FM2 | (KBr): —NH— 3427.3; C=O 1643.3; 1678.0 |

-continued

| No. | RCO | Z | R² | A | NR³R⁴ | n | Remarks | % Yield | MS | R_f | Eluant | IR [cm⁻¹] |
|---|---|---|---|---|---|---|---|---|---|---|---|---|
| 30 | N23 | N—H | AS1 | A1 | C1 | 1 | | 83.3 | ESI: (M + H)⁺ = 833/5/7/9 (Br₂, Cl) | 0.5 | FM2 | (KBr): C=O 1643.3; 1676.0 |
| 31 | N24 | N—H | AS1 | A1 | C1 | 1 | | 100 | ESI: (M + H)⁺ = 843/5/7 (Br₂) | 0.51 | FM2 | (KBr): C=O 1645.2; 1676.0 |
| 63 | N46 | N—H | AS1 | A1 | C1 | 1 | | 100 | ESI: (M + H)⁺ = 764/6/8 (Br₂) | 0.58 | FM2 | (KBr): C=O 1643.3; 1676.0 |
| 68 | N15 | N—H | AS1 | A1 | C6 | 1 | | 80 | ESI: (M + H)⁺ = 833/5/7 (Br₂) | 0.18 | FM1 | (KBr): C=O 1683.8 |
| 69 | N15 | N—H | AS1 | A1 | C5 | 1 | | 74 | ESI: (M + H)⁺ = 854/6/8 (Br₂) | 0.18 | FM1 | (KBr): C=O 1683.8; 1639.4 |
| 70 | N45 | N—H | AS1 | A1 | C6 | 1 | | 89 | ESI: (M + H)⁺ = 897/9/901 (Br₂) | 0.2 | FM1 | (KBr): C=O 1695.3; 1676.0 |
| 71 | N16 | N—H | AS1 | A1 | C5 | 1 | | 82 | ESI: (M + H)⁺ = 874/6/8 (Br₂) | 0.22 | FM1 | (KBr): C=O 1678.0; 1639.4 |
| 72 | N15 | N—H | AS5 | A1 | C1 | 1 | | 97 | ESI: (M + H)⁺ = 838/40/42 (Br₂) | 0.16/0.2 | FM1 | (KBr): C=O 1685.7; 1643.3 |
| 77 | N45 | N—H | AS5 | A1 | C1 | 1 | | 66 | ESI: (M + H)⁺ = 852/4/6 (Br₂) | 0.33/0.4 | FM1 | (KBr): C=O 1683.8; 1645.2 NH₃ 3427.3 |
| 24 | N18 | N—H | AS1 | A1 | C1 | 1 | | 94 | ESI: (M + H)⁺ = 775/7/9 (Br₂) | 0.11 | FM1 | (KBr): C=O 1676.0; 1643.3 |
| 25 | N19 | N—H | AS1 | A1 | C1 | 1 | | 92 | ESI: (M + H)⁺ = 833/5/7 (Br₂) | 0.13 | FM1 | (KBr): C=O 1676.0; 1643.3 |
| 26 | N20 | N—H | AS1 | A1 | C1 | 1 | | 98 | EI: M⁺ = 762/4/6 (Br₂) | 0.11 | FM1 | (KBr): C=O 1676.0; 1643.3 |
| 27 | N21 | N—H | AS1 | A1 | C1 | 1 | | 98 | ESI: (M + H)⁺ = 814/6/8 (Br₂) | 0.04 | FM1 | (KBr): C=O 1676.0; 1645.2 |
| 41 | N34 | N—H | AS1 | A1 | C1 | 1 | | 97 | ESI: (M + H)⁺ = 835/38/40/42 (Br₃) | 0.08 | FM1 | (KBr): C=O 1676.0; 1643.3 |
| 42 | N35 | N—H | AS1 | A1 | C1 | 1 | | 83 | ESI: (M + H)⁺ = 803/5/7 (Br₂) | 0.09 | FM1 | (KBr): C=O 1676.0; 1643.3 |
| 43 | N36 | N—H | AS1 | A1 | C1 | 1 | | 87 | ESI: (M + H)⁺ = 815/7/9 (Br₂) | 0.04 | FM1 | (KBr): C=O 1676.0; 1645.2 |
| 53 | N42 | N—H | AS1 | A1 | C1 | 1 | | 89 | ESI: (M + H)⁺ = 805/7/9 (Br₂) | 0.11 | FM1 | (KBr): C=O 1676.0; 1634.3 |
| 54 | N43 | N—H | AS1 | A1 | C1 | 1 | | 84 | ESI: (M + H)⁺ = 835/7/9/41 (Br₃) | 0.11 | FM1 | (KBr): C=O 1678.0; 1643.3 |
| 55 | N44 | N—H | AS1 | A1 | C1 | 1 | | 95 | ESI: (M + H)⁺ = 796/8/800 (Br₂) | 0.07 | FM1 | (KBr): C=O 1676.0; 1643.3 |
| 67 | N48 | N—H | AS1 | A1 | C1 | 1 | | 90 | ESI: (M + H)⁺ = 797/99/801 (Br₂) | 0.06 | FM1 | (KBr): C=O 1682.9; 1643.3 |
| 184 | N77 | N—H | AS1 | A1 | C4 | 1 | | 88 | ESI: (M + H)⁺ = 855/7/9 (Br₂) | 0.11 | FM1 | (KBr): C=O 1637.5; 1676 |
| 248 | N78 | N—H | AS1 | A1 | C1 | 1 | | 97 | ESI: (M + H)⁺ = 855/7/9 (Br₂) | 0.14 | FM1 | (KBr): C=O 1643.3; 1676; 1772.5 |
| 181 | N75 | N—H | AS1 | A1 | C4 | 1 | | 95 | ESI: (M + H)⁺ = 793/5/7 (Br₂) | 0.04 | FM1 | (KBr): C=O 1637.5; 1676 |
| 182 | N76 | N—H | AS1 | A1 | C4 | 1 | | 93 | ESI: (M + H)⁺ = 793/5/7 (Br₂) | 0.04 | FM1 | (KBr): C=O 1637.5; 1678 |
| 183 | N74 | N—H | AS1 | A1 | C4 | 1 | | 91 | ESI: (M + H)⁺ = 807/9/11 (Br₂) | 0.08 | FM1 | (KBr): C=O 1635.5; 1678 |
| 250 | N15 | N—H | AS1 | A1 | C18 | 1 | | 98 | ESI: (M + H)⁺ = 885/7/9 (Br₂) | 0.14 | FM1 | (KBr): C=O 1633.6; 1680 |
| 251 | N15 | N—H | AS10 | A1 | C4 | 1 | | 84 | ESI: (M + H)⁺ = 837/39/41 (Br₂) | 0.27 | FM1 | (KBr): C=O 1635.5; 1693.4 |
| 252 | N15 | N—H | AS10 | A1 | C4 | 1 | | 87 | ESI: (M + H)⁺ = 837/39/41 (Br₂) | 0.31 | FM1 | (KBr): C=O 1637.5; 1685.7 |
| 253 | N15 | N—H | AS10 | A1 | C1 | 1 | | 82 | ESI: (M + H)⁺ = 838/40/42 (Br₂) | 0.18 | FM1 | (KBr): C=O 1690 |
| 255 | N77 | N—H | AS1 | A1 | C1 | 1 | | 94 | ESI: (M + H)⁺ = 856/8/60 (Br₂) | 0.08 | FM1 | (KBr): C=O 1645; 1676 |
| 256 | N15 | N—H | AS4 | A1 | C18 | 1 | | 74 | ESI: (M + H)⁺ = 884/6/8 (Br₂) | 0.28 | FM1 | (KBr): C=O 1633.6; 1683.8 |
| 271 | N81 | N—H | AS4 | A1 | C8 | 1 | | 76 | ESI: (M + H)⁺ = 874/6/8 (Br₂) | 0.2 | FM1 | (KBr): C=O 1674 |
| 280 | N84 | N—H | AS4 | A1 | C4 | 1 | | 66 | ESI: (M + H)⁺ = 866/8/70 (Br₂) | 0.26 | FM1 | (KBr): C=O 1635.5; 1685.7 |
| | N15 | N—H | AS1 | A1 | C1 | 0 | | 98 | ESI: (M + H)⁺ = 840/2/4 (Br₂) | 0.2 | ButOH/AcOH/H2O = 4/1/1 (v/v/v) | (KBr): C=O 1643; 1680 |
| 179 | N73 | N—H | AS1 | A1 | C4 | 1 | | 86 | ESI: (M + H)⁺ = 779/81/83 (Br₂) | 0.03 | FM1 | (KBr): C=O 1642.8; 1676 |

-continued

| No. | RCO | Z | R² | A | NR³R⁴ | n | Remarks | % Yield | MS | R_f | Eluant | IR [cm⁻¹] |
|---|---|---|---|---|---|---|---|---|---|---|---|---|
|  | N66 | N—H | AS4 | A0 |  | 1 |  | 75 | ESI: (M + H)⁺ = 744/6/8 (Br₂) | 0.3 | FM1 | (KBr): C=O 1620/1666 |
| 516 | N66 | N—H | AS1 | A1 | C1 | 1 | Isomer to No. (154) | 82 |  | 0.1 | FM1 |  |
| 517 | N66 | N—H | AS1 | A1 | C1 | 1 | Isomer to No. (154) | 80 |  | 0.1 | FM1 |  |
| 518 | N66 | N—H | AS1 | A1 | C1 | 1 | Isomer to No. (154) | 89 |  | 0.1 | FM1 |  |
| 521 | N66 | N—H | AS4 | A0 | C17 | 1 | THF/DMF | 75 | ESI: (M + H)⁺ = 744/6/8 (Br₂) | 0.15 | FM1 | (KBr): C=O 1666/1620 |
| 522 | N66 | N—H | AS1 | A0 | C17 | 1 | THF/DMF | 100 | ESI: (M + H)⁺ = 745/7/9 (Br₂) | 0.15 | FM1 | (KBr): C=O 1624/1655 |
| 643 | N66 | CH₂ | AS21 | A0 | C17 | 1 |  | 53 | ESI: (M + H)⁺ = 640 | 0.35 | FM1 | (KBr): C=O 1635/1668 |
|  | N66 | CH₂ | AS2 | A0 | C17 | 1 |  | 100 | EI: M⁺ = 621 | 0.35 | FM1 | (KBr): C=O 1670 |

EXAMPLE 7

Preparation of Compounds of General Formula:

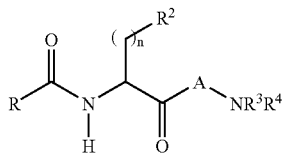

1-[N²—[N-[[[(2-methoxyphenyl)methyl]amino]carbonyl]-3,5-dibromo-D,L-tyrosyl]-L-lysyl]-4-(4-pyridinyl)-piperazine A mixture of 910 mg (1.0 mmol) of 1-[N²—[N-[[[2-(2-methoxy-phenyl)methyl]amino]carbonyl]-3,5-dibromo-D,L-tyrosyl]-N⁶-[(phenylmethoxy)carbonyl]-L-lysyl]-4-(4-pyridinyl)-piperazine, 50 ml of glacial acetic acid, 25 ml of a 33% solution of hydrogen bromide in glacial acetic acid and 2 ml of anisole was stirred overnight at ambient temperature. The reaction mixture was stirred into diethylether and the sticky precipitate formed was suction filtered. The crude product was purified by column chromatography (MN-silica gel 60, Macherey-Nagel, 70-230 mesh ASTM, eluant:ethyl acetate/methanol/conc. aqueous ammonia=8/2/0.2 (v/v/v)). 0.37 g (48% of theory) of an amorphous solid were obtained.

| IR (KBr): | 1630 cm⁻¹ (C=O) |  |
|---|---|---|
| ESI-MS: | (M + H)⁺ = | 774/776/778 (Br₂) |
|  | (M + 2H)⁺⁺ = | 387.7/388.7/389.7 (Br₂) |

The following were prepared analogously (in each case n=1):

| No. | RCO | R² | A | NR³R⁴ | % Yield | MS | R_f | Eluant | IR [cm⁻¹] |
|---|---|---|---|---|---|---|---|---|---|
| 1 | N1 | AS1 | A1 | C1 | 46.9 | ESI: (M + H)⁺ = 788/90/92 (Br₂) | 0.36 | FM1 | (KBr): C=O 1627.8 |
| 2 | N2 | AS1 | A1 | C1 | 100 | ESI: (M + H)⁺ = 788/90/92 (Br₂) | 0.48 | FM2 | (KBr): C=O 1641.3; NH, NH⁺ 3419.6 |
| 4 | N4 | AS1 | A1 | C1 | 2.8 | ESI: (M + H)⁺ = 818/20/22 (Br₂) | 0.52 | FM2 |  |

EXAMPLE 8

Preparation of Compounds of General Formula:

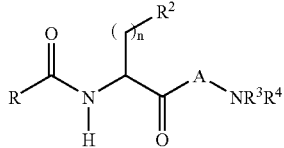

1-[$N^2$—[N-[4-(4-fluorophenyl)-1-oxobutyl]-3,5-dibromo-D-tyrosyl]-$N^6$-[(1.1-dimethylethoxy)carbonyl]-L-lysyl]-4-(4-pyridinyl)-piperazine To a solution of 0.18 g (0.001 mol) 4-(4-fluorophenyl)-butanoic acid in a mixture of 4 ml of dimethylformamide and 10 ml of tetrahydrofuran was added with stirring a mixture of 0.71 g (0.001 mol) 1-[N2-(3,5-dibromo-D-tyrosyl)-$N^6$-[(phenylmethoxy)carbonyl]-L-lysyl]-4-(4-pyridinyl)-piperazine, 0.32 g (0.001 mol) TBTU and 0.13 g (0.001 mol) DIEA and the mixture was stirred in a nitrogen atmosphere for 2 days. The reaction mixture was then evaporated down in vacuo and the remaining residue was taken up in dichloromethane. The organic phase was with 20% aqueous citric acid solution and then extracted with 10% aqueous sodium hydrogen carbonate solution, dried over sodium sulphate, filtered and evaporated down in vacuo. After stirring the residue with ether 0.68 g (77% of theory) of the desired product remain as an amorphous residue.

| | | |
|---|---|---|
| IR (KBr): | 1641, 1676 cm$^{-1}$ (C=O) | |
| $R_f$: | 0.65 (FM2) | |
| ESI-MS: | (M + H)$^+$ = | 875/877/879 (Br$_2$) |
| | (M + H + Na)$^{++}$ = | 449/450/451 (Br$_2$) |

The following were prepared analogously (in each case n=1):

EXAMPLE 9

Preparation of Compounds of General Formula:

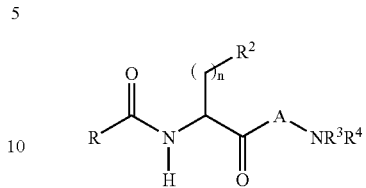

1-[$N^2$—[N-[[[(3-methoxyphenyl)ethyl]amino]carbonyl]-3,5-dichloro-D-tyrosyl]-L-lysyl]-4-(4-pyridinyl)-piperazine-bis-(trifluoroacetate (No. 20)

To a suspension of 0.33 g (2 mmol) of CDT and 1 ml of triethylamine in about 30 ml of tetrahydrofuran, cooled to −10° C., was added dropwise, with stirring, a solution of 1.0 g (1.6 mmol) of 1-[$N^2$(-3.5-dichloro-D-tyrosyl]-$N^6$-[(1.1-dimethylethoxy)carbonyl]-L-lysyl]-4-(4-pyridinyl)-piperazine in 50 ml of tetrahydrofuran within 60 minutes. The reaction mixture was stirred for 1 hour at 0° C., then stirred for 2 hours at ambient temperature, mixed with a tetrahydrofuran solution of 0.24 g (1.6 mmol) of (3-methoxyphenyl)-ethanamine, refluxed for 3 hours and stirred overnight at ambient temperature. After elimination of the solvent in vacuo the residue was purified by column chromatography (MN-silica gel 60, Macherey-Nagel, 70-230 mesh ASTM, eluant:FM1). The resulting intermediate compound was stirred in a mixture of 5 ml of trifluoroacetic acid and 80 ml of dichloromethane overnight, the solvent was eliminated in vacuo and the residue triturated with ether. 709 mg (43% of theory) of the desired compound as an amorphous solid.

| | | |
|---|---|---|
| IR (KBr): | 1643, 1676 cm$^{-1}$ (C=O) | |
| $R_f$: | 0.41 (FM2) | |
| ESI-MS | (M + H)$^+$ = | 700/702/704 (Br$_2$) |
| | (M + 2H)$^{++}$ = | 350.7/351.7/352.7 (Br$_2$) |

| No. | RCO | $R^2$ | A | $NR^3R^4$ | Remarks | % Yield | MS | $R_f$ | Eluant | IR [cm$^{-1}$] |
|---|---|---|---|---|---|---|---|---|---|---|
| 123 | N62 | AS1 | A0 | C1 | DMF/THF as solvent | 20 | ESI: (M + H)$^+$ = 725/7/9 (Br$_2$) | 0.3 | FM 1 | (KBr): C=O 1641.3; 1691.5 |
| 124 | N63 | AS1 | A0 | C1 | DMF/THF as solvent | 53 | ESI: (M + H)$^+$ = 725/7/9 (Br$_2$) | 0.2 | FM 1 | (KBr): C=O 1641.3; 1691.5 |
| 322 | N63 | AS1 | A0 | C8 | DMF/THF as solvent | 19 | EI: M$^+$ = 729/31/33 (Br$_2$) | 0.3 | FM 1 | (KBr): C=O 1629.8; 1695.3 |
| | N11 | AS1 | A3 | C1 | | 46 | ESI: (M + H)$^+$ = 873/5/7 (Br$_2$) | | | (KBr): C=O 1625.9; 1645.2 |
| | N18 | AS1 | A3 | C1 | THF/DMF as solvent | 77 | ESI: (M + H)$^+$ = 875/7/9 (Br$_2$) | 0.78 | FM7 | (KBr): C=O 1641.3 |
| | N20 | AS1 | A3 | C1 | THF/DMF as solvent | 88 | ESI: (M + H)$^+$ = 863/5/7 (Br$_2$) | 0.67 | FM7 | (KBr): C=O 1643.3 |
| | N21 | AS1 | A3 | C1 | THF/DMF as solvent | 78 | ESI: (M + H)$^+$ = 917/6/8 (Br$_2$) | 0.47 | FM7 | (KBr): C=O 1643.3 |
| | N46 | AS1 | A3 | C1 | THF/DMF as solvent | 80 | ESI: (M + H)$^+$ = 905/7/9 (Br$_2$) | 0.65 | FM7 | (KBr): C=O 1643.3 |
| | N43 | AS1 | A3 | C1 | THF/DMF as solvent | 75 | | 0.75 | FM7 | (KBr): C=O 1645.2 |
| | N44 | AS1 | A3 | C1 | THF/DMF as solvent | 79 | ESI: (M + H)$^+$ = 896/98/900 (Br$_2$) | 0.65 | FM7 | (KBr): C=O 1629.8 |

The following were prepared analogously (in each case n=1):

| No. | RCO | R² | A | NR³R⁴ | Remarks | % Yield | MS | $R_f$ | Eluant | IR [cm⁻¹] |
|---|---|---|---|---|---|---|---|---|---|---|
| 23 | N17 | AS1 | A1 | C1 | NEt₃ as base | 55 | ESI: (M + H)⁺ = 798/800/802 (Br₂) | 0.2 | FM1 | (KBr): C=O 1643.3; 1676 |
| 47 | N39 | AS1 | A1 | C1 | NEt₃ as base | 69.4 | ESI: (M + H)⁺ = 676/78/80 (Br₂) | 0.1 | FM1 | (KBr): C=O 1645.2; 1676 |
| 50 | N64 | AS1 | A1 | C1 | NEt₃ as base | 76 | ESI: (M + H)⁺ = 828/830/832 (Br₂) | 0.2 | FM1 | (KBr): C=O 1643.3; 1678 |
| 51 | N40 | AS1 | A1 | C1 | NEt₃ as base; dehydration | 79.7 | ESI: (M + H)⁺ = 826/828/30 (Br₂) | 0.2 | FM1 | (KBr): C=O 1643.3; 1678 |
| 52 | N41 | AS1 | A1 | C1 | NEt₃ as base; dehydration | 21.8 | ESI: (M + H)⁺ = 826/828/30 (Br₂) | 0.2 | FM1 | (KBr): C=O 1645.2; 1679.9 |
| 56 | N16 | AS1 | A1 | C4 | NEt₃ as base | 5 | ESI: (M + H)⁺ = 873/75/77 (Br₂) | 0.3 | FM1 | (KBr): C=O 1637.5; 1676 |
| 57 | N45 | AS1 | A1 | C4 | NEt₃ as base | 32 | ESI: (M + H)⁺ = 867/9/71 (Br₂) | 0.2 | FM1 | (KBr): C=O 1635.5; 1678 |
| 66 | N47 | AS1 | A1 | C4 | NEt₃ as base | 28.4 | ESI: (M + H)⁺ = 764/6/8 (Br₂) | 0.1 | FM1 | (KBr): C=O 1635.5; 1676 |
| 46 | N38 | AS1 | A1 | C1 | NEt₃ as base | 86 | ESI: (M + H)⁺ = 826/28/30 (Br₂) | 0.35 | FM1 | (KBr): C=O 1645.2; 1684 |
| 232 | N66 | AS4 | A1 | C8 | | 69 | ESI: (M + H)⁺ = 872/4/6 (Br₂) | 0.33 | FM1 | (KBr): C=O 1645 |
| 233 | N66 | AS4 | A1 | C1 | THF/DMF as solvent | 16 | ESI: (M + H)⁺ = 867/69/71 (Br₂) | 0.32 | FM1 | (KBr): C=O 1653 |
| 234 | N66 | AS4 | A1 | C4 | | 68 | ESI: (M + H)⁺ = 867/69/71 (Br₂) | 0.42 | FM1 | (KBr): C=O 1645 |
| 235 | N66 | AS1 | A1 | C8 | | 26 | ESI: (M + H)⁺ = 873/5/7 (Br₂) | 0.27 | FM1 | (KBr): C=O 1645 |
| 236 | N71 | AS1 | A1 | C1 | | 30 | ESI: (M + H)⁺ = 880/2/4 (Br₂) | 0.22 | FM1 | (KBr): C=O 1636; 1678 |
| 237 | N71 | AS4 | A1 | C8 | | 28 | ESI: (M + H)⁺ = 884/6/8 (Br₂) | 0.25 | FM1 | |
| 238 | N71 | AS4 | A1 | C1 | | 20 | ESI: (M + H)⁺ = 879/81/83 (Br₂) | 0.3 | FM1 | (KBr): C=O 1641; 1682 |
| 18 | N14 | AS1 | A1 | C1 | Cleaving of Boc protecting group with methanolic HCl solution | 26.3 | ESI: (M + H)⁺ = 813/5/7 (Br₂) | 0.55 | FM2 | (KBr): C=O 1641.3; 1716.5 |
| 17 | N13 | AS1 | A1 | C1 | Cleaving of Boc protecting group with methanolic HCl solution | 55.2 | ESI: (M + H)⁺ = 799/801/803 (Br₂) | 0.55 | FM2 | (KBr): C=O 1639.4 |
| 9 | N6 | AS1 | A1 | C1 | Cleaving of Boc protecting group with methanolic HCl solution | 41.3 | ESI: (M + H)⁺ = 829/31/33 (Br₂) | 0.44 | FM2 | (KBr): C=O 1639.4 |
| 10 | N7 | AS1 | A1 | C1 | Cleaving of Boc protecting group with methanolic HCl solution | 57.6 | ESI: (M + H)⁺ = 829/31/33 (Br₂) | 0.32 | FM2 | (KBr): C=O 1639.4 |
| 20 | N2 | AS5 | A1 | C1 | | 43 | ESI: (M + H)⁺ = 700/2/4 (Br₂) | 0.41 | FM2 | (KBr): C=O 1643.3; 1676.0 |
| 283 | N102 | AS4 | A3 | C4 | NEt₃ as base | 65 | ESI: (M + H)⁺ = 864/6/8 (Br₂) | 0.24 | FM1 | (KBr): C=O 1637.5; 1676 |

EXAMPLE 10

Preparation of Compounds of General Formula:

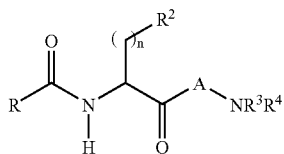

1-[N²—[N-[4-(2,3-dichlorophenyl)-1-piperazinyl] carbonyl]-3,5-dibromo-D-tyrosyl]-L-lysyl]-4-(4-pyridinyl)-piperazine-tris-(trifluoroacetate) (No. 74)

To a solution of 0.35 g (2.1 mmol) of CDT in 50 ml of tetrahydrofuran were added with cooling (0° C.) and stirring 1.0 g (1.4 mmol) of 1-[N²-(3,5-dibromo-D-tyrosyl)-N⁶-[(1,1-dimethylethoxy)carbonyl]-L-lysyl]-4-(4-pyridinyl)-piperazine and the mixture was stirred for 30 minutes at 0° C. and for a further 30 minutes at ambient temperature. After the addition of 0.47 g (1.75 mmol) of 1-(2,3-dichlorophenyl) piperazine-hydrochloride and 0.25 ml of triethylamine the reaction mixture was refluxed for 5 hours and after cooling mixed with 70 ml of saturated aqueous sodium hydrogen carbonate solution. The organic phase was separated off, the aqueous phase was extracted twice with 50 ml of tetrahydrofuran. The combined organic phases were washed with saturated aqueous saline solution, dried over magnesium sulphate, filtered and evaporated down in vacuo. The residue was triturated with ether, suction filtered and then stirred for 2 hours with a mixture of 50 ml of dichloromethane and 5 ml of trifluoroacetic acid. After evaporation of the reaction mixture in vacuo and trituration of the residue with ether, 0.8 g (47% of theory) of an amorphous solid are left.

| IR (KBr): | 1643.3, 1676 cm$^{-1}$ (C=O) | |
|---|---|---|
| $R_f$: | 0.78 (FM7) | |
| ESI-MS: | $(M + H)^+$ = | 867/869/871/873/875 (Br$_2$, Cl$_2$) |
| | $(M + 2H)^{++}$ = | 434/435/436/437 (Br$_2$, Cl$_2$) |

The following were prepared in the same way (in each case n=1):

| No. | RCO | R$^2$ | A | NR$^3$R$^4$ | % Yield | MS | $R_f$ | Eluant | IR [cm$^{-1}$] |
|---|---|---|---|---|---|---|---|---|---|
| 36 | N29 | AS1 | A1 | C1 | 17.3 | ESI: (M + H)$^+$ = 889/91/93 (Br$_2$) | 0.35 | MeOH/NH$_4$OH = 9/1 (v/v) | (KBr): C=O 1643.3; 1674.1 |
| 208 | N15 | AS1 | A1 | C1 | 53.5 | ESI: (M + H)$^+$ = 854/6/8 (Br$_2$) | 0.43 | FM2 | (KBr): C=O 1691.5; 1635.5 |
| 209 | N15 | AS1 | A1 | C1 | 47.7 | ESI: (M + H)$^+$ = 854/6/8 (Br$_2$) | 0.55 | FM2 | (KBr): C=O 1695.3; 1637.5 |
| 210 | N15 | AS1 | A1 | C1 | 28 | ESI: (M + H)$^+$ = 854/6/8 (Br$_2$) | 0.48 | FM2 | (KBr): C=O 1689.5; 1639.4 |
| 75 | N50 | AS1 | A1 | C1 | 16.5 | ESI: (M + H)$^+$ = 867/69/71/73/75 (Br$_2$, Cl$_2$) | 0.63 | FM2 | (KBr): C=O 1643.3; 1676.0; |
| 74 | N49 | AS1 | A1 | C1 | 47 | ESI: (M + H)$^+$ = 867/69/71/73/75 (Br$_2$, Cl$_2$) | 0.65 | FM2 | (KBr): C=O 1643.3; 1676.0 |
| 76 | N51 | AS1 | A1 | C1 | 13.4 | ESI: (M + H)$^+$ = 824/6/8 (Br$_2$) | 0.58 | FM2 | (KBr): C=O 1643.3; 1676.0; CN 2219.9 |
| 79 | N52 | AS1 | A1 | C1 | 11.4 | ESI: (M + H)$^+$ = 901/3/5/7 (Br$_2$, Cl) | 0.59 | FM2 | (KBr): C=O 1645.2; 1676.3 |
| 45 | N37 | AS1 | A1 | C1 | 43 | ESI: (M + H)$^+$ = 784/6/8 (Br$_2$) | 0.6 | FM2 | (KBr): C=O 1643.3; 1678.0 |
| 39 | N32 | AS1 | A1 | C1 | 48.3 | ESI: (M + H)$^+$ = 795/7/9 (Br$_2$) | 0.57 | FM2 | (KBr): C=O 1643.3; 1678.0 |
| 38 | N31 | AS1 | A1 | C1 | 54.1 | ESI: (M + H)$^+$ = 844/6/8 (Br$_2$) | 0.6 | FM2 | (KBr): C=O 1643.3; 1678.0; NO2 1543.0 |
| 37 | N30 | AS1 | A1 | C1 | 61.6 | ESI: (M + H)$^+$ = 813/5/7 (Br$_2$) | 0.6 | FM2 | (KBr): C=O 1643.3; 1676.0 |
| 35 | N28 | AS1 | A1 | C1 | 74.8 | ESI: (M + H)$^+$ = 800/2/4 (Br$_2$) | 0.55 | FM2 | (KBr): C=O 1639.4; |
| 34 | N27 | AS1 | A1 | C1 | 36.8 | ESI: (M + H)$^+$ = 800/2/4 (Br$_2$) | 0.43 | FM2 | (KBr): C=O 1641.3; 1714.6; NH+ 3409.9 |
| 32 | N25 | AS1 | A1 | C1 | 50.0 | ESI: (M + H)$^+$ = 737/39/41 (Br$_2$) | 0.44 | FM2 | (KBr): C=O 1645.2; 1678.3 |
| 33 | N26 | AS1 | A1 | C1 | 42 | ESI: (M + H)$^+$ = 767/69/71 (Br$_2$) | 0.33 | FM2 | (KBr): C=O 1676.0 |
| 40 | N33 | AS1 | A1 | C1 | 14.5 | ESI: (M + H)$^+$ = 802/4/6 (Br$_2$) | 0.58 | FM2 | (KBr): C=O 1643.3; 1676.0 |
| 28 | N6 | AS3 | A1 | C1 | 67.2 | ESI: (M + H)$^+$ = 741/3/5 (Cl$_2$) | 0.43 | FM2 | (KBr): C=O 1641.3; 1716.5 |
| 64 | N23 | AS1 | A1 | C4 | 39 | ESI: (M + H)$^+$ = 832/4/6/8 (Br$_2$, Cl) | 0.68 | FM2 | (KBr): C=O 1627.8; 1678.0 |
| 65 | N15 | AS1 | A1 | C4 | 41 | ESI: (M + H)$^+$ = 853/5/7 (Br$_2$) | 0.61 | FM2 | (KBr): C=O 1631.7; 1695.3 |
| 365 | N111 | AS1 | A1 | C1 | 36.9 | ESI: (M + H)$^+$ = 839/41/43 (Br$_2$) | 0.09 | FM1 | (KBr): C=O 1626/1676 |

EXAMPLE 11

1-[N2—[N-[[[2-(2,5-dimethoxyphenyl)ethyl]amino]carbonyl]-3,5 dibromo-D,L-tyrosyl]-L-lysyl]-4-(4-pyridinyl)-piperazine (No. 3)

A mixture of 0.8 g (0.84 mmol) of 1-[N$^2$—[N-[[2-(2,5-dimethoxyphenyl)ethyl]amino]carbonyl]-3,5-dibromo-D-tyrosyl]-N$^6$-[(phenylmethoxy)carbonyl]-L-lysyl]-4-(4-pyridinyl)-piperazine, 50 ml of glacial acetic acid, 25 ml of a 33% solution of hydrogen bromide in glacial acetic acid and 2 ml of anisole was stirred for 12 hours at ambient temperature. The reaction mixture was stirred into diethylether and the resulting precipitate was suction filtered. The solid residue was purified by column chromatography (MN-silica gel 60, Macherey-Nagel, 70-230 mesh ASTM, eluant:ethyl acetate/methanol/conc. aqueous ammonia=8/2/0.2 (v/v/v)). 0.3 g (44% of theory) of the desired product was obtained as an amorphous solid.

| IR (KBr): | 1643.3 cm$^{-2\ 1}$ (C=O) | |
|---|---|---|
| R$_f$: | 0.17 (ethyl acetate/methanol/conc. aqueous ammonia = 6/4/1) | |
| ESI-MS: | (M + H)$^+$ = | 818/820/822 (Br$_2$) |
| | (M + 2H)$^{++}$ = | 409.5/410.5/411.5 (Br$_2$) |

EXAMPLE 12

1-[N$^2$-[3,5-dibromo-N-[[[2-(3-methoxyphenyl)ethyl]amino]carbonyl]-D-tyrosyl]-L-arginyl]-4-(4-pyridinyl)-piperazine-bis-(trifluoroacetate) (No. 4)

A stirred mixture of 20 ml of trifluoroacetic acid, 1.3 ml of anisole and 0.9 ml of ethanedithiol was mixed with 2.1 g (1.9 mmol) of solid 1-[N$^2$-[3,5-dibromo-N-[[[2-(3-methoxyphenyl)-ethyl]amino]carbonyl]-N$^G$-(2,2,5,7,8-pentamethyl-chroman-6-sulphonyl)-D-tyrosyl]-L-arginyl]-4-(4-pyridinyl)-piperazine whilst cooling with ice and stirred for a further 45 minutes whilst cooling with ice, then for 3 hours at ambient temperature. The resulting precipitate was suction filtered and discarded, the filtrate was evaporated down in vacuo, the residue remaining was mixed with toluene and again evaporated down in vacuo. The resulting solid residue was triturated with a mixture of diethylether and acetone and the white solid formed was suction filtered and dried. 1.7 g (65% of theory) of the desired title compound were obtained.

| IR (KBr): | 1674, 1645 cm$^{-2\ 1}$ (C=O) | |
|---|---|---|
| R$_f$: | 0.15 (FM: BuOH/AcOH/H$_2$O 4/1/1 (v/v/v)) | |
| ESI-MS: | (M + H)$^+$ = | 816/818/820 (Br$_2$) |
| | (M + 2H)$^{++}$ = | 408.6/409.6/410.6 (Br$_2$) |

EXAMPLE 13

Preparation of Compounds of General Formula:

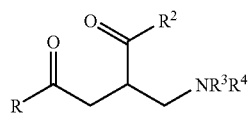

(R,S)-1-[2-(4-amino-3,5-dibromobenzoyl)-4-[4-(3,4-dihydro-2(1H)-oxoquinazolin-3-yl)-1-piperidinyl]-4-oxobutyl]-4-(4-pyridinyl)-piperidine (No. 291)

A mixture of 0.97 g (1.8 mmol) of (R,S)-4-amino-3,5-dibromo-γ-oxo-β-[[4-(4-pyridinyl)-1-piperidinyl]methyl]-benzenebutanoic acid, 0.48 g (1.8 mmol) of 4-(3,4-dihydro-2(1H)-oxoquinazolin-3-yl)-piperidine, 2 ml of triethylamine, 0.58 g (1.8 mmol) of TBTU, 0.24 g (1.8 mmol) of HOBt, 25 ml of THF and 25 ml of DMF was stirred for 4 hours at ambient temperature. The reaction mixture was evaporated down in vacuo, the residue was taken up in a mixture of ethyl acetate and methanol (95/5 (v/v)) and washed with saturated aqueous sodium hydrogen carbonate solution. The organic phase was dried and evaporated down in vacuo. The residue was purified by column chromatography (MN-silica gel 60, Macherey-Nagel, 70-230 mesh ASTM, eluant:ethyl acetate/methanol=9/1 (v/v); then MN-silica gel 60, Macherey-Nagel, 70-230 mesh ASTM, eluant: methylene chloride/ethanol=9/1 (v/v)). 0.2 g (15% of theory) of the desired product were obtained as a white amorphous solid.

| IR (KBr): | 1668.3 cm$^{-1}$ (C=O) | |
|---|---|---|
| R$_f$: | 0.5 (FM2) | |
| ESI-MS: | (M + H)$^+$ = | 737/739/741 (Br$_2$) |
| | (M + Na)$^+$ = | 759/761/763 (Br$_2$) |

The following were prepared analogously:

| No. | RCO | R$^2$ | NR$^3$R$^4$ | % Yield | MS | R$_f$ | Eluant | IR [cm$^{-1}$] |
|---|---|---|---|---|---|---|---|---|
| 291 | N66 | AS4 | C4 | 15 | ESI: (M + H)$^+$ = 737/39/41 (Br$_2$) | 0.36 | CH$_2$Cl$_2$/ EtOH | (KBr): C=O 1668 |
| 296 | N66 | AS4 | C8 | 14 | ESI: (M + H)$^+$ = 743/5/7 (Br$_2$) | 0.66 | FM1 | (KBr): C=O 1668 |
| 302 | N71 | AS4 | C8 | 19 | ESI: (M + H)$^+$ = 755/7/9 (Br$_2$) | 0.54 | FM1 | (KBr): C=O 1682 |

EXAMPLE 14

1-[4-amino-N-[[4-[7-(aminocarbonyl)-3,4-dihydro-2(1H)-oxoquinazolin-3-yl]-1-piperidinyl]carbonyl]-3,5-dibromo-D-phenylalanyl]-4-(4-pyridinyl)-piperdine (No. 312)

a) 1-[4-amino-3,5-dibromo-N-[[4-[3,4-dihydro-7-(methoxycarbonyl)-2(1H)-oxoquinazolin-3-yl]-1-piperidinyl]carbonyl]-D-phenylalanyl]-4-(4-pyridinyl)-piperidine (No. 307)

Prepared analogously to Example 3 from methyl 3,4-dihydro-3-(4-piperidinyl)-2(1H)-oxoquinazoline-7-carboxylate, 1-[4-amino-3,5-dibromo-D-phenylalanyl]-4-(4-pyridinyl)-piperidine and CDT in a yield of 27.2% of theory. Colourless, amorphous substance, Rf 0.5 (eluant:dichloromethane/cyclohexane/methanol/conc. ammonia=7/1.5/1.5/0.2 (v/v/v/v)).

| IR (KBr): | 1718.5, 1670.3, 1618.2 cm$^{-2\ 1}$ (C=O) | |
|---|---|---|
| ESI-MS: | (M + H)+ = | 796/798/800 (Br$_2$) |
| | (M + Na)$^+$ = | 818/820/822 (Br$_2$) |

The following were obtained accordingly:

From methyl-3,4-dihydro-3-(4-piperidinyl)-2(1H)-oxoquinazoline-7-carboxylate, 1-[4-amino-3,5-dibromo-D-phenylalanyl]-4-(1-piperidinyl)-piperidine and CDT in a yield of 30.3% of theory: 1-[4-amino-3,5-dibromo-N-[[4-[3,4-dihydro-7-(methoxycarbonyl)-2(1H)-oxoquinazolin-3-yl]-1-piperidinyl]carbonyl]-D-phenylalanyl]-4-(1-piperidinyl)-piperidine (No. 304), $R_f$=0.75 (FM1).

| IR (KBr): | 1720.4, 1668.3, 1620.1 cm$^{-2\ 1}$ (C=O) |  |
|---|---|---|
| ESI-MS: | (M + H)$^+$ = | 802/804/806 (Br$_2$) |
|  | (M + Na)$^+$ = | 824/826/828 (Br$_2$) |

From methyl-3,4-dihydro-3-(4-piperidinyl)-2(1H)-oxoquinazoline-7-carboxylate, 1-(3,5-dibromo-D-tyrosyl)-4-(1-piperidinyl)-piperidine and CDT in a yield of 35% of theory: 1-[3,5-dibromo-N-[[4-[7-(methoxycarbonyl)-3,4-dihydro-2(1H)-oxoquinazolin-3-yl]-1-piperidinyl]carbonyl]-D-tyrosyl]-4-(1-piperidinyl)-piperidine (No. 422), $R_f$ 0.54 (eluant:dichloromethane/cyclohexane/methanol/conc. ammonia=7/1.5/1.5/0.2 (v/v/v/v)).

| IR (KBr): | 1720.4, 1668.3, 1627.8 cm$^{-2\ 1}$ (C=O) |  |
|---|---|---|
| ESI-MS: | (M + H)$^+$ = | 803/805/807 (Br$_2$) |
|  | (M + Na)$^+$ = | 825/827/829 (Br$_2$) |

From methyl-3,4-dihydro-3-(4-piperidinyl)-2(1H)-oxoquinazoline-7-carboxylate, 1-(3,5-dibromo-D-tyrosyl)-4-(4-pyridinyl)-piperidine and CDT in a yield of 45% of theory: 1-[3,5-dibromro-N-[[4-[7-(methoxycarbonyl)-3,4-dihydro-2(1H)-oxoquinazolin-3-yl]-1-piperidinyl]carbonyl]-D-tyrosyl]-4-(4-pyridinyl)-piperidine (No. 420), $R_f$ 0.56 (FM1).

| IR (KBr): | 1718.5, 1664.5, 1624.0 cm$^{-2\ 1}$ (C=O) |  |
|---|---|---|
| ESI-MS: | (M + H)$^+$ = | 797/799/801 (Br$_2$) |
|  | (M + Na)$^+$ = | 819/821/823 (Br$_2$) | b) 1-[4-amino-3,5-dibromo-N-[[4-[3,4-dihydro-7-(hydroxycarbonyl)-2(1H)-oxoquinazolin-3-yl]-1-piperidinyl]carbonyl]-D-phenylalanyl]-4-(4-pyridinyl)-piperidine (No. 309)

Prepared analogously to Example A37 from 1-[4-amino-3,5-dibromo-N-[[4-[3,4-dihydro-7-(methoxycarbonyl)-2(1H)-oxoquinazolin-3-yl]-1-piperidinyl]carbonyl]-D-phenylalanyl]-4-(4-pyridinyl)-piperidine by saponification with lithium hydroxide in a yield of 95% of theory. Colourless, amorphous substance, $R_f$ 0.25 (eluant:dichloromethane/methanol/conc. ammonia=7.5/2.5/0.5 (v/v/v)).

IR (KBr): 1666.4, 1614.3 cm$^{-1}$ (C=O)
ESI-MS: (M—H)$^-$=780/782/784 (Br$_2$)

The following were obtained accordingly:
From 1-[4-amino-3,5-dibromo-N-[[4-[3,4-dihydro-7-(methoxycarbonyl)-2(1H)-oxoquinazolin-3-yl]-1-piperidinyl]carbonyl]-D-phenylalanyl]-4-(1-piperidinyl)-piperidine in a yield of 60.2% of theory: 1-[4-amino-3,5-dibromo-N-[[4-[3,4-dihydro-7-(hydroxycarbonyl)-2(1H)-oxoquinazolin-3-yl]-1-piperidinyl]carbonyl]-D-phenylalanyl]-4-(1-piperidinyl)-piperidine (No. 306), $R_f$ 0.15 (FM1).

| IR(KBr): | 1635.5 cm$^{-1}$, broad (C=O) |  |
|---|---|---|
| ESI-MS: | (M + H)$^+$ = | 788/790/792 (Br$_2$) |
|  | (M + Na)$^+$ = | 810/812/814 (Br$_2$) |

From 1-[3,5-dibromo-N-[[4-[7-(methoxycarbonyl)-3,4-dihydro-2(1H)-oxoquinazolin-3-yl]-1-piperidinyl]carbonyl]-D-tyrosyl]-4-(1-piperidinyl)-piperidine in a yield of 62% of theory: 1-[3,5-dibromo-N-[[4-[7-(hydroxycarbonyl)-3,4-dihydro-2(1H)-oxoquinazolin-3-yl]-1-piperidinyl]carbonyl]-D-tyrosyl]-4-(1-piperidinyl)-piperidine (No. 423), $R_f$ 0.03 (eluant:dichloromethane/cyclohexane/methanol/conc. ammonia=7/1.5/1.5/0.2 (v/v/v/v)).

IR (KBr): 1635.5 cm$^{-1}$, broad(C=O)
ESI-MS: (M+H)$^+$=789/791/793 (Br$_2$)

From 1-[3,5-dibromo-N-[[4-(1,3-dihydro-5-(methoxycarbonyl)-2(2H)-oxobenzimidazol-1-yl)-1-piperidinyl]carbonyl]-D-tyrosyl]-4-(4-pyridinyl)-piperidine in a yield of 80% of theory: 1-[3,5-dihbrcmo-N-[[4-(1,3-dihydro-5-(hydroxycarbonyl)-2(2H)-oxobenzimidazol-1-yl)-1-piperidinyl]carbonyl]-D-tyrosyl]-4-(4-pyridinyl)-piperidine (No. 151). Colourless, amorphous substance.

| IR(KBr): | 1701.1, 1625.9 cm$^{-1}$ (C=O) |  |
|---|---|---|
| ESI-MS: | (M + H)$^+$ = | 767/769/771 (Br$_2$) |
|  | (M + 2H)$^{++}$ = | 383/384/385 (Br$_2$) |

From 1-[3,5-dibromo-N-[[4-[7-(methoxycarbonyl)-3,4-dihydro-2(1H)-oxoquinazolin-3-yl]-1-piperidinyl]carbonyl]-D-tyrosyl]-4-(4-pyridinyl)-piperidine in a yield of 82% of theory: 1-[3,5-dibromo-N-[[4-[7-(hydroxycarbonyl)-3,4-dihydro-2(1H)-oxoquinazolin-3-yl]-1-piperidinyl]carbonyl]-D-tyrosyl]-4-(4-pyridinyl)-piperidine (No. 421), $R_f$ 0.03 (FM1). Colourless, amorphous substance.

| IR (KBr): | 1625 wide cm$^{-1}$ (C=O) |
|---|---|
| ESI-MS: | (M + H)$^+$ = 783/785/787 (Br$_2$) |
|  | (M + Na)$^+$ = 805/807/809 (Br$_2$) | c) 1-[4-amino-N-[[4-[7-(aminocarbonyl)-3,4-dihydro-2(1H)-oxoquinazolin-3-yl]-1-piperidinyl]carbonyl]-3,5-dibromo-D-phenylalanyl]-4-(4-pyridinyl)-piperidine (No. 312)

Prepared analogously to Example 1 from 1-[4-amino-3,5-dibromo-N-[[4-[3,4-dihydro-7-(hydroxycarbonyl)-2(1H)-oxoquinazolin-3-yl]-1-piperidinyl]carbonyl]-D-phenylalanyl]-4-(4-pyridinyl)-piperidine and ammonium carbonate in the presence of TBTU in a yield of 40.6% of theory. Colourless, amorphous substance, $R_f$ 0.8 (eluant:dichloromethane/methanol/conc. ammonia=7.5/2.5/0.5 (v/v/v)).

| IR (KBr): | 1670.3, 1616.3 cm$^{-1}$ (C=O) |
|---|---|
| ESI-MS: | (M + H)$^+$ = 781/783/785 (Br$_2$) |
|  | (M + Na)$^+$ = 803/805/807 (Br$_2$) |

The following were obtained accordingly:

From 1-[4-amino-3,5-dibromo-N-[[4-[3,4-dihydro-7-(hydroxycarbonyl)-2(1H)-oxoquinazolin-3-yl]-1-piperidinyl]carbonyl]-D-phenylalanyl]-4-(4-pyridinyl)-piperidine and ethanolamine in a yield of 34.6% of theory: 1-[4-amino-3,5-dibromo-N-[[4-[7-(2-hydroxyethylaminocarbonyl)-3,4-dihydro-2(1H)-oxoquinazolin-3-yl]-1-piperidinyl]carbonyl]-D-phenylalanyl]-4-(4-pyridinyl)-piperidine, (No. 313) $R_f$=0.7 (eluant:dichloromethane/methanol/conc. ammonia = 7.5/2.5/0.5 v/v/v).

| IR (KBr): | 1662.5, 1618.2 cm$^{-1}$ (C=O) |
|---|---|
| ESI-MS: | (M + H)$^+$ = 825/827/829 (Br$_2$) |
| | (M + Na)$^+$ = 847/849/851 (Br$_2$) |
| | (M + 2H)$^{++}$ = 413/414/415 (Br$_2$) |
| | (M + H + Na)$^{++}$ = 424/425/426 (Br$_2$) |

From 1-[4-amino-3,5-dibromo-N-[[4-[3,4-dihydro-7-(hydroxycarbonyl)-2(1H)-oxoquinazolin-3-yl]-1-piperidinyl]carbonyl]-D-phenylalanyl]-4-(4-pyridinyl)-piperidine and 1-methylpiperazine in a yield of 44.9% of theory: 1-[4-amino-3,5-dibromo-N-[[4-[7-[(4-methyl-1-piperazinyl)carbonyl]-3,4-dihydro-2(1H)-oxoquinazolin-3-yl]-1-piperidinyl]carbonyl]-D-phenylalanyl]-4-(4-pyridinyl)-piperidine, (No. 430) $R_f$=0.28 (eluant:ethyl acetate/methanol/conc. ammonia=8/1.5/0.3 v/v/v).

| IR (KBr): | 1618.2 cm$^{-1}$ (C=O) |
|---|---|
| ESI-MS: | (M + H)$^+$ = 864/866/868 (Br$_2$) |
| | (M + Na)$^+$ = 886/888/890 (Br$_2$) |
| | (M + 2H)$^{++}$ = 432/433/434.7 (Br$_2$) |

From 1-[4-amino-3,5-dibromo-N-[[4-[3,4-dihydro-7-(hydroxycarbonyl)-2(1H)-oxoquinazolin-3-yl]-1-piperidinyl]carbonyl]-D-phenylalanyl]-4-(4-pyridinyl)-piperidine and methylammonium chloride in a yield of 37% of theory: 1-[4-amino-3,5-dibromo-N-[[4-[7-(methylaminocarbonyl)-3,4-dihydro-2(1H)-oxoquinazolin-3-yl]-1-piperidinyl]carbonyl]-D-phenylalanyl]-4-(4-pyridinyl)-piperidine, (No. 424) $R_f$=0.49 (FM1)

| IR (KBr): | 1662.5, 1622 cm$^{-1}$ (C=O) |
|---|---|
| ESI-MS: | (M + H)$^+$ = 795/797/799 (Br$_2$) |
| | (M + Na)$^+$ = 817/819/821 (Br$_2$) |

From 1-[4-amino-3,5-dibromo-N-[[4-[3,4-dihydro-7-(hydroxycarbonyl)-2(1H)-oxoquinazolin-3-yl]-1-piperidinyl]carbonyl]-D-phenylalanyl]-4-(1-piperidinyl)-piperidine and ammonium carbonate in a yield of 12% of theory: 1-[4-amino-N-[[4-[7-(aminocarbonyl)-3,4-dihydro-2(1H)-oxoquinazolin-3-yl]-1-piperidinyl]carbonyl]-3,5-dibromo-D-phenylalanyl]-4-(1-piperidinyl)-piperidine (No. 310), $R_f$=0.7 (eluant:dichloromethane/methanol/conc. ammonia=7.5/2.5/0.5 v/v/v)).

IR (KBr): 1670.3, 1618.2 cm$^{-1}$ (C=O)

ESI-MS: (M+H)$^+$=787/789/791 (Br$_2$)

From 1-[4-amino-3,5-dibromo-N-[[4-[3,4-dihydro-7-(hydroxycarbonyl)-2(1H)-oxoquinazolin-3-yl]-1-piperidinyl]carbonyl]-D-phenylalanyl]-4-(1-piperidinyl)-piperidine and ethanolamine in a yield of 11.4% of theory: 1-[4-amino-3,5-dibromo-N-[[4-[7-(2-hydroxyethylaminocarbonyl)-3,4-dihydro-2(1H)-oxoquinazolin-3-yl]-1-piperidinyl]carbonyl]-D-phenylalanyl]-4-(1-piperidinyl)-piperidine (No. 311), $R_f$=0.65 (eluant:dichloromethane/methanol/conc. ammonia=7.5/2.5/0.5 (v/v/v)).

| IR (KBr): | 1660.6, 1620.1 cm$^{-1}$ (C=O) |
|---|---|
| ESI-MS: | (M + H)$^+$ = 831/833/835 (Br$_2$) |
| | (M + 2H)$^{++}$ = 416/417/418 (Br$_2$) |
| | (M + H + Na)$^{++}$ = 427/428/429 (Br$_2$) |

EXAMPLE 15

4-(1-acetyl-4-piperidinyl)-1-[4-amino-3,5-dibromo-N-([[4-(3,4-dihydro-2(1H)-oxoquinazolin-3-yl)-1-piperidinyl]-carbonyl]-D-phenylalanyl]-piperidine (No. 372)

a) 1-[4-amino-3,5-dibromo-D-phenylalanyl]-4-[1-(1,1-dimethylethoxycarbonyl)-4-piperidinyl]-piperidine A mixture of 5.60 g (0.01 mol) of 4-amino-3,5-dibromo-N-(9-fluorenylmethoxycarbonyl)-D-phenylalanine, 1.35 g (0.01 mol) HOBt, 3.21 g (0.01 mol) TBTU, 1.29 g (0.01 mol) DIEA, 2.68 g (0.01 mol) 4-[1-(1,1-dimethylethoxycarbonyl)-4-piperidinyl]-piperidine and 150 ml of tetrahydrofuran was stirred for 2 hours at room temperature. After the reaction was complete 20 ml of diethylamine were added and the mixture was stirred for a further 18 hours at room temperature. The reaction mixture was evaporated down in vacuo, the residue was taken up in 200 ml of dichloromethane and washed successively with 100 ml of saturated sodium chloride solution and saturated sodium hydrogen carbonate solution and dried over magnesium sulphate. The reddish oil remaining after elimination of the solvent was purified by column chromatography on silica gel (30-60 µm) using firstly dichloromethane, then FM4 as eluant. The title compound was obtained in the form of a colourless amorphous substance and in a yield of 4.31 g (73.3% of theory).

IR(KBr): 1687.6 cm$^{+1}$ (C=O)

MS: M+=586/588/590 (Br$_2$)

b) 1-[4-amino-3,5-dibromo-N-[[4-(3,4-dihydro-2(1H)-oxoquinazolin-3-yl)-1-piperidinyl]carbonyl]-D-phenylalanyl]-4-[1-(1,1-dimethylethoxycarbonyl)-4-piperidinyl]-piperidine Prepared analogously to Example 4 from 1-[4-amino-3,5-dibromo-D-phenylalanyl]-4-[1-(1,1-dimethylethoxycarbonyl)-4-piperidinyl]-piperidine, CDT and 3,4-dihydro-3-(4-piperidinyl)-2(1H)-quinazolinone in a quantitative yield. Colourless, amorphous substance.

| IR (KBr): | 1676 cm$^{-1}$ (C=O) |
|---|---|
| MS: | (M + H)$^+$ = 844/846/848 (Br$_2$) |
| | (M + Na)$^+$ = 866/868/870 (Br$_2$) | c) 1-[4-amino-3,5-dibromo-N-[[4-(3,4-dihydro-2(1H)-oxoquinazolin-3-yl)-1-piperidinyl]carbonyl]-D-phenylalanyl]-4-(4-piperidinyl)-piperidine (No. 521)

Prepared analogously to Example A1b), but using sodium hydroxide solution instead of ammonia, from 1-[4-amino-3,5-dibromo-N-[[4-(3,4-dihydro-2(1H)-oxoquinazolin-3-yl)-

1-piperidinyl]-carbonyl]-D-phenylalanyl]-4-[1-(1,1-dimethylethoxycarbonyl)-4-piperidinyl]-piperidine by treating with trifluoroacetic acid in a yield of 75% of theory. Colourless, amorphous substance.

| | |
|---|---|
| IR (KBr): | 1666.4, 1620.1 cm$^{-1}$ (C=O) |
| MS: | (M + H)$^+$ = 744/746/748 (Br$_2$) |
| | (M + 2H)$^{++}$ = 372/373/374.5 (Br$_2$) | d) 4-(1-acetyl-4-piperidinyl)-1-[4-amino-3,5-dibromo-N-[[4-(3,4-dihydro-2(1H)-oxoquinazolin-3-yl)-1-piperidinyl]carbonyl]-D-phenylalanyl]-piperidine (No. 372)

A solution of 0.372 g (0.499 mmol) of 1-[4-amino-3,5-dibromo-N-[[4-(3,4-dihydro-2(1H)-oxoquinazolin-3-yl)-1-piperidinyl]carbonyl]-D-phenylalanyl]-4-(4-piperidinyl)-piperidine and 0.07 g (5.5 mmol) of DIEA in 50 ml of dichloromethane was mixed with 0.043 g (5.48 mmol) of acetylene chloride dropwise whilst cooling externally with ice-water and then stirred for 1 hour at room temperature. The solvent was eliminated in vacuo, the residue was stirred with water and filtered. The filter residue was dried in vacuo and purified by column chromatography on silica gel (30-60 µm) using FM4 as eluant. The suitable eluates were evaporated down, the residue was triturated with diethylether and suction filtered. 230 mg (58.5% of theory) of colourless crystals were obtained.

| | |
|---|---|
| IR (KBr): | 1622 cm$^{-1}$ (C=O) |
| MS: | (M + H)$^+$ = 786/788/790 (Br$_2$) |
| | (M + Na)$^+$ = 808/810/812 (Br$_2$) |

The following were obtained accordingly:

1-[4-amino-3,5-dibromo-N-[[4-[3,4-dihydro-2(1H)-oxoquinazolin-3-yl]-1-piperidinyl]carbonyl]-D-phenylalanyl]-4-(1-benzoyl-4-piperidinyl)-piperidine (No. (485).

Colourless crystals
R$_f$ 0.74 (FM1)
IR(KBr): 1626,1668 cm$^{-1}$ (C=O)
ESI-MS: (M+H)$^+$=848/850/852 (Br$_2$)

EXAMPLE 16

1-[4-amino-3,5-dibromo-N-[[4-[3,4-dihydro-2(1H)-oxoquinazolin-3-yl]-1-piperidinyl]carbonyl]-D-phenylalanyl]-4-(1-methylsulfonyl-4-piperidinyl)-piperidine (No. 486)

A solution of 0.372 g (0.499 mmol) of 1-[4-amino-3,5-dibromo-N-[[4-(3,4-dihydro-2(1H)-oxoquinazolin-3-yl)-1-piperidinyl]carbonyl]-D-phenylalanyl]-4-(4-piperidinyl)-piperidine and 0.07 g (5.5 mmol) of DIEA in 50 ml of dichloromethane was mixed dropwise with 0.063 g (5.5 mmol) of methanesulphonylchloride whilst cooling externally with ice-water and then stirred for 1 hour at room temperature. The solvent was eliminated in vacuo, the residue was stirred with water and filtered. The filter residue was dried in vacuo and purified by column chromatography over silica gel (30-60 µm) using initially dichloromethane, then FM4 as eluant. The suitable eluates were evaporated down, the residue was triturated with diethylether and suction filtered. 220 mg (53.5% of theory) of colourless crystals were obtained.

| | |
|---|---|
| IR (KBr): | 1668, 1618 cm$^{-1}$ (C=O) |
| MS: | (M + H)$^+$ = 822/824/826 (Br$_2$) |
| | (M + Na)$^+$ = 844/846/848 (Br$_2$) |
| | (M + K)$^+$ = 860/862/864 (Br$_2$) |

The following were obtained accordingly:

(1) 1-[3,5-dibromo-N-[[4-(3,4-dihydro-2(1H)-oxoquinazolin-3-yl-1-piperidinyl]carbonyl]-4-(methylsulphonyloxy)-D-phenylalanyl]-4-[1-(methylsulphonyl)-4-piperidinyl]-piperidine (No. (523)) in a yield of 12% of theory.

R$_f$ 0.54 (FM1)
IR(KBr): 1628,1665 cm$^{31\ 1}$ (C=O)
ESI-MS: (M+H)$^{+=}$901/903/905 (Br$_2$)

(2) 1-[3,5-dibromo-N-[[4-(3,4-dihydro-2(1H)-oxoquinazolin-3-yl)-1-piperidinyl]carbonyl]-D-tyrosyl]-4-[1-(methylsulphonyl)-4-piperidinyl]-piperidine (No. (524) in a yield of 12% of theory.

R$_f$ 0.50 (FM1)
ESI-MS: (M+H)$_+$=833/825/827 (Br$_2$)

(3) (R,S)-1-[4-[4-(3,4-dihydro-2(1H)-oxoquinazolin-3-yl)-1-piperidinyl]-2-[(1-naphthyl)methyl]-1,4-dioxobutyl]-4-(1-methylsulphonyl-4-piperidinyl)-piperidine (No. (668) in a yield of 56% of theory.

R$_f$ 0. 70 (FM1)
IR(KBr): 1630,1666 cm$^{-1}$ (C=O)
MS: M$^+$=699

EXAMPLE 17

1-[4-amino-3,5-dibromo-N-[[4-[3,4-dihydro-2(1H)-oxoquinazolin-3-yl]-1-piperidinyl]carbonyl]-D-phenylalanyl]-4-[1-(3-carboxy-1-oxopropyl)-4-piperidinyl]-piperidine (No. 487)

A mixture of 0.372 g (0.499 mmol) of 1-[4-amino-3,5-dibromo-N-[[4-(3,4-dihydro-2(1H)-oxoquinazolin-3-yl)-1-piperidinyl]carbonyl]-D-phenylalanyl]-4-(4-piperidinyl)-piperidine, 0.11 g (1.1 mmol) of succinic anhydride and 150 ml of tetrahydrofuran was refluxed for 1 hour. The reaction mixture was freed from solvent in vacuo, the residue was purified by column chromatography on silica gel (30-60 µm) using FM1 as eluant. The suitable eluates were evaporated down, the residue was triturated with diethylether and suction filtered. 175 mg (41.5% of theory) of colourless crystals were obtained.

| IR (KBr): | 1668, 1608 cm$^{-1}$ (C=O) |
| --- | --- |
| MS: | (M − H)$^-$ = 842/844/846 (Br$_2$) |
| | (M + Na)$^+$ = 868/870/872 (Br$_2$) |

EXAMPLE 18

1-[4-amino-3,5-dibromo-N-[[4-[3,4-dihydro-2(1H)-oxoquinazolin-3-yl]-1-piperidinyl]carbonyl]-D-phenylalanyl]-4-(1-hexyl-4-piperidinyl)-piperidine (No. 488)

A mixture of 0.372 g (0.499 mmol) of 1-[4-amino-3,5-dibromo-N-[[4-(3,4-dihydro-2(1H)-oxoquinazolin-3-yl)-1-piperidinyl]carbonyl]-D-phenylalanyl]-4-(4-piperidinyl)-piperidine, 0.05 g (0.499 mmol) of hexanal, 0.03 g (0.5 mmol) of glacial acetic acid and 150 ml of tetrahydrofuran was stirred for 1 hour at room temperature. After the addition of 0.116 g (0.52 mmol) of 95% sodium triacetoxyborohydride the mixture was kept for a further 2.5 hours at room temperature. The solvent was eliminated in vacuo, the residue was divided between 20% aqueous sodium carbonate solution and dichloromethane, the organic phase was dried over magnesium sulphate and evaporated down. The residue was purified by column chromatography on silica gel (30-60 μm) using FM4 as eluant. The suitable eluates were evaporated down, the residue was triturated with diethylether and suction filtered. 100 mg (24.2% of theory) of colourless crystals were obtained.

| IR (KBr): | 1666, 1620 cm$^{-1}$ (C=O) |
| --- | --- |
| MS: | (M + H)$^+$ = 828/830/832 (Br$_2$) |
| | (M + Na)$^+$ = 850/852/854 (Br$_2$) |

The following were obtained accordingly:

(1) 1-[4-amino-3,5-dibromo-N-[[4-[3,4-dihydro-2(1H)-oxoquinazolin-3-yl]-1-piperidinyl]carbonyl]-D-phenylalanyl]-4-(1-cyclopropylmethyl-4-piperidinyl)-piperidine (No. 489) in a yield of 23% of theory.

R$_f$ 0.65 (FM1)
IR(KBr): 1622,1666 cm$^{-1}$ (C=O)
ESI-MS: (M+H)$^+$=798/800/802 (Br$_2$)

(2) 1-[4-amino-3,5-dibromo-N-[[4-[3,4-dihydro-2(1H)-oxoquinazolin-3-yl]-1-piperidinyl]carbonyl]-D-phenylalanyl]-4-[1-(ethoxycarbonylmethyl)-4-piperidinyl]-piperidine (No. (493) in a yield of 43% of theory.

R$_f$ 0.72 (FM1)
IR(KBr): 1620,1666 cm$^{-1}$ (C=O)
ESI-MS: (M+H)$^+$=730/732/734 (Br$_2$)

(3) 1-[3,5-dibromo-N-[[4-(3,4-dihydro-2(1H)-oxoquinazolin-3-yl)-1-piperidinyl]carbonyl]-D-tyrosyl]-4-[1-(cyclopropylmethyl)-4-piperidinyl]-piperidine (No. (525) in a yield of 46.5% of theory.

R$_f$ 0.50 (FM1)
IR(KBr): 1622,1662 cm$^{-1}$ (C=O)
ESI-MS: (M+H)$^+$=799/801/803 (Br$_2$)

EXAMPLE 19

Preparation of Compounds of General Formula:

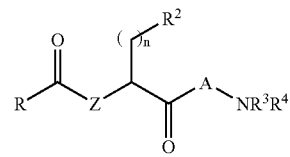

1-[N-[[4-[3,4-dihydro-2(1H)-oxoquinazolin-3-yl]-1-piperidinyl]carbonyl]-3-ethenyl-D,L-phenylalanyl]-4-(hexahydro-1H-1-azepinyl)-piperidine (No. 532)

The mixture of 200 mg (3 mmol) 1-[3-bromo-N-[[4-[3,4-dihydro-2(1H)-oxoquinazolin-3-yl]-1-piperidinyl]carbonyl]-D,L-phenylalanyl]-4-(hexahydro-1H-1-azepinyl)-piperidine, 108 mg (0.33 mMol) vinyl-tributyl tin (ALDRICH No. 27143-8), 50 mg tetrakis-(triphenylphosphine)-palladium (Merck No. 818193), a trace of 2,6-di-tert.-butyl-4-methylphenol and 10 ml anhydrous toluene was refluxed for 5 hours. The cooled reaction mixture was filtered over an activated charcoal filter, the filtrate was evaporated in a vacuum. The residue was purified for elution by column chromatography over silica gel, initially using pure dichloromethane, then methanol/conc. ammonia (9/1 v/v). The suitable eluates were triturated and suction filtered with tert.-butyl-methylether. Yield was 60 mg (32.6% of theory) of colourless crystals of R$_f$ 0.25 (FM1).
MS: M$^+$=612
The following were prepared analogously: (in each case, n=1):

| No. | RCO | Z | R$^2$ | A | NR$^3$R$^4$ | % Yield | MS | Eluant | R$_f$ | IR [cm$^{-1}$] |
| --- | --- | --- | --- | --- | --- | --- | --- | --- | --- | --- |
| 647 | N66 | CH$_2$ | AS40 | A0 | C8 | 75 | EI: M$^+$ = 611 | FM1 | 0.6 | (KBr): C=O 1639/1668 |

-continued

| No. | RCO | Z | R² | A | NR³R⁴ | % Yield | MS | Eluant | $R_f$ | IR [cm⁻¹] |
|---|---|---|---|---|---|---|---|---|---|---|
| 648 | N66 | CH₂ | AS41 | A0 | C8 | 56 | EI: M⁺ = 647 | FM1 | 0.7 | (KBr): C=O 1639/1668 |
| 649 | N66 | CH₂ | AS42 | A0 | C8 | 8 | EI: M⁺ = 648 | FM1 | 0.6 | (KBr): C=O 1635/1668 |
| 650 | N66 | CH₂ | AS43 | A0 | C8 | 11 | EI: M⁺ = 654 | FM1 | 0.6 | (KBr): C=O 1635/1666 |
| 651 | N66 | CH₂ | AS44 | A0 | C8 | 84 | EI: M⁺ = 637 | FM1 | 0.6 | (KBr): C=O 1633/1664 |
| 652 | N66 | CH₂ | AS45 | A0 | C8 | 83 | EI: M⁺ = 613 | FM1 | 0.6 | (KBr): C=O 1637/1667 |

EXAMPLE 20

Preparation of Compounds of General Formula:

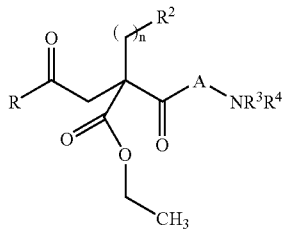

(R,S)-1-[4-[4-(3,4-dihydro-2(1H)-oxoquinazolin-3-yl)-1-piperidinyl]-2-(ethoxycarbonyl)-2-[[1-methyl-1H-indol-3-yl]methyl]-1,4-dioxobutyl]-4-(4-methyl-1-piperazinyl)-piperidine (No. 599)

Produced analogously to Example 1 from (R,S)-4-[4-(3,4-dihydro-2(1H)-oxoquinazolin-3-yl)-1-piperidinyl]-2-(ethoxycarbonyl)-2-[[1-methyl-1H-indol-3-yl]methyl]-4-oxobutanoic acid, 4-(4-methyl-1-piperazinyl)piperidine and TBTU in a yield of 10% of theory. Colourless, amorphous substance of $R_f$=0.2 (dichloromethane/methanol/conc. ammonia 90/10/1 v/v/v).

IR (KBr): 1722, 1662, 1637 cm⁻¹ (C=O)
MS: M⁺=711

Accordingly, (R,S)-1-[4-[4-(amincocarbonylamino)-1-piperidinyl]-2-(ethoxycarbonyl)-2-[[1-methyl-1H-indol-3-yl]methyl]-1,4-dioxobutyl]-4-(4-methyl-1-piperazinyl)-piperidine (No. 601) was obtained from (R,S)-4-[4-(1,3-dihydro-4-phenyl-2(2H)-oxoimidazol-1-yl)-1-piperidinyl]-2-(ethoxycarbonyl)-2-[[1-methyl-1H-indol-3-yl]methyl]-4-oxobutanoic acid, 4-(4-methyl-1-piperazinyl)piperidine and TBTU in a yield of 20% of theory. Colourless, amorphous substance of $R_f$=0.25 (dichloromethane/methanol/conc. ammonia 90/10/1 v/v/v).

| ESI-MS: | (M + H)⁺ = 624 |
|---|---|
| | (M + Na)⁺ = 646 |
| | (M + H + Na)⁺⁺ = 323.8 |

EXAMPLE 21

1-[3,5-dibromo-N-[[4-(1,3-dihydro-2(2H)-oxobenzimidazol-1-yl)-1-piperidinyl]carbonyl]-D-tyrosyl]-4-(hydroxycarbonyl)-piperidine (No. 211)

Produced analogously to Example A38 from 1-[3,5-dibromo-N-[[4-(1,3-dihydro-2(2H)-oxobenzimidazol-1-yl)-1-piperidinyl]carbonyl]-D-tyrosyl]-4-(ethoxycarbonyl)-piperidine and aqueous lithium hydroxide solution in a yield of 79% of theory. Colourless, amorphous substance of $R_f$ 0.54 (ethyl ethanoate/methanol/glacial acetic acid 9/1/0.3 v/v/v).
IR(KBr): 1691.5,1622.0 cm⁻¹ (C=O) ESI-MS: (M–H)⁻= 690/2/4 (Br₂)

EXAMPLE 22

1-[3,5-dibromo-N-[[4-(1,3-dihydro-2(2H)-oxobenzimidazol-1-yl)-1-piperidinyl]carbonyl]-D-tyrosyl]-4-(4-piperidinyl)-piperazine (No. 214)

Produced analogously to Example A24 from 3,5-dibromo-N-[[4-(1,3-dihydro-2(2H)-oxobenzimidazol-1-yl)-1-piperidinyl]carbonyl]-D-tyrosine, 1-(1,1-dimethylethoxycarbonyl)-4-(1-piperazinyl)piperidine and TBTU, and additional conversion of the obtained intermediate product with trifluoroacetic acid (in accordance with Example A1b) in a yield of 4.2% of theory. Colourless, amorphous substance of $R_f$ 0.25 (FM1).
IR(KBr): 1624.0 cm⁻¹ (C=O)
ESI-MS: (M+H)⁺=732/4/6 (Br₂)

EXAMPLE 23

(R)-1-[2-[N-[[4-(1,3-dihydro-2(2H)-oxobenzimidazol-1-yl)-1-piperidinyl]carbonyl]-N-methylamino]-3-(3,5-dibromo-4-hydroxyphenyl)-propyl]-4-(1-piperidinyl)-piperidine (No. 219)

a) 1-(chlorocarbonyl)-4-(1,3-dihydro-2(2H)-oxobenzimidazol-1-yl)-piperidine

To a solution of 3.0 g (13.8 mmol) 4-(1,3-dihydro-2(2H)-oxobenzimidazol-1-yl)piperidine and 2.7 ml (15 mMol) DIEA in 100 ml toluene, a solution of 1.8 ml (14.9 mMol) diphosgene in 15 ml toluene was added dropwise under external cooling with iced water, and the mixture was additionally kept at room temperature for 17 hours. The precipitate was suction filtered, washed with petroleum ether and dissolved in 50 ml dichloromethane. The obtained solution was agitated twice each with 50 ml 7% aqueous sodium hydrogen carbonate solution, dried over sodium sulphate and evaporated in a vacuum. Yield was 3.0 g (78% of theory) of a colourless substance of $R_f$ 0.25 (dichloromethane/acetone 9/1 v/v), which was further processed without more purification.

b) (R)-1-[3-(3,5-dibromo-4-hydroxyphenyl)-2-(N-methylamino)-propyl]-4-(1-piperidinyl)-piperidine To a suspension of 2.3 g (60 mmol) lithium aluminium hydride in 100 ml anhydrous tetrahydrofuran, a solution of 11.0 g (18.66 mmol) 1-[3,5-dibromo-N-(1,1-dimethylethoxycarbonyl)-D-tyrosyl]-4-(1-piperidinyl)piperidine in 100 ml anhydrous tetrahydrofuran was added dropwise at room temperature whilst being stirred. It was stirred for a further 15 minutes at room temperature and then refluxed for 3 hours. 3 ml 20% aqueous ammonium chloride solution was added to the cooled mixture, then it was dried with magnesium sulphate. The filter cake was filtered and washed with 300 ml of an ethyl ethanoate-methanol mixture (1/1 v/v), and the combined filtrates were evaporated in a vacuum. The residue was purified by column chromatography over silica gel using ethyl ethanoate/methanol (8/2 v/v) for elution.

1. 2.9 g (31% of theory) of a colourless substance of $R_f$ 0.13 (eluant: methanol) was isolated from the suitable fractions, which was identified as 1-(3,5-dibromo-N-methyl-D-tyrosyl)-4-(1-piperidinyl)piperidine:

IR(KBr): 1668.3 cm$^{-1}$ (C=O)

MS: M$^+$=501/3/5 (Br$_2$)

and 2. 1.8 g (20% of theory) of a colourless substance of $R_f$ 0.05 (eluant: methanol), which was identified as the sought compound:

| ESI-MS: | (M + H)$^+$ = 488/490/492 (Br$_2$) |
|---|---|
| | (M + 2H)$^{++}$ = 244/245/246.5 (Br$_2$) | c) (R)-1-[2-[N-[[4-(1,3-dihydro-2(2H)-oxobenzimidazol-1-yl)-1-piperidinyl]carbonyl]-N-methylamino]-3-(3,5-dibromo-4-hydroxyphenyl)-propyl]-4-(1-piperidinyl)-piperidine (No. 219)

A solution of 0.57 g (2.02 mmol) 1-(chlorocarbonyl)-4-(1,3-dihydro-2(2H)-oxobenzimidazol-1-yl)-piperidine in 30 ml dimethylformamide was added dropwise to the mixture of 0.9 g (1.84 mmol) (R)-1-[3-(3,5-dibromo-4-hydroxyphenyl)-2-(N-methylamino)-propyl]-4-(1-piperidinyl)-piperidine and 0.65 ml (3.7 mmol) DIEA in a mixture of 50 ml tetrahydrofuran and 20 ml dimethylformamide. It was stirred overnight at room temperature and the deposit was evaporated in a vacuum. The residue was treated with 300 ml of a tetrahydrofuran ethyl ethanoate mixture (1/1 v/v) and the resulting solution was agitated twice each with 100 ml of a saturated aqueous solution of sodium hydrogen carbonate, dried over sodium sulphate and evaporated in a vacuum. The residue was purified over silica gel by column chromatography using dichloromethane/methanol (8.5/1.5 v/v) for elution. 390 mg (29% of theory) of a colourless substance of $R_f$ 0.46 (dichloromethane cyclohexane/methanol/conc. ammonia 75/15/15/2 v/v/v/v) were isolated from the suitable fractions:

IR(KBr): 1695.3, 1624.0 cm$^{-1}$ (C=O)

ESI-MS: (M+H)$^+$=731/3/5 (Br$_2$)

EXAMPLE 24

1-[3,5-dibromo-N-[[4-[5-[(4-morpholinyl)carbonyl]-1,3-dihydro-2(2H)-oxobenzimidazol-1-yl]-1-piperidinyl]carbonyl]-D-tyrosyl]-4-(4-pyridinyl)-piperidine (No. 223)

100 mg (0.6 mMol) N,N'-carbonyldiimidazole was added to a solution of 400 mg (0.5 mMol) 1-[3,5-dibromo-N-[[4-(1,3-dihydro-5-(hydroxycarbonyl)-2(2H)-oxobenzimidazol-1-yl)-1-piperidinyl]carbonyl]-D-tyrosyl]-4-(4-pyridinyl)-piperidine in 10 ml anhydrous tetrahydrofuran at room temperature, heated to 50° C. for 30 minutes and then 90 mg (1 mMol) morpholine was added. After heating to 50-60° C. for two hours, the solution was removed in a vacuum and the residue was purified over silica gel(30-60 μm) by column chromatography, initially using dichloromethane, then dichloromethane/methanol 9/1 (v/v), and finally dichloromethane/methanol/conc. ammonia 9/1/0.2 (v/v/v) as eluants. 250 mg (60% of theory) of an amorphous, colourless substance was yielded from the suitable extracts.

| IR (KBr): | 1712.7, 1625.9 cm$^{-1}$ (C=O) |
|---|---|
| ESI-MS: | (M + H)$^+$ = 838/840/842 (Br$_2$) |
| | (M + 2H)$^{++}$ = 419/420/421.5 (Br$_2$) |

The following were obtained accordingly:

1-[3,5-dibromo-N-[[4-[5-[(4-methyl-1-piperazinyl)carbonyl]-1,3-dihydro-2(2H)-oxobenzimidazol-1-yl]-1-piperidinyl]carbonyl]-D-tyrosyl]-4-(4-pyridinyl)-piperidine (No. 224) from 1-[3,5-dibromo-N-[[4-(1,3-dihydro-5-(hydroxycarbonyl)-2(2H)-oxobenzimidazol-1-yl)-1-piperidinyl]carbonyl]-D-tyrosyl]-4-(4-pyridinyl)piperidine, 1-methylpiperazine and N,N'-carbonyldiimidazole in yield of 52% of theory. Colourless, amorphous substance.

| IR (KBr): | 1710.8, 1625.9 cm$^{-1}$ (C=O) |
|---|---|
| ESI-MS: | (M + H)$^+$ = 851/853/855 (Br$_2$) |
| | (M + 2H)$^{++}$ = 426/427/428 (Br$_2$) |

EXAMPLE 25

1-[4-amino-3,5-dibromo-N-[[4-[3,4-dihydro-2(1H)-oxoquinazolin-3-yl]-1-piperidinyl]carbonyl]-D-phenylalanyl]-4-[1-(carboxymethyl)-4-piperidinyl]-piperidine (No. 494)

Produced analogously to Example A37, but using tetrahydrofuran instead of methanol, from 1-[4-amino-3,5-dibromo-N-[[4-[3,4-dihydro-2(1H)-oxoquinazolin-3-yl]-1-piperidinyl]carbonyl]-D-phenylalanyl]-4-[1-(ethoxycarbonylmethyl)-4-piperidinyl]-piperidine by the action of aqueous lithium hydroxide solution in a yield of 51% of theory. Colourless, amorphous substance.

| ESI-MS: | (M − H)$^−$ = 800/802/804 (Br$_2$) |
|---|---|
| | (M + H)$^+$ = 802/804/806 (Br$_2$) |
| | (M + Na)$^+$ = 824/826/828 (Br$_2$) |

EXAMPLE 26

1-[3,5-dibromo-N-[[4-(3,4-dihydro-2(1H)-oxo-quinazolin-3-yl)-1-piperidinyl]carbonyl]-D-tyrosyl]-4-[1-(hydroxycarbonylmethyl)-4-piperidinyl]-piperidine (No. 526)

Produced analogously to Example 18 from 1-[3,5-dibromo-N-[[4-(3,4-dihydro-2(1H)-oxoquinazolin-3-yl)-1-piperidinyl]carbonyl]-D-tyrosyl]-4-(4-piperidinyl)-piperidine, ethyl glyoxylate and sodium triacetoxyborhydride and additional saponification with soda lye of the 1-[3,5-dibromo-N-[[4-(3,4-dihydro-2(1H)-oxoquinazolin-3-yl)-1-piperidinyl]carbonyl]-D-tyrosyl]-4-[1-(ethoxycarbonylmethyl)-4-piperidinyl]-piperidine, obtained as an intermediate product but not characterised, according to Example A55. A colourless, amorphous substance is obtained in a yield of 35% of theory.

| | |
|---|---|
| IR (KBr): | 1625.9 wide cm$^{-1}$ (C=O) |
| ESI-MS: | (M + H)$^+$ = 803/805/807 (Br$_2$) |
| | (M + Na)$^+$ = 825/827/829 (Br$_2$) |

EXAMPLE 27

1-[4-amino-N-[(4-amino-1-piperidinyl)carbonyl]-3,5-dibromo-D-phenylalanyl]-4-(1-methyl-4-piperidinyl)-piperidine (No. 564)

653 mg (10.4 mMol) 95% sodium cyanoborohydride (Aldrich 15.615-9) was stirred into the mixture of 930 mg (1.48 mMol) 1-[4-amino-3,5-dibromo-N-[(4-oxo-1-piperidinyl)carbonyl]-D-phenylalanyl]-4-(1-methyl-4-piperidinyl)-piperidine, 1143 mg (14.8 mMol) ammonium acetate (Merck No. 1115) and 30 ml anhydrous methanol at room temperature, and was stirred overnight. The deposit was adjusted to pH ≦2 with conc. hydrochloric acid and was evaporated in a vacuum. The residue is taken up in water and made alkaline with 40% soda lye. Exhaustive extraction with dichloromethane followed, then the combined extracts were dried over sodium sulphate and evaporated in a vacuum. The residue was purified over 100 g silica gel (Amicon, 35-70 μm) by column chromatography using dichloromethane/methanol/conc. ammonia(60/40/5 v/v/v) for elution. From the suitable fractions, 250 mg (27% of theory) of the sought substance was isolated as a colourless, amorphous product of R$_f$ 0.15 (dichloromethane/methanol/conc. ammonia 50/50/0.5 v/v/v).

| | |
|---|---|
| IR (KBr): | 1618 wide cm$^{-1}$ (C=O) |
| ESI-MS: | (M + H)$^+$ = 627/629/631 (Br$_2$) |
| | (M + Na)$^+$ = 649/651/653 (Br$_2$) |
| | (M + 2H)$^{++}$ = 314/315/316 (Br$_2$) |

EXAMPLE 28

(R,S)-1-[4-[4-(3,4-Dihydro-2(1H)-oxoquinazolin-3-yl)-1-piperidinyl]-2-[(3,4-dichlorphenyl)methyl]-1,4-dioxobutyl]-4-(hydroxycarbonylmethyl)-piperidine (No. 596)

Produced analogously to Example A55 from (R,S)-1-[4-[4-(3,4-dihydro-2(1H)-oxoquinazolin-3-yl)-1-piperidinyl]-2-[(3,4-dichlorophenyl)methyl]-1,4-dioxobutyl]-4-(ethoxycarbonylmethyl)-piperidine by saponification with soda lye in a yield of 86% of theory. Colourless, amorphous substance of R$_f$ 0.76 (ethyl ethanoate/methanol/glacial acetic acid 70/30/1 v/v/v).

| | |
|---|---|
| IR (KBr): | 1716, 1635 cm$^{-1}$ (C=O) |
| ESI-MS: | (M − H)$^-$ = 613/615/617 (Cl$_2$) |
| | (M + H)$^+$ = 615/617/619 (Cl$_2$) |
| | (M + Na)$^+$ = 637/639/641 (Cl$_2$) |

EXAMPLE 29

1-[N-[[4-[3,4-dihydro-2(1H)-oxoquinazolin-3-yl]-1-piperidinyl]-carbonyl]-3-(1H-tetrazol-5-yl)-D,L-phenylalanyl]-4-(1-piperidinyl)-piperidine (No. 632)

8.5 g (35 mMol) tributyl tin(IV)-azide (Synthesis 1976, 330) was added to a solution of 1.6 g (2.68 mMol) 1-[3-cyano-N-[[4-[3,4-dihydro-2(1H)-oxoquinazolin-3-yl]-1-piperidinyl]carbonyl]-D,L-phenylalanyl]-4-(1-piperidinyl)-piperidine in 400 ml toluene and the mixture was refluxed for 4 days. The residue remaining after dispellation of the solvent was stirred with ethyl ethanoate, the obtained precipitate was suction filtered and purified over silica gel by column chromatography using FM1 as an eluent. After the usual further processing, yield is 400 mg (24% of theory) of colourless crystals of R$_f$ 0.2 (FM1).

| | |
|---|---|
| IR (KBr): | 1653 cm$^{-1}$ (C=O) |
| ESI-MS: | (M + H)$^+$ = 641 |
| | (M + Na)$^+$ = 663 |

The following Examples describe the preparation of pharmaceutically useful forms which contain as active substance any desired compound of general formula I:

EXAMPLE I

Capsules for powder inhalation containing 1 mg of active substance

Composition:
1 capsule for powder inhalation contains:

| | |
|---|---|
| Active substance | 1.0 mg |
| Lactose | 20.0 mg |
| Hard gelatine capsules | 50.0 mg |
| | 71.0 mg |

Method of Preparation:

The active substance is ground to the particle size required for inhalants. The ground active substance is homogeneously mixed with the lactose. The mixture is packed into hard gelatine capsules.

EXAMPLE II

| Inhalable solution for Respimat ® containing 1 mg of active substance | |
|---|---|
| Composition: 1 stroke contains: | |
| Active substance | 1.0 mg |
| Benzalkonium chloride | 0.002 mg |
| Disodium edetate | 0.0075 mg |
| Purified water ad | 15.0 µl |

Method of Preparation:
The active substance and benzalkonium chloride are dissolved in water and transferred into Respimat® cartridges.

EXAMPLE III

| Inhalable solution for nebulisers containing 1 mg of active substance | |
|---|---|
| Composition: 1 vial contains: | |
| Active substance | 0.1 g |
| Sodium chloride | 0.18 g |
| Benzalkonium chloride | 0.002 g |
| Purified water ad | 20.0 ml |

Method of Preparation:
Active substance, sodium chloride and benzalkonium chloride are dissolved in water.

EXAMPLE IV

| Propellant gas metering aerosol containing 1 mg of active substance | |
|---|---|
| Composition: 1 stroke contains: | |
| Active substance | 1.0 mg |
| Lecithin | 0.1% |
| Propellant gas ad | 50.0 µl |

Method of Preparation:
The micronised active substance is homogeneously suspended in a mixture of lecithin and propellant gas. The suspension is transferred into a pressurised container with metering valve.

EXAMPLE V

| Nasal spray containing 1 mg of active substance | |
|---|---|
| Composition: | |
| Active substance | 1.0 mg |
| Sodium chloride | 0.9 mg |
| Benzalkonium chloride | 0.025 mg |
| Disodium edetate | 0.05 mg |
| Purified water ad | 0.1 ml |

Method of Preparation:
The active substance and adjuvants are dissolved in water and transferred into a suitable container.

EXAMPLE VI

| Injectable solution containing 5 mg of active substance per 5 ml | |
|---|---|
| Composition: | |
| Active substance | 5 mg |
| Glucose | 250 mg |
| Human-serum-albumin | 10 mg |
| Glycofurol | 250 mg |
| Water for injections ad | 5 ml |

Preparation:
Glycofurol and glucose are dissolved in water for injections (WfI); human-serum-albumin is added; active substance is dissolved with heating; solution is made up to required volume with WfI; transferred into ampoules under nitrogen gas.

EXAMPLE VII

| Injectable solution containing 100 mg of active substance per 20 ml | |
|---|---|
| Composition: | |
| Active substance | 100 mg |
| Monopotassium dihydrogen phosphate = $KH_2PO_4$ | 12 mg |
| Disodium hydrogen phosphate = $Na_2HPO_4 \cdot 2H_2O$ | 2 mg |
| Sodium chloride | 180 mg |
| Human-serum-albumin | 50 mg |
| Polysorbate 80 | 20 mg |
| Water for injections ad | 20 ml |

Preparation:
Polysorbate 80, sodium chloride, monopotassium dihydrogen phosphate and disodium hydrogen phosphate are dissolved in water for injections (WfI); human-serum-albumin is added; active substance is dissolved with heating; solution is made up to required volume with WfI; transferred into ampoules.

EXAMPLE VIII

| Lyophilisate containing 10 mg of active substance | |
|---|---|
| Composition: | |
| Active substance | 10 mg |
| Mannitol | 300 mg |
| Human-serum-albumin | 20 mg |

Preparation:

Mannitol is dissolved in water for injections (WfI); human-serum-albumin is added; active substance is dissolved with heating; solution is made up to required volume with WfI; transferred into vials and freeze-dried.

| Solvent for lyophilisate: | |
|---|---|
| Polysorbate 80 = Tween 80 | 20 mg |
| Mannitol | 200 mg |
| Water for injections ad | 10 ml |

Preparation:

Polysorbate 80 and mannitol are dissolved in water for injections (WfI) and transferred into ampoules.

EXAMPLE IX

| Tablets containing 20 mg of active substance | |
|---|---|
| Composition: | |
| Active substance | 20 mg |
| Lactose | 120 mg |
| Corn starch | 40 mg |
| Magnesium stearate | 2 mg |
| Povidon K 25 | 18 mg |

Preparation:

Active substance, lactose and corn starch are homogeneously mixed; granulated with an aqueous solution of Povidon; mixed with magnesium stearate; pressed in a tablet press; weight of tablet 200 mg.

EXAMPLE X

| Capsules containing 20 mg of active substance | |
|---|---|
| Composition: | |
| Active substance | 20 mg |
| Corn starch | 80 mg |
| Highly dispersed silicic acid | 5 mg |
| Magnesium stearate | 2.5 mg |

Preparation:

Active substance, corn starch and silicic acid are homogeneously mixed; mixed with magnesium stearate; then the mixture is packed into size 3 hard gelatine capsules using a capsule filling machine.

EXAMPLE XI

| Suppositories containing 50 mg of active substance | |
|---|---|
| Composition: | |
| Active substance | 50 mg |
| Hard fat (adeps solidus) q.s. ad | 1700 mg |

Preparation:

Hard fat is melted at about 38° C.; ground active substance is homogeneously dispersed in the molten hard fat; then after cooling to about 35° C. the melt is poured into chilled moulds.

EXAMPLE XII

| Aqueous solution for nasal application containing 10 mg active substance | |
|---|---|
| Composition: | |
| Active substance | 10.0 mg |
| Hydrochloric acid in quantity required for formation of a neutral salt | 0.01 mg |
| Methylparahydroxybenzoate (PHB) | |
| Propylparahydroxybenzoate (PHB) | 0.005 mg |
| Purified water ad | 1.0 ml |

Preparation:

The active substance is dissolved in purified water; Hydrochloric acid is added until the solution is clear; PHB methyl and propyl esters are added; the solution is made up to required volume with purified water; the solution is sterile-filtered and is transferred into an appropriate container.

EXAMPLE XIII

| Aqueous solution for nasal application containing 5 mg active substance | |
|---|---|
| Composition: | |
| Active substance | 5 mg |
| 1,2-propandiol | 300 mg |
| Hydroxyethyl cellulose | 5 mg |
| Sorbic acid | 1 mg |
| Purified water ad | 1 ml |

Preparation:

The active substance is dissolved in 1,2-propandiol; a hydroxy-ethyl-cellulose solution is prepared in purified water containing sorbic acid and is added to the active substance solution; the solution is sterile-filtered and is transferred into an appropriate container.

EXAMPLE XIV

| Aqueous solution for intravenous application containing 5 mg active substance | |
|---|---|
| Composition: | |
| Active substance | 5 mg |
| 1,2-propandiol | 300 mg |
| Mannitol | 50 mg |
| Water for injections (WfI) ad | 1 ml |

Preparation:

The active substance is dissolved in 1,2-propandiol; the solution is approximately made up to the required volume with WfI; the mannitol is added and the solution is made up to required volume with WfI; the solution is sterile-filtered, transferred into individual containers and autoclaved.

EXAMPLE XV

| Liposomal formulation for intravenous injection containing 7.5 mg active substance | |
|---|---|
| Composition: | |
| Active substance | 7.5 mg |
| Egg-lecithin, e.g. lipoid E 80 | 100.0 mg |
| Cholesterol | 50.0 mg |
| Glycerine | 50.0 mg |
| Water for injections ad | 1.0 ml |

Preparation:

The active substance is dissolved in a mixture of lecithin and cholesterol; the solution is added to a mixture of glycerine and WfI and is homogenised by means of high-pressure homogenisation or microfluidiser technology; the liposomal formulation obtained in this manner is transferred into an appropriate container under aseptic conditions.

EXAMPLE XVI

| Suspension for nasal application containing 20 mg active substance | |
|---|---|
| Composition: | |
| Active substance | 20.0 mg |
| Carboxymethylcellulose (CMC) | 20.0 mg |
| Sodium monohydrogen phosphate/sodium-dihydrogen phosphate buffer pH 6.8 | q.s. |
| Sodium chloride | 8.0 mg |
| Methylparahydroxybenzoate | 0.01 mg |
| Propylparahydroxybenzoate | 0.003 mg |
| Purified water ad | 1.0 ml |

Preparation:

The active substance is suspended in an aqueous CMC solution; the other components are added to the suspension one after another and the suspension is made up to required volume with purified water.

EXAMPLE XVII

| Aqueous solution for subcutaneous application containing 10 mg active substance | |
|---|---|
| Composition: | |
| Active substance | 10.0 mg |
| Sodium monohydrogen phosphate/sodium dihydrogen phosphate buffer q.s. ad pH | 7.0 |
| Sodium chloride | 4.0 mg |
| Water for injections ad | 0.5 ml |

Preparation:

The active substance is dissolved in the phosphate buffer solution, after addition of the sodium chloride the solution is made up to required volume with water. The solution is sterile-filtered and is autoclaved after being transferred into an appropriate container.

EXAMPLE XVIII

| Aqueous solution for subcutaneous application containing 5 mg active substance | |
|---|---|
| Composition: | |
| Active substance | 5.0 mg |
| Polysorbate 80 | 0.5 mg |
| Water for injections ad | 0.5 ml |

Preparation:

The active substance is suspended in the polysorbate 80 solution and is reduced to a particle size of approx. 1 μm by means of a suitable dispersion technique (e.g. wet milling, high-pressure homogenisation, micro-fluidisation, etc.). The suspension is transferred into an appropriate container under aseptic conditions.

The invention claimed is:
1. A compound of the formula I

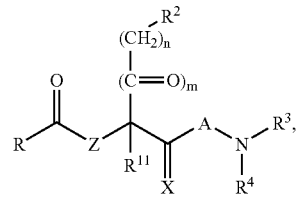

(I)

wherein

R denotes a group of formula

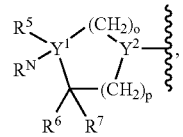

(II)

wherein
- p denotes the number 1,
- o denotes the number 2,
- $Y^1$ denotes the carbon atom,
- $Y^2$ denotes the nitrogen atom,
- $R^5$, $R^6$ and $R^7$ each denote the hydrogen atom,
- $R^N$ denotes a N-(aminocarbonyl)-N-phenylamino group or
- a mono- or bicyclic heterocycle selected from the group consisting of 1,3-dihydro-4-phenyl-2H-2-oxoimidazol-1-yl,
- 1,3-dihydro-5-phenyl-2H-2-oxoimidazol-1-yl,
- 1,3-dihydro-2(2H)-oxobenzimidazol-1-yl,
- 3,4-dihydro-2(1H)-oxothieno [3,4-d]pyrimidin-3-yl,
- 1H-benzimidazol-1-yl,
- 3,4-dihydro-2(1H)-oxoquinazolin-3-yl,
- 3,4-dihydro-2(1H)-oxoquinazolin-1-yl,
- 2,3,4,5-tetrahydro-2(1H)-oxo-1,3-benzodiazepin-3-yl, 2(1H)-oxoquinolin-3-yl, or
1,1-dioxido-3(4H)-oxo-1,2,4-benzothiadiazin-2-yl,
wherein said mono- and bicyclic heterocycles optionally are monosubstituted in the carbon skeleton and/or at the phenyl groups contained in these groups by a chlorine atom, or by a methyl, or hydroxy group, X denotes an oxygen atom or 2 hydrogen atoms, Z denotes a methylene group or the group —$NR^1$, wherein
$R^1$ denotes a hydrogen atom or a methyl group, $R^{11}$ denotes a hydrogen atom, n denotes the number 1 and m denotes the number 0 or n denotes the number 0 and m denotes the number 1, $R^2$ denotes an aromatic group selected from phenyl, 1-naphthyl and 2-naphthyl, wherein said aromatic group optionally is mono- or disubstituted by fluorine, chlorine or bromine atoms, by methyl, methoxy, hydroxy or amino groups and the substituents may be identical or different, or trisubstituted by two bromine atoms and either one hydroxy, one amino, one methyl, one methoxy group or trisubstituted by two chlorine atoms and one hydroxy group or trisubstituted by two methyl groups and either one hydroxy or one methoxy group, or $R^2$ denotes a 1H-indol-3-yl, 1-methyl-1H-indol-3-yl, 1-(1,1-dimethylethoxycarbonyl)-1H-indol-3-yl, 2-thienyl, 3-thienyl or pyridinyl group, A denotes the divalent group of formula

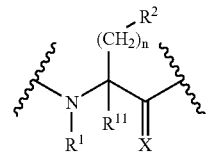
(III)

(linked to the group —$NR^3R^4$ of formula (I) via the carbonyl group)
wherein $R^8$ denotes the hydrogen atom or the methyl group and $R^9$ denotes the hydrogen atom or an unbranched $C_{1-4}$-alkyl group, which may be substituted in the ω-position by an amino, methylamino, dimethylamino or amino iminomethylamino group, $R^3$ denotes a hydrogen atom or a $C_{1-4}$-alkyl group optionally substituted in the ω-position by an amino, methylamino or dimethylamino group, $R^4$ denotes a hydrogen atom, a methyl or ethyl group, or $R^3$ and $R^4$ together with the enclosed nitrogen atom denote a group of general formula

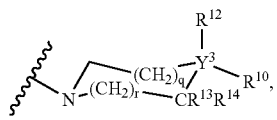
(IV)

wherein
$Y^3$ denotes the carbon atom or, if $R^{12}$ denotes a free pair of electrons, $Y^3$ denotes a nitrogen atom,
r denotes the number 1,
q denotes the number 1, $R^{10}$ denotes a $C_{1-3}$-alkyl group which may be substituted in the ω-position by a dialkylamino group having 1 to 3 carbon atoms in each alkyl moiety, or a phenyl, pyridinyl or diazinyl group, each of which may be substituted in the carbon skeleton by methyl or methoxy group, a 1-pyrrolidinyl, 1-piperidinyl, 4-(dimethylamino)-1-piperidinyl or 4-piperidinyl group, wherein the nitrogen atom of the 4-piperidinyl group may be substituted by an alkyl group having 1 to 3 carbon atoms, $R^{12}$ denotes a hydrogen atom, or a free pair of electrons if $Y^3$ denotes a nitrogen atom, and $R^{13}$ and $R^{14}$ each denote a hydrogen atom, or a tautomer or salt thereof 2. A compound of the formula I according to claim 1, wherein the partial amino acid structure of the formula

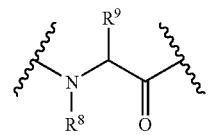
(V)

is in the D- or (R)-configuration and is in the L- or (S)-configuration with regard to the partial amino acid structure of formula

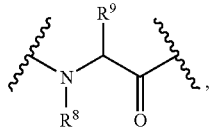
(III)

which may be present in the group A, or wherein the partial structure of formula VI

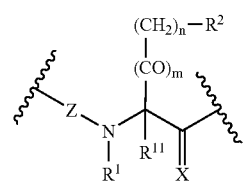
(VI)

is spatially constructed analogously to the (R)-configured partial structure of formula V.

3. A compound selected from the group consisting of:
1-[$N^2$—[N-[4-(1,3-Dihydro-2(2H)-oxobenzimidazol-1-yl)-1-piperidinyl]carbonyl]-3,5-dibromo-D-tyrosyl]-L-lysyl]-4-(4-pyridinyl)-piperazine;

(22) 1-[N2-[N-(4,4-Diphenyl-1-piperidinyl)carbonyl]-3,5-dibromo-D-tyrosyl]-L-lysyl]-4-(4-pyridinyl)-piperazine;

(23) 1-[N2-[N-(4-Phenyl-1-piperidinyl)carbonyl]-3,5-dibromo-D-tyrosyl]-L-lysyl]-4-(4-pyridinyl)-piperazine;

1-[$N^2$—[N-[4-(2-Methoxyphenyl)-1-piperidinyl]carbonyl]-3,5-dibromo-D-tyrosyl]-L-lysyl]-4-(4-pyridinyl)-piperazine;

1-[N²—[N-[4-(3-Methoxyphenyl)-1,2,5,6-tetrahydro-1-piperidinyl]carbonyl]-3,5-dibromo-D-tyrosyl ]-L-lysyl]-4-(4-pyridinyl)-piperazine;

1-[N²—[N-[4-(2-Methoxyphenyl)-1,2,5,6-tetrahydro-1-piperidinyl]carbonyl]-3,5-dibromo-D-tyrosyl ]-L-lysyl]-4-(4-pyridinyl)-piperazine;

1-[N²—[N-(4,4-Diphenyl-1-piperidinyl)carbonyl]-3,5-dibromo-D-tyrosyl]-L-lysyl]-4-(4-pyridinyl)-piperazine;

1-[N²—[N-[4-(1,3-Dihydro-2(2H)-oxobenzimidazol-1-yl)-1-piperidinyl]carbonyl]-4-amino-3,5-dibromo-D-phenylalanyl]-L-lysyl]-4-(4-pyridinyl)-piperidine;

1-[N²—[N-[4-(1,3-Dihydro-2(2H)-oxobenzimidazol-1-yl)-1-piperidinyl]carbonyl]-4-amino-3,5-dibromo-D-phenylalanyl]-L-lysyl]-4-(4-pyridinyl)-piperazine;

1-[N²—[N-[4-(1,3-Dihydro-2(2H)-oxobenzimidazol-1-yl)-1-piperidinyl]carbonyl]-3,5-dibromo-D-tyrosyl ]-N⁶-(1,1-dimethylethoxycarbonyl)-L-lysyl]-4-(2-pyridinyl)-piperazine;

1-[N²—[N-[4-(1,3-Dihydro-2(2H)-oxobenzimidazol-1-yl)-1-piperidinyl]carbonyl]-3,5-dibromo-D-tyrosyl]-L-lysyl]-4-(4-pyridinyl)-piperidine;

1-[N²—[N-[4-(Aminocarbonyl)-1-piperidinyl]carbonyl]-3,5-dibromo-D-tyrosyl]-L-lysyl]-4-(4-pyridinyl)-piperidine;

1-[N²—[N-[4-(1,3-Dihydro-2(2H)-oxobenzimidazol-1-yl)-1-piperidinyl]carbonyl]-3,5-dibromo-D-tyrosyl]-L-lysyl]-4-(2-methoxyphenyl)-piperazine;

1-[N²—[N-[4-(1,3-Dihydro-2(2H)-oxobenzimidazol-1-yl)-1-piperidinyl]carbonyl]-3,5-dibromo-D-tyrosyl]-L-lysyl]-4-(2-pyridinyl)-piperazine;

1-[N²—[N-(4,4-Diphenyl-1-piperidinyl)carbonyl]-3,5-dibromo-D-tyrosyl]-L-lysyl]-4-(2-pyridinyl)-piperazine;

1-[N²—[N-[4-(1,3-Dihydro-2(2H)-oxobenzimidazol-1-yl)-1-piperidinyl]carbonyl]-3,5-dibromo-D,L-phenylalanyl]-L-lysyl]-4-(4-pyridinyl)-piperazine;

1-[N²—[N-[4-(1,3-Dihydro-2(2H)-oxobenzimidazol-1-yl)-1-piperidinyl]carbonyl]-3,5-dibromo-D,L-phenylalanyl]-N⁶-(1,1-dimethylethoxycarbonyl)-L-lysyl]-4-(4-pyridinyl)-piperazine;

1-[N²—[N-[4-(1,3-Dihydro-2(2H)-oxobenzimidazol-1-yl)-1-piperidinyl]carbonyl]-3,5-dibromo-D-tyrosyl]-N⁶-(1,1-dimethylethoxycarbonyl)-L-lysyl]-4-(4-pyridinyl)-piperazine;

1-[N²-[3,5-Dibromo-N-[[4-(2,4(1H,3H)-dioxoquinazolin-3-yl)-1-piperidinyl]carbonyl]-D-tyrosyl]-L-lysyl]-4-(4-pyridinyl)-piperazine;

1-[N²-[3,5-Dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine;

1-[N²—[N-[[4-(Aminocarbonylamino)-1-piperidinyl]carbonyl]-3,5-dibromo-D-tyrosyl]-N⁶-(1,1-dimethylethoxycarbonyl)-L-lysyl]-4-(4-pyridinyl)-piperidine;

1-[N²-[3,5-Dibromo-N-[[4-(methylaminocarbonylamino)-1-piperidinyl]carbonyl]-D-tyrosyl]-N⁶-(1,1-dimethylethoxycarbonyl)-L-lysyl]-4-(4-pyridinyl)-piperidine;

1-[N²-[3,5-Dibromo-N-[[4-[N-(aminocarbonyl)methylamino]-1piperidinyl]carbonyl]-D-tyrosyl]-N⁶-(1,1-dimethylethoxycarbonyl)-L-lysyl]-4-(4-pyridinyl)-piperidine;

1-[N²—N-[[4-(Aminocarbonylamino)-1-piperidinyl]carbonyl]-3,5-dibromo-D-tyrosyl]-L-lysyl]-4-(4-pyridinyl)-piperidine;

1-[N²-[3,5-Dibromo-N-[[4-[N-(methylaminocarbonyl)methylamino]-1-piperidinyl]carbonyl]-D-tyrosyl]-N⁶-(1,1-dimethylethoxycarbonyl)-L-lysyl]-4-(4-pyridinyl)-piperidine;

1-[N²-[3,5-Dibromo-N-[[4-[N-(aminocarbonyl)methylamino]-1-piperidinyl]carbonyl]-D-tyrosyl]-L-lysyl]-4-(4-pyridinyl)-piperidine;

1-[N²-[3,5-Dibromo-N-[[4-[N-(methylaminocarbonyl)amino]-1-piperidinyl]carbonyl]-D-tyrosyl]-L-lysyl]-4-(4-pyridinyl)-piperidine;

1-[N²-[3,5-Dibromo-N-[[4-[N-(methylaminocarbonyl)methylamino]-1-piperidinyl]carbonyl]-D-tyrosyl]-L-lysyl]-4-(4-pyridinyl)-piperidine;

1-[N²—[N-[[4-[N-(Aminocarbonyl)phenylamino]-1-piperidinyl]carbonyl]-3,5-dibromo-D-tyrosyl]-L-lysyl]-4-(4-pyridinyl)-piperidine;

1-[N²—[N-[[4-[2(3H)-Oxobenzoxazol-3-yl]-1-piperidinyl]carbonyl]-3,5-dibromo-D-tyrosyl]-N⁶-(1,1-dimethylethoxycarbonyl)-L-lysyl]-4-(4-pyridinyl)-piperazine;

1-[N²-[3,5-Dibromo-N-[[4-(1,3-dihydro-2(2H)-oxobenzimidazol-1-yl)-1-piperidinyl]carbonyl]-D-tyrosyl]-N⁶-(1,1-dimethylethoxycarbonyl)-L-lysyl]-4-(5-methoxy-4-pyrimidinyl)-piperazine;

1-[N²-[2,5-Dibromo-N-[[4-(1,3-dihydro-2(2H)-oxobenzimidazol-1-yl)-1-piperidinyl]carbonyl]-D-phenylalanyl]-N⁶-(1,1-dimethylethoxycarbonyl)-L-lysyl]-4-(4-pyridinyl)-piperazine;

1-[N²-[3,5-Dibromo-N-[[4-(1,3-dihydro-2(2H)-oxobenzimidazol-1-yl)-1-piperidinyl]carbonyl]-D-tyrosyl]-N⁶-(1,1-dimethylethoxycarbonyl)-L-lysyl]-4-(1-piperidinyl)-piperidine;

1-[N²-[3,5-Dibromo-N-[[4-(1,3-dihydro-2(2H)-oxobenzimidazol-1-yl)-1-piperidinyl ]carbonyl]-D-tyrosyl]-L-lysyl]-4-(1-piperidinyl)-piperidine;

1-[N²-[3,5-Dibromo-N-[[4-(1,3-dihydro-2(2H)-oxobenzimidazol-1-yl)-1-piperidinyl ]carbonyl]-L-tyrosyl]-L-lysyl]-4-(4-pyridinyl)-piperazine;

1-[N²-[3,5-Dibromo-N-[[4-(1,3-dihydro-2(2H)-oxobenzimidazol-1-yl)-1-piperidinyl ]carbonyl]-L-tyrosyl]-D-lysyl]-4-(4-pyridinyl)-piperazine;

1-[N²-[3,5-Dibromo-N-[[4-(1,3-dihydro-2(2H)-oxobenzimidazol-1-yl)-1-piperidinyl ]carbonyl]-D-tyrosyl]-D-lysyl]-4-(4-pyridinyl)-piperazine;

1-[N²-[3,5-Dibromo-N-[[4-(1,3-dihydro-2(2H)-oxobenzimidazol-1-yl)-1-piperidinyl ]carbonyl]-D-tyrosyl]-N⁶,N⁶-dimethyl-L-lysyl]-4-(4-pyridinyl)-piperazine;

1-[N²-[3-Bromo-N-[[4-(1,3-dihydro-2(2H)-oxobenzimidazol-1-yl)-1-piperidinyl ]carbonyl]-D-tyrosyl]-L-lysyl]-4-(1-piperidinyl)-piperidine;

1-[N²-[3-Bromo-N-[[4-(1,3-dihydro-2(2H)-oxobenzimidazol-1-yl)-1-piperidinyl ]carbonyl]-D-tyrosyl]-N⁶-(1,1-dimethylethoxycarbonyl)-L-lysyl]-4-(4-pyridinyl)-piperazine;

1-[N²-[3-Bromo-N-[[4-(1,3-dihydro-2(2H)-oxobenzimidazol-1-yl)-1-piperidinyl ]carbonyl]-D-tyrosyl]-L-lysyl]-4-(4-pyridinyl)-piperazine;

1-[N²-[4-Amino-3,5-dibromo-N-[[4-(1,3-dihydro-2(2H)-oxobenzimidazol-1-yl)-1-piperidinyl ]carbonyl]-D-phenylalanyl]-N⁶,N⁶-dimethyl-L-lysyl]-4-(4-pyridinyl)-piperazine;

1-[N²-[4-Amino-3,5-dibromo-N-[[4-(3,4-dihydro-2(1H)-oxoquinazolin-3-yl)-1-piperidinyl ]carbonyl]-D-phenylalanyl]-L-lysyl]-4-(1-piperidinyl)-piperidine;

1-[N²-[4-Amino-3,5-dibromo-N-[[4-(3,4-dihydro-2(1H)-oxoquinazolin-3-yl)-1-piperidinyl ]carbonyl]-D-phenylalanyl]-L-lysyl]-4-(4-pyridinyl)-piperazine;

1-[N²-[4-Amino-3,5-dibromo-N-[[4-(3,4-dihydro-2(1H)-oxoquinazolin-3-yl)-1-piperidinyl ]carbonyl]-D-phenylalanyl]-L-lysyl]-4-(4-pyridinyl)-piperidine;

1-[N²-[3,5-Dibromo-N-[[4-(3,4-dihydro-2(1H)-oxo-quinazolin-3-yl)-1-piperidinyl]carbonyl]-D-tyrosyl]-L-lysyl]-4-(1-piperidinyl)-piperidine;

1-[N²-[3,5-Dibromo-N-[[4-(1,3-dihydro-4-phenyl-2(2H)-oxoimidazol-1-yl)-1-piperidinyl]carbonyl]-D-tyrosyl]-L-lysyl]-4-(4-pyridinyl)-piperazine;

1-[N²-[4-Amino-3,5-dibromo-N-[[4-(1,3-dihydro-4-phenyl-2(2H)-oxoimidazol-1-yl)-1-piperidinyl]carbonyl]-D-phenylalanyl]-L-lysyl]-4-(1-piperidinyl)-piperidine;

1-[N²-[4-Amino-3,5-dibromo-N-[[4-(1,3-dihydro-4-phenyl-2(2H)-oxoimidazol-1-yl)-1-piperidinyl]carbonyl]-D-phenylalanyl]-L-lysyl]-4-(4-pyridinyl)-piperazine;

1-[N²-[2,5-Dibromo-N-[[4-(1,3-dihydro-2(2H)oxobenz-imidazol-1-yl)-1-piperidinyl]carbonyl]-D-phenylalanyl]-N⁶-(1,1-dimethylethoxycarbonyl)-L-lysyl]-4-(4-pyridinyl)-piperidine;

1-[N²-[3,5-Dibromo-N-[[4-[2(3H)-oxobenzoxazol-3-yl]-1-piperidinyl]carbonyl]-D-tyrosyl]-L-lysyl]-4-(4-pyridinyl)-piperazine;

1-[N²-[3,5-Dibromo-N-[[4-(1,3-dihydro-2(2H)-oxobenz-imidazol-1-yl)-1-piperidinyl]carbonyl]-D-tyrosyl]-L-lysyl]-4-(5-methoxy-4-pyrimidinyl)-piperazine;

1-[N²-[2,5-Dibromo-N-[[4-(1,3-dihydro-2(2H)-oxobenz-imidazol-1-yl)-1-piperidinyl]carbonyl]-D-phenylalanyl]-L-lysyl]-4-(4-pyridinyl)-piperidine;

1-[N²-[2,5-Dibromo-N-[[4-(1,3-dihydro-2(2H)-oxobenz-imidazol-1-yl)-1-piperidinyl]carbonyl]-L-phenylalanyl]-L-lysyl]-4-(4-pyridinyl)-piperidine;

1-[N²-[2,5-Dibromo-N-[[4-(1,3-dihydro-2(2H)-oxobenz-imidazol-1-yl)-1-piperidinyl]carbonyl]-D-phenylalanyl]-L-lysyl]-4-(4-pyridinyl)-piperazine;

1-[N²-[3,5-Dibromo-N-[[4-[N-(Aminocarbonyl)pheny-lamino]-1-piperidinyl]carbonyl]-D-tyrosyl]-N⁶-(1,1-dimethylethoxycarbonyl)-L-lysyl]-4-(4-pyridinyl)-piperazine;

1-[N²-[3,5-Dibromo-N-[[4-[N-(Aminocarbonyl)pheny-lamino]-1-piperidinyl]carbonyl]-D-tyrosyl]-L-lysyl]-4-(4-pyridinyl)-piperazine;

1-[N²-[4-Amino-3,5-dibromo-N-[[4-(1,3-dihydro-2(2H)-oxobenzimidazol-1-yl)-1-piperidinyl]carbonyl]-D-phenylalanyl]-L-lysyl]-4-(5-methoxy-4-pyrimidinyl)-piperazine;

1-[N²-[4-Amino-3,5-dibromo-N-[[4-[N-(methylami-nocarbonyl)phenylamino]-1-piperidinyl]carbonyl]-D-phenylalanyl]-N⁶-(1,1-dimethylethoxycarbonyl)-L-lysyl]-4-(1-piperidinyl)-piperidine;

1-[N²-[4-Amino-3,5-dibromo-N-[[4-[N-(methylami-nocarbonyl)phenylamino]-1-piperidinyl]carbonyl]-D-phenylalanyl]-L-lysyl]-4-(1-piperidinyl)-piperidine;

1-[N²-[4-Amino-3,5-dibromo-N-[[4-(1,3-dihydro-2(2H)-oxobenzimidazol-1-yl)-4-methyl-1-piperidinyl]carbo-nyl]-D-phenylalanyl]-N⁶-(1,1-dimethylethoxycarbo-nyl)-L-lysyl]-4-(4-pyridinyl)-piperidine;

1-[N²-[4-Amino-3,5-dibromo-N-[[4-(1,3-dihydro-2(2H)-oxobenzimidazol-1-yl)-4-methyl-1-piperidinyl]carbo-nyl]-D-phenylalanyl]-L-lysyl]-4-(4-pyridinyl)-piperi-dine;

1-[N²-[3,5-Dibromo-N-[[4-(1,3-dihydro-2(2H)-oxobenz-imidazol-1-yl)-1-piperidinyl]carbonyl]-D-tyrosyl]-L-lysyl]-4-(4-pyridinyl)-piperazine;

1-[N⁶-Acetyl-N²-[3,5-dibromo-N-[[4-(3,4-dihydro-2 (1H)-oxoquinazolin-3-yl)-1-piperidinyl]carbonyl]-D-tyrosyl]-L-lysyl]-4-(4-pyridinyl)-piperazine;

1-[N²-[4-Amino-3,5-dibromo-N-[[4-(3,4-dihydro-2(1H)-oxoquinazolin-3-yl)-1-piperidinyl]carbonyl]-D-pheny-lalanyl]-N⁶,N⁶-dimethyl-L-lysyl]-4-(4-pyridinyl)-pip-erazine;

1-[N²-[3,5-Dibromo-N-[[4-(3,4-dihydro-2(1H)-oxo-quinazolin-3-yl)-1-piperidinyl]carbonyl]-D-tyrosyl]-N⁶,N⁶-dimethyl-L-lysyl]-4-(4-pyridinyl)-piperazine;

1-[N²-[3,5-Dibromo-N-[[4-[1,3-dihydro-4-[3-(trifluo-romethyl)phenyl]-2(2H)-oxoimidazol-1-yl]-1-piperidi-nyl]carbonyl]-D-tyrosyl]-L-lysyl]-4-(4-pyridinyl)-pip-erazine;

1[N2-[3,5-Dibromo-N-[[4-(1,3-dihydro-2(2H)-oxobenz-imidazol-1-yl)-1-piperidinyl]carbonyl]-D-tyrosyl]-N⁶-(1,1-dimethylethoxycarbonyl)-L-lysyl]-4-(4-pyridi-nyl)-piperazine;

1-[N²-[3,5-Dibromo-N-[[4-(3,4-dihydro-2(1H)-oxo-quinazolin-3-yl)-1-piperidinyl]carbonyl]-L-tyrosyl]-D-lysyl]-4-(4-pyridinyl)-piperazine; and 1-[N²-[3,5-Dibromo-N-[[4-(3,4-dihydro-2(1H)-oxo-quinazolin-3-yl)-1-piperidinyl]carbonyl]-L-tyrosyl]-L-lysyl]-4-(4-pyridinyl)-piperazine;

or a tautomer or salt thereof.

4. A physiologically acceptable salt of a compound in accordance with claim 2, 1 or 3.

5. A pharmaceutical composition containing a compound according to claim 2, 1 or 3 or a physiologically acceptable salt thereof, together with an inert carrier or diluent.

* * * * *